US008518975B2

(12) United States Patent
Aslanian et al.

(10) Patent No.: US 8,518,975 B2
(45) Date of Patent: Aug. 27, 2013

(54) GAMMA SECRETASE MODULATORS

(75) Inventors: Robert G. Aslanian, Rockaway, NJ (US); Xianhai Huang, Warren, NJ (US); Anandan Palani, Bridgewater, NJ (US); Jun Qin, Edison, NJ (US); Wei Zhou, Scotch Plains, NJ (US); Xiaohong Zhu, Edison, NJ (US); Robert D. Mazzola, Jr., Stewartsville, NJ (US); Pawan Dhondi, Elizabeth, NJ (US); William J. Greenlee, Teaneck, NJ (US)

(73) Assignee: Merck Sharp + Dohme Corp., Rahway, NJ (US)

( * ) Notice: Subject to any disclaimer, the term of this patent is extended or adjusted under 35 U.S.C. 154(b) by 201 days.

(21) Appl. No.: 12/673,858

(22) PCT Filed: Sep. 4, 2008

(86) PCT No.: PCT/US2008/010370

§ 371 (c)(1),
(2), (4) Date: Dec. 22, 2010

(87) PCT Pub. No.: WO2009/032277

PCT Pub. Date: Mar. 12, 2009

(65) Prior Publication Data

US 2011/0082153 A1 Apr. 7, 2011

Related U.S. Application Data

(60) Provisional application No. 60/970,344, filed on Sep. 6, 2007.

(51) Int. Cl.

| | |
|---|---|
| ***C07D 403/12*** | (2006.01) |
| ***C07D 401/12*** | (2006.01) |
| ***C07D 237/14*** | (2006.01) |
| ***A61K 31/501*** | (2006.01) |
| ***A61K 31/50*** | (2006.01) |
| ***A61K 31/4439*** | (2006.01) |

(52) U.S. Cl.
USPC .................................... 514/341; 546/272.7

(58) Field of Classification Search
USPC .................................... 546/272.7; 514/341
See application file for complete search history.

(56) References Cited

U.S. PATENT DOCUMENTS

| | | | |
|---|---|---|---|
| 2005/0042284 A1 | 2/2005 | Hobden et al. |
| 2006/0004013 A1 | 1/2006 | Kimura et al. |
| 2007/0117798 A1 | 5/2007 | Kimura et al. |
| 2007/0117839 A1 | 5/2007 | Kimura et al. |

FOREIGN PATENT DOCUMENTS

| | | |
|---|---|---|
| WO | 2004/071431 A2 | 8/2004 |
| WO | 2004/110350 A2 | 12/2004 |
| WO | 2005/110422 A2 | 11/2005 |
| WO | 2006/001877 A2 | 1/2006 |
| WO | 2006/045554 A1 | 5/2006 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
PCT/US2008/010370 Search Report, Mar. 9, 2010.

* cited by examiner

*Primary Examiner* — Kahsay T Habte
(74) *Attorney, Agent, or Firm* — Susan L. Hess; Gerard M. Devlin

(57) ABSTRACT

This invention provides novel compounds that are modulators of gamma secretase. The compounds have the formula (I)

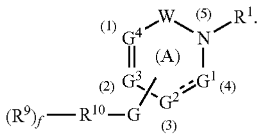

Also disclosed are methods of modulating gamma secretase activity and methods of treating Alzheimer's Disease using the compounds of formula (I).

15 Claims, No Drawings

GAMMA SECRETASE MODULATORS

REFERENCE TO RELATED APPLICATIONS

This application is a 371 of PCT/US2008/010370 filed Sep. 4, 2008, which in turn claims the benefit of U.S. Provisional Application Ser. No. 60/970,344 filed Sep. 6, 2007.

FIELD OF THE INVENTION

The present invention relates to certain heterocyclic compounds useful as gamma secretase modulators (including inhibitors, antagonists and the like), pharmaceutical compositions containing the compounds, and methods of treatment using the compounds and compositions to treat various diseases including central nervous system disorders such as, for example, neurodegenerative diseases such as Alzheimer's disease and other diseases relating to the deposition of amyloid protein. They are especially useful for reducing Amyloid beta (hereinafter referred to as Aβ) production which is effective in the treatment of diseases caused by Aβ such as, for example, Alzheimers and Down Syndrome.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

Aβ protein, which is a metabolite of amyloid precursor protein (hereinafter referred to as APP), is considered to be greatly involved in degeneration and loss of neurons as well as onset of demential conditions (for example, see Klein W L, et al *Proceeding National Academy of Science USA*, Sep. 2, 2003, 100(18), p. 10417-22, suggest a molecular basis for reversible memory loss.

Nitsch R M, and 16 others, Antibodies against β-amyloid slow cognitive decline in Alzheimer's disease, Neuron, May 22, 2003, 38(4), p. 547-554) suggest that the main components of Aβ protein are Aβ40 consisting of 40 amino acids and Aβ42 having two additional amino acids at the C-terminal. The Aβ40 and Aβ42 tend to aggregate (for example, see Jarrell J T et al, *The carboxy terminus of the β amyloid protein is critical for the seeding of amyloid formation: implications for the pathogenesis of Alzheimer's disease*, Biochemistry, May 11, 1993, 32(18), p. 4693-4697) and constitute main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer disease and Down syndrome*, Proceeding National Academy of Science USA, June 1985, 82(12), p. 4245-4249.).

Furthermore, it is known that mutations of APP and presenelin genes, which is observed in familial Alzheimer's disease, increase production of Aβ40 and Aβ42 (for example, see Gouras G K, et al, *Intraneuronal Aβ42 accumulation in human brain*, American Journal of Pathology, January 2000, 156(1), p. 15-20. Also, see Scheuner D, et al, Nature Medicine, August 1996, 2(8), p. 864-870; and Forman M S, et al, *Differential effects of the Swedish mutant amyloid precursor protein on β-amyloid accumulation and secretion in neurons and nonneuronal cells*, Journal of Biological Chemistry, Dec. 19, 1997, 272(51), p. 32247-32253.). Therefore, compounds which reduce production of Aβ40 and Aβ542 are expected as an agent for controlling progress of Alzheimer's disease or for preventing the disease.

These Aβs are produced when APP is cleaved by beta secretase and subsequently clipped by gamma secretase. In consideration of this, creation of inhibitors of γ secretase and β secretase has been attempted for the purpose of reducing production of Aβs. Many of these secretase inhibitors already known are peptides or peptidomimetics such as L-685,458. L-685,458, an aspartyl protease transition stale mimic, is a potent inhibitor of amyloid β-protein precursor γ-secretase activity, Biochemistry, Aug. 1, 2000, 39(30), p. 8698-8704).

Also of interest in connection with the present invention are: US 2007/0117798 (Eisai, published May 24, 2007); US 2007/0117839 (Eisai, published May 24, 2007); US 2006/0004013 (Eisai, published Jan. 5, 2006); WO 2005/110422 (Boehringer Ingelheim, published Nov. 24, 2005); WO 2006/045554 (Cellzone A G, published May 4, 2006); WO 2004/110350 (Neurogenetics, published Dec. 23, 2004); WO 2004/071431 (Myriad Genetics, published Aug. 26, 2004); US 2005/0042284 (Myriad Genetics, published Feb. 23, 2005) and WO 2006/001877 (Myriad Genetics, published Jan. 5, 2006).

There is a need for new compounds, formulations, treatments and therapies to treat diseases and disorders associated with Aβ. It is, therefore, an object of this invention to provide compounds useful in the treatment or prevention or amelioration of such diseases and disorders.

SUMMARY OF THE INVENTION

In its many embodiments, the present invention provides a novel class of compounds as gamma secretase modulators (including inhibitors, antagonists and the like), methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the Aβ using such compounds or pharmaceutical compositions.

The compounds of this invention (e.g., the compounds of Formula (I), and the compounds 50.1-190.1) can be useful as gamma secretase modulators and can be useful in the treatment and prevention of diseases such as, for example, Alzheimers disease, mild cognitive impairment (MCI), Downs Syndrome, Glaucoma (Guo et. al., Proc. Natl. Acad. Sci. USA 104, 13444-13449 (2007)), Cerebral amyloid angiopathy, stroke or dementia (Frangione et al., Amyloid: J. Protein folding Disord. 8, suppl. 1, 36-42 (2001), Microgliosis and brain inflammation (M P Lamber, Proc. Natl. Acad. Sci. USA 95, 6448-53 (1998)), Olfactory function loss (Getchell, et. al. Neurobiology of Aging, 663-673, 24, 2003).

This invention provides novel compounds, that are gamma secretase modulators, of the formula:

(I)

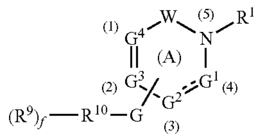

or a pharmaceutically acceptable salt, ester, or solvate thereof, wherein all substituents are defined below.

Another embodiment of this invention is directed to a compound of formula (I).

Another embodiment of this invention is directed to a pharmaceutically acceptable salt of a compound of formula (I).

Another embodiment of this invention is directed to a pharmaceutically acceptable ester of a compound of formula (I).

Another embodiment of this invention is directed to a solvate of a compound of formula (I).

Another embodiment of this invention is directed to a compound of formula (I) in isolated form.

Another embodiment of this invention is directed to a compound of formula (I) in pure form.

Another embodiment of this invention is directed to a compound of formula (I) in pure and isolated form.

Another embodiment of this invention is directed to a compound selected from the group consisting of compounds 1.1 to 49.1 and 191.1 to 274.1 (and in one example, 1.1 to 49.1, and in another example 191.1 to 262.1, and in another example 263.1 to 274.1).

Another embodiment of this invention is directed to a compound selected from the group consisting of 1.1 to 49.1 and 191.1 to 274.1 (and in one example, 1.1 to 49.1, and in another example 191.1 to 262.1, and in another example 263.1 to 274.1).

Another embodiment of this invention is directed to a compound selected from the group consisting of 1.1 to 49.1 and 191.1 to 274.1 (and in one example, 1.1 to 49.1, and in another example 191.1 to 262.1, and in another example 263.1 to 274.1).

Another embodiment of this invention is directed to a compound selected from the group consisting of 1.1 to 49.1 and 191.1 to 274.1 (and in one example, 1.1 to 49.1, and in another example 191.1 to 262.1, and in another example 263.1 to 274.1).

Another embodiment of this invention is directed to a pharmaceutically acceptable salt of a compound selected from the group consisting of 1.1 to 49.1 and 191.1 to 274.1 (and in one example, 1.1 to 49.1, and in another example 191.1 to 262.1, and in another example 263.1 to 274.1).

Another embodiment of this invention is directed to a pharmaceutically acceptable ester of a compound selected from the group consisting of 1.1 to 49.1 and 191.1 to 274.1 (and in one example, 1.1 to 49.1, and in another example 191.1 to 262.1, and in another example 263.1 to 274.1).

Another embodiment of this invention is directed to a solvate of a compound selected from the group consisting of 1.1 to 49.1 and 191.1 to 274.1 (and in one example, 1.1 to 49.1, and in another example 191.1 to 262.1, and in another example 263.1 to 274.1).

Another embodiment of this invention is directed to a compound selected from the group consisting of compounds 50.1 to 190.1 (and in one embodiment the compound is selected from the group consisting of 50.1-118.1, and in another embodiment the compound is selected from the group consisting of 119.1-190.1).

Another embodiment of this invention is directed to a compound selected from the group consisting of 50.1 to 190.1 in pure and isolated form (and in one embodiment the compound is selected from the group consisting of 50.1-118.1, and in another embodiment the compound is selected from the group consisting of 119.1-190.1).

Another embodiment of this invention is directed to a compound selected from the group consisting of 50.1 to 190.1 in pure form (and in one embodiment the compound is selected from the group consisting of 50.1-118.1, and in another embodiment the compound is selected from the group consisting of 119.1-190.1).

Another embodiment of this invention is directed to a compound selected from the group consisting of 50.1 to 190.1 in isolated form (and in one embodiment the compound is selected from the group consisting of 50.1-118.1, and in another embodiment the compound is selected from the group consisting of 119.1-190.1).

Another embodiment of this invention is directed to a pharmaceutically acceptable salt of a compound selected from the group consisting of 50.1 to 190.1 (and in one embodiment the compound is selected from the group consisting of 50.1-118.1, and in another embodiment the compound is selected from the group consisting of 119.1-190.1).

Another embodiment of this invention is directed to a pharmaceutically acceptable ester of a compound selected from the group consisting of 50.1 to 190.1 (and in one embodiment the compound is selected from the group consisting of 50.1-118.1, and in another embodiment the compound is selected from the group consisting of 119.1-190.1).

Another embodiment of this invention is directed to a solvate of a compound selected from the group consisting of 50.1 to 190.1 (and in one embodiment the compound is selected from the group consisting of 50.1-118.1, and in another embodiment the compound is selected from the group consisting of 119.1-190.1).

Another embodiment is directed to a pharmaceutical composition comprising an effective amount of one or more (e.g., one) compounds of formula (I) and a pharmaceutically acceptable carrier.

Another embodiment is directed to a pharmaceutical composition comprising an effective amount of a pharmaceutically acceptable salt of one or more (e.g., one) compounds of formula (I) and a pharmaceutically acceptable carrier.

Another embodiment is directed to a pharmaceutical composition comprising an effective amount of a pharmaceutically acceptable ester of one or more (e.g., one) compounds of formula (I) and a pharmaceutically acceptable carrier.

Another embodiment is directed to a pharmaceutical composition comprising an effective amount of a solvate of one or more (e.g., one) compounds of formula (I) and a pharmaceutically acceptable carrier.

Another embodiment of this invention is directed to a pharmaceutical composition comprising an effective amount of one or more (e.g., one) compounds of formula (I), and an effective amount of one or more (e.g., one) other pharmaceutically active ingredients (e.g.) drugs, and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising an effective amount of one or more (e.g., one) compounds of formula (I), and effective amount of one or more BACE inhibitors, and a pharmaceutically acceptable carrier.

Another embodiment of this invention is directed to a pharmaceutical composition comprising an effective amount of one or more (e.g., one) compounds of formula (I), and effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds of formula (I), and effective amount of one or more muscarinic antagonists (e.g., $m_1$ or $m_2$ antagonists), and a pharmaceutically acceptable carrier.

The compounds of formula (I) can be useful as gamma secretase modulators and can be useful in the treatment and prevention of diseases such as, for example, central nervous system disorders such as Alzheimers disease and Downs Syndrome.

Thus, another embodiment of this invention is directed to a method for modulating (including inhibiting, antagonizing and the like) gamma-secretase comprising administering an effective (i.e., therapeutically effective) amount of one or more (e.g., one) compounds of formula (I) to a patient in need of such treatment.

Another embodiment of this invention is directed to a method for modulating (including inhibiting, antagonizing and the like) gamma-secretase, comprising administering an effective (i.e., therapeutically effective) amount of a compound of formula (I) to a patient in need of treatment.

Another embodiment of this invention is directed to a method of treating one or more neurodegenerative diseases, comprising administering an effective (i.e., therapeutically effective) amount of one or more (e.g., one) compounds of formula (I) to a patient in need of treatment.

Another embodiment of this invention is directed to a method of treating one or more neurodegenerative diseases, comprising administering an effective (i.e., therapeutically effective) amount of a compound of formula (I) to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of one or more (e.g., one) compounds of formula (I) to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of a compound of formula (I) to a patient in need of treatment.

Another embodiment of this invention is directed to a method of treating Alzheimer's disease, comprising administering an effective (i.e., therapeutically effective) amount of one or more (e.g., one) compounds of formula (I) to a patient in need of treatment.

Another embodiment of this invention is directed to a method of treating Alzheimer's disease, comprising administering an effective (i.e., therapeutically effective) amount of a compound of formula (I) to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (I) and the administration of one or more (e.g., one) other pharmaceutical active ingredients (e.g., drugs). The compounds of formula (I) and the other drugs can be administered separately (i.e., each is in its own separate dosage form), or the compounds of formula (I) can be combined with the other drugs in the same dosage form.

Thus, other embodiments of this invention are directed to any one of the methods of treatment, or methods of inhibiting, described herein, wherein the compound of formula (I) is used in combination with an effective amount of one or more other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Thus, another embodiment of this invention is directed to a method of treating Alzheimer's disease comprising administering one or more (e.g., one) compounds of formula (I) in combination with an effective amount of one or more other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchiolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe), to a patient in need of such treatment.

Another embodiment of this invention is directed to a method of treating Alzheimer's disease, comprising administering an effective (i.e., therapeutically effective) amount of one or more (e.g., one) compounds of formula (I), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1 H -inden-1-one hydrochloride, i.e., donepezil hydrochloride, available as the Aricept® brand of donepezil hydrochloride), to a patient in need of treatment.

This invention also provides a method of treating Alzheimer's disease, comprising administering an effective (i.e., therapeutically effective) amount of a compound of formula (I), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1 H -inden-1-one hydrochloride, i.e., donepezil hydrochloride, available as the Aricept® brand of donepezil hydrochloride), to a patient in need of treatment.

This invention also provides a method of treating Alzheimer's disease, comprising administering an effective (i.e., therapeutically effective) amount of one or more (e.g., one) compounds of formula (I), in combination with an effective (i.e., therapeutically effective) amount of one or more compounds selected from the group consisting of Aβ antibody inhibitors, gamma secretase inhibitors and beta secretase inhibitors.

This invention also provides a method of treating Alzheimer's disease, comprising administering an effective (i.e., therapeutically effective) amount of one or more (e.g., one)

compounds of formula (I), in combination with an effective (i.e., therapeutically effective) amount of one or more BACE inhibitors.

This invention also provides a method of treating Downs syndrome, comprising administering an effective (i.e., therapeutically effective) amount of one or more (e.g., one) compounds of formula (I) to a patient in need of treatment.

This invention also provides a method of treating Downs syndrome, comprising administering an effective (i.e., therapeutically effective) amount of a compound of formula (I) to a patient in need of treatment.

This invention also provides a method of treating Downs syndrome, comprising administering an effective (i.e., therapeutically effective) amount of one or more (e.g., one) compounds of formula (I), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1 H -inden-1-one hydrochloride, i.e., donepezil hydrochloride, available as the Aricept® brand of donepezil hydrochloride), to a patient in need of treatment.

This invention also provides a method of treating Downs syndrome, comprising administering an effective (i.e., therapeutically effective) amount of a compound of formula (I), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1 H -inden-1-one hydrochloride, i.e., donepezil hydrochloride, available as the Aricept® brand of donepezil hydrochloride), to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula (I) and the administration of an effective amount of one or more (e.g., one) other pharmaceutical active ingredients (e.g., drugs).

This invention also provides a method of treating mild cognitive impairment, comprising administering an effective amount of one or more (e.g., one) compounds of formula (I) to a patient in need of treatment.

This invention also provides a method of treating glaucoma, comprising administering an effective amount of one or more (e.g., one) compounds of formula (I) to a patient in need of treatment.

This invention also provides a method of treating cerebral amyloid angiopathy, comprising administering an effective amount of one or more (e.g., one) compounds of formula (I) to a patient in need of treatment.

This invention also provides a method of treating stroke, comprising administering an effective amount of one or more (e.g., one) compounds of formula (I) to a patient in need of treatment.

This invention also provides a method of treating dementia, comprising administering an effective amount of one or more (e.g., one) compounds of formula (I) to a patient in need of treatment.

This invention also provides a method of treating microgliosis, comprising administering an effective amount of one or more (e.g., one) compounds of formula (I) to a patient in need of treatment.

This invention also provides a method of treating brain inflammation, comprising administering an effective amount of one or more (e.g., one) compounds of formula (I) to a patient in need of treatment.

This invention also provides a method of treating olfactory function loss, comprising administering an effective amount of one or more (e.g., one) compounds of formula (I) to a patient in need of treatment.

This invention also provides pharmaceutical compositions comprising a combination of an effective amount of one or more (e.g., one) compounds of formula (I), in combination with an effective amount of one or more compounds selected from the group consisting of cholinesterase inhibitors, Aβ antibody inhibitors, gamma secretase inhibitors and beta secretase inhibitors. The pharmaceutical compositions also comprise a pharmaceutically acceptable carrier.

Other embodiments of this invention are directed to any one of the methods described above wherein the compound of formula (I) is a compound selected from the group consisting of 1.1 to 49.1 and 191.1 to 274.1 (and in one example, 1.1 to 49.1, and in another example 191.1 to 262.1, and in another example 263.1 to 274.1).

This invention also provides combinations (i.e., pharmaceutical compositions) comprising an effective (i.e., therapeutically effective) amount of one or more (e.g., one) compounds of formula (I), in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1 H -inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described above), the combined quantities of the compound of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

This invention also provides a kit comprising, in separate containers, in a single package, pharmaceutical compositions for use in combination, wherein one container comprises an effective amount of a compound selected from the group consisting of 1.1 to 49.1 and 191.1 to 274.1 (and in one example, 1.1 to 49.1, and in another example 191.1 to 262.1, and in another example 263.1 to 274.1), in a pharmaceutically acceptable carrier, and another container (i.e., a second container) comprises an effective amount of another pharmaceutically active ingredient (as described above), the combined quantities of the compound selected from the group consisting of 1.1 to 49.1 and 191.1 to 274.1 (and in one example, 1.1 to 49.1, and in another example 191.1 to 262.1, and in another example 263.1 to 274.1), and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Compounds of formula (I) include compounds of formulas: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Thus, a compound of the formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), or (IAF1) can be used instead of a compound of formula (I) in any one of the embodiments directed to the compounds of formula (I).

DETAILED DESCRIPTION OF THE INVENTION

This invention provides compounds, useful as gamma secretase modulators, of formula (I):

(I)

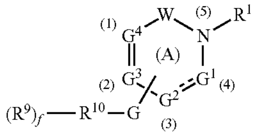

or a pharmaceutically acceptable salt, ester, or solvate thereof, wherein:

G, $G^1$, $G^2$, $G^3$, $G^4$, $R^1$, $R^9$, $R^{10}$, and W are each independently selected;

(A) in the ring in formula (I) is a reference letter to identify the ring;

the numbers (1), (2), (3), (4), and (5) are reference numbers to identify positions of the Ring (A);

the dotted line (‐) between positions (3) and (4) represents an optional bond;

d is 0 or 1 (and those skilled in the art will appreciate that when d is 0 in the —$N(R^2)_d$— moiety there is no substituent on the N, thus, the moiety —$N(R^2)_d$— is —N═ or —NH— when d is 0, i.e., when d is 0 in a moiety there is the appropriate number of H atoms on the N to fill the required valences);

f is 1;

m is 0 to 6;

n is 1 to 5;

p is 0 to 5;

q is 0, 1 or 2, and each q is independently selected (and those skilled in the art will appreciate that when q is 0 in the moiety —$C(R^{21})_q$ this means that there is no $R^{21}$ substituent on the carbon, and the —$C(R^{21})_q$ moiety is —CH═ or —$CH_2$—, i.e., when q is 0 in a moiety there is the appropriate number of H atoms on the carbon to fill the required valences);

r is 1 to 3;

t is 1 or 2;

W is selected from the group consisting of: —C(O)—, —$S(O)_2$—, —S(O)—, and —C(═$NR^2$)—;

the moiety -G-$R^{10}$—$(R^9)_f$ is bound through G to positions (1) or (2), and when G is bound to (1) then $G^4$ is a —C—, and when G is bound to (2) then $G^3$ is a —C—;

G is selected from the group consisting of: a direct bond (i.e., $R^{10}$ is bound directly to ring A, at $G^3$ or $G^4$ for example), —C(O)—, —(C═$NR^2$)—, —(C═$C(R^6)_2$)—, —$CHR^3$— (e.g., —CHOH), $C(R^4)_2$, —$CF_2$—, —$N(R^2)$— (and in one example, —NH—), —O—, —S—, —$S(O)_t$, —$CR^4$(OH)—, —$CR^4(OR^4)$—, —C═C—, alkynyl, —$(CH_2)_rN(R^2)$—, —$(CHR^4)_rN(R^2)$—, —$(C(R^4)_2)_rN(R^2)$—, —$N(R^2)(CH_2)_r$, —$N(R^2)(CHR^4)_r$—, —$N(R^2)(C(R^4)_2)_r$—$(CH_2)_r$—O—, —$(CHR^4)_r$—O—, —$(C(R^4)_2)_r$—O—, —O—$(CH_2)_r$—O—$(CHR^4)_r$—, —O—$(C(R^4)_2)_r$—$(CH_2)_r$—O—C(O)—, —$(CHR^4)_r$—O—C(O)—, —$(C(R^4)_2)_r$—O—C(O)—, —C(O)—O—$(CH_2)_r$—, —C(O)—O—$(CHR^4)_r$—, —C(O)—O—$(C(R^4)_2)_r$—$C(O)NR^5$—, —O—C(O)—, —C(O)—O—, —O—C(O)—$NR^5$—, —$NR^5$C(O)—, —$(CH_2)_rNR^5$—C(O)—, —$(CHR^4)_rNR^5$—C(O)—, —$(C(R^4)_2)_rNR^5$—C(O)—, —$C(O)NR^5(CH_2)_r$—, —$C(O)NR^5(CHR^4)_r$—$C(O)NR^5(C(R^4)_2)_r$—$NR^5S(O)_t$—$(CH_2)_rNR^5S(O)_t$—$(CHR^4)_rNR^6S(O)_t$—$(C(R^4)_2)_rNR^5S(O)_t$—$S(O)_tNR^5$—, —$S(O)_tNR^5(CH_2)_r$—$S(O)_tNR^5(CHR^4)_r$—$S(O)_tNR^5(C(R^4)_2)_r$—$NR^5$—C(O)—O—, —$NR^5$—C(O)—$NR^5$—, —$NR^5$—$S(O)_t$—$NR^5$—, —$NR^5$—C(═$NR^2$)—$NR^5$—, —$NR^5$—C(═$NR^2$)—O—, —O—C(═$NR^2$)—$NR^5$—, —$C(R^4)$═N—O—, —O—N═$C(R^4)$—, —O—$C(R^4)$═N—, —N═$C(R^4)$—O—, —$(CH_2)_{2\text{-}3}$— (i.e., 2 to 3 —$CH_2$— groups), —$(C(R^4)_2)_{2\text{-}3}$— (i.e., there are 2 to 3 —$C(R^4)_2$ groups), —$(CHR^4)_{2\text{-}3}$— (i.e., there are 2 to 3 —$(CHR^4)$— groups), cycloalkyl (e.g., $C_3$ to $C_{10}$ cycloalkyl), and heterocycloalkyl (comprising 1 to 4 heteroatoms independently selected from the group consisting of: —O—, —$NR^2$—, —S—, —S(O)—, and —$S(O)_2$);

$G^1$ is selected from the group consisting of: a direct bond (i.e., the N at (5) is bonded directly to $G^2$, and Ring A is a five membered ring), —O—, —$C(R^{21})_q$, —$N(R^2)_d$—, —C(O)—, —C(═$NR^2$)—, —S—, —$S(O)_2$, and —S(O)—; and with the proviso that when the optional double bond between (3) and (4) is present then:

(a) q for the —$C(R^{21})_q$ group is 0 or 1 (and when 0 there is a H on the carbon), and (b) d for the —$N(R^2)_d$— group is 0 (and there is no H on the N due to the double bond between positions (3) and (4)); and (c) $G^1$ is not —O—, —C(O)—, —C(═$NR^2$)—, —S—, —$S(O)_2$, or S(O)—;

$G^2$ is selected from the group consisting of: a direct bond (i.e., $G^1$ is bonded directly to $G^3$, and Ring A is a five membered ring), —O—, —$C(R^{21})_q$, —$N(R^2)_d$—, —C(O)—, —C(═$NR^2$)—, —S—, —$S(O)_2$, and —S(O)—; and with the proviso that when the optional double bond between (3) and (4) is present then:

(a) q for the —$C(R^{21})_q$ group is 0 or 1 (and when 0 there is a H on the carbon), and (b) d for the —$N(R^2)_d$— group is 0 (and there is no H on the N due to the double bond between positions (3) and (4)); and (c) $G^2$ is not —O—, —C(O)—, —C(═$NR^2$)—, —S—, —$S(O)_2$, or —S(O)—;

$G^3$ is selected from the group consisting of: —$C(R^{21})_q$ wherein q is 0 or 1 (and when 0 there is a H on the carbon), and —$N(R^2)_d$ wherein d is 0 (and there is no H on the N due to the double bond between positions (1) and (2)); and with the proviso that when moiety G is bound to position (2), then $G^3$ is carbon (i.e., the group $G^3$ is the group —$C(R^{21})_q$ wherein q is 0 and the resulting H on the C is replaced by moiety G);

$G^4$ is selected from the group consisting of: —C($R^{21}$)$_q$ wherein q is 0 or 1 (and when 0 there is a H on the carbon), and —N($R^2$)$_d$ wherein d is 0 (and there is no H on the N due to the double bond between positions (1) and (2)); and with the proviso that when moiety G is bound to position (1), then $G^4$ is carbon (i.e., the group $G^4$ is the group —C($R^{21}$)$_q$ wherein q is 0 and the resulting H on the C is replaced by moiety G); and $R^1$ is selected from the group consisting of: alkyl-, alkenyl-, alkynyl-, aryl-, arylalkyl-, alkylaryl-, cycloalkyl, cycloalkenyl, cycloalkylalkyl-, fused benzocycloalkyl- (i.e., benzofusedcycloalkyl-), fused benzoheterocycloalkyl- (i.e., benzofusedheterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylaryl (i.e., cycloalkyfusedlaryl-), fused heterocycloalkylaryl- (i.e., heterocycloalkylfusedaryl-), fused cycloalkyl heteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarylfusedcycloalkylalkyl-), fused heteroaryl heterocycloalkylalkyl- (i.e., heteroarylfusedheterocycloalkylalkyl-), fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), fused heterocycloalkylheteroarylalkyl- (i.e., heterocycloalkylfusedheteroarylalkyl-), heteroaryl-, heteroarylalkyl-, heterocyclyl-, heterocyclenyl-, and heterocyclyalkyl-; wherein each of said alkyl-, alkenyl-, alkynyl-, aryl-, arylalkyl-, alkylaryl-, cycloalkyl, cycloalkenyl, cycloalkylalkyl-, fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, fused heterocycloalkylheteroarylalkyl-, heteroaryl, heteroarylalkyl-, heterocyclyl, heterocyclenyl and heterocyclyalkyl-$R^1$ groups is optionally substituted with 1-5 independently selected $R^{21}$ groups;

$R^2$ is selected from the group consisting of: H, —OH, —O-alkyl (i.e., alkoxy), —O-(halo substituted alkyl) (such as, for example, —O-fluoroalkyl), —NH($R^4$), —N($R^4$)$_2$ (wherein each $R^4$ is independently selected), —$NH_2$, —S($R^4$), —S(O)$R^4$, —S(O)(O$R^4$), —S(O)$_2R^4$, —S(O)$_2$(O$R^4$), —S(O)NH$R^4$, —S(O)N($R^4$)$_2$ (wherein each $R^4$ is independently selected), —S(O)$NH_2$, —S(O)$_2$NH$R^4$, —S(O)$_2$N($R^4$)$_2$ (wherein each $R^4$ is independently selected), —S(O)$_2NH_2$, —CN, —C(O)$_2R^4$, —C(O)NH$R^4$, —C(O)N($R^4$)$_2$ (wherein each $R^4$ is independently selected), —C(O)$NH_2$, —C(O)$R^4$, unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected $R^{21}$ groups;

$R^3$ is selected from the group consisting of: H, —OH, halo, —O-alkyl (i.e., alkoxy), —O-(halo substituted alky) (such as, for example, —O-fluoroalkyl), —NH($R^4$), —N($R^4$)$_2$ (wherein each $R^4$ is independently selected), —$NH_2$, —S($R^4$), —S(O)$R^4$, —S(O)(O$R^4$), —S(O)$_2R^4$, —S(O)$_2$(O$R^4$), —S(O)NH$R^4$, —S(O)$_N$($R^4$)$_2$, —S(O)$NH_2$, —S(O)$_2$NH$R^4$, —S(O)$_2$N($R^4$)$_2$, —S(O)$_2NH_2$, —CN, —C(O)$_2R^4$, —C(O)NH$R^4$, —C(O)N($R^4$)$_2$, —C(O)$NH_2$, —C(O)$R^4$, unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected $R^{21}$ groups;

Each $R^4$ is independently selected from the group consisting of: unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected $R^{21}$ groups;

Each $R^5$ is independently selected from the group consisting of: H, unsubstituted alkyl, substituted alkyl, unsubstituted alkenyl, substituted alkenyl, unsubstituted alkynyl, substituted alkynyl, unsubstituted cycloalkyl, substituted cycloalkyl, unsubstituted aryl, substituted aryl, unsubstituted heteroaryl and substituted heteroaryl; wherein said substituted groups are substituted with one or more (e.g., 1 to 5) substituents independently selected from: $R^{21}$.

$R^9$ is selected from the group consisting of: arylalkoxy-, heteroarylalkoxy-, arylalkylamino-, heteroarylalkylamino-, aryl, arylalkyl-, heteroaryl, heteroarylalkyl-, heterocyclyl, heterocyclenyl, and heterocyclyalkyl-, wherein each of said $R^9$ arylalkoxy-, heteroarylalkoxy-, arylalkylamino-, heteroarylalkylamino-, aryl, arylalkyl-, heteroaryl, heteroarylalkyl-, heterocyclyl, heterocyclenyl, and heterocyclyalkyl- is optionally substituted with 1-5 independently selected $R^{21}$ groups;

$R^{10}$ is selected from the group consisting of: aryl-, arylalkyl-, alkylaryl-, heteroaryl-, heteroarylalkyl-, cycloalkyl-, cycloalkenyl, cycloalkylalkyl-, heterocyclyl-, heterocyclenyl-, heterocyclylalkyl, heterocyclyalkenyl-,

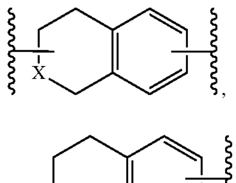
,
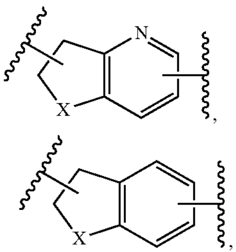
,
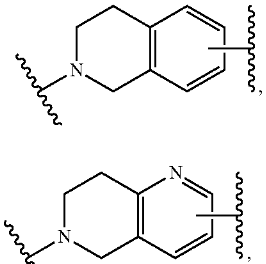
,
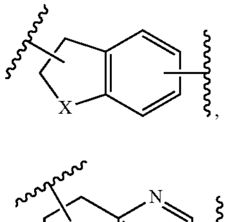
,
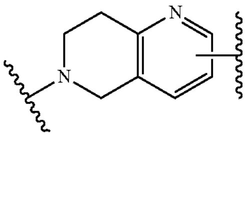
,
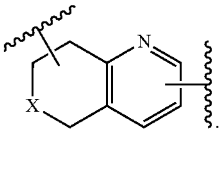
.

-continued and 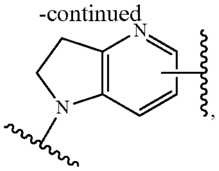

wherein X is selected from the group consisting of: O, —N($R^{14}$)— and —S—; and wherein each of said $R^{10}$ moieties is optionally substituted with 1-5 independently selected $R^{21}$ groups;

$R^{14}$ is selected from the group consisting of H, alkyl, alkenyl, alkynyl, cycloalkyl, cycloalkylalkyl, cycloalkenyl, heterocyclyl, heterocyclenyl, heterocyclylalkyl, heterocyclyalkenyl-, aryl, arylalkyl, heteroaryl, heteroarylalkyl, —CN, —C(O)$R^{15}$, —C(O)O$R^{15}$, —C(O)N($R^{15}$)($R^{16}$), —S(O)N($R^{15}$)($R^{16}$), —$S(O)_2$N($R^{15}$)($R^{16}$), —C(═NO$R^{15}$)$R^{16}$, and —P(O)(O$R^{15}$)(O$R^{16}$);

$R^{15}$, $R^{16}$ and $R^{17}$ are independently selected from the group consisting of H, alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, $(R^{18})_n$-alkyl, $(R^{18})_n$-cycloalkyl, $(R^{18})_n$-cycloalkylalkyl, $(R^{18})_n$-heterocyclyl, $(R^{18})_n$-heterocyclylalkyl, $(R^{18})_n$-aryl, $(R^{18})_n$-arylalkyl, $(R^{18})_n$-heteroaryl and $(R^{18})_n$-heteroarylalkyl;

Each $R^{18}$ is independently selected from the group consisting of alkyl, alkenyl, alkynyl, aryl, arylalkyl, arylalkenyl, arylalkynyl, —$NO_2$, halo, heteroaryl, HO-alkyoxyalkyl, —$CF_3$, —CN, alkyl-CN, —C(O)$R^{19}$, —C(O)OH, —C(O)O$R^{19}$, —C(O)NH$R^{20}$, —C(O)$NH_2$, —C(O)$NH_2$—C(O)N$(alkyl)_2$, —C(O)N(alkyl)(aryl), —C(O)N(alkyl)(heteroaryl), —S$R^{19}$, —$S(O)_2R^{20}$, —S(O)$NH_2$, —S(O)NH(alkyl), —S(O)N(alkyl)(alkyl), —S(O)NH(aryl), —$S(O)_2NH_2$, —$S(O)_2$NH$R^{19}$, —$S(O)_2$NH(heterocyclyl), —$S(O)_2$N$(alkyl)_2$, —$S(O)_2$N(alkyl)(aryl), —O$CF_3$, —OH, —O$R^{20}$, —O-heterocyclyl, —O-cycloalkylalkyl, —O-heterocyclylalkyl, —$NH_2$, —NH$R^{20}$, —N$(alkyl)_2$, —N$(arylalkyl)_2$, —N(arylalkyl)-(heteroarylalkyl), —NHC(O)$R^{20}$, —NHC(O)$NH_2$, —NHC(O)NH(alkyl), —NHC(O)N(alkyl)(alkyl), —N(alkyl)C(O)NH(alkyl), —N(alkyl)C(O)N(alkyl)(alkyl), —NH$S(O)_2R^{20}$, —NH$S(O)_2$NH(alkyl), —NH$S(O)_2$N(alkyl)(alkyl), —N(alkyl)$S(O)_2$NH(alkyl) and —N(alkyl)$S(O)_2$N(alkyl)(alkyl); or two $R^{18}$ moieties on adjacent carbons can be linked together to form a

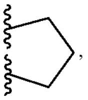, 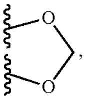, or 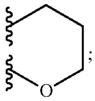;

$R^{19}$ is selected from the group consisting of: alkyl, cycloalkyl, aryl, arylalkyl and heteroarylalkyl;

$R^{20}$ is selected from the group consisting of: alkyl, cycloalkyl, aryl, halo substituted aryl, arylalkyl, heteroaryl and heteroarylalkyl;

Each $R^{21}$ is independently selected from the group consisting of: alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —O$R^{15}$, —C(O)$R^{15}$, —C(O)O$R^{15}$, —C(O)N($R^{15}$)($R^{16}$), —$SF_5$, —O$SF_5$, —Si$(R^{15})_3$ wherein each $R^{15}$ is independently selected, —S$R^{15}$, —S(O)N($R^{15}$)($R^{16}$), —CH($R^{15}$)($R^{16}$), —$S(O)_2$N($R^{15}$)($R^{16}$), —C(═NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —$CH_2$—N($R^{15}$)C(O)N($R^{16}$)($R^{17}$), —$CH_2$—$R^{15}$; —$CH_2$N($R^{15}$)($R^{16}$), —N($R^{15}$)S(O)$R^{16}$, —N($R^{15}$)$S(O)_2R^{16}$, —$CH_2$—N($R^{15}$)$S(O)_2R^{16}$, —N($R^{15}$)$S(O)_2$N($R^{16}$)($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —S(O)$R^{15}$, ═NO$R^{15}$, —$N_3$, —$NO_2$, —$S(O)_2R^{15}$, —O—N═C$(R^4)_2$ (wherein each $R^4$ is independently selected), and —O—N═C$(R^4)_2$ wherein $R^4$ is taken together with the carbon atom to which they are bound to form a 5 to 10 membered ring, said ring optionally containing 1 to 3 heteroatoms selected from the group consisting of —O—, —S—, —S(O)—, —$S(O)_2$—, and —N$R^2$—; wherein each of said alkyl, alkenyl, alkynyl, cycloalkyl, cycloalkylalkyl, cycloalkenyl, heterocycloalkyl, heterocycloalkylalkyl, aryl, arylalkyl, heteroaryl, and heteroarylalkyl $R^{21}$ groups is optionally substituted with 1 to 5 independently selected $R^{22}$ groups;

Each $R^{22}$ group is independently selected from the group consisting of alkyl, cycloalkyl, cycloalkenyl, heterocycloalkyl, aryl, heteroaryl, halo, —$CF_3$, —CN, —O$R^{15}$, —C(O)$R^{15}$, —C(O)O$R^{15}$, -alkyl-C(O)O$R^{15}$, C(O)N($R^{15}$)($R^{16}$), —$SF_5$, —O$SF_5$, —Si$(R^{15})_3$ wherein each $R^{15}$ is independently selected, —S$R^{15}$, —S(O)N($R^{15}$)($R^{16}$), —$S(O)_2$N($R^{15}$)($R^{16}$), —C(═NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —N($R^{15}$)S(O)$R^{16}$, —N($R^{15}$)$S(O)_2R^{16}$, —$CH_2$—N($R^{15}$)$S(O)_2R^{16}$, —N($R^{15}$)$S(O)_2$N($R^{16}$)($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —$N_3$, ═NO$R^{15}$, —$NO_2$, —S(O)$R^{15}$ and —$S(O)_2R^{15}$; and provided that:

(a) Ring A does not have two adjacent —O— atoms in the ring; and (b) Ring A does not have two adjacent sulfur groups in the ring (i.e., when there is a —S—, —S(O)— or —$S(O)_2$ group at one position in Ring A, then the adjacent positions in Ring A are not —S—, —S(O)— or —$S(O)_2$); and (c) Ring A does not have an —O— atom adjacent to a sulfur group (i.e., Ring A does not have an —O— atom adjacent to a —S—, —S(O)— or —$S(O)_2$); and (d) When $G^1$ is N, then $G^2$ is not —O—; and (e) When $G^1$ is —O—, then $G^2$ is not N; and (f) When $G^1$ is N, then $G^2$ is not —S—; and (g) When $G^1$ is —S—, then $G^2$ is not N; and (h) When $G^1$ is a direct bond, and $G^2$ is —O—, then $G^3$ is not N; and (i) When $G^2$ is a direct bond, and $G^1$ is —O—, then $G^3$ is not N; and (j) When $G^1$ is N, and $G^3$ is N, then $G^2$ is not N; and (k) When $G^2$ is N, and $G^3$ is N, then $G^1$ is not N; and (l) When $G^1$ is N, and $G^2$ is N, then $G^3$ is not N; and (m) When no —$SF_5$ moiety or no —O$SF_5$ moiety or no —Si$(R^{15})_3$ moiety is present, and W is C(═O) or C(═N$R^2$), and $G^1$ is C$(R^{21})_q$, and $G^2$ is C$(R^{21})_q$, and $G^3$ is C$(R^{21})_q$, and $G^4$ is C, and G is bound to $G^4$, and the optional bond between $G^1$ and $G^2$ is present (i.e, there is a double bond between positions (3) and (4), including a double bond formed by tautomerization), then $R^1$ is not alkyl-, alkenyl-, alkynyl-, aryl, arylalkyl-, alkylaryl-, cycloalkyl, cycloalkenyl, or cycloalkylalkyl-; and (n) When W is C(═O), and $G^1$ is C$(R^{21})_q$, and $G^2$ is C$(R^{21})_q$, and $G^3$ is C$(R^{21})_q$, and $G^4$ is C, and G is bound to $G^4$, then G is not CH$R^3$; and (o) When W is C(═O), and $G^1$ is $C(R^{21})_q$, and $G^2$ is $C(R^{21})_q$, and $G^3$ is $C(R^{21})_q$, and $G^4$ is C, and G is bound to $G^4$, and the optional bond between $G^1$ and $G^2$ is not present (i.e, there is a single bond between positions (3) and (4)), then $R^1$ is not a fused 2-aminopyridylcycloalkyl- moiety; and (p) When W is C(═O), and $G^1$ is $C(R^{21})_q$, and $G^2$ is $C(R^{21})_q$, and $G^3$ is N, and $G^4$ is C, and G is bound to $G^4$, and the optional bond between $G^1$ and $G^2$ is not present (i.e, there is a single bond between positions (3) and (4)), then $R^1$ is not a fused 2-aminopyridylcycloalkyl moiety; and (q) When W is C(═O), and $G^1$ is $N(R^2)_d$, and $G^2$ is C(═O), and $G^3$ is $C(R^{21})_q$, and $G^4$ is C, and G is bound to $G^4$, then $R^{21}$ for said $G^3$ is not $—NR^{15}R^{16}$, that is, $G^3$ is not the moiety:

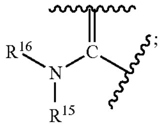

and (r) When $G^1$ is $C(═NR^2)$, and $G^2$ is a direct bond, and $G^3$ is N, and $G^4$ is C, and G is bound to $G^4$, then G is not $CHR^3$.

The fused 2-aminopyridylcycloalkyl moiety in provisos (o) and (p) above is the moiety:

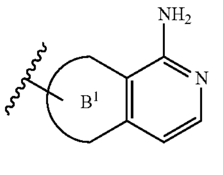

wherein $B^1$ represents a cycloalkyl ring.

In one embodiment of this invention, no $—SF_5$ group is present, no $—SF_5$ group is present, no $—Si(R^{15})_3$ is present, W is C(═O) or $C(═NR^2)$, $G^1$ is $C(R^{21})_q$, $G^2$ is $C(R^{21})_q$, $G^3$ is $C(R^{21})_q$, $G^4$) G is C, G is bound to $G^4$, and the optional bond between $G^1$ and $G^2$ is present (i.e, there is a double bond between positions (3) and (4), including a double bond formed by tautomerization), and $R^1$ is selected from the group consisting of: fused benzocycloalkyl- (i.e., benzofusedcycloalkyl-), fused benzoheterocycloalkyl- (i.e., benzofused-heterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylary-l (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarylfusedcycloalkylalkyl-), fused heteroarylheterocycloalkylalkyl- (i.e., heteroarylfusedheterocycloalkylalkyl)-, fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), fused heterocycloalkylheteroarylalkyl- (i.e., heterocycloalkylfusedheteroarylalkyl-), heteroaryl-, heteroarylalkyl-, heterocyclyl-, heterocyclenyl-, and heterocyclylalkyl-; wherein each of said fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, fused heterocycloalkylheteroarylalkyl-, heteroaryl, heteroarylalkyl-, heterocyclyl, heterocyclenyl and heterocyclyalkyl-$R^1$ groups is optionally substituted with 1-5 independently selected $R^{21}$ groups.

In another embodiment of this invention at least one group (e.g., 1 to 2) selected from the group consisting of: $—SF_5$, $—OSF_5$, and $—Si(R^{15})_3$ (wherein each $R^{15}$ is independently selected) is present, and W is C(═O) or $C(═NR^2)$, and $G^1$ is $C(R^{21})_q$, and $G^2$ is $C(R^{21})_q$, and $G^3$ is $C(R^{21})_q$, and $G^4$ is C, and G is bound to $G^4$, and the optional bond between $G^1$ and $G^2$ is present (i.e, there is a double bond between positions (3) and (4), including a double bond formed by tautomerization), and $R^1$ is selected from the group consisting of: alkyl-, alkenyl-, alkynyl-, aryl-, arylalkyl-, alkylaryl-, cycloalkyl, cycloalkenyl, cycloalkylalkyl-, fused benzocycloalkyl- (i.e., benzofusedcycloalkyl-), fused benzoheterocycloalkyl- (i.e., benzofusedheterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylaryl (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarylfusedcycloalkylalkyl-), fused heteroarylheterocycloalkylalkyl- (i.e., heteroarylfusedheterocycloalkylalkyl-), fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), fused heterocycloalkylheteroarylalkyl- (i.e., heterocycloalkylfusedheteroarylalkyl-), heteroaryl-, heteroarylalkyl-, heterocyclyl-, heterocyclenyl-, and heterocyclyalkyl-; wherein each of said alkyl-, alkenyl-, alkynyl-, aryl-, arylalkyl-, alkylaryl-, cycloalkyl, cycloalkenyl, cycloalkylalkyl-, fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, fused heterocycloalkylheteroarylalkyl-, heteroaryl, heteroarylalkyl-, heterocyclyl, heterocyclenyl and heterocyclyalkyl-$R^1$ groups is optionally substituted with 1-5 independently selected $R^{21}$ groups (wherein the total number of substituents on the substituted $R^1$ groups is from 1 to 5). In one example of this embodiment, one $—SF_5$ group is present. In another example of this embodiment two $—SF_5$ groups are present. In another example of this embodiment, one $—OSF_5$ group is present. In another example of this embodiment two $—OSF_5$ groups are present. In another example of this embodiment, one $—Si(R^{15})_3$ group is present. In another example of this embodiment two $—Si(R^{15})_3$ groups are present.

In another embodiment of this invention at least one group (e.g., 1 to 2) selected from the group consisting of: —$SF_5$, —$OSF_5$ and —$Si(R^{15})_3$ (wherein each $R^{15}$ is the same or different alkyl group) is present, and W is C(═O) or C(═$NR^2$), and $G^1$ is $C(R^{21})_q$, and $G^2$ is $C(R^{21})_q$, and $G^3$ is $C(R^{21})_q$, and $G^4$ is C, and G is bound to $G^4$, and the optional bond between $G^1$ and $G^2$ is present (i.e, there is a double bond between positions (3) and (4), including a double bond formed by tautomerization), and $R^1$ is selected from the group consisting of: alkyl-, alkenyl-, alkynyl-, aryl-, arylalkyl-, alkylaryl-, cycloalkyl, cycloalkenyl, cycloalkylalkyl-, fused benzocycloalkyl- (i.e., benzofusedcycloalkyl-), fused benzoheterocycloalkyl- (i.e., benzofusedheterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylaryl (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarylfusedcycloalkylalkyl-), fused heteroarylheterocycloalkylalkyl- (i.e., heteroarylfusedheterocycloalkylalkyl-), fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), fused heterocycloalkylheteroarylalkyl- (i.e., heterocycloalkylfusedheteroarylalkyl-), heteroaryl-, heteroarylalkyl-, heterocyclyl-, heterocyclenyl-, and heterocyclyalkyl-; wherein each of said alkyl-, alkenyl-, alkynyl-, aryl-, arylalkyl-, alkylaryl-, cycloalkyl, cycloalkenyl, cycloalkylalkyl-, fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, fused heterocycloalkylheteroarylalkyl-, heteroaryl, heteroarylalkyl-, heterocyclyl, heterocyclenyl and heterocyclyalkyl-$R^1$ groups is optionally substituted with 1-5 independently selected $R^{21}$ groups (wherein the total number of substituents on the substituted $R^1$ groups is from 1 to 5). In one example of this embodiment, one —$SF_5$ group is present. In another example of this embodiment two —$SF_5$ groups are present. In another example of this embodiment, one —$OSF_5$ group is present. In another example of this embodiment two —$OSF_5$ groups are present. In another example of this embodiment, one —$Si(R^{15})_3$ group is present. In another example of this embodiment two —$Si(R^{15})_3$ groups are present.

In another embodiment of this invention at least one group (e.g., 1 to 2) selected from the group consisting of: —$SF_5$, —$OSF_5$ and —$Si(CH_3)_3$ is present, and W is C(═O) or C(═$NR^2$), and $G^1$ is $C(R^{21})_q$, and $G^2$ is $C(R^{21})_q$, and $G^3$ is $C(R^{21})_q$, and $G^4$ is C, and G is bound to $G^4$, and the optional bond between $G^1$ and $G^2$ is present (i.e, there is a double bond between positions (3) and (4), including a double bond formed by tautomerization), and $R^1$ is selected from the group consisting of: alkyl-, alkenyl-, alkynyl-, aryl-, arylalkyl-, alkylaryl-, cycloalkyl, cycloalkenyl, cycloalkylalkyl-, fused benzocycloalkyl- (i.e., benzofusedcycloalkyl-), fused benzoheterocycloalkyl- (i.e., benzofusedheterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylaryl (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarylfusedcycloalkylalkyl-), fused heteroarylheterocycloalkylalkyl- (i.e., heteroarylfusedheterocycloalkylalkyl-), fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), fused heterocycloalkylheteroarylalkyl- (i.e., heterocycloalkylfusedheteroarylalkyl-), heteroaryl-, heteroarylalkyl-, heterocyclyl-, heterocyclenyl-, and heterocyclyalkyl-; wherein each of said alkyl-, alkenyl-, alkynyl-, aryl-, arylalkyl-, alkylaryl-, cycloalkyl, cycloalkenyl, cycloalkylalkyl-, fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, fused heterocycloalkylheteroarylalkyl-, heteroaryl, heteroarylalkyl-, heterocyclyl, heterocyclenyl and heterocyclyalkyl-$R^1$ groups is optionally substituted with 1-5 independently selected $R^{21}$ groups (wherein the total number of substituents on the substituted $R^1$ groups is from 1 to 5). In one example of this embodiment, one —$SF_5$ group is present. In another example of this embodiment two —$SF_5$ groups are present. In another example of this embodiment, one —$OSF_5$ group is present. In another example of this embodiment two —$OSF_5$ groups are present. In another example of this embodiment, one —$Si(CH_3)_3$ group is present. In another example of this embodiment two —$Si(CH_3)_3$ groups are present.

In another embodiment of this invention W is C(═O), $G^1$ is $C(R^{21})_q$, $G^2$ is $C(R^{21})_q$, $G^3$ is $C(R^{21})_q$, $G^4$ is C, G is bound to $G^4$, and G is selected from the group consisting of: a direct bond (i.e., $R^{10}$ is bound directly to ring A, at $G^3$ or $G^4$ for example), —C(O)—, —(C═$NR^2$)—, —(C═$C(R^6)_2$)—, $C(R^4)_2$, —$CF_2$—, —$N(R^2)$— (and in one example, —NH—), —O—, —S—, —$S(O)_t$, —$CR^4(OH)$—, —$CR^4(OR^4)$—, —C═C—, alkynyl, —$(CH_2)_rN(R^2)$—, —$(CHR^4)_rN(R^2)$—, —$(C(R^4)_2)_rN(R^2>$, —$N(R^2)(CH_2)_r$—$N(R^2)(CHR^4)_r$—, —$N(R^2)(C(R^4)_2)_r$—$(CH_2)_r$—O—, —$(CHR^4)_r$—O—, —$(C(R^4)_2)_r$—O—, —O—$(CH_2)_r$—O—$(CHR^4)_r$—, —O—$(C(R^4)_2)_r$—, —$(CH_2)_r$—O—C(O)—, —$(CHR^4)_r$—O—C(O)—, —$(C(R^4)_2)_r$—O—C(O)—, —C(O)—O—$(CH_2)_r$—, —C(O)—O—$(CHR^4)_r$—, —C(O)—$(C(R^4)_2)_r$—, —C(O)$NR^5$—, —O—C(O)—, —$C(R^4)_2)_rNR^5$—, —$NR^5(CH_2)_r$—, —$(CH_2)_rNR^5$—C(O)—, —$(CHR^4)_rNR^5$—C(O)—, —$(C(R^4)_2)_rNR^5$—C(O)—, —C(O)$NR^5(CH_2)_r$—C(O)$NR^5(CHR^4)_r$—C(O)$NR^5(C(R^4)_2)_r$—$NR^5S(O)_t$—$(CH_2)_rNR^5S(O)_t$—$(CHR^4)_rNR^5S(O)_t$—$(C(R^4)_2)_rNR^5S(O)_t$—$S(O)_tNR^5$—, —$S(O)_tNR^5(CH_2)_r$—$S(O)_tNR^5(CHR^4)_r$—, —$S(O)_tNR^5(C(R^4)_2)_r$—$NR^5$—C(O)—O—, —$NR^5$—C(O)—$NR^5$—, —$NR^5$—$S(O)_t$—$NR^5$—, —$NR^5$—C(═$NR^2$)—$NR^5$—, —$NR^5$—C(═$NR^2$)—O—, —O—C(═$NR^2$)—$NR^5$—, —$C(R^4)$═N—O—, —O—N═$C(R^4)$—, —O—$C(R^4)$═N—, —N═$C(R^4)$—O—, —$(CH_2)_{2\text{-}3}$— (i.e., 2 to 3 —$CH_2$— groups), —$(C(R^4)_2)_{2\text{-}3}$— (i.e., there are 2 to 3 —$(C(R^4)_2$ groups), —$(CHR^4)_{2\text{-}3}$— (i.e., there are 2 to 3

—(CHR$^4$)— groups), cycloalkyl (e.g., C$_3$ to C$_{10}$ cycloalkyl), and heterocycloalkyl (comprising 1 to 4 heteroatoms independently selected from the group consisting of: —O—, —NR$^2$—, —S—, —S(O)—, and —S(O)$_2$).

In another embodiment of this invention, W is C(=O), G$^1$ is C(R$^{21}$)$_q$, G$^2$ is C(R$^{21}$)$_q$, G$^3$ is C(R$^{21}$)$_q$, G$^4$ is C, G is bound to G$^4$, the optional bond between G$^1$ and G$^2$ is not present (i.e, there is a single bond between positions (3) and (4)), and R$^1$ is selected from the group consisting of: alkyl-, alkenyl-, alkynyl-, aryl-, arylalkyl-, alkylaryl-, cycloalkyl, cycloalkenyl, cycloalkylalkyl-, fused benzocycloalkyl- (i.e., benzofusedcycloalkyl-), fused benzoheterocycloalkyl- (i.e., benzofusedheterocycloalkyl-), fused heteroarylheterocycloalkyl- (i.e., heteroarylfusedheterocycloalkyl-), fused cycloalkylary-l (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarylfusedcycloalkylalkyl-), fused heteroarylheterocycloalkylalkyl- (i.e., heteroarylfusedheterocycloalkylalkyl)-, fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), fused heterocycloalkylheteroarylalkyl- (i.e., heterocycloalkylfusedheteroarylalkyl-), heteroaryl-, heteroarylalkyl-, heterocyclyl-, heterocyclenyl-, and heterocyclyalkyl-; wherein each of said alkyl-, alkenyl-, alkynyl-, aryl-, arylalkyl-, alkylaryl-, cycloalkyl, cycloalkenyl, cycloalkylalkyl-, fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, fused heterocycloalkylheteroarylalkyl-, heteroaryl, heteroarylalkyl-, heterocyclyl, heterocyclenyl and heterocyclyalkyl-R$^1$ groups is optionally substituted with 1-5 independently selected R$^{21}$ groups.

In another embodiment of this invention, W is C(=O), G$^1$ is C(R$^{21}$)$_q$, G$^2$ is C(R$^{21}$)$_q$, G$^3$ is C(R$^{21}$)$_q$, 20 C G$^4$ is C, G is bound to G$^4$, the optional bond between G$^1$ and G$^2$ is not present (i.e, there is a single bond between positions (3) and (4)), and R$^1$ is selected from the group consisting of: R$^1$ is selected from the group consisting of: alkyl-, alkenyl-, alkynyl-, aryl-, arylalkyl-, alkylaryl-, cycloalkyl, cycloalkenyl, cycloalkylalkyl-, fused benzocycloalkyl- (i.e., benzofusedcycloalkyl-), fused benzoheterocycloalkyl- (i.e., benzofusedheterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylary-l (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarylfusedcycloalkylalkyl-), fused heteroarylheterocycloalkylalkyl- (i.e., heteroarylfusedheterocycloalkylalkyl)-, fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), fused heterocycloalkylheteroarylalkyl- (i.e., heterocycloalkylfusedheteroarylalkyl-), heteroaryl-, heteroarylalkyl-, heterocyclyl-, heterocyclenyl-, and heterocyclyalkyl-; wherein each of said alkyl-, alkenyl-, alkynyl-, aryl-, arylalkyl-, alkylaryl-, cycloalkyl, cycloalkenyl, cycloalkylalkyl-, fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, fused heterocycloalkylheteroarylalkyl-, heteroaryl, heteroarylalkyl-, heterocyclyl, heterocyclenyl and heterocyclyalkyl-R$^1$ groups is optionally substituted with 1-5 independently selected R$^{21}$ groups, and provided that said fused heteroarylcycloalkyl- (i.e., heteroarylfusedcycloalkyl-) substituent is not a fused 2-aminopyridylcycloalkyl-moiety.

In another embodiment of this invention, W is C(=O), G$^1$ is C(R$^{21}$)$_q$, G$^2$ is C(R$^{21}$)$_q$, G$^3$ is N, G$^4$ is C, G is bound to G$^4$, the optional bond between G$^1$ and G$^2$ is not present (i.e, there is a single bond between positions (3) and (4)), and R$^1$ is selected from the group consisting of: R$^1$ is selected from the group consisting of: alkyl-, alkenyl-, alkynyl-, aryl-, arylalkyl-, alkylaryl-, cycloalkyl, cycloalkenyl, cycloalkylalkyl-, fused benzocycloalkyl- (i.e., benzofusedcycloalkyl-), fused benzoheterocycloalkyl- (i.e., benzofusedheterocycloalkyl-), fused heteroarylheterocycloalkyl- (i.e., heteroarylfusedheterocycloalkyl-), fused cycloalkylary-l (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarylfusedcycloalkylalkyl-), fused heteroarylheterocycloalkylalkyl- (i.e., heteroarylfusedheterocycloalkylalkyl)-, fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), fused heterocycloalkylheteroarylalkyl- (i.e., heterocycloalkylfusedheteroarylalkyl-), heteroaryl-, heteroarylalkyl-, heterocyclyl-, heterocyclenyl-, and heterocyclyalkyl-; wherein each of said alkyl-, alkenyl-, alkynyl-, aryl-, arylalkyl-, alkylaryl-, cycloalkyl, cycloalkenyl, cycloalkylalkyl-, fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, fused heterocycloalkylheteroarylalkyl-, heteroaryl, heteroarylalkyl-, heterocyclyl, heterocyclenyl and heterocyclyalkyl-R$^1$ groups is optionally substituted with 1-5 independently selected R$^{21}$ groups.

In another embodiment of this invention, W is C(=O), G$^1$ is C(R$^{21}$)$_q$, G$^2$ is C(R$^{21}$)$_q$, G$^3$ is N, G$^4$ is C, G is bound to G$^4$, the optional bond between G$^1$ and G$^2$ is not present (i.e, there is a single bond between positions (3) and (4)), and R$^1$ is selected from the group consisting of: R$^1$ is selected from the group consisting of: alkyl-, alkenyl-, alkynyl-, aryl-, arylalkyl-, alkylaryl-, cycloalkyl, cycloalkenyl, cycloalkylalkyl-, fused benzocycloalkyl- (i.e., benzofusedcycloalkyl-), fused benzoheterocycloalkyl- (i.e., benzofusedheterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylary-l (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarytfusedcycloalkylalkyl-), fused heteroarylheterocycloalkylalkyl- (i.e., heteroarylfusedheterocycloalkylalkyl)-, fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), fused heterocycloalkylheteroarylalkyl- (i.e., heterocycloalkylfusedheteroarylalkyl-), heteroaryl-, heteroarylalkyl-, heterocyclyl-, heterocyclenyl-, and heterocyclyalkyl-; wherein each of said alkyl-, alkenyl-, alkynyl-, aryl-, arylalkyl-, alkylaryl-, cycloalkyl, cycloalkenyl, cycloalkylalkyl-, fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkyl heteroarylalkyl-, fused heterocycloalkylheteroarylalkyl-, heteroaryl, heteroarylalkyl-, heterocyclyl, heterocyclenyl and heterocyclyalkyl-$R^1$ groups is optionally substituted with 1-5 independently selected $R^{21}$ groups, and provided that said fused heteroarylcycloalkyl- (i.e., heteroarylfusedcycloalkyl-) substituent is not a fused 2-aminopyridylcycloalkyl-moiety.

In another embodiment of this invention, W is C(=O), $G^1$ is $N(R^2)_d$, $G^2$ is C(=O), $G^4$ is C, G is bound to $G^4$, $G^3$ is $C(R^{21})_q$, and $R^{21}$ for said $G^3$ moiety is selected from the group consisting of: alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, $—OR^{15}$, $—C(O)R^{15}$, $—C(O)OR^{15}$, $—C(O)N(R^{15})(R^{16})$, $—SR^{15}$, $—S(O)N(R^{15})(R^{16})$, $—CH(R^{15})(R^{16})$, $—S(O)_2N(R^{15})(R^{15})$, $—C(=NOR^{15})R^{16}$, $—P(O)(OR^{15})(OR^{16})$, -alkyl-$N(R^{15})(R^{16})$, $—N(R^{15})C(O)R^{16}$, $—CH_2—N(R^{15})C(O)R^{16}$, $—CH_2—N(R^{15})C(O)N(R^{16})(R^{17})$, $—CH_2—R^{15}$; $—CH_2N(R^{15})(R^{16})$, $—N(R^{15})S(O)R^{16}$, $—N(R^{15})S(O)_2R^{16}$, $—CH_2—N(R^{15})S(O)_2R^{16}$, $—N(R^{15})S(O)_2N(R^{16})(R^{17})$, $—N(R^{15})S(O)N(R^{16})(R^{17})$, $—N(R^{15})C(O)N(R^{16})(R^{17})$, $—CH_2—N(R^{15})C(O)N(R^{16})(R^{17})$, $—N(R^{15})C(O)OR^{16}$, $—CH_2—N(R^{15})C(O)OR^{16}$, $—S(O)R^{15}$, $=NOR^{15}$, $—N_3$, $—NO_2$, $—S(O)_2R^{15}$, $—O—N=C(R^4)_2$ (wherein each $R^4$ is independently selected), and $—O—N=C(R^4)_2$ wherein $R^4$ is taken together with the carbon atom to which they are bound to form a 5 to 10 membered ring, said ring optionally containing 1 to 3 heteroatoms selected from the group consisting of —O—, —S—, —S(O)—, $—S(O)_2—$, and $—NR^2—$; wherein each of said alkyl, alkenyl, alkynyl, cycloalkyl, cycloalkylalkyl, cycloalkenyl, heterocycloalkyl, heterocycloalkylalkyl, aryl, arylalkyl, heteroaryl, and heteroarylalkyl $R^{21}$ groups is optionally substituted with 1 to 5 independently selected $R^{22}$ groups; and each $R^{22}$ group is independently selected from the group consisting of alkyl, cycloalkyl, cycloalkenyl, heterocycloalkyl, aryl, heteroaryl, halo, $—CF_3$, —CN, $—OR^{15}$, $—C(O)R^{15}$, $—C(O)OR^{15}$, -alkyl-$C(O)OR^{15}$, $C(O)N(R^{15})(R^{16})$, $—SR^{15}$, $—S(O)N(R^{15})(R^{16})$, $—S(O)_2N(R^{15})(R^{16})$, $—C(=NOR^{15})R^{16}$, $—P(O)(OR^{15})(OR^{16})$, $—N(R^{15})(R^{16})$, -alkyl-$N(R^{15})(R^{16})$, $—N(R^{15})C(O)R^{16}$, $—CH_2—N(R^{15})C(O)R^{16}$, $—N(R^{15})S(O)R^{16}$, $—N(R^{15})S(O)_2R^{16}$, $—CH_2—N(R^{15})S(O)_2R^{16}$, $—N(R^{15})S(O)_2N(R^{16})(R^{17})$, $—N(R^{15})S(O)N(R^{16})(R^{17})$, $—N(R^{15})C(O)N(R^{16})(R^{17})$, $—CH_2—N(R^{15})C(O)N(R^{16})(R^{17})$, $—N(R^{15})C(O)OR^{16}$, $—CH_2—N(R^{15})C(O)OR^{16}$, $—N_3$, $=NOR^{15}$, $—NO_2$, $—S(O)R^{15}$ and $—S(O)_2R^{15}$.

In another embodiment of this invention $G^1$ is $C(=NR^2)$, $G^2$ is a direct bond, $G^3$ is N, $G^4$ is C, G is bound to $G^4$, and G is selected from the group consisting of: a direct bond (i.e., $R^{10}$ is bound directly to ring A, at $G^3$ or $G^4$ for example), —C(O)—, $—(C=NR^2)—$, $—(C=C(R^6)_2)—$, $C(R^4)_2$, $—CF_2—$, $—N(R^2)—$ (and in one example, —NH—), —O—, —S—, $—S(O)_t$, $—CR^4(OH)—$, $—CR^4(OR^4)—$, —C=C—, alkynyl, $—(CH_2)_rN(R^2)—$, $—(CHR^4)_rN(R^2)—$, $—(C(R^4)_2)_rN(R^2)—$, $—N(R^2)(CH_2)_r$—$N(R^2)(CHR^4)_r—$, $—N(R^2)(C(R^4)_2)_r$—$(CHR^4)_r—O—$, $—(C(R^4)_2)_r—O—$, $—O—(CH_2)_r$—$O—(CHR^4)_r$—$O—(C(R^4)_2)_r$—$(CH_2)_r—O—C(O)—$, $—(CHR^4)_r$—$(C(R^4)_2)_r$—O—C(O)—, $—C(O)—O—(CH_2)_r$—$C(O)—O—(CHR^4)_r$—$C(O)—O—(C(R^4)_2)_r$—$C(O)NR^5—$, —O—C(O)—, —C(O)—O—, $—O—C(O)—NR^5—$, $—NR^5C(O)—$, $—(CH_2)_rNR^5—C(O)—$, $—(CHR^4)_rNR^5—C(O)—$, $—(C(R^4)_2)_rNR^5—C(O)—$, $—C(O)NR^5(CH_2)_r—$, $—C(O)NR^5(CHR^4)_r$—$C(O)NR^5(C(R^4)_2)_r$—$NR^5S(O)_t$—$(CH_2)_rNR^5S(O)_t$—$(CHR^4)_rNR^5S(O)_t$—$(C(R^4)_2)_rNR^5S(O)_t$—$S(O)_tNR^5—$, $—S(O)_tNR^5(CH_2)_r—$, $—S(O)_tNR^5(CHR^4)_r—$, $—S(O)_tNR^5(C(R^4)_2)_r$—$NR^5—C(O)—O—$, $—NR^5—C(O)—NR^5—$, $—NR^5—S(O)_t—NR^5—$, $—NR^5—C(=NR^2)—NR^5—$, $—NR^5—C(=NR^2)—O—$, $—O—C(=NR^2)—NR^5—$, $—C(R^4)=N—O—$, $—O—N=C(R^4)—$, $—O—C(R^4)=N—$, $—N=C(R^4)—O—$, $—(CH_2)_{2-3}—$ (i.e., 2 to 3 $—CH_2—$ groups), $—(C(R^4)_2)_{2-3}—$ (i.e., there are 2 to 3 $—(C(R^4)_2$ groups), $—(CHR^4)_{2-3}—$ (i.e., there are 2 to 3 $—(CHR^4)—$ groups), cycloalkyl (e.g., $C_3$ to $C_{10}$ cycloalkyl), and heterocycloalkyl (comprising 1 to 4 heteroatoms independently selected from the group consisting of: —O—, $—NR^2—$, —S—, —S(O)—, and $—S(O)_2$).

Those skilled in the art will appreciate that when W is —S(O)—, the —S(O)— moiety can be:

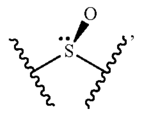

or the —S(O)— moiety can be;

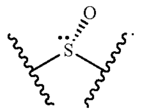

In another embodiment of this invention the moiety -G-$R^{10}$—$(R^9)_f$ is bound through G to position (1).

In another embodiment of this invention the moiety -G-$R^{10}$—$(R^9)_f$ is bound through G to position (2).

Examples of the cycloalkyl G moiety include, for example, cyclopropyl, cyclobutyl, cyclopentyl and cyclohexyl. In one example the cycloalkyl ring carbon by which said cycloalkyl moiety is bound to positions (1) or (2) is different from the cycloalkyl ring carbon by which said cycloalkyl moiety is bound to moiety $R^{10}$. In another example said cycloalkyl ring is bound to positions (1) or (2) and the $R^{10}$ moiety by the same cycloalkyl ring carbon.

The heterocycloalkyl G moiety comprises, for example, 1 to 4 heteroatoms selected from the group consisting of —O—, —$NR^2$—, —S—, —S(O)—, and —$S(O)_2$. In another example the heterocycloalkyl G moiety comprises 1 to 3 heteroatoms. In another example the heterocycloalkyl G moiety comprises 1 to 2 heteroatoms. In another example the heterocycloalkyl G moiety comprises 1 heteroatom. The heteroatoms in said heterocycloalkyl G moiety are independently selected from the group consisting of —O—, —$NR^2$—, —S—, —S(O)—, and —$S(O)_2$. In one example the heterocycloalkyl moiety is bound to the $R^{10}$ moiety and positions (1) or (2) by the same heterocycloalkyl ring atom. In another example, the heterocycloalkyl moiety is bound to the $R^{10}$ moiety and positions (1) or (2) by different heterocycloalkyl ring atoms. The heterocycloalkyl ring atoms that bind the heterocycloalkyl moiety to $R^{10}$ and positions (1) or (2) are selected from the group consisting of carbon and nitrogen.

In one embodiment of this invention the $R^9$-$R^{10}$— moiety is:

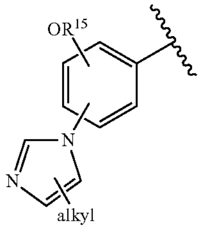

or

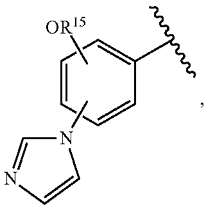

, and G is selected from the group consisting of: a direct bond (i.e., $R^{10}$ is bound directly to ring A, at $G^3$ or $G^4$ for example), —C(O)—, —(C═$NR^2$)—, —(C═C($R^6$)$_2$)—, —$CHR^3$— (e.g., —CHOH), C($R^4$)$_2$, —N($R^2$)— (and in one example, —NH—), —O—, —S—, —S(O)$_t$, —$CR^4$(OH)—, —$CR^4$($OR^4$)—, alkynyl, —($CH_2$)$_r$N($R^2$)—, —($CHR^4$)$_r$N($R^2$)—, —(C($R^4$)$_2$)$_r$N($R^2$)—, —N($R^2$)($CH_2$)$_r$—, —N($R^2$)($CHR^4$)$_r$—, —N($R^2$)(C($R^4$)$_2$)$_r$—, —($CH_2$)$_r$—O—, —($CHR^4$)$_r$—O—, —(C($R^4$)$_2$)$_r$—O—, —O—($CH_2$)$_r$—, —O—($CHR^4$)$_r$—, —O—(C($R^4$)$_2$)$_r$—, —($CH_2$)$_r$—O—C(O)—, —($CHR^4$)$_r$—O—, C(O)—, —C($R^4$)$_2$)$_r$—O—C(O)—, —C(O)—O—($CH_2$)$_r$—, —C(O)—O—($CHR^4$)$_r$—, —C(O)—O—(C($R^4$)$_2$)$_r$—, —C(O)$NR^5$—, —O—C(O)—, —C(O)—O—, —O—C(O)—$NR^5$—, —$NR^5$C(O)—, —($CH_2$)$_r$$NR^5$—C(O)—, —($CHR^4$)$_r$$NR^5$—C(O)—, —(C($R^4$)$_2$)$_r$$NR^5$—C(O)—, —C(O)$NR^5$($CH_2$)$_r$—, —C(O)$NR^5$($CHR^4$)$_r$—, —C(O)$NR^5$(C($R^4$)$_2$)$_r$—, —$NR^5$S(O)$_t$—, —($CH_2$)$_r$$NR^5$S(O)$_t$—, —($CHR^4$)$_r$$NR^5$S(O)$_t$—, —(C($R^4$)$_2$)$_r$$NR^5$S(O)$_t$—, —S(O)$_t$$NR^5$—, —S(O)$_t$$NR^5$($CH_2$)$_r$—S(O)$_t$$NR^5$($CHR^4$)$_r$—, —S(O)$_t$$NR^5$(C($R^4$)$_2$)$_r$—$NR^5$—C(O)—O—, —$NR^5$—C(O)—$NR^5$—, —$NR^5$—S(O)$_t$—$NR^5$—, —$NR^5$—C(═$NR^2$)—$NR^5$—, —$NR^5$—C(═$NR^2$)—O—, —O—C(═$NR^2$)—$NR^5$—, —C($R^4$)═N—O—, —O—N═C($R^4$)—, —O—C($R^4$)═N—, —N═C($R^4$)—O—, —($CH_2$)$_{2-3}$— (i.e., 2 to 3 —$CH_2$— groups), —(C($R^4$)$_2$)$_{2-3}$— (i.e., there are 2 to 3 —(C($R^4$)$_2$ groups), —($CHR^4$)$_{2-3}$— (i.e., there are 2 to 3 —($CHR^4$)— groups), cycloalkyl (e.g., $C_3$ to $C_{10}$ cycloalkyl), and heterocycloalkyl (comprising 1 to 4 heteroatoms independently selected from the group consisting of: —O—, —$NR^2$—, —S—, —S(O)—, and —$S(O)_2$).

In one embodiment of this invention the $R^9$-$R^{10}$— moiety is:

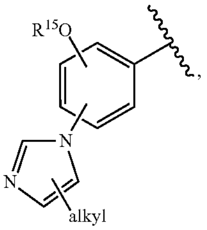

and G is selected from the group consisting of: a direct bond (i.e., $R^{10}$ is bound directly to ring A, at $G^3$ or $G^4$ for example), —(C═$NR^2$)—, —(C═C($R^6$)$_2$)—, —$CHR^3$— (e.g., —CHOH), C($R^4$)$_2$, —N($R^2$)— (and in one example, —NH—), —O—, —S—, —S(O)$_t$, —$CR^4$(OH)—, —$CR^4$($OR^4$)—, alkynyl, —($CH_2$)$_r$N($R^2$)—, —($CHR^4$)$_r$N($R^2$)—, —(C($R^4$)$_2$)$_r$N($R^2$)—, —N($R^2$)($CH_2$)$_r$—N($R^2$)($CHR^4$)$_r$—, —N($R^2$)(C($R^4$)$_2$)$_r$—, —($CH_2$)$_r$—O—, —($CHR^4$)$_r$—O—, —(C($R^4$)$_2$)$_r$—O—, —O—($CH_2$)$_r$—O—($CHR^4$)$_r$—O—(C($R^4$)$_2$)$_r$—, —($CH_2$)$_r$—O—C(O)—, —($CHR^4$)$_r$—O—C(O)—, —(C($R^4$)$_2$)$_r$—O—C(O)—O—($CH_2$)$_r$—C(O)—O—($CHR^4$)$_r$—, —C(O)—O—(C($R^4$)$_2$)$_r$—, —C(O)$NR^5$—, —O—C(O)—, —C(O)—O—, —O—C(O)—$NR^5$—, —$NR^5$C(O)—, —($CH_2$)$_r$$NR^5$—C(O)—, —($CHR^4$)$_r$$NR^5$—C(O)—, —(C($R^4$)$_2$)$_r$$NR^5$—C(O)—, —C(O)$NR^5$($CH_2$)$_r$—C(O)$NR^5$($CHR^4$)$_r$—, —C(O)$NR^5$(C($R^4$)$_2$)$_r$—$NR^5$S(O)$_t$—($CH_2$)$_r$$NR^5$S(O)$_t$—($CHR^4$)$_r$$NR^5$S(O)$_t$—, —(C($R^4$)$_2$)$_r$$NR^5$S(O)$_t$—S(O)$_t$$NR^5$—, —S(O)$_t$$NR^5$($CH_2$)$_r$—S(O)$_t$$NR^5$($CHR^4$)$_r$—, —S(O)$_t$$NR^5$(C($R^4$)$_2$)$_r$—$NR^5$—C(O)—O—, —$NR^5$—C(O)—$NR^5$—, —$NR^5$—S(O)$_t$—$NR^5$—, —$NR^5$—C(═$NR^2$)—$NR^5$—, —$NR^5$—C(═$NR^2$)—O—, —O—C(═$NR^2$)—$NR^5$—, —C($R^4$)═N—O—, —O—N═C($R^4$)—, —O—C($R^4$)═N—, —N═C($R^4$)—O—, —($CH_2$)$_{2-3}$— (i.e., 2 to 3 —$CH_2$— groups), —(C($R^4$)$_2$)$_{2-3}$— (i.e., there are 2 to 3 —(C($R^4$)$_2$ groups), —($CHR^4$)$_{2-3}$— (i.e., there are 2 to 3 —($CHR^4$)— groups), cycloalkyl (e.g., $C_3$ to $C_{10}$ cycloalkyl), and heterocycloalkyl (comprising 1 to 4 heteroatoms independently selected from the group consisting of: —O—, —$NR^2$—, —S—, —S(O)—, and —$S(O)_2$).

In one embodiment of this invention the $R^9$-$R^{10}$— moiety is:

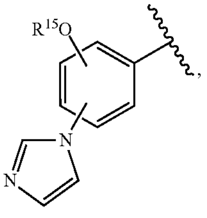

and G is selected from the group consisting of: a direct bond (i.e., $R^{10}$ is bound directly to ring A, at $G^3$ or $G^4$ for example), —C(O)—, —(C═$NR^2$)—, —(C═C($R^6$)$_2$)—, —$CHR^3$— (e.g., —CHOH), C($R^4$)$_2$, —$CF_2$—, —N($R^2$)— (and in one example, —NH—), —O—, —S—, —S(O)$_t$, —$CR^4$(OH)—, —$CR^4$($OR^4$)—, alkynyl, —($CH_2$)$_r$N($R^2$)—, —($CHR^4$)$_r$N($R^2$)—, —(C($R^4$)$_2$)$_r$N($R^2$)—, —N($R^2$)($CH_2$)$_r$—N($R^2$)

$(CHR^4)_r$—, —$N(R^2)(C(R^4)_2)_r$—$(CH_2)_r$—O—, —$(CHR^4)_r$—O—, —$(C(R^4)_2)_r$—O—, —O—$(CH_2)_r$, —O—$(CHR^4)_r$—O—$(C(R^4)_2)_r$—, —$(CH_2)_r$—, —C(O)—, —$(CHR^4)_r$—O—C(O)—, —$(C(R^4)_2)_r$—O—C(O)—, —C(O)—O—$(CH_2)_r$—C(O)—O—$(CHR^4)_r$—, —C(O)—O—$(C(R^4)_2)_r$—, —C(O)$NR^5$—, —O—C(O)—, —C(O)—O—, —O—C(O)—$NR^5$—, —$NR^5C(O)$—, —$(CH_2)_rNR^5$—C(O)—, —$(CHR^4)_rNR^5$—C(O)—, —$(C(R^4)_2)_rNR^5$—, —C(O)—, —C(O)$NR^5(CH_2)_r$—C(O)$NR^5(CHR^4)_r$—, —C(O)$NR^5(C(R^4)_2)_r$—$NR^5S(O)_t$—, —$(CH_2)_rNR^5S(O)_t$—$(CHR^4)_rNR^5S(O)_t$—, $(C(R^4)_2)_rNR^5S(O)_t$—, —$S(O)_tNR^5$—, —$S(O)_tNR^5(CH_2)_r$—, —$S(O)_tNR^5(CHR^4)_r$—, —$S(O)_tNR^5(C(R^4)_2)_r$—$NR^5$—C(O)—O—, —$NR^5$—C(O)—$NR^5$—, —$NR^5$—$S(O)_t$—$NR^5$—, —$NR^5$—C(=$NR^2$)—$NR^5$—, —$NR^5$—C(=$NR^2$)—O—, —O—C(=$NR^2$)—$NR^5$—, —$C(R^4)$=N—O—, —O—N=$C(R^4)$—, —O—$C(R^4)$=N—, —N=$C(R^4)$—O—, —$(CH_2)_{2-3}$— (i.e., 2 to 3 —$CH_2$— groups), —$(C(R^4)_2)_{2-3}$— (i.e., there are 2 to 3 —$(C(R^4)_2$ groups), —$(CHR^4)_{2-3}$— (i.e., there are 2 to 3 —$(CHR^4)$— groups), cycloalkyl (e.g., $C_3$ to $C_{10}$ cycloalkyl), and heterocycloalkyl (comprising 1 to 4 heteroatoms independently selected from the group consisting of: —O—, —$NR^2$—, —S—, —S(O)—, and —$S(O)_2$).

In another embodiment of this invention the $R^9$-$R^{10}$— moiety is:

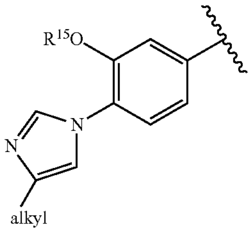

or

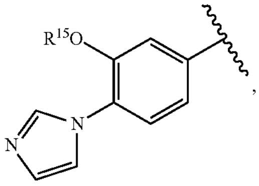

, and G is selected from the group consisting of: a direct bond (i.e., $R^{10}$ is bound directly to ring A, at $G^3$ or $G^4$ for example), —C(O)—, —(C=$NR^2$)—, —(C=$C(R^6)_2$)—, —$CHR^3$— (e.g., —CHOH), $C(R^4)_2$, —$CF_2$—, —$N(R^2)$— (and in one example, —NH—), —O—, —S—, —$S(O)_t$, —$CR^4(OH)$—, —$CR^4(OR^4)$—, alkynyl, —$(CH_2)_rN(R^2)$—, —$(CHR^4)_rN(R^2)$—, —$(C(R^4)_2)_rN(R^2)$—, —$N(R^2)(CH_2)_r$—$N(R^2)(CHR^4)_r$—, —$N(R^2)(C(R^4)_2)_r$—$(CH_2)_r$—O—, —$(CHR^4)_r$—O—, —$(C(R^4)_2)_r$—O—, —O—$(CH_2)_r$—O—$(CHR^4)_r$—, —O—$(C(R^4)_2)_r$—$(CH_2)_r$—O—C(O)—, —$(CHR^4)_r$—O—C(O)—, —$(C(R^4)_2)_r$—O—C(O)—, —C(O)—O—$(CH_2)_r$—C(O)—O—$(CHR^4)_r$—, —C(O)—O—$(C(R^4)_2)_r$—, —C(O)$NR^5$—, —O—C(O)—, —O—C(O)—$NR^5$—, —$NR^5C(O)$—, —$(CH_2)_rNR^5$—C(O)—, —$(CHR^4)_rNR^5$—C(O)—, —$(C(R^4)_2)_rNR^5$—C(O)—, —C(O)$NR^5(CH_2)_r$—C(O)$NR^5(CHR^4)_r$—, —C(O)$NR^5(C(R^4)_2)_r$—$NR^5S(O)_t$—$(CH_2)_rNR^5S(O)_t$—$(CHR^4)_rNR^5S(O)_t$—, —$(C(R^4)_2)_rNR^5S(O)_t$—$S(O)_tNR^5$—, —$S(O)_tNR^5(CH_2)_r$—$S(O)_tNR^5(CHR^4)_r$—, —$S(O)NR^5(C(R^4)_2)_r$—$NR^5$—C(O)—O—, —$NR^5$—C(O)—$NR^5$—, —$NR^5$—$S(O)_t$—$NR^5$—, —$NR^5$—C(=$NR^2$)—$NR^5$—, —$NR^5$—C(=$NR^2$)—O—, —O—C(=$NR^2$)—$NR^5$—, —$C(R^4)$=N—O—, —O—N=$C(R^4)$—, —O—$C(R^4)$=N—, —N=$C(R^4)$—O—, —$(CH_2)_{2-3}$— (i.e., 2 to 3 —$CH_2$— groups), —$(C(R^4)_2)_{2-3}$— (i.e., there are 2 to 3 —$(C(R^4)_2$ groups), —$(CHR^4)_{2-3}$— (i.e., there are 2 to 3 —$(CHR^4)$— groups), cycloalkyl (e.g., $C_3$ to $C_{10}$ cycloalkyl), and heterocycloalkyl (comprising 1 to 4 heteroatoms independently selected from the group consisting of: —O—, —$NR^2$—, —S—, —S(O)—, and —$S(O)_2$).

In another embodiment of this invention the $R^9$-$R^{10}$— moiety is:

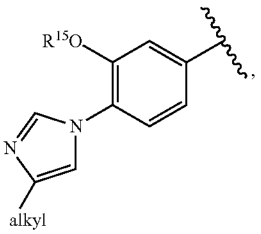

, and G is selected from the group consisting of: a direct bond (i.e., $R^{10}$ is bound directly to ring A, at $G^3$ or $G^4$ for example), —C(O)—, —(C=$NR^2$)—, —(C=$C(R^6)_2$)—, —$CHR^3$— (e.g., —CHOH), $C(R^4)_2$, —$CF_2$—, —$N(R^2)$— (and in one example, —NH—), —O—, —S—, —$S(O)_t$, —$CR^4(OH)$—, —$CR^4(OR^4)$—, alkynyl, —$(CH_2)_rN(R^2)$—, —$(CHR^4)_rN(R^2)$—, —$(C(R^4)_2)_rN(R^2)$—, —$N(R^2)(CH_2)_r$—$N(R^2)(CHR^4)_r$—, —$N(R^2)(C(R^4)_2)_r$—, —$(CHR^4)_r$—O—, —$(C(R^4)_2)_r$—O—, —O—$(CH_2)_r$—O—$(CHR^4)_r$—, —O—$(C(R^4)_2)_r$—, —$(CH_2)_r$—$(CHR^4)_r$—O—C(O)—, —$(C(R^4)_2)_r$—O—C(O)—, —C(O)—O—$(CH_2)_r$—, —C(O)—O—$(CHR^4)_r$—, —C(O)—O—$(C(R^4)_2)_r$—, —C(O)$NR^5$—, —O—C(O)—, —C(O)—O—, —O—C(O)—$NR^5$—, —$NR^5C(O)$—, —$(CH_2)_rNR^5$—C(O)—, —$(CHR^4)_rNR^5$—C(O)—, —$(C(R^4)_2)_rNR^5$—C(O)—, —C(O)$NR^5(CH_2)_r$—, —C(O)$NR^5(CHR^4)_r$—, —C(O)$NR^5(C(R^4)_2)_r$—, —$NR^5S(O)_t$—, —$(CH_2)_rNR^5S(O)_t$—, —$(CHR^4)_rNR^5S(O)_t$—, —$(C(R^4)_2)_rNR^5S(O)_t$—$S(O)_tNR^5$—, —$S(O)_tNR^5(CH_2)_r$—$S(O)_tNR^5(CHR^4)_r$—, —$S(O)_tNR^5(C(R^4)_2)_r$—$NR^5$—C(O)—O—, —$NR^5$—C(O)—$NR^5$—, —$NR^5$—$S(O)_t$—$NR^5$—, —$NR^5$—C(=$NR^2$)—$NR^5$—, —$NR^5$—C(=$NR^2$)—O—, —O—C(=$NR^2$)—$NR^5$—, —$C(R^4)$=N—O—, —O—N=$C(R^4)$—, —O—$C(R^4)$=N—, —N=$C(R^4)$—O—, —$(CH_2)_{2-3}$— (i.e., 2 to 3 —$CH_2$— groups), —$(C(R^4)_2)_{2-3}$— (i.e., there are 2 to 3 —$(C(R^4)_2$ groups), —$(CHR^4)_{2-3}$— (i.e., there are 2 to 3 —$(CHR^4)$— groups), cycloalkyl (e.g., $C_3$ to $C_{10}$ cycloalkyl), and heterocycloalkyl (comprising 1 to 4 heteroatoms independently selected from the group consisting of: —O—, —$NR^2$—, —S—, —S(O)—, and —$S(O)_2$).

In another embodiment of this invention the $R^9$-$R^{10}$— moiety is:

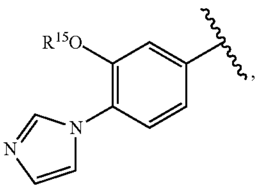

, and G is selected from the group consisting of: a direct bond (i.e., $R^{10}$ is bound directly to ring A, at $G^3$ or $G^4$ for example), —C(O)—, —(C=$NR^2$)—, —(C=$C(R^6)_2$)—, —$CHR^3$— (e.g., —CHOH), $C(R^4)_2$, —$CF_2$—, —$N(R^2)$— (and in one example, —NH—), —O—, —S—, —$S(O)_t$, —$CR^4(OH)$—, —$CR^4(OR^4)$—, alkynyl, —$(CH_2)_rN(R^2)$—, —$(CHR^4)_rN(R^2)$—, —$(C(R^4)_2)_rN(R^2)$—, —$N(R^2)(CH_2)_r$—$N(R^2)(CHR^4)_r$—, —$N(R^2)(C(R^4)_2)_r$—, —$(CH_2)_r$—, —$(CHR^4)_r$—O—, —$(C(R^4)_2)_r$—O—, —O—$(CH_2)_r$—O—$(CHR^4)_r$—O—$(C(R^4)_2)_r$—, —$(CH_2)_r$—$(CHR^4)_r$—O—C(O)—, —(C (R$^4$)$_2$)$_r$—O—C(O)—, —C(O)—O—(CH$_2$)$_r$—, —C(O)—O—(CHR$^4$)$_r$—, —C(O)—O—(C(R$^4$)$_2$)$_r$—, —C(O)NR$^5$—, —O—C(O)—NR$^5$—, —NR$^5$C(O)—, —(CH$_2$)$_r$NR$^5$—C(O)—, —(CHR$^4$)$_r$NR$^5$—C(O)—, —(C(R$^4$)$_2$)$_r$NR$^5$—C(O)—, —C(O)NR$^5$(CH$_2$)$_r$—C(O)NR$^5$(CHR$^4$)$_r$—, —C(O)NR$^5$(C(R$^4$)$_2$)$_r$—, —NR$^5$S(O)$_t$—, —(CH$_2$)$_r$NR$^5$S(O)$_t$—, —(CHR$^4$)$_r$NR$^5$S(O)$_t$—, —(C(R$^4$)$_2$)$_r$NR$^5$S(O)$_t$—S(O)$_t$NR$^5$—, —S(O)$_t$NR$^6$(CH$_2$)$_r$—S(O)$_t$NR$^5$(CHR$^4$)$_r$—, —S(O)$_t$NR$^5$(C(R$^4$)$_2$)$_r$—NR$^5$—C(O)—O—, —NR$^5$—C(O)—NR$^5$—, —NR$^5$—S(O)$_t$—NR$^5$—, —NR$^5$—C(=NR$^2$)—NR$^5$—, —NR$^5$—C(=NR$^2$)—O—, —O—C(=NR$^2$)—NR$^5$—, —C(R$^4$)=N—O—, —O—N=C(R$^4$)—, —O—C(R$^4$)=N—, —N=C(R$^4$)—O—, —(CH$_2$)$_{2-3}$— (i.e., 2 to 3 —CH$_2$— groups), —(C(R$^4$)$_2$)$_{2-3}$— (i.e., there are 2 to 3 —(C(R$^4$)$_2$ groups), —(CHR$^4$)$_{2-3}$— (i.e., there are 2 to 3 —(CHR$^4$)— groups), cycloalkyl (e.g., C$_3$ to C$_{10}$ cycloalkyl), and heterocycloalkyl (comprising 1 to 4 heteroatoms independently selected from the group consisting of: —O—, —NR$^2$—, —S—, —S(O)—, and —S(O)$_2$).

In another embodiment of this invention the R$^9$-R$^{10}$— moiety is:

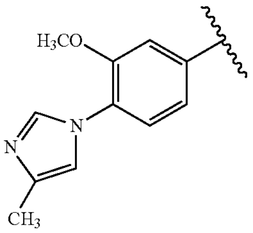

or

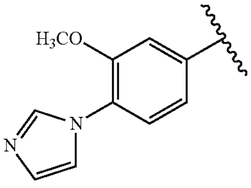

and G is selected from the group consisting of: a direct bond (i.e., R$^{10}$ is bound directly to ring A, at G$^3$ or G$^4$ for example), —C(O)—, —(C=NR$^2$)—, —(C=C(R$^6$)$_2$)—, —CHR$^3$— (e.g., —CHOH), C(R$^4$)$_2$, —CF$_2$—, —N(R$^2$)— (and in one example, —NH—), —O—, —S—, —S(O)$_t$, —CR$^4$(OH)—, —CR$^4$(OR$^4$)—, alkynyl, —(CH$_2$)$_r$N(R$^2$)—, —(CHR$^4$)$_r$N(R$^2$)—, —(C(R$^4$)$_2$)$_r$N(R$^2$)—, —N(R$^2$)(CH$_2$)$_r$—N(R$^2$)(CHR$^4$)$_r$—, —N(R$^2$)(C(R$^4$)$_2$)$_r$—, —(CH$_2$)$_r$—, —(CHR$^4$)$_r$—O—, —(C(R$^4$)$_2$)$_r$—O—, —O—(CH$_2$)$_r$, —O—(C(R$^4$)$^r$, —O—(C(R$^4$)$_2$)$_r$—(CH$_2$)$_r$—O—C(O)—, —(CHR$^4$)$_r$—O—C(O)—, —(C(R$^4$)$_2$)$_r$—O—C(O)—, —C(O)—O—(CH$_2$)$_r$—C(O)—O—(CHR$^4$)$_r$—, —C(O)—O—(C(R$^4$)$_2$)$_r$—, —C(O)NR$^5$—, —O—C(O)—, —C(O)—O—, —O—C(O)—NR$^5$—, —NR$^5$C(O)—, —(CH$_2$)$_r$NR$^5$—C(O)—, —(CHR$^4$)$_r$NR$^5$—C(O)—, —(C(R$^4$)$_2$)$_r$NR$^5$—, —C(O)—, —C(O)NR$^5$(CH$_2$)$_r$—C(O)NR$^5$(CHR$^4$)$_r$—, —C(O)NR$^5$(C(R$^4$)$_2$)$_r$—NR$^6$S(O)$_t$—(CH$_2$)$_r$NR$^5$S(O)$_t$—, —(CHR$^4$)$_r$NR$^6$S(O)$_t$ —(C(R$^4$)$_2$)$_r$NR$^5$S(O)$_t$—, —S(O)$_t$NR$^5$—, —S(O)$_t$NR$^5$(CH$_2$)$_r$—S(O)$_t$NR$^5$(CHR$^4$)$_r$—, —S(O)$_t$NR$^5$(C(R$^4$)$_2$)$_r$—NR$^5$—C(O)—O—, —NR$^5$—C(O)—NR$^5$—, —NR$^5$—S(O)$_t$—NR$^5$—, —NR$^5$—C(=NR$^2$)—NR$^5$—, —NR$^5$—C(=NR$^2$)—O—, —O—C(=NR$^2$)—NR$^5$—, —C(R$^4$)=N—O—, —O—N=C(R$^4$)—, —O—C(R$^4$)=N—, —N=C(R$^4$)—O—, —(CH$_2$)$_{2-3}$— (i.e., 2 to 3 —CH$_2$— groups), —(C(R$^4$)$_2$)$_{2-3}$— (i.e., there are 2 to 3 —(C(R$^4$)$_2$ groups), —(CHR$^4$)$_{2-3}$— (i.e., there are 2 to 3 —(CHR$^4$)— groups), cycloalkyl (e.g., C$_3$ to C$_{10}$ cycloalkyl), and heterocycloalkyl (comprising 1 to 4 heteroatoms independently selected from the group consisting of: —O—, —NR$^2$—, —S—, —S(O)—, and —S(O)$_2$).

In another embodiment of this invention the R$^9$-R$^{10}$— moiety is:

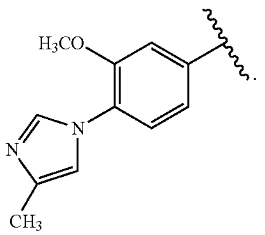 [SMILES: *c1ccc(-n2cnc(C)c2)c(OC)c1]

and G is selected from the group consisting of: a direct bond (i.e., R$^{10}$ is bound directly to ring A, at G$^3$ or G$^4$ for example), —C(O)—, —(C=NR$^2$)—, —(C=C(R$^6$)$_2$)—, —CHR$^3$— (e.g., —CHOH), C(R$^4$)$_2$, —CF$_2$—, —N(R$^2$)— (and in one example, —NH—), —O—, —S—, —S(O)$_t$, —CR$^4$(OH)—, —CR$^4$(OR$^4$)—, alkynyl, —(CH$_2$)$_r$N(R$^2$)—, —(CHR$^4$)$_r$N(R$^2$)—, —(C(R$^4$)$_2$)$_r$N(R$^2$)—, —N(R$^2$)(CH$_2$)$_r$—N(R$^2$)(CHR$^4$)$_r$—, —N(R$^2$)(C(R$^4$)$_2$)$_r$—(CH$_2$)$_r$—O—, —(CHR$^4$)$_r$—O—, —(C(R$^4$)$_2$)$_r$—O—(CH$_2$)$_r$—O—(CHR$^4$)$_r$—O—(C(R$^4$)$_2$)$_r$—(CH$_2$)$_r$—(CHR$^4$)$_r$—O—C(O)—, —(C(R$^4$)$_2$)$_r$—C(O)—O—(CH$_2$)$_r$—, —C(O)—O—(CHR$^4$)$_r$—, —C(O)—O—(C(R$^4$)$_2$)$_r$—, —C(O)NR$^5$—, —O—C(O)—, —C(O)—O—, —O—C(O)—NR$^5$—, —NR$^5$C(O)—, —(CH$_2$)$_r$NR$^5$—C(O)—, —(CHR$^4$)$_r$NR$^5$—C(O)—, —(C(R$^4$)$_2$)$_r$NR$^5$—C(O)—, —C(O)NR$^5$(CH$_2$)$_r$—C(O)NR$^5$(CHR$^4$)$_r$—C(O)NR$^5$(C(R$^4$)$_2$)$_r$—NR$^5$S(O)$_t$—(CH$_2$)$_r$NR$^5$S(O)$_t$—(CHR$^4$)$_r$NR$^5$S(O)$_t$—, —(C(R$^4$)$_2$)$_r$NR$^5$S(O)$_t$—, —S(O)$_t$NR$^5$—, —S(O)$_t$NR$^5$(CH$_2$)$_r$—S(O)$_t$NR$^5$(CHR$^4$)$_r$—, —S(O)$_t$NR$^5$(C(R$^4$)$_2$)$_r$—NR$^5$—C(O)—O—, —NR$^5$—C(O)—NR$^5$—, —NR$^5$—S(O)$_t$NR$^5$—, —NR$^5$—C(=NR$^2$)—NR$^5$—, —NR$^5$—C(=NR$^2$)—O—, —O—C(=NR$^2$)—NR$^5$—, —C(R$^4$)=N—O—, —O—N=C(R$^4$)—, —O—C(R$^4$)=N—, —N=C(R$^4$)—O—, —(CH$_2$)$_{2-3}$— (i.e., 2 to 3 —CH$_2$— groups), —(C(R$^4$)$_2$)$_{2-3}$— (i.e., there are 2 to 3 —(C(R$^4$)$_2$ groups), —(CHR$^4$)$_{2-3}$— (i.e., there are 2 to 3 —(CHR$^4$)— groups), cycloalkyl (e.g., C$_3$ to C$_{10}$ cycloalkyl), and heterocycloalkyl (comprising 1 to 4 heteroatoms independently selected from the group consisting of: —O—, —NR$^2$—, —S—, —S(O)—, and —S(O)$_2$).

In another embodiment of this invention the R$^9$-R$^{10}$— moiety is:

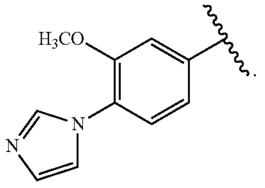

and G is selected from the group consisting of: a direct bond (i.e., R$^{10}$ is bound directly to ring A, at G$^3$ or G$^4$ for example), —C(O)—, —(C=NR$^2$)—, —(C=C(R$^6$)$_2$)—, —CHR$^3$— (e.g., —CHOH), C(R$^4$)$_2$, —CF$_2$—, —N(R$^2$)— (and in one example, —NH—), —O—, —S—, —S(O)$_t$, —CR$^4$(OH)—, —CR$^4$(OR$^4$)—, alkynyl, —(CH$_2$)$_r$N(R$^2$)—, —(CHR$^4$)$_r$N(R$^2$)—, —(C(R$^4$)$_2$)$_r$N(R$^2$)—, —N(R$^2$)(CH$_2$)$_r$—N(R$^2$)(CHR$^4$)$_r$—, —N(R$^2$)(C(R$^4$)$_2$)$_r$—(CH$_2$)$_r$—O—, —(CHR$^4$)$_r$—O—, —(C(R$^4$)$_2$)$_r$—O—, —O—(CH$_2$)$_r$, —O—(CHR$^4$)$_r$—O—(C(R$^4$)$_2$)$_r$—, —(CH$_2$)$_r$—, O—C(O)—, —(CHR$^4$)$_r$—O—C(O)—, —(C(R$^4$)$_2$)$_r$—C(O)O—(CH$_2$)$_r$—, —C(O)—

O—(CHR$^4$)$_r$—, —C(O)—O—(C(R$^4$)$_2$)$_r$—, —C(O)NR$^5$—, —O—C(O)—NR$^5$—, —NR$^5$C(O)—, —(CH$_2$)$_r$NR$^5$—C(O)—, —(CHR$^4$)$_r$NR$^5$—C(O)—, —(C(R$^4$)$_2$)$_r$NR$^5$—C(O)—, —C(O)NR$^5$(CH$_2$)$_r$—C(O)NR$^5$(CHR$^4$)$_r$ —C(O)NR$^5$(C(R$^4$)$_2$)$_r$—NR$^5$S(O)$_t$—(CH$_2$)$_r$NR$^5$S(O)$_t$—(CHR$^4$)$_r$NR$^5$S(O)$_t$—, —(C(R$^4$)$_2$)$_r$NR$^5$S(O)$_t$—, —S(O)$_t$NR$^5$—, —S(O)$_t$NR$^5$(CH$_2$)$_r$—S(O)$_t$NR$^5$(CHR$^4$)$_r$—, —S(O)$_t$NR$^5$(C(R$^4$)$_2$)$_r$ —NR$^5$—C(O)—O—, —NR$^5$—C(O)—NR$^5$—, —NR$^5$—S(O)$_t$—NR$^5$—, —NR$^5$—C(=NR$^2$)—NR$^5$—, —NR$^5$—C(=NR$^2$)—O—, —O—C(=NR$^2$)—NR$^5$—, —C(R$^4$)=N—O—, —O—N=C(R$^4$)—, —O—C(R$^4$)=N—, —N=C(R$^4$)—O—, —(CH$_2$)$_{2\text{-}3}$— (i.e., 2 to 3 —CH$_2$— groups), —(C(R$^4$)$_2$)$_{2\text{-}3}$— (i.e., there are 2 to 3 —(C(R$^4$)$_2$ groups), —(CHR$^4$)$_{2\text{-}3}$— (i.e., there are 2 to 3 —(CHR$^4$)— groups), cycloalkyl (e.g., C$_3$ to C$_{10}$ cycloalkyl), and heterocycloalkyl (comprising 1 to 4 heteroatoms independently selected from the group consisting of: —O—, —NR$^2$—, —S—, —S(O)—, and —S(O)$_2$).

In another embodiment of this invention G is selected from the group consisting of: a direct bond (i.e., R$^{10}$ is bound directly to ring A, at G$^3$ or G$^4$ for example), —C(O)—, —(C=NR$^2$)—, —(C=C(R$^6$)$_2$)—, —CHR$^3$— (e.g., —CHOH), C(R$^4$)$_2$, —CF$_2$—, —N(R$^2$)— (and in one example, —NH—), —O—, —S—, —S(O)$_t$, —CR$^4$(OH)—, —CR$^4$(OR$^4$)—, alkynyl, —(CH$_2$)$_r$N(R$^2$)—, —(CHR$^4$)$_r$N(R$^2$)—, —(C(R$^4$)$_2$)$_r$N(R$^2$)—, —N(R$^2$)(CH$_2$)$_r$—N(R$^2$)(CHR$^4$)$_r$—, —N(R$^2$)(C(R$^4$)$_2$)$_r$—, —(CH$_2$)$_r$—O—, —(CHR$^4$)$_r$—O—, —(C(R$^4$)$_2$)$_r$—O—, —O—(CH$_2$)$_r$—O—(CHR$^4$)$_r$—, —O—(C(R$^4$)$_2$)$_r$—, —(CH$_2$)$_r$—O—, —(CHR$^4$)$_r$ —O—, —(C(R$^4$)$_2$)$_r$—O—C(O)—, —C(O)—O—(CH$_2$)$_r$— C(O)—O—(CHR$^4$)$_r$—, —C(O)—O—(C(R$^4$)$_2$)$_r$—O—C(O)—, —C(O)—O—, —O—C(O)—NR$^5$—, —NR$^5$C(O)—, —(CH$_2$)$_r$NR$^5$—C(O)—, —(CHR$^4$)$_r$NR$^5$—C(O)—, —(C(R$^4$)$_2$)$_r$NR$^5$—C(O)—, —C(O)NR$^5$(CH$_2$)$_r$—C(O)NR$^5$(CHR$^4$)$_r$—C(O)NR$^5$(C(R$^4$)$_2$)$_r$—, —NR$^5$S(O)$_t$—(CH$_2$)$_r$ NR$^5$S(O)$_t$—, —(CHR$^4$)$_r$NR$^5$S(O)$_t$—(C(R$^4$)$_2$)$_r$NR$^5$S(O)$_t$—, —S(O)$_t$NR$^5$—, —S(O)$_t$NR$^5$(CH$_2$)$_r$—S(O)$_t$NR$^5$(CHR$^4$)$_r$—S(O)$_t$NR$^5$(C(R$^4$)$_2$)$_r$—, —NR$^5$—C(O)—O—, —NR$^5$—C(O)—NR$^5$—, —NR$^5$—S(O)—NR$^5$—, —NR$^5$—C(=NR$^2$)—NR$^5$—, —NR$^5$—C(=NR$^2$)—O—, —O—C(=NR$^2$)—NR$^5$—, —C(R$^4$)=N—O—, —O—N=C(R$^4$)—, —O—C(R$^4$)=N—, —N=C(R$^4$)—O—, —(CH$_2$)$_{2\text{-}3}$— (i.e., 2 to 3 —CH$_2$— groups), —(C(R$^4$)$_2$)$_{2\text{-}3}$— (i.e., there are 2 to 3 —(C(R$^4$)$_2$ groups), —(CHR$^4$)$_{2\text{-}3}$— (i.e., there are 2 to 3 —(CHR$^4$)— groups), cycloalkyl (e.g., C$_3$ to C$_{10}$ cycloalkyl), and heterocycloalkyl (comprising 1 to 4 heteroatoms independently selected from the group consisting of: —O—, —NR$^2$—, —S—, —S(O)—, and —S(O)$_2$).

In another embodiment of this invention G is selected from the group consisting of: a direct bond (i.e., R$^{10}$ is bound directly to either G$^3$ or G$^4$), cycloalkyl (e.g., C$_3$ to C$_{10}$, and also for example, cyclopropyl, cyclobutyl, cyclopentyl and cyclohexyl, and wherein in one example the cycloalkyl ring carbon by which said cycloalkyl moiety is bound to positions (1) or (2) is different from the cycloalkyl ring carbon by which said cycloalkyl moiety is bound to moiety R$^{10}$, and wherein in another example said cycloalkyl ring is bound to positions (1) or (2) and the R$^{10}$ moiety by the same cycloalkyl ring carbon), heterocycloalkyl (wherein said heterocycloalkyl comprises 1 to 4 heteroatoms, and in one example, 1 to 4 heteroatoms, and in another example 1 to 3 heteroatoms, and in another example 1 to 2 heteroatoms, and in another example 1 heteroatom, and wherein said heteroatoms are selected from the group consisting of —O—, —NR$^2$—, —S—, —S(O)—, and —S(O)$_2$, and wherein in one example said heterocycloalkyl moiety is bound to the R$^{10}$ moiety and positions (1) or (2) by the same heterocycloalkyl ring atom, and in another example said heterocycloalkyl moiety is bound to the R$^{10}$ moiety and positions (1) or (2) by different heterocycloalkyl ring atoms, and wherein the heterocycloalkyl ring atoms that bind the heterocycloalkyl moiety to R$^{10}$ and positions (1) or (2) are selected from the group consisting of carbon and nitrogen), —C=C—, —CF$_2$— alkynyl (e.g., —C≡C—), —NH—, —N(R$^2$)— (and in one example, —NH—), —O—, —CR$^4$(OH)—, —CR$^4$(OR$^4$)—, —(CH$_2$)$_r$N(R$^2$)—, —N(R$^2$)(CH$_2$)$_r$ —(CH$_2$)$_{2\text{-}10}$—, —(C(R$^4$)$_2$)$_r$— (wherein each R$^4$ is independently selected), —(CHR$^4$)$_{2\text{-}10}$— (wherein each R$^4$ is independently selected), —S—, —S(O)—, and —S(O)$_2$.

In another embodiment of this invention G is selected from the group consisting of: a direct bond, and —N(R$^2$) (e.g., —NH—).

In another embodiment of this invention G is a cycloalkyl.

In another embodiment of this invention G is a heterocycloalkyl.

In another embodiment of this invention G is —C=C—.

In another embodiment of this invention G is —CF$_2$—.

In another embodiment of this invention G is alkynyl.

In another embodiment of this invention G is —O—.

In another embodiment of this invention G is —CR$^4$(OH)—.

In another embodiment of this invention G is —CR$^4$(OR$^4$)—.

In another embodiment of this invention G is —(CH$_2$)$_r$N(R$^2$)—.

In another embodiment of this invention G is —N(R$^2$)(CH$_2$)$_r$—.

In another embodiment of this invention G is —(CH$_2$)$_{2\text{-}10}$—.

In another embodiment of this invention G is —(C(R$^4$)$_2$)$_r$— (wherein each R$^4$ is independently selected).

In another embodiment of this invention G is —(CHR$^4$)$_{2\text{-}10}$— (wherein each R$^4$ is independently selected).

In another embodiment of this invention G is —S—.

In another embodiment of this invention G is —S(O)—.

In another embodiment of this invention G is —S(O)$_2$.

In another embodiment of this invention G$^1$ is a direct bond.

In another embodiment of this invention G$^1$ is —O—.

In another embodiment of this invention G$^1$ is —C(R$^{21}$)$_q$.

In another embodiment of this invention G$^1$ is —N(R$^2$)$_d$—.

In another embodiment of this invention G$^1$ is —C(O)—.

In another embodiment of this invention G$^1$ is —C(=NR$^2$)—.

In another embodiment of this invention G$^1$ is —S—.

In another embodiment of this invention G$^1$ is —S(O)$_2$.

In another embodiment of this invention G$^1$ is —S(O)—.

In another embodiment of this invention G$^2$ is a direct bond.

In another embodiment of this invention G$^2$ is —O—.

In another embodiment of this invention G$^2$ is —C(R$^{21}$)$_q$.

In another embodiment of this invention G$^2$ is —N(R$^2$)$_d$—.

In another embodiment of this invention G$^2$ is —C(O)—.

In another embodiment of this invention G$^2$ is —C(=NR$^2$)—.

In another embodiment of this invention G$^2$ is —S—.

In another embodiment of this invention G$^2$ is —S(O)$_2$.

In another embodiment of this invention G$^2$ is —S(O)—.

In another embodiment of this invention at least one (e.g., 1 to 2) R$^{21}$ is selected from the group consisting of: —SF$_5$, —OSF$_5$ and —Si(R$^{15}$)$_3$, wherein each R$^{15}$ is independently selected.

In another embodiment of this invention at least one R$^{21}$ is selected from the group consisting of: —SF$_5$ and —Si(R$^{15}$)$_3$, and each R$^{15}$ is the same or different alkyl group.

In another embodiment of this invention at least one $R^{21}$ is selected from the group consisting of: —$SF_5$, —$OSF_5$ and —$Si(CH_3)_3$.

In another embodiment of this invention one of the $R^{21}$ groups is selected from the group consisting of: —$SF_5$, $OSF_5$ and —$Si(R^{15})_3$.

In another embodiment of this invention one of the $R^{21}$ groups is selected from the group consisting of: —$SF_5$, $OSF_5$ and —$Si(R^{15})_3$, and each $R^{15}$ is the same or different alkyl group.

In another embodiment of this invention one of the $R^{21}$ groups is selected from the group consisting of: —$SF_5$, —$OSF_5$ and —$Si(CH_3)_3$.

In another embodiment of this invention two of the $R^{21}$ groups are selected from the group consisting of: —$SF_5$, $OSF_5$ and —$Si(R^{15})_3$, wherein each $R^{15}$ is independently selected.

In another embodiment of this invention two of the $R^{21}$ groups are selected from the group consisting of: —$SF_5$, $OSF_5$ and —$Si(R^{15})_3$, and each $R^{15}$ is the same or different alkyl group.

In another embodiment of this invention two of the $R^{21}$ groups are selected from the group consisting of: —$SF_5$, —$OSF_5$ and —$Si(CH_3)_3$.

In another embodiment of this invention at least one (e.g., 1 to 2) $R^{21}$ is selected from the group consisting of: —$SF_5$ and —$Si(R^{15})_3$, wherein each $R^{15}$ is independently selected.

In another embodiment of this invention at least one $R^{21}$ is selected from the group consisting of: —$SF_5$ and —$Si(R^{15})_3$, and each $R^{15}$ is the same or different alkyl group.

In another embodiment of this invention at least one $R^{21}$ is selected from the group consisting of: —$SF_5$ and —$Si(CH_3)_3$.

In another embodiment of this invention one of the $R^{21}$ groups is selected from the group consisting of: —$SF_5$ and —$Si(R^{15})_3$.

In another embodiment of this invention one of the $R^{21}$ groups is selected from the group consisting of: —$SF_5$ and —$Si(R^{15})_3$, and each $R^{15}$ is the same or different alkyl group.

In another embodiment of this invention one of the $R^{21}$ groups is selected from the group consisting of: —$SF_5$ and —$Si(CH_3)_3$.

In another embodiment of this invention two of the $R^{21}$ groups are selected from the group consisting of: —$SF_5$ and —$Si(R^{15})_3$, wherein each $R^{15}$ is independently selected.

In another embodiment of this invention two of the $R^{21}$ groups are selected from the group consisting of: —$SF_5$ and —$Si(R^{15})_3$, and each $R^{15}$ is the same or different alkyl group.

In another embodiment of this invention two of the $R^{21}$ groups are selected from the group consisting of: —$SF_5$ and —$Si(CH_3)_3$.

In another embodiment of this invention one of the $R^{21}$ groups is —$SF_5$.

In another embodiment of this invention two of the $R^{21}$ groups are —$SF_5$.

In another embodiment of this invention one of the $R^{21}$ groups is —$OSF_5$.

In another embodiment of this invention two of the $R^{21}$ groups are —$OSF_5$.

In another embodiment of this invention one of the $R^{21}$ groups is —$Si(R^{15})_3$.

In another embodiment of this invention one of the $R^{21}$ groups is —$Si(R^{15})_3$ and each $R^{15}$ is the same or different alkyl group.

In another embodiment of this invention one of the $R^{21}$ groups is —$Si(CH_3)_3$.

In another embodiment of this invention two of the $R^{21}$ groups are the same or different —$Si(R^{15})_3$, wherein each $R^{15}$ is independently selected.

In another embodiment of this invention two of the $R^{21}$ groups are the same or different —$Si(R^{15})_3$ and each $R^{15}$ is the same or different alkyl group.

In another embodiment of this invention two of the $R^{21}$ groups are —$Si(CH_3)_3$.

In another embodiment of this invention $R^{21}$ is selected from the group consisting of: alkyl, —$OR^{15}$, —$C(O)OR^{15}$, —$C(O)NR^{15}R^{16}$, and alkyl substituted with 1 to 5 independently selected $R^{22}$ groups (e.g., halo, such as, for example, F, Cl, and Br).

In another embodiment of this invention $R^{21}$ is selected from the group consisting of: alkyl, —$OR^{15}$, —$C(O)OR^{15}$, —$C(O)NR^{15}R^{16}$, and alkyl substituted with 1 to 5 independently selected $R^{22}$ groups (e.g., halo, such as, for example, F, Cl, and Br, and wherein in one example the alkyl substituted $R^{21}$ group is —$CF_3$), wherein $R^{15}$ and $R^{16}$ are independently selected from the group consisting of: H, alkyl, $(R^{18})_n$-arylalkyl- (wherein, for example, n is 1, and $R^{18}$ is —$OR^{20}$, and $R^{20}$ is alkyl (e.g., methyl), cycloalkyl (e.g., cyclobutyl), and $(R^{18})_n$-alkyl (e.g, n is 1, $R^{18}$ is —$OR^{20}$, and $R^{20}$ is alkyl (e.g., methyl).

In another embodiment of this invention $R^{21}$ is selected from the group consisting of: (a) alkyl, —$OR^{15}$ (wherein $R^{15}$ is alkyl, e.g., methyl and ethyl), (b) —$C(O)OR^{15}$ (wherein $R^{15}$ is alkyl, e.g., methyl), (c) —$C(O)NR^{15}R^{16}$ (wherein $R^{15}$ and $R^{16}$ are independently selected from the group consisting of: H, alkyl, $(R^{18})_n$-arylalkyl- (wherein, for example, n is 1, and $R^{18}$ is —$OR^{20}$, and $R^{20}$ is alkyl (e.g., methyl), cycloalkyl (e.g., cyclobutyl), and $(R^{18})_n$-alkyl (e.g., n is 1, $R^{18}$ is —$OR^{20}$, and $R^{20}$ is alkyl (e.g., methyl), and in one example, only one of $R^{15}$ and $R^{16}$ is H), and (d) alkyl substituted with 1 to 5 independently selected $R^{22}$ groups (e.g., halo, such as, for example, F, Cl, and Br, and wherein in one example the alkyl substituted $R^{21}$ group is —$CF_3$).

In another embodiment of this invention $R^{10}$ is aryl.

In another embodiment of this invention $R^{10}$ aryl is aryl and said aryl is phenyl.

In another embodiment of this invention $R^{10}$ is aryl substituted with one or more $R^{21}$ groups.

In another embodiment of this invention $R^{10}$ is aryl substituted with one or more $R^{21}$ groups, and said aryl is phenyl, i.e., said $R^{15}$ group is phenyl substituted with one or more $R^{21}$ groups.

In another embodiment of this invention $R^{10}$ is phenyl substituted with one or more $R^{21}$ groups, and each $R^{21}$ group is the same or different —$OR^{15}$ group.

In another embodiment of this invention $R^{10}$ is phenyl substituted with one or more $R^{21}$ groups, and each $R^{21}$ group is the same or different —$OR^{15}$ group, and said $R^{15}$ is alkyl, and each alkyl is independently selected.

In another embodiment of this invention $R^{10}$ is phenyl substituted with one $R^{21}$ group, and said $R^{21}$ group is —$OR^{15}$, and said $R^{15}$ is alkyl.

In another embodiment of this invention $R^{10}$ is phenyl substituted with one $R^{21}$ group, and said $R^{21}$ group is —$OR^{15}$, and said $R^{15}$ is alkyl, and said alkyl is methyl.

In another embodiment of this invention $R^{10}$ is heteroaryl.

In another embodiment of this invention $R^{10}$ is heteroaryl substituted with one or more $R^{21}$ groups.

In another embodiment of this invention $R^9$ is heteroaryl.

In another embodiment of this invention $R^9$ is heteroaryl substituted with one or more $R^{21}$ groups.

In another embodiment of this invention $R^9$ is heteroaryl substituted with one or more $R^{21}$ groups, and said $R^{21}$ groups are the same or different alkyl.

In another embodiment of this invention $R^9$ is heteroaryl substituted with one $R^{21}$ group, and said $R^{21}$ is alkyl.

In another embodiment of this invention $R^9$ is heteroaryl substituted with one $R^{21}$ group, and said $R^{21}$ is alkyl, and said alkyl is methyl.

In another embodiment of this invention $R^9$ is heteroaryl and said heteroaryl is imidazoyl.

In another embodiment of this invention $R^9$ is imidazolyl substituted with one or more $R^{21}$ groups.

In another embodiment of this invention $R^9$ is imidazolyl substituted with one or more $R^{21}$ groups, and said $R^{21}$ groups are the same or different alkyl.

In another embodiment of this invention $R^9$ is imidazolyl substituted with one $R^{21}$ group, and said $R^{21}$ is alkyl.

In another embodiment of this invention $R^9$ is imidazolyl substituted with one $R^{21}$ group, and said $R^{21}$ is alkyl, and said alkyl is methyl.

In another embodiment of this invention $R^9$ is arylalkoxy-.

In another embodiment of this invention $R^9$ is phenylalkoxy-.

In another embodiment of this invention $R^9$ is:

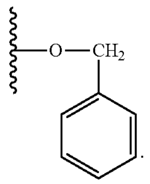 [SMILES: *OCc1ccccc1]

In another embodiment of this invention $R^{10}$ is selected from the group consisting of aryl and aryl substituted with one or more $R^{21}$ groups, and said $R^9$ group is selected from the group consisting of heteroaryl and heteroaryl substituted with one or more $R^{21}$ groups, wherein each $R^{21}$ is independently selected.

In another embodiment of this invention $R^{10}$ is phenyl substituted with one or more $R^{21}$ groups, and said $R^9$ is imidazolyl substituted with one or more $R^{21}$ groups, wherein each $R^{21}$ is independently selected.

In another embodiment of this invention $R^{10}$ is phenyl substituted with one $R^{21}$ group, and said $R^9$ is imidazolyl substituted with one $R^{21}$ group, wherein each $R^{21}$ is independently selected.

In another embodiment of this invention $R^{10}$ is phenyl substituted with one or more independently selected —$OR^{15}$ groups, and said $R^9$ is imidazolyl substituted with one or more independently selected alkyl groups.

In another embodiment of this invention $R^{10}$ is phenyl substituted with one or more independently selected —$OR^{15}$ groups, and said $R^9$ is imidazolyl substituted with one or more independently selected alkyl groups, and each $R^{15}$ is the same or different alkyl group.

In another embodiment of this invention $R^{10}$ is phenyl substituted with one —$OR^{15}$ group, and said $R^9$ is imidazolyl substituted with one alkyl group.

In another embodiment of this invention $R^{10}$ is phenyl substituted with one —$OR^{15}$ group, and said $R^9$ is imidazolyl substituted with one alkyl group, and $R^{15}$ is alkyl, and wherein the $R^{15}$ alkyl group, and the alkyl group on said imidazolyl are independently selected.

In another embodiment of this invention $R^{10}$ is phenyl substituted with one —$OR^{15}$ group, and said $R^9$ is imidazolyl substituted with one methyl group, and $R^{15}$ is methyl.

In another embodiment of this invention $R^{10}$ is selected from the group consisting of aryl and aryl substituted with one or more $R^{21}$ groups, and said $R^9$ group is arylalkoxy (such as, for example, phenylalkoxy-, such as for example, —O—$CH_2$-phenyl).

In another embodiment of this invention $R^{10}$ is phenyl substituted with one or more $R^{21}$ groups, and said $R^9$ group is arylalkoxy- (such as, for example, phenylalkoxy-, such as for example, —O—$CH_2$-phenyl).

In another embodiment of this invention $R^{10}$ is phenyl substituted with one $R^{21}$ group, and said $R^9$ is group is arylalkoxy- (such as, for example, phenylalkoxy-, such as for example, —O—$CH_2$-phenyl).

In another embodiment of this invention $R^{10}$ is phenyl substituted with one or more independently selected —$OR^{15}$ groups, and said $R^9$ group is arylalkoxy- (such as, for example, phenylalkoxy-, such as for example, —O—$CH_2$-phenyl).

In another embodiment of this invention $R^{10}$ is phenyl substituted with one or more independently selected —$OR^{15}$ groups, each $R^{15}$ is the same or different alkyl group, and said $R^9$ group is arylalkoxy- (such as, for example, phenylalkoxy-, such as for example, —O—$CH_2$-phenyl).

In another embodiment of this invention $R^{10}$ is phenyl substituted with one —$OR^{15}$ group, said $R^9$ group is arylalkoxy- (such as, for example, phenylalkoxy-, such as for example, —O—$CH_2$-phenyl).

In another embodiment of this invention $R^{10}$ is phenyl substituted with one —$OR^{15}$ group, and $R^{15}$ is alkyl, and said $R^9$ group is arylalkoxy- (such as, for example, phenylalkoxy-, such as for example, —O—$CH_2$-phenyl).

In another embodiment of this invention $R^{10}$ is phenyl substituted with one —$OR^{15}$ group, $R^{15}$ is methyl, and said $R^9$ group is arylalkoxy- (such as, for example, phenylalkoxy-, such as for example, —O—$CH_2$-phenyl).

In another embodiment of this invention the $R^9$-$R^{10}$— moiety is:

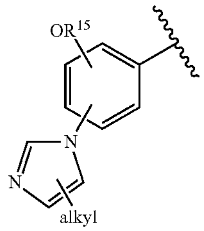

or

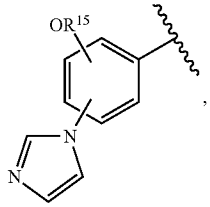

,

In another embodiment of this invention the $R^9$-$R^{10}$— moiety is:

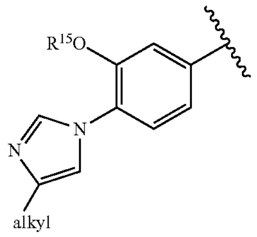

or

-continued

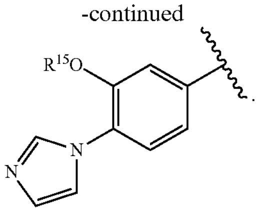

In another embodiment of this invention the $R^9$-$R^{10}$— moiety is:

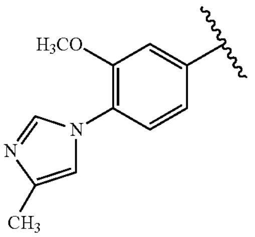

or

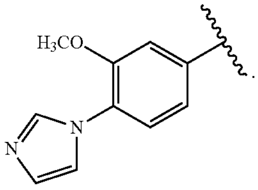

In another embodiment of this invention the $R^9$-$R^{10}$— moiety is:

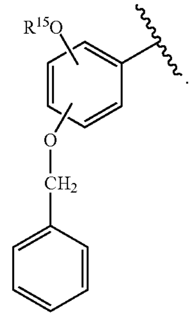

In another embodiment of this invention the $R^9$-$R^{10}$— moiety is:

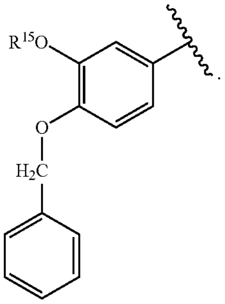

In another embodiment of this invention the $R^9$-$R^{10}$— moiety is:

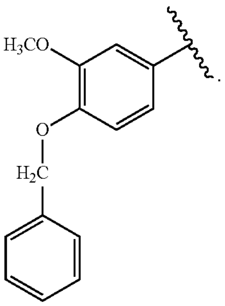

In one embodiment, $R^1$ is selected from the group consisting of: fused benzocycloalkyl- (i.e., benzofusedcycloalkyl-), fused benzoheterocycloalkyl- (i.e., benzofusedheterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylary-l (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarylfusedcycloalkylalkyl-), fused heteroarylheterocycloalkylalkyl- (i.e., heteroarylfusedheterocycloalkylalkyl)-, fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), fused heterocycloalkylheteroarylalkyl- (i.e., heterocycloalkylfusedheteroarylalkyl-); wherein each of said fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, and fused heterocycloalkylheteroarylalkyl-$R^1$ groups is optionally substituted with 1-5 independently selected $R^{21}$ groups.

In one embodiment, $R^1$ is selected from the group consisting of: fused benzocycloalkyl- (i.e., benzofusedcycloalkyl-), fused benzoheterocycloalkyl- (i.e., benzofusedheterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylary-l (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarylfusedcycloalkylalkyl-), fused heteroarylheterocycloalkylalkyl- (i.e., heteroarylfusedheterocycloalkylalkyl)-, fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), fused heterocycloalkylheteroarylalkyl- (i.e., heterocycloalkylfusedheteroarylalkyl-); wherein each of said fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, and fused heterocycloalkylheteroarylalkyl-$R^1$ groups is substituted with 1-5 independently selected $R^{21}$ groups. In one example, the $R^{21}$ groups are halo (e.g., F).

In one embodiment, $R^1$ is selected from the group consisting of: fused benzocycloalkyl- (i.e., benzofusedcycloalkyl-), fused benzoheterocycloalkyl- (i.e., benzofusedheterocycloalkyl-), fused heteroarylcycloalkyl- (i.e., heteroarylfusedcycloalkyl-), fused heteroarylheterocycloalkyl- (i.e., heteroarylfusedheterocycloalkyl-), fused cycloalkylary-l (i.e., cycloalkyfusedlaryl-), fused heterocycloalkylaryl- (i.e., heterocycloalkylfusedaryl-), fused cycloalkylheteroaryl- (i.e., cycloalkylfusedheteroaryl-), fused heterocycloalkylheteroaryl- (i.e., heterocycloalkylfusedheteroaryl-), fused benzocycloalkylalkyl- (i.e., benzofusedcycloalkylalkyl-), fused benzoheterocycloalkylalkyl- (i.e., benzofusedheterocycloalkylalkyl-), fused heteroarylcycloalkylalkyl- (i.e., heteroarylfusedcycloalkylalkyl-), fused heteroarylheterocycloalkylalkyl- (i.e., heteroarylfusedheterocycloalkylalkyl)-, fused cycloalkylarylalkyl- (i.e., cycloalkyfusedlarylalkyl-), fused heterocycloalkylarylalkyl- (i.e., heterocycloalkylfusedarylalkyl-), fused cycloalkylheteroarylalkyl- (i.e., cycloalkylfusedheteroarylalkyl-), and fused heterocycloalkylheteroarylalkyl- (i.e., heterocycloalkylfusedheteroarylalkyl-).

Examples of the cycloalkyl groups of the fused $R^1$ moieties for the compounds of this invention include, but are not limited to: cyclopentyl and cyclohexyl. Thus, in one embodiment the cycloalkyl group of the fused $R^1$ moieties is cyclopentyl. In another embodiment the cycloalkyl group of the fused $R^1$ moieties is cyclohexyl.

Examples of the aryl groups of the fused $R^1$ moieties for the compounds of this invention include, but are not limited to: phenyl.

Examples of the heteroaryl groups of the fused $R^1$ moieties for the compounds of this invention include, but are not limited to: pyridyl, thienyl, and thiazolyl. Thus, in one embodiment the heteroaryl group of the fused $R^1$ moieties is pyridyl. In another embodiment the heteroaryl group of the fused $R^1$ moieties is thienyl. In another embodiment the heteroaryl group of the fused $R^1$ moieties is thiazolyl.

Examples of the heterocycloalkyl groups of the fused $R^1$ moieties for the compounds of this invention include, but are not limited to: tetrahydrofuranyl, pyrrolidinyl, tetrahydropyranyl, piperidinyl, piperazinly, and morpholinyl. Thus, on one embodiment the heterocycloalkyl group of the fused $R^1$ moieties is tetrahydrofuranyl. In another embodiment the heterocycloalkyl group of the fused $R^1$ moieties is pyrrolidinyl. In another embodiment the heterocycloalkyl group of the fused $R^1$ moieties is tetrahydropyranyl. In another embodiment the heterocycloalkyl group of the fused $R^1$ moieties is piperidinyl. In another embodiment the heterocycloalkyl group of the fused $R^1$ moieties is piperazinyl. In another embodiment the heterocycloalkyl group of the fused $R^1$ moieties is morpholinyl.

In another embodiment, $R^1$ is selected from the group consisting of: alkyl-, alkenyl-, alkynyl-, aryl-, arylalkyl-, alkylaryl-, cycloalkyl, cycloalkenyl, cycloalkylalkyl-, heteroaryl-, heteroarylalkyl-, heterocyclyl-, heterocyclenyl-, and heterocyclyalkyl-; wherein each of said alkyl-, alkenyl-, alkynyl-, aryl-, arylalkyl-, alkylaryl-, cycloalkyl, cycloalkenyl, cycloalkylalkyl-, heteroaryl, heteroarylalkyl-, heterocyclyl, heterocyclenyl and heterocyclyalkyl-$R^1$ groups is optionally substituted with 1-5 independently selected $R^{21}$ groups.

In another embodiment, $R^1$ is selected from the group consisting of: alkyl-, alkenyl-, alkynyl-, aryl-, arylalkyl-, alkylaryl-, cycloalkyl, cycloalkenyl, cycloalkylalkyl-, heteroaryl-, heteroarylalkyl-, heterocyclyl-, heterocyclenyl-, and heterocyclyalkyl-; wherein each of said alkyl-, alkenyl-l, alkynyl-, aryl-, arylalkyl-, alkylaryl-, cycloalkyl, cycloalkenyl, cycloalkylalkyl-, heteroaryl, heteroarylalkyl-, heterocyclyl, heterocyclenyl and heterocyclyalkyl-$R^1$ groups is substituted with 1-5 independently selected $R^{21}$ groups.

In another embodiment, $R^1$ is selected from the group consisting of: alkyl-, alkenyl-, alkynyl-, aryl-, arylalkyl-, alkylaryl-, cycloalkyl, cycloalkenyl, cycloalkylalkyl-, heteroaryl-, heteroarylalkyl-, heterocyclyl-, heterocyclenyl-, and heterocyclyalkyl-.

In another embodiment, $R^1$ is fused benzocycloalkyl- (i.e., benzofusedcycloalkyl-), optionally substituted with 1-5 independently selected $R^{21}$ groups. Examples of this fused $R^1$ substituent include, for example, benzocyclopentyl- optionally substituted with 1-5 independently selected $R^{21}$ groups, and benzocyclohexyl- optionally substituted with 1-5 independently selected $R^{21}$ groups. Thus, in one example, $R^1$ is

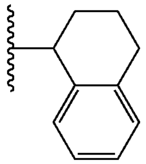 [SMILES: *C1CCCc2ccccc21]

optionally substituted with 1-5 independently selected $R^{21}$ groups. In another example, $R^1$ is

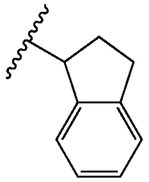 [SMILES: *C1CCc2ccccc21]

optionally substituted with 1-5 independently selected $R^{21}$ groups. Another embodiment is directed to the above fused benzocycloalkyl-$R^1$ substituents wherein said substituents are substituted with 1-5 independently selected $R^{21}$ groups. Another embodiment is directed to the above fused benzocycloalkyl-$R^1$ substituents wherein said substituents are not substituted with 1-5 independently selected $R^{21}$ groups.

In another embodiment, $R^1$ is fused benzoheterocycloalkyl- (i.e., benzofusedheterocycloalkyl-), optionally substituted with 1-5 independently selected $R^{21}$ groups. Examples of this fused $R^1$ substituent include, for example, benzotetrahydrofuranyl-, benzopyrrolidinyl-, benzotetrahydrppyranyl-, benzopiperidinyl-, benzopiperazinyl-, and benzomorpholinyl-, wherein each of said benzotetrahydrofuranyl-, benzopyrrolidinyl-, benzotetrahydrppyranyl-, and benzopiperidinyl-, benzopiperazinyl-, and benzomorpholinyl-$R^1$ substituent is optionally substituted with 1-5 independently selected $R^{21}$ groups. Another embodiment is directed to the above fused benzoheterocycloalkyl-$R^1$ substituents wherein said substituents are substituted with 1-5 independently selected $R^{21}$ groups. Another embodiment is directed to the above fused benzoheterocycloalkyl-$R^1$ substituents wherein said substituents are not substituted with 1-5 independently selected $R^{21}$ groups.

In another embodiment, $R^1$ is a fused benzoheterocycloalkyl- (i.e., benzofusedheterocycloalkyl-) of the formula:

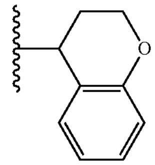

optionally substituted with 1-5 independently selected $R^{21}$ groups. Another embodiment is directed to the above fused benzoheterocycloalkyl-$R^1$ substituent wherein said substituent is substituted with 1-5 independently selected $R^{21}$ groups. Another embodiment is directed to the above fused benzoheterocycloalkyl-$R^1$ substituent wherein said substituent is not substituted with 1-5 independently selected $R^{21}$ groups.

In another embodiment, $R^1$ is fused heteroarylcycloalkyl- (i.e., heteroarylfusedcycloalkyl-), optionally substituted with 1-5 independently selected $R^{21}$ groups. Examples of this fused $R^1$ substituent include, for example, substituents wherein the heteroaryl moiety is selected from the group consisting of: pyridyl, thienyl, and thiazolyl, and the cycloalkyl moiety is selected from the group consisting of: cyclopentyl and cyclohexyl. Thus, examples of this fused $R^1$ substituent include, for example, pyridylcyclopentyl-, pyridylcyclohexyl-, thienylcyclopentyl-, thienylcyclohexyl-, thiazolylcyclopentyl and thiazolylcyclohexyl, wherein said $R^1$ substituents are optionally substituted with 1-5 independently selected $R^{21}$ groups. Another embodiment is directed to the above fused heteroarylcycloalkyl-$R^1$ substituents wherein said substituents are substituted with 1-5 independently selected $R^{21}$ groups. Another embodiment is directed to the above fused heteroarylcycloalkyl-$R^1$ substituents wherein said substituents are not substituted with 1-5 independently selected $R^{21}$ groups.

In another embodiment, $R^1$ is fused heteroarylheterocycloalkyl- (i.e., heteroarylfusedheterocycloalkyl-), optionally substituted with 1-5 independently selected $R^{21}$ groups. Examples of this fused $R^1$ substituent include, for example, substituents wherein the heteroaryl moiety is selected from the group consisting of: pyridyl, thienyl, and thiazolyl, and the heterocycloalkyl moiety is selected from the group consisting of: tetrahydrofuranyl, pyrrolidinyl, tetrahydropyranyl, piperidinyl, piperazinyl, and morpholinyl. Thus, examples of this fused $R^1$ substituent include, for example, pyridyltetrahydrofuranyl-, pyridylpyrrolidinyl-, pyridyltetrahydropyranyl-, pyridylpiperidinyl-, pyridylpiperazinyl-, pyridylmorpholinyl-, thienyltetrahydrofuranyl-, thienylpyrrolidinyl-, thienyltetrahydropyranyl-, thienylpiperidinyl-, thienylpiperazinyl-, thienylmorpholinyl-, thiazolyltetrahydrofuranyl-, thiazolylpyrrolidinyl-, thiazolyltetrahydropyranyl-, thiazolylpiperidinyl-, and thiazolylpiperazinyl-, thiazolylmorpholinyl-, wherein said $R^1$ substituents are optionally substituted with 1-5 independently selected $R^{21}$ groups. Another embodiment is directed to the above fused heteroarylheterocycloalkyl-$R^1$ substituents wherein said substituents are substituted with 1-5 independently selected $R^{21}$ groups. Another embodiment is directed to the above fused heteroarylheterocycloalkyl-$R^1$ substituents wherein said substituents are not substituted with 1-5 independently selected $R^{21}$ groups.

In another embodiment, $R^1$ is fused cycloalkylaryl- (i.e., cycloalkyfusedlaryl-), optionally substituted with 1-5 independently selected $R^{21}$ groups. Examples of this fused $R^1$ substituent include, for example, cyclopentylphenyl- and cyclohexylphenyl-, wherein said fused $R^1$ substituents are optionally substituted with 1-5 independently selected $R^{21}$ groups. Another embodiment is directed to the above fused cycloalkylaryl-$R^1$ substituents wherein said substituents are substituted with 1-5 independently selected $R^{21}$ groups. Another embodiment is directed to the above fused cycloalkylaryl-$R^1$ substituents wherein said substituents are not substituted with 1-5 independently selected $R^{21}$ groups.

In another embodiment, $R^1$ is fused heterocycloalkylaryl- (i.e., heterocycloalkylfusedaryl-), optionally substituted with 1-5 independently selected $R^{21}$ groups. Examples of this fused $R^1$ substituent include, for example, tetrahydrofuranylphenyl-, pyrrolidinylphenyl-, tetrahydropyranylphenyl-, piperidinylphenyl-, piperazinylphenyl-, and morpholinylphenyl-, wherein said fused $R^1$ substituents are optionally substituted with 1-5 independently selected $R^{21}$ groups. Another embodiment is directed to the above fused heterocycloalkylaryl-$R^1$ substituents wherein said substituents are substituted with 1-5 independently selected $R^{21}$ groups. Another embodiment is directed to the above fused heterocycloalkylaryl-$R^1$ substituents wherein said substituents are not substituted with 1-5 independently selected $R^{21}$ groups.

In another embodiment, $R^1$ is fused cycloalkylheteroaryl- (i.e., cycloalkylfusedheteroaryl-), optionally substituted with 1-5 independently selected $R^{21}$ groups. Examples of this fused $R^1$ substituent include, for example, substituents wherein the cycloalkyl moiety is selected from the group consisting of: cyclopentyl and cyclohexyl, and the heteroaryl moiety is selected from the group consisting of: pyridyl, thienyl, and thiazolyl. Thus, examples of this fused $R^1$ moiety include, for example, cyclopentylpyridyl-, cyclopentylthienyl-, cyclopentylthiazolyl-, cyclohexylpyridyl-, cyclohexylthienyl-, and cyclohexylthiazolyl-, wherein the fused $R^1$ substituents are optionally substituted with 1-5 independently selected $R^{21}$ groups. Another embodiment is directed to the above fused cycloalkylheteroaryl-$R^1$ substituents wherein said substituents are substituted with 1-5 independently selected $R^{21}$ groups. Another embodiment is directed to the above fused cycloalkylheteroaryl-$R^1$ substituents wherein said substituents are not substituted with 1-5 independently selected $R^{21}$ groups.

In another embodiment, $R^1$ is fused heterocycloalkylheteroaryl- (i.e., heterocycloalkylfusedheteroaryl)-, optionally substituted with 1-5 independently selected $R^{21}$ groups. Examples of this fused $R^1$ substituent include, for example, substituents wherein the heterocycloalkyl moiety is selected from the group consisting of: tetrahydrofuranyl, pyrrolidinyl, tetrahydropyranyl, piperidinyl, piperazinyl, and morpholinyl, and the heteroaryl moiety is selected from the group consisting of: pyridyl, thienyl, and thiazolyl. Thus, examples of this fused $R^1$ substituent include, for example, tetrahydrofuranylpyridyl-, tetrahydrofuranylthienyl-, tetrahydrofuranylthiazolyl-, pyrrolidinylpyridyl-, pyrrolidinylthienyl-, pyrrolidinylthiazolyl-, tetrahydropyranylpyridyl-, tetrahydropyranylthienyl-, tetrahydropyranylthiazolyl-, piperidinylpyridyl-, piperidinyithienyl-, piperidinyithiazolyl-, piperazinylpyridyl-, piperazinylthienyl-, piperazinylthiazolyl-, morpholinylpyridyl-, morpholinylthienyl-, and morpholinylthiazolyl-, wherein the fused $R^1$ substituents are optionally substituted with 1-5 independently selected $R^{21}$ groups. Another embodiment is directed to the above fused heterocycloalkylheteroaryl-$R^1$ substituents wherein said substituents are substituted with 1-5 independently selected $R^{21}$ groups. Another embodiment is directed to the above fused heterocycloalkylheteroaryl-$R^1$ substituents wherein said substituents are not substituted with 1-5 independently selected $R^{21}$ groups.

In another embodiment, $R^1$ is fused benzocycloalkylalkyl- (i.e., benzofusedcycloalkylalkyl-), optionally substituted with 1-5 independently selected $R^{21}$ groups. Examples of this fused $R^1$ substituent include, for example, benzocyclopentylalkyl- (such as, for example, benzocyclopentyl-$CH_2$—), and benzocyclohexylalkyl- (such as, for example, benzocyclohexyl-$CH_2$—), optionally substituted with 1-5 independently selected $R^{21}$ groups. In one example the fused $R^1$ moiety is:

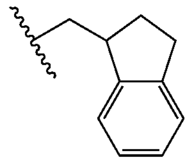 [SMILES: *CC1CCc2ccccc21]

optionally substituted with 1-5 independently selected $R^{21}$ groups. In another example the fused $R^1$ moiety is:

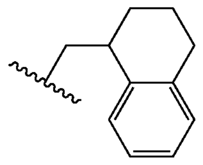 [SMILES: *CC1CCCc2ccccc21]

optionally substituted with 1-5 independently selected $R^{21}$ groups. Another embodiment is directed to the above fused benzocycloalkylalkyl-$R^1$ substituents wherein said substituents are substituted with 1-5 independently selected $R^{21}$ groups. Another embodiment is directed to the above fused benzocycloalkylalkyl-$R^1$ substituents wherein said substituents are not substituted with 1-5 independently selected $R^{21}$ groups.

In another embodiment, $R^1$ is fused benzoheterocycloalkylalkyl- (i.e., benzofusedheterocycloalkylalkyl-), optionally substituted with 1-5 independently selected $R^{21}$ groups. Examples of this fused $R^1$ substituent include, for example, benzotetetrahydrofuranylalkyl- (such as, for example, benzotetetrahydrofuranyl-$CH_2$—), benzotepyrrolidinylalkyl- (such as, for example, benzopyrrolidinyl-$CH_2$—), benzotetetrahydropyranylalkyl- (such as, for example, benzotetetrahydropyranyl-$CH_2$—), benzopiperidinylalkyl- (such as, for example, benzopiperidinyl-$CH_2$—), benzopiperazinylalkyl- (such as, for example, benzo piperazinyl-$CH_2$—), and benzomorpholinylalkyl- (such as, for example, benzomorpholinyl-$CH_2$—), wherein the fused $R^1$ substituents are optionally substituted with 1-5 independently selected $R^{21}$ groups. Another embodiment is directed to the above fused benzoheterocycloalkylalkyl-$R^1$ substituents wherein said substituents are substituted with 1-5 independently selected $R^{21}$ groups. Another embodiment is directed to the above fused benzoheterocycloalkylalkyl-$R^1$ substituents wherein said substituents are not substituted with 1-5 independently selected $R^{21}$ groups.

In another embodiment, $R^1$ is fused heteroarylcycloalkylalkyl- (i.e., heteroarylfusedcycloalkylalkyl-), optionally substituted with 1-5 independently selected $R^{21}$ groups. Examples of this fused $R^1$ substituent include, for example, substituents wherein the heteroaryl moiety is selected from the group consisting of: pyridyl, thienyl, and thiazolyl, and the cycloalkyl moiety is selected from the group consisting of: cyclopentyl and cyclohexyl. Examples of this fused $R^1$ substituent, include, for example, pyridylcyclopentylalkyl- (such as, for example, pyridylcyclopentyl-$CH_2$—), pyridylcyclohexylalkyl- (such as, for example, pyridylcyclohexyl-$CH_2$—), thienylcyclopentylalkyl- (such as, for example, thienylcyclopentyl-$CH_2$—), thienylcyclohexylalkyl- (such as, for example, thienylcyclohexyl-$CH_2$—), thiazolylcyclopentylalkyl- (such as, for example, thiazolylcyclopentyl-$CH_2$—), and thiazolylcyclohexylalkyl- (such as, for example, thiazolylcyclohexyl-$CH_2$—), wherein the fused $R^1$ substituents are optionally substituted with 1-5 independently selected $R^{21}$ groups. Another embodiment is directed to the above fused heteroarylcycloalkylalkyl-$R^1$ substituents wherein said substituents are substituted with 1-5 independently selected $R^{21}$ groups. Another embodiment is directed to the above fused heteroarylcycloalkylalkyl-$R^1$ substituents wherein said substituents are not substituted with 1-5 independently selected $R^{21}$ groups.

In another embodiment, $R^1$ is fused heteroarylheterocycloalkylalkyl- (i.e., heteroarylfusedheterocycloalkylalkyl)-, optionally substituted with 1-5 independently selected $R^{21}$ groups. Examples of this fused $R^1$ moiety include, for example, substituents wherein the heteroaryl moiety is selected from the group consisting of: pyridyl, thienyl and thiazolyl, and the heterocycloalkyl moiety is selected from the group consisting of: tetrahydrofuranyl, pyrrolidinyl, tetrahydropyranyl, piperidinyl, piperazinyl, and morpholinyl. Examples of this fused $R^1$ moiety include, for example, pyridyltetrahydrofuranylalkyl- (such as, for example, pyridyltetrahydrofuranyl-$CH_2$—), pyridylpyrrolidinyalkyl- (such as, for example, pyridylpyrrolidiny-$CH_2$—), pyridyltetrahydropyranylalkyl- (such as, for example, pyridyltetrahydropyranylalkyl-$CH_2$—), pyridylpiperidinylalkyl- (such as, for example, pyridylpiperidinylalkyl-$CH_2$—), pyridylpiperazinylalkyl- (such as, for example, pyridylpiperazinylalkyl-$CH_2$—), pyridylmorpholinylalkyl- (such as, for example, pyridylmorpholinylalkyl-$CH_2$—), thienyltetrahydrofuranylalkyl- (such as, for example, thienyltetrahydrofuranylalkyl-$CH_2$—), thienylpyrrolidinylalkyl- (such as, for example, thienylpyrrolidinylalkyl-$CH_2$—), thienyltetrahydropyranylalkyl- (such as, for example, thienyltetrahydropyranylalkyl-$CH_2$—), thienylpiperidinylalkyl- (such as, for example, thienylpiperidinylalkyl-$CH_2$—), thienylpiperazinylalkyl- (such as, for example, thienylpiperazinylalkyl-$CH_2$—), thienylmorpholinylalkyl- (such as, for example, thienylmorpholinylalkyl-$CH_2$—), thiazolyltetrahydrofuranylalkyl- (such as, for example, thiazolyltetrahydrofuranylalkyl-$CH_2$—), thiazolylpyrrolidinylalkyl- (such as, for example, thiazolylpyrrolidinylalkyl-$CH_2$—), thiazolyltetrahydropyranylalkyl- (such as, for example, thiazolyltetrahydropyranylalkyl-$CH_2$—), thiazolylpiperidinylalkyl- (such as, for example, thiazolylpiperidinylalkyl-$CH_2$—), thiazolylpiperazinylalkyl- (such as, for example, thiazolylpiperazinylalkyl-$CH_2$—), and thiazolylmorpholinylalkyl- (such as, for example, thiazolylmorpholinylalkyl-$CH_2$—), wherein said $R^1$ substituents are optionally substituted with 1-5 independently selected $R^{21}$ groups. Another embodiment is directed to the above fused heteroarylheterocycloalkylalkyl-$R^1$ substituents wherein said substituents are substituted with 1-5 independently selected $R^{21}$ groups. Another embodiment is directed to the above fused heteroarylheterocycloalkylalkyl-$R^1$ substituents wherein said substituents are not substituted with 1-5 independently selected $R^{21}$ groups.

In another embodiment, $R^1$ is fused cycloalkylarylalkyl- (i.e., cycloalkyfusedlarylalkyl-), optionally substituted with 1-5 independently selected $R^{21}$ groups. Examples of this fused $R^1$ substituent include, for example, cyclopentylphenylalkyl- (such as, for example, cyclopentylphenyl-$CH_2$—), and cyclohexylphenylalkyl- (such as, for example, cyclohexylphenyl$CH_2$—), wherein the fused $R^1$ substituents are optionally substituted with 1-5 independently selected $R^{21}$ groups. One example of the fused $R^1$ substituent is:

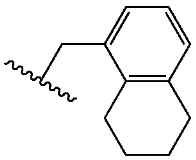 [SMILES: *Cc1cccc2c1CCCC2]

optionally substituted with 1-5 independently selected $R^{21}$ groups. Another example of the fused $R^1$ group is:

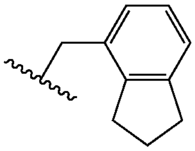 [SMILES: *Cc1cccc2c1CCC2]

optionally substituted with 1-5 independently selected $R^{21}$ groups. Another embodiment is directed to the above fused cycloalkylarylalkyl-$R^1$ substituents wherein said substituents are substituted with 1-5 independently selected $R^{21}$ groups. Another embodiment is directed to the above fused cycloalkylarylalkyl-$R^1$ substituents wherein said substituents are not substituted with 1-5 independently selected $R^{21}$ groups.

In another embodiment, $R^1$ is fused heterocycloalkylarylalkyl- (i.e., heterocycloalkylfusedarylalkyl-), optionally substituted with 1-5 independently selected $R^{21}$ groups. Examples of this fused $R^1$ substituent include, for example, tetrahydrofuranylphenylalkyl- (such as, for example, tetrahydrofuranylphenyl-$CH_2$—), pyrrolidinylphenylalkyl- (such as, for example, pyrrolidinylphenylalkyl-$CH_2$—), tetrahydropyranylphenylalkyl- (such as, for example, tetrahydropyranylphenylalkyl-$CH_2$—), piperidinylphenylalkyl- (such as, for example, piperidinylphenylalkyl-$CH_2$—), piperazinylphenylalkyl- (such as, for example, piperazinylphenylalkyl-$CH_2$—), and morpholinylphenylalkyl- (such as, for example, morpholinylphenylalkyl-$CH_2$—), wherein the $R^1$ substituents are optionally substituted with 1-5 independently selected $R^{21}$ groups. Another embodiment is directed to the above fused heterocycloalkylarylalkyl-$R^1$ substituents wherein said substituents are substituted with 1-5 independently selected $R^{21}$ groups. Another embodiment is directed to the above fused heterocycloalkylarylalkyl-$R^1$ substituents wherein said substituents are not substituted with 1-5 independently selected $R^{21}$ groups.

In another embodiment, $R^1$ is fused cycloalkylheteroarylalkyl- (i.e., cycloalkylfusedheteroarylalkyl-), optionally substituted with 1-5 independently selected $R^{21}$ groups. Examples of this fused $R^1$ substituent include, for example, substituents wherein the cycloalkyl moiety is selected from the group consisting of: cyclopentyl and cyclohexyl, and the heteroaryl moiety is selected from the group consisting of: pyridyl, thienyl, and thiazolyl. Thus, examples of this fused $R^1$ moiety include, for example, cyclopentylpyridylalkyl- (such as, for example, cyclopentylpyridylalkyl-$CH_2$—), cyclopentylthienylalkyl- (such as, for example, cyclopentylthienylalkyl-$CH_2$—), cyclopentylthiazolylalkyl- (such as, for example, cyclopentylthiazolylalkyl-$CH_2$—), cyclohexylpyridylalkyl- (such as, for example, cyclohexylpyridylalkyl-$CH_2$—) cyclohexylthienylalkyl- (such as, for example, cyclohexylthienylalkyl-$CH_2$—), and cyclohexylthiazolylalkyl- (such as, for example, cyclohexylthiazolylalkyl-$CH_2$—), wherein the fused $R^1$ substituents are optionally substituted with 1-5 independently selected $R^{21}$ groups. Another embodiment is directed to the above fused cycloalkylheteroarylalkyl-$R^1$ substituents wherein said substituents are substituted with 1-5 independently selected $R^{21}$ groups. Another embodiment is directed to the above fused cycloalkylheteroarylalkyl-$R^1$ substituents wherein said substituents are not substituted with 1-5 independently selected $R^{21}$ groups.

In another embodiment, $R^1$ is fused heterocycloalkylheteroarylalkyl- (i.e., heterocycloalkylfusedheteroarylalkyl-), optionally substituted with 1-5 independently selected $R^{21}$ groups. Examples of this fused $R^1$ substituent include, for example, substituents wherein the heterocycloalkyl moiety is selected from the group consisting of: tetrahydrofuranyl, pyrrolidinyl, tetrahydropyranyl, piperidinyl, piperazinyl, and morpholinyl, and the heteroaryl moiety is selected from the group consisting of: pyridyl, thienyl, and thiazolyl. Thus, examples of this fused $R^1$ substituent include, for example, tetrahydrofuranylpyridylalkyl- (such as, for example, tetrahydrofuranylpyridyl-$CH_2$—), tetrahydrofuranylthienylalkyl- (such as, for example, tetrahydrofuranylthienyl-$CH_2$—), tetrahydrofuranylthiazolylalkyl- (such as, for example, tetrahydrofuranylthiazolyl-$CH_2$—), pyrrolidinylpyridylalkyl- (such as, for example, pyrrolidinylpyridyl-$CH_2$—), pyrrolidinylthienylalkyl- (such as, for example, pyrrolidinylthienyl-$CH_2$—), pyrrolidinylthiazolylalkyl- (such as, for example, pyrrolidinylthiazolyl-$CH_2$—), tetrahydropyranylpyridylalkyl- (such as, for example, tetrahydropyranylpyridyl-$CH_2$—), tetrahydropyranylthienylalkyl- (such as, for example, tetrahydropyranylthienyl-$CH_2$—), tetrahydropyranylthiazolylalkyl- (such as, for example, tetrahydropyranylthiazolyl-$CH_2$—), piperidinylpyridylalkyl- (such as, for example, piperidinylpyridyl-$CH_2$—), piperidinylthienylalkyl- (such as, for example, piperidinylthienyl-$CH_2$—), piperidinylthiazolylalkyl- (such as, for example, piperidinylthiazolyl-$CH_2$—), piperazinylpyridylalkyl- (such as, for example, piperazinylpyridyl-$CH_2$—), piperazinylthienylalkyl- (such as, for example, piperazinylthienyl-$CH_2$—), piperazinylthiazolylalkyl- (such as, for example, piperazinylthiazolyl-$CH_2$—), morpholinylpyridylalkyl- (such as, for example, morpholinylpyridyl-$CH_2$—), morpholinylthienylalkyl- (such as, for example, morpholinylthienyl-$CH_2$—), and morpholinylthiazolylalkyl- (such as, for example, morpholinylthiazolyl-$CH_2$—), wherein the fused $R^1$ substituents are optionally substituted with 1-5 independently selected $R^{21}$ groups. Another embodiment is directed to the above fused heterocycloalkylheteroarylalkyl-$R^1$ substituents wherein said substituents are substituted with 1-5 independently selected $R^{21}$ groups. Another embodiment is directed to the above fused heterocycloalkylheteroarylalkyl-$R^1$ substituents wherein said substituents are not substituted with 1-5 independently selected $R^{21}$ groups.

In another embodiment of this invention $R^1$ is substituted with $R^{21}$ groups, and at least one (e.g. 1 to 2) of the $R^{21}$ groups is selected from the group consisting of: —$SF_5$, —$OSF_5$ and —$Si(R^{15})_3$, wherein each $R^{15}$ is independently selected.

In another embodiment of this invention $R^1$ is substituted with $R^{21}$ groups, and at least one (e.g. 1 to 2) of the $R^{21}$ groups is selected from the group consisting of: —$SF_5$, —$OSF_5$ and —$Si(R^{15})_3$, and each $R^{15}$ is the same or different alkyl group.

In another embodiment of this invention $R^1$ is substituted with $R^{21}$ groups, and at least one (e.g. 1 to 2) of the $R^{21}$ groups is selected from the group consisting of: —$SF_5$, —$OSF_5$ and —$Si(CH_3)_3$.

In another embodiment of this invention $R^1$ is substituted with $R^{21}$ groups, and one $R^{21}$ group is selected from the group consisting of: —$SF_5$, —$OSF_5$ and —$Si(R^{15})_3$, wherein each $R^{15}$ is independently selected.

In another embodiment of this invention $R^1$ is substituted with $R^{21}$ groups, and one $R^{21}$ group is selected from the group consisting of: —$SF_5$, —$OSF_5$ and —$Si(R^{15})_3$, and each $R^{15}$ is the same or different alkyl group.

In another embodiment of this invention $R^1$ is substituted with $R^{21}$ groups, and one $R^{21}$ group is selected from the group consisting of: —$SF_5$, —$OSF_5$ and —$Si(CH_3)_3$.

In another embodiment of this invention $R^1$ is substituted with $R^{21}$ groups, and two $R^{21}$ groups are selected from the group consisting of: —$SF_5$, —$OSF_5$ and —$Si(R^{15})_3$, wherein each $R^{15}$ is independently selected.

In another embodiment of this invention $R^1$ is substituted with $R^{21}$ groups, and two $R^{21}$ groups are selected from the group consisting of: —$SF_5$, —$OSF_5$ and —$Si(R^{15})_3$, and each $R^{15}$ is the same or different alkyl group.

In another embodiment of this invention $R^1$ is substituted with $R^{21}$ groups, and two $R^{21}$ groups are selected from the group consisting of: —$SF_5$, —$OSF_5$ and —$Si(CH_3)_3$.

In another embodiment of this invention $R^1$ is substituted with $R^{21}$ groups, and one $R^{21}$ group is —$SF_5$.

In another embodiment of this invention $R^1$ is substituted with $R^{21}$ groups, and two $R^{21}$ groups are —$SF_5$.

In another embodiment of this invention $R^1$ is substituted with $R^{21}$ groups, and one $R^{21}$ group is —$OSF_5$.

In another embodiment of this invention $R^1$ is substituted with $R^{21}$ groups, and two $R^{21}$ groups are —$OSF_5$.

In another embodiment of this invention $R^1$ is substituted with $R^{21}$ groups, and one $R^{21}$ group is —$Si(R^{15})_3$, wherein each $R^{15}$ is independently selected.

In another embodiment of this invention $R^1$ is substituted with $R^{21}$ groups, and one $R^{21}$ group is —$Si(R^{15})_3$ and each $R^{15}$ is the same or different alkyl group.

In another embodiment of this invention $R^1$ is substituted with $R^{21}$ groups, and one $R^{21}$ group is —$Si(CH_3)_3$.

In another embodiment of this invention $R^1$ is substituted with $R^{21}$ groups, and two of the $R^{21}$ groups are the same or different —$Si(R^{15})_3$, wherein each $R^{15}$ is independently selected.

In another embodiment of this invention $R^1$ is substituted with $R^{21}$ groups, and two of the $R^{21}$ groups are the same or different —$Si(R^{15})_3$ group, and each $R^{15}$ is the same or different alkyl group.

In another embodiment of this invention $R^1$ is substituted with $R^{21}$ groups, and two of the $R^{21}$ group are —$Si(CH_3)_3$.

In another embodiment of this invention $R^1$ is an alkyl group substituted with one or more independently selected $R^{21}$ groups.

In another embodiment of this invention $R^1$ is:

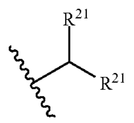

wherein each $R^{21}$ is independently selected, and each $R^{21}$ is independently unsubstituted or substituted with one or more independently selected $R^{22}$ groups.

In another embodiment of this invention $R^1$ is:

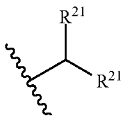

wherein one $R^{21}$ is an unsubstituted or substituted alkyl group.

In another embodiment of this invention $R^1$ is:

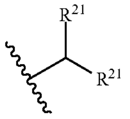

wherein one $R^{21}$ is an unsubstituted alkyl group.

In another embodiment of this invention $R^1$ is:

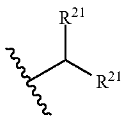

wherein one $R^{21}$ is a substituted alkyl group.

In another embodiment of this invention $R^1$ is:

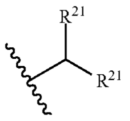

wherein one $R^{21}$ is an unsubstituted or substituted alkyl group, and the other $R^{21}$ is an unsubstituted or substituted aryl (e.g., phenyl) group.

In another embodiment of this invention $R^1$ is:

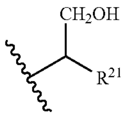

and $R^{21}$ is unsubstituted or substituted with one or more independently selected $R^{22}$ groups.

In another embodiment of this invention $R^1$ is:

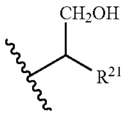

and $R^{21}$ is unsubstituted aryl (e.g., phenyl) or aryl (e.g., phenyl) substituted with one or more independently selected $R^{22}$ groups.

In another embodiment of this invention $R^1$ is an alkyl group substituted with one $R^{21}$ group.

In another embodiment of this invention $R^1$ is an alkyl group substituted with one $R^{21}$ group, and said $R^{21}$ group is substituted with one or more independently selected $R^{22}$ groups.

In another embodiment of this invention $R^1$ is:

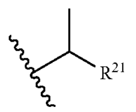

wherein $R^{21}$ is unsubstituted or substituted with one or more independently selected $R^{22}$ groups.

In another embodiment of this invention $R^1$ is an alkyl group substituted with one $R^{21}$ group, and said $R^{21}$ group is an aryl group.

In another embodiment of this invention $R^1$ is an alkyl group substituted with one $R^{21}$ group, and said $R^{21}$ group is an aryl group, said aryl is phenyl.

In another embodiment of this invention $R^1$ is an ethyl group substituted with one $R^{21}$ group, and said $R^{21}$ group is an aryl group, said aryl is phenyl.

In another embodiment of this invention $R^1$ is a methyl group substituted with one $R^{21}$ group, and said $R^{21}$ group is an aryl group, said aryl is phenyl.

In another embodiment of this invention $R^1$ is an alkyl group substituted with one $R^{21}$ group, and said $R^{21}$ group is an aryl group, and said aryl group is substituted with one or more $R^{22}$ groups.

In another embodiment of this invention $R^1$ is an alkyl group substituted with one $R^{21}$ group, and said $R^{21}$ group is an aryl group, and said aryl group is substituted with one or more $R^{22}$ groups, and each $R^{22}$ group is the same or different halo.

In another embodiment of this invention $R^1$ is an alkyl group substituted with one $R^{21}$ group, and said $R^{21}$ group is an aryl group, and said aryl group is substituted with 1 to 3 $R^{22}$ groups, and each $R^{22}$ group is the same or different halo.

In another embodiment of this invention $R^1$ is an alkyl group substituted with one $R^{21}$ group, and said $R^{21}$ group is an aryl group, and said aryl group is substituted with one or two $R^{22}$ halo groups, and each $R^{22}$ group is the same or different halo.

In another embodiment of this invention $R^1$ is an alkyl group substituted with one $R^{21}$ group, and said $R^{21}$ group is an aryl group, and said aryl group is substituted with one or two $R^{22}$ F groups.

In another embodiment of this invention $R^1$ is an alkyl group substituted with one $R^{21}$ group, and said $R^{21}$ group is phenyl, and said phenyl is substituted with one or more $R^{22}$ groups.

In another embodiment of this invention $R^1$ is an alkyl group substituted with one $R^{21}$ group, and said $R^{21}$ group is phenyl, and said phenyl is substituted with one or more $R^{22}$ groups, and each $R^{22}$ group is the same or different halo.

In another embodiment of this invention $R^1$ is an alkyl group substituted with one $R^{21}$ group, and said $R^{21}$ group is phenyl, and said phenyl is substituted with one or two $R^{22}$ halo groups, and each $R^{22}$ group is the same or different halo.

In another embodiment of this invention $R^1$ is an alkyl group substituted with one $R^{21}$ group, and said $R^{21}$ group is phenyl, and said phenyl is substituted with one or two $R^{22}$ F groups.

In another embodiment of this invention $R^1$ is an ethyl group substituted with one $R^{21}$ group, and said $R^{21}$ group is an aryl group, and said aryl group is substituted with one or more $R^{22}$ groups.

In another embodiment of this invention $R^1$ is a methyl group substituted with one $R^{21}$ group, and said $R^{21}$ group is an aryl group, and said aryl group is substituted with one or more $R^{22}$ groups.

In another embodiment of this invention $R^1$ is an ethyl group substituted with one $R^{21}$ group, and said $R^{21}$ group is phenyl, and said phenyl is substituted with one or more $R^{22}$ groups.

In another embodiment of this invention $R^1$ is a methyl group substituted with one $R^{21}$ group, and said $R^{21}$ group is phenyl, and said phenyl is substituted with one or more $R^{22}$ groups.

In another embodiment of this invention $R^1$ is an ethyl group substituted with one $R^{21}$ group, and said $R^{21}$ group is phenyl, and said phenyl is substituted with one or two $R^{22}$ halo groups, and each $R^{22}$ group is the same or different halo.

In another embodiment of this invention $R^1$ is a methyl group substituted with one $R^{21}$ group, and said $R^{21}$ group is phenyl, and said phenyl is substituted with one or two $R^{22}$ halo groups, and each $R^{22}$ group is the same or different halo.

In another embodiment of this invention $R^1$ is an ethyl group substituted with one $R^{21}$ group, and said $R^{21}$ group is phenyl, and said phenyl is substituted with one or two $R^{22}$ F groups.

In another embodiment of this invention $R^1$ is a methyl group substituted with one $R^{21}$ group, and said $R^{21}$ group is phenyl, and said phenyl is substituted with one or two $R^{22}$ F groups.

In another embodiment of this invention $R^1$ is an ethyl group substituted with one $R^{21}$ group, and said $R^{21}$ group is phenyl, and said phenyl is substituted with one $R^{22}$ halo group.

In another embodiment of this invention $R^1$ is a methyl group substituted with one $R^{21}$ group, and said $R^{21}$ group is phenyl, and said phenyl is substituted with one $R^{22}$ halo group.

In another embodiment of this invention $R^1$ is an ethyl group substituted with one $R^{21}$ group, and said $R^{21}$ group is phenyl, and said phenyl is substituted with one $R^{22}$ F group.

In another embodiment of this invention $R^1$ is a methyl group substituted with one $R^{21}$ group, and said $R^{21}$ group is phenyl, and said phenyl is substituted with one $R^{22}$ F group.

In another embodiment of this invention $R^1$ is an alkyl group substituted with one $R^{21}$ group, and said $R^{21}$ group is an aryl group, and said aryl group is substituted with one or more $R^{22}$ groups, and at least one (e.g., 1 to 2) $R^{22}$ group is selected from the group consisting of: $-SF_5$, $-OSF_5$ and $-Si(R^{15})_3$, wherein each $R^{15}$ is independently selected.

In another embodiment of this invention $R^1$ is an alkyl group substituted with one $R^{21}$ group, and said $R^{21}$ group is an aryl group, and said aryl group is substituted with one or more $R^{22}$ groups, and at least one (e.g., 1 to 2) $R^{22}$ group is selected from the group consisting of: $-SF_5$, $-OSF_5$ and $-Si(R^{15})_3$, and each $R^{15}$ is the same or different alkyl group.

In another embodiment of this invention $R^1$ is an alkyl group substituted with one $R^{21}$ group, and said $R^{21}$ group is an aryl group, and said aryl group is substituted with one or more $R^{22}$ groups, and at least one (e.g., 1 to 2) $R^{22}$ group is selected from the group consisting of: $-SF_5$, $-OSF_5$ and $-Si(CH_3)_3$.

In another embodiment of this invention $R^1$ is an alkyl group substituted with one $R^{21}$ group, and said $R^{21}$ group is phenyl, and said phenyl is substituted with one or more $R^{22}$ groups, and at least one (e.g., 1 to 2) $R^{22}$ is selected from the group consisting of: $-SF_5$, $-OSF_5$ and $-Si(R^{15})_3$, wherein each $R^{15}$ is independently selected.

In another embodiment of this invention $R^1$ is an alkyl group substituted with one $R^{21}$ group, and said $R^{21}$ group is phenyl, and said phenyl is substituted with one or more $R^{22}$ groups, and at least one (e.g., 1 to 2) $R^{22}$ is selected from the group consisting of: —$SF_5$, —$OSF_5$ and —$Si(R^{15})_3$, and each $R^{15}$ is the same or different alkyl group.

In another embodiment of this invention $R^1$ is an alkyl group substituted with one $R^{21}$ group, and said $R^{21}$ group is phenyl, and said phenyl is substituted with one or more $R^{22}$ groups, and at least one (e.g., 1 to 2) $R^{22}$ is selected from the group consisting of: —$SF_5$, —$OSF_5$ and —$Si(CH_3)_3$.

In another embodiment of this invention $R^1$ is an alkyl group substituted with one $R^{21}$ group, and said $R^{21}$ group is phenyl, and said phenyl is substituted with one or more $R^{22}$ groups, and one of the $R^{22}$ groups is selected from the group consisting of: —$SF_5$, —$OSF_5$ and —$Si(R^{15})_3$.

In another embodiment of this invention $R^1$ is an alkyl group substituted with one $R^{21}$ group, and said $R^{21}$ group is phenyl, and said phenyl is substituted with one or more $R^{22}$ groups, and one of the $R^{22}$ groups is selected from the group consisting of: —$SF_5$, —$OSF_5$ and —$Si(R^{15})_3$, and each $R^{15}$ is the same or different alkyl group.

In another embodiment of this invention $R^1$ is an alkyl group substituted with one $R^{21}$ group, and said $R^{21}$ group is phenyl, and said phenyl is substituted with one or more $R^{22}$ groups, and one of the $R^{22}$ groups is selected from the group consisting of: —$SF_5$, —$OSF_5$ and —$Si(CH_3)_3$.

In another embodiment of this invention $R^1$ is an alkyl group substituted with one $R^{21}$ group, and said $R^{21}$ group is phenyl, and said phenyl is substituted with one or more $R^{22}$ groups, and two of the $R^{22}$ groups are selected from the group consisting of: —$SF_5$, —$OSF_5$ and —$Si(R^{15})_3$.

In another embodiment of this invention $R^1$ is an alkyl group substituted with one $R^{21}$ group, and said $R^{21}$ group is phenyl, and said phenyl is substituted with one or more $R^{22}$ groups, and two of the $R^{22}$ groups are selected from the group consisting of: —$SF_5$, —$OSF_5$ and —$Si(R^{15})_3$, and each $R^{15}$ is the same or different alkyl group.

In another embodiment of this invention $R^1$ is an alkyl group substituted with one $R^{21}$ group, and said $R^{21}$ group is phenyl, and said phenyl is substituted with one or more $R^{22}$ groups, and two of the $R^{22}$ groups are selected from the group consisting of: —$SF_5$, —$OSF_5$ and —$Si(CH_3)_3$.

In another embodiment of this invention $R^1$ is an alkyl group substituted with one $R^{21}$ group, and said $R^{21}$ group is phenyl, and said phenyl is substituted with one or more $R^{22}$ groups, and one of the $R^{22}$ groups is —$SF_5$.

In another embodiment of this invention $R^1$ is an alkyl group substituted with one $R^{21}$ group, and said $R^{21}$ group is phenyl, and said phenyl is substituted with one or more $R^{22}$ groups, and two of the $R^{22}$ groups are —$SF_5$.

In another embodiment of this invention $R^1$ is an alkyl group substituted with one $R^{21}$ group, and said $R^{21}$ group is phenyl, and said phenyl is substituted with one or more $R^{22}$ groups, and one of the $R^{22}$ groups is —$OSF_5$.

In another embodiment of this invention $R^1$ is an alkyl group substituted with one $R^{21}$ group, and said $R^{21}$ group is phenyl, and said phenyl is substituted with one or more $R^{22}$ groups, and two of the $R^{22}$ groups are —$OSF_5$.

In another embodiment of this invention $R^1$ is an alkyl group substituted with one $R^{21}$ group, and said $R^{21}$ group is phenyl, and said phenyl is substituted with one or more $R^{22}$ groups, and one of the $R^{22}$ groups is —$Si(R^{15})_3$.

In another embodiment of this invention $R^1$ is an alkyl group substituted with one $R^{21}$ group, and said $R^{21}$ group is phenyl, and said phenyl is substituted with one or more $R^{22}$ groups, and one of the $R^{22}$ groups is —$Si(R^{15})_3$, and each $R^{15}$ is the same or different alkyl group.

In another embodiment of this invention $R^1$ is an alkyl group substituted with one $R^{21}$ group, and said $R^{21}$ group is phenyl, and said phenyl is substituted with one or more $R^{22}$ groups, and one of the $R^{22}$ groups is —$Si(CH_3)_3$.

In another embodiment of this invention $R^1$ is an alkyl group substituted with one $R^{21}$ group, and said $R^{21}$ group is phenyl, and said phenyl is substituted with one or more $R^{22}$ groups, and two of the $R^{22}$ groups are —$Si(R^{15})_3$.

In another embodiment of this invention $R^1$ is an alkyl group substituted with one $R^{21}$ group, and said $R^{21}$ group is phenyl, and said phenyl is substituted with one or more $R^{22}$ groups, and two of the $R^{22}$ groups are —$Si(R^{15})_3$, and each $R^{15}$ is the same or different alkyl group.

In another embodiment of this invention $R^1$ is an alkyl group substituted with one $R^{21}$ group, and said $R^{21}$ group is phenyl, and said phenyl is substituted with one or more $R^{22}$ groups, and two of the $R^{22}$ groups are —$Si(CH_3)_3$.

In another embodiment of this invention $R^1$ is an alkyl group substituted with one $R^{21}$ group, and said $R^{21}$ group is phenyl, and said phenyl is substituted with one or more $R^{22}$ groups, and each $R^{22}$ group is the same or different halo.

In another embodiment of this invention $R^1$ is an alkyl group substituted with one $R^{21}$ group, and said $R^{21}$ group is phenyl, and said phenyl is substituted with one or two $R^{22}$ halo groups, and each $R^{22}$ group is the same or different halo.

In another embodiment of this invention $R^1$ is an alkyl group substituted with one $R^{21}$ group, and said $R^{21}$ group is phenyl, and said phenyl is substituted with one or two $R^{22}$ F groups.

In another embodiment of this invention $R^1$ is an ethyl group substituted with one $R^{21}$ group, and said $R^{21}$ group is an aryl group, and said aryl group is substituted with one or more $R^{22}$ groups.

In another embodiment of this invention $R^1$ is a methyl group substituted with one $R^{21}$ group, and said $R^{21}$ group is an aryl group, and said aryl group is substituted with one or more $R^{22}$ groups.

In another embodiment of this invention $R^1$ is an ethyl group substituted with one $R^{21}$ group, and said $R^{21}$ group is phenyl, and said phenyl is substituted with one or more $R^{22}$ groups.

In another embodiment of this invention $R^1$ is a methyl group substituted with one $R^{21}$ group, and said $R^{21}$ group is phenyl, and said phenyl is substituted with one or more $R^{22}$ groups.

In another embodiment of this invention $R^1$ is an ethyl group substituted with one $R^{21}$ group, and said $R^{21}$ group is phenyl, and said phenyl is substituted with one or two $R^{22}$ halo groups, and each $R^{22}$ group is the same or different halo.

In another embodiment of this invention $R^1$ is a methyl group substituted with one $R^{21}$ group, and said $R^{21}$ group is phenyl, and said phenyl is substituted with one or two $R^{22}$ halo groups, and each $R^{22}$ group is the same or different halo.

In another embodiment of this invention $R^1$ is an ethyl group substituted with one $R^{21}$ group, and said $R^{21}$ group is phenyl, and said phenyl is substituted with one or two $R^{22}$ F groups.

In another embodiment of this invention $R^1$ is a methyl group substituted with one $R^{21}$ group, and said $R^{21}$ group is phenyl, and said phenyl is substituted with one or two $R^{22}$ F groups.

In another embodiment of this invention $R^1$ is an ethyl group substituted with one $R^{21}$ group, and said $R^{21}$ group is phenyl, and said phenyl is substituted with one $R^{22}$ halo group.

In another embodiment of this invention $R^1$ is a methyl group substituted with one $R^{21}$ group, and said $R^{21}$ group is phenyl, and said phenyl is substituted with one $R^{22}$ halo group.

In another embodiment of this invention $R^1$ is an ethyl group substituted with one $R^{21}$ group, and said $R^{21}$ group is phenyl, and said phenyl is substituted with one $R^{22}$ F group.

In another embodiment of this invention $R^1$ is a methyl group substituted with one $R^{21}$ group, and said $R^{21}$ group is phenyl, and said phenyl is substituted with one $R^{22}$ F group.

In another embodiment of this invention $R^1$ is selected from the group consisting of:

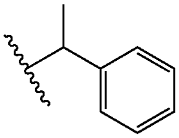
,
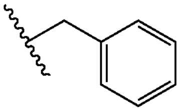
,

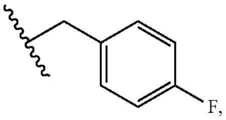
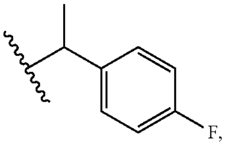

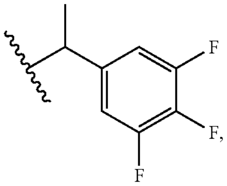
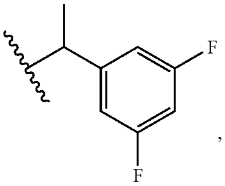
,

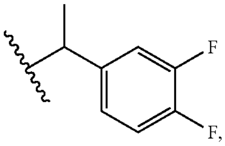
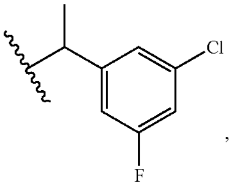
,

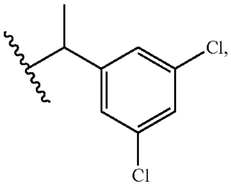
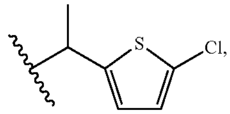

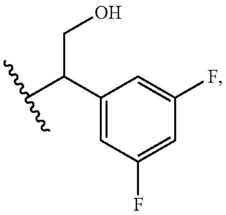
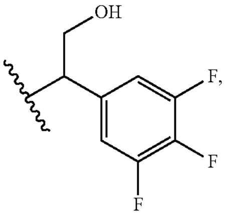

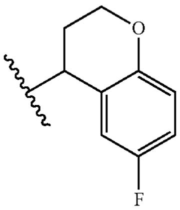
,
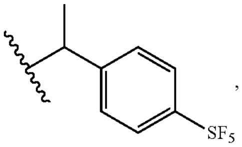
,

-continued

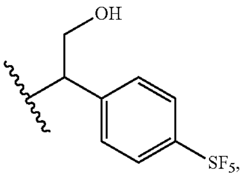
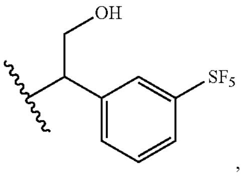
,

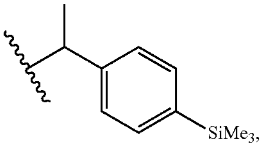
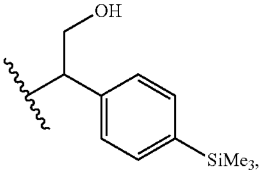

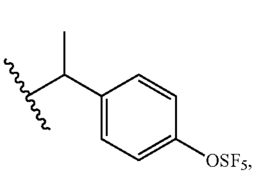
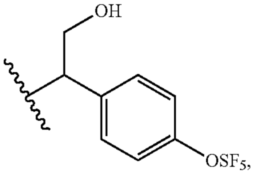

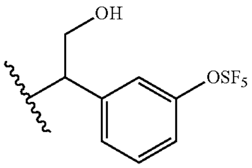
and
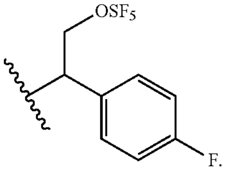

In another embodiment of this invention $R^1$ is selected from the group consisting of:

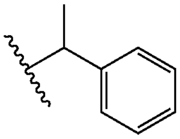
,
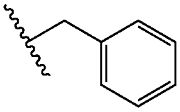
,

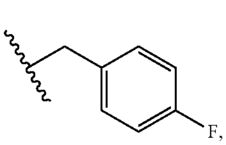
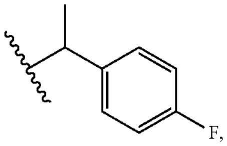

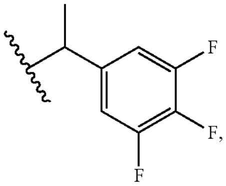
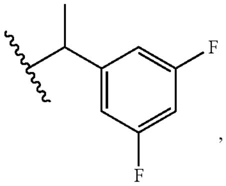
,

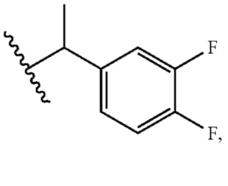
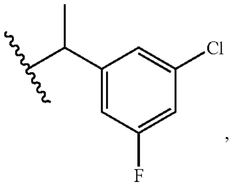
,

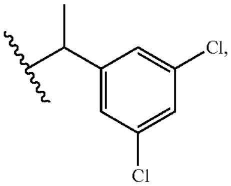
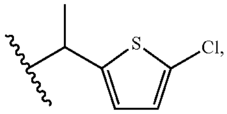

-continued
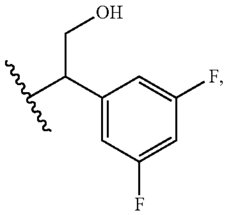
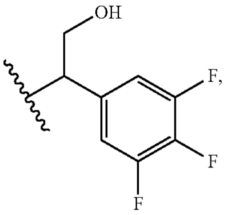
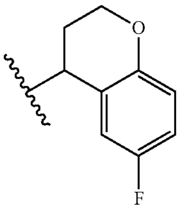
,
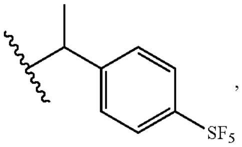
,
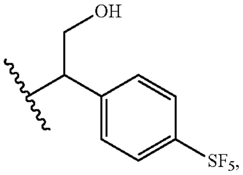
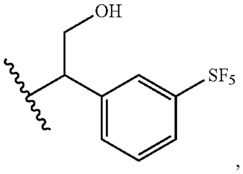
,
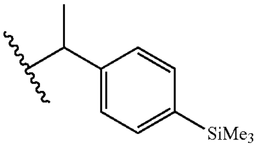
and
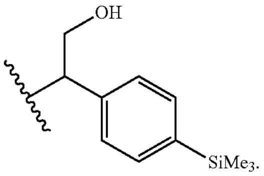
In another embodiment of this invention $R^1$ is selected from the group consisting of:
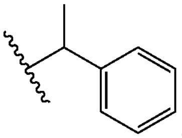
,
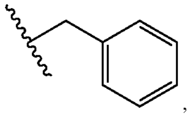
,
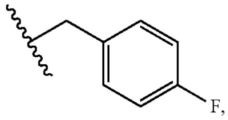
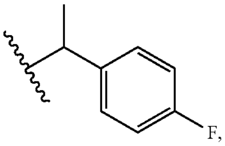
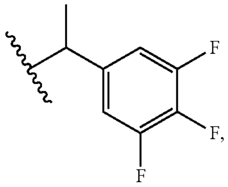
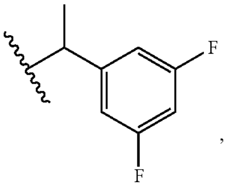
,
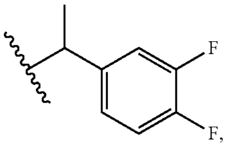
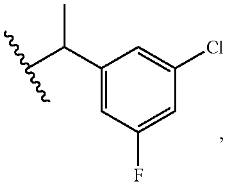
,
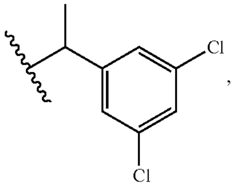
,
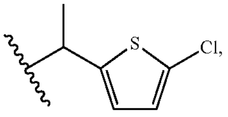
-continued
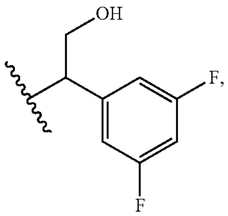
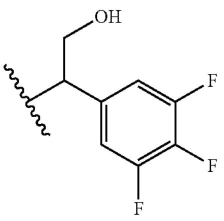
and
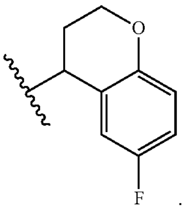
.
In another embodiment of this invention $R^1$ is selected from the group consisting of:
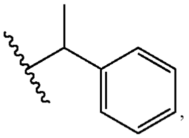
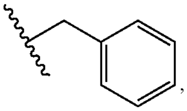
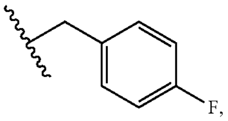
and
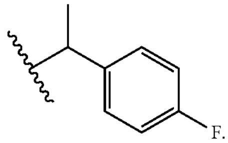
In another embodiment of this invention $R^1$ is selected from the group consisting of:
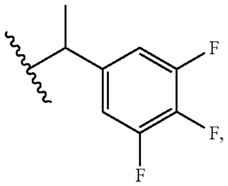
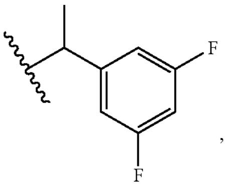
,
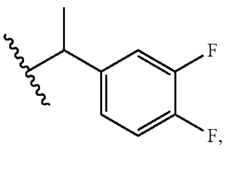
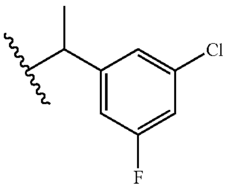
,
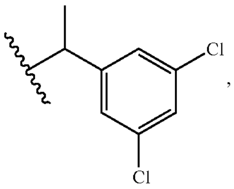
,
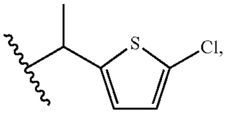
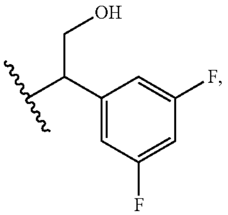
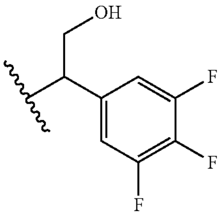
and -continued

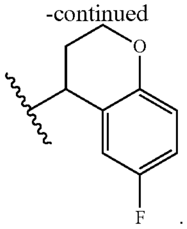

In another embodiment $R^1$ is selected from the group consisting of:

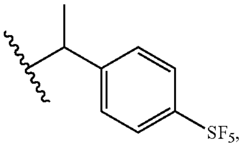

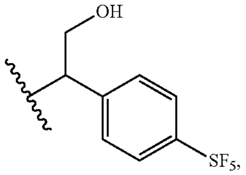

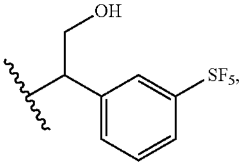

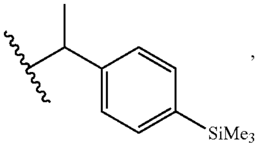

,

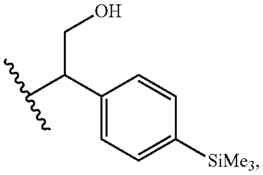

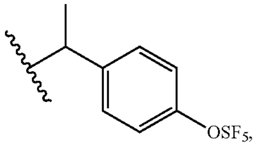

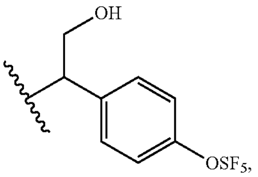

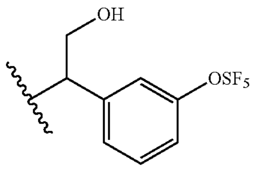

, and

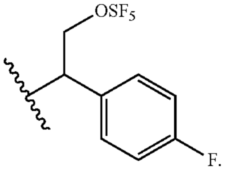

In another embodiment $R^1$ is selected from the group consisting of:

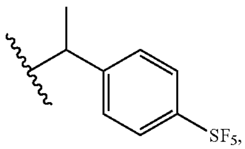

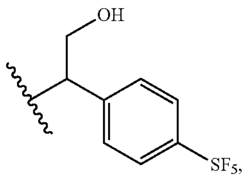

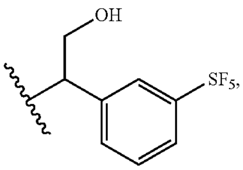

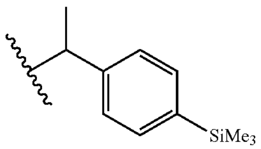

and

-continued

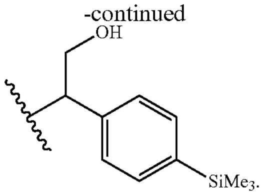

In another embodiment $R^1$ is selected from the group consisting of:

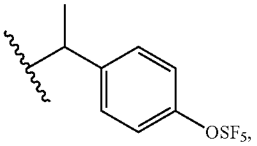

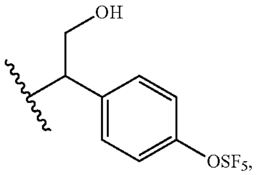

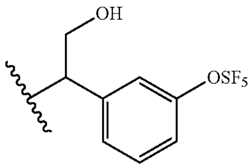

and

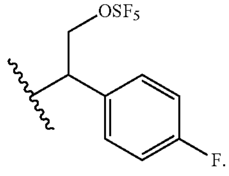

In another embodiment of this invention $R^{10}$ is selected from the group consisting of aryl and aryl substituted with one or more $R^{21}$ groups, and said $R^9$ group is selected from the group consisting of heteroaryl and heteroaryl substituted with one or more $R^{21}$ groups, and wherein each $R^{21}$ is independently selected.

In another embodiment of this invention: (a) $R^1$ is an alkyl group substituted with one $R^{21}$ group, or (b) $R^1$ is an alkyl group substituted with one $R^{21}$ group, and said $R^{21}$ group is substituted with one or more independently selected $R^{22}$ groups, and (c) $R^{10}$ is selected from the group consisting of aryl and aryl substituted with one or more independently selected $R^{21}$ groups, and (d) $R^9$ is selected from the group consisting of heteroaryl and heteroaryl substituted with one or more independently selected $R^{21}$ groups.

In another embodiment of this invention: (a) $R^1$ is an alkyl group substituted with one phenyl group, or (b) $R^1$ is an alkyl group substituted with one phenyl group, and said phenyl group is substituted with one or more independently selected $R^{22}$ groups, and (c) $R^{10}$ is selected from the group consisting of phenyl and phenyl substituted with one or more independently selected $R^{21}$ groups, and (d) $R^9$ is selected from the group consisting of imidazolyl and imidazolyl substituted with one or more independently selected $R^{21}$ groups.

In another embodiment of this invention: (a) $R^1$ is a methyl or ethyl group substituted with one phenyl, or (b) $R^1$ is an methyl or alkyl group substituted with one phenyl, and said phenyl is substituted with one or more independently selected halos, and (c) $R^{10}$ is selected from the group consisting of phenyl and phenyl substituted with one or more independently selected —$OR^{15}$ groups, and (d) $R^9$ is selected from the group consisting of imidazolyl and imidazolyl substituted with one or more independently selected alkyl groups.

In another embodiment of this invention: (a) $R^1$ is a methyl or ethyl group substituted with one phenyl, or (b) $R^1$ is an methyl or alkyl group substituted with one phenyl, and said phenyl is substituted with one or two independently selected halos, and (c) $R^{10}$ is selected from the group consisting of phenyl and phenyl substituted with one or two independently selected —$OR^{15}$ groups, wherein $R^{15}$ is alkyl, and (d) $R^9$ is selected from the group consisting of imidazolyl and imidazolyl substituted with one or two independently selected alkyl groups.

In another embodiment of this invention: (a) $R^1$ is a methyl or ethyl group substituted with one phenyl, or (b) $R^1$ is an methyl or alkyl group substituted with one phenyl, and said phenyl is substituted with one or two F, and (c) $R^{10}$ is selected from the group consisting of phenyl and phenyl substituted with one or two independently selected —$OR^{15}$ groups, wherein $R^{15}$ is methyl, and (d) $R^9$ is selected from the group consisting of imidazolyl and imidazolyl substituted with one or two independently selected methyl groups.

In another embodiment of this invention: (a) $R^1$ is a methyl or ethyl group substituted with one phenyl, or (b) $R^1$ is an methyl or alkyl group substituted with one phenyl, and said phenyl is substituted with one or two F, and (c) $R^{10}$ is phenyl substituted with one —$OR^{15}$ group, wherein $R^{15}$ is methyl, and (d) $R^9$ is selected from the group consisting of imidazolyl and imidazolyl substituted with one methyl group.

In another embodiment of this invention $R^1$ is selected from the group consisting of:

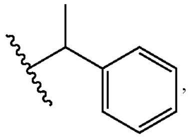, 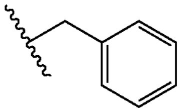,

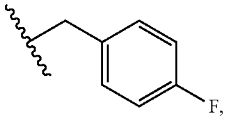 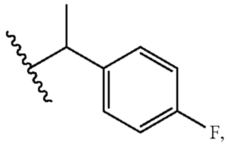

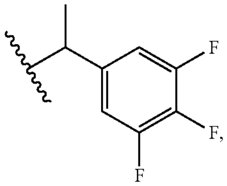 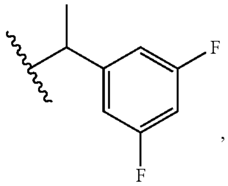 ,

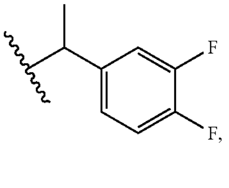 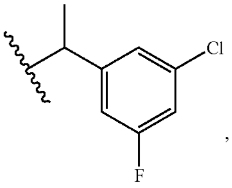 ,

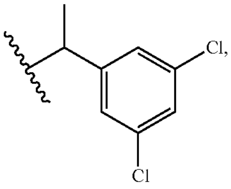 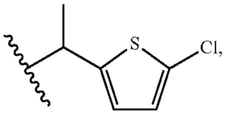

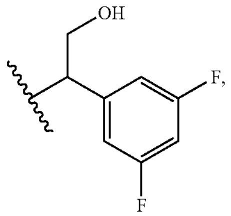 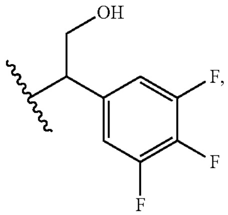

-continued

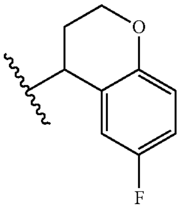, 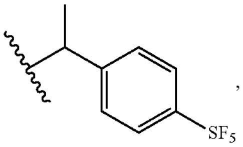 ,

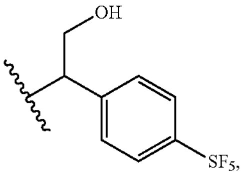 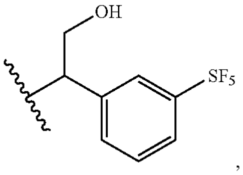 ,

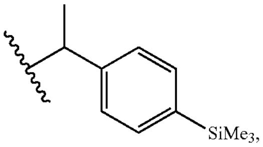 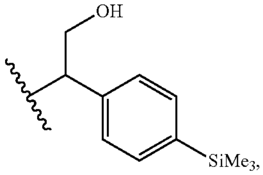

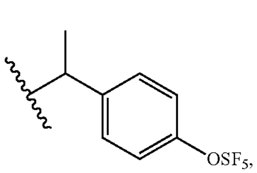 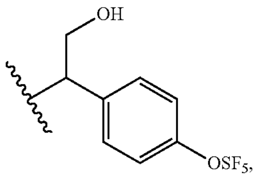

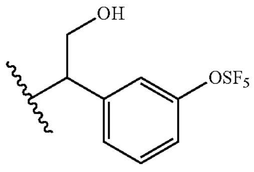 and 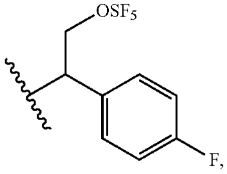

and the $R^9$-$R^{10}$— moiety is:

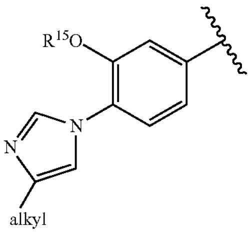 or 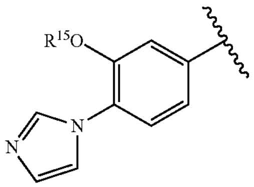.

In another embodiment of this invention $R^1$ is selected from the group consisting of:

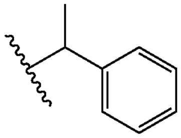, 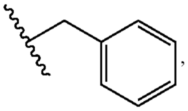,

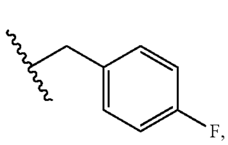 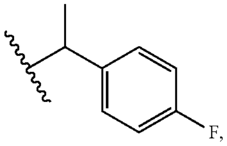

-continued
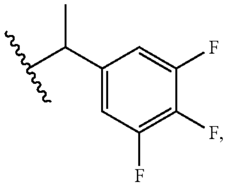 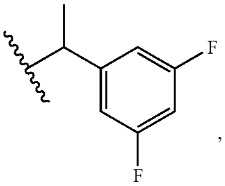,
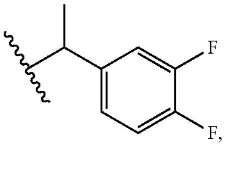 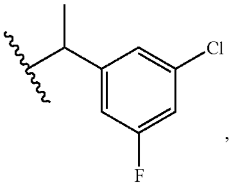,
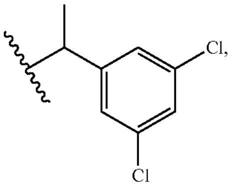 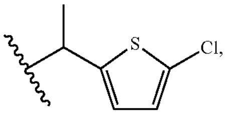
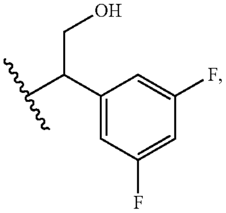 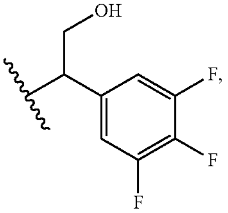
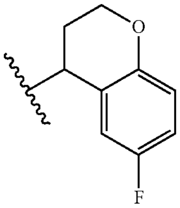, 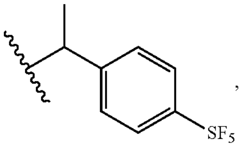,
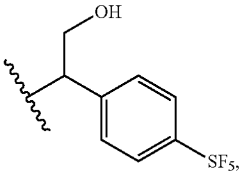 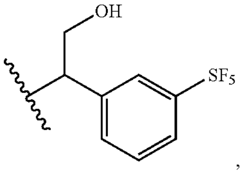,
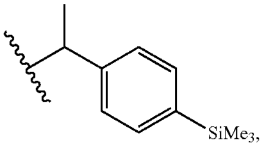 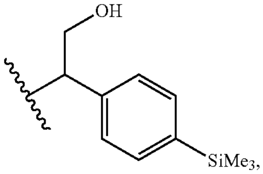
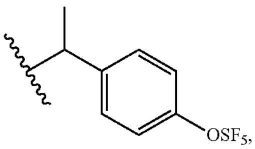 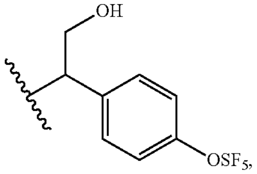
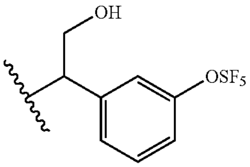 and 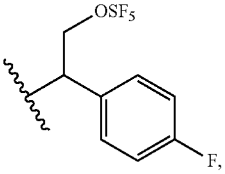
and
the $R^9$-$R^{10}$— moiety is:
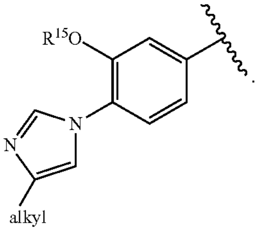
In another embodiment of this invention $R^1$ is selected from the group consisting of:
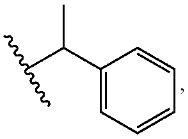 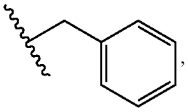
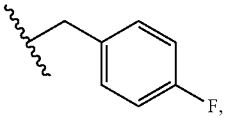 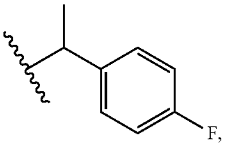
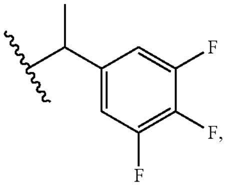 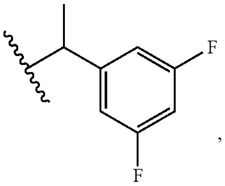
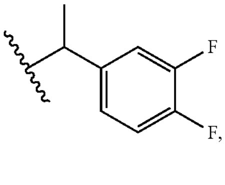 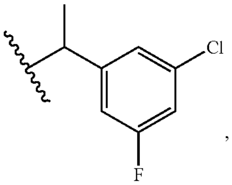
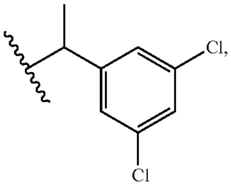 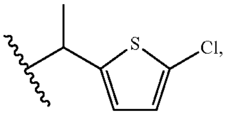
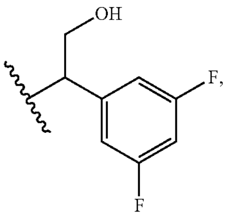 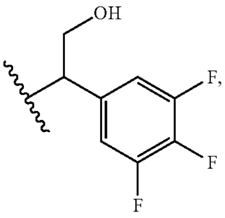
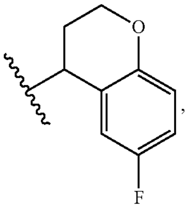 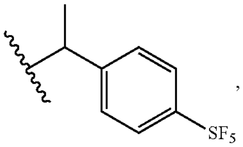, -continued
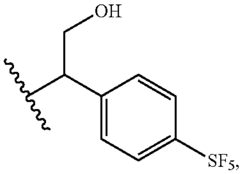
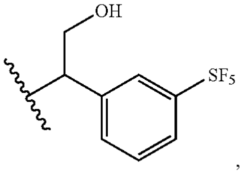
,
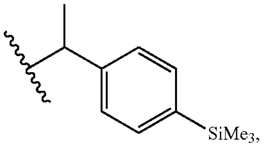
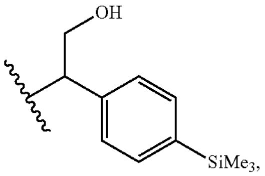
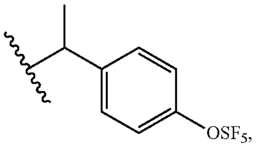
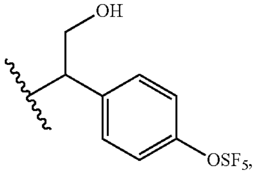
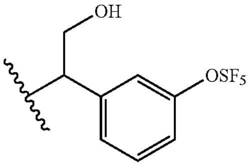
and
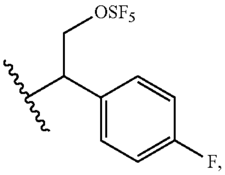
and
the $R^9$-$R^{10}$— moiety is:
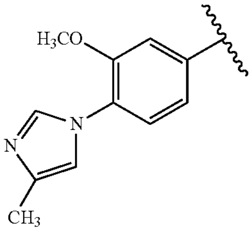
or
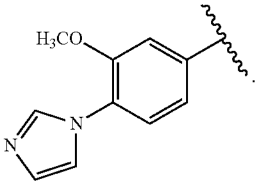
In another embodiment of this invention $R^1$ is selected from the group consisting of:
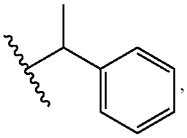
,
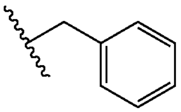
,
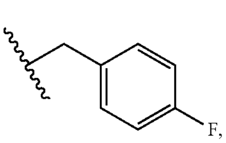
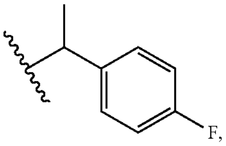
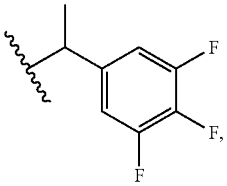
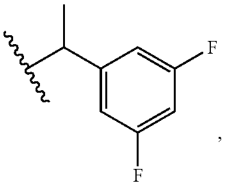
,
-continued
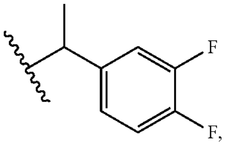
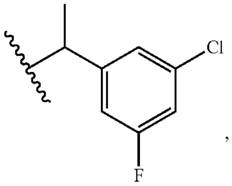
,
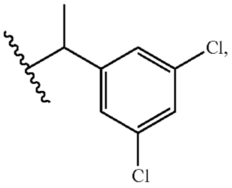
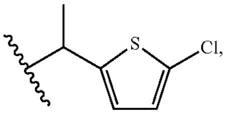
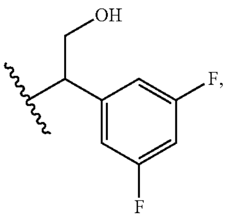
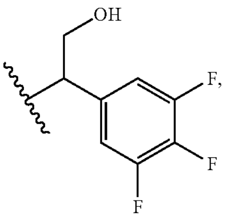
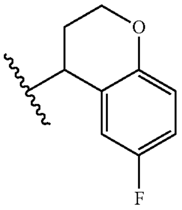
,
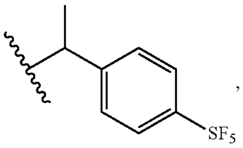
,
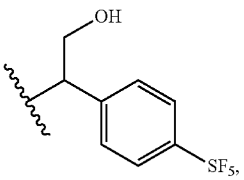
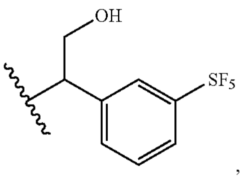
,
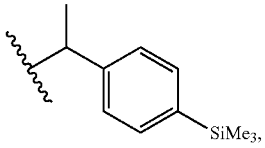
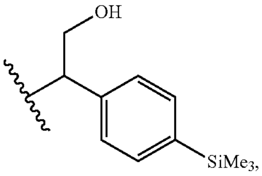
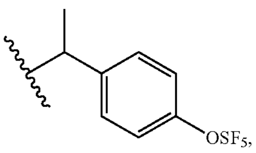
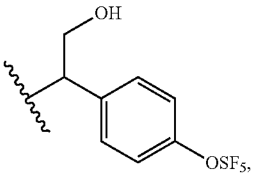
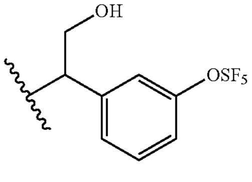
and
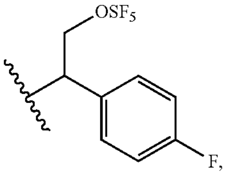

and
the $R^9$-$R^{10}$— moiety is:
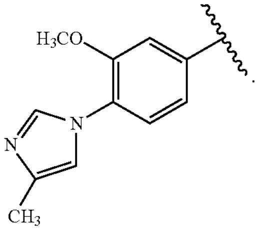
In another embodiment of this invention $R^1$ is selected from the group consisting of:
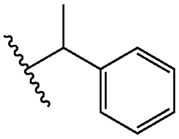,
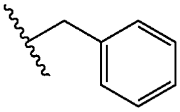,
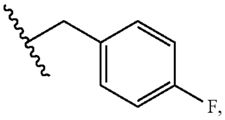
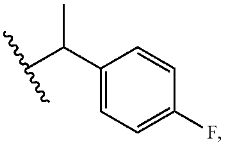
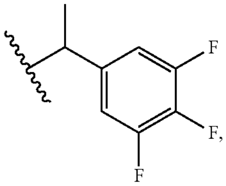
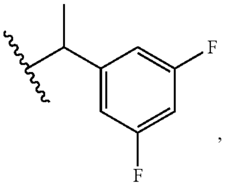,
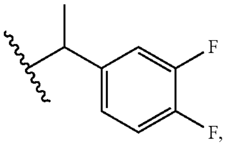
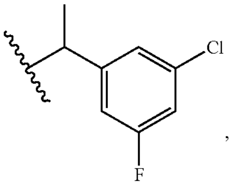,
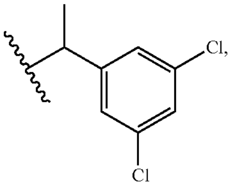
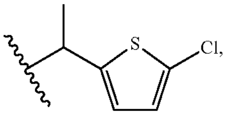
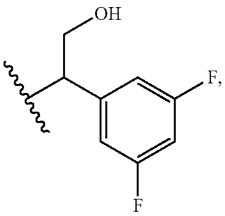
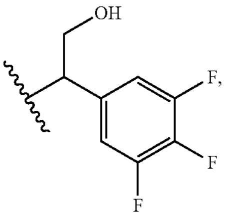
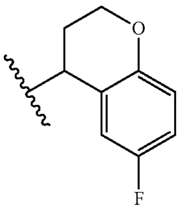,
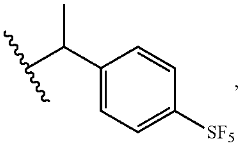,
-continued
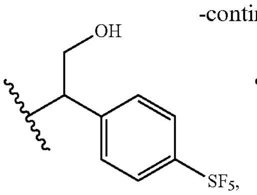
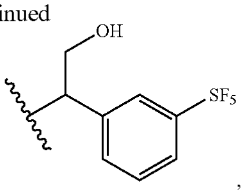,
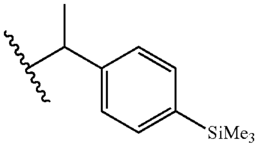
and
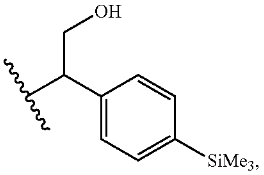
and
the $R^9$-$R^{10}$— moiety is:
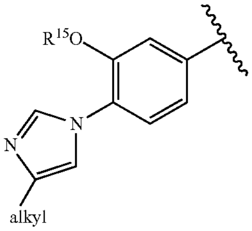
or
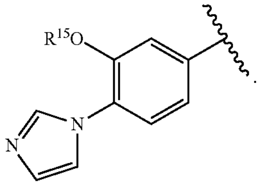
In another embodiment of this invention $R^1$ is selected from the group consisting of:
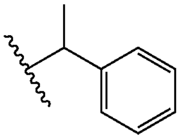,
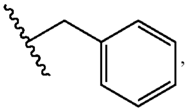,
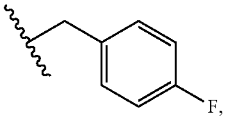
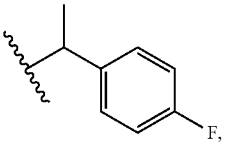
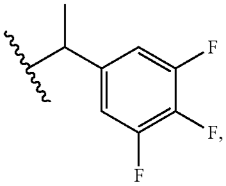
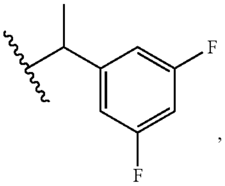,
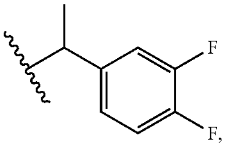
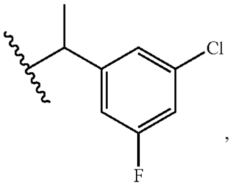,
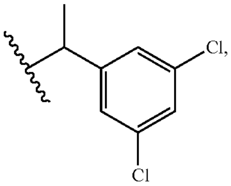
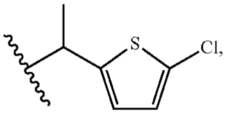

-continued
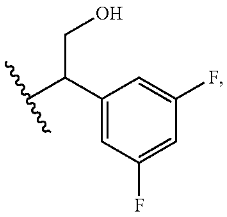
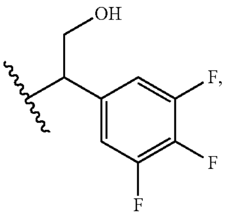
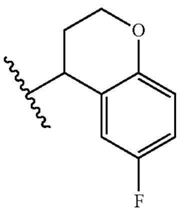
,
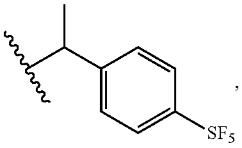
,
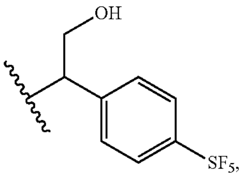
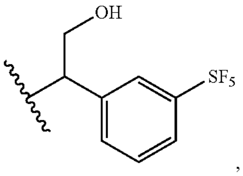
,
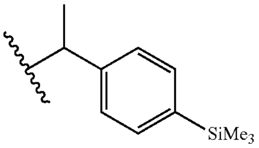
and
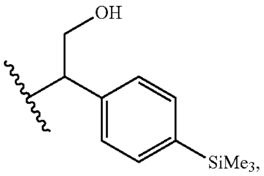
and
the $R^9$-$R^{10}$— moiety is:
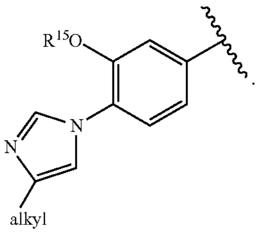
In another embodiment of this invention $R^1$ is selected from the group consisting of:
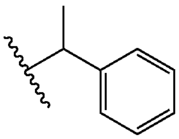
,
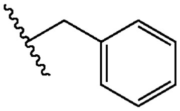
,
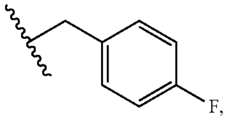
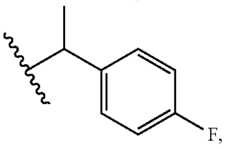
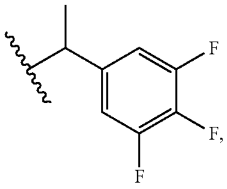
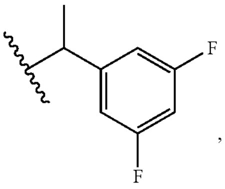
,
-continued
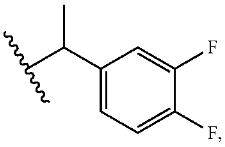
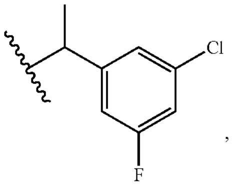
,
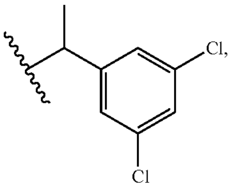
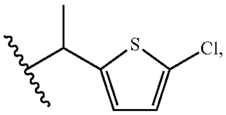
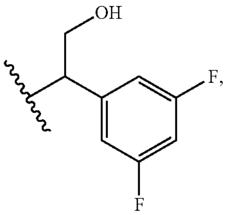
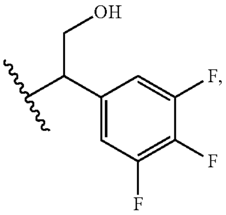
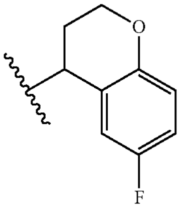
,
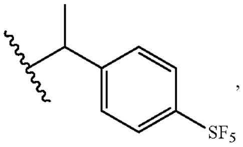
,
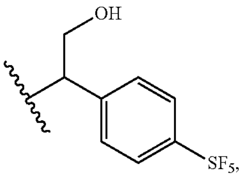
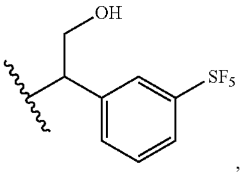
,
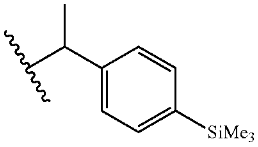
and
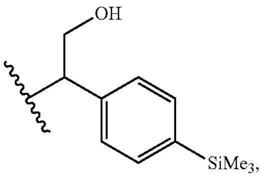
and
the $R^9$-$R^{10}$— moiety is:
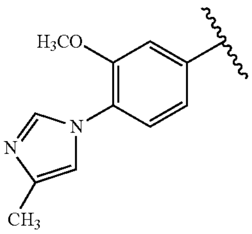
or
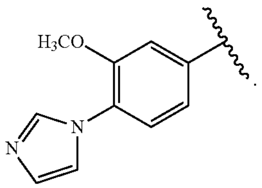

In another embodiment of this invention $R^1$ is selected from the group consisting of:
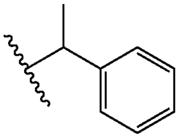, 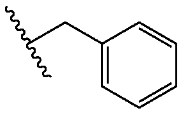,
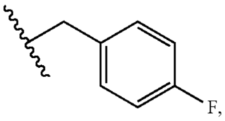, 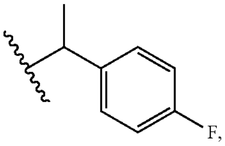,
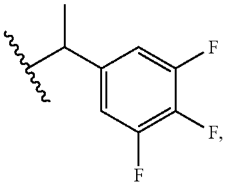, 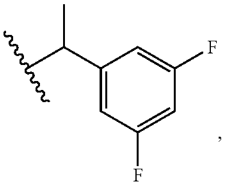,
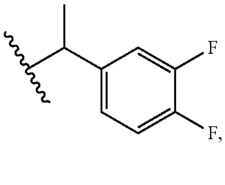, 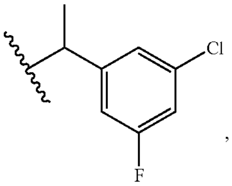,
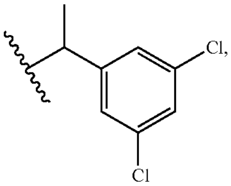, 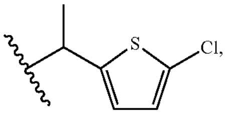,
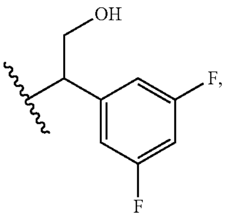, 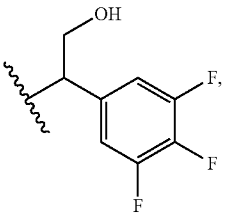,
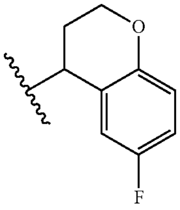, 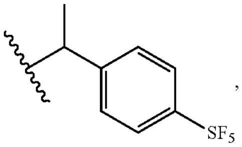,
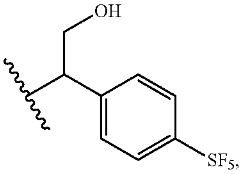, 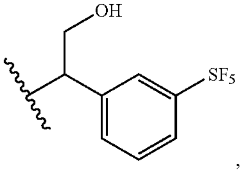,
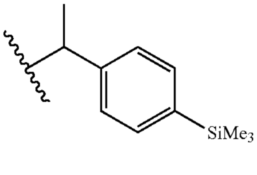 and 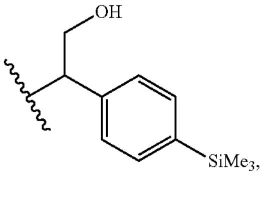,
and
the $R^9$-$R^{10}$— moiety is:
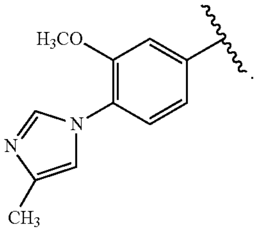 [SMILES: *c1ccc(-n2cnc(C)c2)c(OC)c1].
In another embodiment of this invention $R^1$ is selected from the group consisting of:
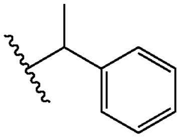, 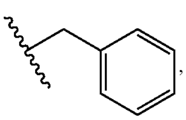,
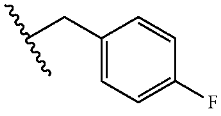 and 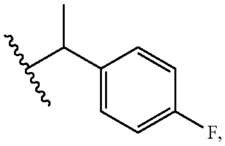,
and
wherein the $R^9$-$R^{10}$— moiety is:
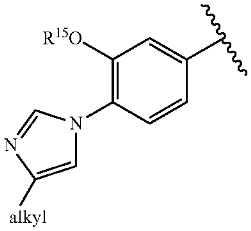 or 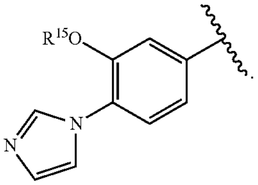.
In another embodiment of this invention $R^1$ is selected from the group consisting of:
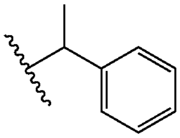, 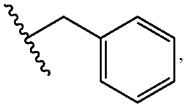,
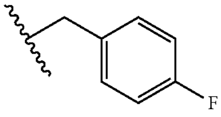 and 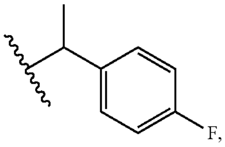, and wherein the $R^9$-$R^{10}$— moiety is:

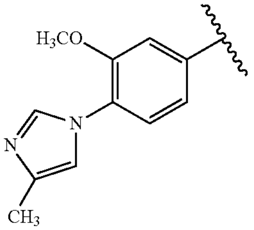 or 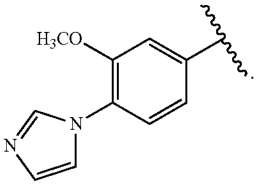.

In another embodiment of this invention $R^1$ is selected from the group consisting of:

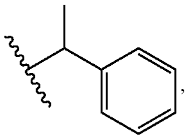, 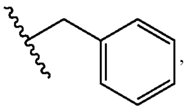,

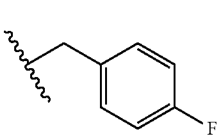 and 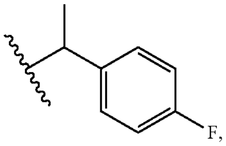, and wherein the $R^9$-$R^{10}$— moiety is:

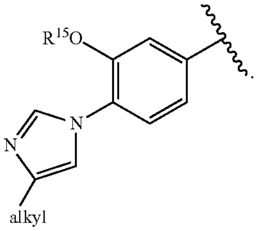.

In another embodiment of this invention $R^1$ is selected from the group consisting of:

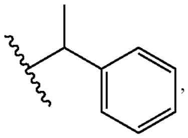, 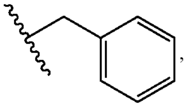,

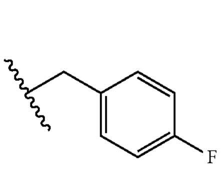 and 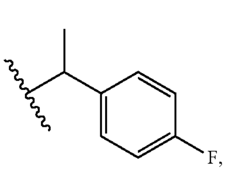, and wherein the $R^9$-$R^{10}$— moiety is:

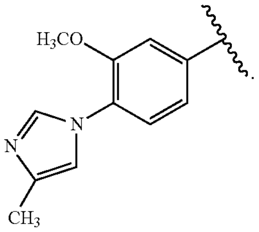.

In another embodiment of this invention $R^1$ is selected from the group consisting of:

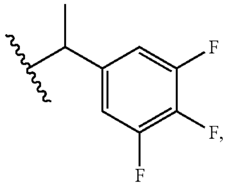 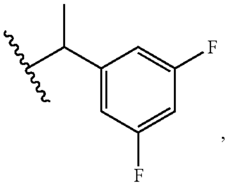,

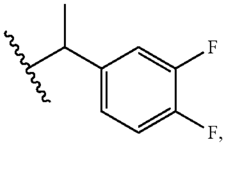 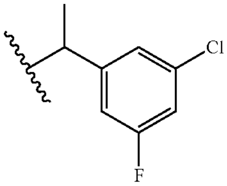,

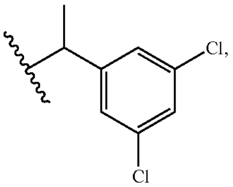 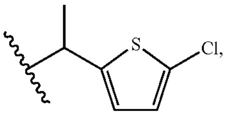

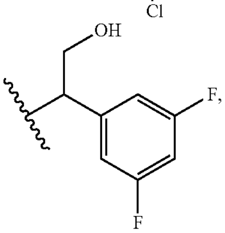 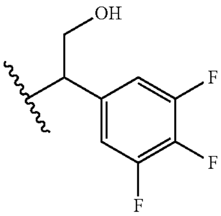 and

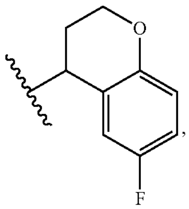, and the $R^9$-$R^{10}$— moiety is:

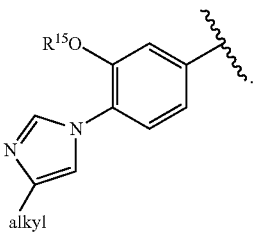.

In another embodiment of this invention $R^1$ is selected from the group consisting of:

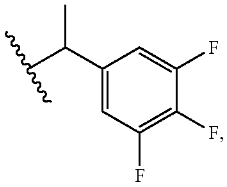
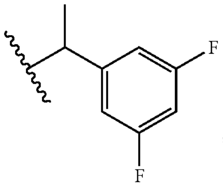
,
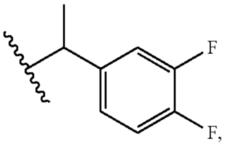
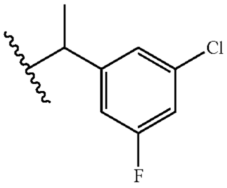
,
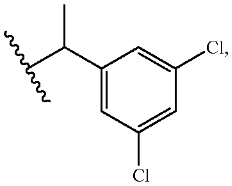
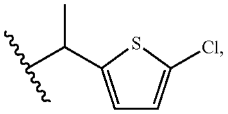
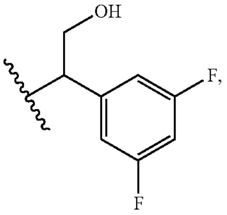
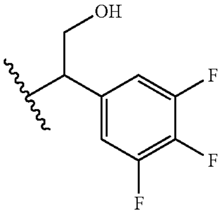
and
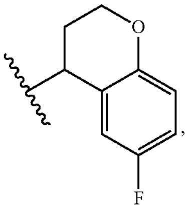

and the $R^9$-$R^{10}$— moiety is:

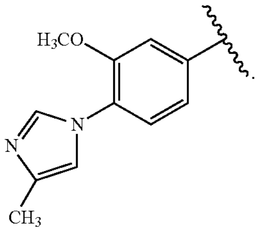 [SMILES: *c1ccc(-n2cnc(C)c2)c(OC)c1]

In another embodiment of this invention $R^1$ is selected from the group consisting of:

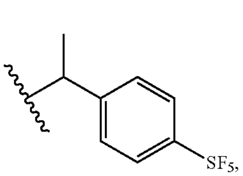
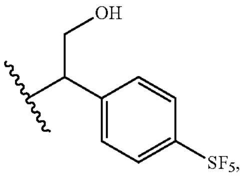

-continued

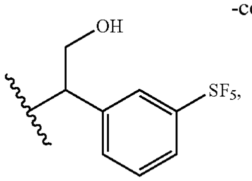
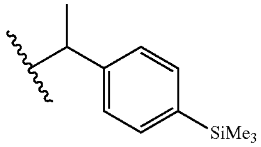
and
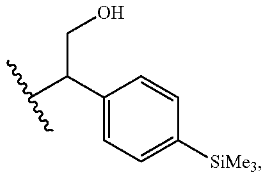

and the $R^9$-$R^{10}$— moiety is:

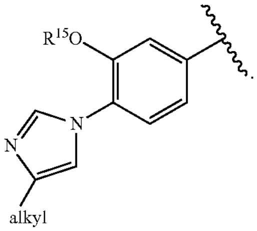

In another embodiment of this invention $R^1$ is selected from the group consisting of:

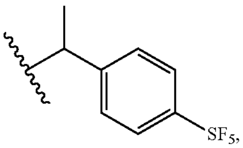
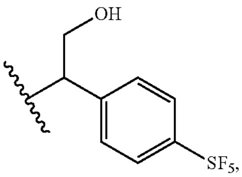
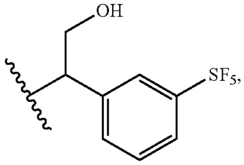
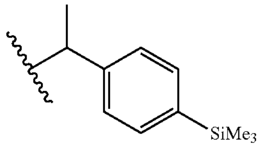
and
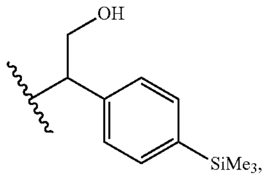

and the $R^9$-$R^{10}$— moiety is:

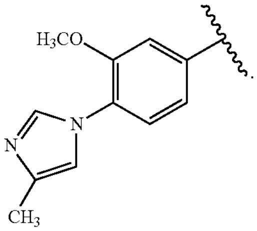 [SMILES: *c1ccc(-n2cnc(C)c2)c(OC)c1]

In another embodiment of this invention $R^1$ is selected from the group consisting of:

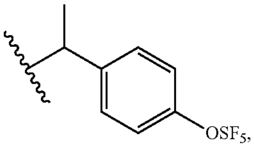,
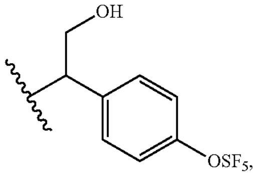,
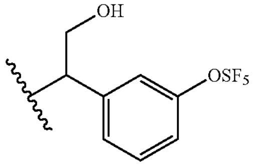 and
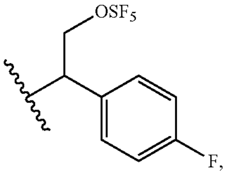, and
the $R^9$-$R^{10}$— moiety is:

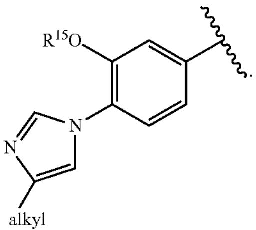.

In another embodiment of this invention $R^1$ is selected from the group consisting of:

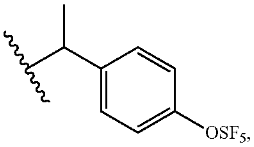,
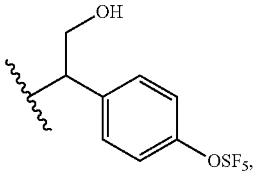,
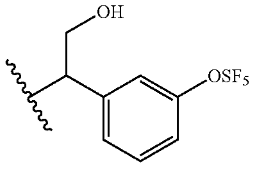 and
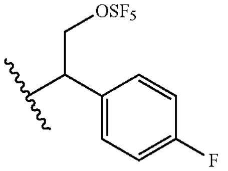

and
the $R^9$-$R^{10}$— moiety is:

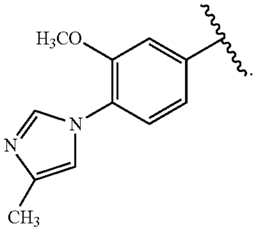.

In another embodiment of this invention W is —C(O)—.

In another embodiment of this invention W is —S(O)—.

In another embodiment of this invention W is —$S(O)_2$—.

In another embodiment of this invention W is —C(=$NR^2$)—.

In another embodiment W is —C(=$NR^2$)— wherein $R^2$ is selected from the group consisting of: —OH, —O-alkyl (i.e., alkoxy), —O-(halo substituted alkyl) (such as, for example, —O-fluoroalkyl), —NH($R^4$), —N$(R^4)_2$ (wherein each $R^4$ is independently selected), —$NH_2$, —S($R^4$), —S(O)$R^4$, —S(O)($OR^4$), —$S(O)_2R^4$, —$S(O)_2(OR^4)$, —S(O)$NHR^4$, —S(O)N$(R^4)_2$ (wherein each $R^4$ is independently selected), —S(O)$NH_2$, —$S(O)_2NHR^4$, —$S(O)_2N(R^4)_2$ (wherein each $R^4$ is independently selected), —$S(O)_2NH_2$, —CN, —$C(O)_2R^4$, —C(O)$NHR^4$, —C(O)N$(R^4)_2$ (wherein each $R^4$ is independently selected), —C(O)$NH_2$, and —C(O)$R^4$.

In another embodiment of this invention G is —NH—.

In another embodiment of this invention G is a direct bond.

In another embodiment, of this invention: (a) $R^1$ is a methyl or ethyl group substituted with one phenyl, or (b) $R^1$ is an methyl or alkyl group substituted with one phenyl, and said phenyl is substituted with one or two independently selected halos, and (c) $R^{10}$ is selected from the group consisting of phenyl and phenyl substituted with one or two independently selected —$OR^{15}$ groups, wherein $R^{15}$ is alkyl, and (d) $R^9$ is selected from the group consisting of imidazolyl and imidazolyl substituted with one or two independently selected alkyl groups, and (e) G is selected from the group consisting of —NH—, and a direct bond.

In another embodiment of this invention: (a) $R^1$ is a methyl or ethyl group substituted with one phenyl, or (b) $R^1$ is an methyl or alkyl group substituted with one phenyl, and said phenyl is substituted with one or two F, and (c) $R^{10}$ is phenyl substituted with one —$OR^{15}$ group, wherein $R^{15}$ is methyl, and (d) $R^9$ is selected from the group consisting of imidazolyl and imidazolyl substituted with one methyl group, and (e) G is selected from the group consisting of —NH—, and a direct bond.

In another embodiment of this invention $R^1$ is selected from the group consisting of:

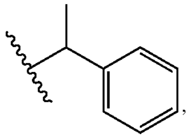,
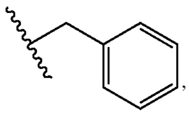,
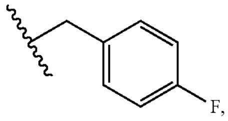,
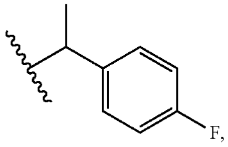,
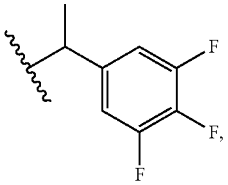,
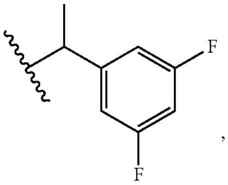,
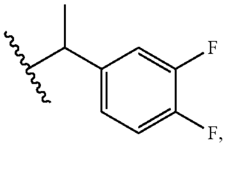,
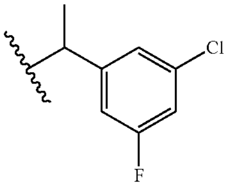, -continued

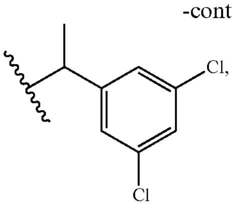, 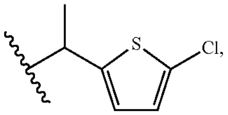,

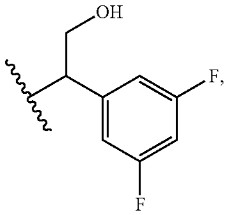, 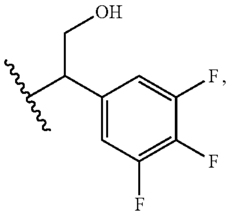,

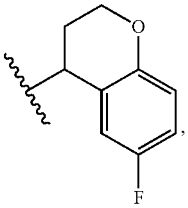, 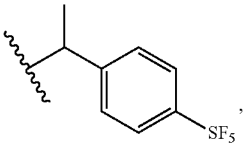,

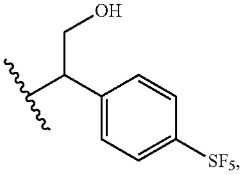, 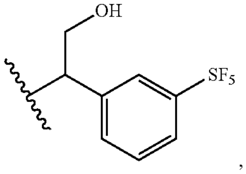,

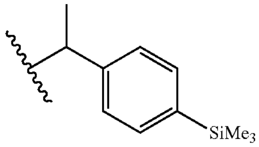 and 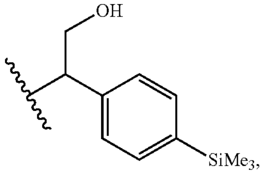, and the $R^9$-$R^{10}$— moiety is:

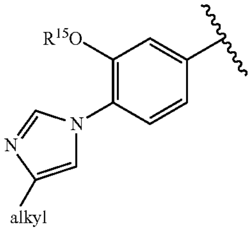

or

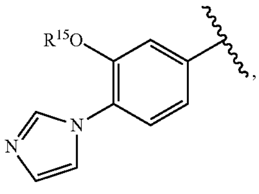, and

G is selected from the group consisting of —NH—, and a direct bond.

In another embodiment of this invention $R^1$ is selected from the group consisting of:

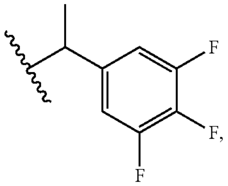, 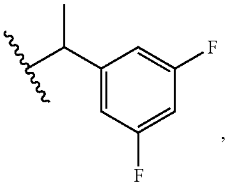,

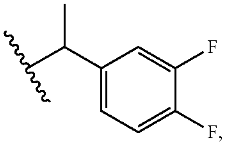, 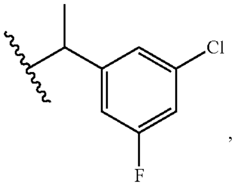,

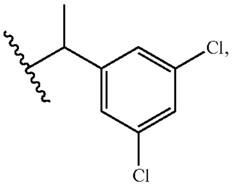, 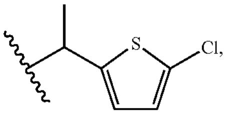,

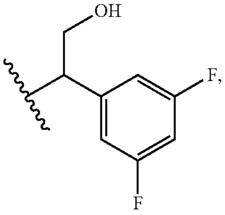, 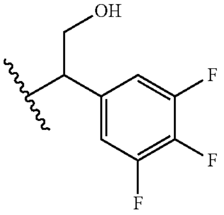 and

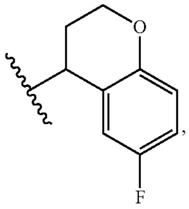, and the $R^9$-$R^{10}$— moiety is:

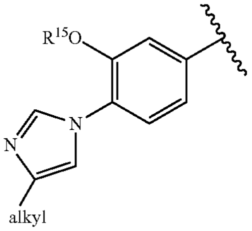

or

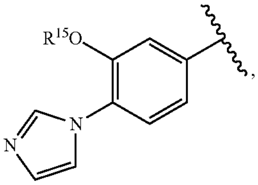, and

G is selected from the group consisting of —NH—, and a direct bond.

In another embodiment of this invention $R^1$ is selected from the group consisting of:

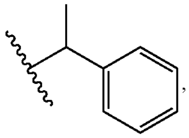, 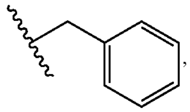,

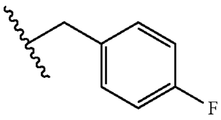 and 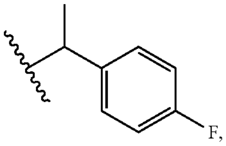

and wherein the $R^9$-$R^{10}$— moiety is:

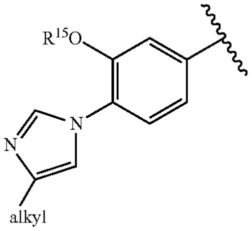 or

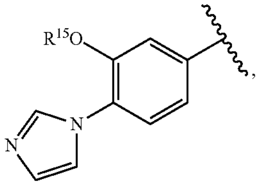

and

G is selected from the group consisting of —NH—, and a direct bond.

In another embodiment of this invention $R^1$ is selected from the group consisting of:

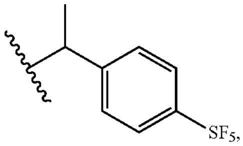

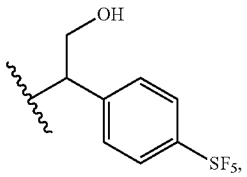

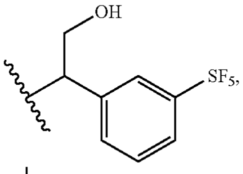

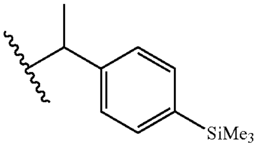 and

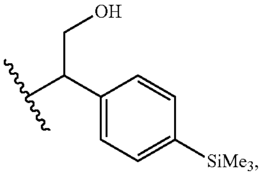

and wherein the $R^9$-$R^{10}$— moiety is:

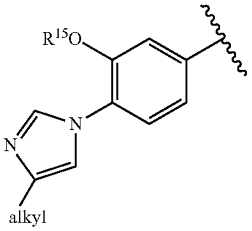 or

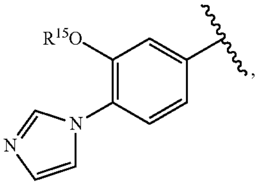

and

G is selected from the group consisting of —NH—, and a direct bond.

In another embodiment of this invention $R^1$ is selected from the group consisting of:

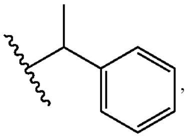, 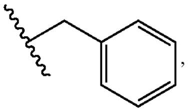,

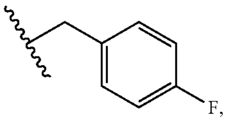 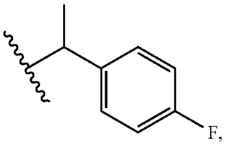

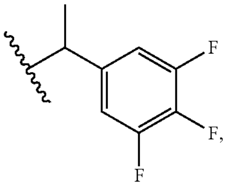 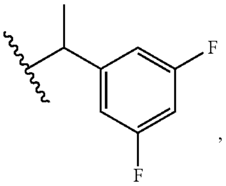,

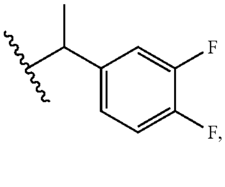 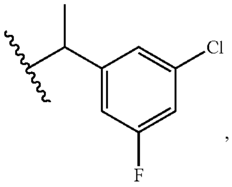,

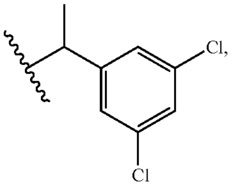 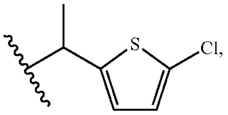

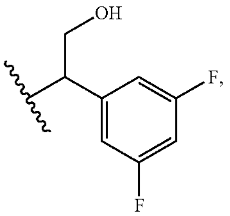 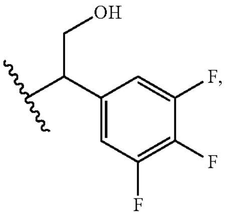

-continued

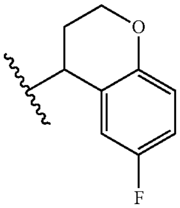,
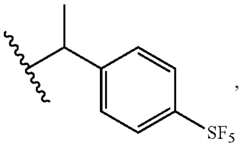,
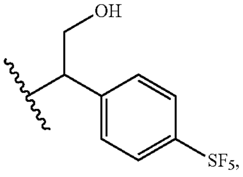
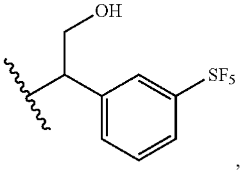,
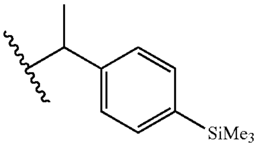
and
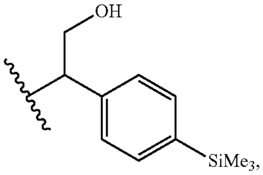

and the $R^9$-$R^{10}$— moiety is:

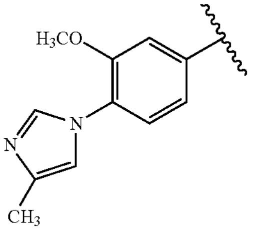
or
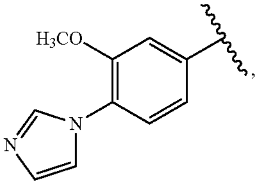

and

G is selected from the group consisting of —NH—, and a direct bond.

In another embodiment of this invention $R^1$ is selected from the group consisting of:

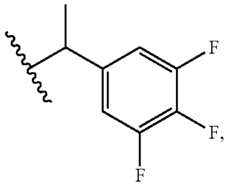
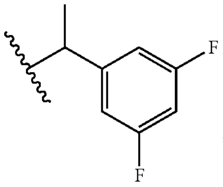,
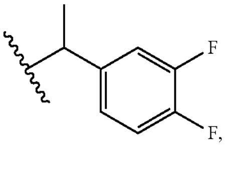
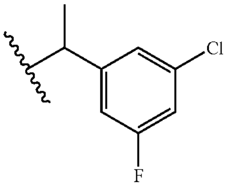,

-continued

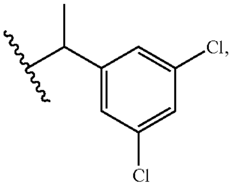
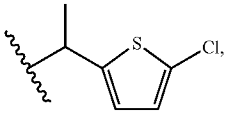
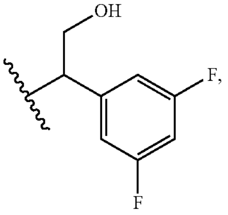
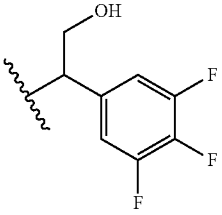
and
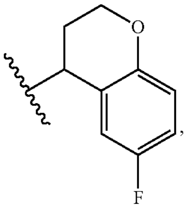

and the $R^9$-$R^{10}$— moiety is:

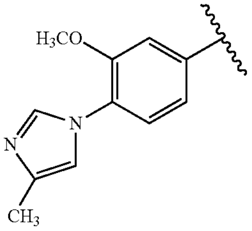
or
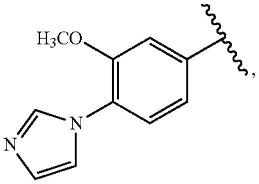

and

G is selected from the group consisting of —NH—, and a direct bond.

In another embodiment of this invention $R^1$ is selected from the group consisting of:

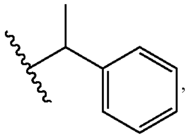
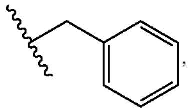
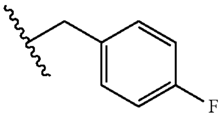
and
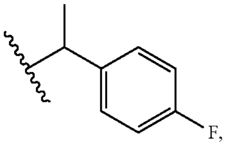

and wherein the $R^9$-$R^{10}$— moiety is:

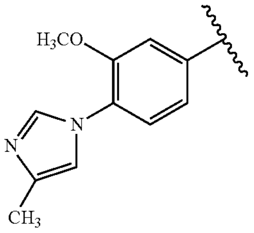

or

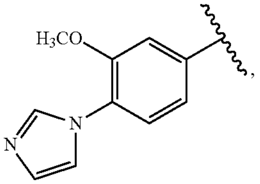

and

G is selected from the group consisting of —NH—, and a direct bond.

In another embodiment of this invention $R^1$ is selected from the group consisting of:

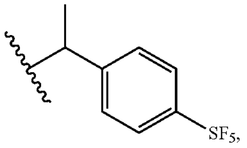

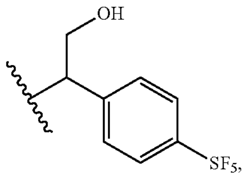

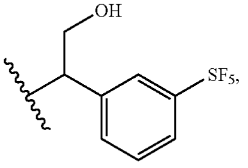

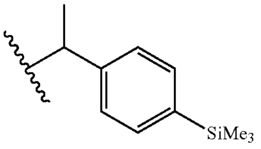

and

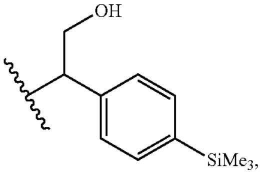

and wherein the $R^9$-$R^{10}$— moiety is:

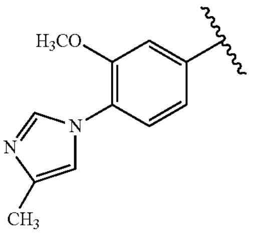

or

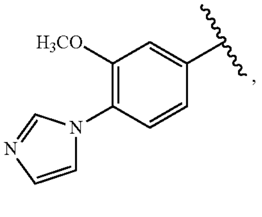

and

G is selected from the group consisting of —NH—, and a direct bond.

In another embodiment of this invention: (a) $R^1$ is a methyl or ethyl group substituted with one phenyl, or (b) $R^1$ is an methyl or alkyl group substituted with one phenyl, and said phenyl is substituted with one or two F, and (c) $R^{10}$ is phenyl substituted with one —$OR^{15}$ group, wherein $R^{15}$ is methyl, and (d) $R^9$ is selected from the group consisting of imidazolyl and imidazolyl substituted with one methyl group, and (e) G is selected from the group consisting of —NH—, and a direct bond, and (f) W is —C(O)—.

In another embodiment of this invention $R^1$ is selected from the group consisting of:

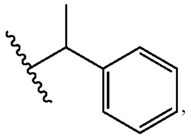

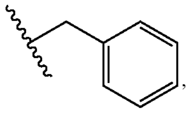

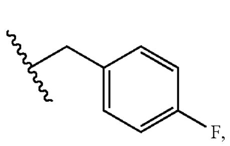

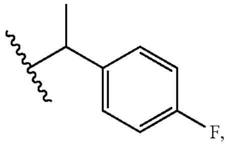

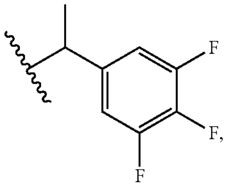

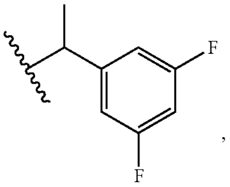

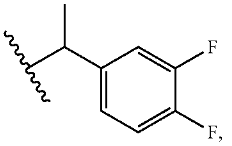

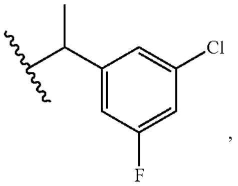

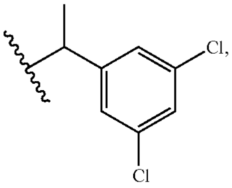

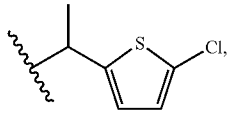

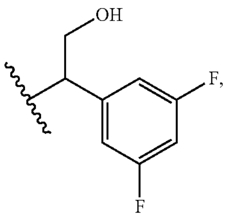

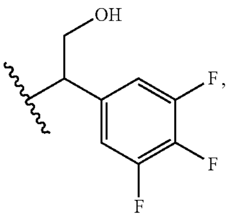

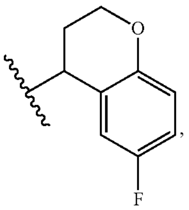

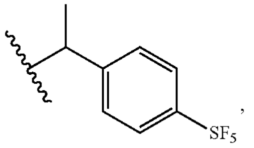

-continued

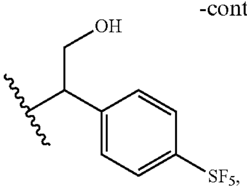

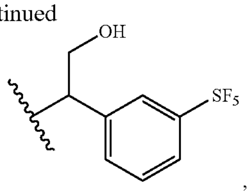

,

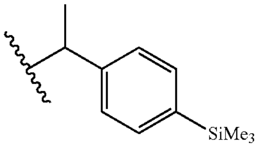

and

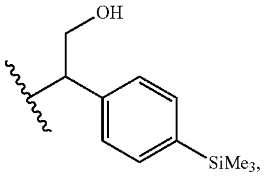

and the $R^9$-$R^{10}$— moiety is:

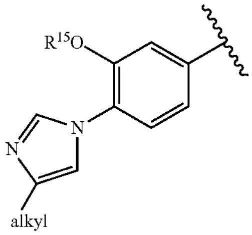

or

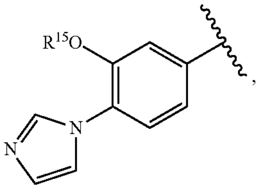

and

G is selected from the group consisting of —NH—, and a direct bond, and W is —C(O)—.

In another embodiment of this invention $R^1$ is selected from the group consisting of:

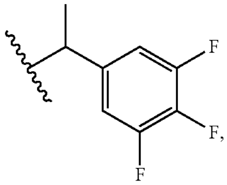

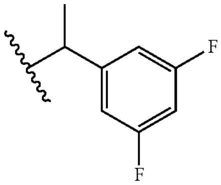

,

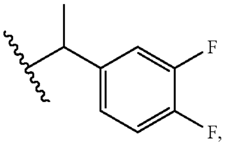

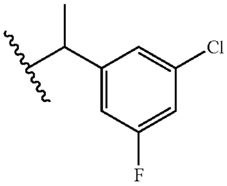

,

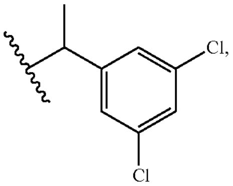

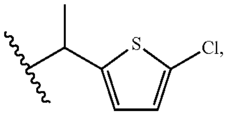

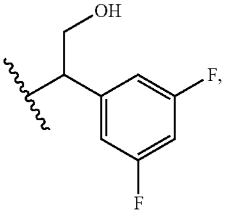

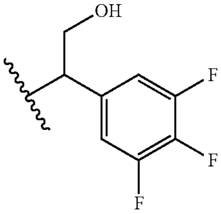

and

-continued

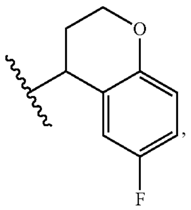

and the $R^9$-$R^{10}$— moiety is:

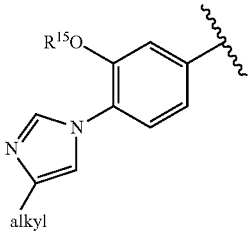

or

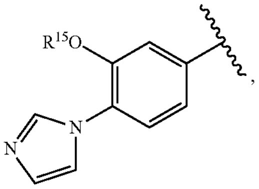

and

G is selected from the group consisting of —NH—, and a direct bond, and W is —C(O)—.

In another embodiment of this invention $R^1$ is selected from the group consisting of:

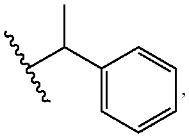

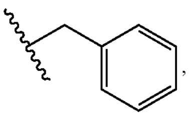

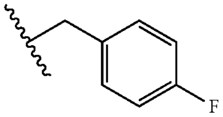

and

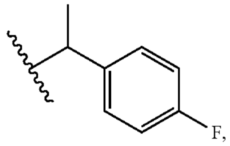

and wherein the $R^9$-$R^{10}$— moiety is:

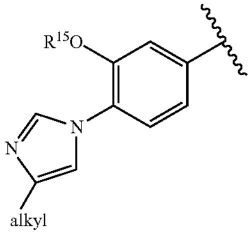

or

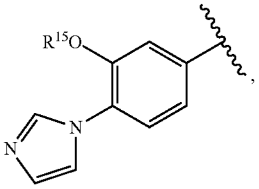

and

G is selected from the group consisting of —NH—, and a direct bond, and W is —C(O)—.

In another embodiment of this invention $R^1$ is selected from the group consisting of:

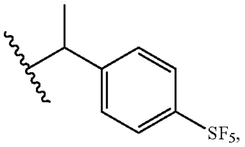
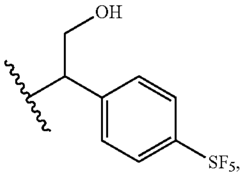

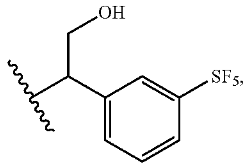
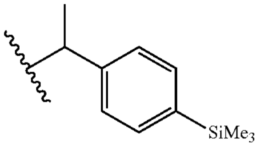
and

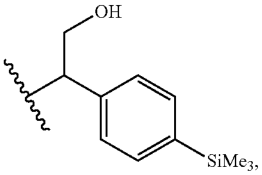

and wherein the $R^9$-$R^{10}$— moiety is:

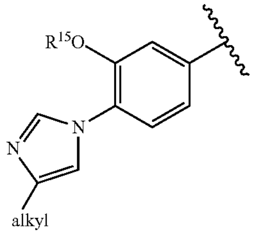
or
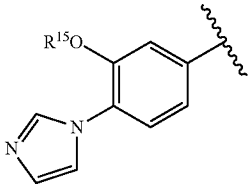
, and

G is selected from the group consisting of —NH—, and a direct bond, and W is —C(O)—.

In another embodiment of this invention $R^1$ is selected from the group consisting of:

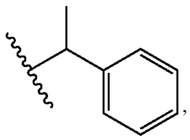
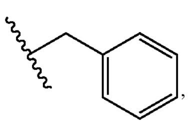

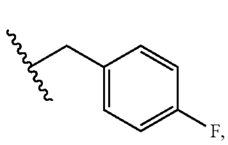
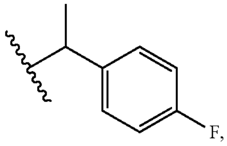

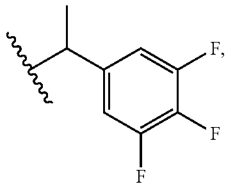
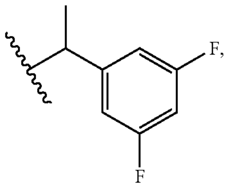

-continued

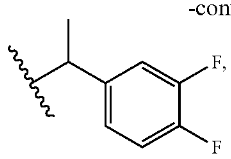
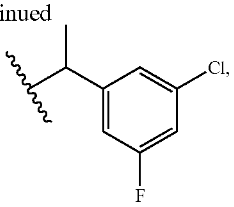

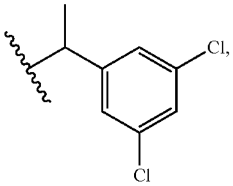
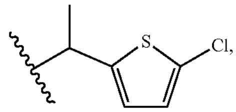

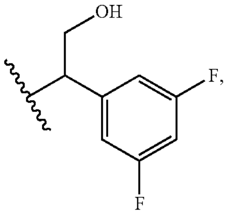
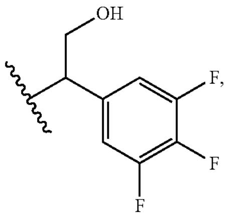

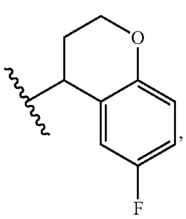
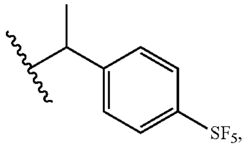

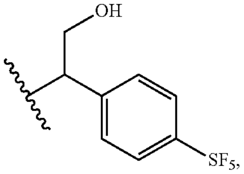
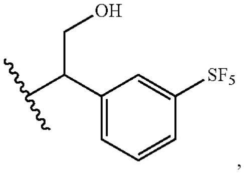
,

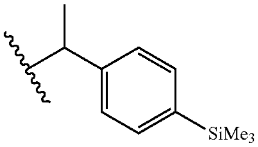
and
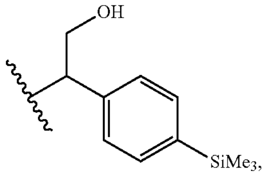

and the $R^9$-$R^{10}$— moiety is:

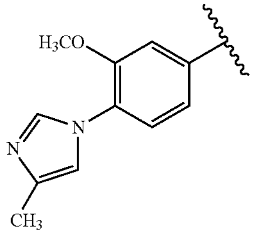
or
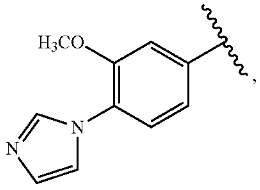

and

G is selected from the group consisting of —NH—, and a direct bond, and W is —C(O)—.

In another embodiment of this invention $R^1$ is selected from the group consisting of:

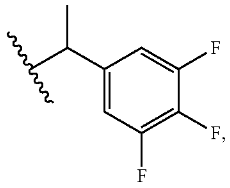
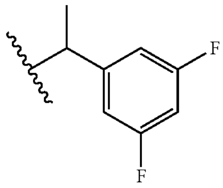
,

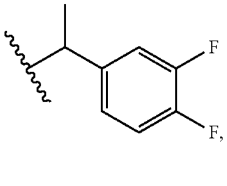
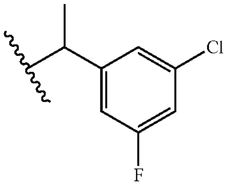
,

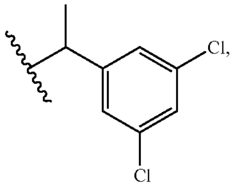
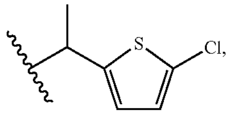

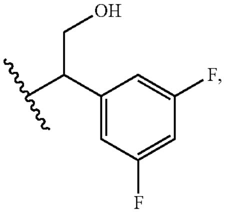
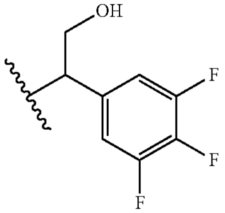
and

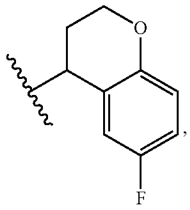
, and
the $R^9$-$R^{10}$— moiety is:

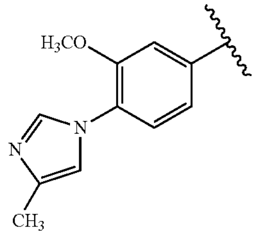
or
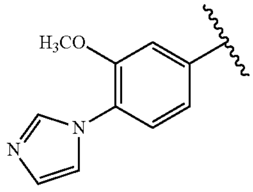
, and
G is selected from the group consisting of —NH—, and a direct bond, and W is —C(O)—.

In another embodiment of this invention $R^1$ is selected from the group consisting of:

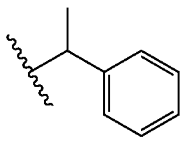
,
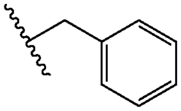
,

-continued

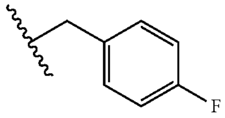
and
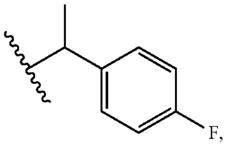

and
wherein the $R^9$-$R^{10}$— moiety is:

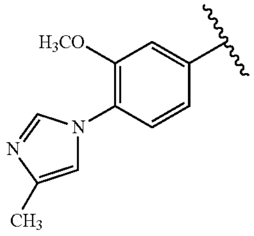
or
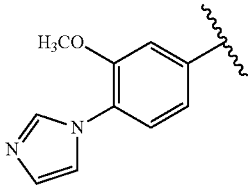
, and
G is selected from the group consisting of —NH—, and a direct bond, and W is —C(O)—.

In another embodiment of this invention $R^1$ is selected from the group consisting of:

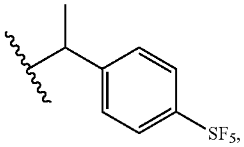
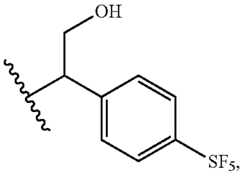
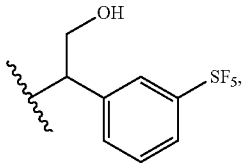
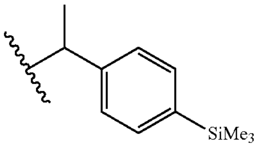
and
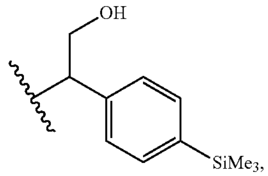

and
wherein the $R^9$-$R^{10}$— moiety is:

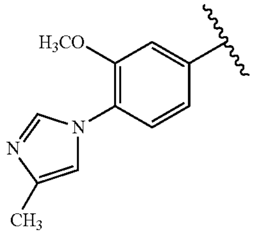
or
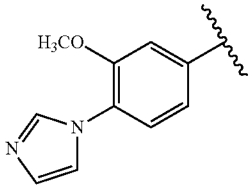
, and

G is selected from the group consisting of —NH—, and a direct bond, and W is —C(O)—.

In another embodiment of this invention: (a) $R^1$ is a methyl or ethyl group substituted with one phenyl, or (b) $R^1$ is an methyl or alkyl group substituted with one phenyl, and said phenyl is substituted with one or two F, and (c) $R^{10}$ is phenyl substituted with one —$OR^{15}$ group, wherein $R^{15}$ is methyl, and (d) $R^9$ is selected from the group consisting of imidazolyl and imidazolyl substituted with one methyl group, and (e) G is selected from the group consisting of —NH—, and a direct bond, and (f) W is —S(O)—.

In another embodiment of this invention $R^1$ is selected from the group consisting of:

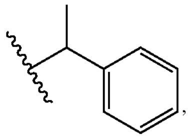,
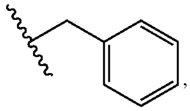,
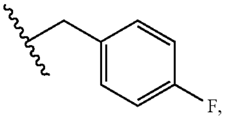,
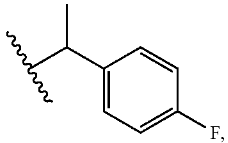,
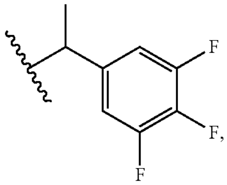,
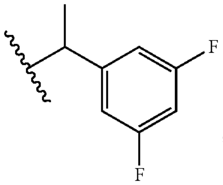,
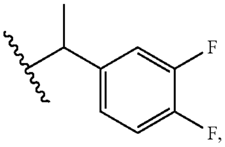,
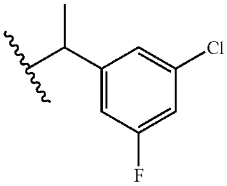,
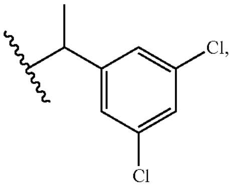,
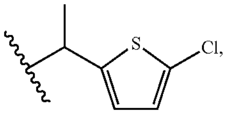,
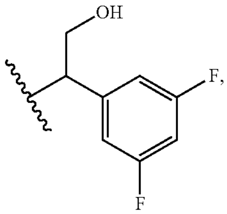,
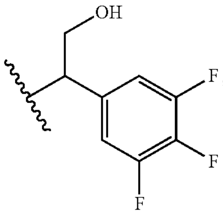,
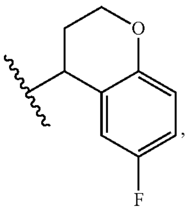,
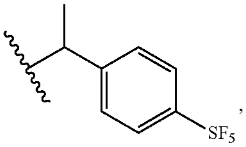, -continued

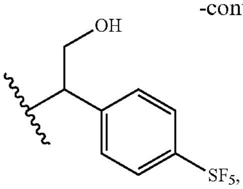,
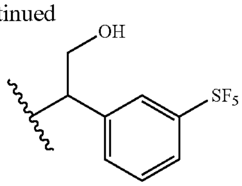,
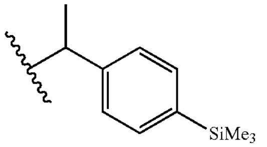 and
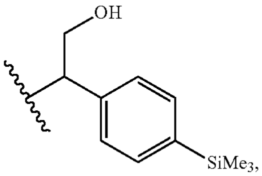, and the $R^9$-$R^{10}$— moiety is:

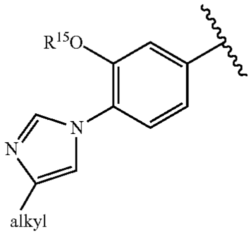 or
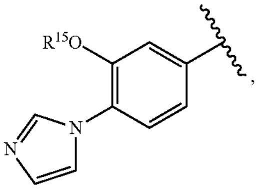, and

G is selected from the group consisting of —NH—, and a direct bond, and W is —S(O)—.

In another embodiment of this invention $R^1$ is selected from the group consisting of:

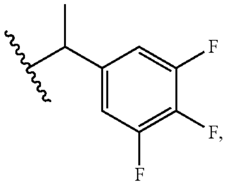,
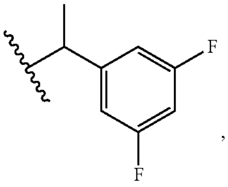,
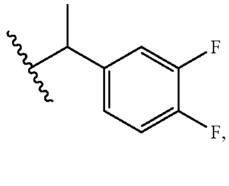,
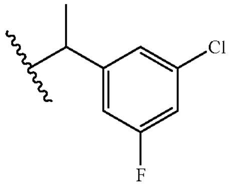,
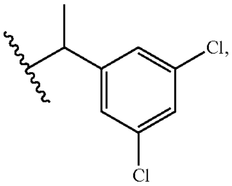,
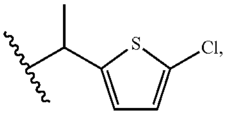,
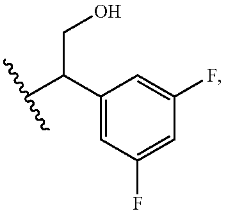 and
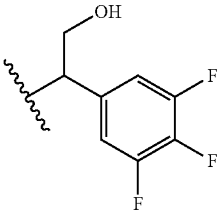

-continued

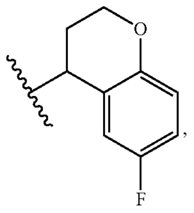

and the $R^9$-$R^{10}$— moiety is:

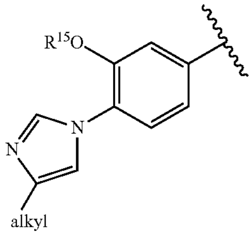

or

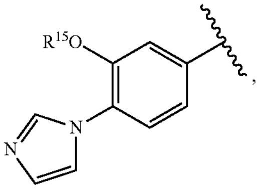

and

G is selected from the group consisting of —NH—, and a direct bond, and W is —S(O)—.

In another embodiment of this invention $R^1$ is selected from the group consisting of:

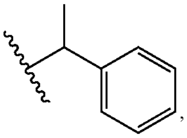

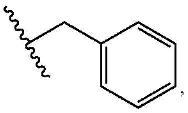

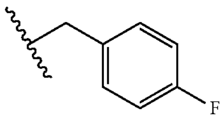

and

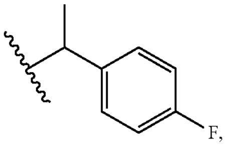

and wherein the $R^9$-$R^{10}$— moiety is:

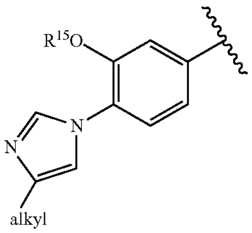

or

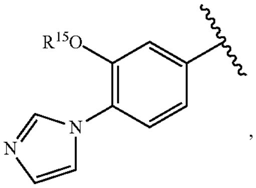

and

G is selected from the group consisting of —NH—, and a direct bond, and W is —S(O)—.

In another embodiment of this invention $R^1$ is selected from the group consisting of:

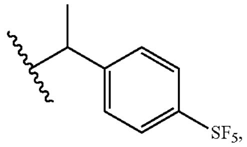

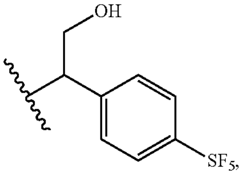

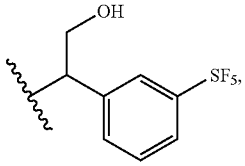

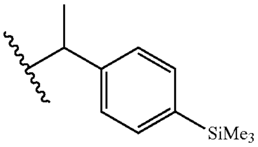

and

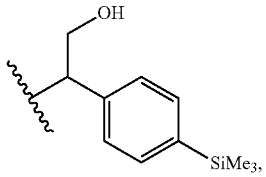

and wherein the $R^9$-$R^{10}$— moiety is:

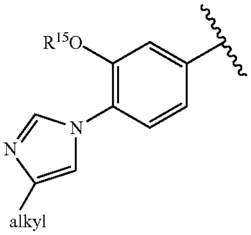

or

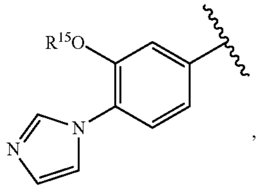

and

G is selected from the group consisting of —NH—, and a direct bond, and W is —S(O)—.

In another embodiment of this invention $R^1$ is selected from the group consisting of:

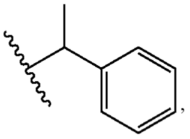

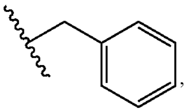

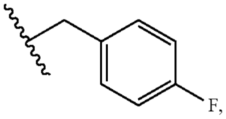

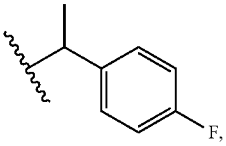

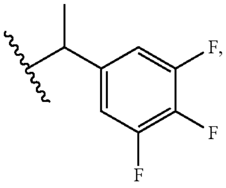

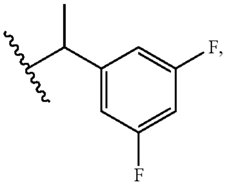

-continued

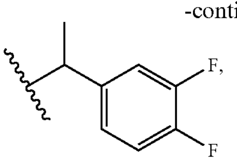 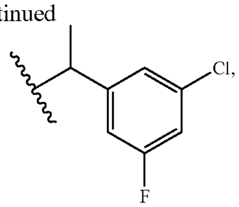

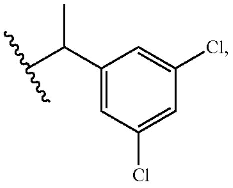 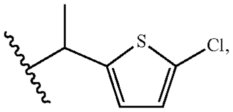

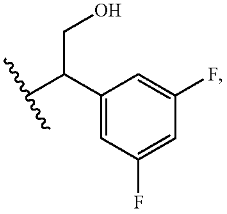 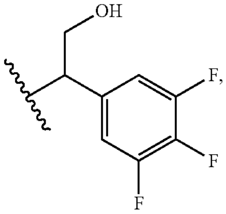

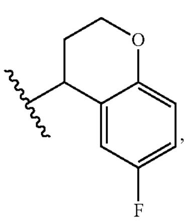 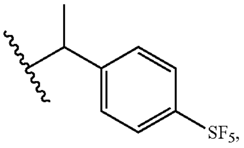

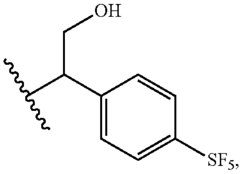 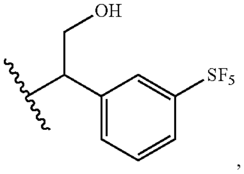 ,

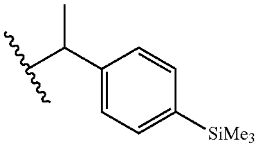 and 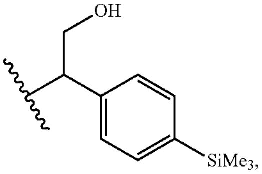

and the $R^9$-$R^{10}$— moiety is:

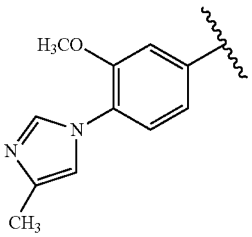 or 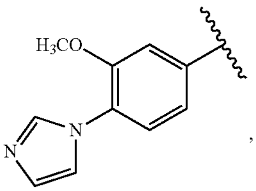 , and

G is selected from the group consisting of —NH—, and a direct bond, and W is —S(O)—.

In another embodiment of this invention $R^1$ is selected from the group consisting of:

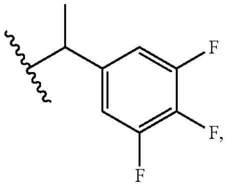 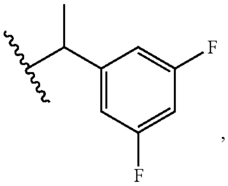 ,

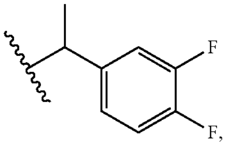 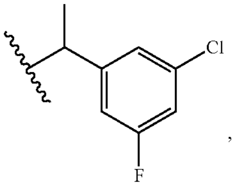 ,

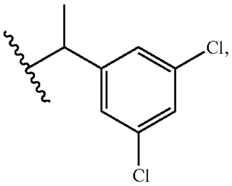 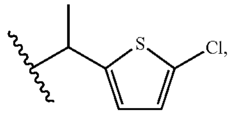

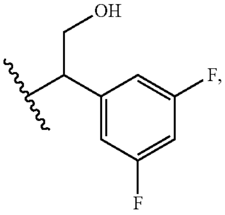 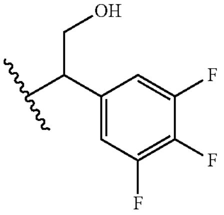 and

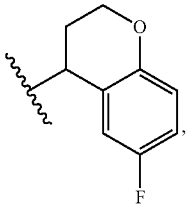

and the $R^9$-$R^{10}$— moiety is:

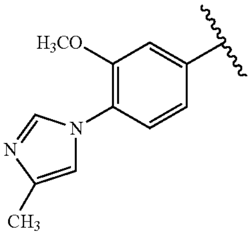 or 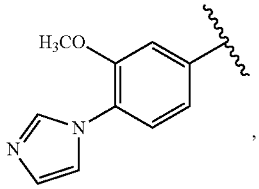 , and

G is selected from the group consisting of —NH—, and a direct bond, and W is —S(O)—.

In another embodiment of this invention $R^1$ is selected from the group consisting of:

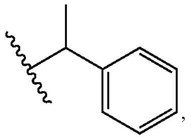 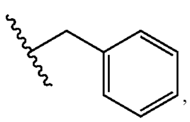

-continued

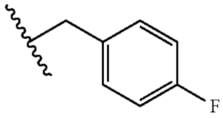

and

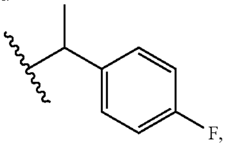

and
wherein the $R^9$-$R^{10}$— moiety is:

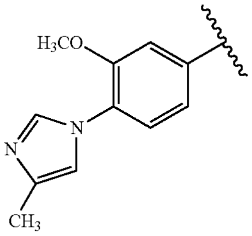

or

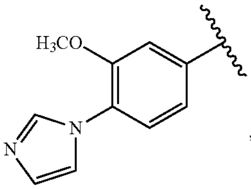

, and
G is selected from the group consisting of —NH—, and a direct bond, and W is —S(O)—.

In another embodiment of this invention $R^1$ is selected from the group consisting of:

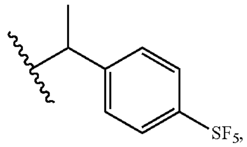

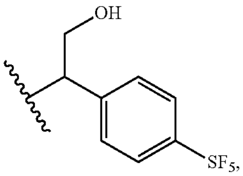

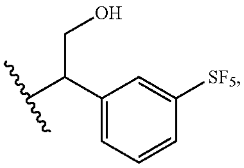

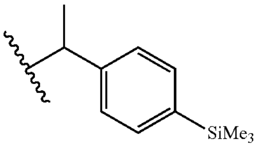

and

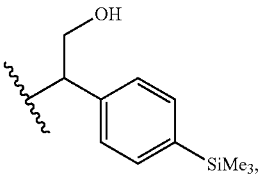

and
wherein the $R^9$-$R^{10}$— moiety is:

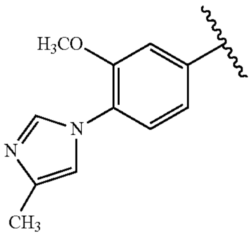

or

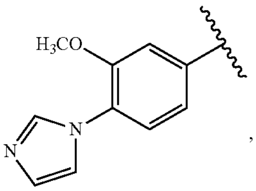

, and
G is selected from the group consisting of —NH—, and a direct bond, and W is —S(O)—.

In another embodiment of this invention: (a) $R^1$ is a methyl or ethyl group substituted with one phenyl, or (b) $R^1$ is an methyl or alkyl group substituted with one phenyl, and said phenyl is substituted with one or two F, and (c) $R^{10}$ is phenyl substituted with one —$OR^{15}$ group, wherein $R^{15}$ is methyl, and (d) $R^9$ is selected from the group consisting of imidazolyl and imidazolyl substituted with one methyl group, and (e) G is selected from the group consisting of —NH—, and a direct bond, and (f) W is —$S(O)_2$—.

In another embodiment of this invention $R^1$ is selected from the group consisting of:

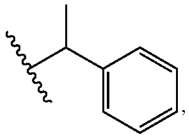

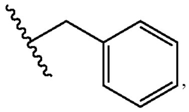

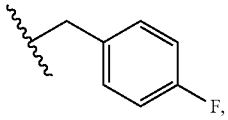

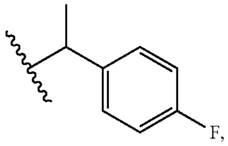

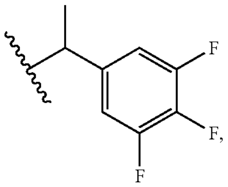

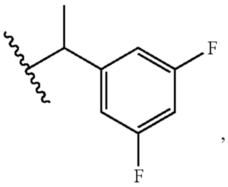

,

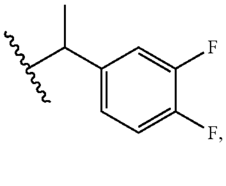

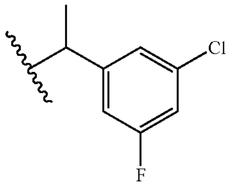

,

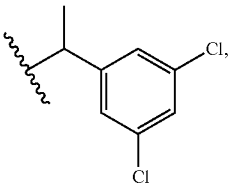

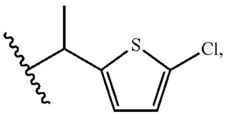

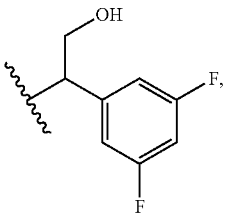

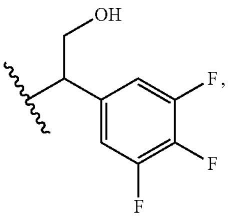

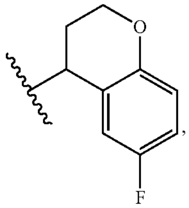

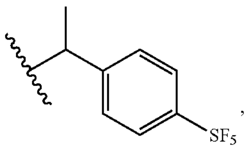

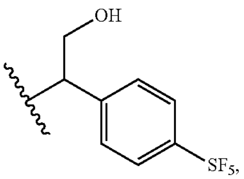

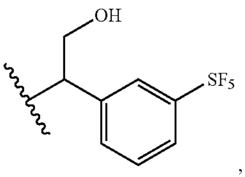

,

-continued

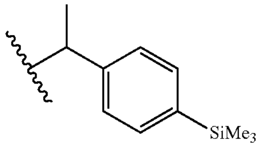 and 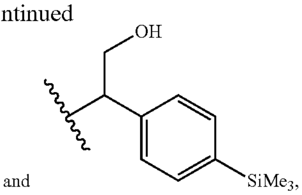

and
the $R^9$-$R^{10}$— moiety is:

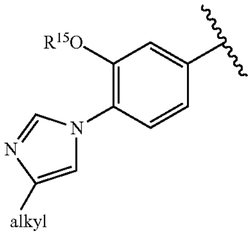 or 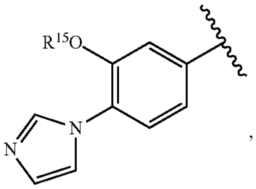, and
G is selected from the group consisting of —NH—, and a direct bond, and W is —$S(O)_2$—.

In another embodiment of this invention $R^1$ is selected from the group consisting of:

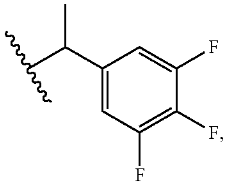 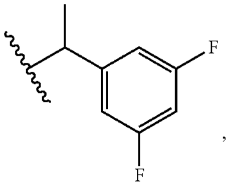,

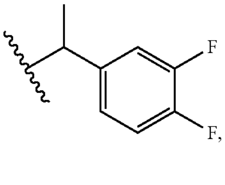 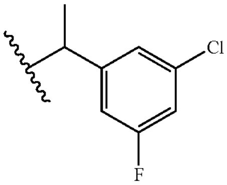,

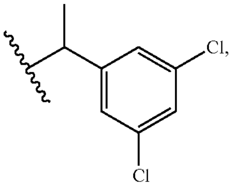 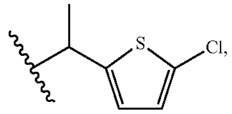

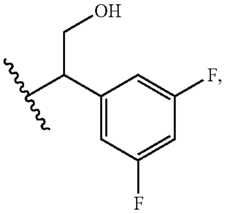 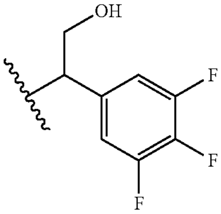 and

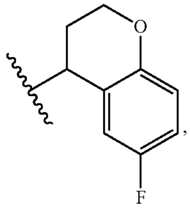, and
the $R^9$-$R^{10}$— moiety is:

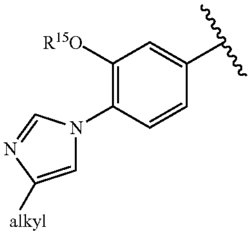 or 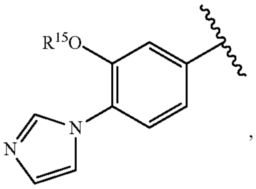, and
G is selected from the group consisting of —NH—, and a direct bond, and W is —$S(O)_2$—.

In another embodiment of this invention $R^1$ is selected from the group consisting of:

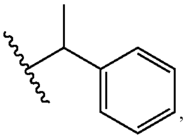, 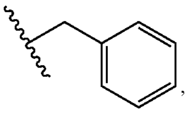,

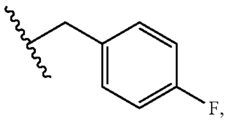 and 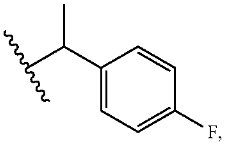

and
wherein the $R^9$-$R^{10}$— moiety is:

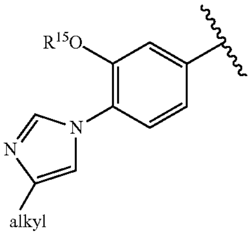 or 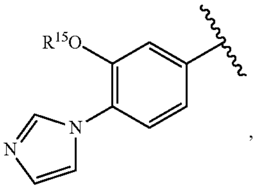, and
G is selected from the group consisting of —NH—, and a direct bond, and W is —$S(O)_2$—.

In another embodiment of this invention $R^1$ is selected from the group consisting of:

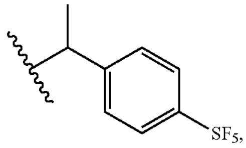 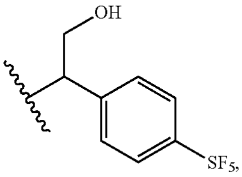

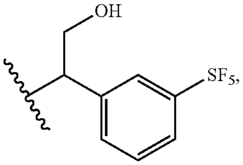 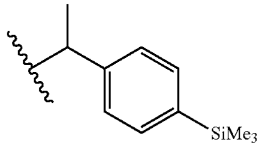 and

-continued

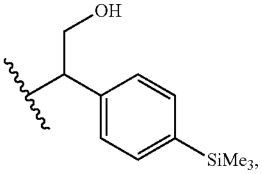

and wherein the $R^9$-$R^{10}$— moiety is:

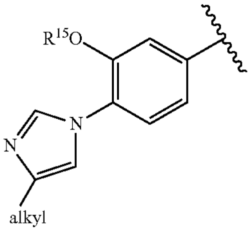

or

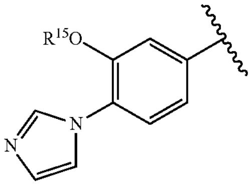

, and

G is selected from the group consisting of —NH—, and a direct bond, and W is —$S(O)_2$—.

In another embodiment of this invention $R^1$ is selected from the group consisting of:

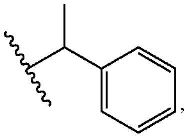

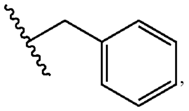

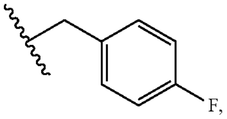

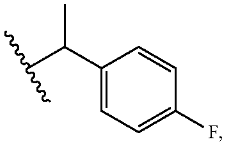

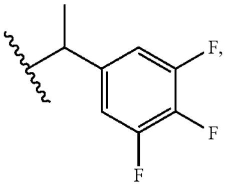

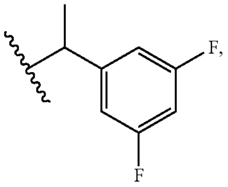

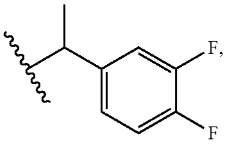

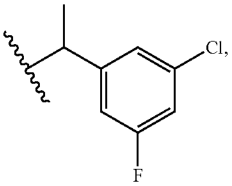

-continued

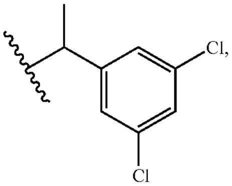

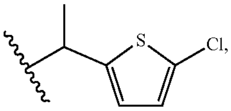

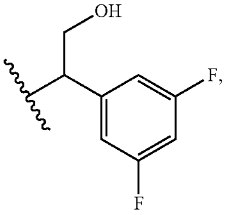

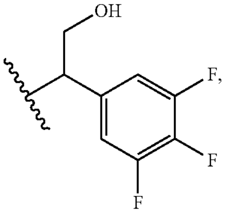

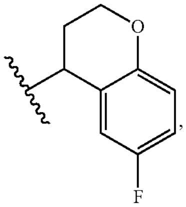

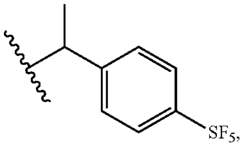

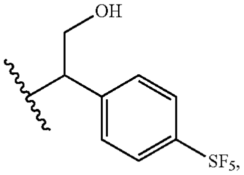

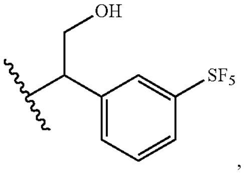

,

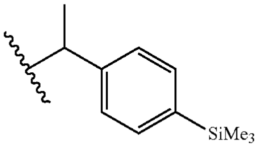

and

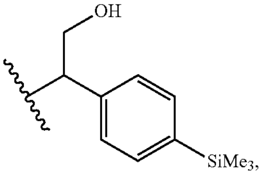

and the $R^9$-$R^{10}$— moiety is:

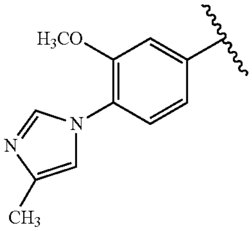

or

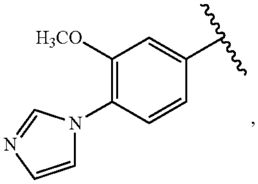

, and

G is selected from the group consisting of —NH—, and a direct bond, and W is —$S(O)_2$—.

In another embodiment of this invention $R^1$ is selected from the group consisting of:

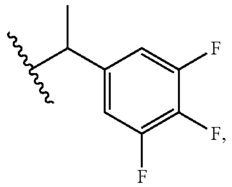 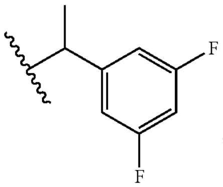 ,

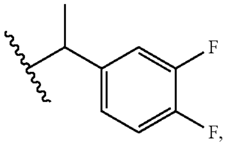 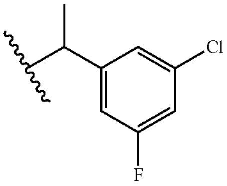 ,

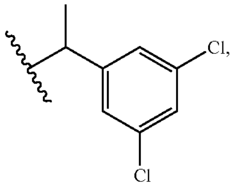 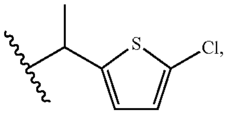

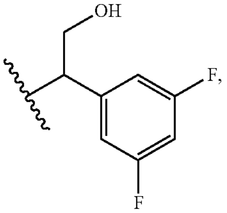 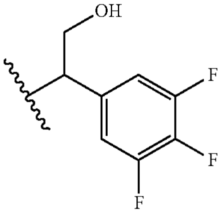 and

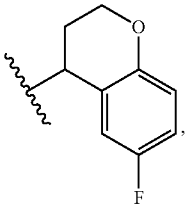

and the $R^9$-$R^{10}$— moiety is:

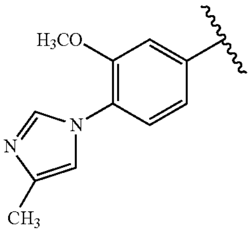 or 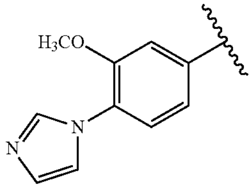 , and

G is selected from the group consisting of —NH—, and a direct bond, and W is —$S(O)_2$—.

In another embodiment of this invention $R^1$ is selected from the group consisting of:

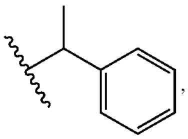 , 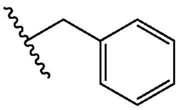 ,

-continued

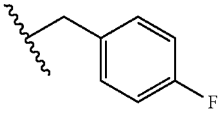 and 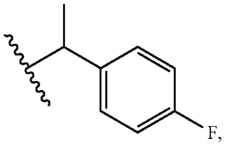

and wherein the $R^9$-$R^{10}$— moiety is:

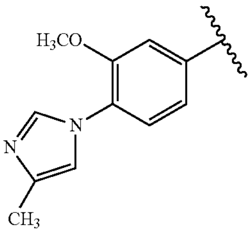 or

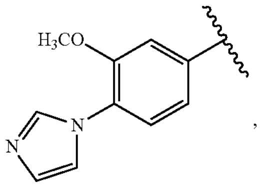 , and

G is selected from the group consisting of —NH—, and a direct bond, and W is —$S(O)_2$—.

In another embodiment of this invention $R^1$ is selected from the group consisting of:

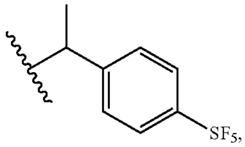 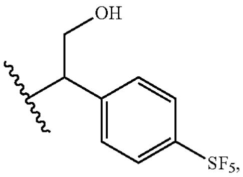

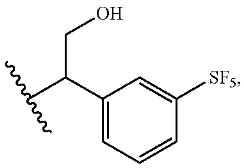 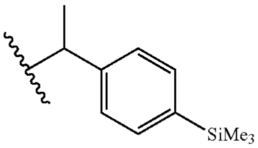 and

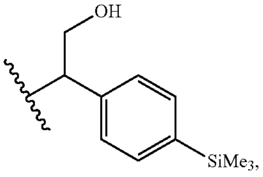

and wherein the $R^9$-$R^{10}$— moiety is:

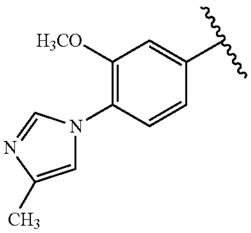 or

-continued

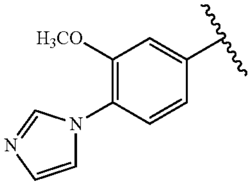

, and

G is selected from the group consisting of —NH—, and a direct bond, and W is —$S(O)_2$—.

In another embodiment of this invention: (a) $R^1$ is a methyl or ethyl group substituted with one phenyl, or (b) $R^1$ is an methyl or alkyl group substituted with one phenyl, and said phenyl is substituted with one or two F, and (c) $R^{10}$ is phenyl substituted with one —$OR^{15}$ group, wherein $R^{15}$ is methyl, and (d) $R^9$ is selected from the group consisting of imidazolyl and imidazolyl substituted with one methyl group, and (e) G is selected from the group consisting of —NH—, and a direct bond, and (f) W is —C(=$NR^2$)—.

In another embodiment of this invention $R^1$ is selected from the group consisting of:

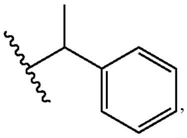

,

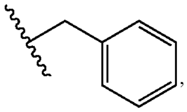

,

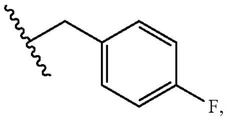

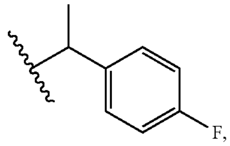

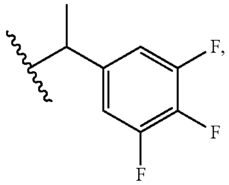

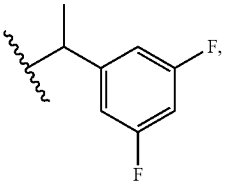

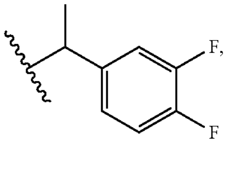

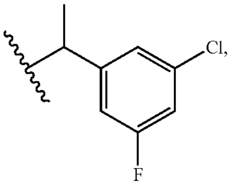

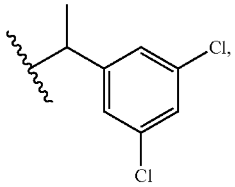

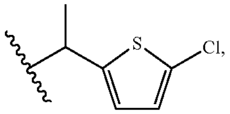

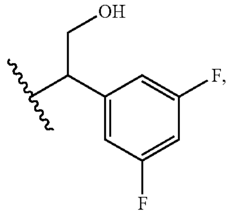

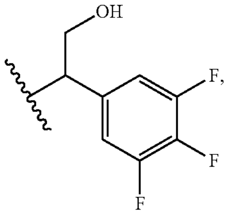

-continued

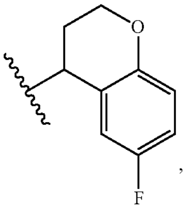

,

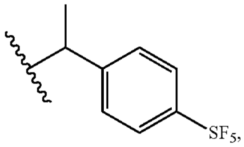

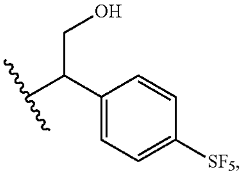

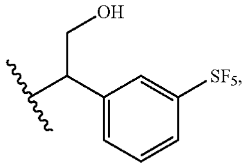

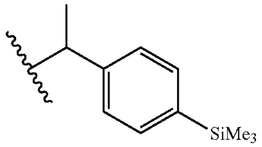

and

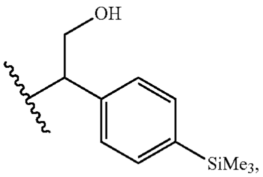

and the $R^9$-$R^{10}$— moiety is:

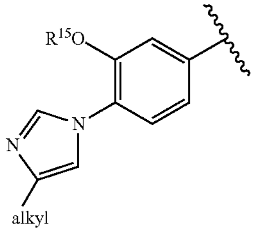

or

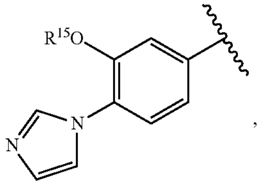

, and

G is selected from the group consisting of —NH—, and a direct bond, and W is —C(=$NR^2$)—.

In another embodiment of this invention $R^1$ is selected from the group consisting of:

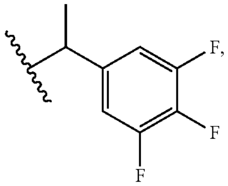

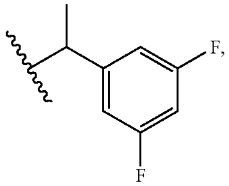

-continued

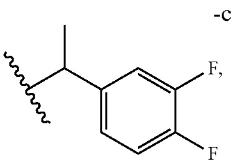
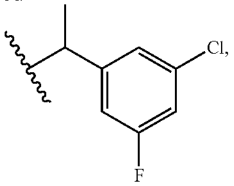
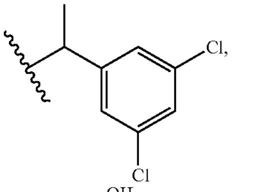
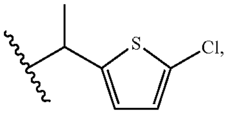
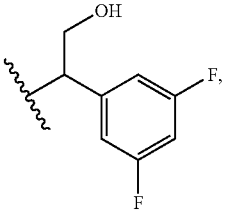
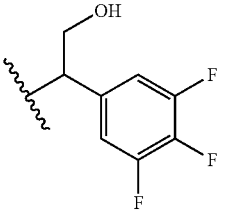
and
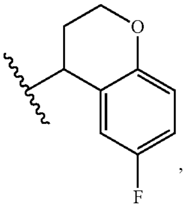
, and the $R^9$-$R^{10}$— moiety is:

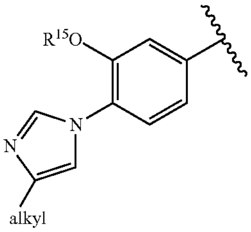
or
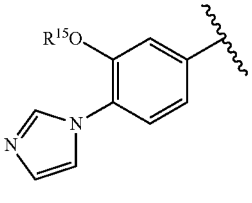
, and

G is selected from the group consisting of —NH—, and a direct bond, and W is —C(=NR$^2$)—.

In another embodiment of this invention $R^1$ is selected from the group consisting of:

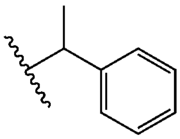
,
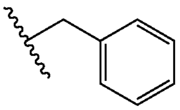
,

-continued

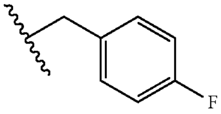
and
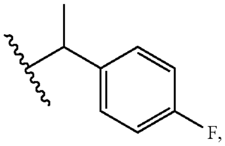

wherein the $R^9$-$R^{10}$— moiety is:

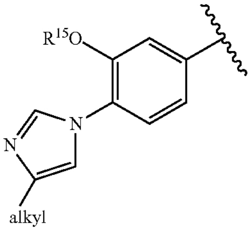
or
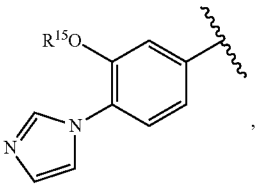
, and

G is selected from the group consisting of —NH—, and a direct bond, and W is —C(=NR$^2$)—.

In another embodiment of this invention $R^1$ is selected from the group consisting of:

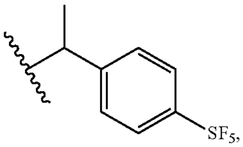
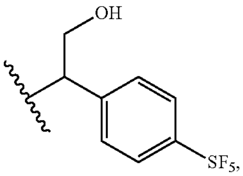
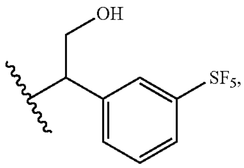
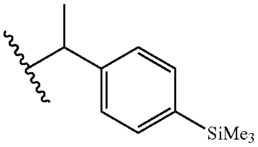
and
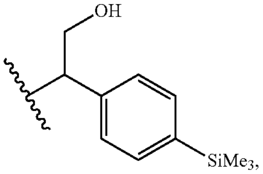

and wherein the $R^9$-$R^{10}$— moiety is:

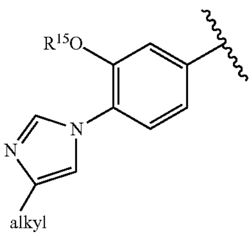
or

-continued

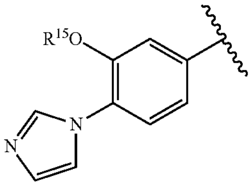

, and

G is selected from the group consisting of —NH—, and a direct bond, and W is —C(=NR$^2$)—.

In another embodiment of this invention $R^1$ is selected from the group consisting of:

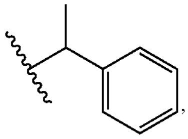
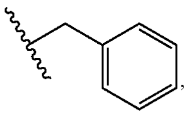
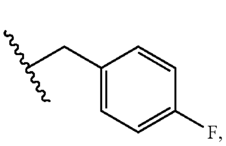
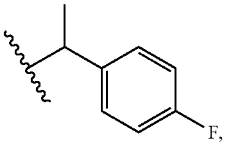
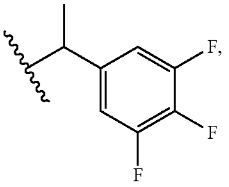
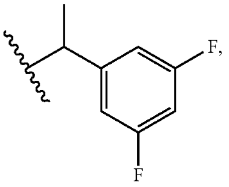
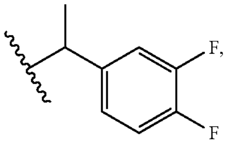
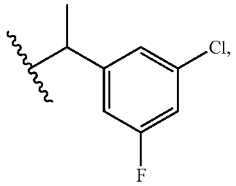
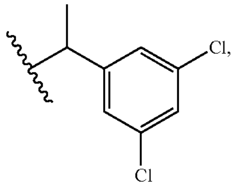
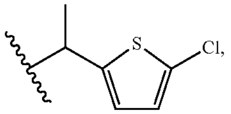
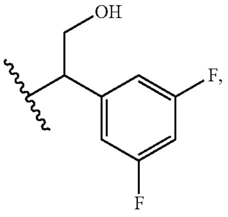
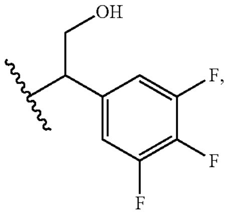
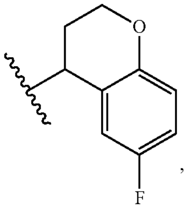

,

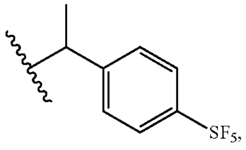

-continued

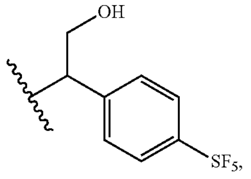
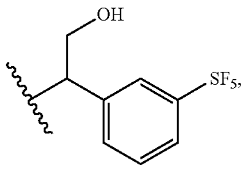
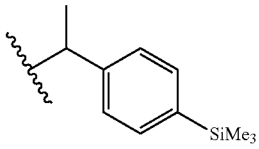

and

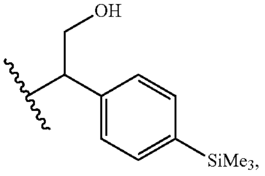

and the $R^9$-$R^{10}$— moiety is:

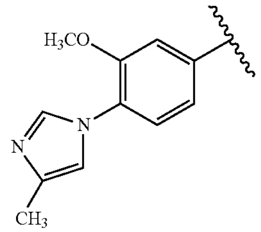

or

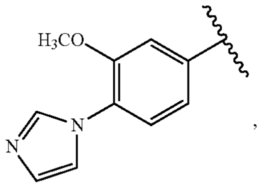

, and

G is selected from the group consisting of —NH—, and a direct bond, and W is —C(=NR$^2$)—.

In another embodiment of this invention $R^1$ is selected from the group consisting of:

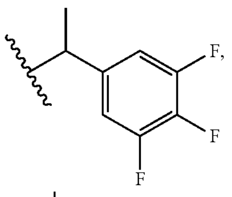
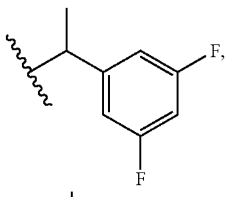
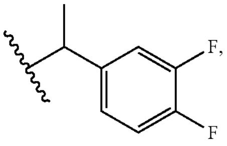
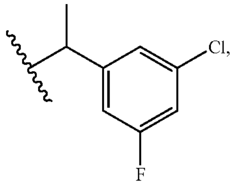

-continued

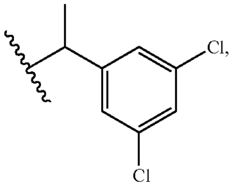
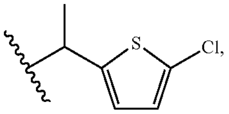

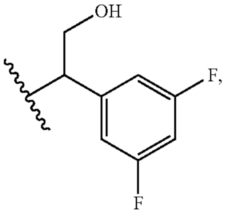
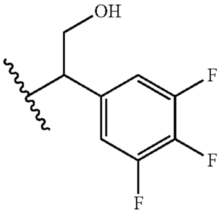 and

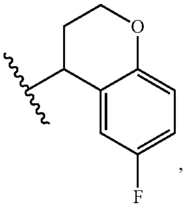, and the $R^9$-$R^{10}$— moiety is:

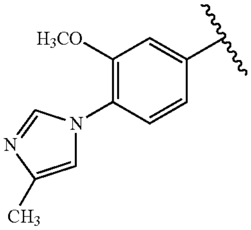 or 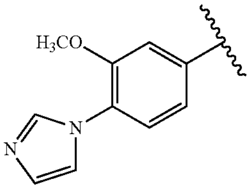, and

G is selected from the group consisting of —NH—, and a direct bond, and W is —C(═$NR^2$)—.

In another embodiment of this invention $R^1$ is selected from the group consisting of:

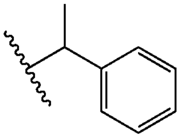, 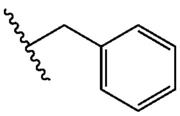,

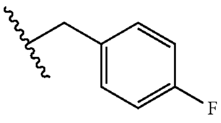 and 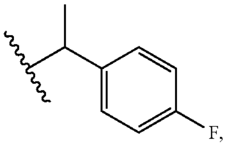

and wherein the $R^9$-$R^{10}$— moiety is:

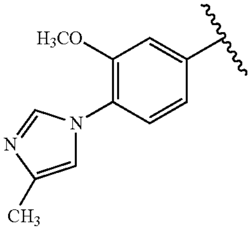 or 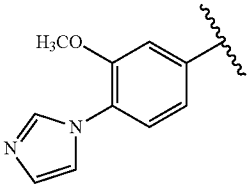, and

G is selected from the group consisting of —NH—, and a direct bond, and W is —C(═$NR^2$)—.

In another embodiment of this invention $R^1$ is selected from the group consisting of:

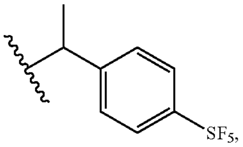
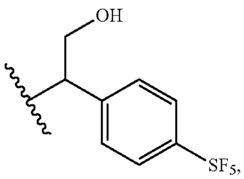

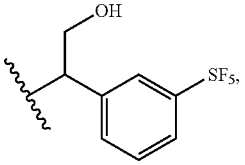
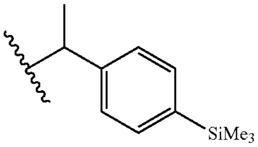 and

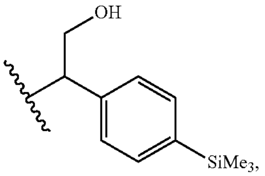

and wherein the $R^9$-$R^{10}$— moiety is:

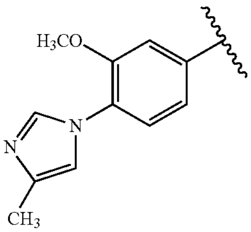 or 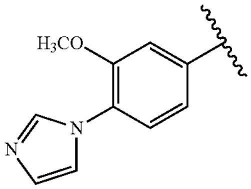, and

G is selected from the group consisting of —NH—, and a direct bond, and W is —C(═$NR^2$)—.

Other embodiments of this invention are directed to compounds of formula (I) wherein $R^1$ is selected from the group consisting of: benzofusedcycloalkyl (i.e., fused benzocycloalkyl), fused benzoheterocycloalkyl, fused heteroarylcycloalkyl, fused heteroarylheterocycloalkyl, and wherein said $R^1$ groups are optionally substituted with 1-5 independently selected $R^{21}$ groups. In one example, the $R^{21}$ groups are halo (e.g., F).

Examples of the fused ring $R^1$ groups include, but are not limited to:

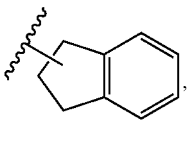, 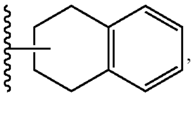, 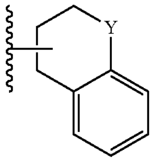,

-continued

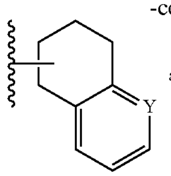

and

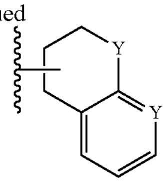

wherein each Y is independently selected from the group consisting of: —O—, —$NR^{14}$— and), —$C(R^{21})_q$—, wherein q is as defined above (i.e., 0, 1 or 2 and each $R^{21}$ is independently selected), and wherein $R^{14}$ and $R^{21}$ are as defined for formula (I). Examples of these $R^1$ groups include, for example:

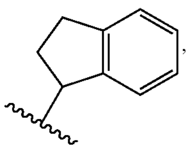

,

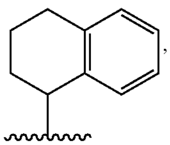

,

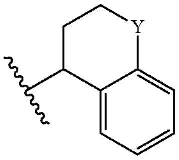

,

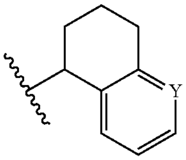

and

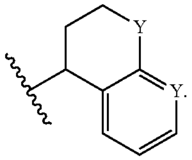

Compounds of formula (I) also include compounds wherein $R^1$ is an alkyl group (e.g., ethyl) substituted with one $R^{21}$ group. Examples of said $R^1$ groups include alkyl (e.g., methyl or ethyl) substituted with the $R^{21}$ moiety aryl (e.g., phenyl or naphthyl). Examples of said $R^1$ groups also include alkyl (e.g., methyl or ethyl) substituted with the $R^{21}$ moiety aryl (e.g., phenyl or naphthyl), which in turn is substituted with one or more (e.g., one or two) independently selected $R^{22}$ groups (e.g., $R^{22}$ is halo, such as, for example, F).

Examples of the substituted $R^1$ alkyl groups include, but are not limited to:

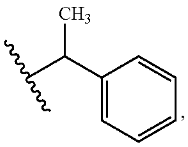

,

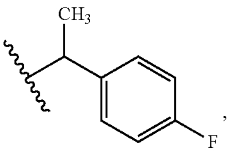

,

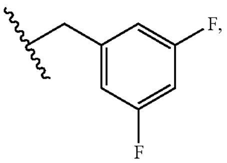

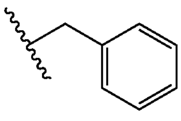

, and

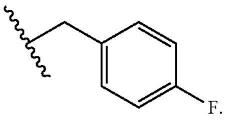

Examples of the substituted $R^1$ alkyl groups also include, for example,

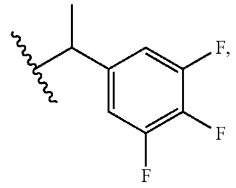

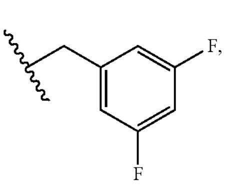

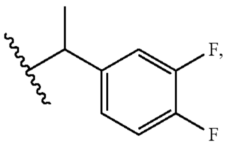

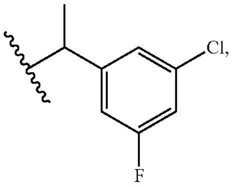

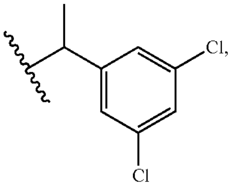

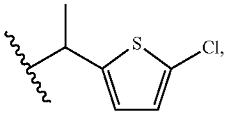

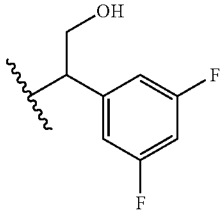

and

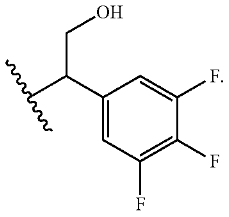

Examples of the substituted $R^1$ alkyl groups also include, for example,

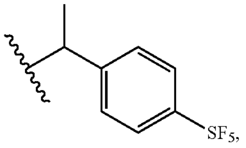

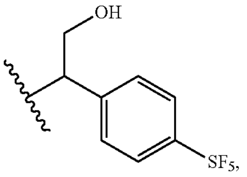

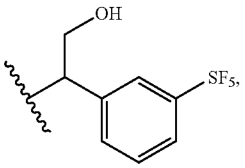

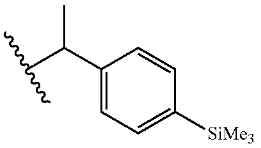

and

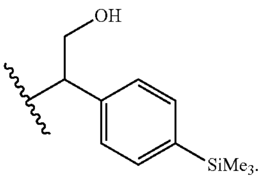

Other embodiments of this invention are directed to compounds of formula (I) wherein $R^1$ is a cycloalkyl group (e.g., cyclopropyl or cyclobutyl) substituted with one $R^{21}$ group (e.g., aryl, such as, for example, phenyl), or a cycloalkyl group (e.g., cyclopentyl or cyclohexyl) substituted with one $R^{21}$ group (e.g., aryl, such as, for example, phenyl) which in turn is substituted with one or more (e.g., one or two) independently selected $R^{22}$ groups (e.g., halo, such as, for example, F). In one example the $R^{21}$ group is bound to the same carbon of the $R^1$ group that binds the $R^1$ group to the rest of the molecule.

Examples of the cycloalkyl $R^1$ groups include, but are not limited to:

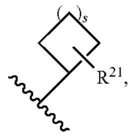

such as, for example,

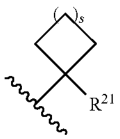

wherein s is 0 (i.e., the ring is cyclopropyl), or 1 (i.e., the ring is cyclobutyl). Examples of these $R^1$ groups include, but are not limited to:

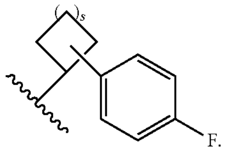

such as, for example,

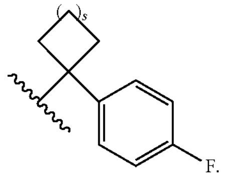

wherein s is 0 (i.e., the ring is cyclopropyl), or 1 (i.e., the ring is cyclobutyl).

Other embodiments of this invention are directed to compounds of formula (I) wherein $R^1$ is

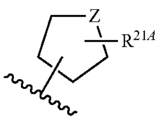

such as, for example, 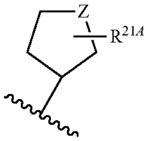 or 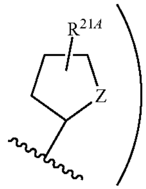

wherein Z is selected from the group consisting of: (1) —O—, (2) —$NR^{14}$—, (3) —$C(R^{21})_q$— wherein q is 0, 1 or 2, and each $R^{21}$ is independently selected, (4) —$C(R^{21})_q$—$C(R^{21})_q$— wherein each q is independently 0, 1 or 2 and each $R^{21}$ is independently selected, (5) —$(C(R^{21})_q)_q$—O—$(C(R^{21})_q)_q$— wherein each q is independently 0, 1 or 2, and each $R^{21}$ is independently selected, and (6) —$(C(R^{21})_q)_q$—$N(R^{14})$—$(C(R^{21})_q)_q$— wherein each q is independently 0, 1 or 2, and each $R^{21}$ is independently selected. $R^{21A}$ is defined the same as $R^{21}$ for formula (I). Examples of $R^{21A}$ include, but are not limited to, aryl (e.g., phenyl) and aryl (e.g., phenyl) substituted with one or more (e.g., one or two, or one) independently selected $R^{22}$ groups (e.g., halo, such as, for example, F). Examples of this $R^1$ include, but are not limited to:

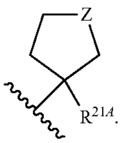

Thus, examples of this $R^1$ group include, but are not limited to:

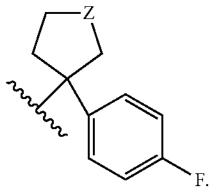

Examples of $R^1$ also include, but are not limited to:

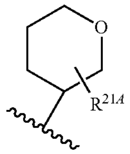 such as, for example, 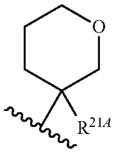,

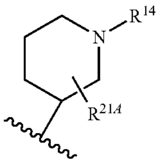 such as, for example, 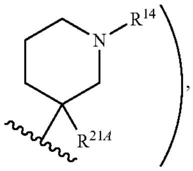,

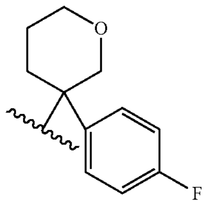 and 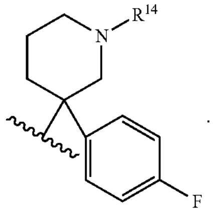.

Examples of the $R^1$ group

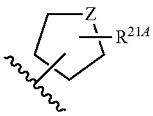

also include, but are not limited to:

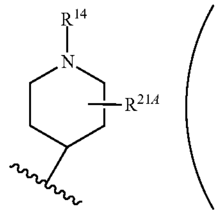

such as, for example,

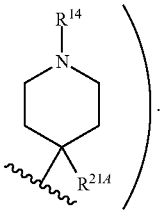

Examples of the $R^1$ group

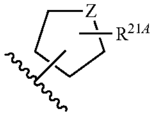

also include, but are not limited to:

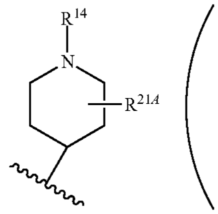

such as, for example,

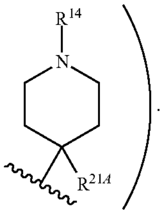

Examples of the $R^1$ group

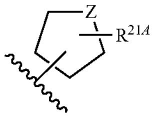

also include, but are not limited to:

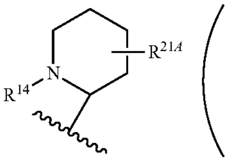

such as, for example,

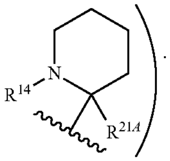

Examples of the $R^1$ group

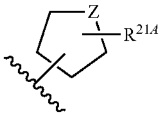

also include, but are not limited to:

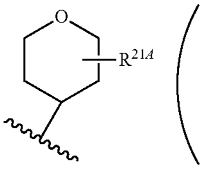

such as, for example,

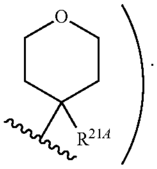

Examples of the $R^1$ group

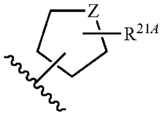

also include, but are not limited to:

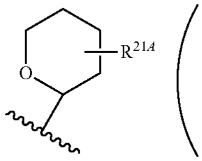

such as, for example,

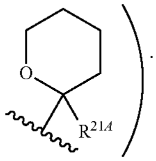

Other embodiments of this invention are directed to compounds of formula (I) wherein $R^{10}$ is aryl (e.g., phenyl) or aryl (e.g., phenyl) substituted with one or more (e.g., one or two, or one) $R^{21}$ groups (e.g., $-OR^{15}$, wherein, for example, $R^{15}$ is alkyl, such as, for example, methyl), and $R^9$ is heteroaryl (e.g., imidazolyl) or heteroaryl (e.g., imidazolyl) substituted with one or more (e.g., one or two, or one) $R^{21}$ groups (e.g., alkyl, such as, for example, methyl).

Thus, examples of the

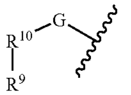

moiety of the compounds of this invention include, but are not limited to:

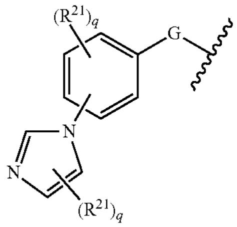

wherein q is 0, 1 or 2, such as, for example,

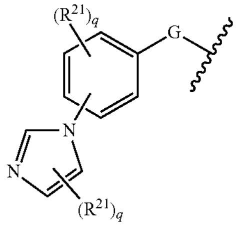

such as, for example,

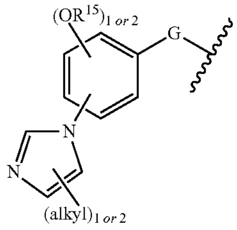

wherein $R^{15}$ is alkyl (e.g., methyl), such as, for example,

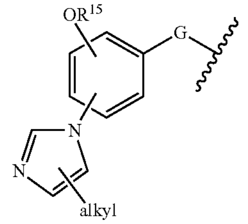

wherein $R^{15}$ is alkyl (e.g., methyl), such as, for example,

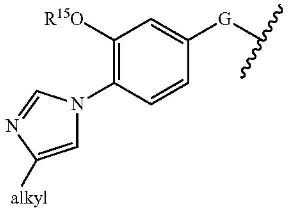

wherein $R^{15}$ is alkyl (e.g., methyl), such as, for example,

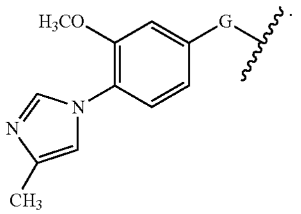

Examples of the

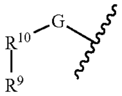

moiety of the compounds of this invention include, but are not limited to:

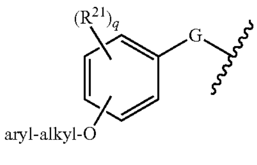

wherein q is 0, 1 or 2, and wherein said aryl-alkyl-O— group is optionally substituted with 1 to 5 (e.g. 1 to 3) independently selected $R^{21}$ groups.

Examples of the

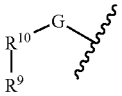

moiety of the compounds of this invention include, but are not limited to:

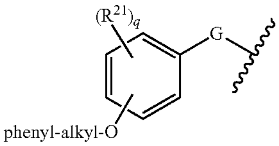

wherein q is 0, 1 or 2, and wherein said phenyl-alkyl-O— group is optionally substituted with 1 to 5 (e.g. 1 to 3) independently selected $R^{21}$ groups.

Examples of the

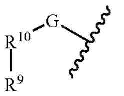

moiety of the compounds of this invention include, but are not limited to:

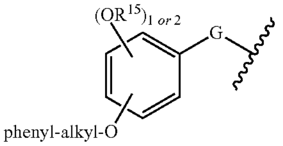

wherein said phenyl-alkyl-O— group is optionally substituted with 1 to 5 (e.g. 1 to 3) independently selected $R^{21}$ groups.

Examples of the

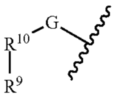

moiety of the compounds of this invention include, but are not limited to:

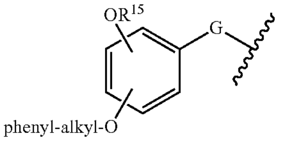

wherein said phenyl-alkyl-O— group is optionally substituted with 1 to 5 (e.g. 1 to 3) independently selected $R^{21}$ groups.

Examples of the

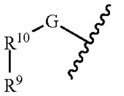

moiety of the compounds of this invention include, but are not limited to:

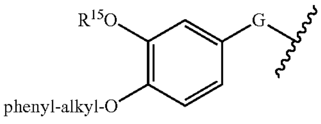

wherein said phenyl-alkyl-O— group is optionally substituted with 1 to 5 (e.g. 1 to 3) independently selected $R^{21}$ groups.

Examples of the

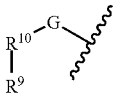

moiety of the compounds of this invention include, but are not limited to:

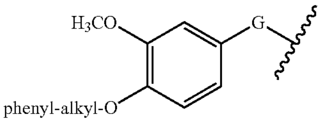

wherein said phenyl-alkyl-O— group is optionally substituted with 1 to 5 (e.g. 1 to 3) independently selected $R^{21}$ groups.

Examples of the

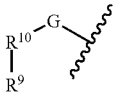

moiety of the compounds of this invention include, but are not limited to:

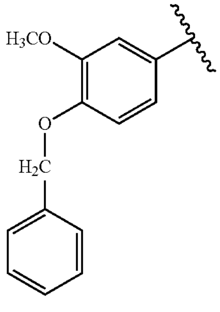 [SMILES: *c1ccc(OCc2ccccc2)c(OC)c1]

wherein said phenyl-$CH_2$—O— group is optionally substituted with 1 to 5 (e.g. 1 to 3) independently selected $R^{21}$ groups.

Examples of the

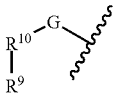

moiety of the compounds of this invention include, but are not limited to:

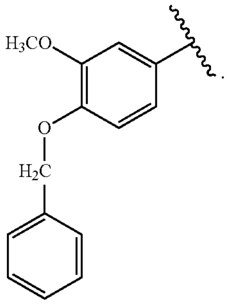 [SMILES: *c1ccc(OCc2ccccc2)c(OC)c1]

Other embodiments of this invention are directed to the compounds of formula (I) wherein $R^{10}$ is heteroaryl or heteroaryl substituted with one or more $R^{21}$ groups, and $R^9$ is heteroaryl (e.g., imidazolyl) or heteroaryl (e.g., imidazolyl) substituted with one or more (e.g., one or two, or one) $R^{21}$ groups (e.g., alkyl, such as, for example, methyl).

In another embodiment of the compounds of formula (I) $R^{10}$ is aryl substituted with one $R^{21}$ group, wherein said $R^{21}$ group is —$OR^{15}$. In one example, $R^{15}$ is alkyl. In another example $R^{15}$ is methyl.

In another embodiment of the compounds of formula (I) $R^{10}$ is phenyl substituted with one $R^{21}$ group, wherein said $R^{21}$ group is —$OR^{15}$. In one example, $R^{15}$ is alkyl. In another example $R^{15}$ is methyl.

In another embodiment of the compounds of formula (I) $R^{10}$ is heteroaryl.

In another embodiment of the compounds of formula (I) $R^9$ is heteroaryl.

In another embodiment of the compounds of formula (I) $R^9$ is heteroaryl substituted with one or more (e.g., one) independently selected $R^{21}$ groups.

In another embodiment of the compounds of formula (I) $R^9$ is heteroaryl substituted with one or more (e.g., one) independently selected $R^{21}$ groups, wherein each $R^{21}$ group is the same or different alkyl group (e.g., methyl).

In another embodiment of the compounds of formula (I) $R^9$ is heteroaryl substituted with one $R^{21}$ group.

In another embodiment of the compounds of formula (I) $R^9$ is heteroaryl substituted with one $R^{21}$ group, wherein $R^{21}$ is an alkyl group (e.g., methyl).

In another embodiment of the compounds of formula (I) $R^9$ is imidazolyl.

In another embodiment of the compounds of formula (I) $R^9$ is imidazolyl substituted with one or more (e.g., one) independently selected $R^{21}$ groups.

In another embodiment of the compounds of formula (I) $R^9$ is imidazolyl substituted with one or more (e.g., one) independently selected $R^{21}$ groups, wherein each $R^{21}$ group is the same or different alkyl group (e.g., methyl).

In another embodiment of the compounds of formula (I) $R^9$ is imidazolyl substituted with one $R^{21}$ group.

In another embodiment of the compounds of formula (I) $R^9$ is imidazolyl substituted with one $R^{21}$ group, wherein $R^{21}$ is an alkyl group (e.g., methyl).

In another embodiment of the compounds of formula (I) $R^9$ is heteroaryl, optionally substituted with one or more $R^{21}$ groups, and $R^{10}$ is aryl optionally substituted with one or more (e.g., one) $R^{21}$ groups.

In another embodiment of the compounds of formula (I) $R^9$ is heteroaryl, optionally substituted with one $R^{21}$ group, and $R^{10}$ is aryl optionally substituted with one $R^{21}$ group.

In another embodiment of the compounds of formula (I) $R^9$ is heteroaryl, optionally substituted with one or more $R^{21}$ groups, and $R^{10}$ is phenyl optionally substituted with one or more (e.g., one) $R^{21}$ groups.

In another embodiment of the compounds of formula (I) $R^9$ is heteroaryl, optionally substituted with one $R^{21}$ group, and $R^{10}$ is phenyl optionally substituted with one $R^{21}$ group.

In another embodiment of the compounds of formula (I) $R^9$ is imidazolyl, optionally substituted with one or more $R^{21}$ groups, and $R^{10}$ is aryl optionally substituted with one or more (e.g., one) $R^{21}$ groups.

In another embodiment of the compounds of formula (I) $R^9$ is imidazolyl, optionally substituted with one $R^{21}$ group, and $R^{10}$ is aryl optionally substituted with one $R^{21}$ group.

In another embodiment of the compounds of formula (I) $R^9$ is imidazolyl, optionally substituted with one or more $R^{21}$ groups, and $R^{10}$ is phenyl optionally substituted with one or more (e.g., one) $R^{21}$ groups.

In another embodiment of the compounds of formula (I) $R^9$ is imidazolyl, optionally substituted with one $R^{21}$ group, and $R^{10}$ is phenyl optionally substituted with one $R^{21}$ group.

In another embodiment of the compounds of formula (I) $R^9$ is heteroaryl, optionally substituted with one or more $R^{21}$ groups, $R^{10}$ is aryl optionally substituted with one or more (e.g., one) $R^{21}$ groups, W is —C(O)—. In one example the $R^{21}$ groups for $R^9$ are independently selected from alkyl. In another example of this embodiment the $R^{21}$ groups for $R^{10}$ are independently selected from —$OR^{15}$ (wherein, for example, $R^{15}$ is alkyl, such as, for example, methyl). In one example of this embodiment $R^9$ is substituted with one $R^{21}$ group. In another example of this embodiment $R^{10}$ is substituted with one $R^{21}$ group. In another example of this embodiment $R^9$ is substituted with one $R^{21}$ group, and $R^{10}$ is substituted with one $R^{21}$ group, each $R^{21}$ being independently selected. In another example of this embodiment the $R^9$ is substituted with one $R^{21}$ group and said $R^{21}$ group is alkyl (e.g., methyl), and $R^{10}$ is substituted with one $R^{21}$ group and this $R^{21}$ group is —$OR^{15}$ (wherein $R^{15}$ is, for example, alkyl, such as, for example, methyl).

Other embodiments of the compounds of formula (I) are directed to any one of the above embodiments wherein $R^9$ is:

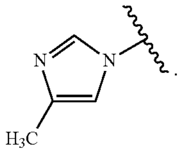

Other embodiments of the compounds of formula (I) are directed to any one of the above embodiments wherein $R^{10}$ is:

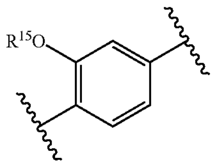

(wherein the —$OR^{15}$ is ortho to the carbon to which $R^9$ is bound to, i.e., the $R^9$-$R^{10}$— moiety is:

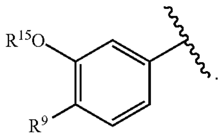

Other embodiments for the compounds of formula (I) are directed to any one of the above embodiments wherein $R^{10}$ is:

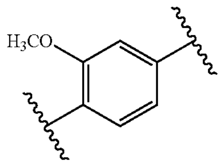 [SMILES: *c1ccc(*)c(OC)c1]

(wherein the —$OCH_3$ is ortho to the carbon to which $R^9$ is bound to, i.e., the $R^9$-$R^{10}$— moiety is:

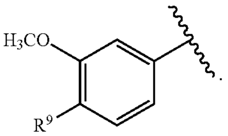

In another embodiment of the compounds of formula (I) $R^1$ is benzofusedcycloalkyl.

In another embodiment of the compounds of formula (I) $R^1$ is:

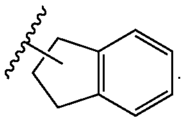

In another embodiment of the compounds of formula (I) $R^1$ is:

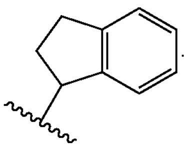 [SMILES: *C1CCc2ccccc21]

In another embodiment of the compounds of formula (I) $R^1$ is:

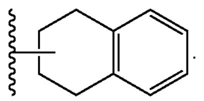

In another embodiment of the compounds of formula (I) $R^1$ is:

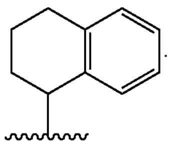 [SMILES: *C1CCCc2ccccc21]

In another embodiment of the compounds of formula (I) $R^1$ is alkyl substituted with one $R^{21}$ group.

In another embodiment of the compounds of formula (I) $R^1$ is alkyl substituted with one $R^{21}$ group, and said alkyl is

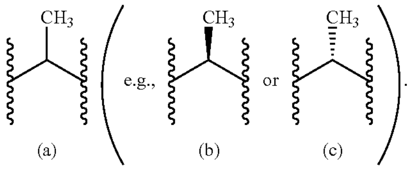

(a) e.g., (b) or (c)

In another embodiment of the compounds of formula (I) $R^1$ is alkyl (e.g., (a), (b) or (c) described above) substituted with one $R^{21}$ group wherein said $R^{21}$ group is aryl.

In another embodiment of the compounds of formula (I) $R^1$ is alkyl (e.g., (a), (b) or (c) described above) substituted with one $R^{21}$ group wherein said $R^{21}$ group is phenyl.

In another embodiment of the compounds of formula (I) $R^1$ is alkyl (e.g., (a), (b) or (c) described above) substituted with one $R^{21}$ group wherein said $R^{21}$ group is naphthyl.

In another embodiment of the compounds of formula (I) $R^1$ is alkyl substituted with one $R^{21}$ group, and said $R^{21}$ group is substituted with two independently selected $R^{22}$ groups.

In another embodiment of the compounds of formula (I) $R^1$ is alkyl substituted with one $R^{21}$ group, and said $R^{21}$ group is substituted with one $R^{22}$ group.

In another embodiment of the compounds of formula (I) $R^1$ is alkyl substituted with one $R^{21}$ group, wherein said alkyl group is (a) (e.g., (b) or (c)), as described above, and said $R^{21}$ group is substituted with two independently selected $R^{22}$ groups.

In another embodiment of the compounds of formula (I) $R^1$ is alkyl substituted with one $R^{21}$ group, wherein said alkyl group is (a) (e.g., (b) or (c)), as described above, and said $R^{21}$ group is substituted with one $R^{22}$ group.

In another embodiment of the compounds of formula (I) $R^1$ is alkyl substituted with one $R^{21}$ group, wherein said $R^{21}$ group is aryl, and said $R^{21}$ group is substituted with two independently selected $R^{22}$ groups.

In another embodiment of the compounds of formula (I) $R^1$ is alkyl substituted with one $R^{21}$ group, wherein said $R^{21}$ group is aryl, and said $R^{21}$ group is substituted with one $R^{22}$ group.

In another embodiment of the compounds of formula (I) $R^1$ is alkyl substituted with one $R^{21}$ group, wherein said $R^{21}$ group is aryl, said alkyl group is (a) (e.g., (b) or (c)), as described above, and said $R^{21}$ group is substituted with two independently selected $R^{22}$ groups.

In another embodiment of the compounds of formula (I) $R^1$ is alkyl substituted with one $R^{21}$ group, wherein said $R^{21}$ group is aryl, wherein said alkyl group is (a) (e.g., (b) or (c)), as described above, and said $R^{21}$ group is substituted with one $R^{22}$ group.

In another embodiment of the compounds of formula (I) $R^1$ is alkyl substituted with one $R^{21}$ group, wherein said $R^{21}$ group is aryl, said $R^{21}$ group is substituted with two independently selected $R^{22}$ groups, and each $R^{22}$ is halo.

In another embodiment of the compounds of formula (I) $R^1$ is alkyl substituted with one $R^{21}$ group, wherein said $R^{21}$ group is aryl, and said $R^{21}$ group is substituted with one $R^{22}$ group, and said $R^{22}$ is halo.

In another embodiment of the compounds of formula (I) $R^1$ is alkyl substituted with one $R^{21}$ group, wherein said $R^{21}$ group is aryl, said alkyl group is (a) (e.g., (b) or (c)), as described above, and said $R^{21}$ group is substituted with two independently selected $R^{22}$ groups, and each $R^{22}$ is halo.

In another embodiment of the compounds of formula (I) $R^1$ is alkyl substituted with one $R^{21}$ group, wherein said $R^{21}$ group is aryl, wherein said alkyl group is (a) (e.g., (b) or (c)), as described above, and said $R^{21}$ group is substituted with one $R^{22}$ group. and said $R^{22}$ is halo.

In another embodiment of the compounds of formula (I) $R^1$ is alkyl substituted with one $R^{21}$ group, wherein said $R^{21}$ group is aryl, said $R^{21}$ group is substituted with two independently selected $R^{22}$ groups, and each $R^{22}$ is F.

In another embodiment of the compounds of formula (I) $R^1$ is alkyl substituted with one $R^{21}$ group, wherein said $R^{21}$ group is aryl, and said $R^{21}$ group is substituted with one $R^{22}$ group, and said $R^{22}$ is F.

In another embodiment of the compounds of formula (I) $R^1$ is alkyl substituted with one $R^{21}$ group, wherein said $R^{21}$ group is aryl, said alkyl group is (a) (e.g., (b) or (c)), as described above, and said $R^{21}$ group is substituted with two independently selected $R^{22}$ groups, and each $R^{22}$ is F.

In another embodiment of the compounds of formula (I) $R^1$ is alkyl substituted with one $R^{21}$ group, wherein said $R^{21}$ group is aryl, wherein said alkyl group is (a) (e.g., (b) or (c)), as described above, and said $R^{21}$ group is substituted with one $R^{22}$ group. and said $R^{22}$ is F.

In another embodiment of the compounds of formula (I) $R^1$ is:

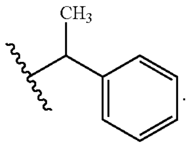 [SMILES: *C(C)c1ccccc1]

In another embodiment of the compounds of formula (I) $R^1$ is:

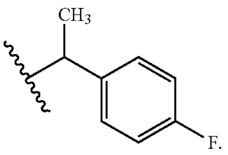 [SMILES: *C(C)c1ccc(F)cc1]

In another embodiment of the compounds of formula (I) $R^1$ is:

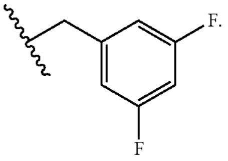 [SMILES: *Cc1cc(F)cc(F)c1]

In another embodiment of the compounds of formula (I) $R^1$ is:

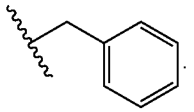

In another embodiment of the compounds of formula (I) $R^1$ is:

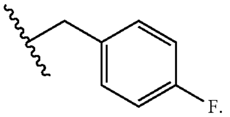

In another embodiment of the compounds of formula (I) $R^1$ is:

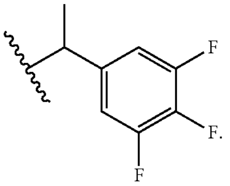

In another embodiment of the compounds of formula (I) $R^1$ is:

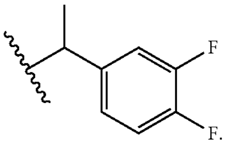 [SMILES: *C(C)c1ccc(F)c(F)c1]

In another embodiment of the compounds of formula (I) $R^1$ is:

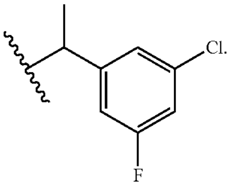 [SMILES: *C(C)c1cc(F)cc(Cl)c1]

In another embodiment of the compounds of formula (I) $R^1$ is:

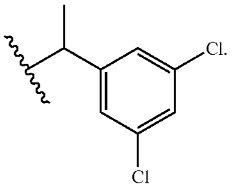 [SMILES: *C(C)c1cc(Cl)cc(Cl)c1]

In another embodiment of the compounds of formula (I) $R^1$ is:

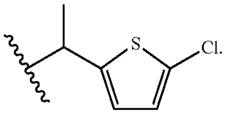 [SMILES: *C(C)c1ccc(Cl)s1]

In another embodiment of the compounds of formula (I) $R^1$ is:

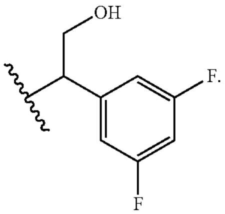 [SMILES: *C(CO)c1cc(F)cc(F)c1]

In another embodiment of the compounds of formula (I) $R^1$ is:

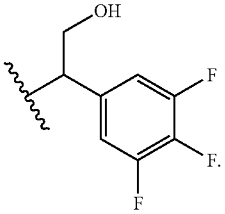 [SMILES: *C(CO)c1cc(F)c(F)c(F)c1]

In another embodiment of the compounds of formula (I) $R^1$ is:

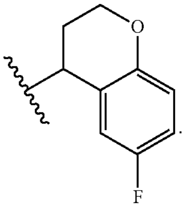 [SMILES: *C1CCOc2ccc(F)cc21]

In another embodiment of the compounds of formula (I) $R^1$ is:

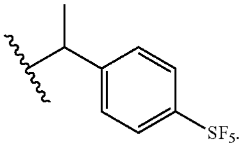

In another embodiment of the compounds of formula (I) $R^1$ is:

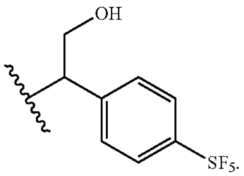

In another embodiment of the compounds of formula (I) $R^1$ is:

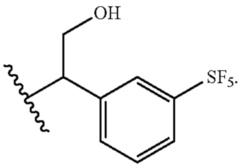

In another embodiment of the compounds of formula (I) $R^1$ is:

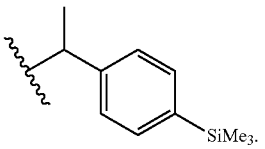

In another embodiment of the compounds of formula (I) $R^1$ is:

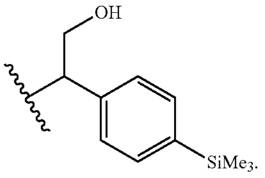

In another embodiment of the compounds of formula (I) $R^1$ is:

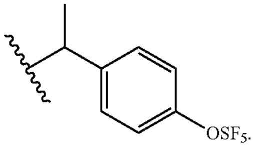

In another embodiment of the compounds of formula (I) $R^1$ is:

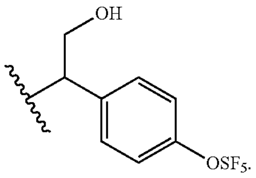

In another embodiment of the compounds of formula (I) $R^1$ is:

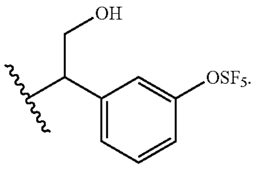

In another embodiment of the compounds of formula (I) $R^1$ is:

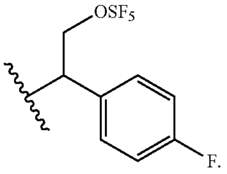

In another embodiment of this invention the compound of formula (I) is a compound of the formula:

(IA)

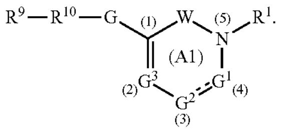

In another embodiment of this invention the compound of formula (I) is a compound of the formula:

(IA)

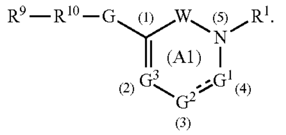

wherein the optional bond is absent, i.e., the compound of formula (IA) is:

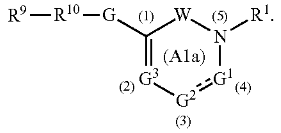

In another embodiment of this invention the compound of formula (I) is a compound of the formula:

(IB)

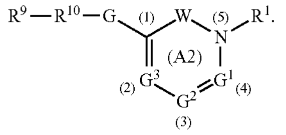

In another embodiment of this invention the compound of formula (I) is a compound of the formula:

(IC)

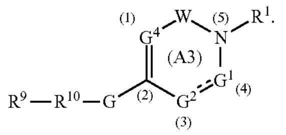

In another embodiment of this invention the compound of formula (I) is a compound of the formula:

(IC)

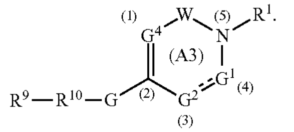

wherein the optional bond is absent, i.e., the compound of formula (IC) is:

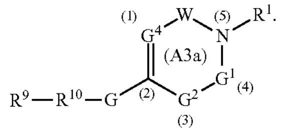

In another embodiment of this invention the compound of formula (I) is a compound of the formula:

(ID)

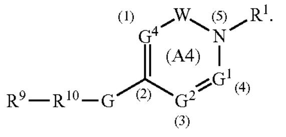

In another embodiment of this invention the compound of formula (I) is a compound of the formula:

(IE)

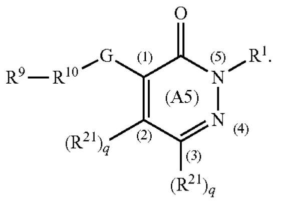

wherein each q is independently 0 or 1, and each $R^{21}$ is independently selected.

In another embodiment of this invention the compound of formula (I) is a compound of the formula (IE) wherein: (a) $R^{21}$ at position (2) is —$OR^{15}$, and q at (3) is 0, or (b) $R^{21}$ at position (3) is —$OR^{15}$, and q at (2) is 0, or (c) q at positions (2) and (3) is 0.

In another embodiment of this invention the compound of formula (I) is a compound of the formula (IE) wherein: (a) $R^{21}$ at position (2) is —$OR^{15}$ and $R^{15}$ is alkyl, and q at position (3) is 0, or (b) $R^{21}$ at position (3) is —$OR^{15}$ and $R^{15}$ is alkyl, and q at position (2) is 0, or (c) q at positions (2) and (3) is 0.

In another embodiment of this invention the compound of formula (I) is a compound of the formula (IE) wherein: (a) $R^{21}$ at position (2) is —$OR^{15}$ and $R^{15}$ is alkyl, and q at position (3) is 0, or (b) $R^{21}$ at position (3) is —$OR^{15}$ and $R^{15}$ is alkyl, and q at position (2) is 0, or (c) q at positions (2) and (3) is 0, and (d) said $R^{15}$ alkyl groups are methyl or ethyl.

In another embodiment of this invention the compound of formula (I) is a compound of the formula (IE) wherein: (a) q at position (2) is 0, (b) $R^{21}$ at position (3) is —$OR^{15}$ wherein $R^{15}$ is selected from the group consisting of: alkyl, cycloalkylalkyl, and -alkyl-$(R^{18})_n$, and wherein said $R^{18}$ is —$OR^{20}$, and said $R^{20}$ is alkyl. Examples of said $R^{21}$ moiety include but are not limited to: —$OCH_3$, —$OCH_2CH_3$, —$O(CH_2)_2OCH_3$, and —$CH_2$-cyclopropyl.

In another embodiment of this invention the compound of formula (I) is a compound of the formula (IE) wherein: G is selected from the group consisting of: —NH—, and a direct bond.

The In another embodiment of this invention the compound of formula (I) is a compound of the formula (IE) wherein: (a) $R^{21}$ at (2) is —$OR^{15}$, and q at (3) is 0, or (b) $R^{21}$ at (3) is —$OR^{15}$, and q at (2) is 0, or (c) q at (2) and (3) is 0, and (d) G is selected from the group consisting of: —NH—, and a direct bond.

In another embodiment of this invention the compound of formula (I) is a compound of the formula (IE) wherein: (a) q at position (2) is 0, and (b) $R^{21}$ at position (3) is —$OR^{15}$ wherein $R^{15}$ is selected from the group consisting of: alkyl, cycloalkylalkyl, and -alkyl-$(R^{18})_n$, and wherein said $R^{18}$ is —$OR^{20}$, and said $R^{20}$ is alkyl, and (c) G is selected from the group consisting of: —NH—, and a direct bond. Examples of said $R^{21}$ moiety include but are not limited to: —$OCH_3$, —$O(CH_2)_2OCH_3$, and —$CH_2$-cyclopropyl.

In another embodiment of this invention the compound of formula (I) is a compound of the formula (IE) wherein: (a) $R^{21}$ at (2) is —$OR^{15}$, and q at (3) is 0, or (b) $R^{21}$ at (3) is —$OR^{15}$, and q at (2) is 0, or (c) q at (2) and (3) is 0, and (d) G is selected from the group consisting of: —NH—, and a direct bond, and (e) said $R^{15}$ is alkyl.

The In another embodiment of this invention the compound of formula (I) is a compound of the formula (IE) wherein: (a) $R^{21}$ at (2) is —$OR^{15}$, and q at (3) is 0, or (b) $R^{21}$ at (3) is —$OR^{15}$, and q at (2) is 0, or (c) q at (2) and (3) is 0, and (d) G is selected from the group consisting of: —NH—, and a direct bond, and (e) said $R^{15}$ is methyl or ethyl.

In another embodiment of this invention the compound of formula (I) is a compound of the formula (IE) wherein: (a) G is selected from the group consisting of: —NH—, and a direct bond, and (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IE) wherein: (a) q at position (2) is 0, and (b) $R^{21}$ at position (3) is —$OR^{15}$ wherein $R^{15}$ is selected from the group consisting of: alkyl, cycloalkylalkyl, and -alkyl-$(R^{18})_n$, and wherein said $R^{18}$ is —$OR^{29}$, and said $R^{29}$ is alkyl, (c) G is selected from the group consisting of: —NH—, and a direct bond, (d) $R^1$ is a methyl or ethyl group substituted with one phenyl, or (e) $R^1$ is an methyl or ethyl group substituted with one phenyl, and said phenyl is substituted with one or two F, (f) $R^{10}$ is phenyl substituted with one —$OR^{15}$ group, wherein $R^{15}$ is methyl, and (g) $R^9$ is selected from the group consisting of imidazolyl and imidazolyl substituted with one methyl group. Examples of said $R^{21}$ moiety include but are not limited to: —$OCH_3$, —$O(CH_2)_2OCH_3$, and —$CH_2$-cyclopropyl.

In another embodiment of this invention the compound of formula (I) is a compound of the formula (IE) wherein: (a) G is selected from the group consisting of: —NH—, and a direct bond, and (b) $R^1$ is selected from the group consisting of:

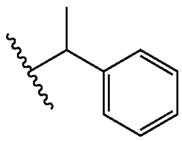
,
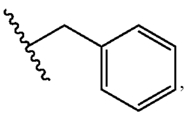
,

-continued
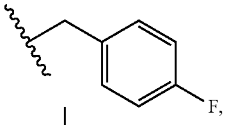
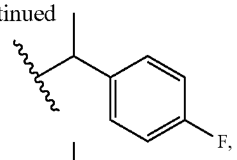
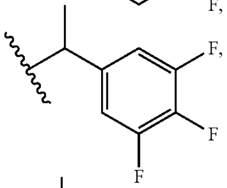
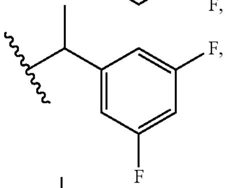
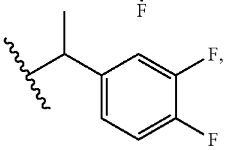
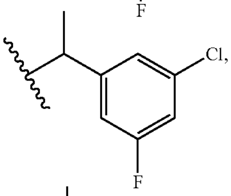
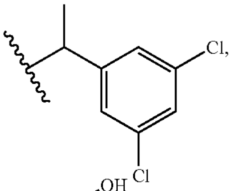
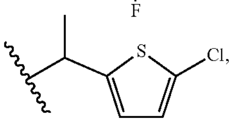
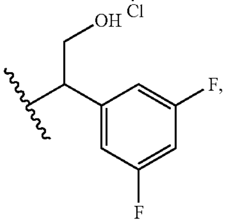
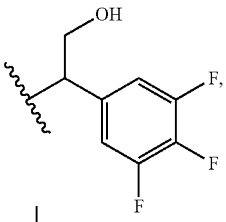
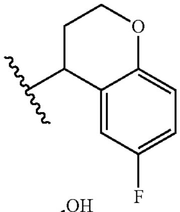
,
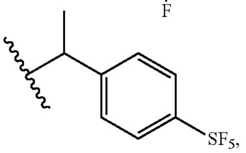
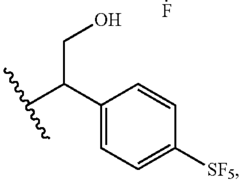
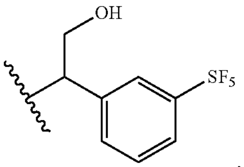
,
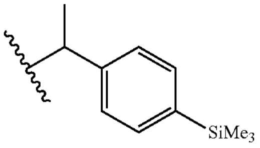
and
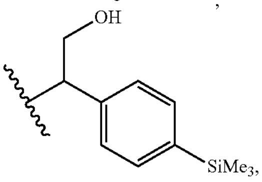
and
wherein the $R^9$-$R^{10}$— moiety is:
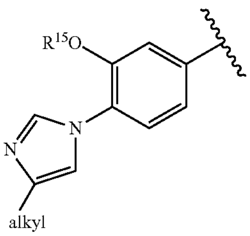
or
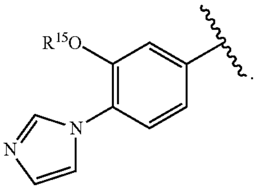
.
In another embodiment of this invention the compound of formula (I) is a compound of the formula (IE) wherein: (a) G is selected from the group consisting of: —NH—, and a direct bond, and (b) $R^1$ is selected from the group consisting of:
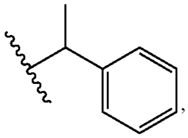
,
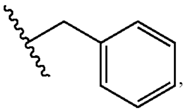
,
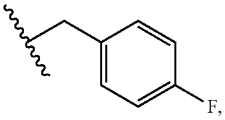
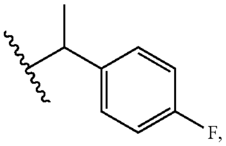
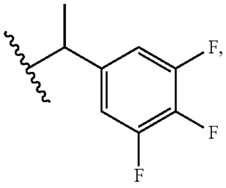
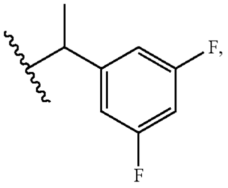
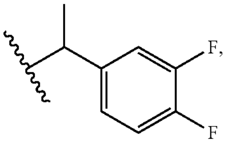
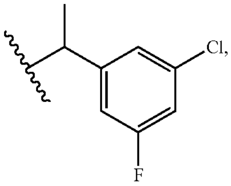
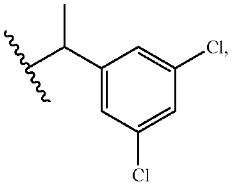
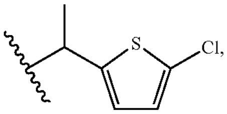
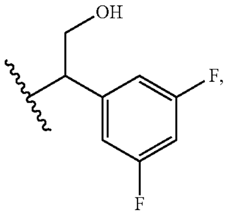
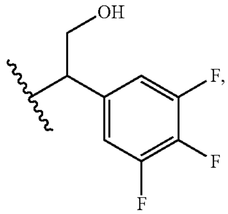
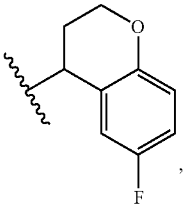
,
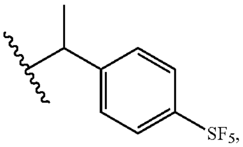
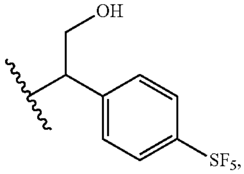
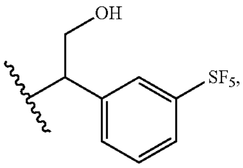

-continued

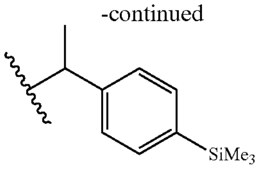

and

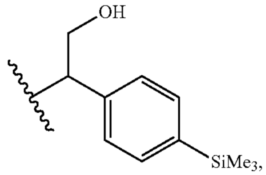

and wherein the $R^9$-$R^{10}$— moiety is:

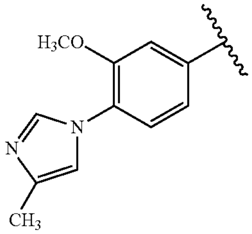

or

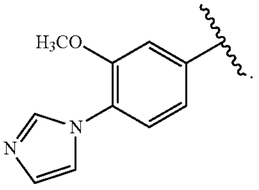

In another embodiment of this invention the compound of formula (I) is a compound of the formula (IE) wherein: (a) G is selected from the group consisting of: —NH—, and a direct bond, and (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^{21}$ at position (2) is —$OR^{15}$, and $R^{15}$ is alkyl, and q for the $R^{21}$ at position (3) is 0, or (g) $R^{21}$ at position (3) is —$OR^{15}$, and $R^{15}$ is alkyl, and q for the $R^{21}$ at position (2) is 0, or (h) q at positions (2) and (3) is 0.

In another embodiment of this invention the compound of formula (I) is a compound of the formula (IE1):

(IE1)

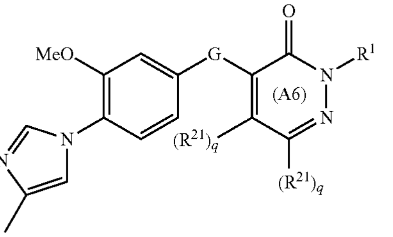

wherein each q is independently 0 or 1, and each $R^{21}$ is independently selected.

In another embodiment of this invention the compound of formula (I) is a compound of the formula (IF):

(IF)

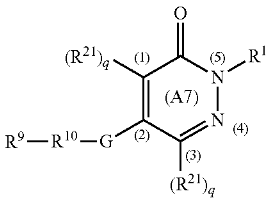

wherein each q is independently 0 or 1, and each $R^{21}$ is independently selected.

In another embodiment of this invention the compound of formula (I) is a compound of the formula (IF) wherein $R^{21}$ at position (3) is —$OR^{15}$ and q at position (1) is 0, or wherein q at positions (1) and (3) are 0.

In another embodiment of this invention the compound of formula (I) is a compound of the formula (IF) wherein $R^{21}$ at position (3) is —$OR^{15}$ and q at position (1) is 0, or wherein q at positions (1) and (3) are 0, and wherein $R^{15}$ is alkyl.

In another embodiment of this invention the compound of formula (I) is a compound of the formula (IF) wherein $R^{21}$ at position (3) is —$OR^{15}$ and q at position (1) is 0, or wherein q at positions (1) and (3) are 0, and wherein $R^{15}$ is methyl or ethyl.

In another embodiment of this invention the compound of formula (I) is a compound of the formula (IF) wherein: (a) q at position (1) is 0, (b) $R^{21}$ at position (3) is —$OR^{15}$ wherein $R^{15}$ is selected from the group consisting of: alkyl, cycloalkylalkyl, and -alkyl-$(R^{18})_n$, and wherein said $R^{15}$ is —$OR^{20}$, and said $R^{20}$ is alkyl. Examples of said $R^{21}$ moiety include but are not limited to: —$OCH_3$, —$OCH_2CH_3$, —$O(CH_2)_2OCH_3$, and —$CH_2$-cyclopropyl.

In another embodiment of this invention the compound of formula (I) is a compound of the formula (IF) wherein G is selected from the group consisting of: —NH—, and a direct bond.

In another embodiment of this invention the compound of formula (I) is a compound of the formula (IF) wherein: (a) G is selected from the group consisting of: —NH—, and a direct bond, and (b) wherein $R^{21}$ at position (3) is —$OR^{15}$ and q at position (1) is 0, or wherein q at positions (1) and (3) are 0.

In another embodiment of this invention the compound of formula (I) is a compound of the formula (IF) wherein: (a) q at position (1) is 0, and (b) $R^{21}$ at position (3) is —$OR^{15}$ wherein $R^{15}$ is selected from the group consisting of: alkyl, cycloalkylalkyl, and -alkyl-$(R^{15})_n$, and wherein said $R^{18}$ is —$OR^{20}$, and said $R^{20}$ is alkyl, and (c) G is selected from the group consisting of: —NH—, and a direct bond. Examples of said $R^{21}$ moiety include but are not limited to: —$OCH_3$, —$O(CH_2)_2OCH_3$, and —$CH_2$-cyclopropyl.

In another embodiment of this invention the compound of formula (I) is a compound of the formula (IF) wherein: (a) G is selected from the group consisting of: —NH—, and a direct bond, and (b) wherein $R^{21}$ at position (3) is —$OR^{15}$ and q at position (1) is 0, or wherein q at positions (1) and (3) are 0, and (c) wherein $R^{15}$ is alkyl.

In another embodiment of this invention the compound of formula (I) is a compound of the formula (IF) wherein: (a) G is selected from the group consisting of: —NH—, and a direct bond, and (b) wherein $R^{21}$ at position (3) is —$OR^{15}$ and q at position (1) is 0, or wherein q at positions (1) and (3) are 0, and (c) wherein $R^{15}$ is methyl or ethyl.

In another embodiment of this invention the compound of formula (I) is a compound of the formula (IF) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IF) wherein: (a) q at position (1) is 0, and (b) $R^{21}$ at position (3) is —$OR^{15}$ wherein $R^{15}$ is selected from the group consisting of: alkyl, cycloalkylalkyl, and -alkyl-$(R^{18})_n$, and wherein said $R^{18}$ is —$OR^{29}$, and said $R^{29}$ is alkyl, (c) G is selected from the group consisting of: —NH—, and a direct bond, (d) $R^1$ is a methyl or ethyl group substituted with one phenyl, or (e) $R^1$ is an methyl or ethyl group substituted with one phenyl, and said phenyl is substituted with one or two F, (f) $R^{10}$ is phenyl substituted with one —$OR^{15}$ group, wherein $R^{15}$ is methyl, and (g) $R^9$ is selected from the group consisting of imidazolyl and imidazolyl substituted with one methyl group. Examples of said $R^{21}$ moiety include but are not limited to: —$OCH_3$, —$O(CH_2)_2OCH_3$, and —$CH_2$-cyclopropyl.

In another embodiment of this invention the compound of formula (I) is a compound of the formula (IF) wherein G is selected from the group consisting of: —NH—, and a direct bond, and $R^1$ is selected from the group consisting of:

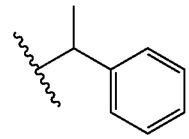,
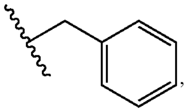,
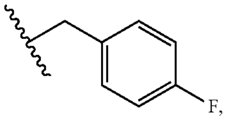
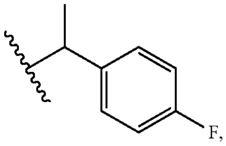
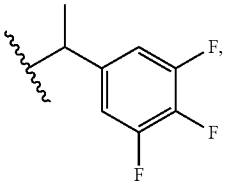
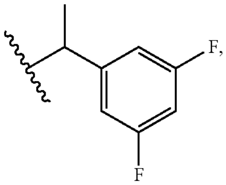
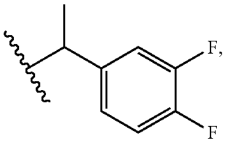
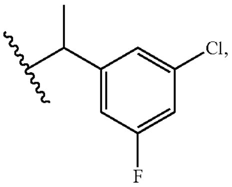
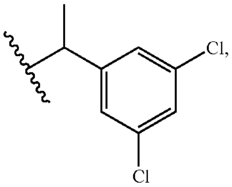
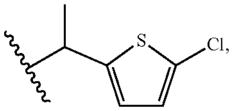
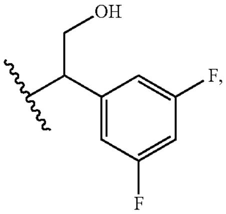
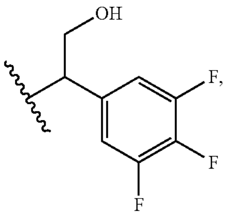
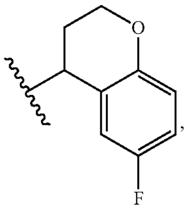,
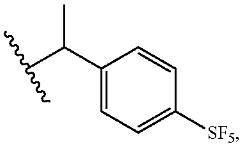
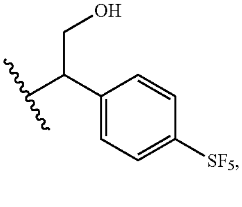
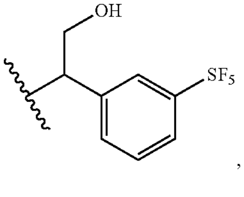, -continued

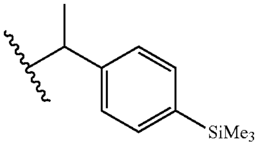 and
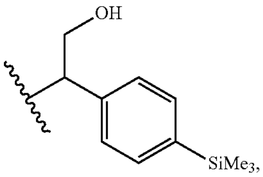

and wherein the $R^9$-$R^{10}$— moiety is:

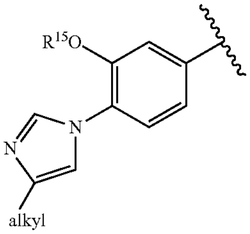 or
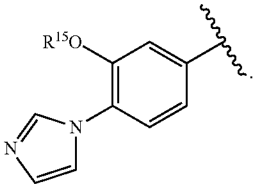

In another embodiment of this invention the compound of formula (I) is a compound of the formula (IF) wherein: G is selected from the group consisting of: —NH—, and a direct bond, and wherein $R^1$ is selected from the group consisting of:

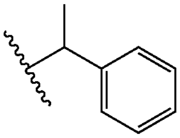,
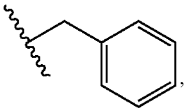,
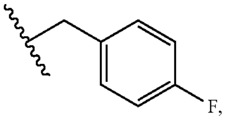
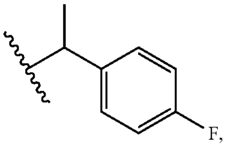
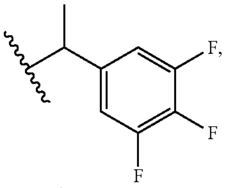
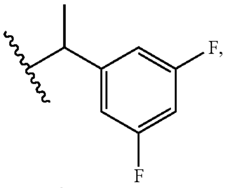
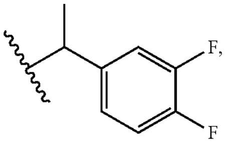
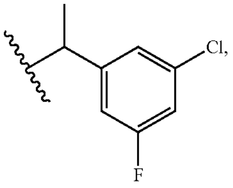
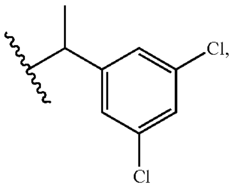
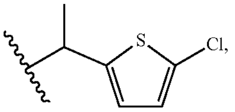
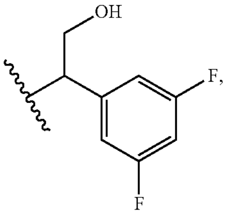
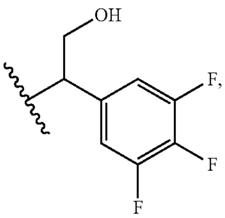

-continued

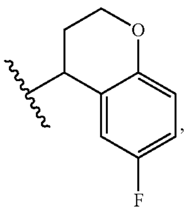,

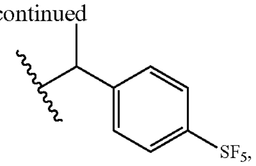

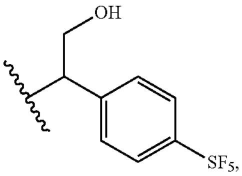

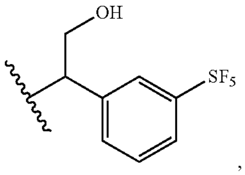,

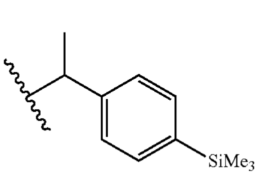 and

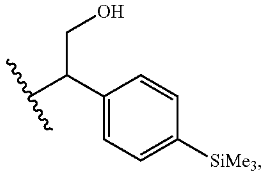

and wherein the $R^9$-$R^{10}$— moiety is:

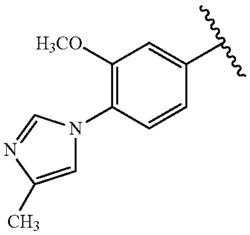 or

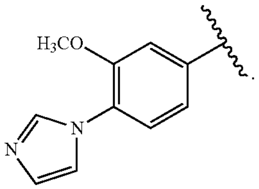.

In another embodiment of this invention the compound of formula (I) is a compound of the formula (IF) wherein: (a) G is selected from the group consisting of: —NH—, and a direct bond, (b) $R^1$ is a methyl or ethyl group substituted with one phenyl, or (c) is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^{21}$ at position (3) is —$OR^{15}$, and $R^{15}$ is alkyl, and q for the $R^{21}$ at position (1) is 0, or wherein q at positions (1) and (3) are 0.

In another embodiment of this invention the compound of formula (I) is a compound of the formula (IF1):

(IF1)

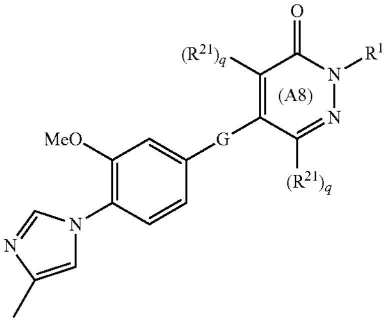

wherein each q is independently 0 or 1, and each $R^{21}$ is independently selected.

In another embodiment of this invention the compound of formula (I) is a compound of the formula:

(IG)

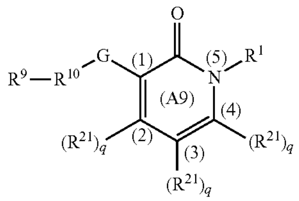

wherein each q is independently 0 or 1, and each $R^{21}$ is independently selected.

In another embodiment of this invention the compound of formula (I) is a compound of the formula (IG) wherein: (a) q at positions (2) and (4) is 0, and $R^{21}$ at (3) is —$C(O)OR^{15}$, or (b) q at positions (2) and (4) is 0, and $R^{21}$ at (3) is —$C(O)NR^{15}R^{16}$, or (c) q at positions (2), (3) and (4) is 0.

In another embodiment of this invention the compound of formula (I) is a compound of the formula (IG) wherein: (a) q at positions (2) and (4) is 0, and $R^{21}$ at (3) is —$C(O)OR^{15}$, or (b) q at positions (2) and (4) is 0, and $R^{21}$ at (3) is —$C(O)NR^{15}R^{16}$, or (c) q at positions (2), (3) and (4) is 0, and (c) $R^{15}$ is alkyl in said —$C(O)OR^{15}$ group, and in said —$C(O)NR^{15}R^{16}$ group one of $R^{15}$ or $R^{16}$ is H, and the other is selected from the group consisting of: $(R^{18})_n$-arylalkyl-, $(R^{18})_n$-alkyl-, and cycloalkyl.

In another embodiment of this invention the compound of formula (I) is a compound of the formula (IG) wherein: (a) q at positions (2) and (4) is 0, and $R^{21}$ at (3) is —$C(O)OR^{15}$, or (b) q at positions (2) and (4) is 0, and $R^{21}$ at (3) is —$C(O)NR^{15}R^{16}$, or (c) q at positions (2), (3) and (4) is 0, and (c) $R^{15}$ is alkyl in said —$C(O)OR^{15}$ group, and in said —$C(O)NR^{15}R^{16}$ group one of $R^{15}$ or $R^{16}$ is H, and the other is selected from the group consisting of: $(R^{18})_n$-arylalkyl-, $(R^{18})_n$-alkyl-, and cycloalkyl, and (d) said $R^{15}$ alkyl group in said —$C(O)OR^{15}$ group is methyl, and (e) in said —$C(O)NR^{15}R^{16}$ group the $R^{18}$ is —$OR^{20}$, n is 1, $R^{20}$ is alkyl, said cycloalkyl is cyclobutyl, and said arylalkyl- is benzyl.

In another embodiment of this invention the compound of formula (I) is a compound of the formula (IG) wherein G is selected from the group consisting of: —NH—, and a direct bond.

In another embodiment of this invention the compound of formula (I) is a compound of the formula (IG) wherein: (a) G is selected from the group consisting of: —NH—, and a direct bond, (b) q at positions (2) and (4) is 0, and $R^{21}$ at position (3) is —$C(O)OR^{15}$, or (c) q at positions (2) and (4) is 0, and $R^{20}$ at position (3) is —$C(O)NR^{15}R^{16}$, or (d) q at positions (2), (3) and (4) is 0.

In another embodiment of this invention the compound of formula (I) is a compound of the formula (IG) wherein: (a) G is selected from the group consisting of: —NH—, and a direct bond, (b) q at positions (2) and (4) is 0, and $R^{21}$ at position (3) is —$C(O)OR^{15}$, or (c) q at positions (2) and (4) is 0, and $R^{21}$ at position (3) is —$C(O)NR^{15}R^{16}$, or (d) q at positions (2), (3) and (4) is 0, (e) $R^{15}$ is alkyl in said —$C(O)OR^{15}$ group, and (f) in said —$C(O)NR^{15}R^{16}$ group one of $R^{15}$ or $R^{16}$ is H, and the other is selected from the group consisting of: $(R^{18})_n$-arylalkyl-, $(R^{18})_n$-alkyl-, and cycloalkyl.

In another embodiment of this invention the compound of formula (I) is a compound of the formula (IG) wherein: (a) G is selected from the group consisting of: —NH—, and a direct bond, (b) q at positions (2) and (4) is 0, and $R^{21}$ at position (3) is —$C(O)OR^{15}$, or (c) q at positions (2) and (4) is 0, and $R^{21}$ at position (3) is —$C(O)NR^{15}R^{16}$, or (d) q at positions (2), (3) and (4) is 0, (e) said $R^{15}$ alkyl group in said —$C(O)OR^{15}$ group is methyl, and (f) in said —C(O)NR$^{15}$R$^{16}$ group the R$^{18}$ is —OR$^{20}$, n is 1, R$^{20}$ is alkyl, said cycloalkyl is cyclobutyl, and said arylalkyl- is benzyl.

In another embodiment of this invention the compound of formula (I) is a compound of the formula (IG) wherein: (a) G is selected from the group consisting of: —NH—, and a direct bond, (b) R$^1$ is a methyl or ethyl group substituted with one phenyl, or (c) R$^1$ is an methyl or ethyl group substituted with one phenyl, and said phenyl is substituted with one or two F, and (d) R$^{10}$ is phenyl substituted with one —OR$^{15}$ group, wherein R$^{15}$ is methyl, and (e) R$^9$ is selected from the group consisting of imidazolyl and imidazolyl substituted with one methyl group.

In another embodiment of this invention the compound of formula (I) is a compound of the formula (IG) wherein: (a) G is selected from the group consisting of: —NH—, and a direct bond, and R$^1$ is selected from the group consisting of:

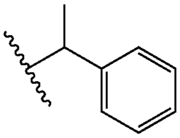,
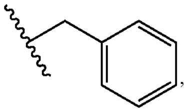,
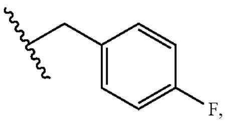
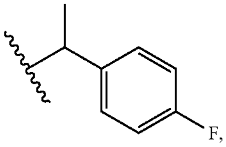
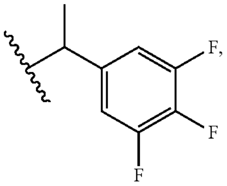
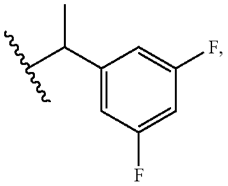
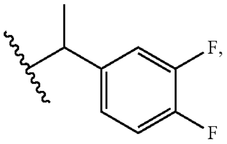
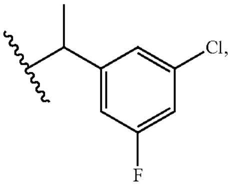
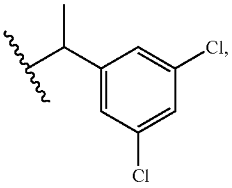
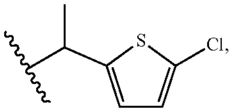
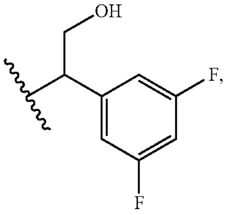
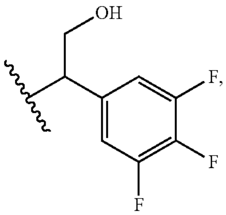
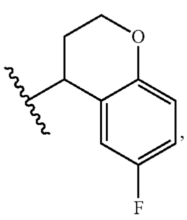,
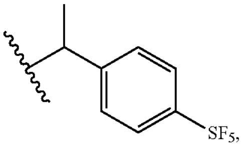

-continued

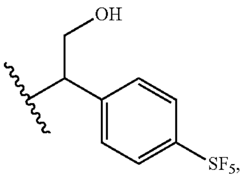
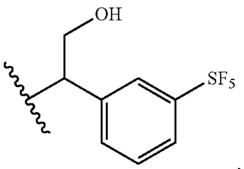,
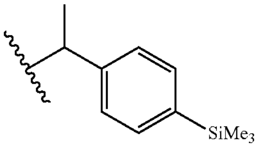 and
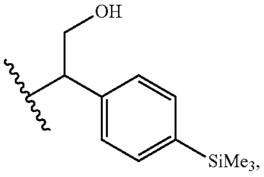

and wherein the R$^9$-R$^{10}$— moiety is:

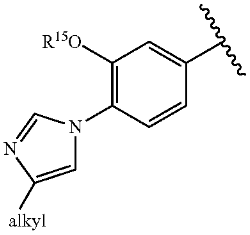
or
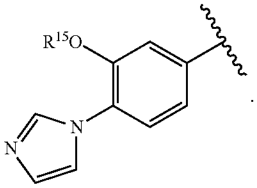.

In another embodiment of this invention the compound of formula (I) is a compound of the formula (IG) wherein: (a) G is selected from the group consisting of: —NH—, and a direct bond, and R$^1$ is selected from the group consisting of:

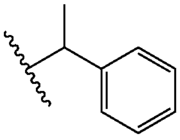,
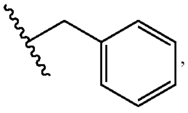,
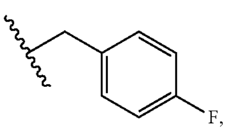
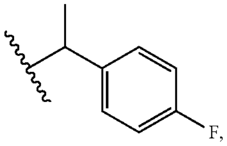
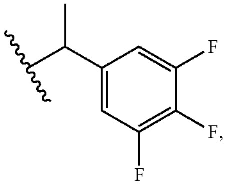
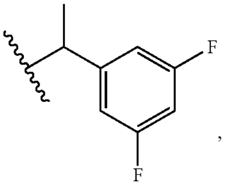,
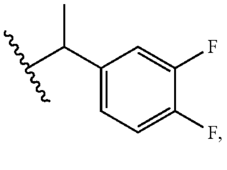
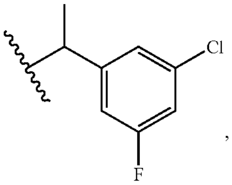, -continued

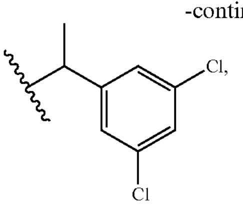

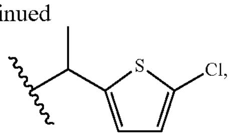

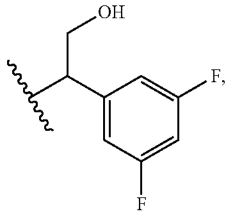

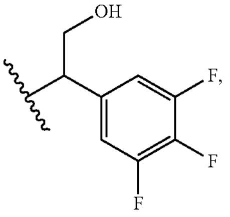

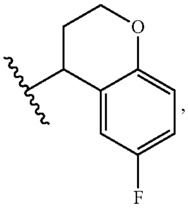

,

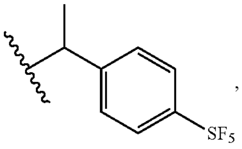

,

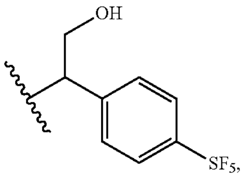

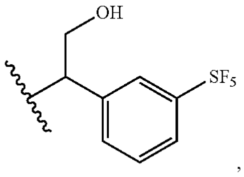

,

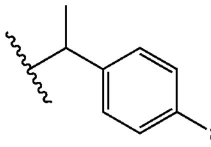

and

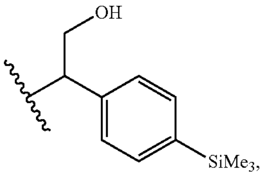

and wherein the $R^9$-$R^{10}$— moiety is

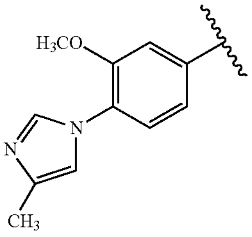

or

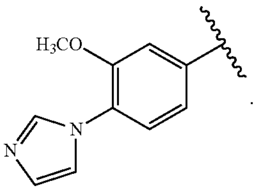

.

In another embodiment of this invention the compound of formula (I) is a compound of the formula (IG) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, (f) q at positions (2) and (4) is 0, and $R^{21}$ at position (3) is —C(O)$OR^{15}$, or (g) q at positions (2) and (4) is 0, and $R^{21}$ at position (3) is —C(O)$NR^{15}R^{16}$, or (h) q at positions (2), (3) and (4) is 0.

In another embodiment of this invention the compound of formula (I) is a compound of the formula (IG) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, (f) q at positions (2) and (4) is 0, and $R^{21}$ at position (3) is —C(O)$OR^{15}$, or (g) q at positions (2) and (4) is 0, and $R^{21}$ at position (3) is —C(O)$NR^{15}R^{16}$, or (h) q at positions (2), (3) and (4) is 0, (i) $R^{15}$ is alkyl in said —C(O)$OR^{15}$ group, and (j) in said —C(O)$NR^{15}R^{16}$ group one of $R^{15}$ or $R^{16}$ is H, and the other is selected from the group consisting of: $(R^{18})_n$-arylalkyl-, $(R^{18})_n$-alkyl-, and cycloalkyl.

In another embodiment of this invention the compound of formula (I) is a compound of the formula (IG1):

(IG1)

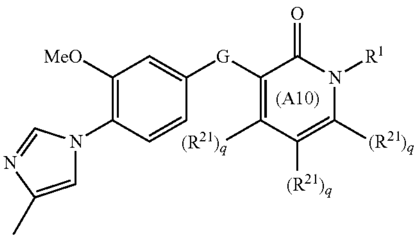

wherein each q is independently 0 or 1, and each $R^{21}$ is independently selected.

In another embodiment of this invention the compound of formula (I) is a compound of the formula (IH):

(IH)

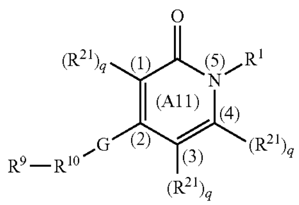

wherein each q is independently 0 or 1, and each $R^{21}$ is independently selected.

In another embodiment of this invention the compound of formula (I) is a compound of the formula (IH) wherein G is selected from the group consisting of: —NH—, and a direct bond.

In another embodiment of this invention the compound of formula (I) is a compound of the formula (IH) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IH) wherein: G is selected from the group consisting of: —NH—, and a direct bond, and wherein $R^1$ is selected from the group consisting of:

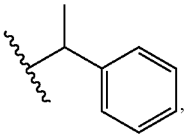,
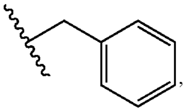,
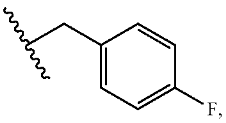
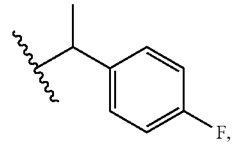
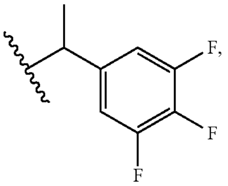
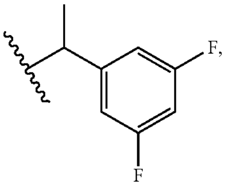
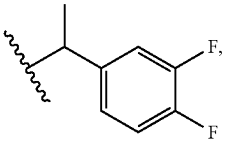
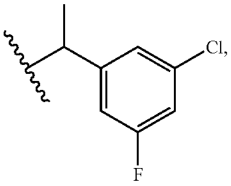
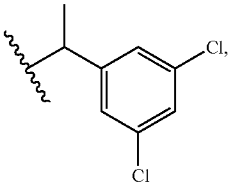
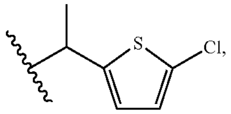
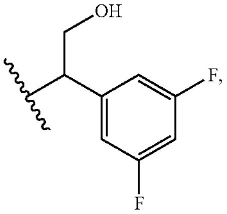
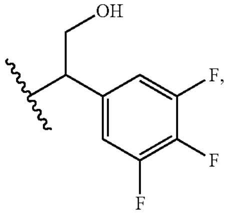
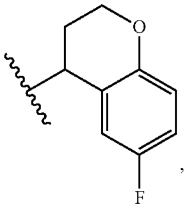,
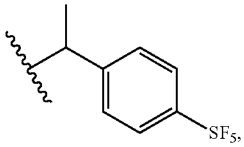
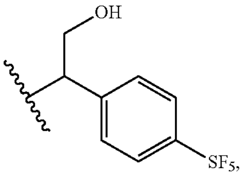
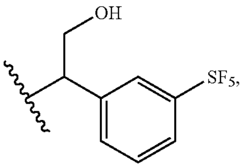

-continued

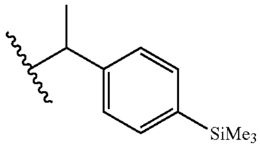 and

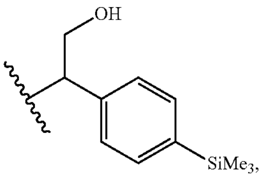

and wherein the $R^9$-$R^{10}$— moiety is:

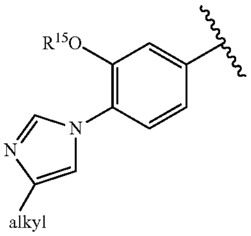 or

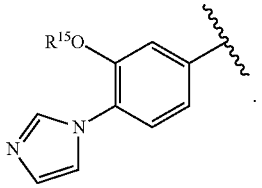

In another embodiment of this invention the compound of formula (I) is a compound of the formula (IH) wherein G is selected from the group consisting of: —NH—, and a direct bond, and wherein $R^1$ is selected from the group consisting of:

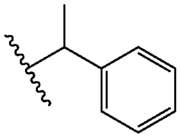,
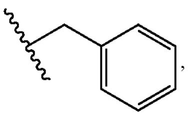,
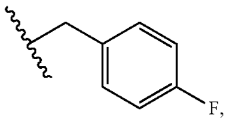
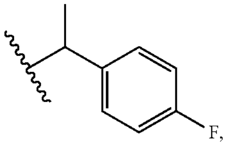
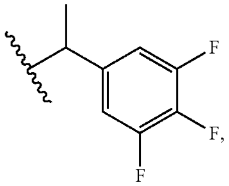
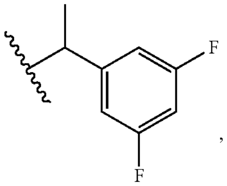
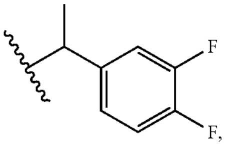
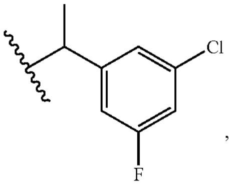

-continued

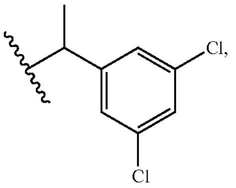

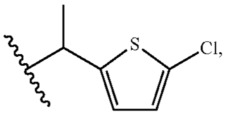

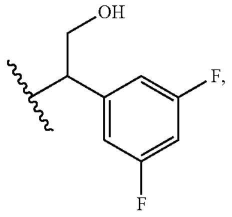

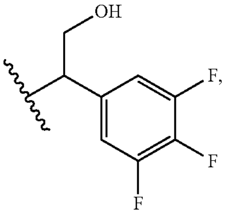

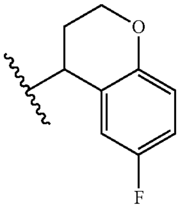

,

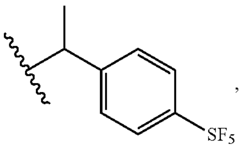

,

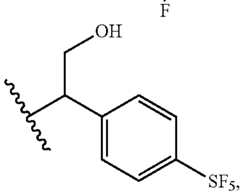

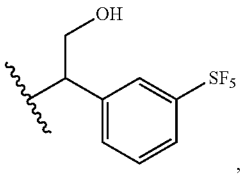

,

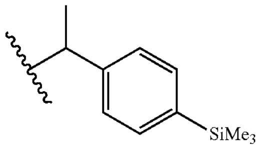

and

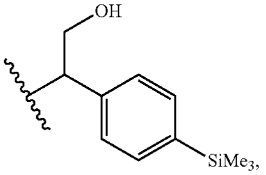

and wherein the $R^9$-$R^{10}$— moiety is:

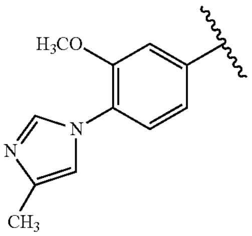

or

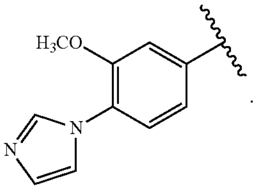

.

In another embodiment of this invention the compound of formula (I) is a compound of the formula (IH) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) q at positions (1) and (4) is 0, and $R^{21}$ at position (3) is —C(O)$OR^{15}$, or (g) q at positions (1) and (4) is 0, and $R^{21}$ at position (3) is —C(O)$NR^{15}R^{16}$, or (h) q at positions (1), (3) and (4) is 0.

In another embodiment of this invention the compound of formula (I) is a compound of the formula (IH) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^{15}$ is alkyl in said —C(O)$OR^{15}$ group, and (g) in said —C(O)$NR^{15}R^{16}$ group one of $R^{15}$ or $R^{16}$ is H, and the other is selected from the group consisting of: $(R^{18})_n$-arylalkyl-, $(R^{18})_n$-alkyl-, and cycloalkyl.

In another embodiment of this invention the compound of formula (I) is a compound of the formula (IH1):

(IH1)

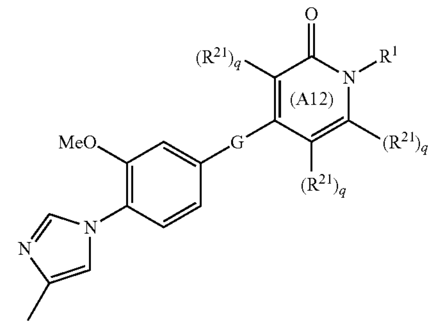

wherein each q is independently 0 or 1, and each $R^{21}$ is independently selected.

In another embodiment of this invention the compound of formula (I) is a compound of the formula:

(IJ)

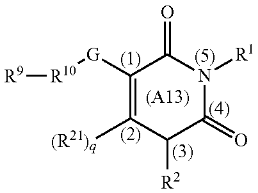

wherein q is 0 or 1.

In another embodiment of this invention the compound of formula (I) is a compound of the formula (IJ) wherein G is selected from the group consisting of: —NH—, and a direct bond.

In another embodiment of this invention the compound of formula (I) is a compound of the formula (IJ) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IJ) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

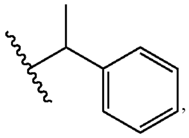
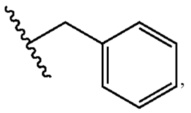
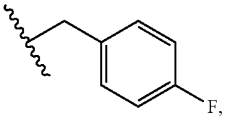
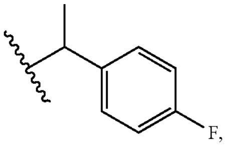
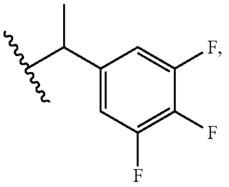
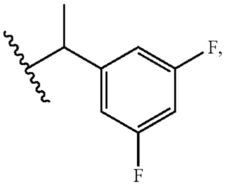
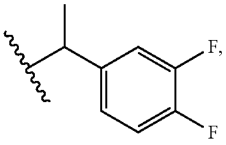
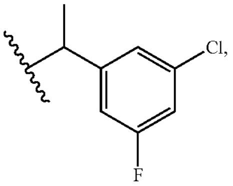
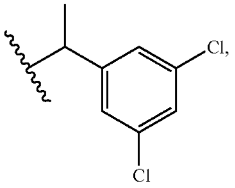
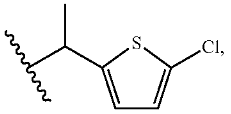
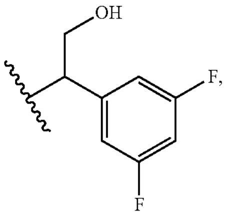
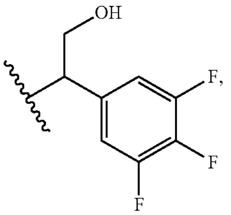
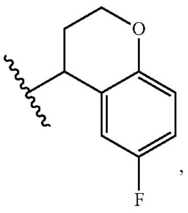
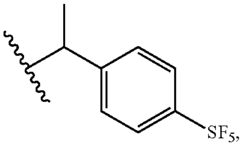
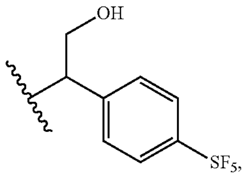
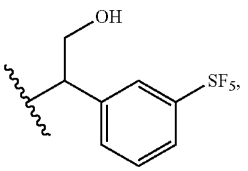

-continued

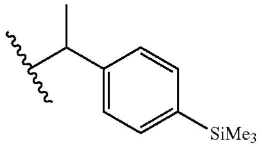
and
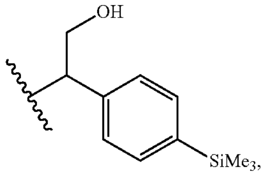

and wherein the $R^9$-$R^{10}$— moiety is:

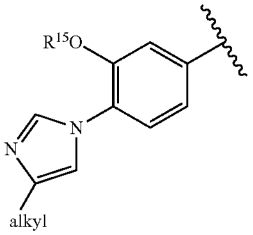
or
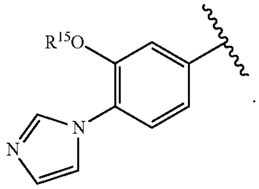

In another embodiment of this invention the compound of formula (I) is a compound of the formula (IJ) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

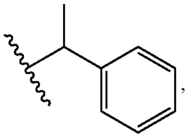
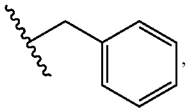
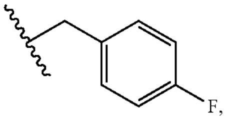
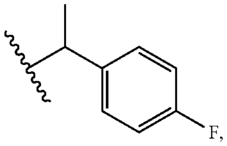
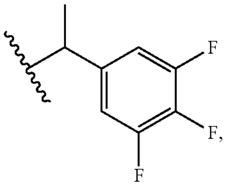
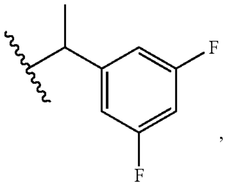

-continued

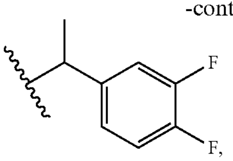
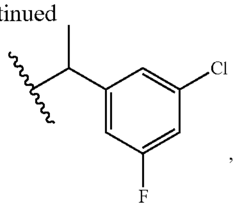
,
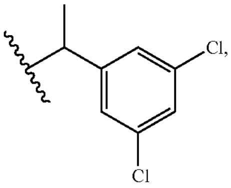
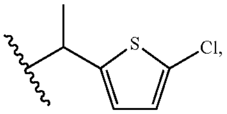
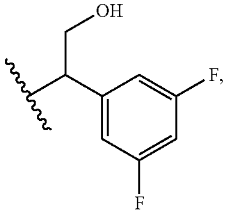
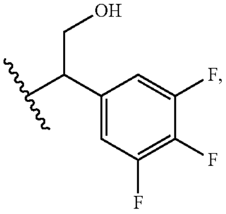
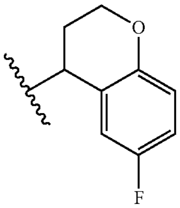
,
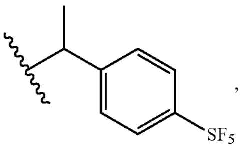
,
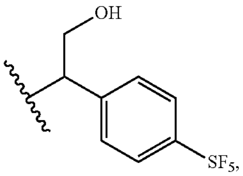
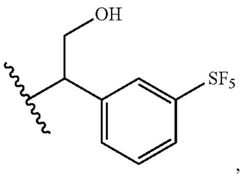
,
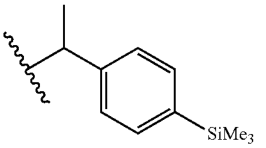
and
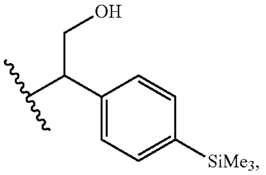

and wherein the $R^9$-$R^{10}$— moiety is:

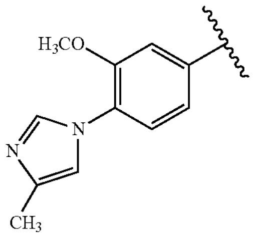
or
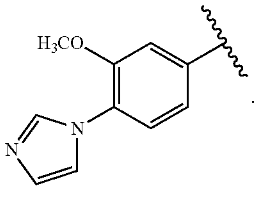
.

In another embodiment of this invention the compound of formula (I) is a compound of the formula (IJI):

(IJ1)

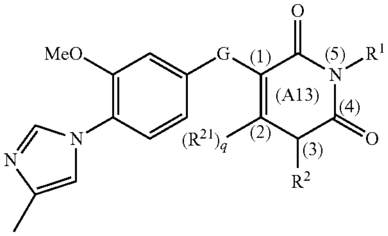

wherein q is 0 or 1.

In another embodiment of this invention the compound of formula (I) is a compound of the formula (IK):

(IK)

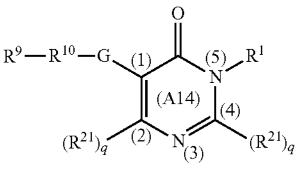

wherein each q is independently 0 or 1, and each $R^{21}$ is independently selected.

In another embodiment of this invention the compound of formula (I) is a compound of the formula (IK) wherein G is selected from the group consisting of: —NH—, and a direct bond.

In another embodiment of this invention the compound of formula (I) is a compound of the formula (IK) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IK) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

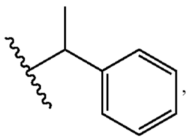
,
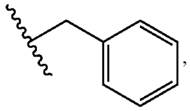
,
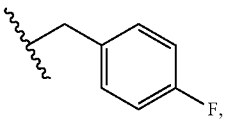
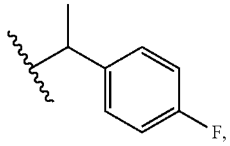

-continued

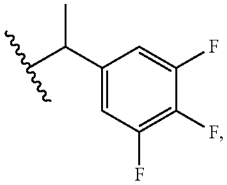 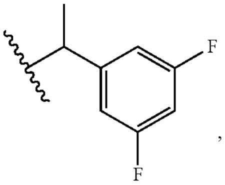,

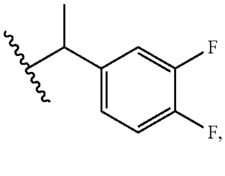 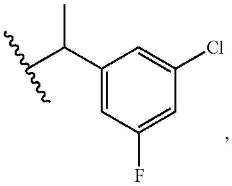,

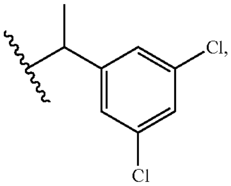 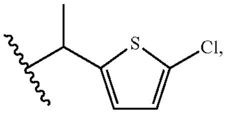

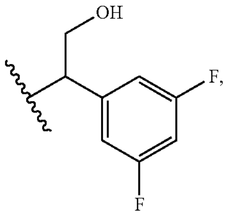 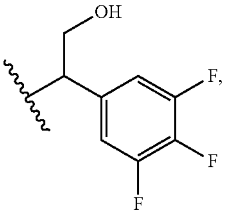

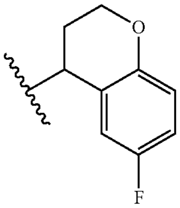, 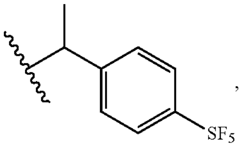,

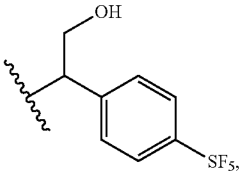 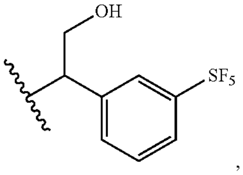,

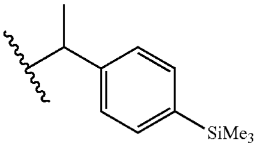 and 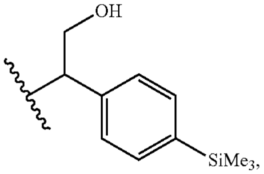

and
wherein the $R^9$-$R^{10}$— moiety is:

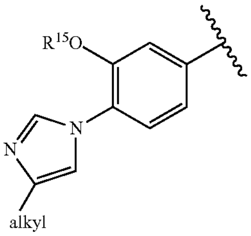 or

-continued

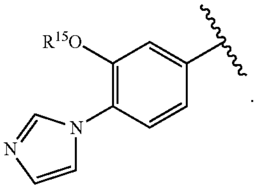.

In another embodiment of this invention the compound of formula (I) is a compound of the formula (IK) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

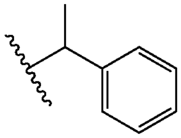, 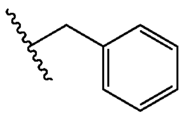,

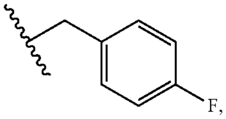 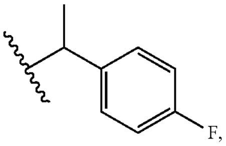

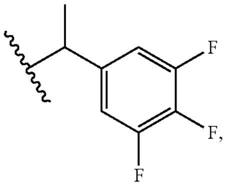 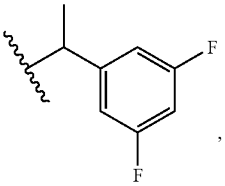,

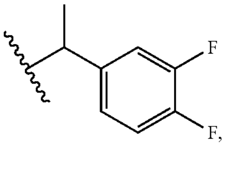 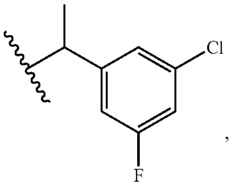,

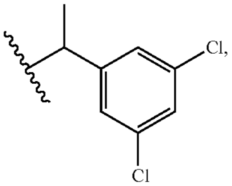 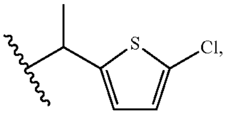

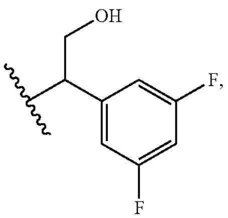 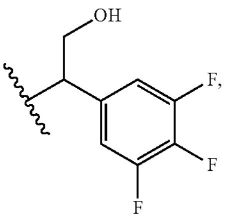

-continued

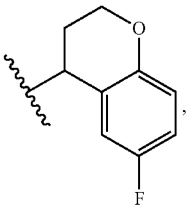

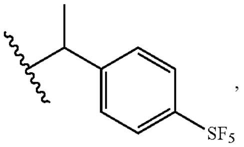

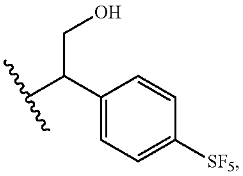

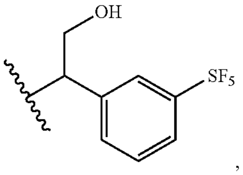

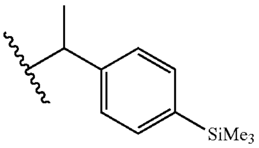

and

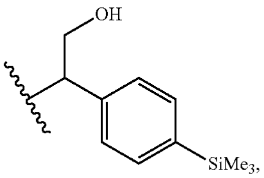

and wherein the $R^9$-$R^{10}$— moiety is:

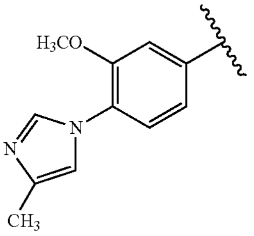

or

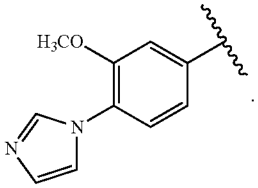

In another embodiment of this invention the compound of formula (I) is a compound of the formula (IK1):

(IK1)

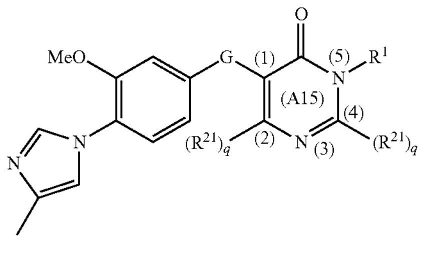

wherein each q is independently 0 or 1.

In another embodiment of this invention the compound of formula (I) is a compound of the formula (IL):

(IL)

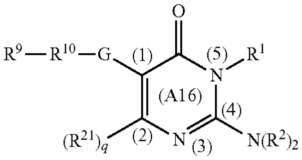

wherein q is 0 or 1, and each $R^2$ is independently selected.

In another embodiment of this invention the compound of formula (I) is a compound of the formula (IL) wherein G is selected from the group consisting of: —NH—, and a direct bond.

In another embodiment of this invention the compound of formula (I) is a compound of the formula (IL) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IL) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

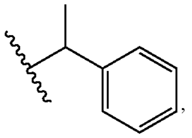

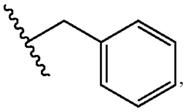

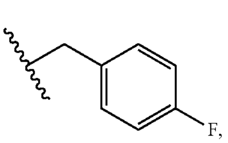

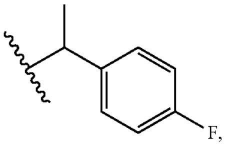

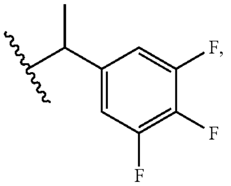

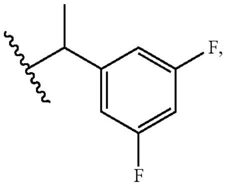

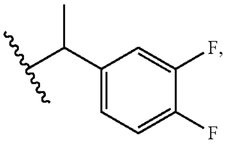

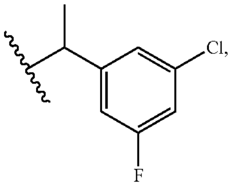

-continued

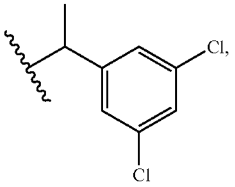

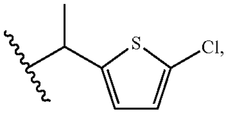

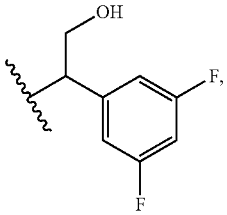

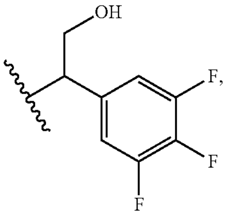

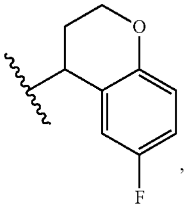

,

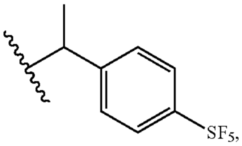

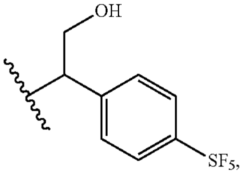

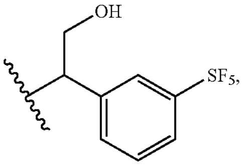

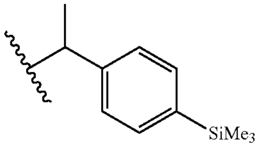

and

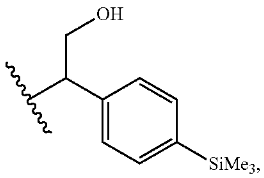

and wherein the $R^9$-$R^{10}$— moiety is:

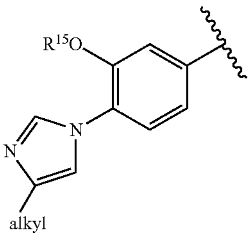

or

-continued

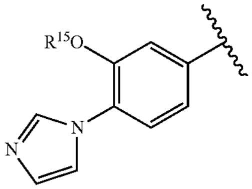

.

In another embodiment of this invention the compound of formula (I) is a compound of the formula (IL) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{10}$ group, wherein $R^{15}$ is methyl, and (e) $R^9$ is selected from the group consisting of imidazolyl and imidazolyl substituted with one methyl group, and (f) $R^1$ is selected from the group consisting of:

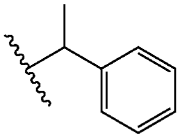

,

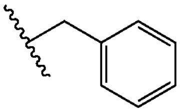

,

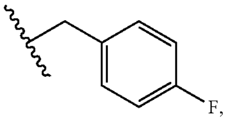

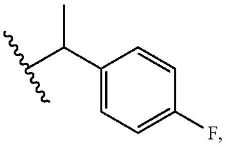

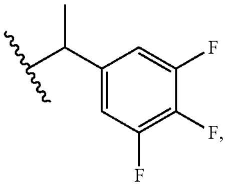

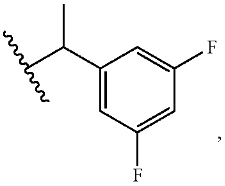

,

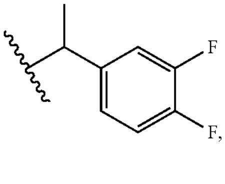

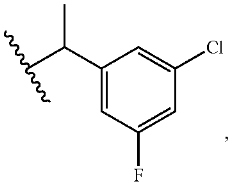

,

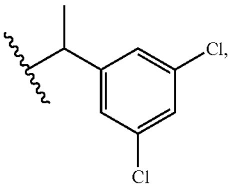

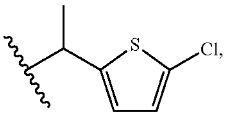

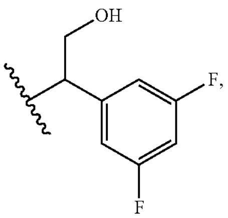

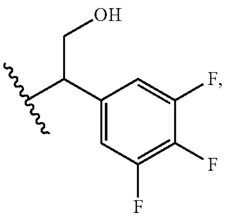

-continued

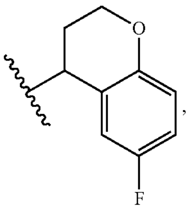,
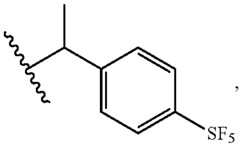,

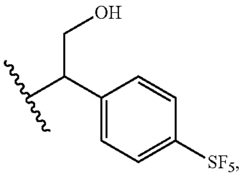
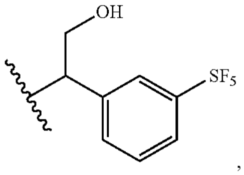,

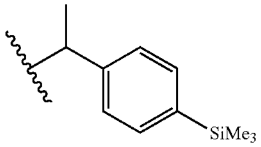 and 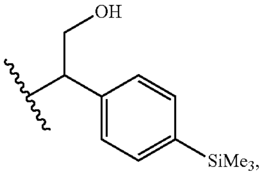

and wherein the $R^9$-$R^{10}$— moiety is:

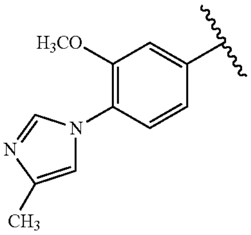

or

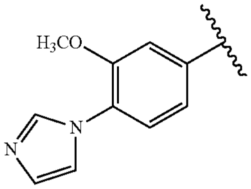.

In another embodiment of this invention the compound of formula (I) is a compound of the formula (IL1):

(IL1)

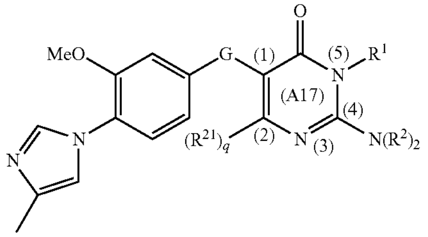

wherein q is 0 or 1, and each $R^2$ is independently selected.

In another embodiment of this invention the compound of formula (I) is a compound of the formula (ID:

(IL2)

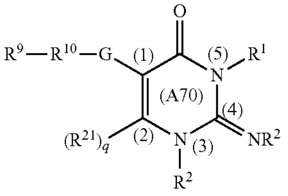

wherein q is 0 or 1, and each $R^2$ is independently selected.

In another embodiment of this invention the compound of formula (I) is a compound of the formula (IL) wherein G is selected from the group consisting of: —NH—, and a direct bond.

In another embodiment of this invention the compound of formula (I) is a compound of the formula (IL) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IL) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

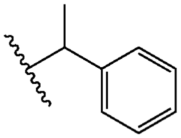, 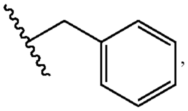,

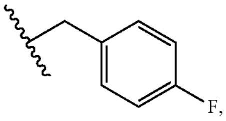 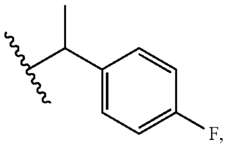

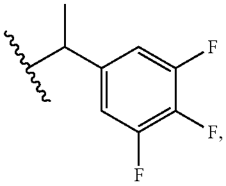 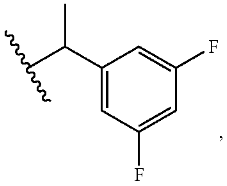,

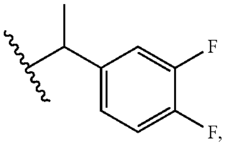 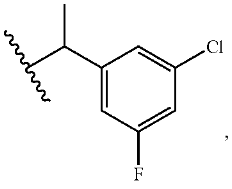,

-continued

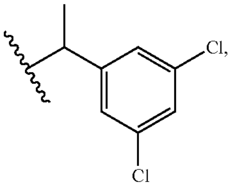
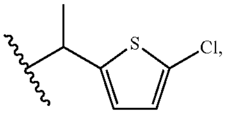

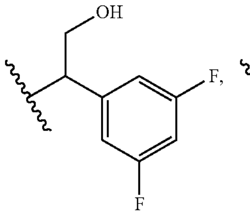
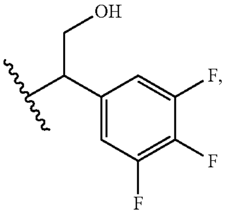

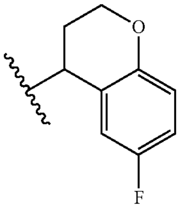,
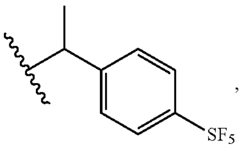,

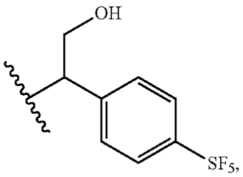
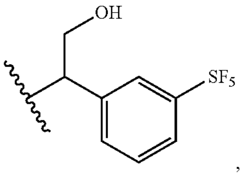,

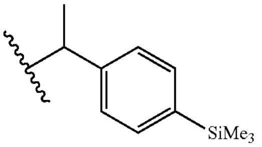 and
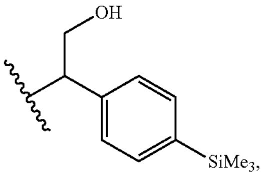

and
wherein the $R^9$-$R^{10}$— moiety is:

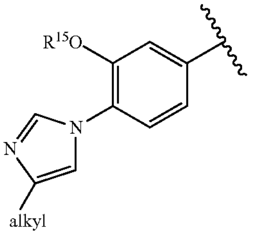

or

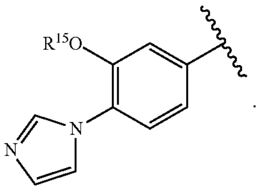.

In another embodiment of this invention the compound of formula (I) is a compound of the formula (IL) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

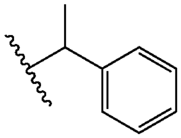,
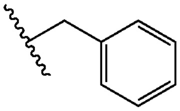,

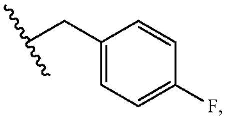
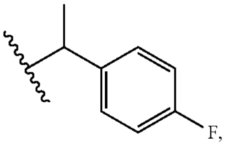

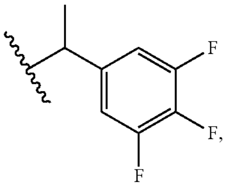
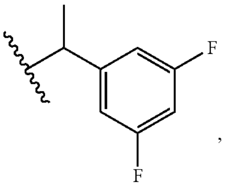,

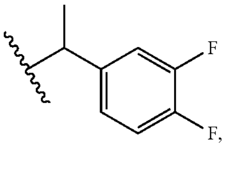
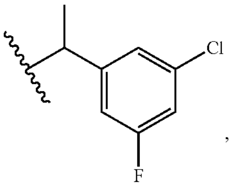,

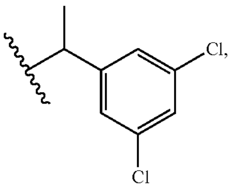
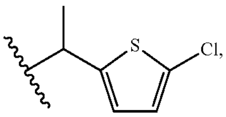

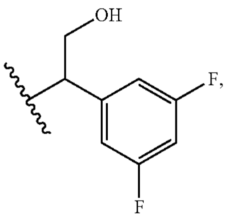
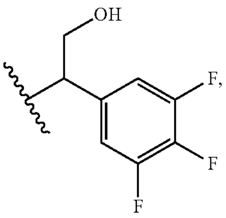

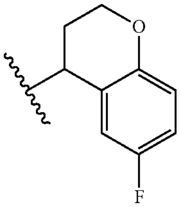,
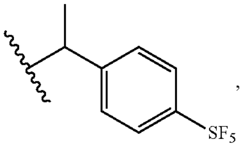,

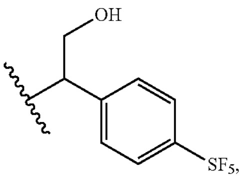
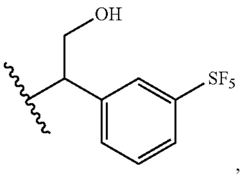,

-continued

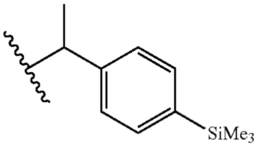

and

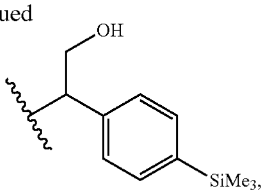

and wherein the $R^9$-$R^{10}$— moiety is:

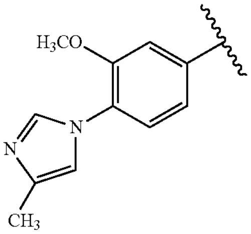

or

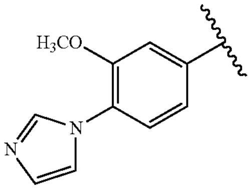

In another embodiment of this invention the compound of formula (I) is a compound of the formula (IL3):

(IL3)

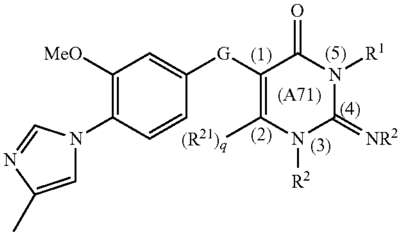

wherein q is 0 or 1, and each $R^2$ is independently selected.

In another embodiment of this invention the compound of formula (I) is a compound of the formula (IJ2):

(IJ2)

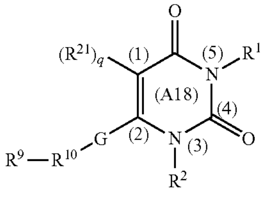

wherein q is 0 or 1.

In another embodiment of this invention the compound of formula (I) is a compound of the formula (IJ2) wherein G is selected from the group consisting of: —NH—, and a direct bond.

In another embodiment of this invention the compound of formula (I) is a compound of the formula (IJ2) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IJ2) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

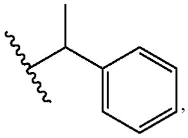

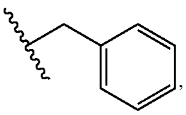

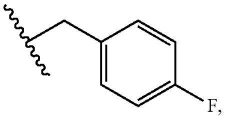

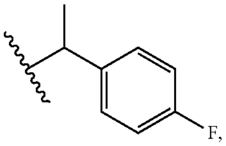

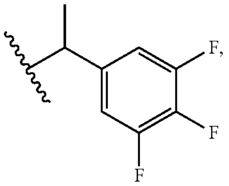

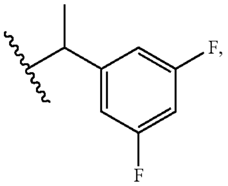

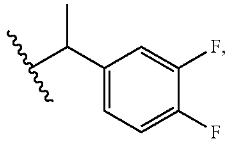

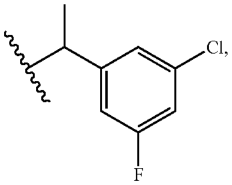

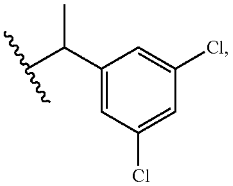

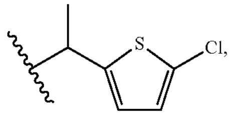

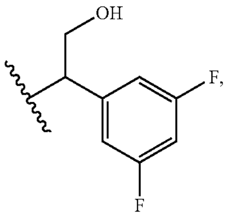

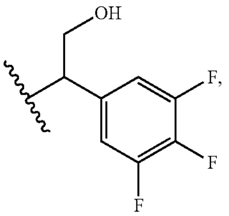

-continued

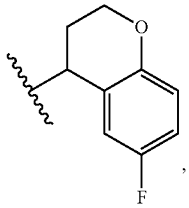,

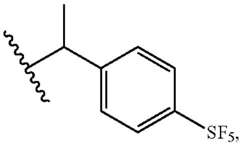

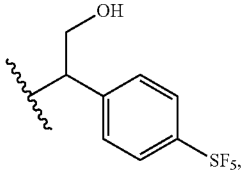

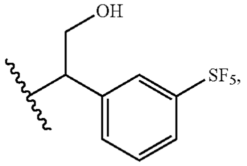

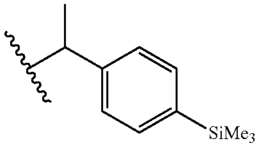 and

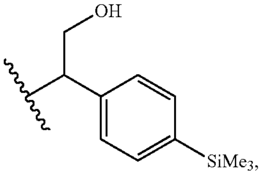

and wherein the $R^9$-$R^{10}$— moiety is:

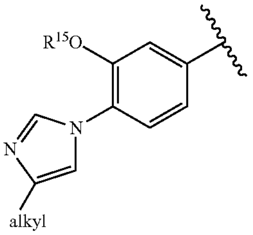

or

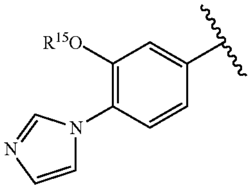

.

In another embodiment of this invention the compound of formula (I) is a compound of the formula (IJ2) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, (f) $R^1$ is selected from the group consisting of:

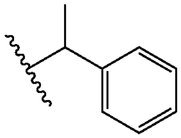,

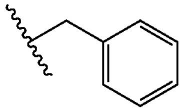,

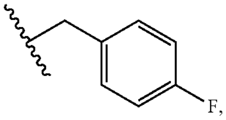

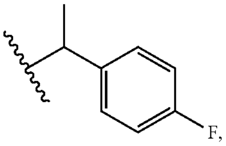

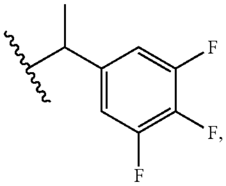

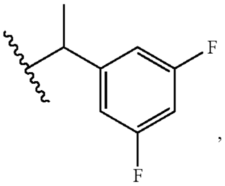,

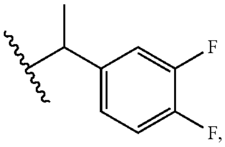

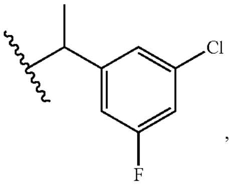,

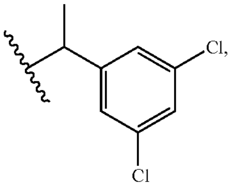

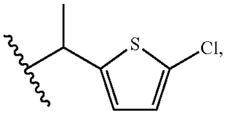

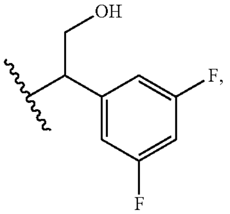

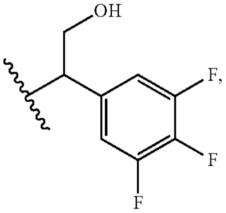

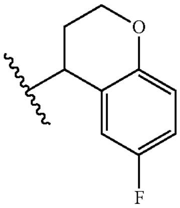,

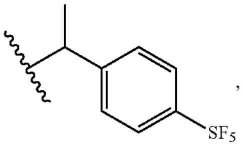,

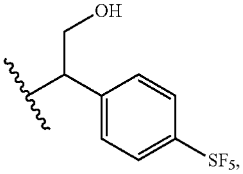

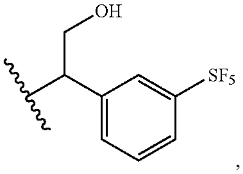,

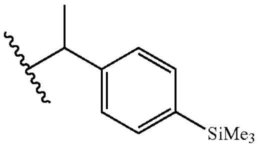 and

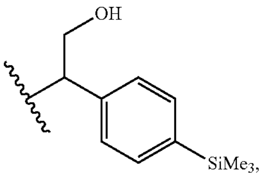

and wherein the $R^9$-$R^{10}$— moiety is:

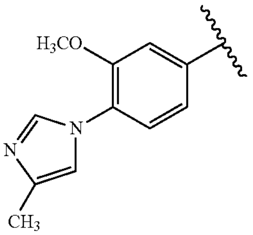

or

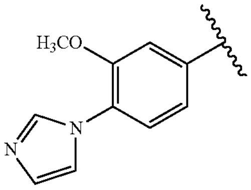

.

In another embodiment of this invention the compound of formula (I) is a compound of the formula (IJ3):

(IJ3)

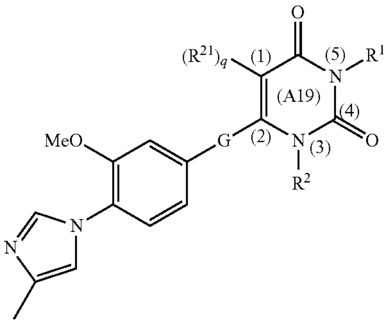

wherein q is 0 or 1.

In another embodiment of this invention the compound of formula (I) is a compound of the formula (IM):

(IM)

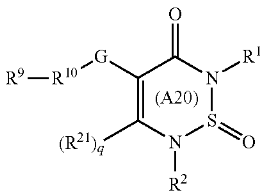

wherein q is 0 or 1.

In another embodiment of this invention the compound of formula (I) is a compound of the formula (IM) wherein G is selected from the group consisting of: —NH—, and a direct bond.

In another embodiment of this invention the compound of formula (I) is a compound of the formula (IM) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IM) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

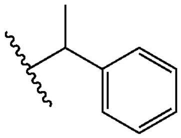

,

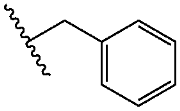

,

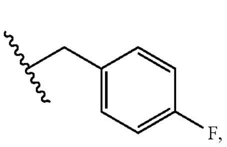

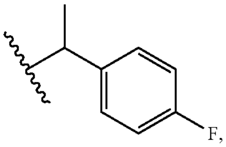

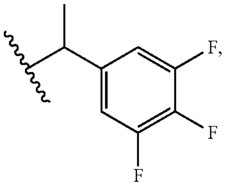

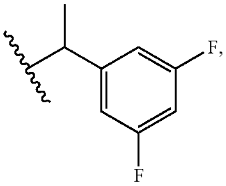

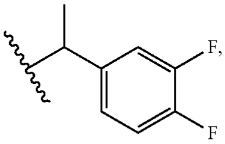

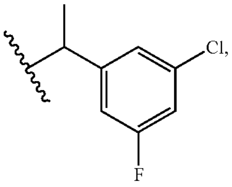

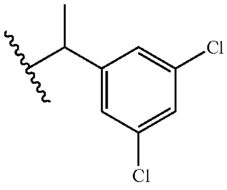

,

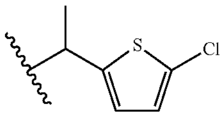

,

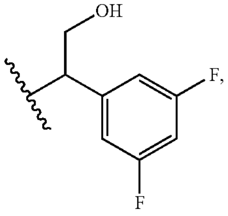

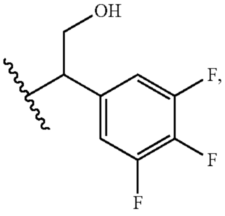

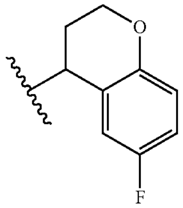

,

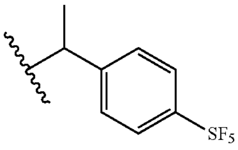

,

-continued

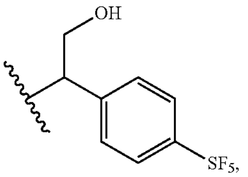

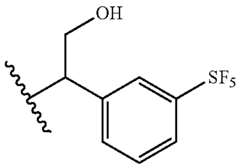

,

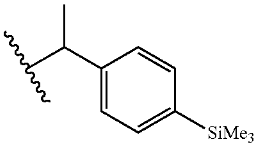

and

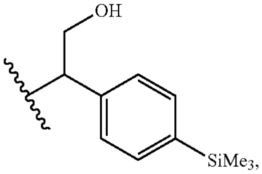

and wherein the $R^9$-$R^{10}$— moiety is:

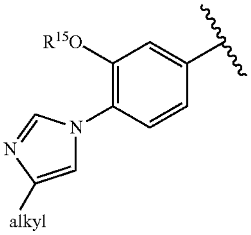

or

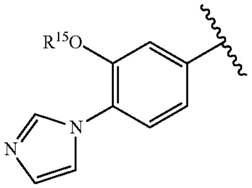

.

In another embodiment of this invention the compound of formula (I) is a compound of the formula (IM) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

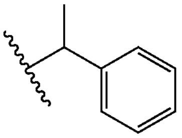

,

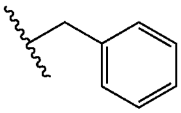

,

-continued

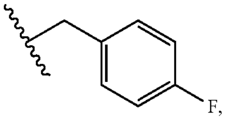

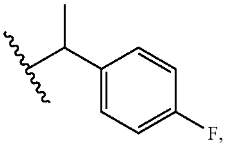

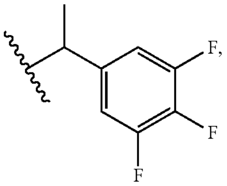

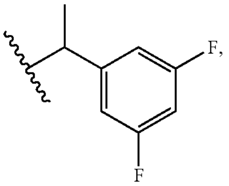

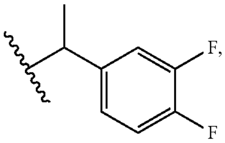

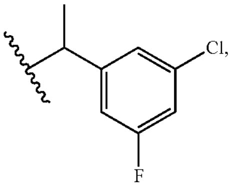

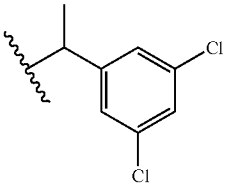

,

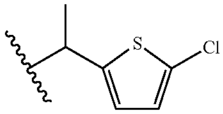

,

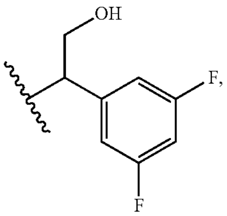

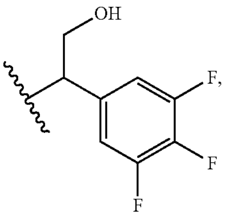

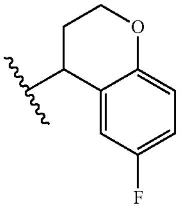

,

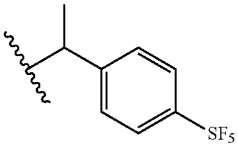

,

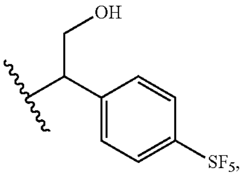

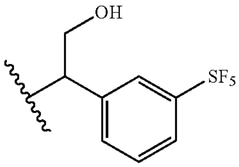

,

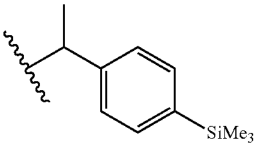

and

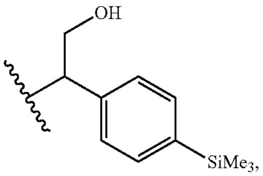

and wherein the $R^9$-$R^{10}$— moiety is:

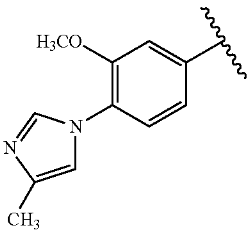

or

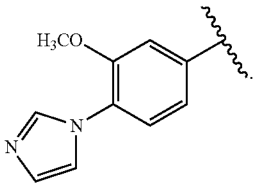

In another embodiment of this invention the compound of formula (I) is a compound of the formula (IM1):

(IM1)

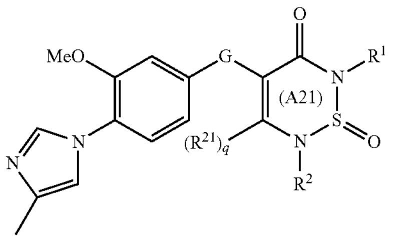

wherein q is 0 or 1.

In another embodiment of this invention the compound of formula (I) is a compound of the formula (IN):

(IN)

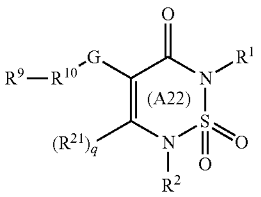

wherein q is 0 or 1.

In another embodiment of this invention the compound of formula (I) is a compound of the formula (IN) wherein G is selected from the group consisting of: —NH—, and a direct bond.

In another embodiment of this invention the compound of formula (I) is a compound of the formula (IN) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IN) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

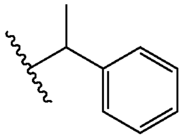
,
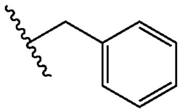
,

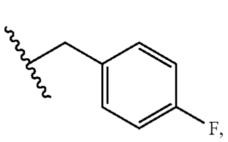

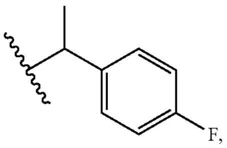

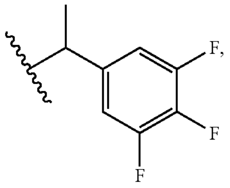

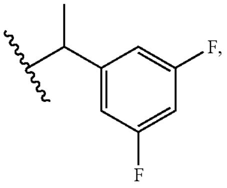

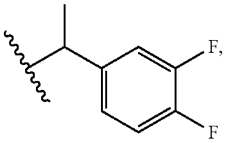

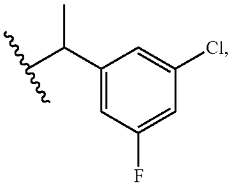

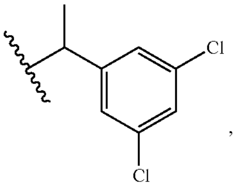
,
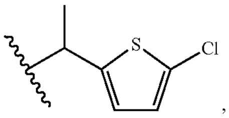
,

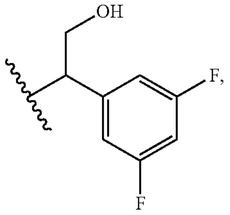

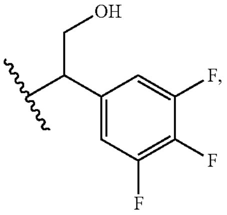

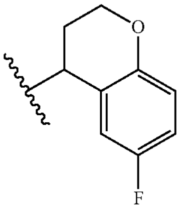
,
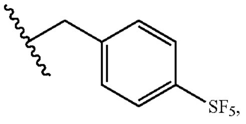

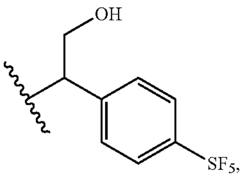

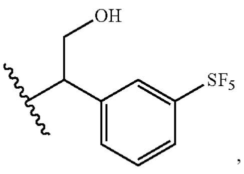
,

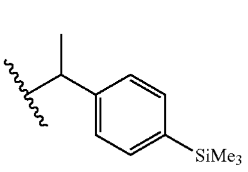

and

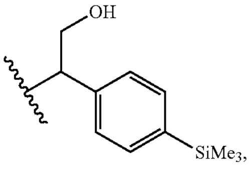

and wherein the $R^9$-$R^{10}$— moiety is:

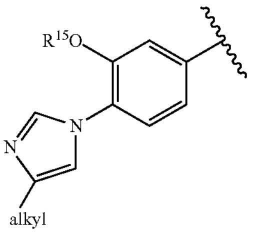
or
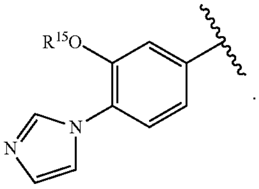

In another embodiment of this invention the compound of formula (I) is a compound of the formula (IN) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

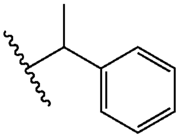
,
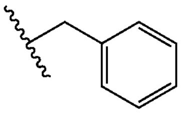
,
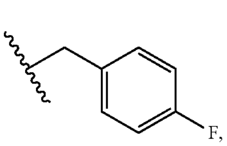
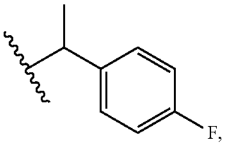
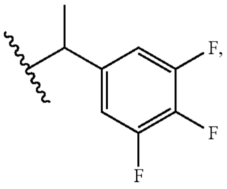
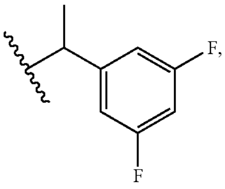
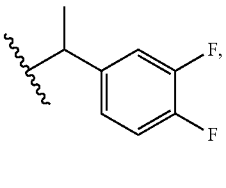
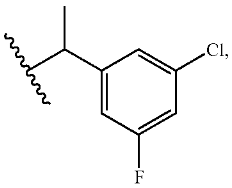
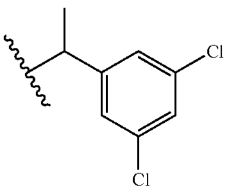
,
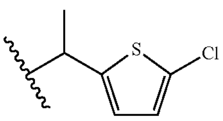
,
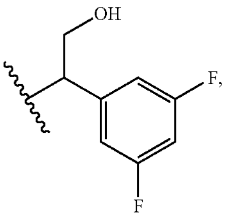
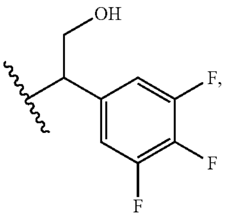

-continued

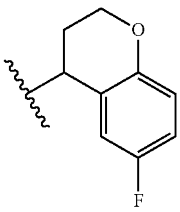
,
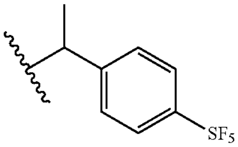
,
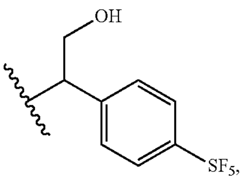
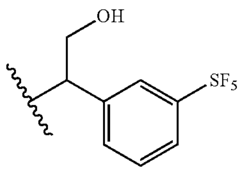
,
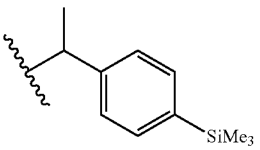
and
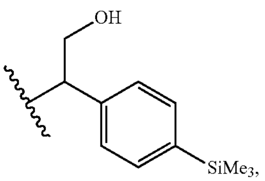

and wherein the $R^9$-$R^{10}$— moiety is:

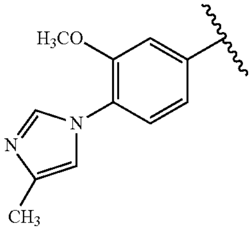
or
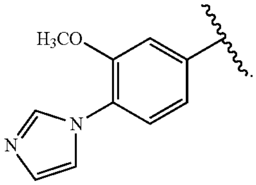

In another embodiment of this invention the compound of formula (I) is a compound of the formula (IN1):

(IN1)

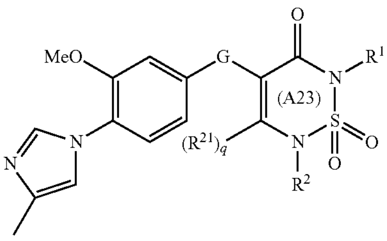

wherein q is 0 or 1.

In another embodiment of this invention the compound of formula (I) is a compound of the formula (10):

(IO)

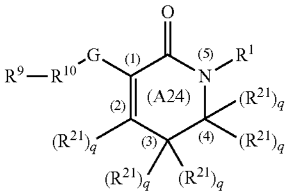

wherein each q is independently 0 or 1, and each $R^{20}$ is independently selected.

In another embodiment of this invention the compound of formula (I) is a compound of the formula (10) wherein G is selected from the group consisting of: —NH—, and a direct bond.

In another embodiment of this invention the compound of formula (I) is a compound of the formula (10) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (10) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

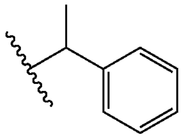,
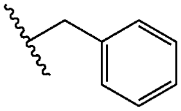,
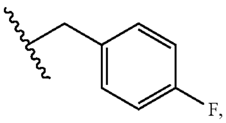,
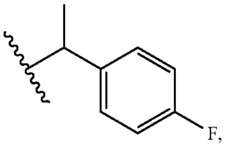,
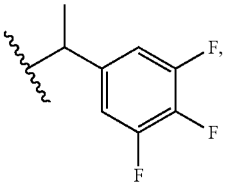,
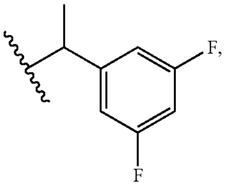,
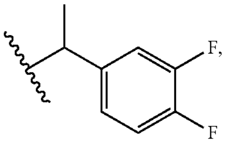,
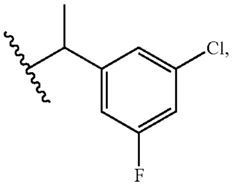, -continued

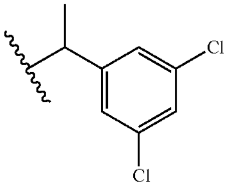,
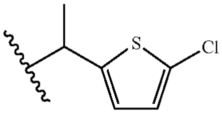,
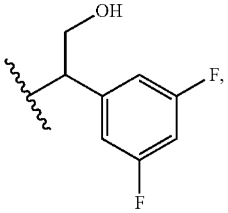,
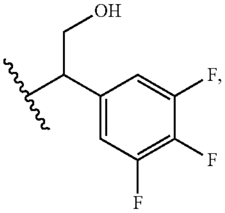,
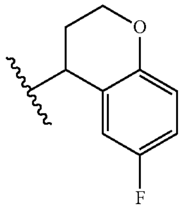,
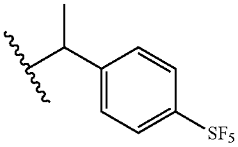,
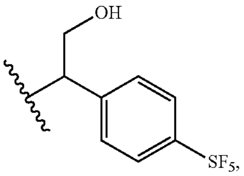,
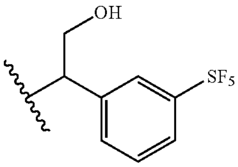,
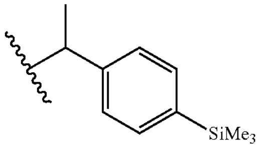 and
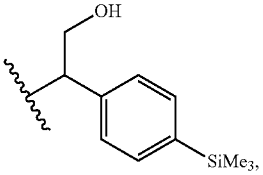, and wherein the $R^9$-$R^{10}$— moiety is:

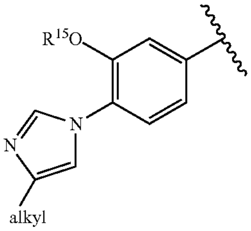

or

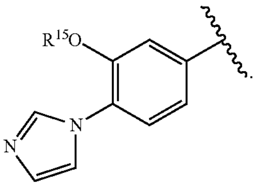.

In another embodiment of this invention the compound of formula (I) is a compound of the formula (10) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

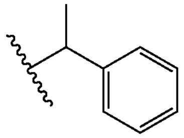
,
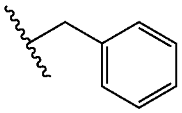
,
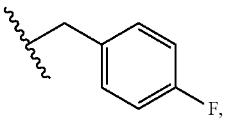
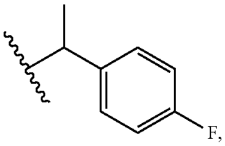
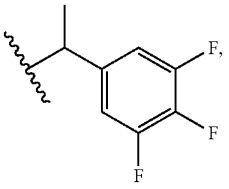
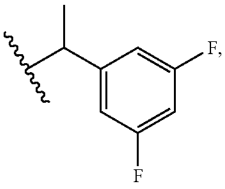
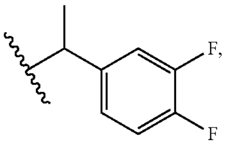
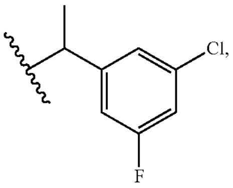
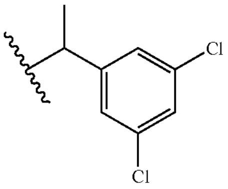
,
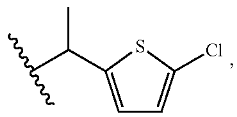
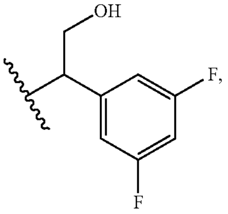
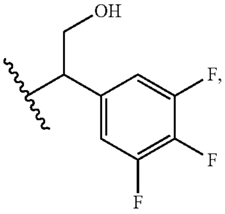
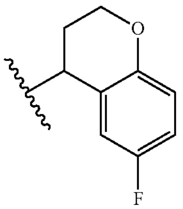
,
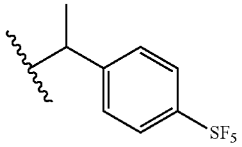
,
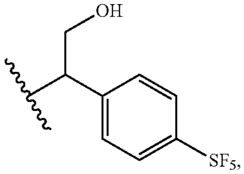
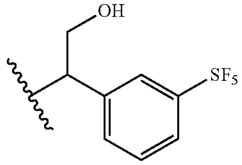
,
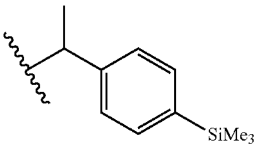
and -continued

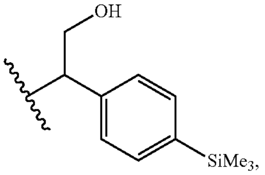

and wherein the $R^9$-$R^{10}$— moiety is:

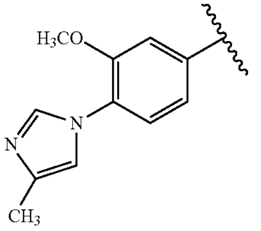
or
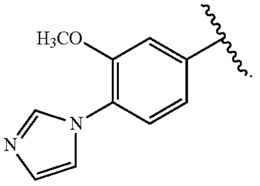

In another embodiment of this invention the compound of formula (I) is a compound of the formula (101):

(IO1)

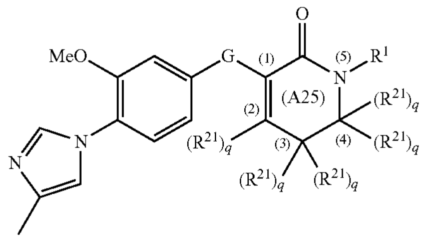

wherein each q is independently 0 or 1, and each $R^{21}$ is independently selected.

In another embodiment of this invention the compound of formula (I) is a compound of the formula (IP):

(IP)

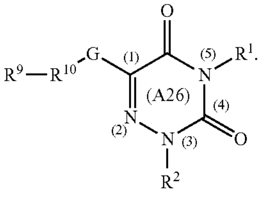

In another embodiment of this invention the compound of formula (I) is a compound of the formula (IP) wherein G is selected from the group consisting of: —NH—, and a direct bond.

In another embodiment of this invention the compound of formula (I) is a compound of the formula (IP) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IP) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

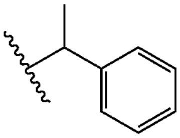
,
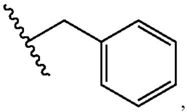
,
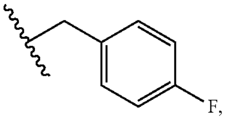
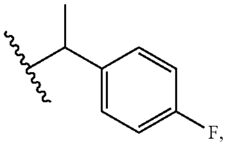
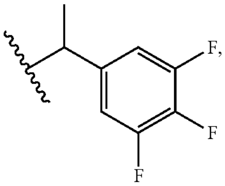
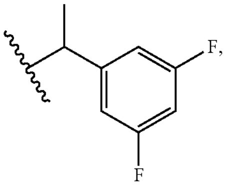
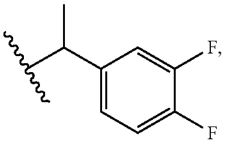
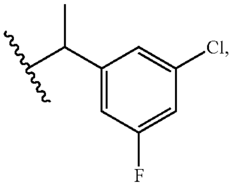
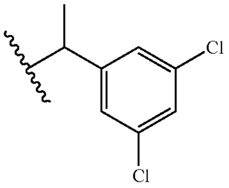
,
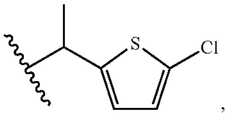
,
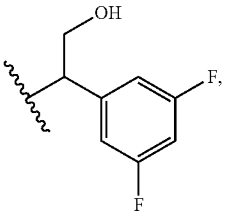
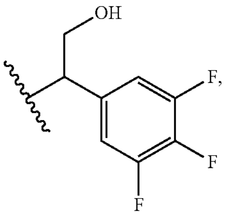
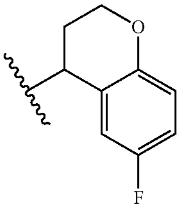
,
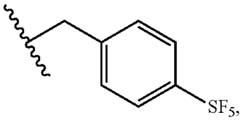

-continued

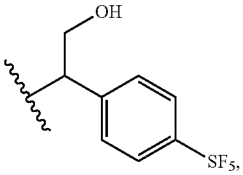
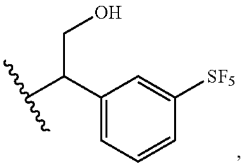
,
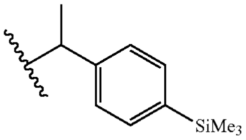
and
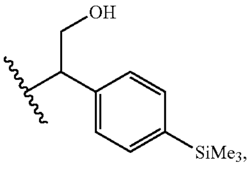

and wherein the $R^9$-$R^{10}$— moiety is:

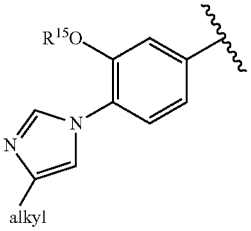
or
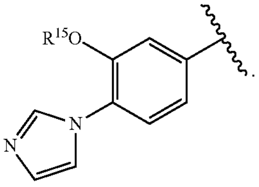

In another embodiment of this invention the compound of formula (I) is a compound of the formula (IP) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

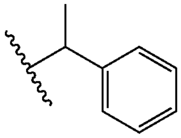
,
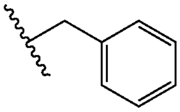
,
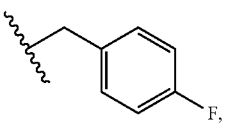
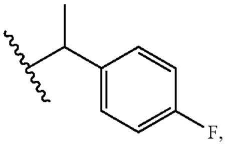
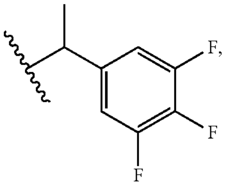
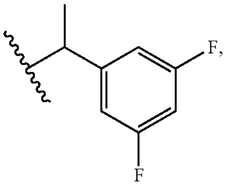

-continued

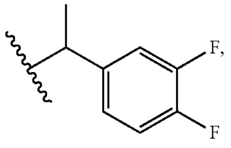

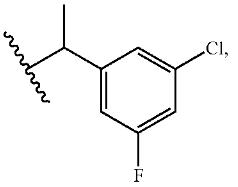

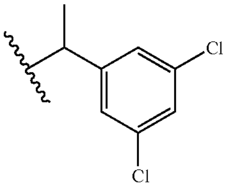

,

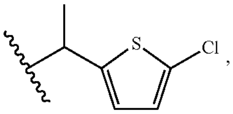

,

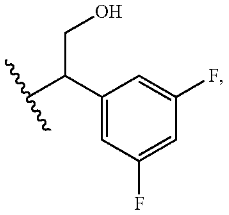

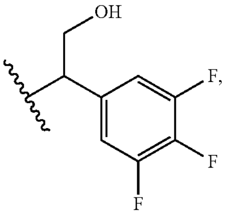

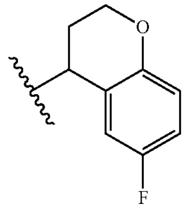

,

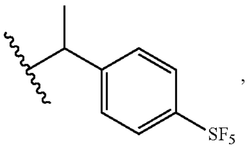

,

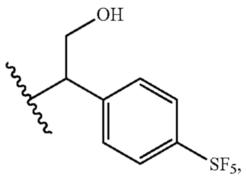

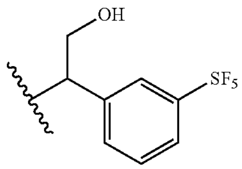

,

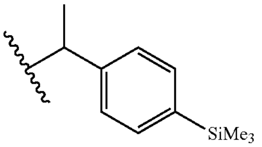

and

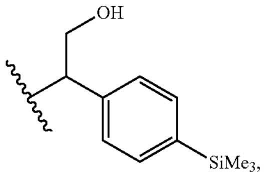

and wherein the $R^9$-$R^{10}$— moiety is:

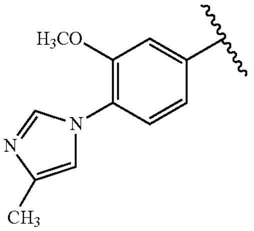

or

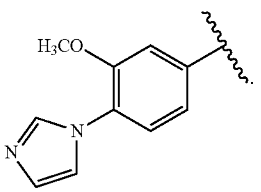

In another embodiment of this invention the compound of formula (I) is a compound of the formula (IP1):

(IP1)

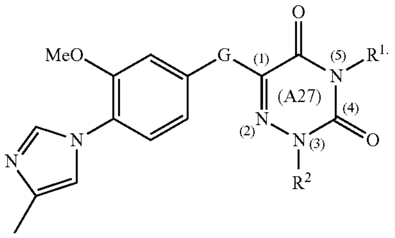

In another embodiment of this invention the compound of formula (I) is a compound of the formula (IQ):

(IQ)

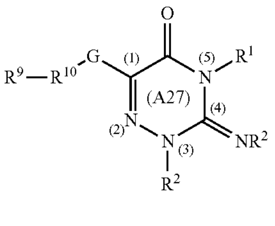

wherein each $R^2$ is independently selected.

In another embodiment of this invention the compound of formula (I) is a compound of the formula (IQ) wherein G is selected from the group consisting of: —NH—, and a direct bond.

In another embodiment of this invention the compound of formula (I) is a compound of the formula (IQ) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IQ) wherein: (a) G is selected from the group consisting of: —NH—, and a direct bond (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

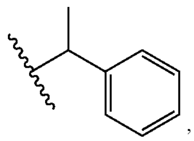

,

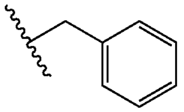

,

-continued

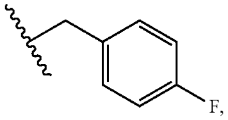
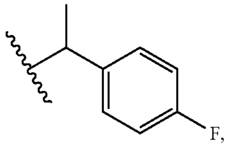
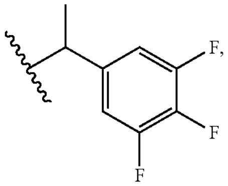
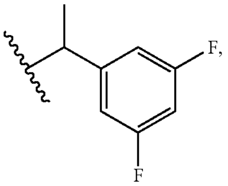
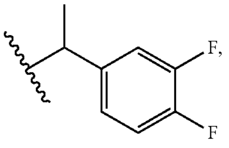
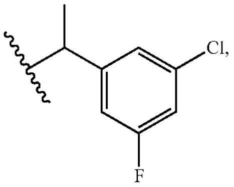
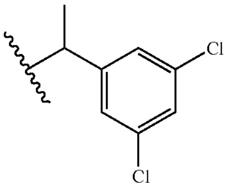
,
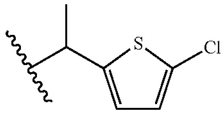
,
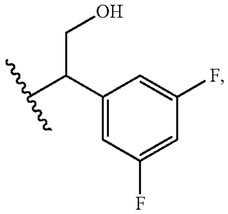
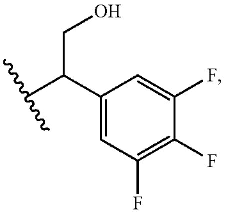
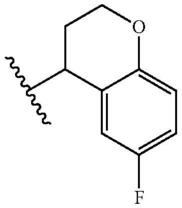
,
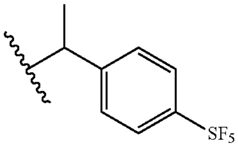
,
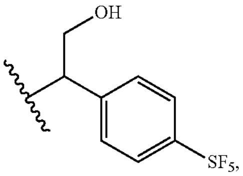
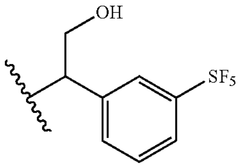
,
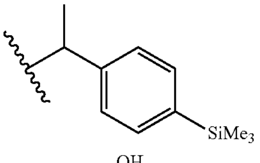
and
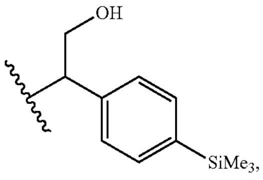

and wherein the $R^9$-$R^{10}$— moiety is:

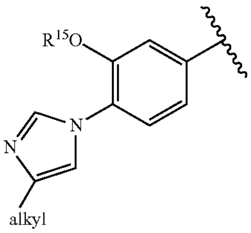
or
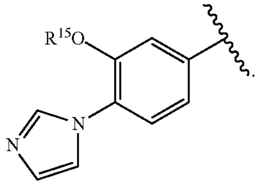

In another embodiment of this invention the compound of formula (I) is a compound of the formula (IQ) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

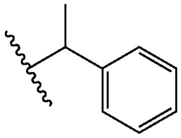
,
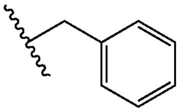
,
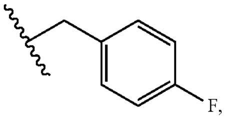
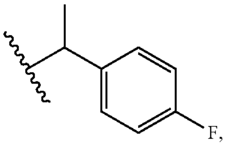
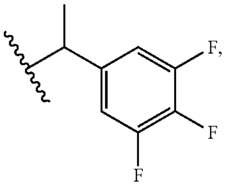
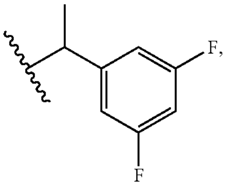
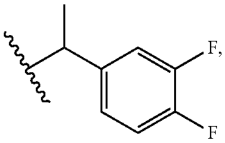
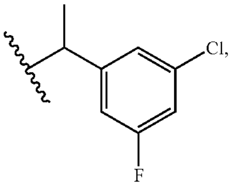
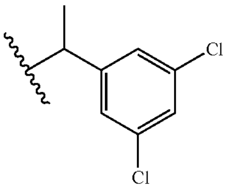
,
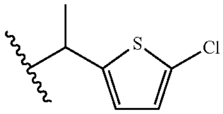
,
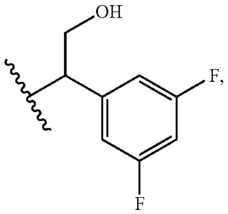
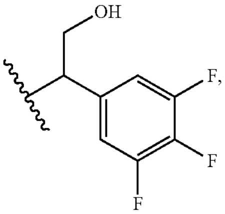

-continued

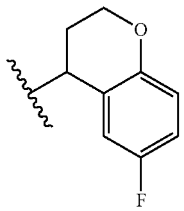
,
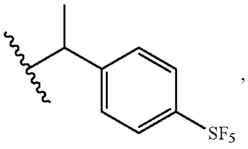
,
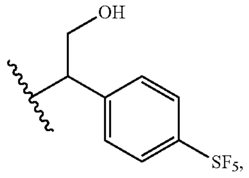
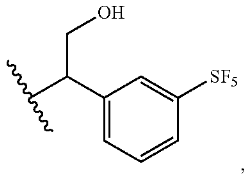
,
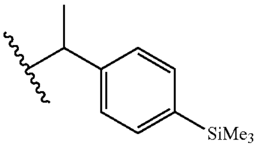
and
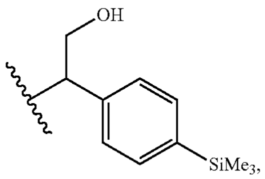

and
wherein the $R^9$-$R^{10}$— moiety is:

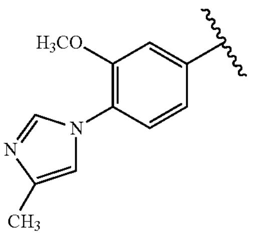
or
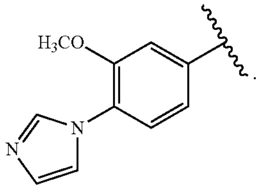
.

In another embodiment of this invention the compound of formula (I) is a compound of the formula (IQ1):

(IQ1)

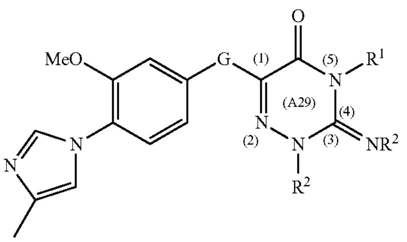

wherein each $R^2$ is independently selected.

In another embodiment of this invention the compound of formula (I) is a compound of the formula (IR):

(IR)

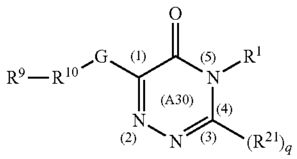

wherein q is 0 or 1.

In another embodiment of this invention the compound of formula (I) is a compound of the formula (IR) wherein G is selected from the group consisting of: —NH—, and a direct bond.

In another embodiment of this invention the compound of formula (I) is a compound of the formula (IR) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IR) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

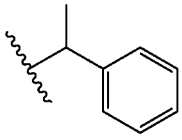
,
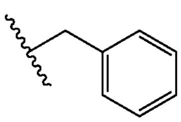
,
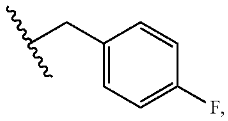
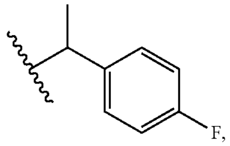
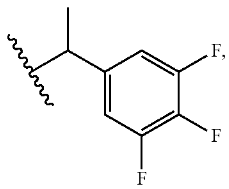
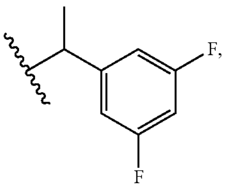
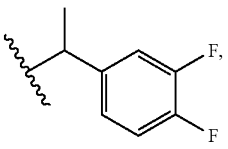
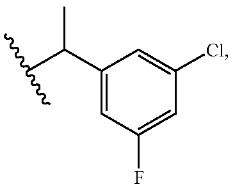

-continued

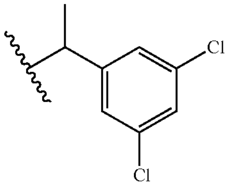

,

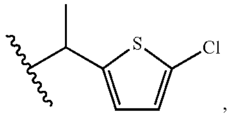

,

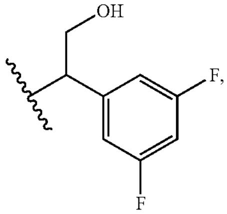

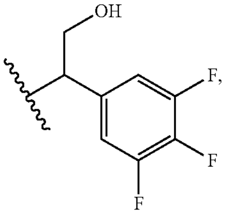

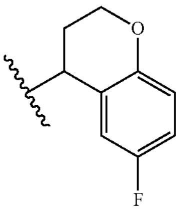

,

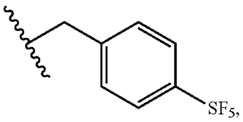

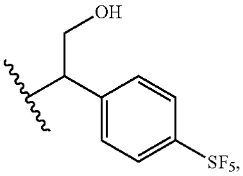

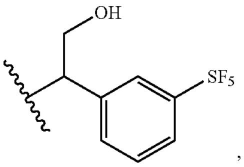

,

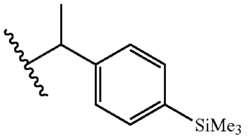

and

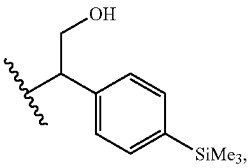

and wherein the $R^9$-$R^{10}$— moiety is:

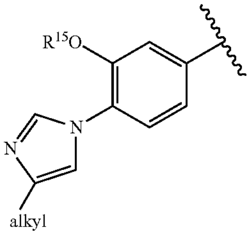

or

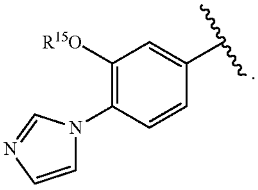

In another embodiment of this invention the compound of formula (I) is a compound of the formula (IR) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

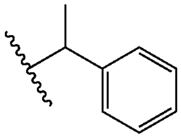

,

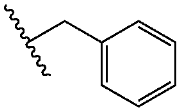

,

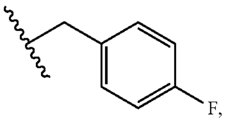

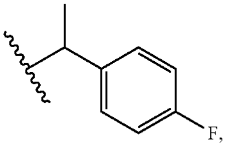

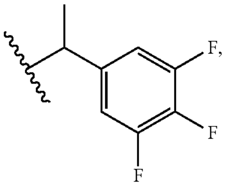

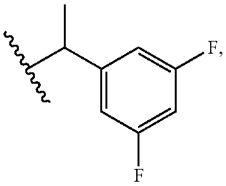

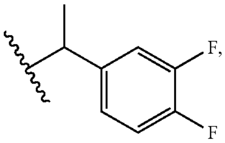

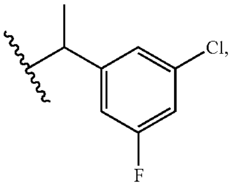

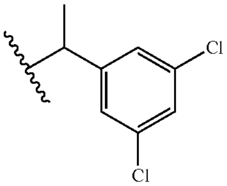

,

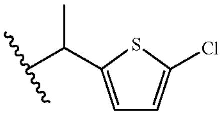

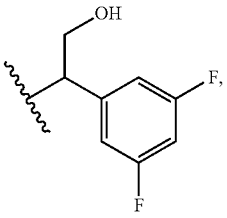

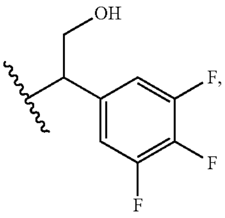

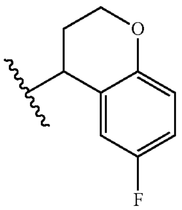

,

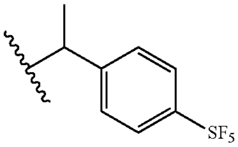

,

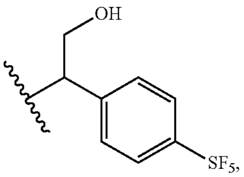

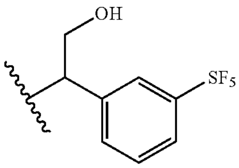

,

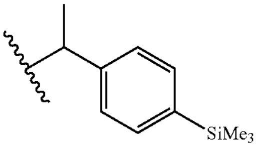

and

-continued

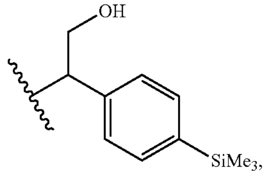

and
wherein the $R^9$-$R^{10}$— moiety is:

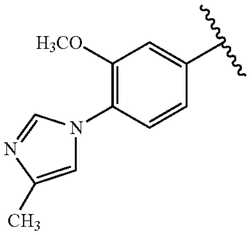

or

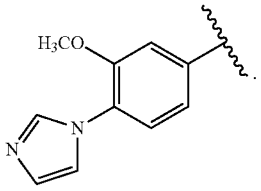

In another embodiment of this invention the compound of formula (I) is a compound of the formula (IR1):

(IR1)

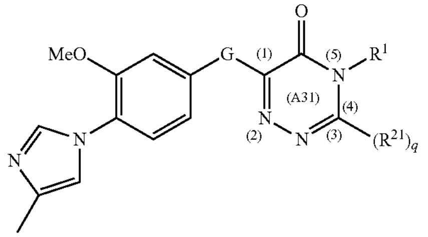

wherein q is 0 or 1.

In another embodiment of this invention the compound of formula (I) is a compound of the formula (IS):

(IS)

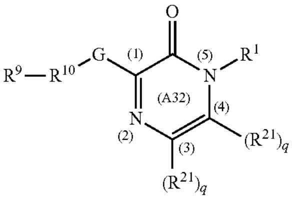

wherein q is 0 or 1.

In another embodiment of this invention the compound of formula (I) is a compound of the formula (IS) wherein G is selected from the group consisting of: —NH—, and a direct bond.

In another embodiment of this invention the compound of formula (I) is a compound of the formula (IS) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IS) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

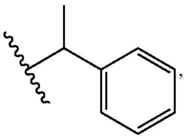
,
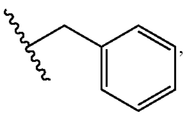
,
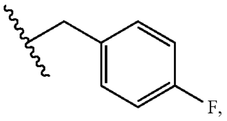
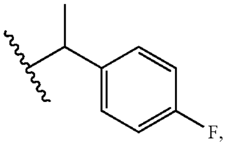
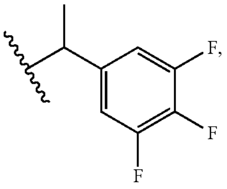
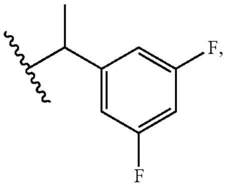
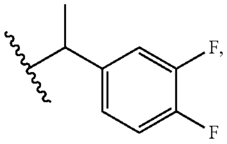
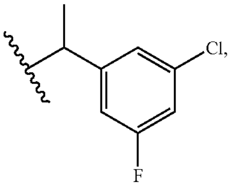
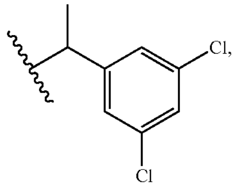
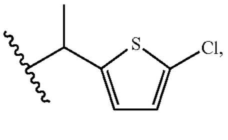
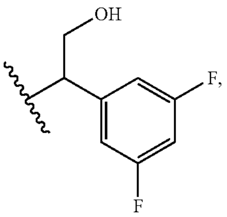
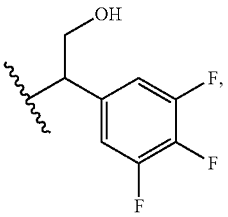
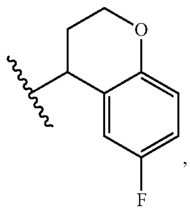
,
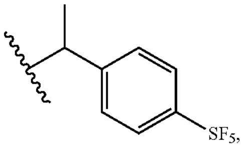

-continued

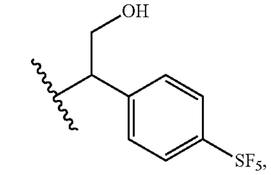

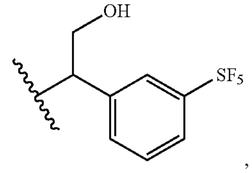

,

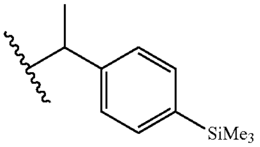

and

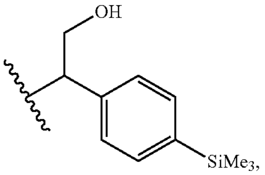

and wherein the $R^9$-$R^{10}$— moiety is:

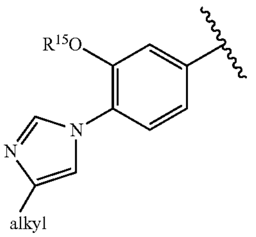

or

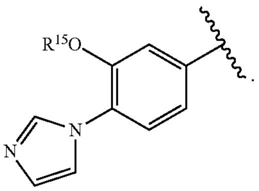

.

In another embodiment of this invention the compound of formula (I) is a compound of the formula (IS) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

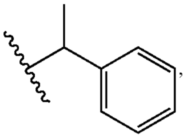

,

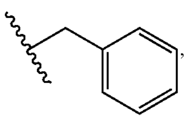

,

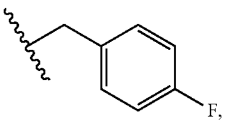

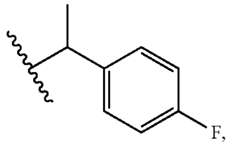

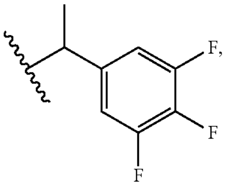

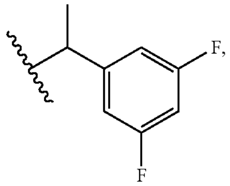

-continued

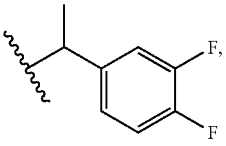

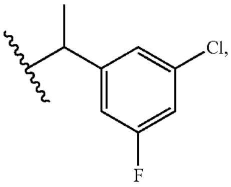

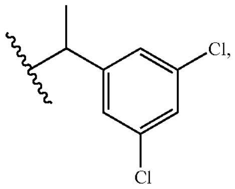

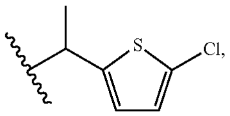

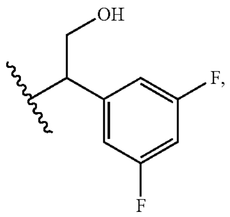

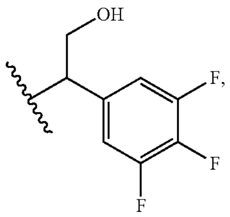

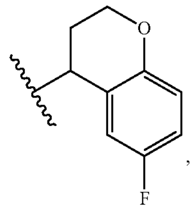

,

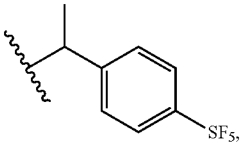

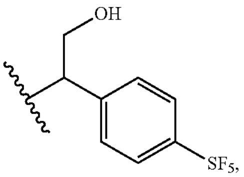

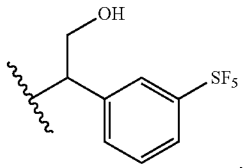

,

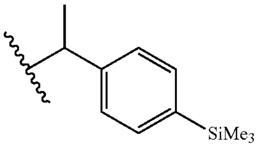

and

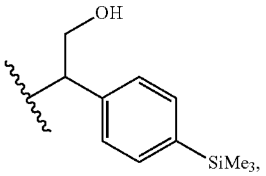

and wherein the $R^9$-$R^{10}$— moiety is:

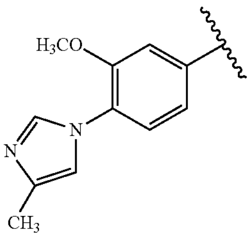

or

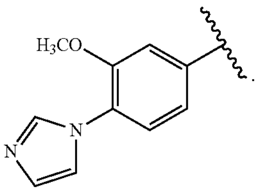

.

In another embodiment of this invention the compound of formula (I) is a compound of the formula (IS1):

(IS1)

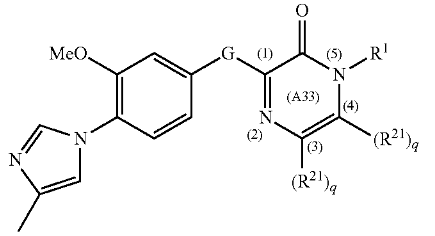

wherein each q is independently 0 or 1, and each $R^{21}$ is independently selected.

In another embodiment of this invention the compound of formula (I) is a compound of the formula (IT):

(IT)

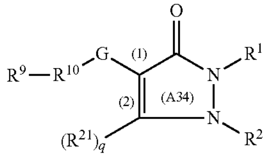

wherein q is 0 or 1.

In another embodiment of this invention the compound of formula (I) is a compound of the formula (IT) wherein G is selected from the group consisting of: —NH—, and a direct bond.

In another embodiment of this invention the compound of formula (I) is a compound of the formula (IT) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IT) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) wherein $R^1$ is selected from the group consisting of:

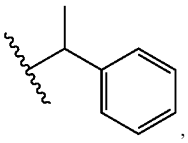 , 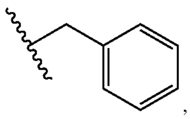 ,

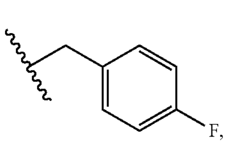 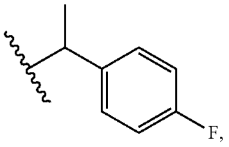

-continued

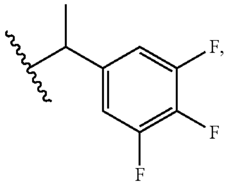 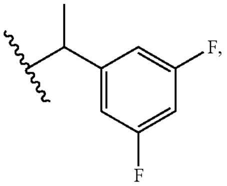

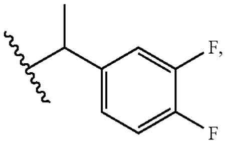 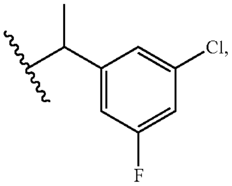

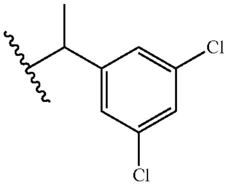 , 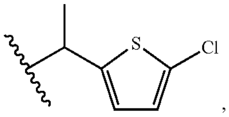 ,

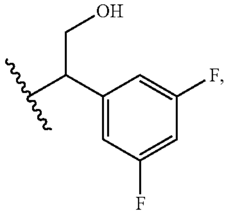 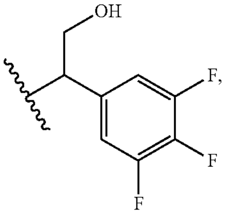

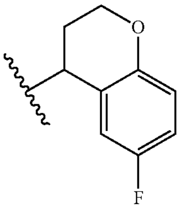 , 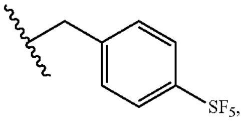

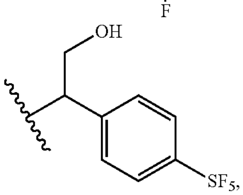 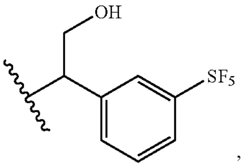 ,

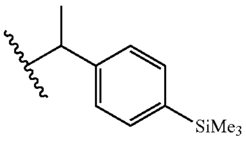 and 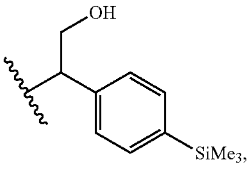

and wherein the $R^9$-$R^{10}$— moiety is:

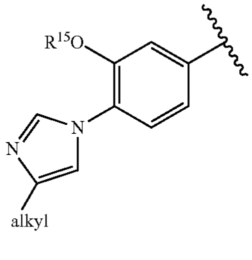 or 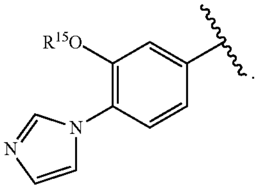 .

In another embodiment of this invention the compound of formula (I) is a compound of the formula (IT) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) wherein $R^1$ is selected from the group consisting of:

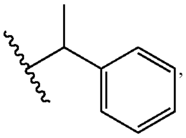

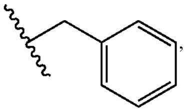

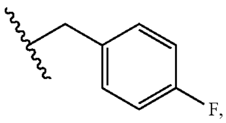

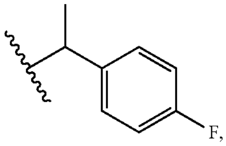

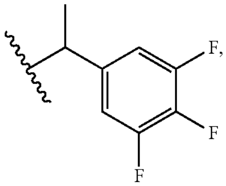

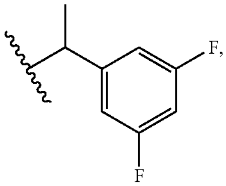

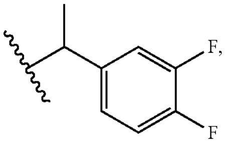

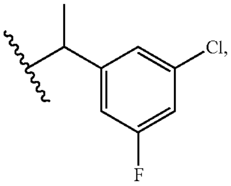

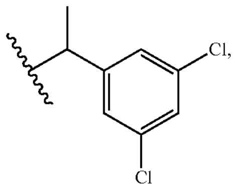

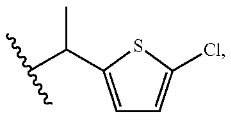

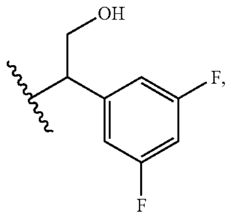

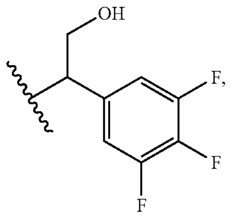

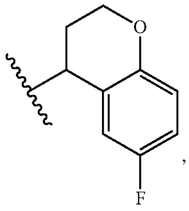
,

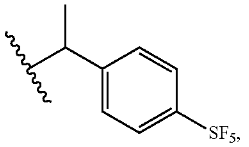

-continued

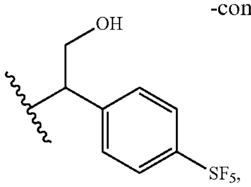

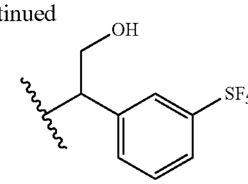
,

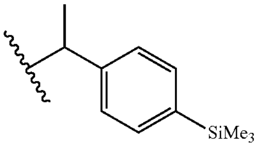
and

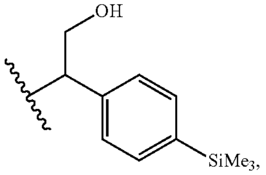

and wherein the $R^9$-$R^{10}$— moiety is:

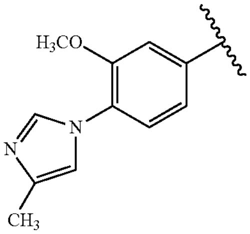
or

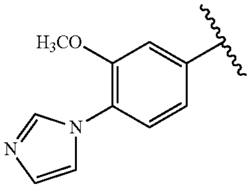
.

In another embodiment of this invention the compound of formula (I) is a compound of the formula (IT1):

(IT1)

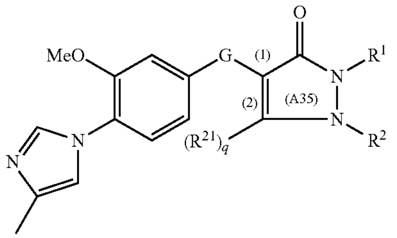

wherein each q is 0 or 1.

In another embodiment of this invention the compound of formula (I) is a compound of the formula (IU):

(IU)

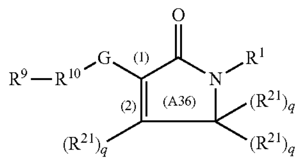

wherein each q is independently 0 or 1, and each $R^{21}$ for each q is independently selected.

In another embodiment of this invention the compound of formula (I) is a compound of the formula (IU) wherein: G is selected from the group consisting of: —NH—, and a direct bond.

In another embodiment of this invention the compound of formula (I) is a compound of the formula (IU) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IU) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

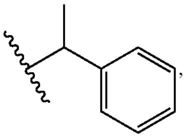
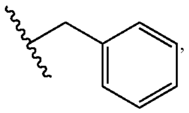
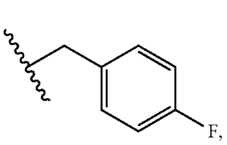
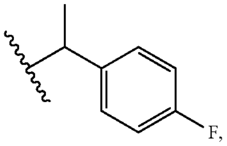
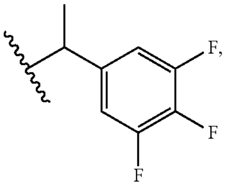
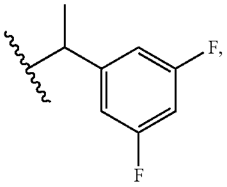
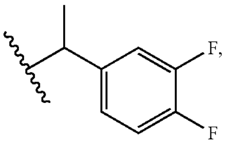
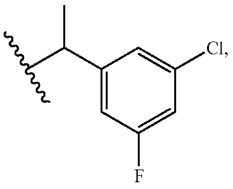
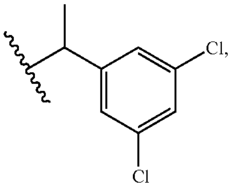
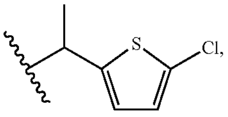
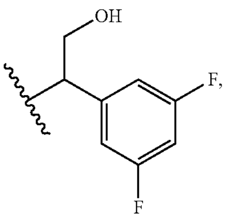
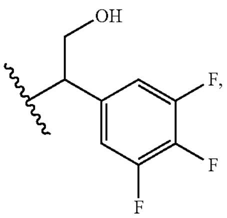

-continued

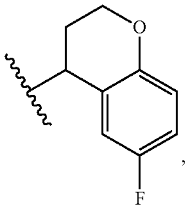
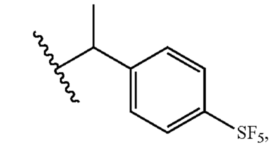
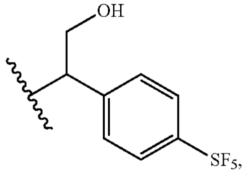
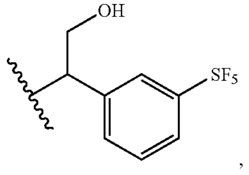
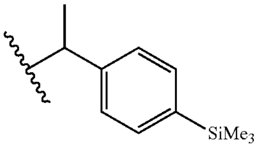
and
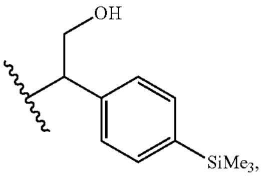

and wherein the $R^9$-$R^{10}$— moiety is:

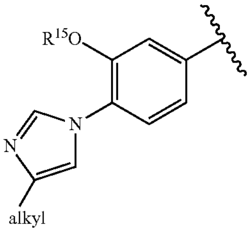
or
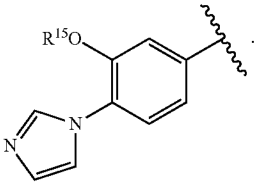

In another embodiment of this invention the compound of formula (I) is a compound of the formula (IU) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

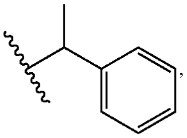
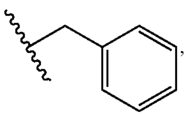
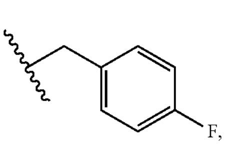
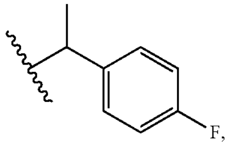

-continued

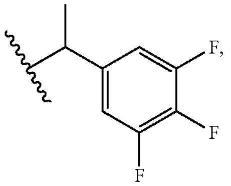 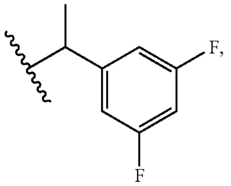

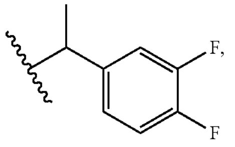 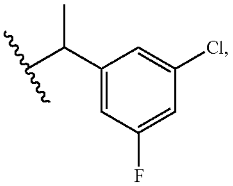

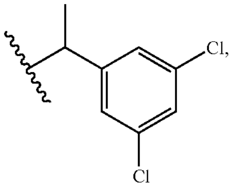 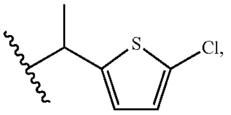

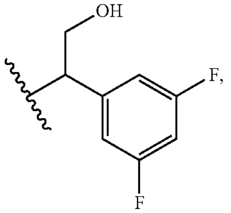 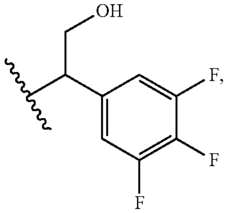

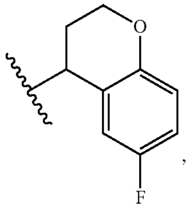, 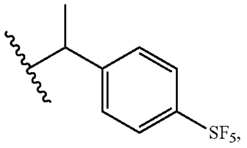

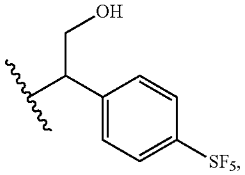 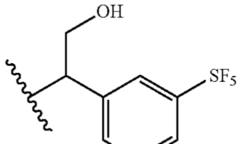,

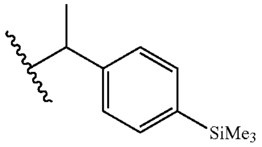 and 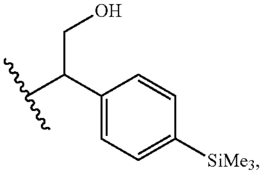

and wherein the $R^9$-$R^{10}$— moiety is:

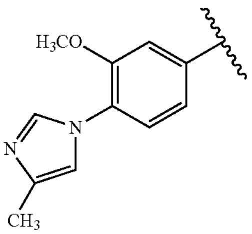 or 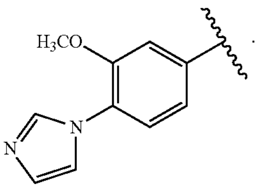.

In another embodiment of this invention the compound of formula (I) is a compound of the formula (IU1):

(IU1)

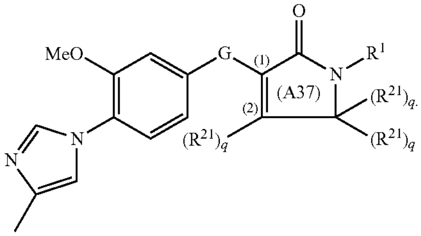

wherein each q is independently 0 or 1, and each $R^{21}$ for each q is independently selected.

In another embodiment of this invention the compound of formula (I) is a compound of the formula (IV):

(IV)

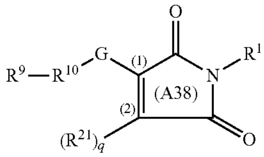

wherein q is 0 or 1.

In another embodiment of this invention the compound of formula (I) is a compound of the formula (IV) wherein G is selected from the group consisting of: —NH—, and a direct bond.

In another embodiment of this invention the compound of formula (I) is a compound of the formula (IV) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (e) (d) $R^{10}$ is phenyl substituted with one —$OR^{15}$ group, wherein $R^{15}$ is methyl, and (f) $R^9$ is selected from the group consisting of imidazolyl and imidazolyl substituted with one methyl group.

In another embodiment of this invention the compound of formula (I) is a compound of the formula (IV) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (e) (d) $R^{10}$ is phenyl substituted with one —$OR^{15}$ group, wherein $R^{15}$ is methyl, and (f) $R^9$ is selected from the group consisting of imidazolyl and imidazolyl substituted with one methyl group, and (g) $R^1$ is selected from the group consisting of:

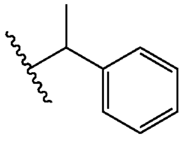, 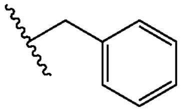,

-continued

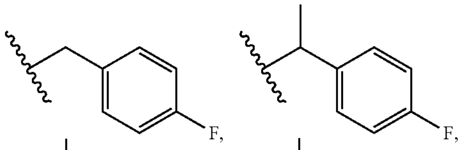

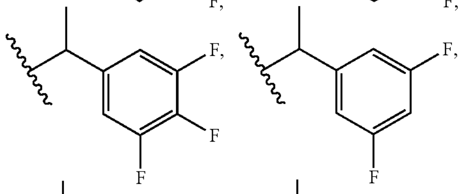

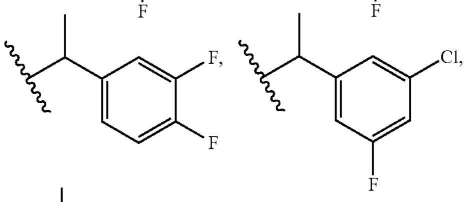

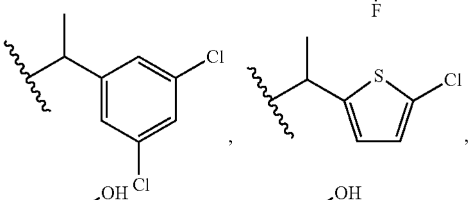

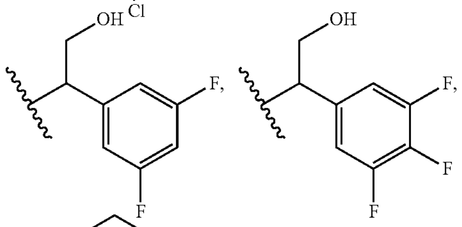

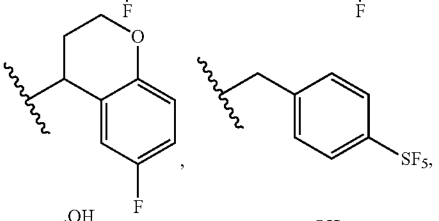

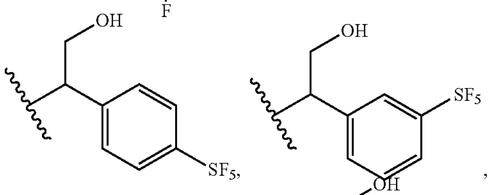

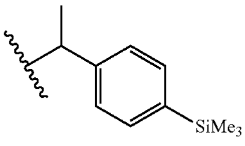

and

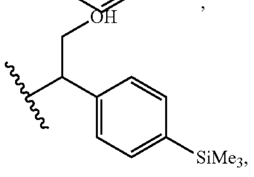

and wherein the $R^9$-$R^{10}$— moiety is:

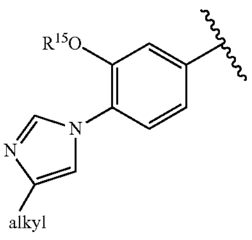

or

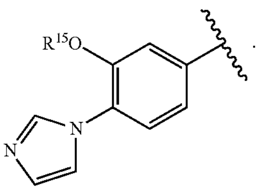

In another embodiment of this invention the compound of formula (I) is a compound of the formula (IV) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (e) (d) $R^{10}$ is phenyl substituted with one —$OR^{15}$ group, wherein $R^{15}$ is methyl, and (f) $R^9$ is selected from the group consisting of imidazolyl and imidazolyl substituted with one methyl group, and (g) $R^1$ is selected from the group consisting of:

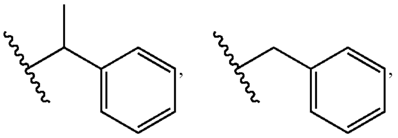

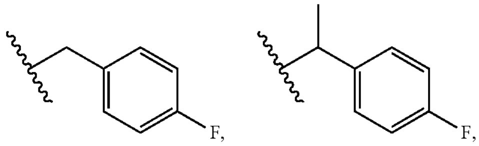

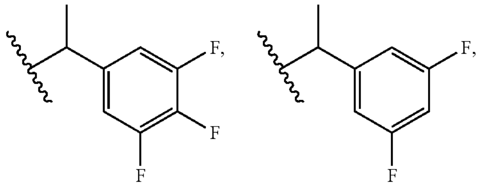

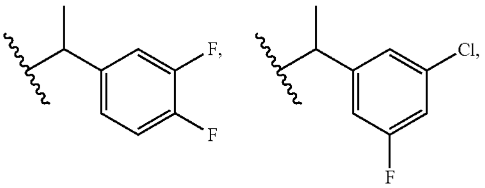

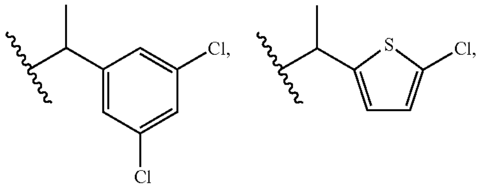

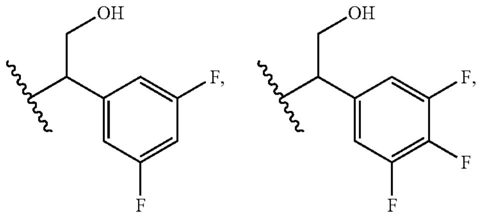

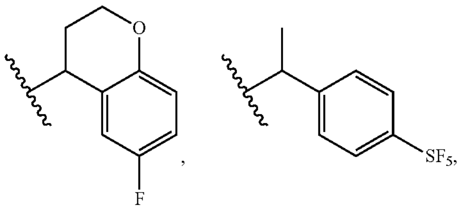

-continued

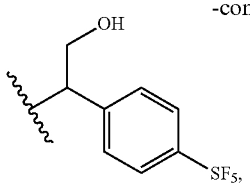

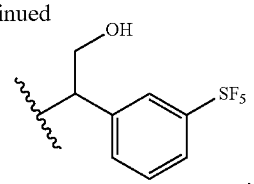

,

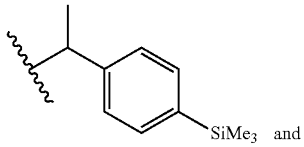

and

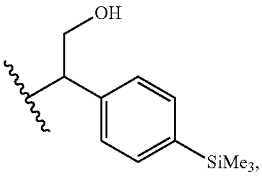

and
wherein the $R^9$-$R^{10}$— moiety is:

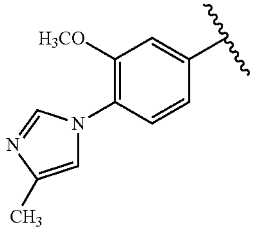

or

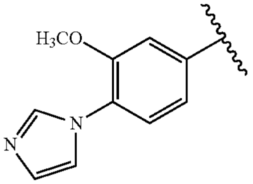

.

In another embodiment of this invention the compound of formula (I) is a compound of the formula (IV1):

(IV1)

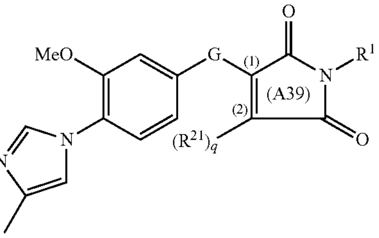

wherein q is 0 or 1.

In another embodiment of this invention the compound of formula (I) is a compound of the formula (IW):

(IW)

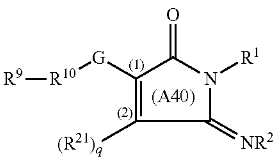

wherein q is 0 or 1.

In another embodiment of this invention the compound of formula (I) is a compound of the formula (IW) wherein G is selected from the group consisting of: —NH—, and a direct bond.

In another embodiment of this invention the compound of formula (I) is a compound of the formula (IW) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IW) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

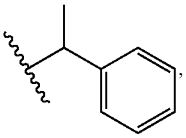

,

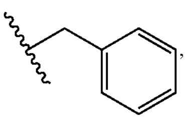

,

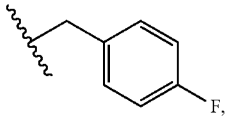

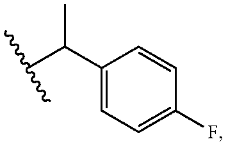

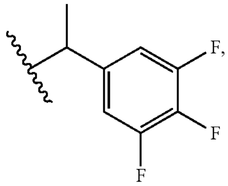

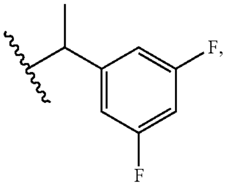

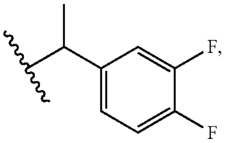

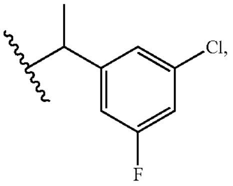

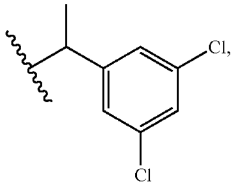

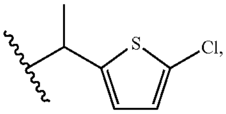

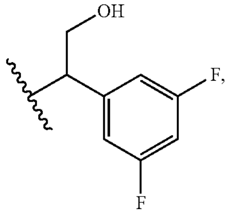

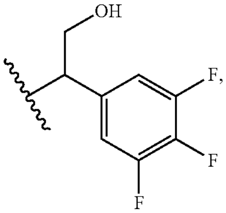

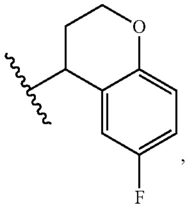

,

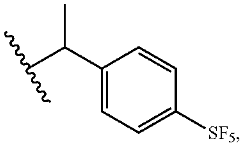

-continued

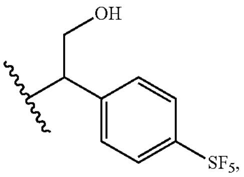

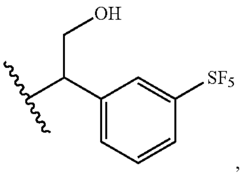

,

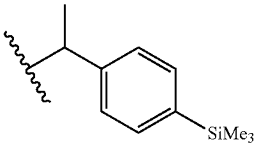

and

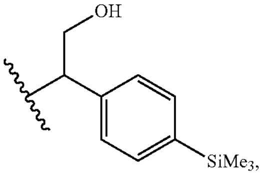

and wherein the $R^9$-$R^{10}$— moiety is:

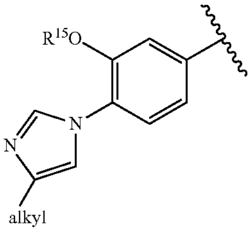

or

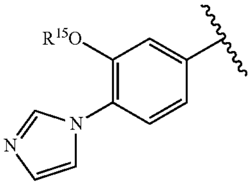

.

In another embodiment of this invention the compound of formula (I) is a compound of the formula (IW) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{10}$ group, wherein $R^{15}$ is methyl, and (e) $R^9$ is selected from the group consisting of imidazolyl and imidazolyl substituted with one methyl group, and (f) $R^1$ is selected from the group consisting of:

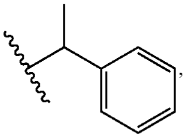

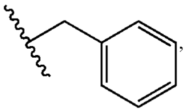

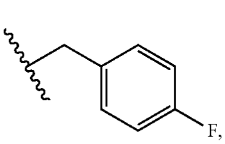

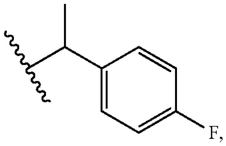

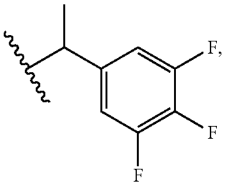

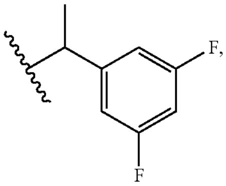

-continued

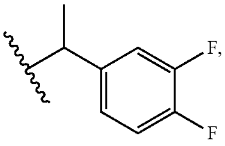

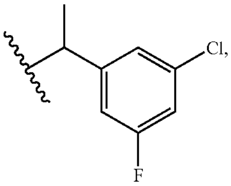

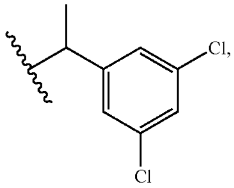

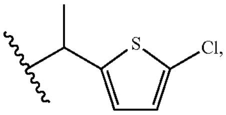

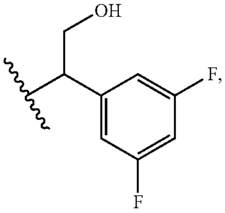

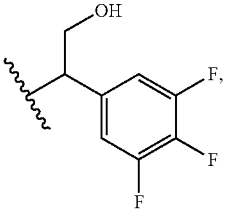

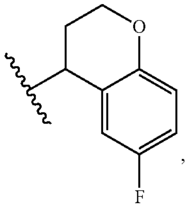

,

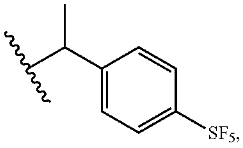

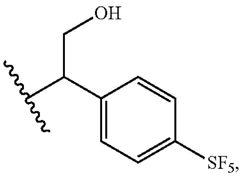

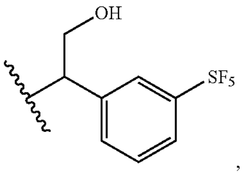

,

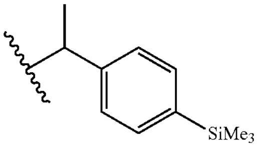

and

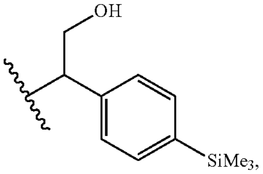

and wherein the $R^9$-$R^{10}$— moiety is:

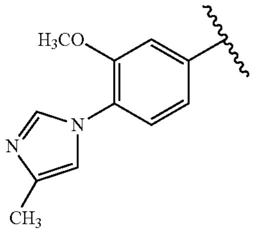

or

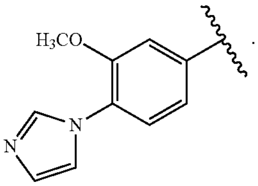

.

In another embodiment of this invention the compound of formula (I) is a compound of the formula (IWI):

(IW1)

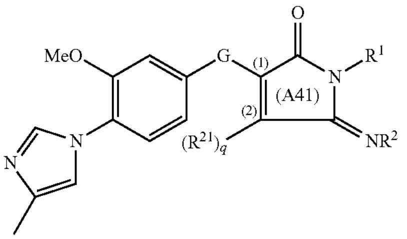

wherein q is 0 or 1.

In another embodiment of this invention the compound of formula (I) is a compound of the formula (IX):

(IX)

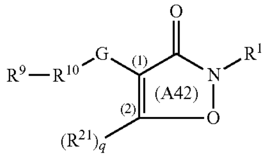

wherein q is 0 or 1.

In another embodiment of this invention the compound of formula (I) is a compound of the formula (IX) wherein G is selected from the group consisting of: —NH—, and a direct bond.

In another embodiment of this invention the compound of formula (I) is a compound of the formula (IX) wherein: (a) G is selected from the group consisting of: —NH—, and a direct bond, (b) is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IX) wherein: (a) G is selected from the group consisting of: —NH—, and a direct bond, (b) is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

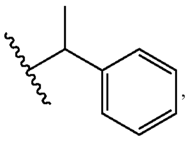, 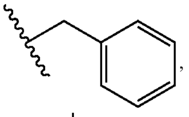,

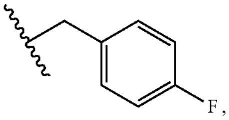 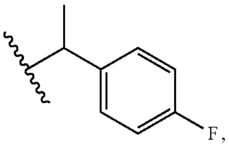

-continued

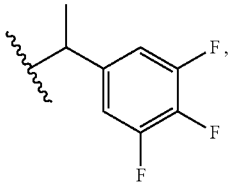 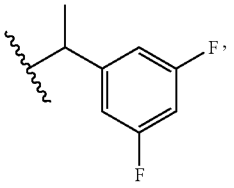

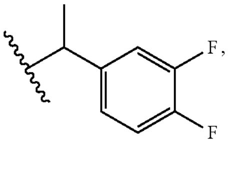 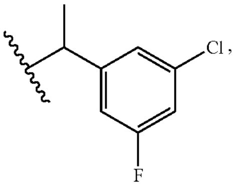

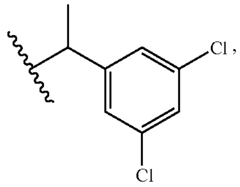 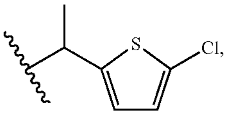

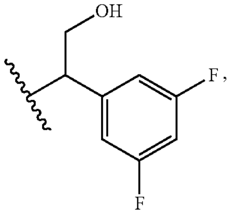 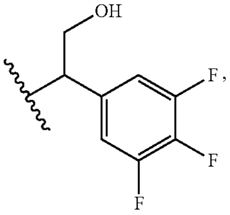

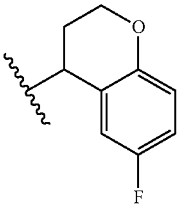, 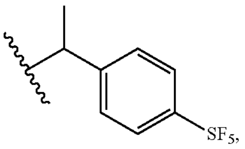

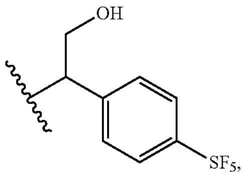 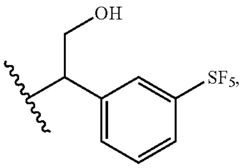

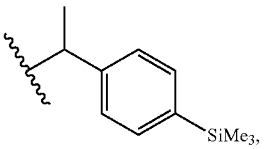 and 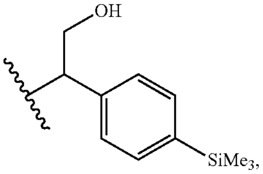

and wherein the $R^9$-$R^{10}$— moiety is:

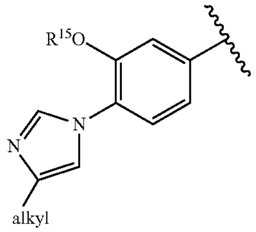 or 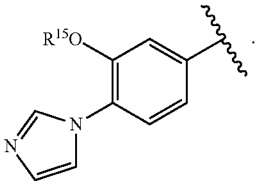.

In another embodiment of this invention the compound of formula (I) is a compound of the formula (IX) wherein: (a) G is selected from the group consisting of: —NH—, and a direct bond, (b) is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

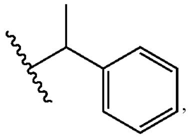
,
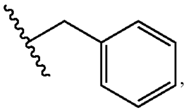
,
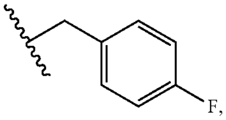
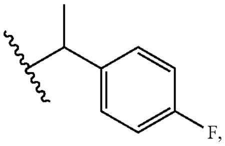
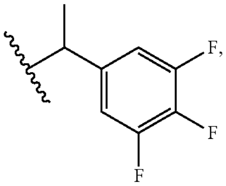
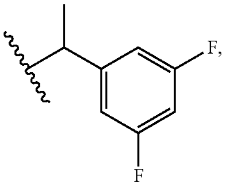
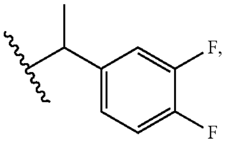
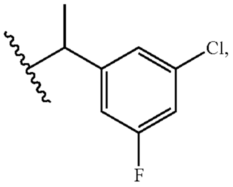
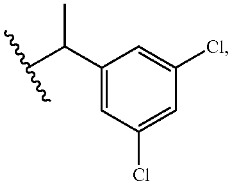
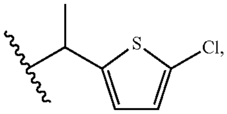
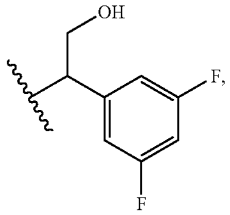
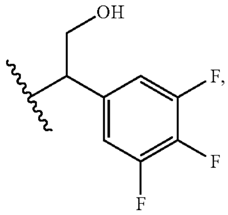
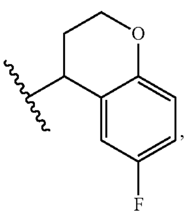
,
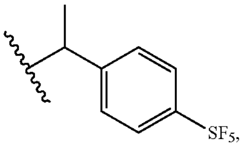
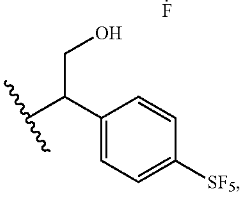
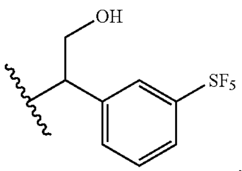
, -continued

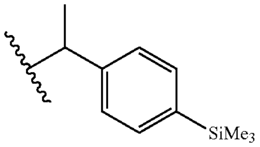
and
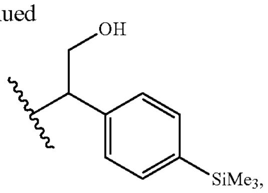

and wherein the $R^9$-$R^{10}$— moiety is:

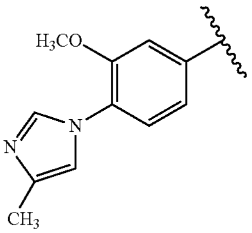
or
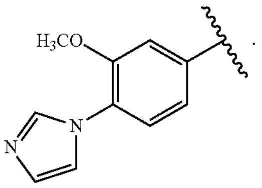
.

In another embodiment of this invention the compound of formula (I) is a compound of the formula (IX1):

(IX1)

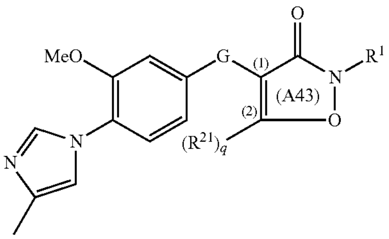

wherein q is 0 or 1.

In another embodiment of this invention the compound of formula (I) is a compound of the formula (IY):

(IY)

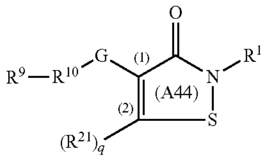

wherein q is 0 or 1.

In another embodiment of this invention the compound of formula (I) is a compound of the formula (IY) wherein G is selected from the group consisting of: —NH—, and a direct bond.

In another embodiment of this invention the compound of formula (I) is a compound of the formula (IY) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IY) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

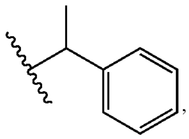

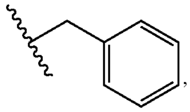

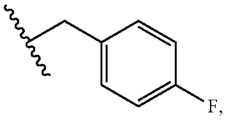

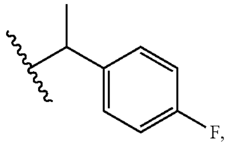

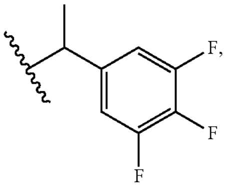

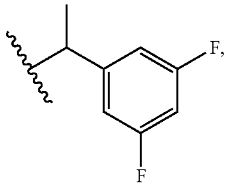

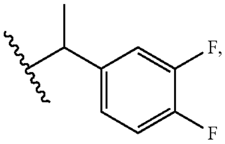

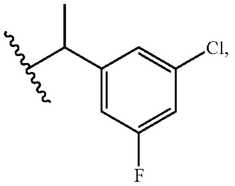

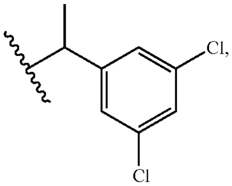

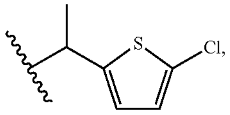

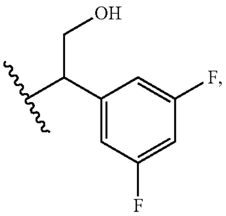

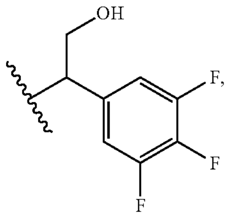

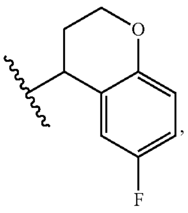

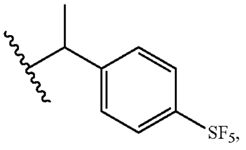

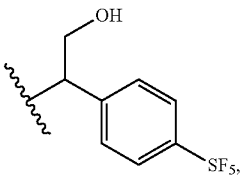

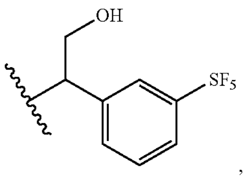

-continued

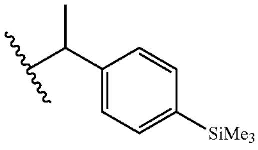

and

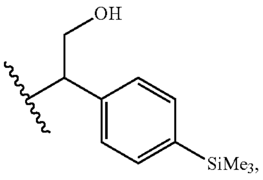

and wherein the $R^9$-$R^{10}$— moiety is:

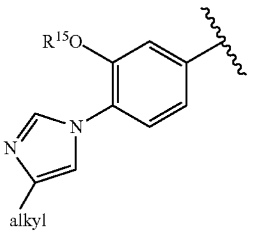

or

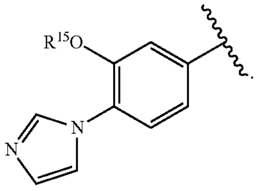

In another embodiment of this invention the compound of formula (I) is a compound of the formula (IY) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

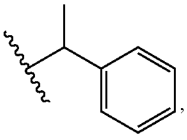

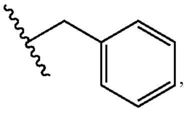

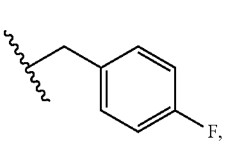

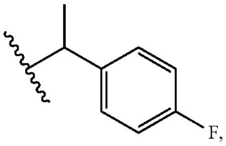

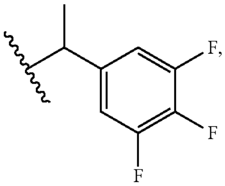

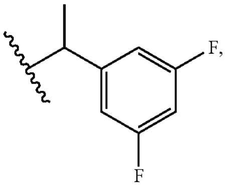

-continued

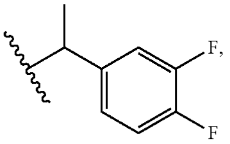
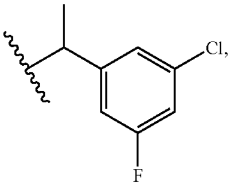
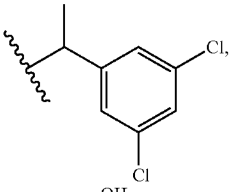
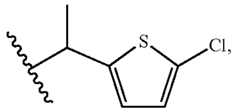
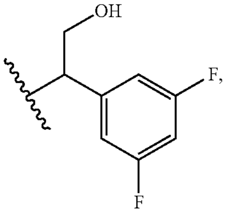
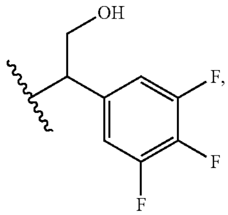
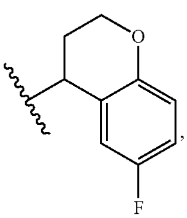,
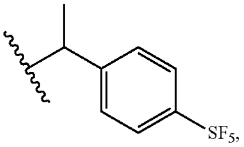
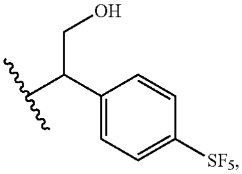
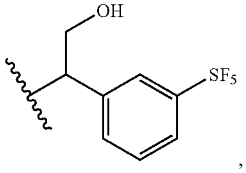,
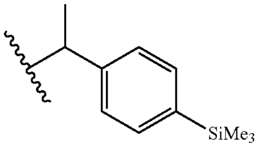 and
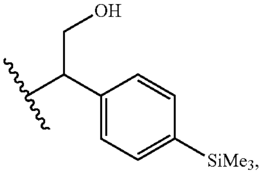

and wherein the $R^9$-$R^{10}$— moiety is:

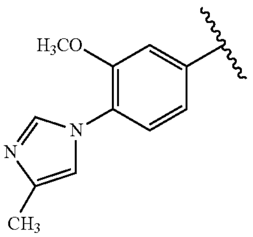

or

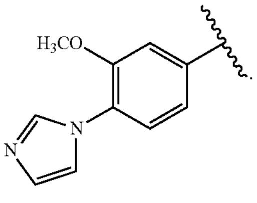

In another embodiment of this invention the compound of formula (I) is a compound of the formula (IY1):

(IY1)

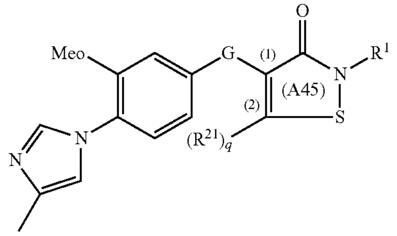

wherein q is 0 or 1.

In another embodiment of this invention the compound of formula (I) is a compound of the formula (IZ):

(IZ)

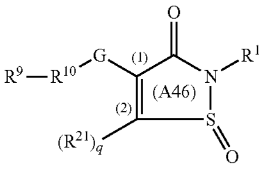

wherein q is 0 or 1.

In another embodiment of this invention the compound of formula (I) is a compound of the formula (IZ) wherein G is selected from the group consisting of: —NH—, and a direct bond.

In another embodiment of this invention the compound of formula (I) is a compound of the formula (IZ) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IZ) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

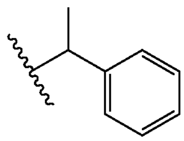,
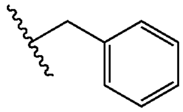,
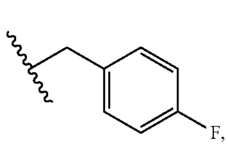
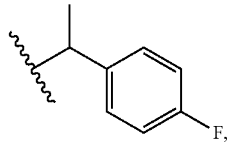

-continued

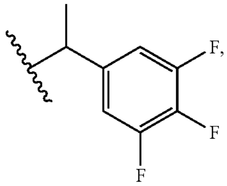 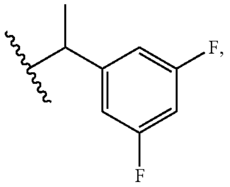

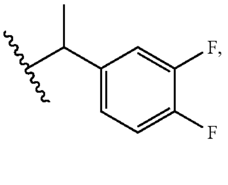 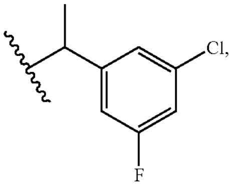

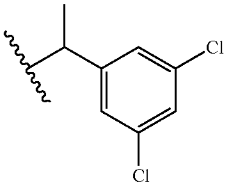 , 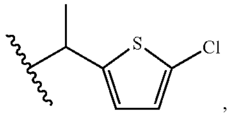 ,

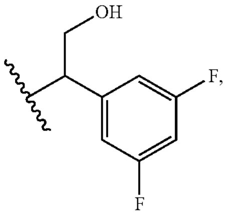 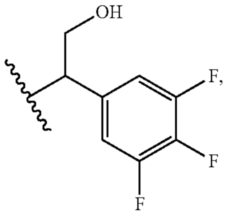

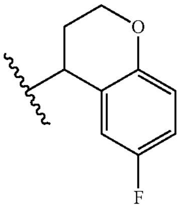 , 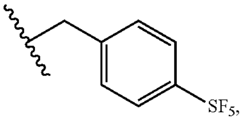

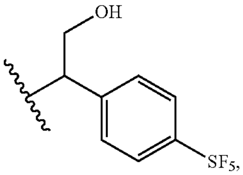 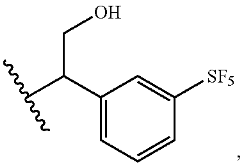 ,

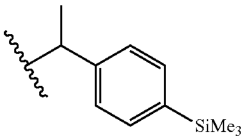 and 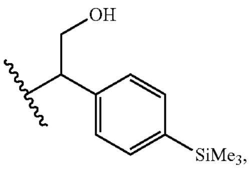

and wherein the $R^9$-$R^{10}$— moiety is:

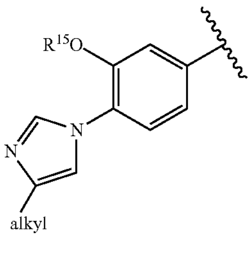 or

-continued

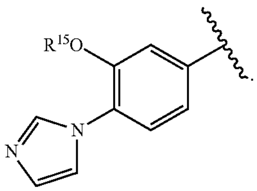

In another embodiment of this invention the compound of formula (I) is a compound of the formula (IZ) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) $R^1$ is selected from the group consisting of:

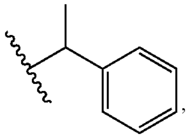 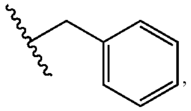

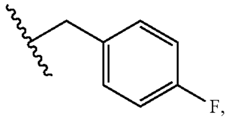 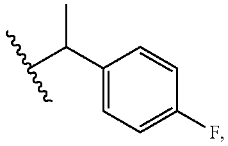

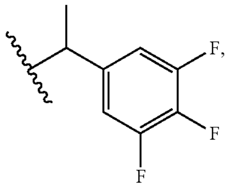 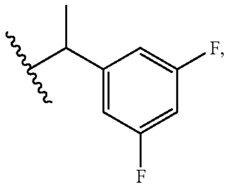

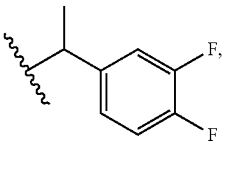 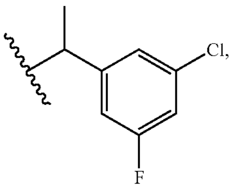

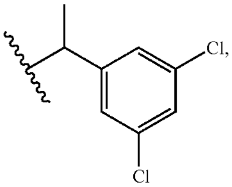 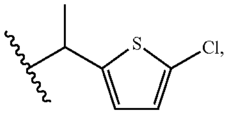

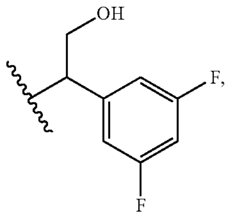 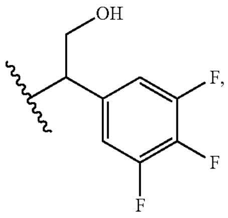

-continued

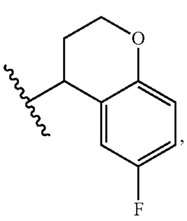

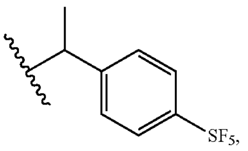

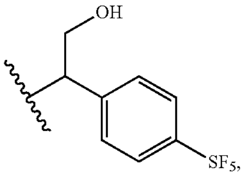

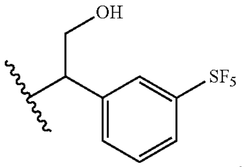

,

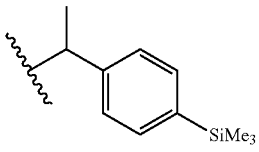

and

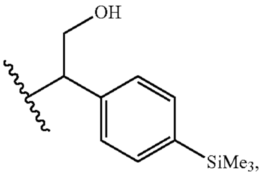

and wherein the $R^9$-$R^{10}$— moiety is:

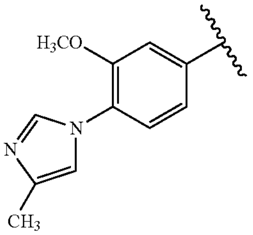

or

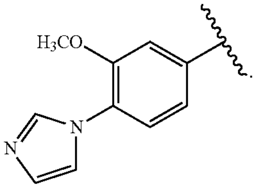

In another embodiment of this invention the compound of formula (I) is a compound of the formula (IZ1):

(IZ1)

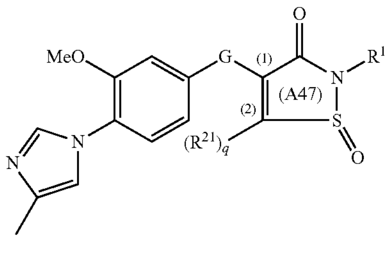

wherein q is 0 or 1.

In another embodiment of this invention the compound of formula (I) is a compound of the formula (IAB):

(IAB)

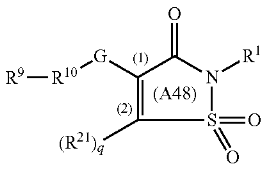

wherein q is 0 or 1.

In another embodiment of this invention the compound of formula (I) is a compound of the formula (IAB) wherein G is selected from the group consisting of: —NH—, and a direct bond.

In another embodiment of this invention the compound of formula (I) is a compound of the formula (IAB) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IAB) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, (f) $R^1$ is selected from the group consisting of:

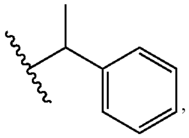

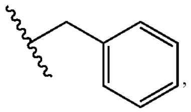

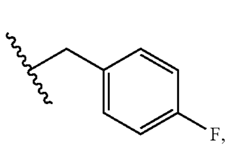

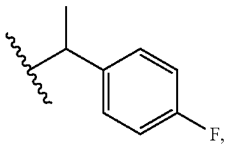

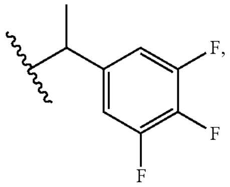

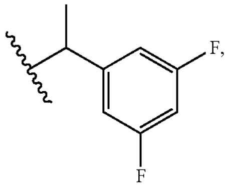

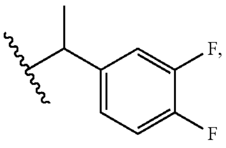

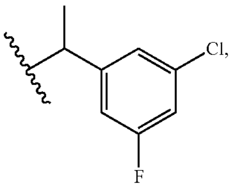

-continued

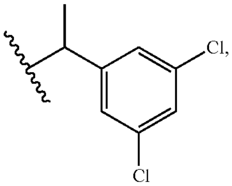

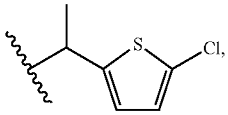

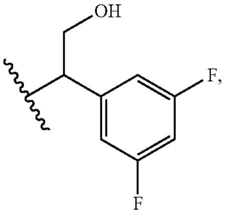

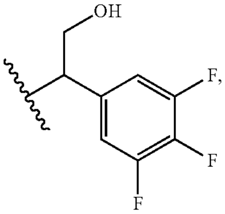

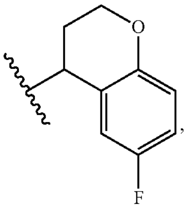
,

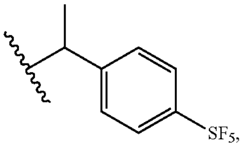

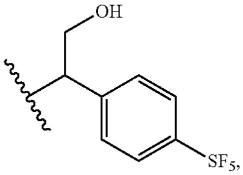

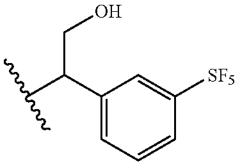
,

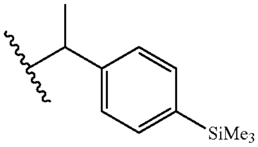
and

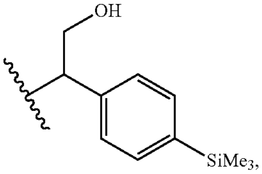

and wherein the $R^9$-$R^{10}$— moiety is:

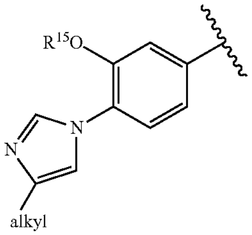
or

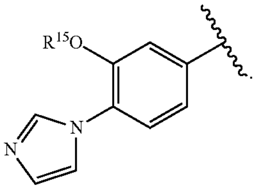

In another embodiment of this invention the compound of formula (I) is a compound of the formula (IAB) wherein: (a) G is selected from the group consisting of: —NH—, and a direct bond, (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, (f) $R^1$ is selected from the group consisting of:

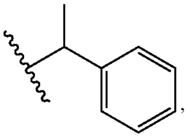

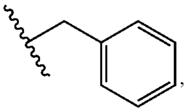

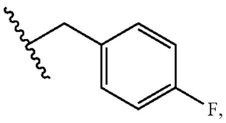

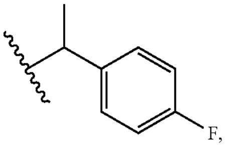

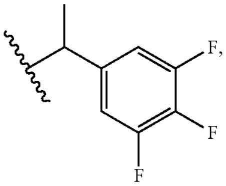

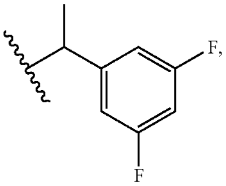

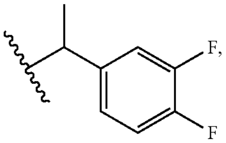

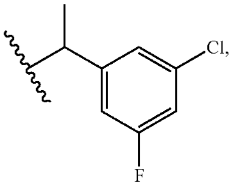

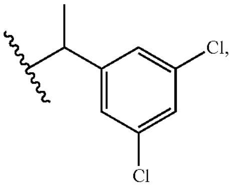

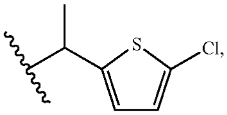

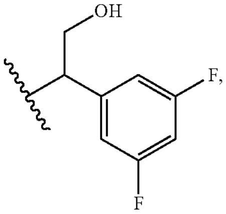

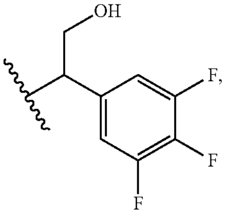

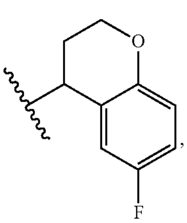

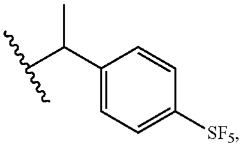

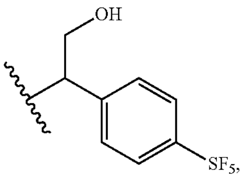

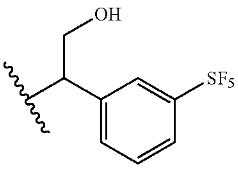
,

-continued

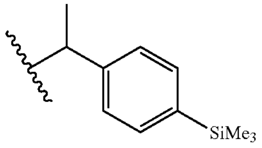

and

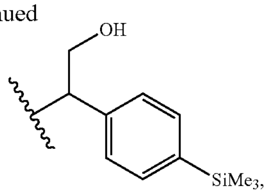

and wherein the $R^9$-$R^{10}$— moiety is:

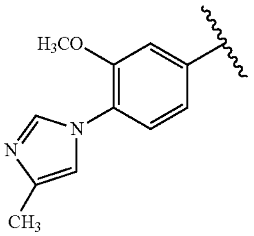

or

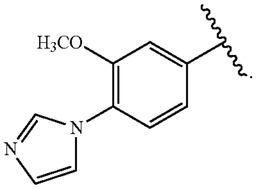

In another embodiment of this invention the compound of formula (I) is a compound of the formula (IAB1):

(IAB1)

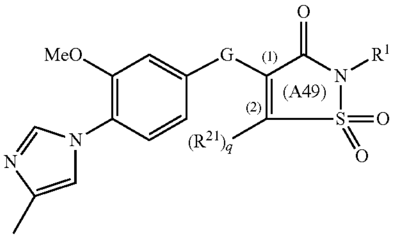

wherein q is 0 or 1.

In another embodiment of this invention the compound of formula (I) is a compound of the formula:

(IAC3)

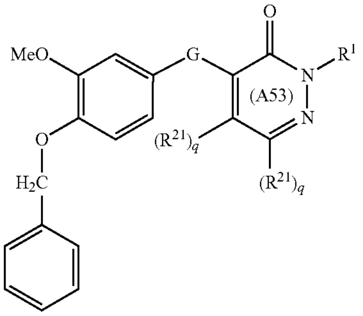

wherein each q is independently 0 or 1, and each $R^{21}$ is independently selected.

In another embodiment of this invention the compound of formula (I) is a compound of the formula:

(IAC6)

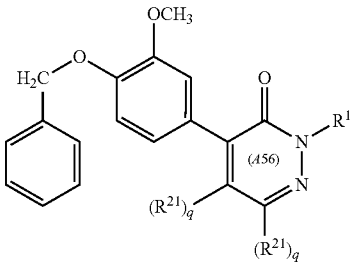

wherein each q is independently 0 or 1, and each $R^{21}$ is independently selected.

In another embodiment of this invention the compound of formula (I) is a compound of the formula:

(IAD3)

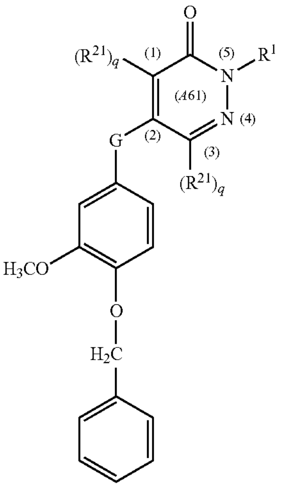

wherein each q is independently 0 or 1, and each $R^{21}$ is independently selected.

In another embodiment of this invention the compound of formula (I) is a compound of the formula:

(IAD6)

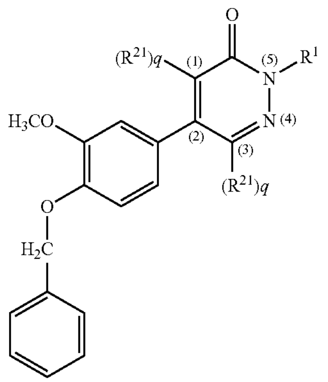

wherein each q is independently 0 or 1, and each $R^{21}$ is independently selected.

In another embodiment of this invention the compound of formula (I) is a compound of the formula:

(IAE)

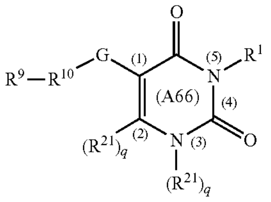

wherein each q is independently 0 or 1, and each $R^{21}$ is independently selected.

In another embodiment of this invention the compound of formula (I) is a compound of the formula (IAE) wherein: q at position (2) is 0 and q at position (3) is 1.

In another embodiment of this invention the compound of formula (I) is a compound of the formula (IAE) wherein: q at position (2) is 0 and q at position (3) is 1, and $R^{21}$ is arylalkyl (e.g., benzyl).

In another embodiment of this invention the compound of formula (I) is a compound of the formula (IAE) wherein: G is selected from the group consisting of: —NH—, and a direct bond.

In another embodiment of this invention the compound of formula (I) is a compound of the formula (IAE) wherein: G is —NH—.

The In another embodiment of this invention the compound of formula (I) is a compound of the formula (IAE) wherein: (a) q at position (2) is 0 and q at position (3) is 1, and (b) G is selected from the group consisting of: —NH—, and a direct bond.

The In another embodiment of this invention the compound of formula (I) is a compound of the formula (IAE) wherein: (a) q at position (2) is 0 and q at position (3) is 1, and $R^{21}$ is arylalkyl (e.g., benzyl), and (b) G is selected from the group consisting of: —NH—, and a direct bond.

In another embodiment of this invention the compound of formula (I) is a compound of the formula (IAE) wherein: (a) G is selected from the group consisting of: —NH—, and a direct bond, and (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IAE) wherein: (a) q at position (2) is 0 and q at position (3) is 1, (b) G is selected from the group consisting of: —NH—, and a direct bond, (c) $R^1$ is a methyl or ethyl group substituted with one phenyl, or (d) $R^1$ is an methyl or ethyl group substituted with one phenyl, and said phenyl is substituted with one or two F, (e) $R^{10}$ is phenyl substituted with one —$OR^{15}$ group, wherein $R^{15}$ is methyl, and (f) $R^9$ is selected from the group consisting of imidazolyl and imidazolyl substituted with one methyl group.

In another embodiment of this invention the compound of formula (I) is a compound of the formula (IAE) wherein: (a) q at position (2) is 0 and q at position (3) is 1, and $R^{21}$ is arylalkyl (e.g., benzyl), (b) G is selected from the group consisting of: —NH—, and a direct bond, (c) $R^1$ is a methyl or ethyl group substituted with one phenyl, or (d) $R^1$ is an methyl or ethyl group substituted with one phenyl, and said phenyl is substituted with one or two F, (e) $R^{10}$ is phenyl substituted with one —$OR^{15}$ group, wherein $R^{15}$ is methyl, and (f) $R^9$ is selected from the group consisting of imidazolyl and imidazolyl substituted with one methyl group.

In another embodiment of this invention the compound of formula (I) is a compound of the formula (IAE) wherein: (a) G is selected from the group consisting of: —NH—, and a direct bond, and (b) $R^1$ is selected from the group consisting of:

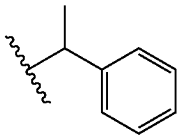,
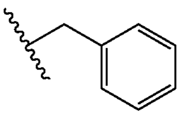,
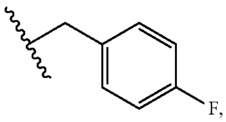, and
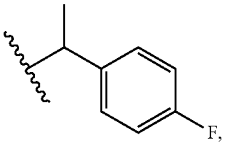, and wherein the $R^9$-$R^{10}$— moiety is:

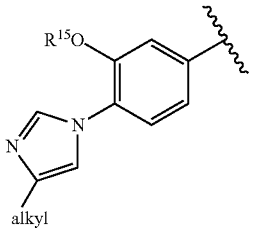 or 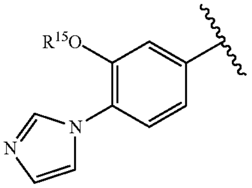.

In another embodiment of this invention the compound of formula (I) is a compound of the formula (IAE) wherein: (a) G is selected from the group consisting of: —NH—, and a direct bond, and (b) $R^1$ is selected from the group consisting of:

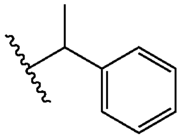,
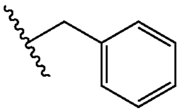,
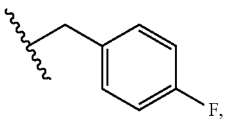, and
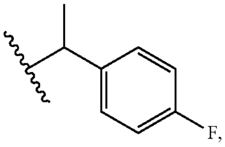, and wherein the $R^9$-$R^{10}$— moiety is:

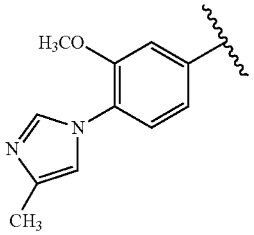 or 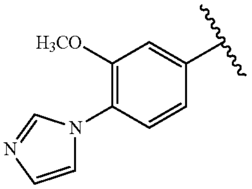.

In another embodiment of this invention the compound of formula (I) is a compound of the formula (IAE) wherein: (a)

G is selected from the group consisting of: —NH—, and a direct bond, and (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) q at position (2) is 0 and q at position (3) is 1, and $R^{21}$ is arylalkyl (e.g., benzyl).

In another embodiment of this invention the compound of formula (I) is a compound of the formula (IAE1):

(IAE1)

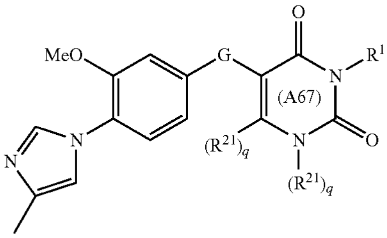

wherein each q is independently 0 or 1, and each $R^{21}$ is independently selected.

In another embodiment of this invention the compound of formula (I) is a compound of the formula:

(IAF)

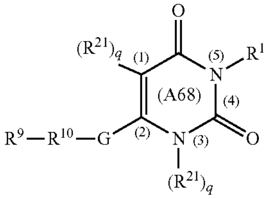

wherein each q is independently 0 or 1, and each $R^{21}$ is independently selected.

In another embodiment of this invention the compound of formula (I) is a compound of the formula (IAF) wherein: (a) q at position (1) is 0 and q at position (3) is 1.

In another embodiment of this invention the compound of formula (I) is a compound of the formula (IAF) wherein: (a) q at position (1) is 0 and q at position (3) is 1, and $R^{21}$ is arylalkyl (e.g., benzyl).

In another embodiment of this invention the compound of formula (I) is a compound of the formula (IAF) wherein: G is selected from the group consisting of: —NH—, and a direct bond.

In another embodiment of this invention the compound of formula (I) is a compound of the formula (IAF) wherein: G is —NH—.

The In another embodiment of this invention the compound of formula (I) is a compound of the formula (IAF) wherein: (a) q at position (1) is 0 and q at position (3) is 1, and (b) G is selected from the group consisting of: —NH—, and a direct bond.

The In another embodiment of this invention the compound of formula (I) is a compound of the formula (IAF) wherein: (a) q at position (1) is 0 and q at position (3) is 1, and $R^{21}$ is arylalkyl (e.g., benzyl), and (b) G is selected from the group consisting of: —NH—, and a direct bond.

In another embodiment of this invention the compound of formula (I) is a compound of the formula (IAF) wherein: (a) G is selected from the group consisting of: —NH—, and a direct bond, and (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group.

In another embodiment of this invention the compound of formula (I) is a compound of the formula (IAF) wherein: (a) q at position (1) is 0 and q at position (3) is 1, (b) G is selected from the group consisting of: —NH—, and a direct bond, (c) $R^1$ is a methyl or ethyl group substituted with one phenyl, or (d) $R^1$ is an methyl or ethyl group substituted with one phenyl, and said phenyl is substituted with one or two F, (e) $R^{10}$ is phenyl substituted with one —$OR^{15}$ group, wherein $R^{15}$ is methyl, and (f) $R^9$ is selected from the group consisting of imidazolyl and imidazolyl substituted with one methyl group.

In another embodiment of this invention the compound of formula (I) is a compound of the formula (IAF) wherein: (a) q at position (1) is 0 and q at position (3) is 1, and $R^{21}$ is arylalkyl (e.g., benzyl), (b) G is selected from the group consisting of: —NH—, and a direct bond, (c) $R^1$ is a methyl or ethyl group substituted with one phenyl, or (d) $R^1$ is an methyl or ethyl group substituted with one phenyl, and said phenyl is substituted with one or two F, (e) $R^{10}$ is phenyl substituted with one —$OR^{15}$ group, wherein $R^{15}$ is methyl, and (f) $R^9$ is selected from the group consisting of imidazolyl and imidazolyl substituted with one methyl group.

In another embodiment of this invention the compound of formula (I) is a compound of the formula (IAF) wherein: (a) G is selected from the group consisting of: —NH—, and a direct bond, and (b) $R^1$ is selected from the group consisting of:

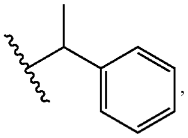

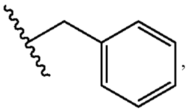

and

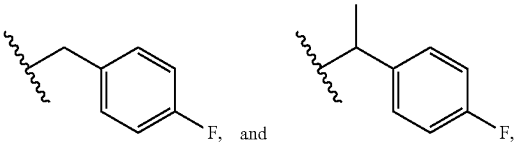

and wherein the $R^9$-$R^{10}$— moiety is:

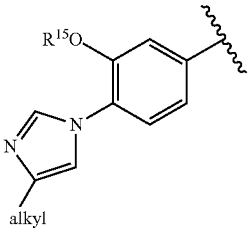

or

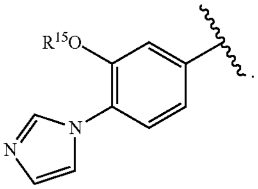

In another embodiment of this invention the compound of formula (I) is a compound of the formula (IAF) wherein: (a)

G is selected from the group consisting of: —NH—, and a direct bond, and (b) $R^1$ is selected from the group consisting of:

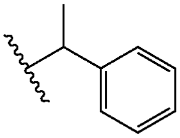,
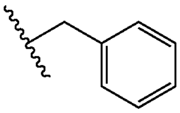,
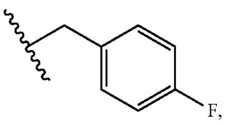, and
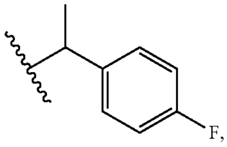, and
wherein the $R^9$-$R^{10}$— moiety is:

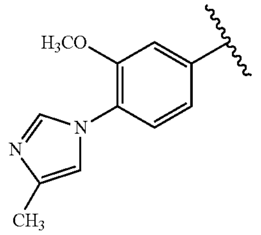
or
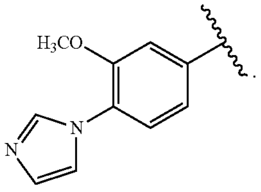.

In another embodiment of this invention the compound of formula (I) is a compound of the formula (IAF) wherein: (a) G is selected from the group consisting of: —NH—, and a direct bond, and (b) $R^1$ is a methyl or ethyl group substituted with one phenyl, or (c) $R^1$ is an methyl or ethyl group substituted with one phenyl, and said phenyl is substituted with one or two F, and (d) $R^{10}$ is phenyl substituted with one —$OR^{15}$ group, wherein $R^{15}$ is methyl, and (e) $R^9$ is selected from the group consisting of imidazolyl and imidazolyl substituted with one methyl group, and (f) q at position (1) is 0 and q at position (3) is 1, and $R^{21}$ is arylalkyl (e.g., benzyl).

In another embodiment of this invention the compound of formula (I) is a compound of the formula (IAF1):

(IAF1)

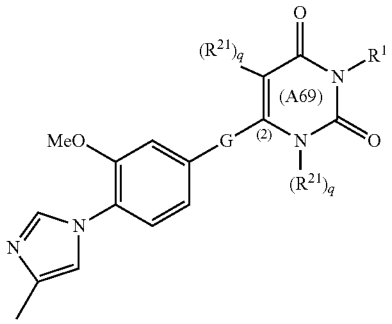

wherein each q is independently 0 or 1, and each $R^{21}$ is independently selected.

Other embodiments of this invention are directed to any one of the embodiments directed to compounds of the formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IO1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1) wherein $R^1$ is selected from the group consisting of:

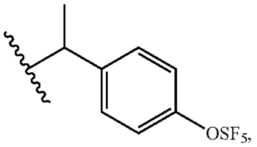,
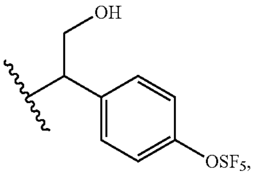,
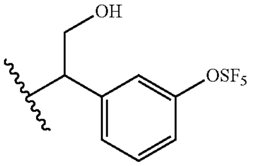 and
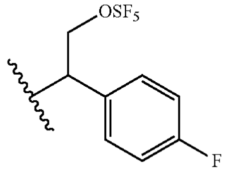.

Representative compounds of formula (I) include, but are not limited to, compounds 1.1-49.1 in Table 1.

TABLE 1

| Compound Number | Structure | LCMS |
|---|---|---|
| 1.1 | 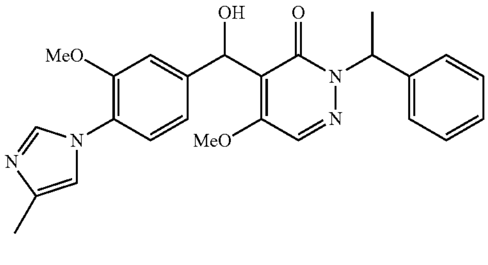 [SMILES: COc1cc(C(O)c2c(OC)cnn(C(C)c3ccccc3)c2=O)ccc1-n1cnc(C)c1] | 447.2 |

TABLE 1-continued
| Compound Number | Structure | LCMS |
|---|---|---|
| 2.1 | 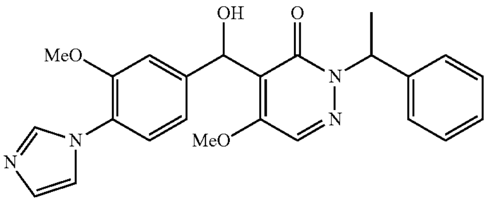 [SMILES: COc1cc(C(O)c2c(OC)cnn(C(C)c3ccccc3)c2=O)ccc1-n1ccnc1] | 433.2 |
| 3.1 | 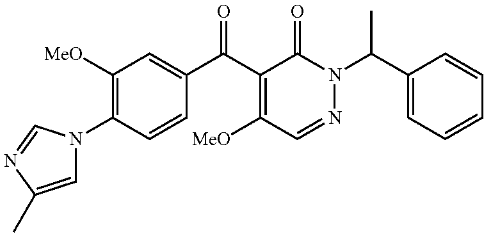 [SMILES: COc1cc(C(=O)c2c(OC)cnn(C(C)c3ccccc3)c2=O)ccc1-n1cnc(C)c1] | 445.2 |
| 4.1 | 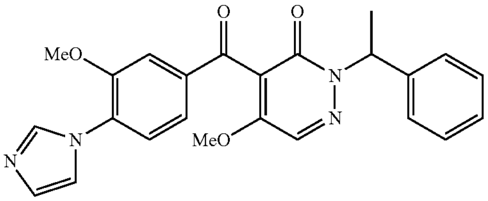 [SMILES: COc1cc(C(=O)c2c(OC)cnn(C(C)c3ccccc3)c2=O)ccc1-n1ccnc1] | 431.2 |
| 5.1 | 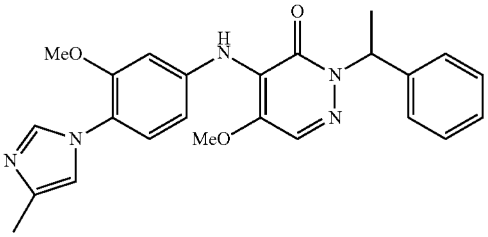 [SMILES: COc1cc(Nc2c(OC)cnn(C(C)c3ccccc3)c2=O)ccc1-n1cnc(C)c1] | 432.2 |
| 6.1 | 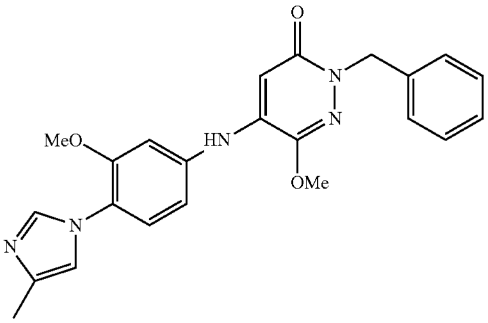 [SMILES: COc1cc(Nc2cc(=O)n(Cc3ccccc3)nc2OC)ccc1-n1cnc(C)c1] | 418.2 |
| 7.1 | 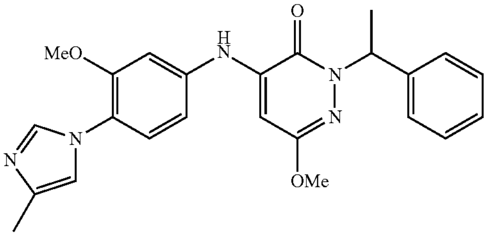 [SMILES: COc1cc(Nc2ccc(-n3cnc(C)c3)c(OC)c2)c(=O)n(C(C)c2ccccc2)n1] | 418.2 |

TABLE 1-continued
| Compound Number | Structure | LCMS |
| --- | --- | --- |
| 8.1 | 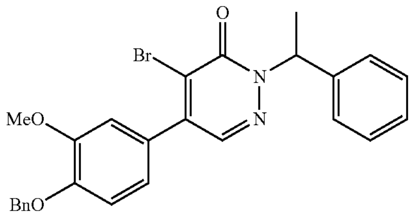 [SMILES: COc1cc(-c2cnn(C(C)c3ccccc3)c(=O)c2Br)ccc1OCc1ccccc1] | 491.0 |
| 9.1 | 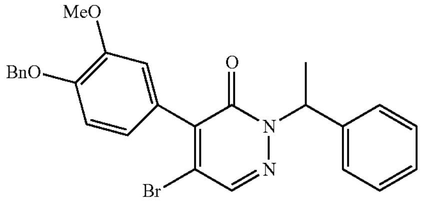 [SMILES: COc1cc(-c2c(Br)cnn(C(C)c3ccccc3)c2=O)ccc1OCc1ccccc1] | 491.0 |
| 10.1 | 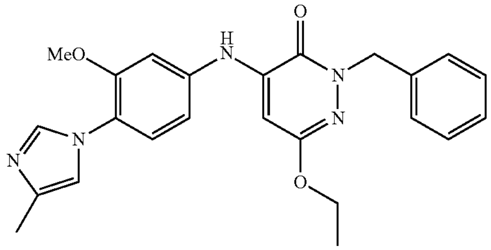 [SMILES: CCOc1cc(Nc2ccc(-n3cnc(C)c3)c(OC)c2)c(=O)n(Cc2ccccc2)n1] | 432.2 |
| 11.1 | 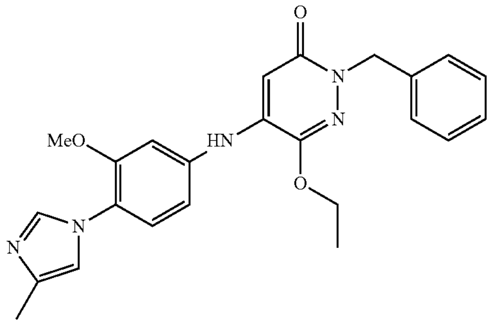 [SMILES: CCOc1nn(Cc2ccccc2)c(=O)cc1Nc1ccc(-n2cnc(C)c2)c(OC)c1] | 432.2 |
| 12.1 | 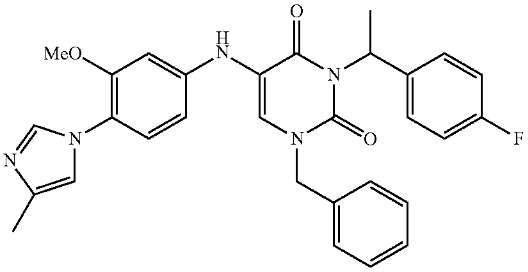 [SMILES: COc1cc(Nc2cn(Cc3ccccc3)c(=O)n(C(C)c3ccc(F)cc3)c2=O)ccc1-n1cnc(C)c1] | 526.3 |
| 13.1 | 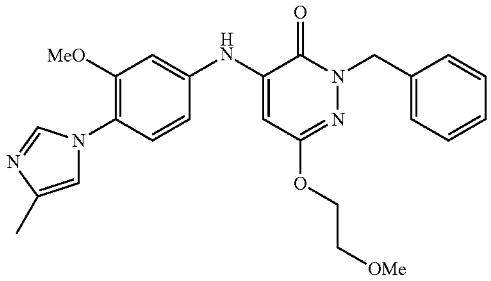 [SMILES: COCCOc1cc(Nc2ccc(-n3cnc(C)c3)c(OC)c2)c(=O)n(Cc2ccccc2)n1] | 462.3 |

TABLE 1-continued
| Compound Number | Structure | LCMS |
|---|---|---|
| 14.1 | 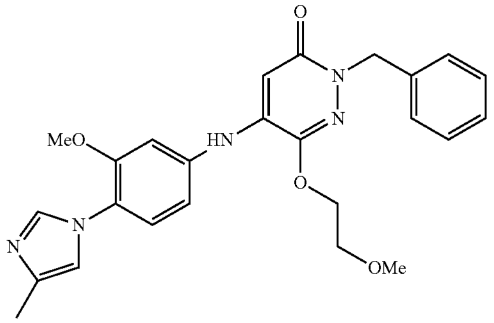 [SMILES: COCCOc1nn(Cc2ccccc2)c(=O)cc1Nc1ccc(-n2cnc(C)c2)c(OC)c1] | 462.3 |
| 15.1 | 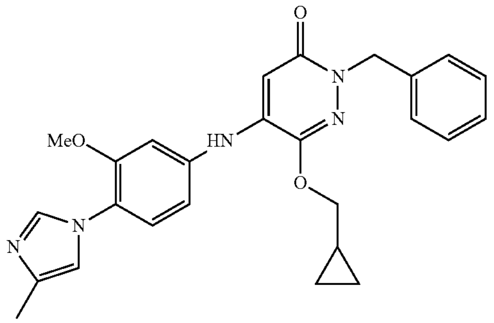 [SMILES: COc1cc(Nc2cc(=O)n(Cc3ccccc3)nc2OCC2CC2)ccc1-n1cnc(C)c1] | 458.3 |
| 16.1 | 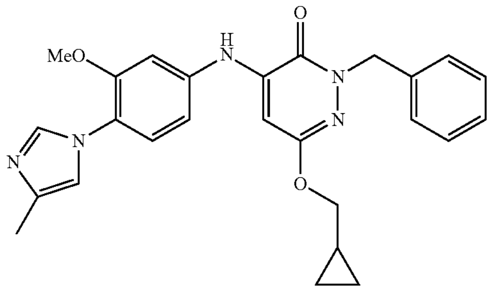 [SMILES: COc1cc(Nc2cc(OCC3CC3)nn(Cc3ccccc3)c2=O)ccc1-n1cnc(C)c1] | 458.3 |
| 17.1 | 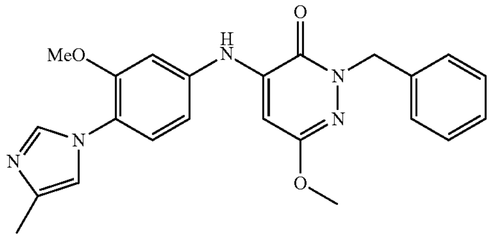 [SMILES: COc1cc(Nc2ccc(-n3cnc(C)c3)c(OC)c2)c(=O)n(Cc2ccccc2)n1] | 419.2 |
| 18.1 | 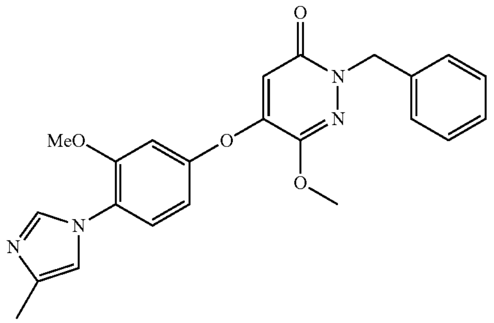 [SMILES: COc1cc(Oc2cc(=O)n(Cc3ccccc3)nc2OC)ccc1-n1cnc(C)c1] | 419.2 |

TABLE 1-continued
| Compound Number | Structure | LCMS |
| --- | --- | --- |
| 19.1 | 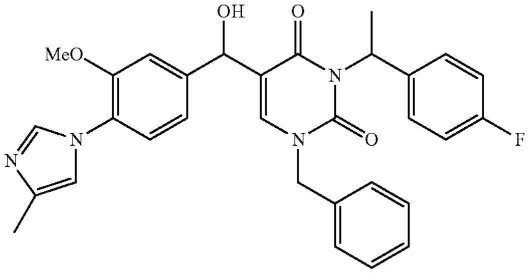 [SMILES: COc1cc(C(O)c2cn(Cc3ccccc3)c(=O)n(C(C)c3ccc(F)cc3)c2=O)ccc1-n1cnc(C)c1] | 541.3 |
| 20.1 | 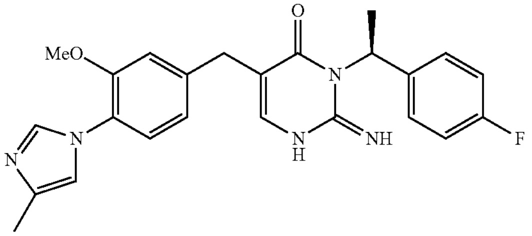 [SMILES: COc1cc(Cc2c[nH]c(=N)n([C@@H](C)c3ccc(F)cc3)c2=O)ccc1-n1cnc(C)c1] | 434.2 |
| 21.1 | 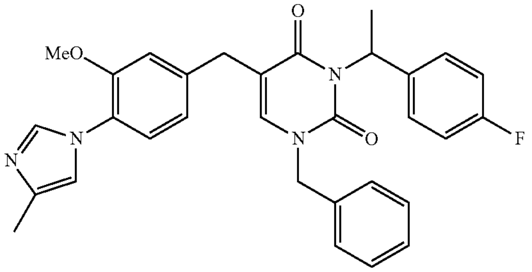 [SMILES: COc1cc(Cc2cn(Cc3ccccc3)c(=O)n(C(C)c3ccc(F)cc3)c2=O)ccc1-n1cnc(C)c1] | 539.3 |
| 22.1 | 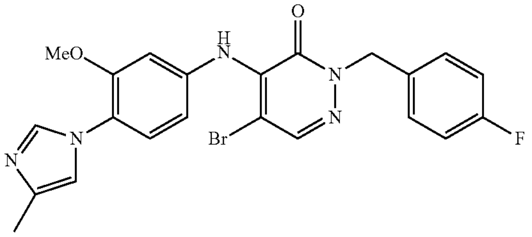 [SMILES: COc1cc(Nc2c(Br)cnn(Cc3ccc(F)cc3)c2=O)ccc1-n1cnc(C)c1] | 486.3 |
| 23.1 | 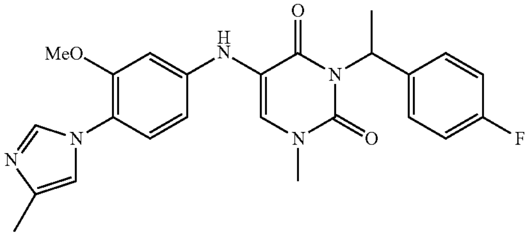 [SMILES: COc1cc(Nc2cn(C)c(=O)n(C(C)c3ccc(F)cc3)c2=O)ccc1-n1cnc(C)c1] | 450.2 |
| 24.1 | 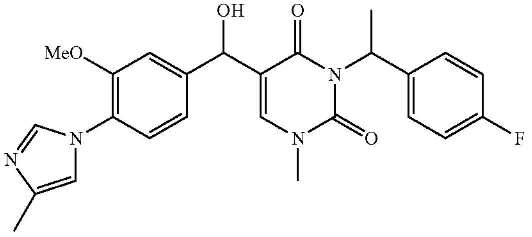 [SMILES: COc1cc(C(O)c2cn(C)c(=O)n(C(C)c3ccc(F)cc3)c2=O)ccc1-n1cnc(C)c1] | 465.3 |

TABLE 1-continued
| Compound Number | Structure | LCMS |
|---|---|---|
| 25.1 | 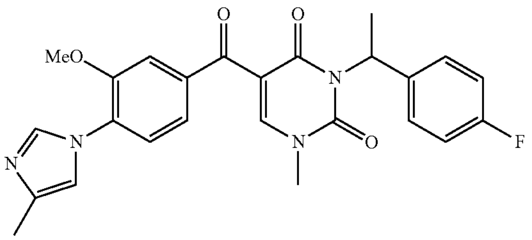 [SMILES: COc1cc(C(=O)c2cn(C)c(=O)n(C(C)c3ccc(F)cc3)c2=O)ccc1-n1cnc(C)c1] | 463.3 |
| 26.1 | 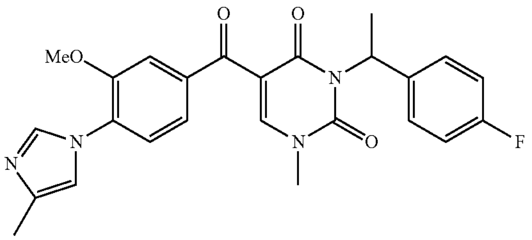 [SMILES: COc1cc(C(=O)c2cn(C)c(=O)n(C(C)c3ccc(F)cc3)c2=O)ccc1-n1cnc(C)c1] | 449.2 |
| 27.1 | 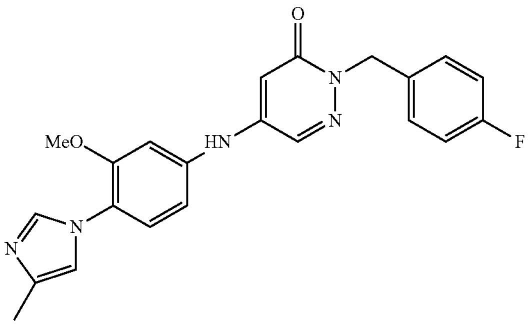 [SMILES: COc1cc(Nc2cnn(Cc3ccc(F)cc3)c(=O)c2)ccc1-n1cnc(C)c1] | 406.2 |
| 28.1 | 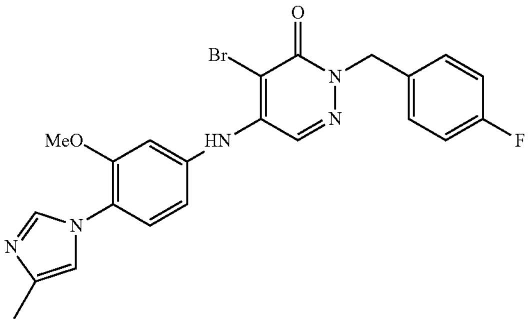 [SMILES: COc1cc(Nc2cnn(Cc3ccc(F)cc3)c(=O)c2Br)ccc1-n1cnc(C)c1] | 486.3 |
| 29.1 | 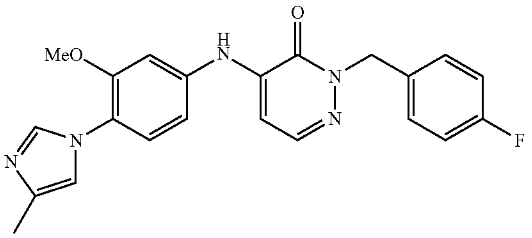 [SMILES: COc1cc(Nc2ccnn(Cc3ccc(F)cc3)c2=O)ccc1-n1cnc(C)c1] | 406.2 |

TABLE 1-continued
| Compound Number | Structure | LCMS |
|---|---|---|
| 30.1 | 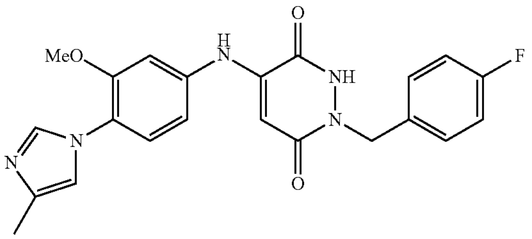 [SMILES: COc1cc(Nc2cc(=O)n(Cc3ccc(F)cc3)[nH]c2=O)ccc1-n1cnc(C)c1] | 422.2 |
| 31.1 | 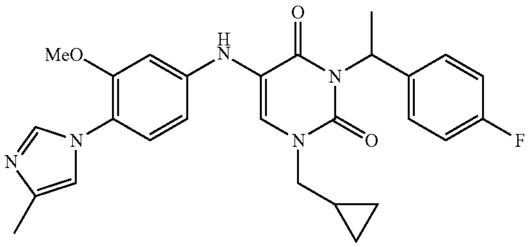 [SMILES: COc1cc(Nc2cn(CC3CC3)c(=O)n(C(C)c3ccc(F)cc3)c2=O)ccc1-n1cnc(C)c1] | 490.3 |
| 32.1 | 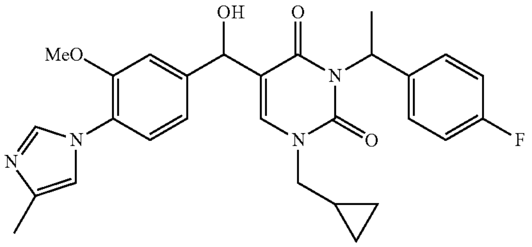 [SMILES: COc1cc(C(O)c2cn(CC3CC3)c(=O)n(C(C)c3ccc(F)cc3)c2=O)ccc1-n1cnc(C)c1] | 505.3 |
| 33.1 | 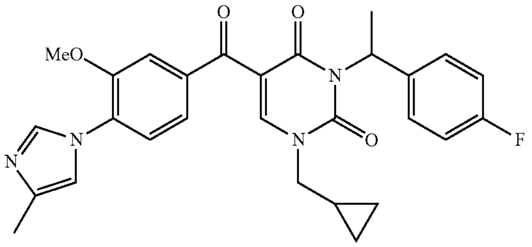 [SMILES: COc1cc(C(=O)c2cn(CC3CC3)c(=O)n(C(C)c3ccc(F)cc3)c2=O)ccc1-n1cnc(C)c1] | 503.3 |
| 34.1 | 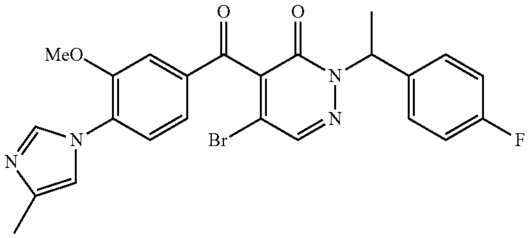 [SMILES: COc1cc(C(=O)c2c(Br)cnn(C(C)c3ccc(F)cc3)c2=O)ccc1-n1cnc(C)c1] | 500.3 |
| 35.1 | 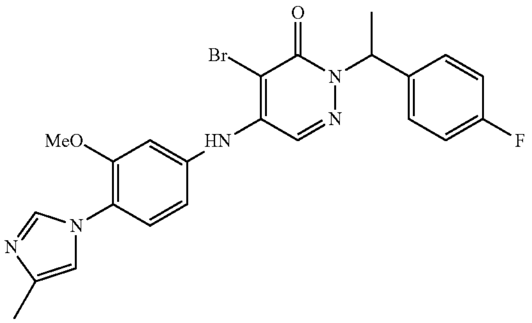 [SMILES: COc1cc(Nc2cnn(C(C)c3ccc(F)cc3)c(=O)c2Br)ccc1-n1cnc(C)c1] | 500.3 |

TABLE 1-continued
| Compound Number | Structure | LCMS |
|---|---|---|
| 36.1 | 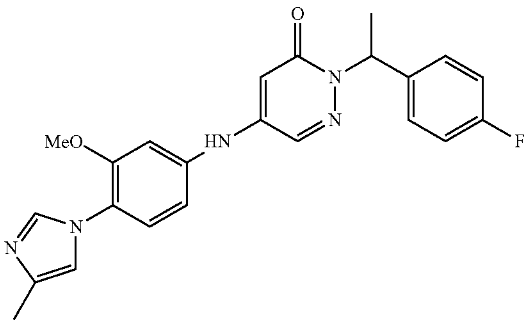 [SMILES: COc1cc(Nc2cnn(C(C)c3ccc(F)cc3)c(=O)c2)ccc1-n1cnc(C)c1] | 420.2 |
| 37.1 | 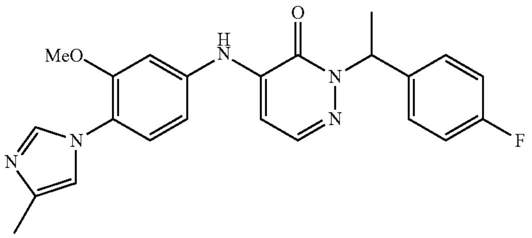 [SMILES: COc1cc(Nc2ccnn(C(C)c3ccc(F)cc3)c2=O)ccc1-n1cnc(C)c1] | 420.2 |
| 38.1 | 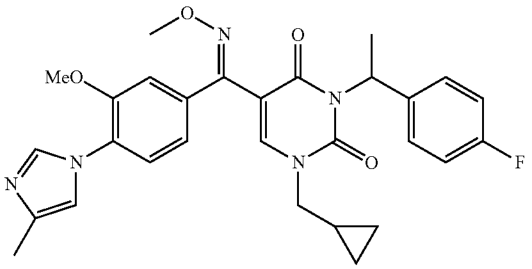 [SMILES: CO/N=C(\c1ccc(-n2cnc(C)c2)c(OC)c1)c1cn(CC2CC2)c(=O)n(C(C)c2ccc(F)cc2)c1=O] | 532.2 |
| 39.1 | 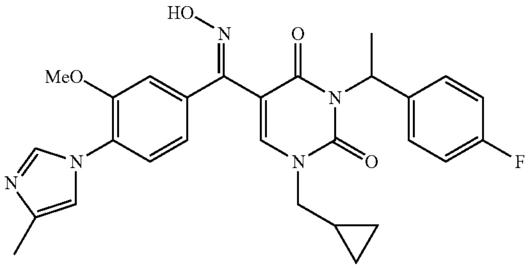 [SMILES: COc1cc(/C(=N\O)c2cn(CC3CC3)c(=O)n(C(C)c3ccc(F)cc3)c2=O)ccc1-n1cnc(C)c1] | 518.3 |
| 40.1 | 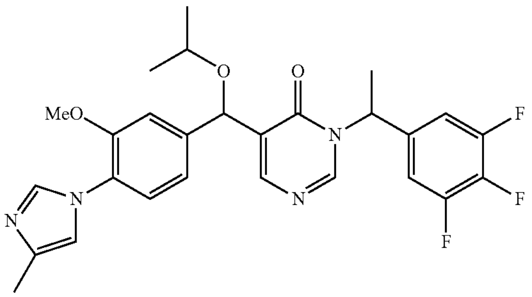 [SMILES: COc1cc(C(OC(C)C)c2cncn(C(C)c3cc(F)c(F)c(F)c3)c2=O)ccc1-n1cnc(C)c1] | 513.3 |

TABLE 1-continued
| Compound Number | Structure | LCMS |
|---|---|---|
| 41.1 | 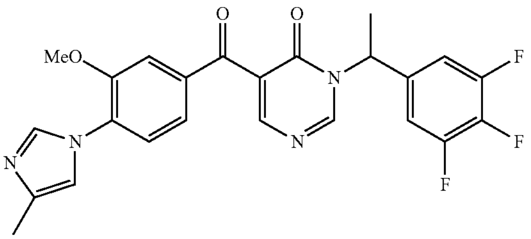 [SMILES: COc1cc(C(=O)c2cncn(C(C)c3cc(F)c(F)c(F)c3)c2=O)ccc1-n1cnc(C)c1] | 469.3 |
| 42.1 | 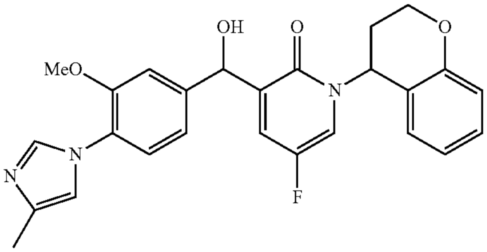 [SMILES: COc1cc(C(O)c2cc(F)cn(C3CCOc4ccccc43)c2=O)ccc1-n1cnc(C)c1] | 462.2 |
| 43.1 | 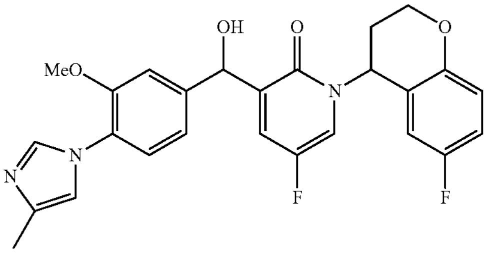 | 480.3 |
| 44.1 | 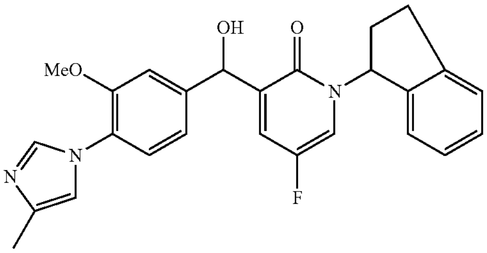 [SMILES: COc1cc(C(O)c2cc(F)cn(C3CCc4ccccc43)c2=O)ccc1-n1cnc(C)c1] | 446.2 |
| 45.1 | 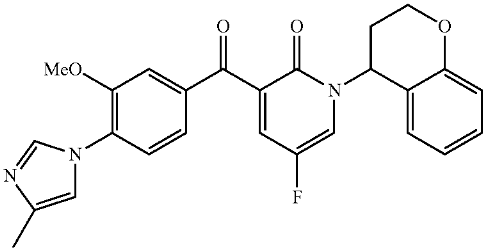 [SMILES: COc1cc(C(=O)c2cc(F)cn(C3CCOc4ccccc43)c2=O)ccc1-n1cnc(C)c1] | 460.3 |
| 46.1 | 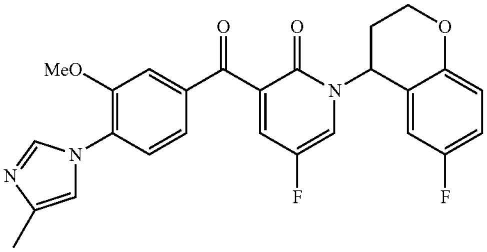 | 478.3 |

TABLE 1-continued
| Compound Number | Structure | LCMS |
|---|---|---|
| 47.1 | 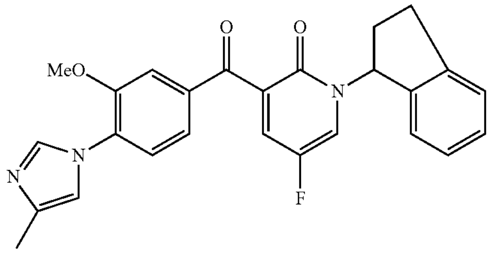 [SMILES: COc1cc(C(=O)c2cc(F)cn(C3CCc4ccccc43)c2=O)ccc1-n1cnc(C)c1] | 444.2 |
| 48.1 | 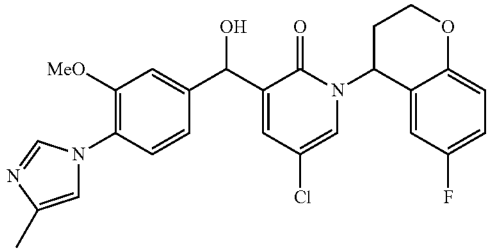 [SMILES: COc1cc(C(O)c2cc(Cl)cn(C3CCOc4ccc(F)cc43)c2=O)ccc1-n1cnc(C)c1] | 496.3 |
| 49.1 | 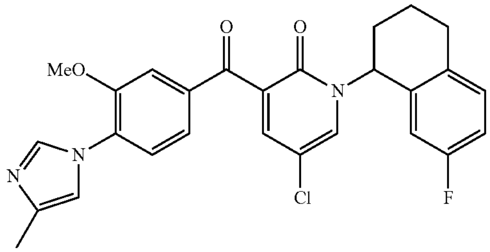 [SMILES: COc1cc(C(=O)c2cc(Cl)cn(C3CCCc4ccc(F)cc43)c2=O)ccc1-n1cnc(C)c1] | 494.3 |
Representative compounds of formula (I) also include, but are not limited to, compounds 191.1-262.1 in Table 2.
TABLE 2
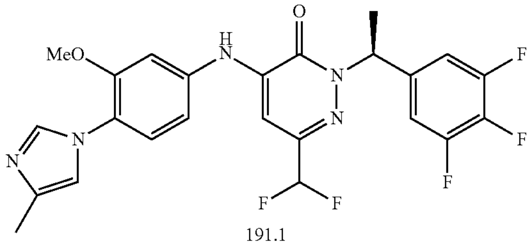 [SMILES: COc1cc(Nc2cc(C(F)F)nn([C@@H](C)c3cc(F)c(F)c(F)c3)c2=O)ccc1-n1cnc(C)c1]
191.1
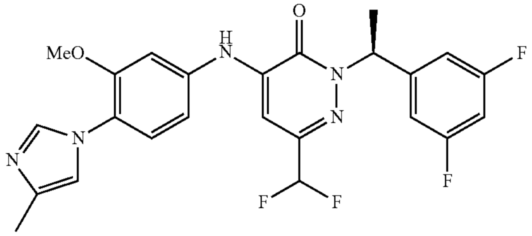
192.1
TABLE 2-continued
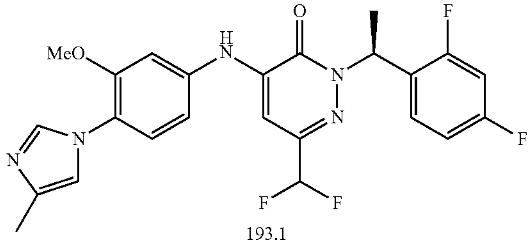 [SMILES: COc1cc(Nc2cc(C(F)F)nn([C@@H](C)c3ccc(F)cc3F)c2=O)ccc1-n1cnc(C)c1]
193.1
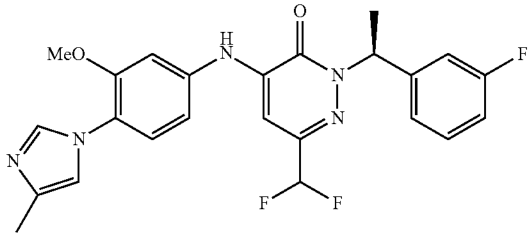
194.1

TABLE 2-continued
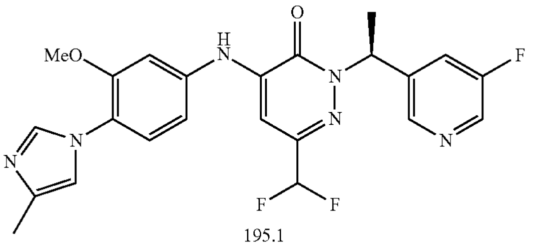 [SMILES: COc1cc(Nc2cc(C(F)F)nn([C@@H](C)c3cncc(F)c3)c2=O)ccc1-n1cnc(C)c1]
195.1
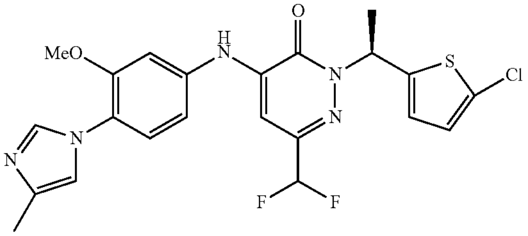
196.1
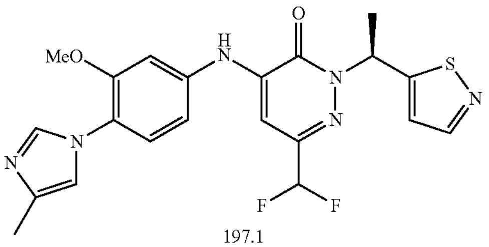 [SMILES: COc1cc(Nc2cc(C(F)F)nn([C@@H](C)c3ccns3)c2=O)ccc1-n1cnc(C)c1]
197.1
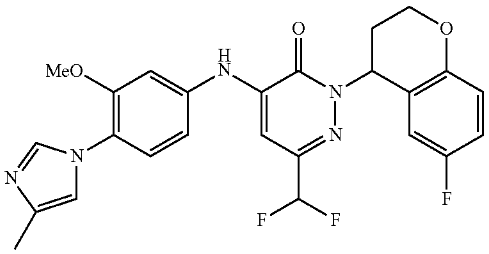
198.1
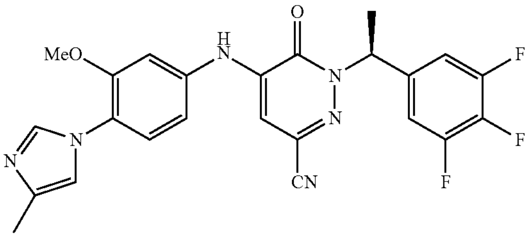
199.1
TABLE 2-continued
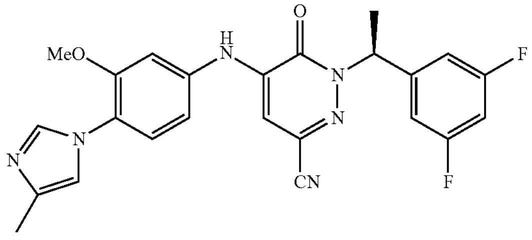
200.1
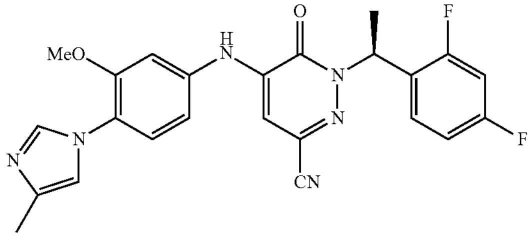
201.1
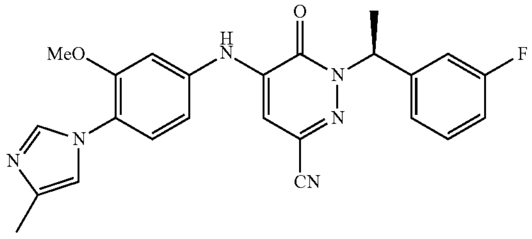
202.1
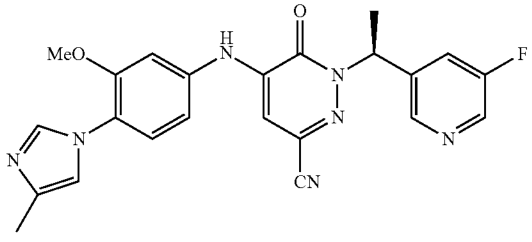
203.1
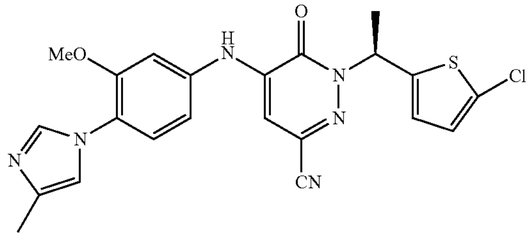
204.1

TABLE 2-continued
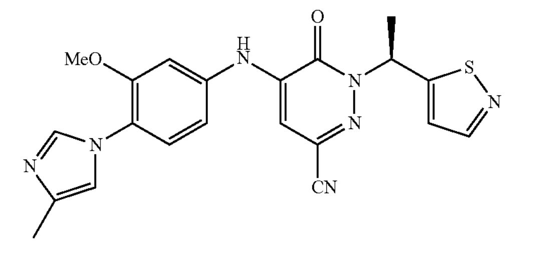
205.1
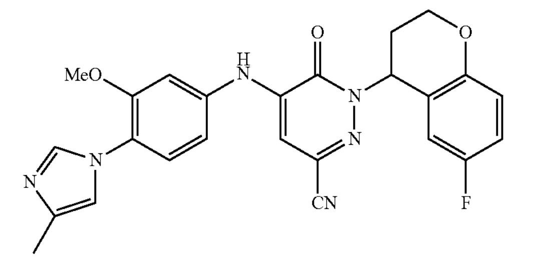
206.1
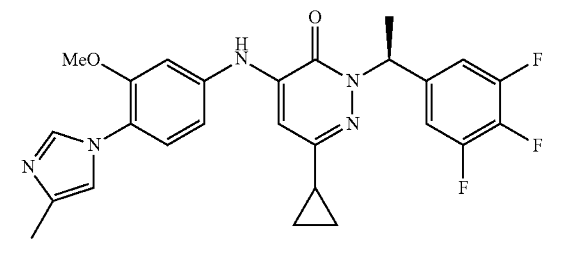
207.1
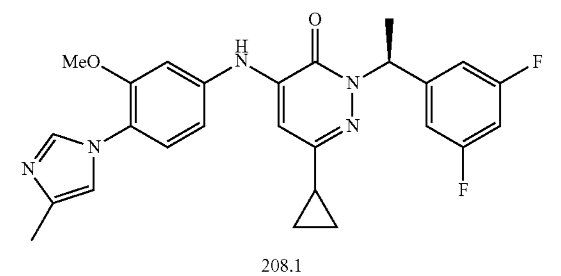 [SMILES: COc1cc(Nc2cc(C3CC3)nn([C@@H](C)c3cc(F)cc(F)c3)c2=O)ccc1-n1cnc(C)c1]
208.1
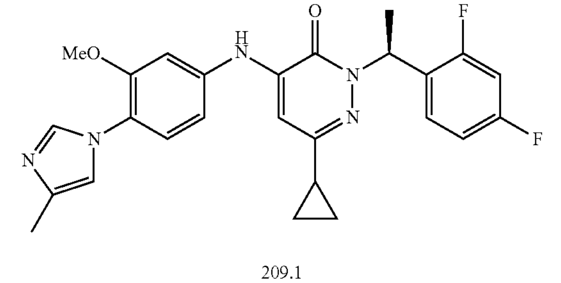 [SMILES: COc1cc(Nc2cc(C3CC3)nn([C@@H](C)c3ccc(F)cc3F)c2=O)ccc1-n1cnc(C)c1]
209.1
TABLE 2-continued
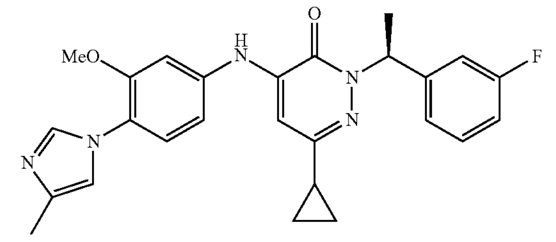
210.1
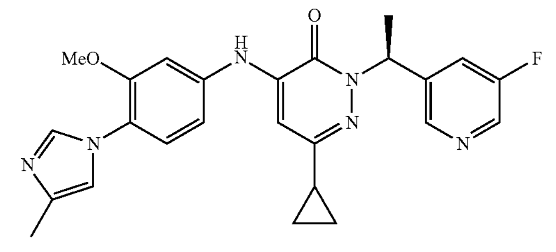
211.1
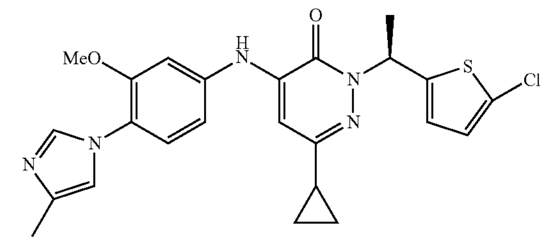
212.1
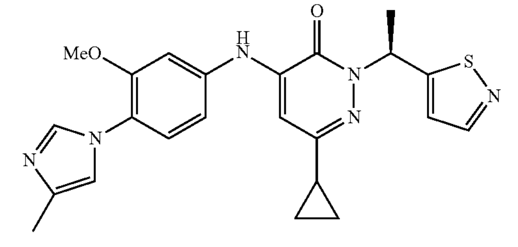
213.1
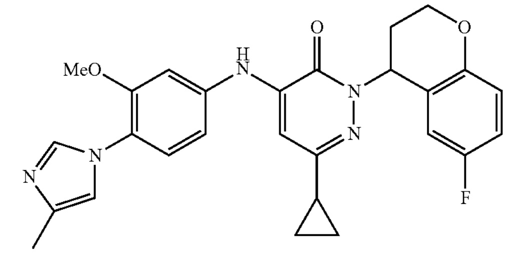
214.1

TABLE 2-continued
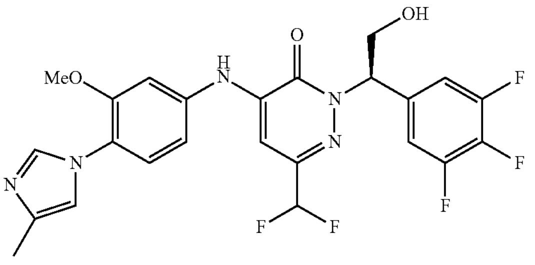
215.1
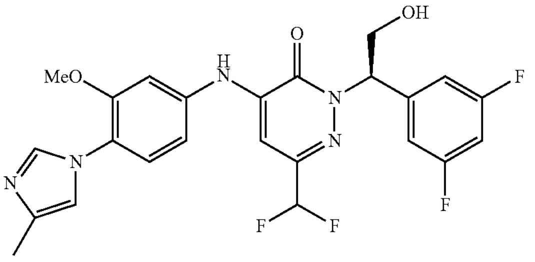
216.1
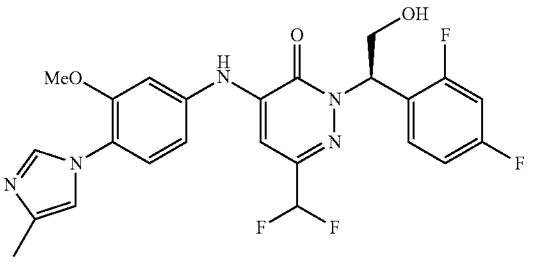
217.1
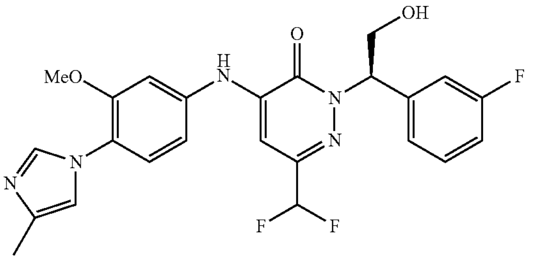
218.1
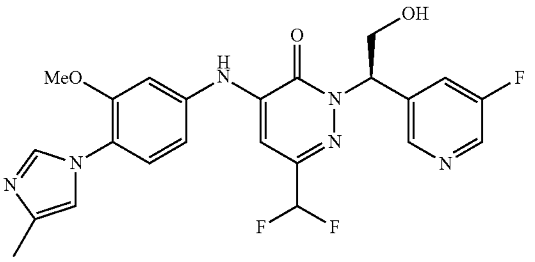
219.1
TABLE 2-continued
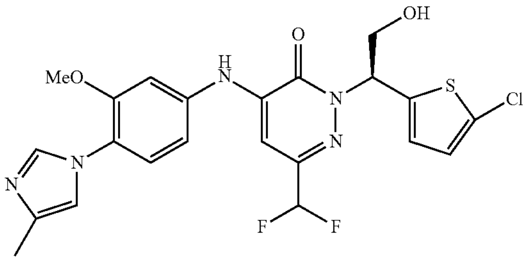
220.1
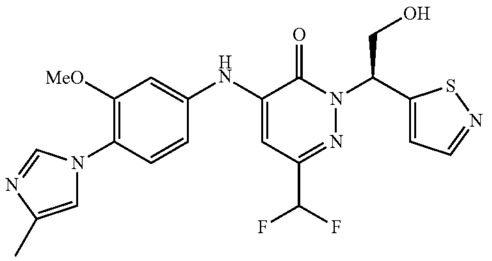
221.1
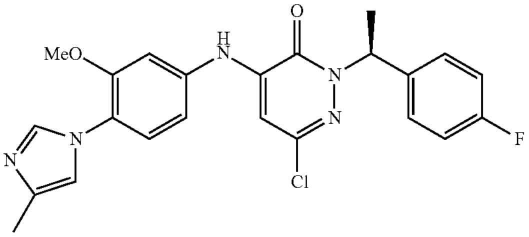
222.1
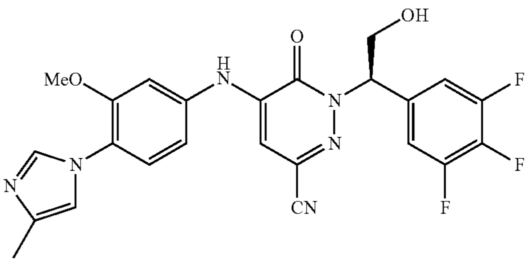
223.1
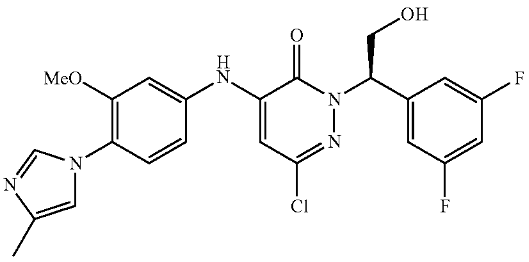
224.1

TABLE 2-continued
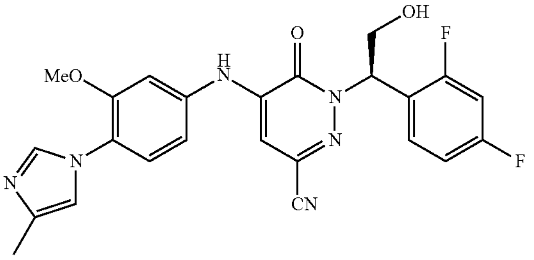
225.1
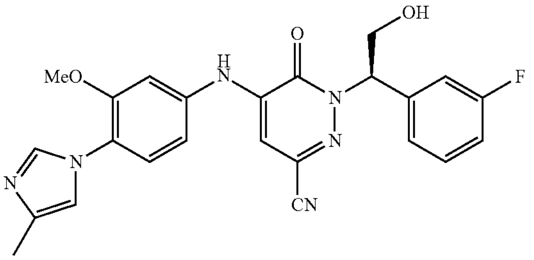
226.1
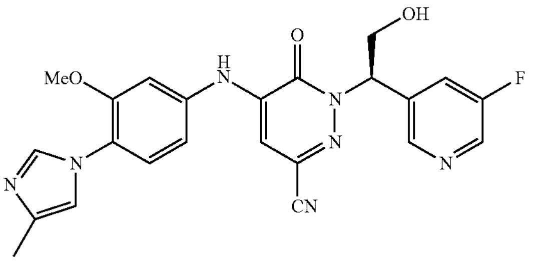
227.1
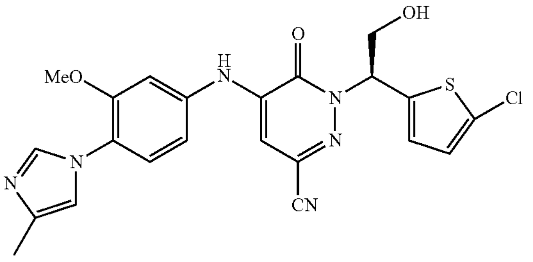
228.1
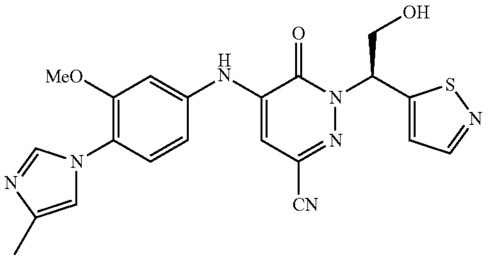
229.1
TABLE 2-continued
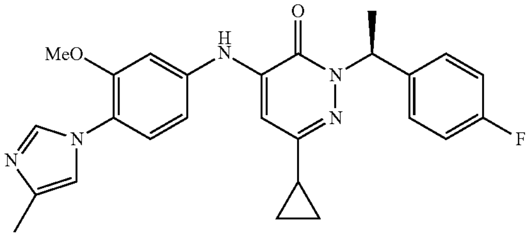
230.1
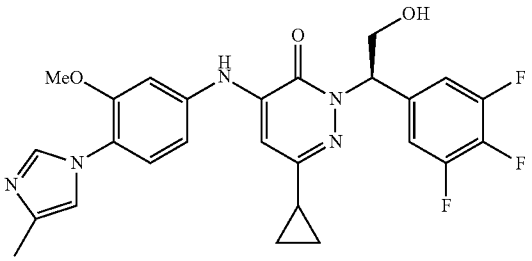
231.1
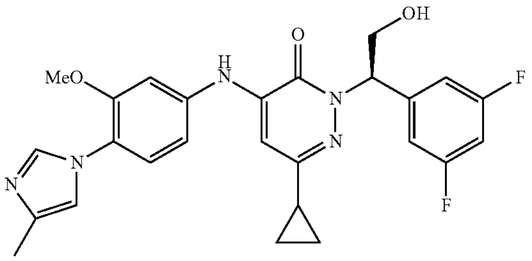
232.1
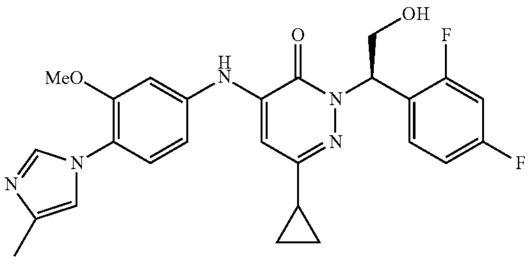
233.1
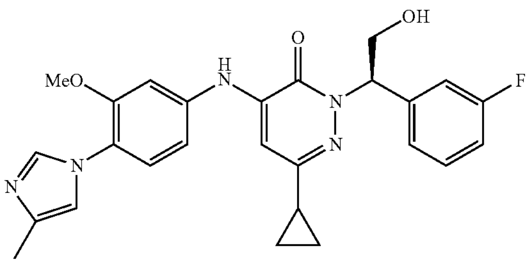
234.1

TABLE 2-continued
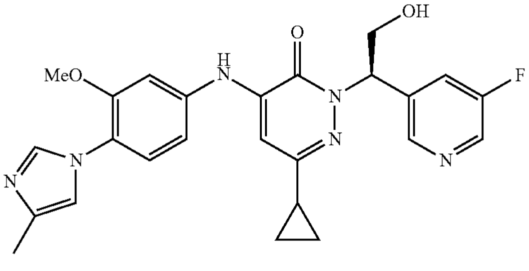
235.1
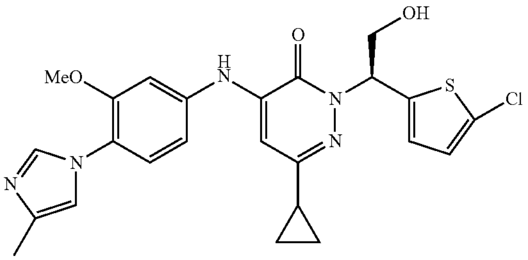
236.1
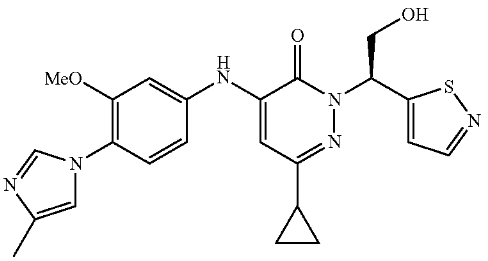
237.1
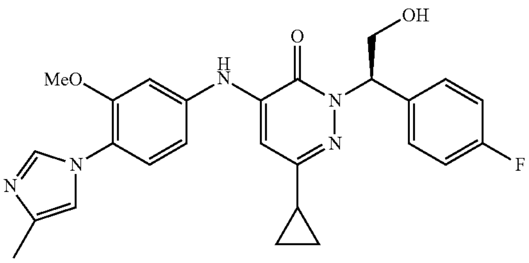
238.1
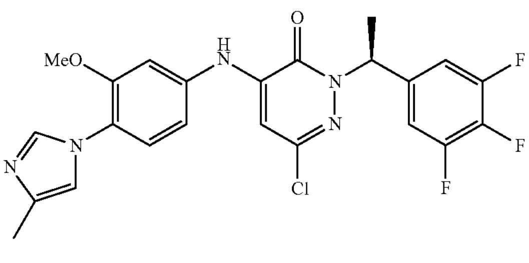
239.1
TABLE 2-continued
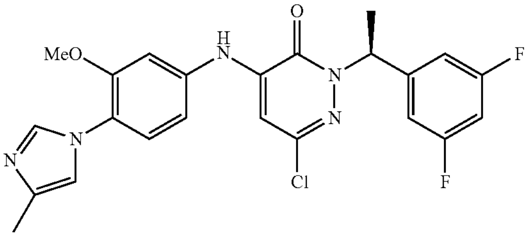
240.1
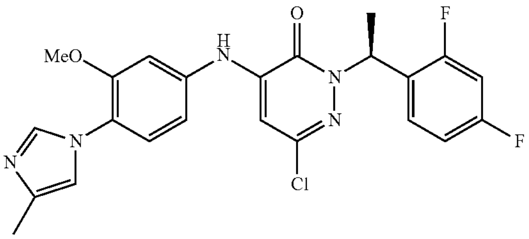
241.1
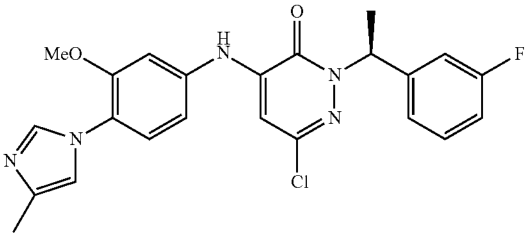
242.1
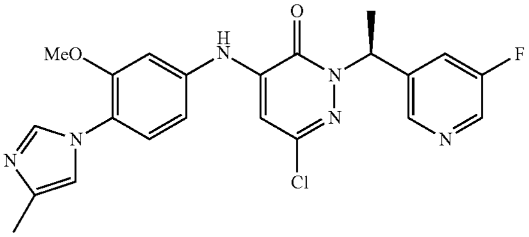
243.1
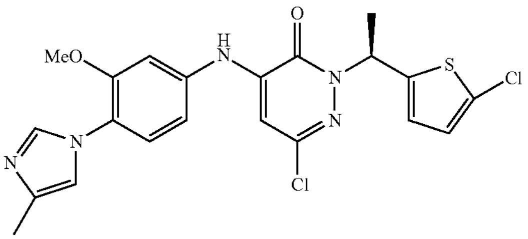
244.1

TABLE 2-continued
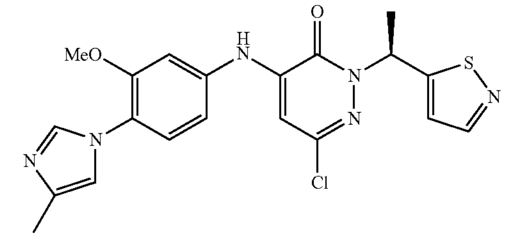
245.1
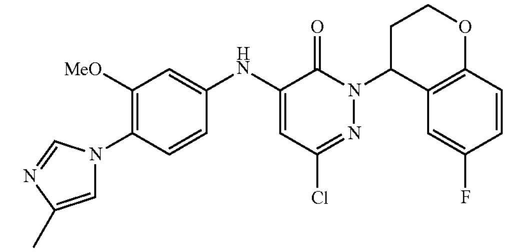
246.1
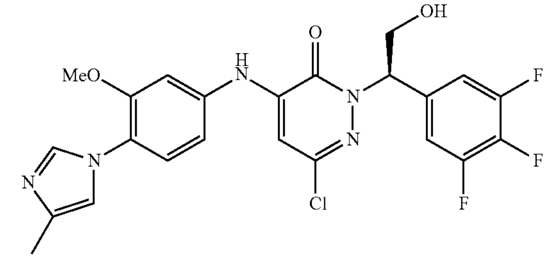
247.1
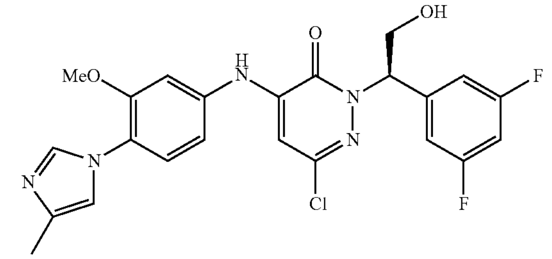
248.1
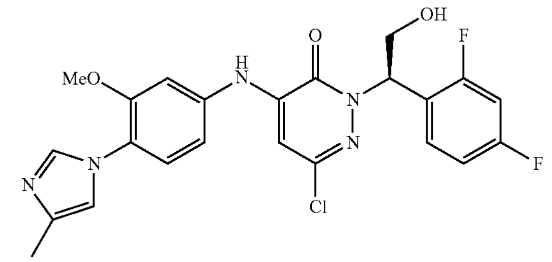
249.1
TABLE 2-continued
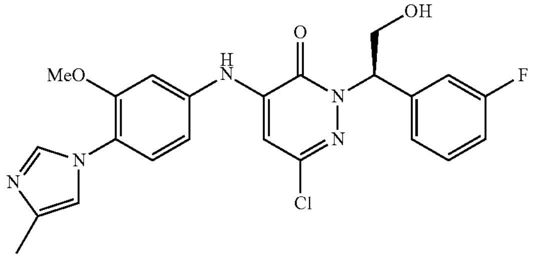
250.1
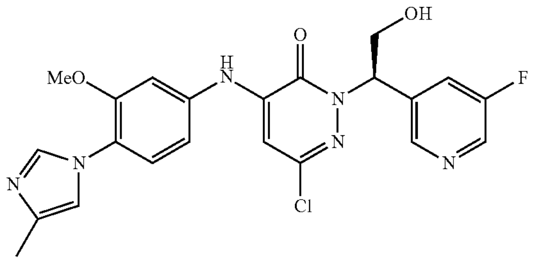
251.1
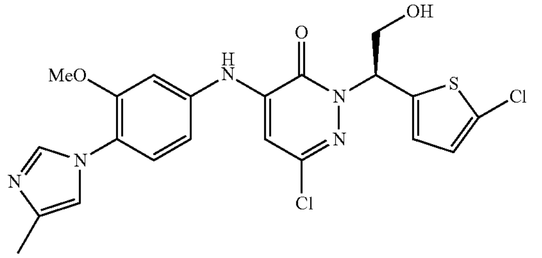
252.1
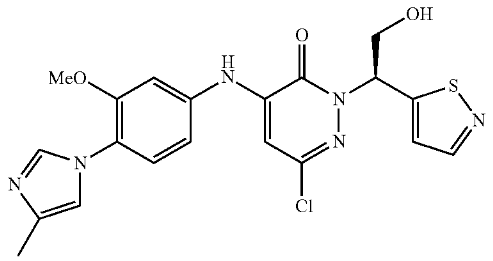
253.1
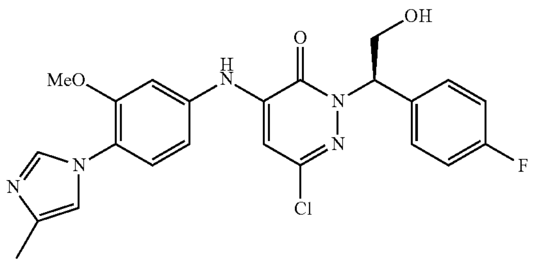
254.1

TABLE 2-continued
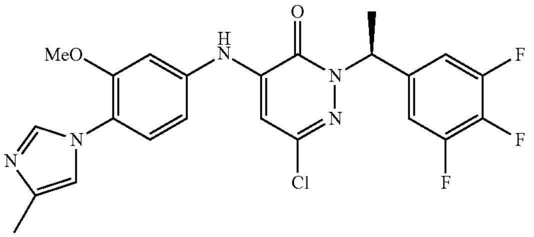
255.1
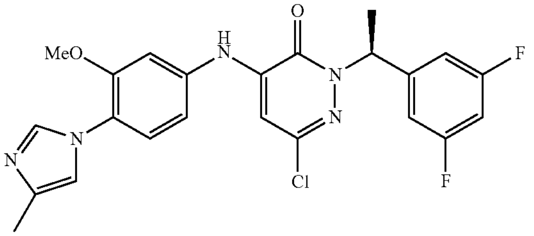
256.1
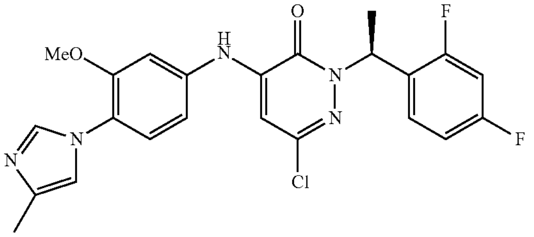
257.1
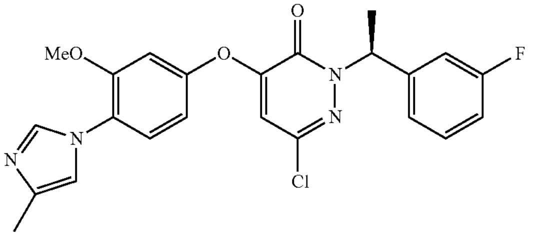
258.1
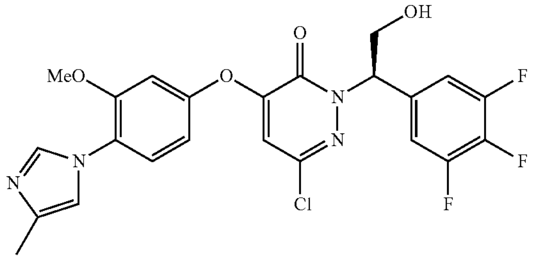
259.1
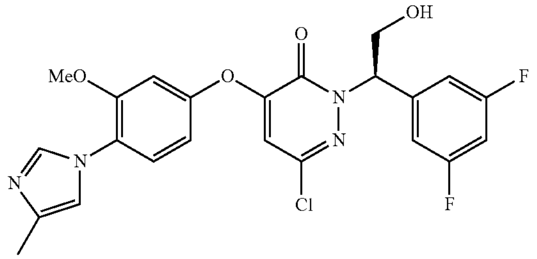
260.1
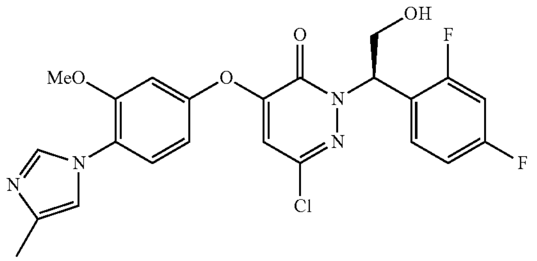
261.1
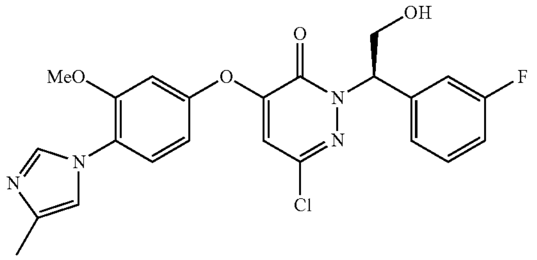
262.1
This invention is also directed to compounds 50.1-118.1 in Table 3.
TABLE 3
| Compound number | Structure | LCMS |
| --- | --- | --- |
| 50.1 | 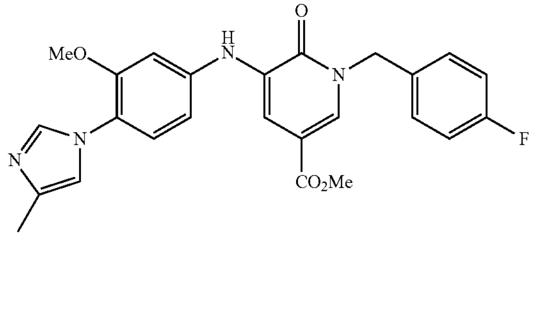 [SMILES: COC(=O)c1cc(Nc2ccc(-n3cnc(C)c3)c(OC)c2)c(=O)n(Cc2ccc(F)cc2)c1] | 463.3 |

TABLE 3-continued
| Compound number | Structure | LCMS |
|---|---|---|
| 51.1 | 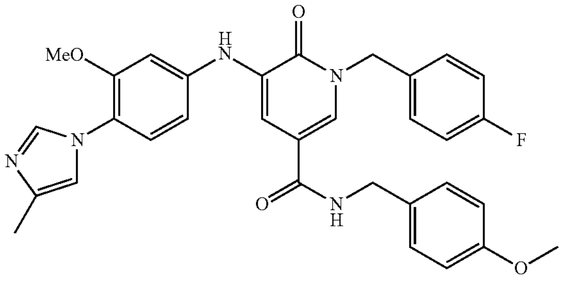 [SMILES: COc1ccc(CNC(=O)c2cc(Nc3ccc(-n4cnc(C)c4)c(OC)c3)c(=O)n(Cc3ccc(F)cc3)c2)cc1] | 568.3 |
| 52.1 | 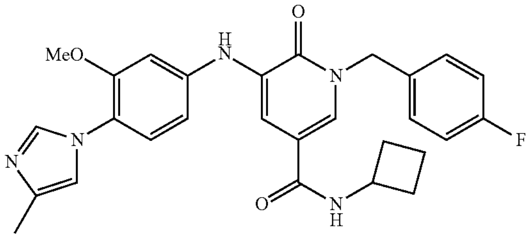 [SMILES: COc1cc(Nc2cc(C(=O)NC3CCC3)cn(Cc3ccc(F)cc3)c2=O)ccc1-n1cnc(C)c1] | 502.3 |
| 53.1 | 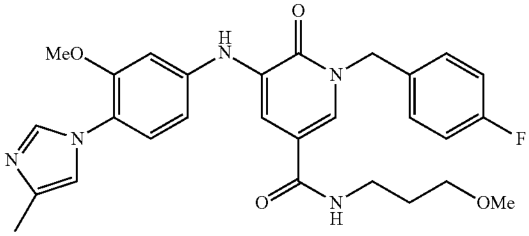 [SMILES: COCCCNC(=O)c1cc(Nc2ccc(-n3cnc(C)c3)c(OC)c2)c(=O)n(Cc2ccc(F)cc2)c1] | 520.3 |
| 54.1 | 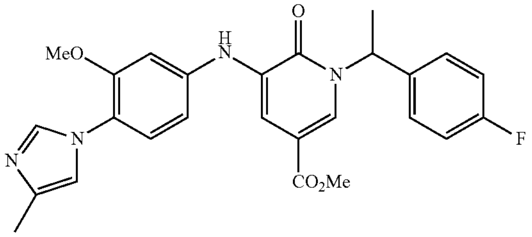 [SMILES: COC(=O)c1cc(Nc2ccc(-n3cnc(C)c3)c(OC)c2)c(=O)n(C(C)c2ccc(F)cc2)c1] | 477.3 |
| 55.1 | 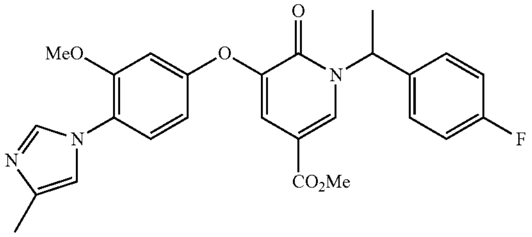 [SMILES: COC(=O)c1cc(Oc2ccc(-n3cnc(C)c3)c(OC)c2)c(=O)n(C(C)c2ccc(F)cc2)c1] | 478.3 |
| 56.1 | 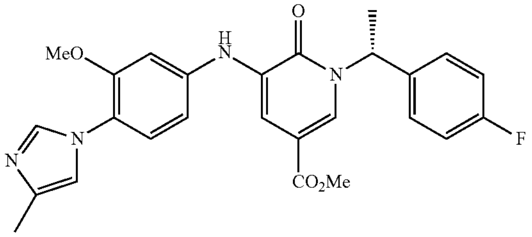 [SMILES: COC(=O)c1cc(Nc2ccc(-n3cnc(C)c3)c(OC)c2)c(=O)n([C@H](C)c2ccc(F)cc2)c1] | 477.3 |

TABLE 3-continued
| Compound number | Structure | LCMS |
| --- | --- | --- |
| 57.1 | 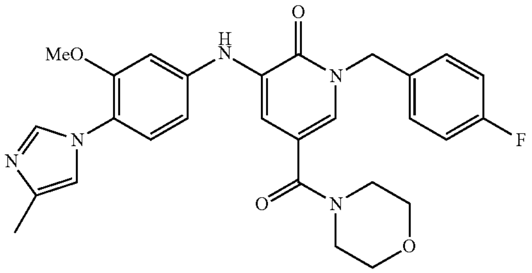 [SMILES: COc1cc(Nc2cc(C(=O)N3CCOCC3)cn(Cc3ccc(F)cc3)c2=O)ccc1-n1cnc(C)c1] | 518.3 |
| 58.1 | 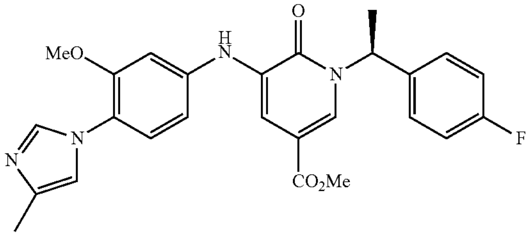 | 477.3 |
| 59.1 | 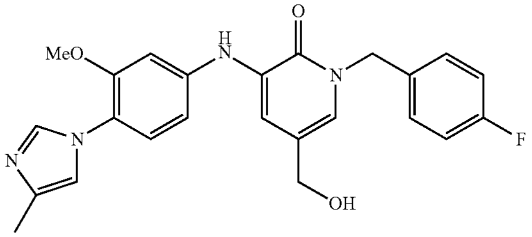 [SMILES: COc1cc(Nc2cc(CO)cn(Cc3ccc(F)cc3)c2=O)ccc1-n1cnc(C)c1] | 435.2 |
| 60.1 | 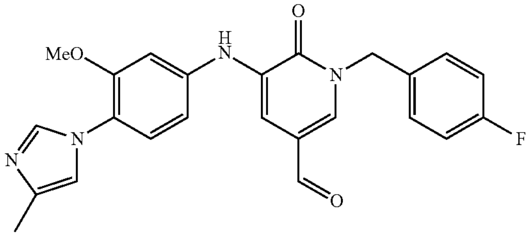 [SMILES: COc1cc(Nc2cc(C=O)cn(Cc3ccc(F)cc3)c2=O)ccc1-n1cnc(C)c1] | 433.2 |
| 61.1 | 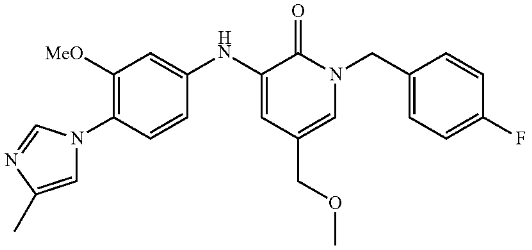 [SMILES: COCc1cc(Nc2ccc(-n3cnc(C)c3)c(OC)c2)c(=O)n(Cc2ccc(F)cc2)c1] | 449.2 |
| 62.1 | 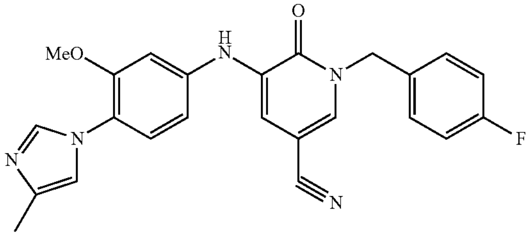 [SMILES: COc1cc(Nc2cc(C#N)cn(Cc3ccc(F)cc3)c2=O)ccc1-n1cnc(C)c1] | 430.2 |

TABLE 3-continued
| Compound number | Structure | LCMS |
|---|---|---|
| 63.1 | 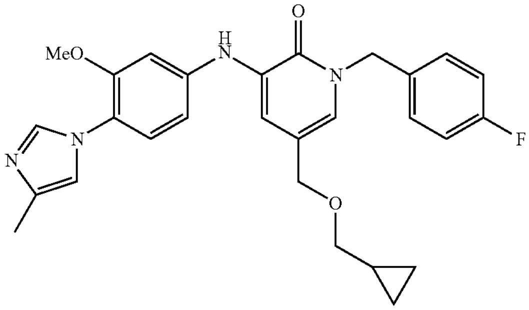 [SMILES: COc1cc(Nc2cc(COCC3CC3)cn(Cc3ccc(F)cc3)c2=O)ccc1-n1cnc(C)c1] | 489.3 |
| 64.1 | 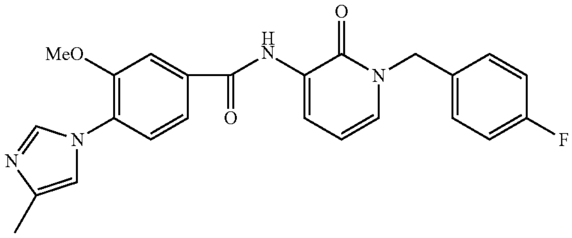 [SMILES: COc1cc(C(=O)Nc2cccn(Cc3ccc(F)cc3)c2=O)ccc1-n1cnc(C)c1] | 433.2 |
| 65.1 | 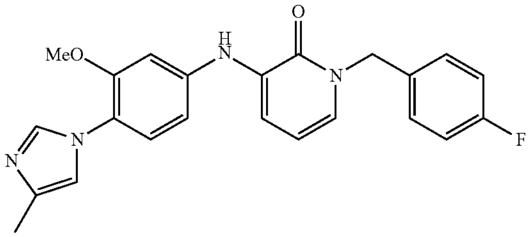 [SMILES: COc1cc(Nc2cccn(Cc3ccc(F)cc3)c2=O)ccc1-n1cnc(C)c1] | 405.2 |
| 66.1 | 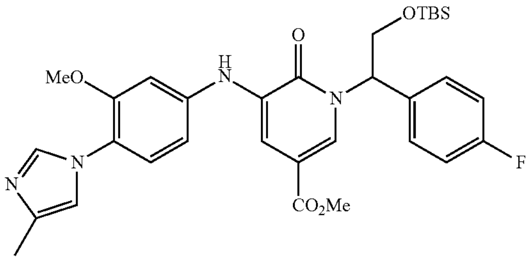 [SMILES: COC(=O)c1cc(Nc2ccc(-n3cnc(C)c3)c(OC)c2)c(=O)n(C(CO[Si](C)(C)C(C)(C)C)c2ccc(F)cc2)c1] | 607.3 |
| 67.1 | 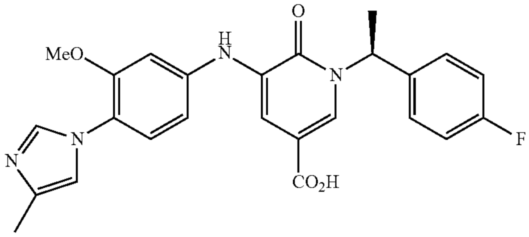 [SMILES: COc1cc(Nc2cc(C(=O)O)cn([C@@H](C)c3ccc(F)cc3)c2=O)ccc1-n1cnc(C)c1] | 463.3 |
| 68.1 | 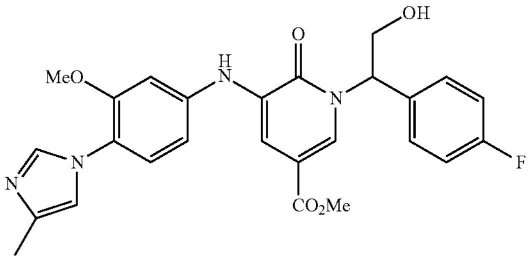 [SMILES: COC(=O)c1cc(Nc2ccc(-n3cnc(C)c3)c(OC)c2)c(=O)n(C(CO)c2ccc(F)cc2)c1] | 493.3 |

TABLE 3-continued
| Compound number | Structure | LCMS |
| --- | --- | --- |
| 69.1 | 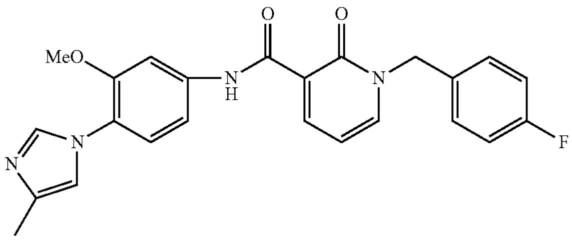 [SMILES: COc1cc(NC(=O)c2cccn(Cc3ccc(F)cc3)c2=O)ccc1-n1cnc(C)c1] | 433.2 |
| 70.1 | 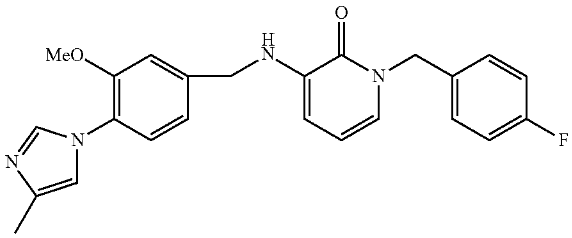 [SMILES: COc1cc(CNc2cccn(Cc3ccc(F)cc3)c2=O)ccc1-n1cnc(C)c1] | 419.2 |
| 71.1 | 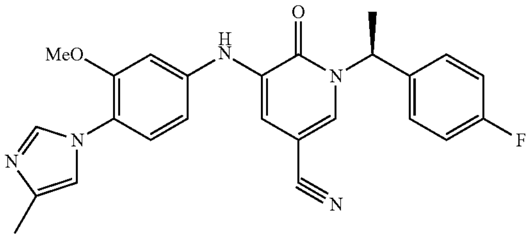 [SMILES: COc1cc(Nc2cc(C#N)cn([C@@H](C)c3ccc(F)cc3)c2=O)ccc1-n1cnc(C)c1] | 444.2 |
| 72.1 | 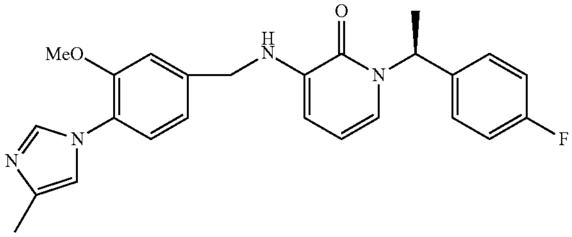 [SMILES: COc1cc(CNc2cccn([C@@H](C)c3ccc(F)cc3)c2=O)ccc1-n1cnc(C)c1] | 433.2 |
| 73.1 | 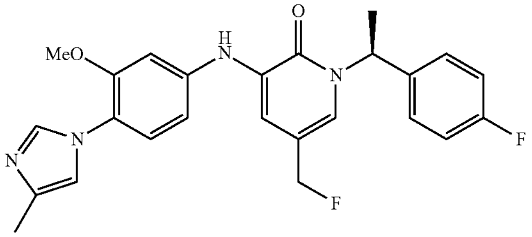 [SMILES: COc1cc(Nc2cc(CF)cn([C@@H](C)c3ccc(F)cc3)c2=O)ccc1-n1cnc(C)c1] | 451.2 |
| 74.1 | 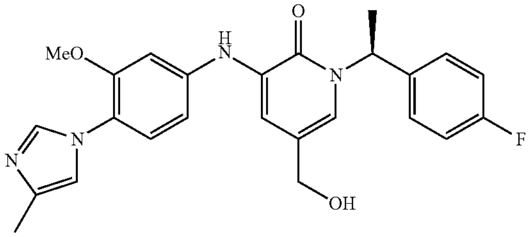 [SMILES: COc1cc(Nc2cc(CO)cn([C@@H](C)c3ccc(F)cc3)c2=O)ccc1-n1cnc(C)c1] | 449.2 |

TABLE 3-continued
| Compound number | Structure | LCMS |
|---|---|---|
| 75.1 | 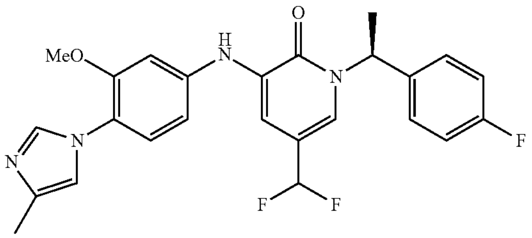 [SMILES: COc1cc(Nc2cc(C(F)F)cn([C@@H](C)c3ccc(F)cc3)c2=O)ccc1-n1cnc(C)c1] | 469.3 |
| 76.1 | 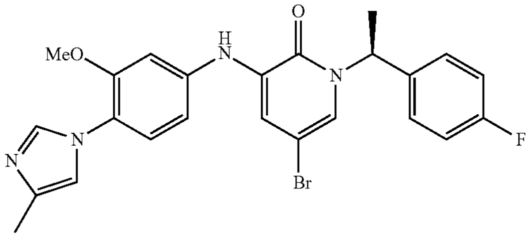 | 497.3 |
| 77.1 | 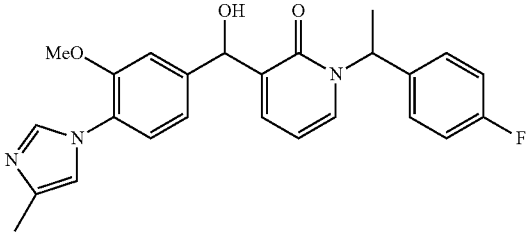 [SMILES: COc1cc(C(O)c2cccn(C(C)c3ccc(F)cc3)c2=O)ccc1-n1cnc(C)c1] | 434.2 |
| 78.1 | 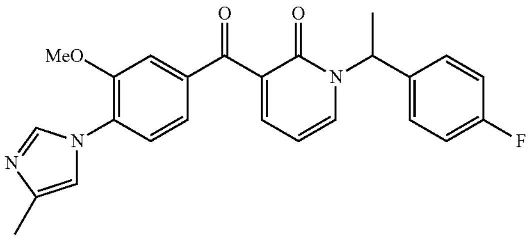 [SMILES: COc1cc(C(=O)c2cccn(C(C)c3ccc(F)cc3)c2=O)ccc1-n1cnc(C)c1] | 432.2 |
| 79.1 | 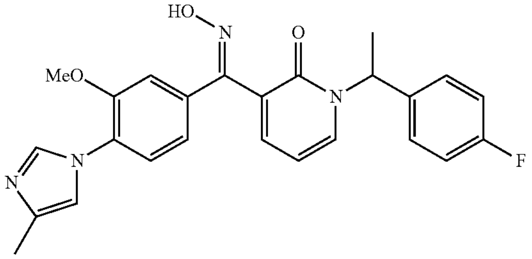 [SMILES: COc1cc(/C(=N\O)c2cccn(C(C)c3ccc(F)cc3)c2=O)ccc1-n1cnc(C)c1] | 447.2 |
| 80.1 | 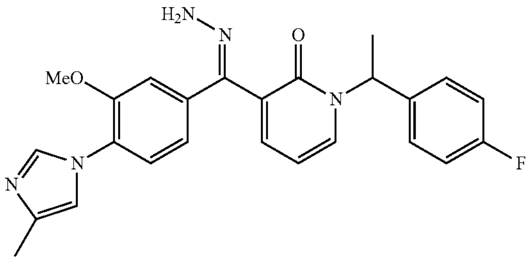 [SMILES: COc1cc(/C(=N\N)c2cccn(C(C)c3ccc(F)cc3)c2=O)ccc1-n1cnc(C)c1] | 446.2 |

TABLE 3-continued
| Compound number | Structure | LCMS |
|---|---|---|
| 81.1 | 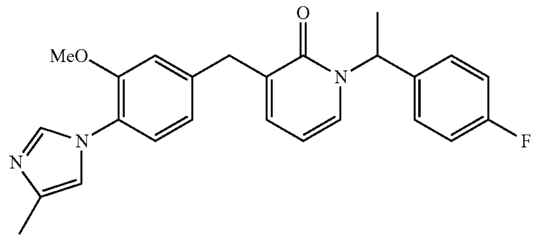 [SMILES: COc1cc(Cc2cccn(C(C)c3ccc(F)cc3)c2=O)ccc1-n1cnc(C)c1] | 418.2 |
| 82.1 | 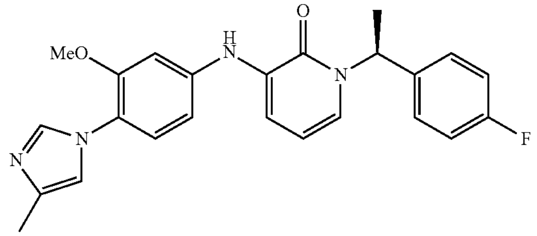 [SMILES: COc1cc(Nc2cccn([C@@H](C)c3ccc(F)cc3)c2=O)ccc1-n1cnc(C)c1] | 419.2 |
| 83.1 | 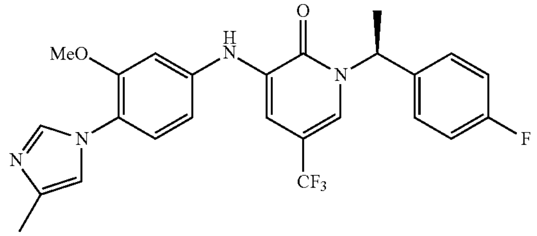 [SMILES: COc1cc(Nc2cc(C(F)(F)F)cn([C@@H](C)c3ccc(F)cc3)c2=O)ccc1-n1cnc(C)c1] | 487.3 |
| 84.1 | 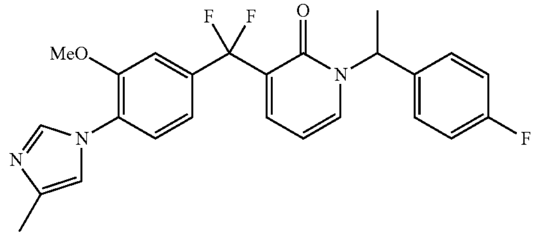 [SMILES: COc1cc(C(F)(F)c2cccn(C(C)c3ccc(F)cc3)c2=O)ccc1-n1cnc(C)c1] | 454.2 |
| 85.1 | 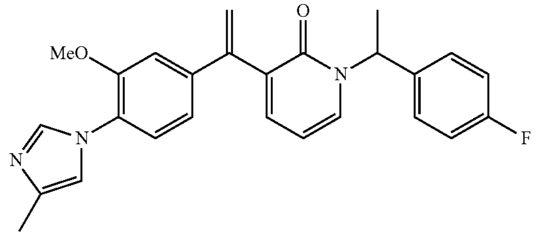 | 430.2 |
| 86.1 | 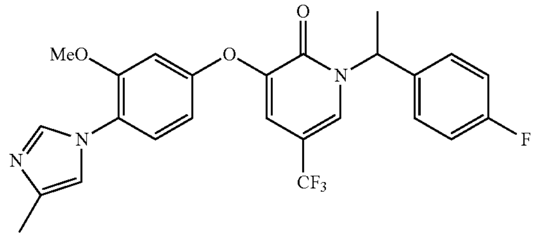 [SMILES: COc1cc(Oc2cc(C(F)(F)F)cn(C(C)c3ccc(F)cc3)c2=O)ccc1-n1cnc(C)c1] | 488.3 |

TABLE 3-continued
| Compound number | Structure | LCMS |
|---|---|---|
| 87.1 | 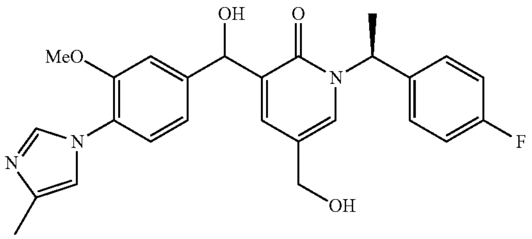 [SMILES: COc1cc(C(O)c2cc(CO)cn([C@@H](C)c3ccc(F)cc3)c2=O)ccc1-n1cnc(C)c1] | 464.3 |
| 88.1 | 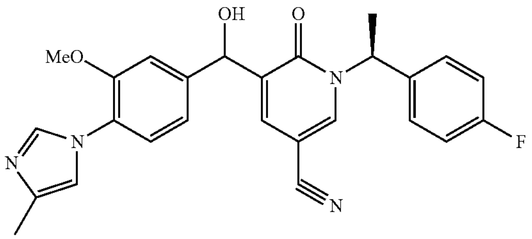 [SMILES: COc1cc(C(O)c2cc(C#N)cn([C@@H](C)c3ccc(F)cc3)c2=O)ccc1-n1cnc(C)c1] | 459.3 |
| 89.1 | 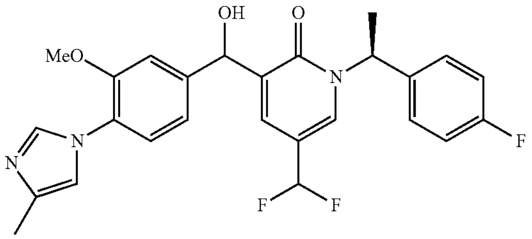 [SMILES: COc1cc(C(O)c2cc(C(F)F)cn([C@@H](C)c3ccc(F)cc3)c2=O)ccc1-n1cnc(C)c1] | 484.3 |
| 90.1 | 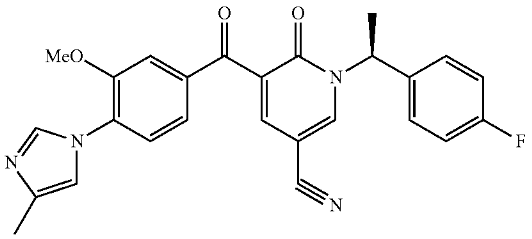 | 457.3 |
| 91.1 | 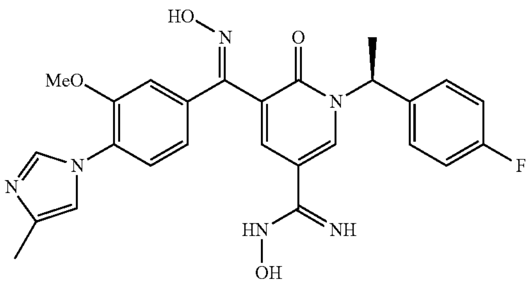 [SMILES: COc1cc(/C(=N\O)c2cc(C(=N)NO)cn([C@@H](C)c3ccc(F)cc3)c2=O)ccc1-n1cnc(C)c1] | 505.3 |
| 92.1 | 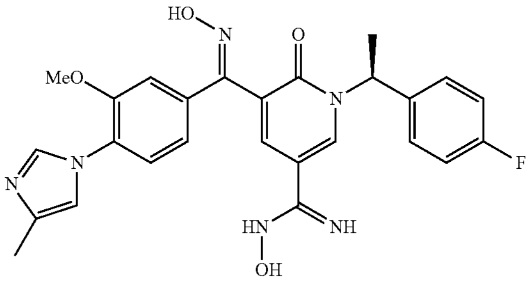 [SMILES: COc1cc(/C(=N\O)c2cc(C(=N)NO)cn([C@@H](C)c3ccc(F)cc3)c2=O)ccc1-n1cnc(C)c1] | 482.3 |

TABLE 3-continued
| Compound number | Structure | LCMS |
|---|---|---|
| 93.1 | 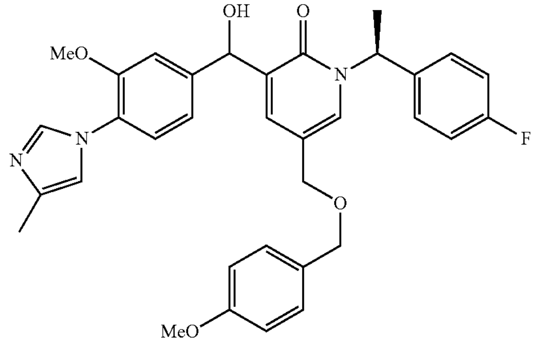 [SMILES: COc1ccc(COCc2cc(C(O)c3ccc(-n4cnc(C)c4)c(OC)c3)c(=O)n([C@@H](C)c3ccc(F)cc3)c2)cc1] | 584.3 |
| 94.1 | 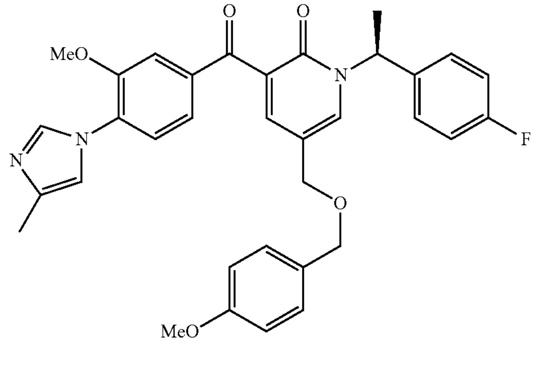 [SMILES: COc1ccc(COCc2cc(C(=O)c3ccc(-n4cnc(C)c4)c(OC)c3)c(=O)n([C@@H](C)c3ccc(F)cc3)c2)cc1] | 582.3 |
| 95.1 | 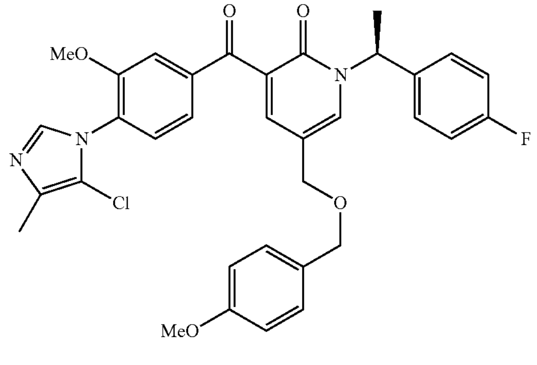 [SMILES: COc1ccc(COCc2cc(C(=O)c3ccc(-n4cnc(C)c4Cl)c(OC)c3)c(=O)n([C@@H](C)c3ccc(F)cc3)c2)cc1] | 616.3 |
| 96.1 | 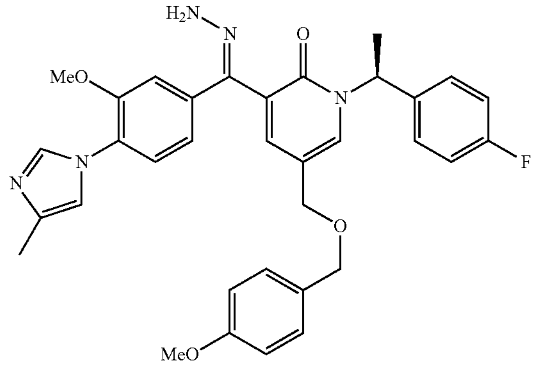 [SMILES: COc1ccc(COCc2cc(/C(=N/N)c3ccc(-n4cnc(C)c4)c(OC)c3)c(=O)n([C@@H](C)c3ccc(F)cc3)c2)cc1] | 596.3 |

TABLE 3-continued
| Compound number | Structure | LCMS |
|---|---|---|
| 97.1 | 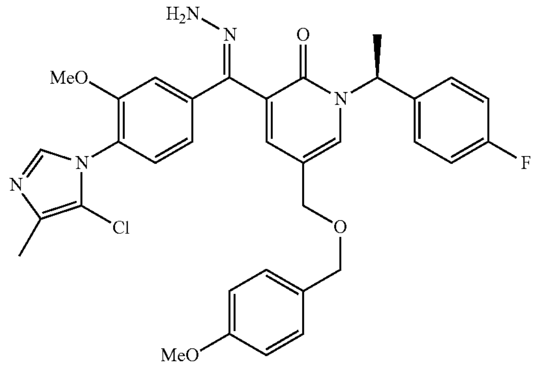 [SMILES: COc1ccc(COCc2cc(/C(=N/N)c3ccc(-n4cnc(C)c4Cl)c(OC)c3)c(=O)n([C@@H](C)c3ccc(F)cc3)c2)cc1] | 630.3 |
| 98.1 | 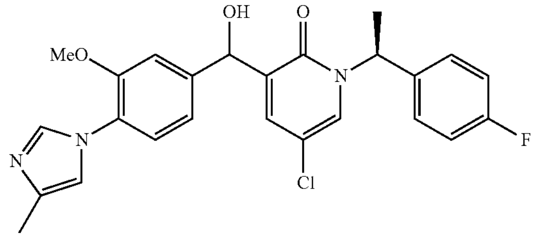 [SMILES: COc1cc(C(O)c2cc(Cl)cn([C@@H](C)c3ccc(F)cc3)c2=O)ccc1-n1cnc(C)c1] | 468.3 |
| 99.1 | 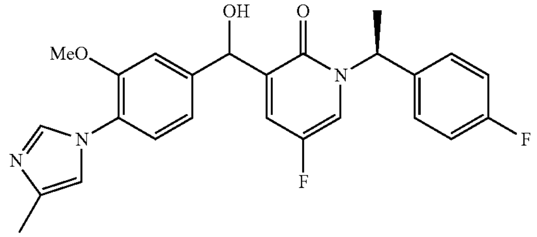 [SMILES: COc1cc(C(O)c2cc(F)cn([C@@H](C)c3ccc(F)cc3)c2=O)ccc1-n1cnc(C)c1] | 452.2 |
| 100.1 | 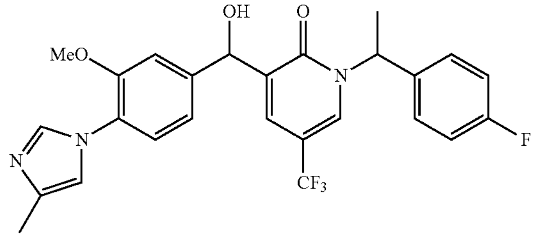 [SMILES: COc1cc(C(O)c2cc(C(F)(F)F)cn(C(C)c3ccc(F)cc3)c2=O)ccc1-n1cnc(C)c1] | 502.3 |
| 101.1 | 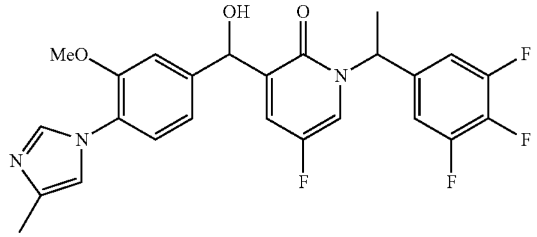 [SMILES: COc1cc(C(O)c2cc(F)cn(C(C)c3cc(F)c(F)c(F)c3)c2=O)ccc1-n1cnc(C)c1] | 488.3 |
| 102.1 | 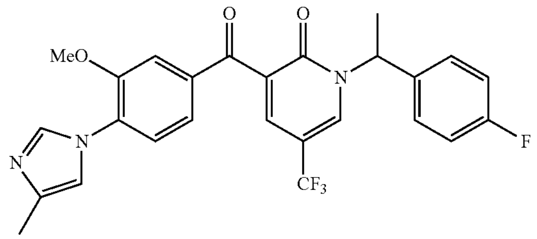 [SMILES: COc1cc(C(=O)c2cc(C(F)(F)F)cn(C(C)c3ccc(F)cc3)c2=O)ccc1-n1cnc(C)c1] | 500.3 |

TABLE 3-continued
| Compound number | Structure | LCMS |
| --- | --- | --- |
| 103.1 | 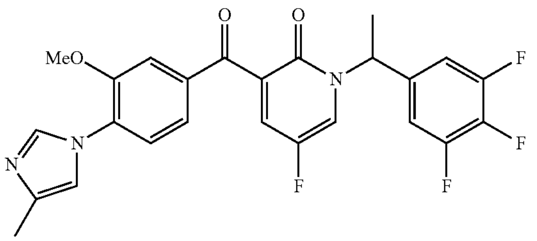 [SMILES: COc1cc(C(=O)c2cc(F)cn(C(C)c3cc(F)c(F)c(F)c3)c2=O)ccc1-n1cnc(C)c1] | 486.3 |
| 104.1 | 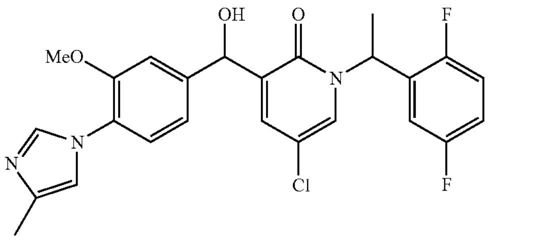 [SMILES: COc1cc(C(O)c2cc(Cl)cn(C(C)c3cc(F)ccc3F)c2=O)ccc1-n1cnc(C)c1] | 486.3 |
| 105.1 | 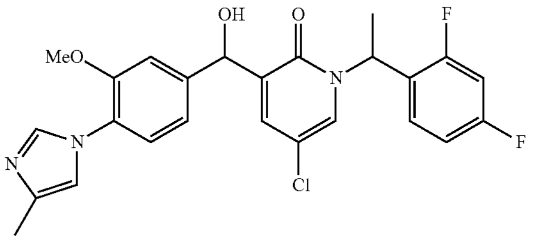 [SMILES: COc1cc(C(O)c2cc(Cl)cn(C(C)c3ccc(F)cc3F)c2=O)ccc1-n1cnc(C)c1] | 486.3 |
| 106.1 | 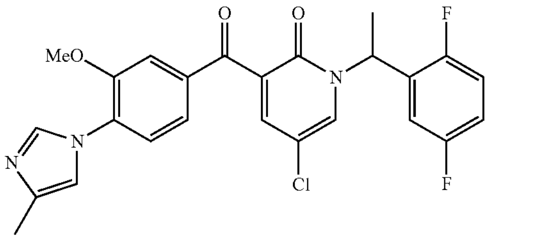 [SMILES: COc1cc(C(=O)c2cc(Cl)cn(C(C)c3cc(F)ccc3F)c2=O)ccc1-n1cnc(C)c1] | 484.3 |
| 107.1 | 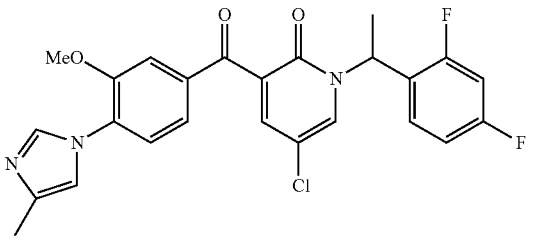 [SMILES: COc1cc(C(=O)c2cc(Cl)cn(C(C)c3ccc(F)cc3F)c2=O)ccc1-n1cnc(C)c1] | 484.3 |
| 108.1 | 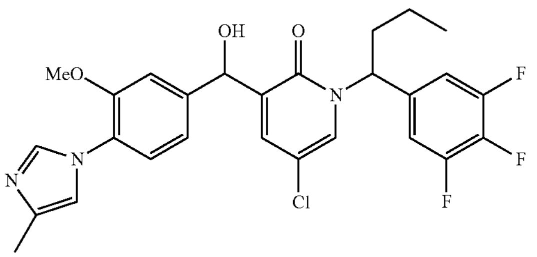 | 532.3 |

TABLE 3-continued
| Compound number | Structure | LCMS |
| --- | --- | --- |
| 109.1 | 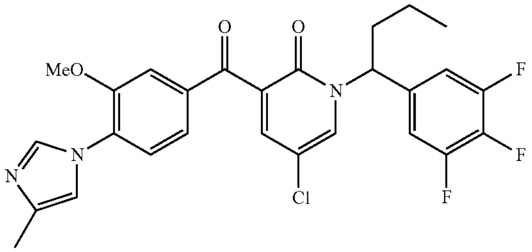 | 530.3 |
| 110.1 | 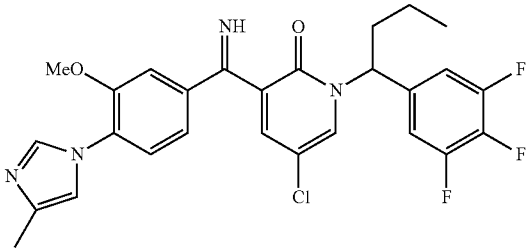 [SMILES: CCCC(c1cc(F)c(F)c(F)c1)n1cc(Cl)cc(C(O)c2ccc(-n3cnc(C)c3)c(OC)c2)c1=O] | 529.3 |
| 111.1 | 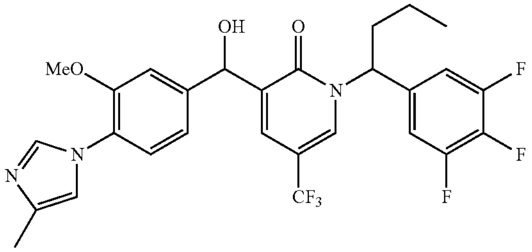 [SMILES: CCCC(c1cc(F)c(F)c(F)c1)n1cc(C(F)(F)F)cc(C(O)c2ccc(-n3cnc(C)c3)c(OC)c2)c1=O] | 566.3 |
| 112.1 | 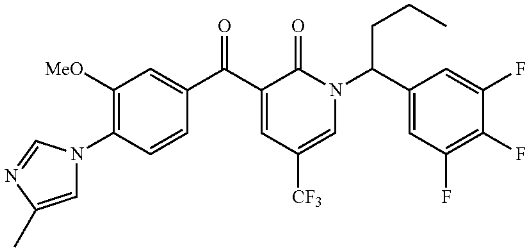 [SMILES: CCCC(c1cc(F)c(F)c(F)c1)n1cc(C(F)(F)F)cc(C(=O)c2ccc(-n3cnc(C)c3)c(OC)c2)c1=O] | 564.3 |
| 113.1 | 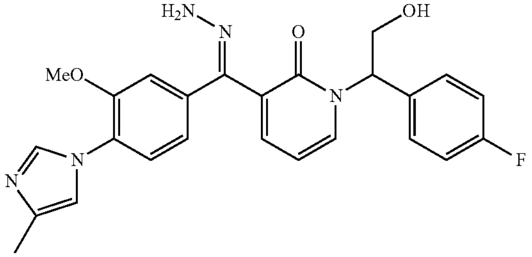 [SMILES: COc1cc(/C(=N\N)c2cccn(C(CO)c3ccc(F)cc3)c2=O)ccc1-n1cnc(C)c1] | 462.3 |
| 114.1 | 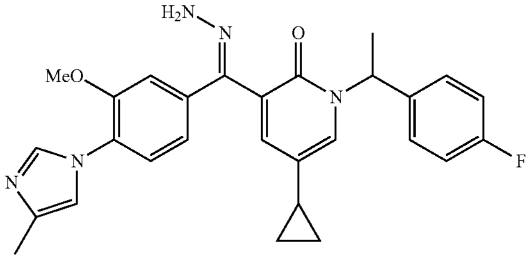 [SMILES: COc1cc(/C(=N\N)c2cc(C3CC3)cn(C(C)c3ccc(F)cc3)c2=O)ccc1-n1cnc(C)c1] | 486.3 |

TABLE 3-continued
| Compound number | Structure | LCMS |
|---|---|---|
| 115.1 | 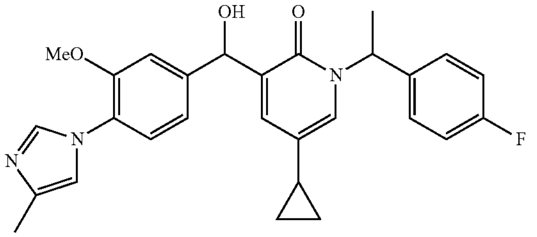 [SMILES: COc1cc(C(O)c2cc(C3CC3)cn(C(C)c3ccc(F)cc3)c2=O)ccc1-n1cnc(C)c1] | 474.3 |
| 116.1 | 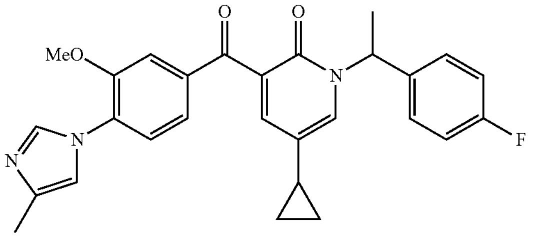 [SMILES: COc1cc(C(=O)c2cc(C3CC3)cn(C(C)c3ccc(F)cc3)c2=O)ccc1-n1cnc(C)c1] | 472.3 |
| 117.1 | 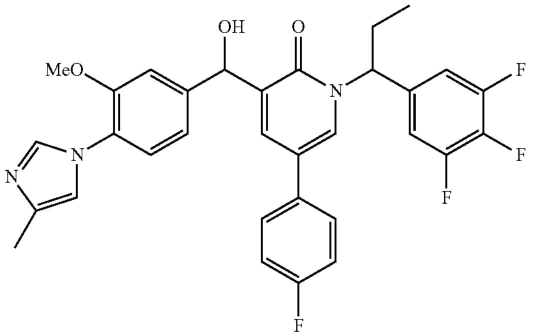 [SMILES: CCC(c1cc(F)c(F)c(F)c1)n1cc(-c2ccc(F)cc2)cc(C(O)c2ccc(-n3cnc(C)c3)c(OC)c2)c1=O] | 578.3 |
| 118.1 | 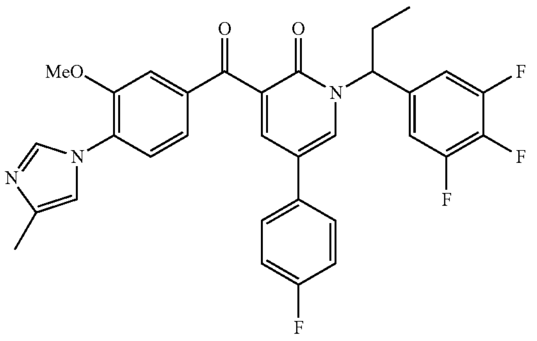 [SMILES: CCC(c1cc(F)c(F)c(F)c1)n1cc(-c2ccc(F)cc2)cc(C(=O)c2ccc(-n3cnc(C)c3)c(OC)c2)c1=O] | 576.3 |
This invention is also directed to compounds 119.1-190.1 in Table 4.
TABLE 4
119.1
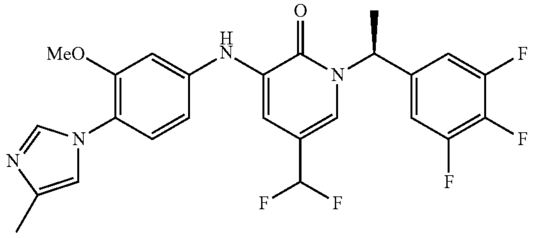 [SMILES: COc1cc(Nc2cc(C(F)F)cn([C@@H](C)c3cc(F)c(F)c(F)c3)c2=O)ccc1-n1cnc(C)c1]

TABLE 4-continued
120.1
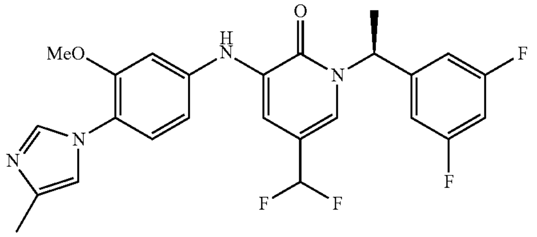
121.1
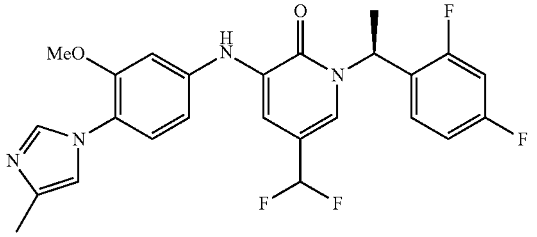 [SMILES: COc1cc(Nc2cc(C(F)F)cn([C@@H](C)c3ccc(F)cc3F)c2=O)ccc1-n1cnc(C)c1]
122.1
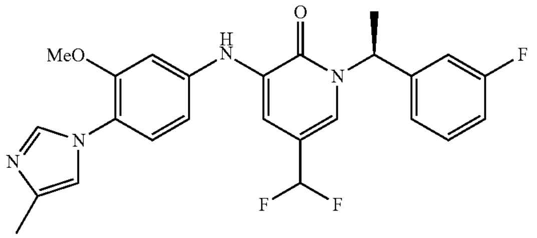 [SMILES: COc1cc(Nc2cc(C(F)F)cn([C@@H](C)c3cccc(F)c3)c2=O)ccc1-n1cnc(C)c1]
123.1
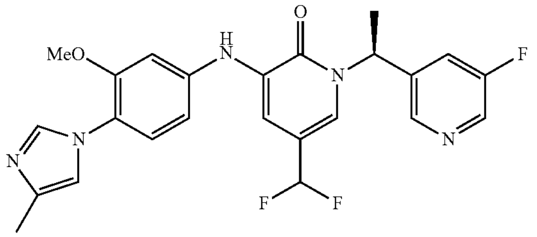 [SMILES: COc1cc(Nc2cc(C(F)F)cn([C@@H](C)c3cncc(F)c3)c2=O)ccc1-n1cnc(C)c1]
124.1
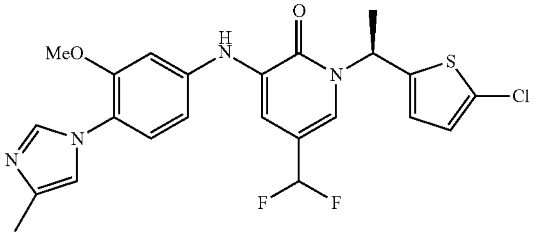 [SMILES: COc1cc(Nc2cc(C(F)F)cn([C@@H](C)c3ccc(Cl)s3)c2=O)ccc1-n1cnc(C)c1]
125.1
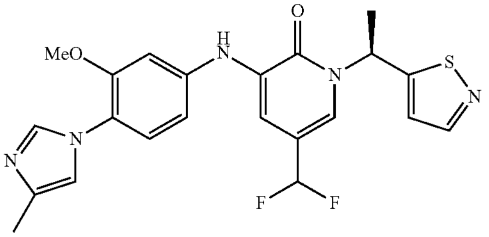 [SMILES: COc1cc(Nc2cc(C(F)F)cn([C@@H](C)c3ccns3)c2=O)ccc1-n1cnc(C)c1]

TABLE 4-continued
126.1
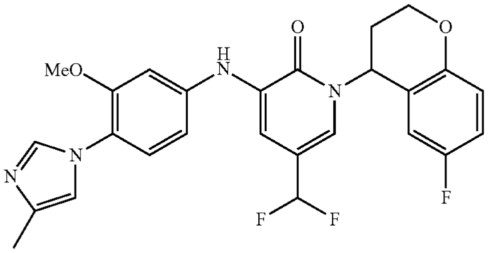 [SMILES: COc1cc(Nc2cc(C(F)F)cn(C3CCOc4ccc(F)cc43)c2=O)ccc1-n1cnc(C)c1]
127.1
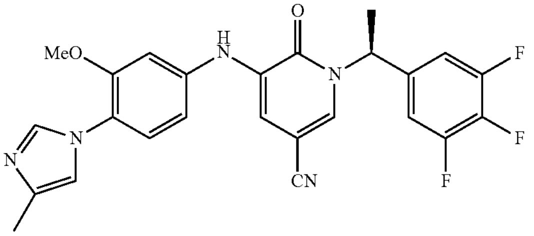 [SMILES: COc1cc(Nc2cc(C#N)cn([C@@H](C)c3cc(F)c(F)c(F)c3)c2=O)ccc1-n1cnc(C)c1]
128.1
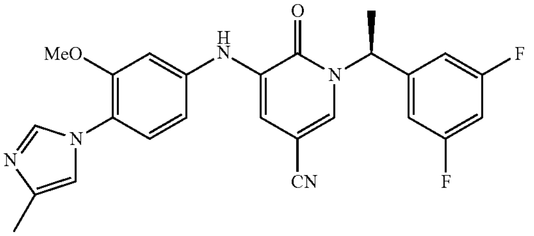 [SMILES: COc1cc(Nc2cc(C#N)cn([C@@H](C)c3cc(F)cc(F)c3)c2=O)ccc1-n1cnc(C)c1]
129.1
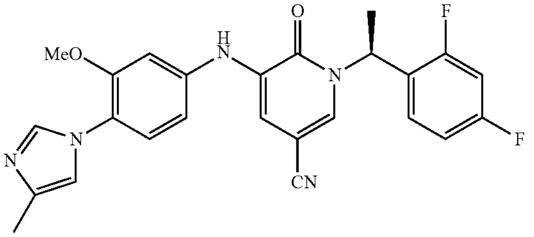 [SMILES: COc1cc(Nc2cc(C#N)cn([C@@H](C)c3ccc(F)cc3F)c2=O)ccc1-n1cnc(C)c1]
130.1
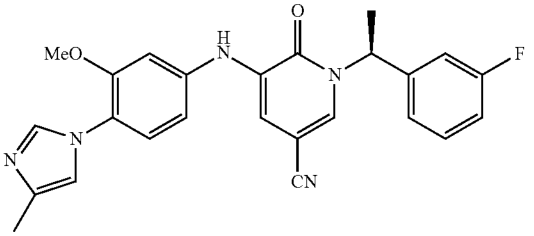 [SMILES: COc1cc(Nc2cc(C#N)cn([C@@H](C)c3cccc(F)c3)c2=O)ccc1-n1cnc(C)c1]
131.1
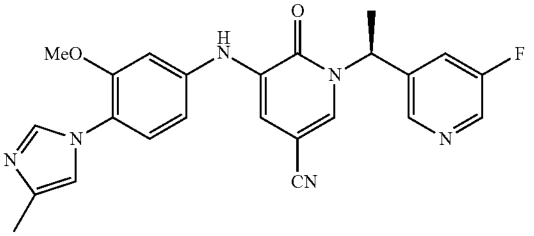 [SMILES: COc1cc(Nc2cc(C#N)cn([C@@H](C)c3cncc(F)c3)c2=O)ccc1-n1cnc(C)c1]

TABLE 4-continued
132.1
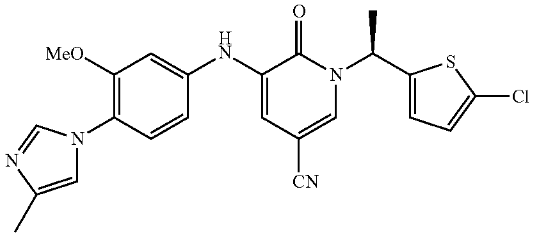
133.1
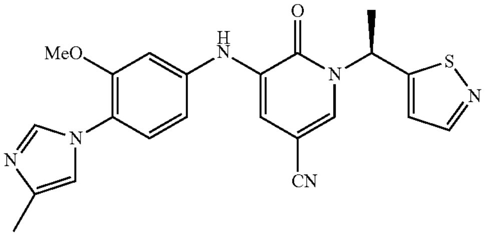 [SMILES: COc1cc(Nc2cc(C#N)cn([C@@H](C)c3ccns3)c2=O)ccc1-n1cnc(C)c1]
134.1
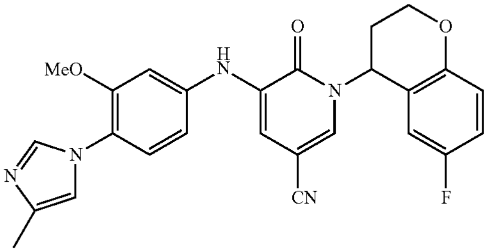 [SMILES: COc1cc(Nc2cc(C#N)cn(C3CCOc4ccc(F)cc43)c2=O)ccc1-n1cnc(C)c1]
135.1
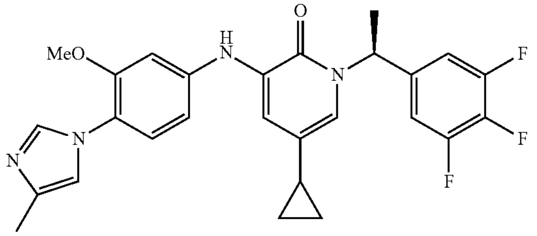 [SMILES: COc1cc(Nc2cc(C3CC3)cn([C@@H](C)c3cc(F)c(F)c(F)c3)c2=O)ccc1-n1cnc(C)c1]
136.1
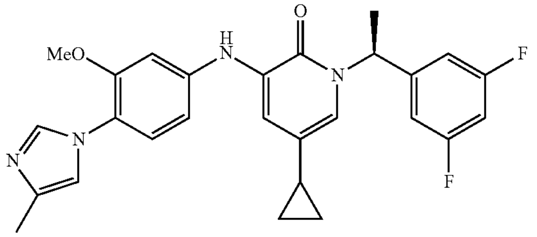 [SMILES: COc1cc(Nc2cc(C3CC3)cn([C@@H](C)c3cc(F)cc(F)c3)c2=O)ccc1-n1cnc(C)c1]
137.1
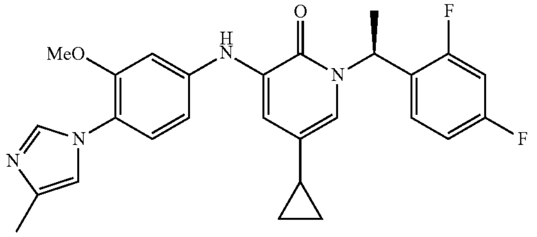 [SMILES: COc1cc(Nc2cc(C3CC3)cn([C@@H](C)c3ccc(F)cc3F)c2=O)ccc1-n1cnc(C)c1]

TABLE 4-continued
138.1
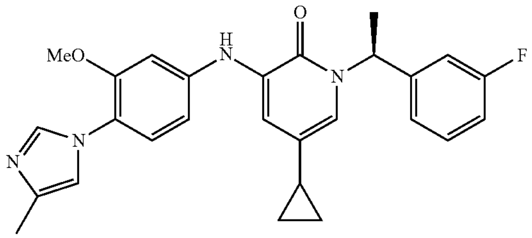 [SMILES: COc1cc(Nc2cc(C3CC3)cn([C@@H](C)c3cccc(F)c3)c2=O)ccc1-n1cnc(C)c1]
139.1
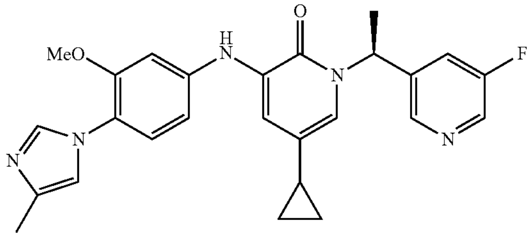 [SMILES: COc1cc(Nc2cc(C3CC3)cn([C@@H](C)c3cncc(F)c3)c2=O)ccc1-n1cnc(C)c1]
140.1
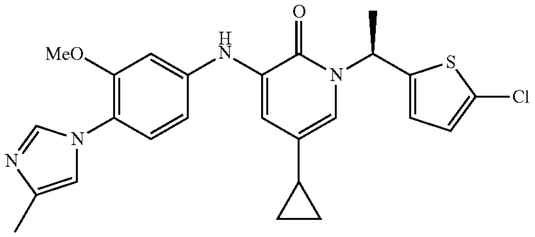 [SMILES: COc1cc(Nc2cc(C3CC3)cn([C@@H](C)c3ccc(Cl)s3)c2=O)ccc1-n1cnc(C)c1]
141.1
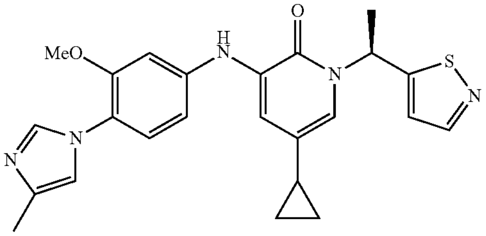 [SMILES: COc1cc(Nc2cc(C3CC3)cn([C@@H](C)c3ccns3)c2=O)ccc1-n1cnc(C)c1]
142.1
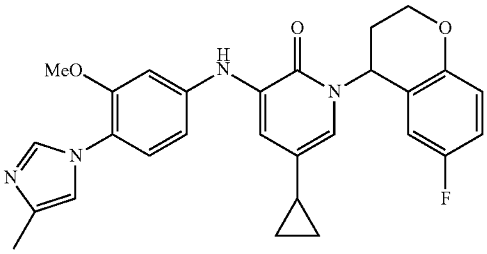 [SMILES: COc1cc(Nc2cc(C3CC3)cn(C3CCOc4ccc(F)cc43)c2=O)ccc1-n1cnc(C)c1]
143.1
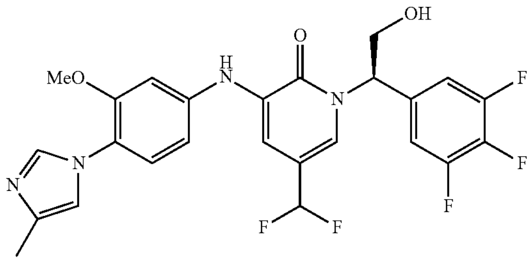 [SMILES: COc1cc(Nc2cc(C(F)F)cn([C@@H](CO)c3cc(F)c(F)c(F)c3)c2=O)ccc1-n1cnc(C)c1]

TABLE 4-continued
144.1
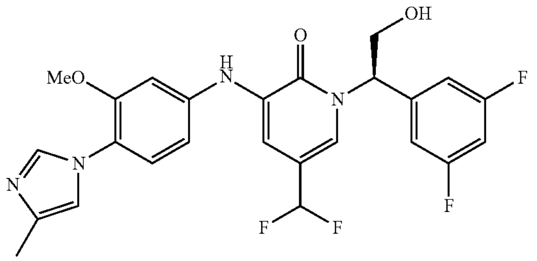 [SMILES: COc1cc(Nc2cc(C(F)F)cn([C@@H](CO)c3cc(F)cc(F)c3)c2=O)ccc1-n1cnc(C)c1]
145.1
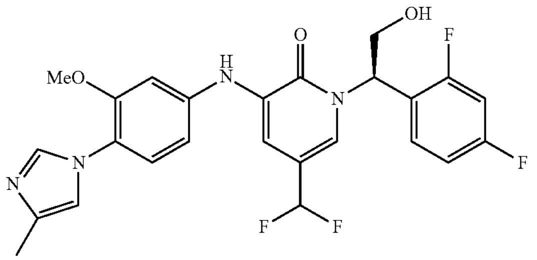 [SMILES: COc1cc(Nc2cc(C(F)F)cn([C@@H](CO)c3ccc(F)cc3F)c2=O)ccc1-n1cnc(C)c1]
146.1
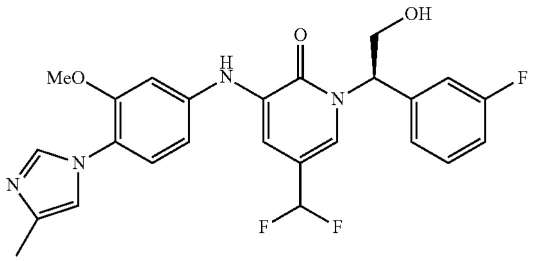
147.1
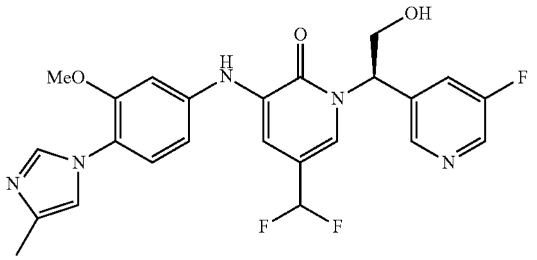 [SMILES: COc1cc(Nc2cc(C(F)F)cn([C@@H](CO)c3cccc(F)c3)c2=O)ccc1-n1cnc(C)c1]
148.1
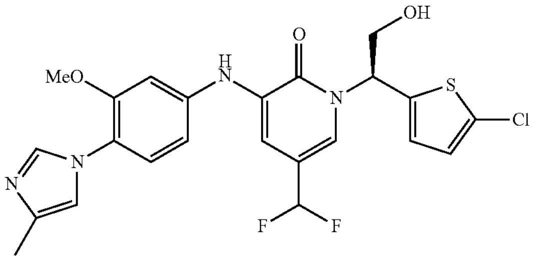 [SMILES: COc1cc(Nc2cc(C(F)F)cn([C@@H](CO)c3ccc(Cl)s3)c2=O)ccc1-n1cnc(C)c1]

TABLE 4-continued
149.1
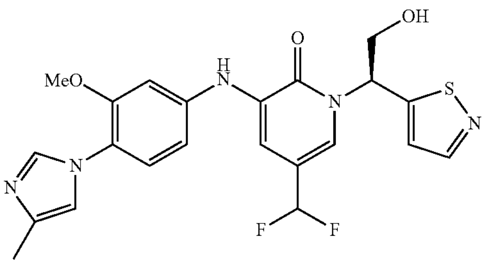 [SMILES: COc1cc(Nc2cc(C(F)F)cn([C@@H](CO)c3ccns3)c2=O)ccc1-n1cnc(C)c1]
150.1
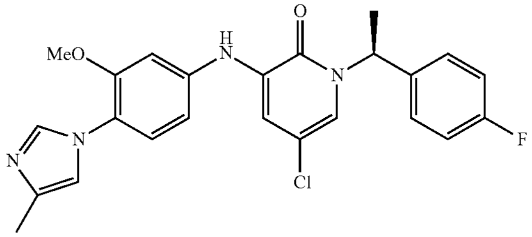 [SMILES: COc1cc(Nc2cc(Cl)cn([C@@H](C)c3ccc(F)cc3)c2=O)ccc1-n1cnc(C)c1]
151.1
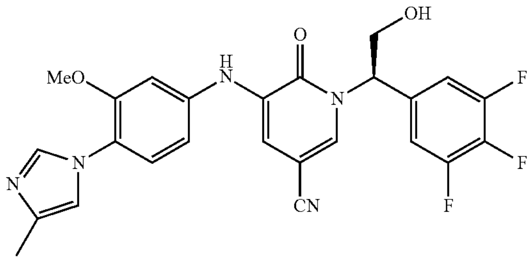 [SMILES: COc1cc(Nc2cc(C#N)cn([C@@H](CO)c3cc(F)c(F)c(F)c3)c2=O)ccc1-n1cnc(C)c1]
152.1
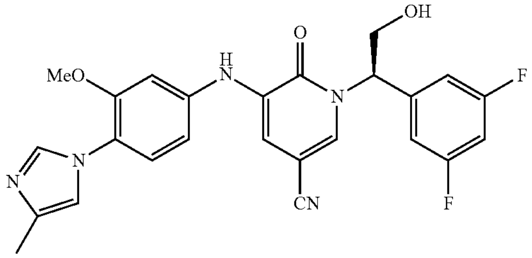
153.1
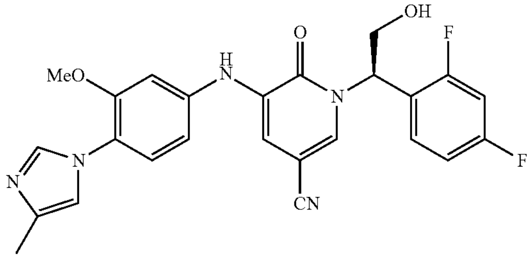 [SMILES: COc1cc(Nc2cc(C#N)cn([C@@H](CO)c3ccc(F)cc3F)c2=O)ccc1-n1cnc(C)c1]

TABLE 4-continued
154.1
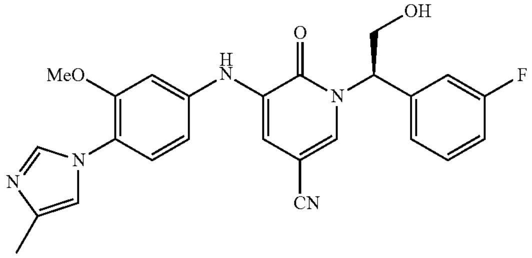 [SMILES: COc1cc(Nc2cc(C#N)cn([C@@H](CO)c3cccc(F)c3)c2=O)ccc1-n1cnc(C)c1]
155.1
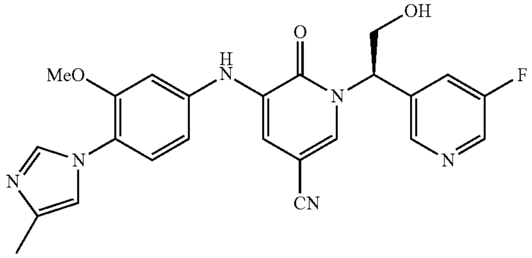 [SMILES: COc1cc(Nc2cc(C#N)cn([C@@H](CO)c3cncc(F)c3)c2=O)ccc1-n1cnc(C)c1]
156.1
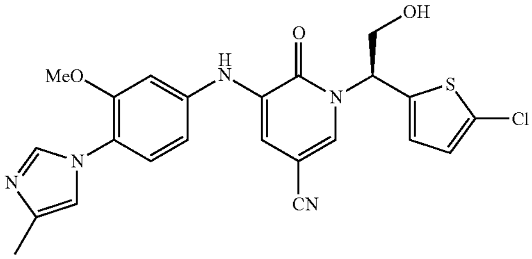 [SMILES: COc1cc(Nc2cc(C#N)cn([C@@H](CO)c3ccc(Cl)s3)c2=O)ccc1-n1cnc(C)c1]
157.1
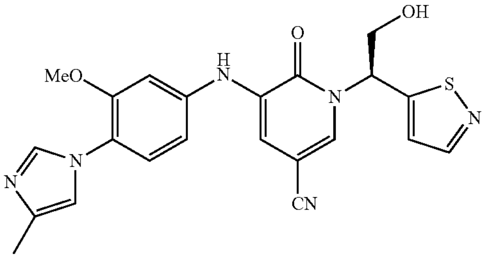 [SMILES: COc1cc(Nc2cc(C#N)cn([C@@H](CO)c3ccns3)c2=O)ccc1-n1cnc(C)c1]
158.1
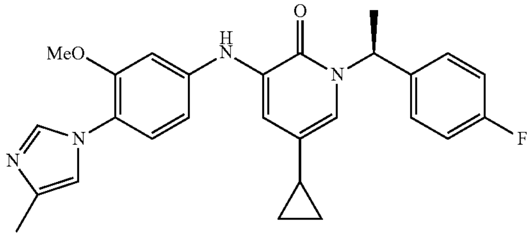 [SMILES: COc1cc(Nc2cc(C3CC3)cn([C@@H](C)c3ccc(F)cc3)c2=O)ccc1-n1cnc(C)c1]

TABLE 4-continued
159.1
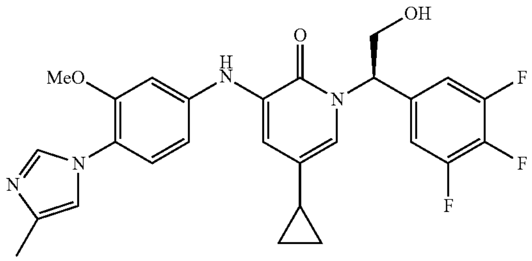 [SMILES: COc1cc(Nc2cc(C3CC3)cn([C@@H](CO)c3cc(F)c(F)c(F)c3)c2=O)ccc1-n1cnc(C)c1]
160.1
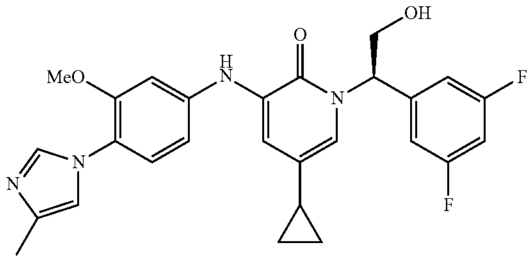 [SMILES: COc1cc(Nc2cc(C3CC3)cn([C@@H](CO)c3cc(F)cc(F)c3)c2=O)ccc1-n1cnc(C)c1]
161.1
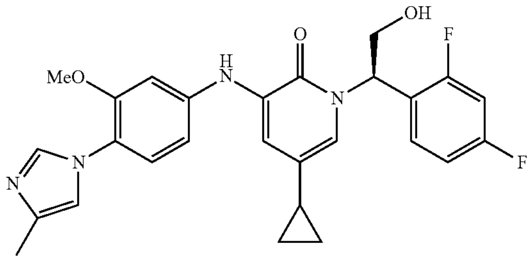 [SMILES: COc1cc(Nc2cc(C3CC3)cn([C@@H](CO)c3ccc(F)cc3F)c2=O)ccc1-n1cnc(C)c1]
162.1
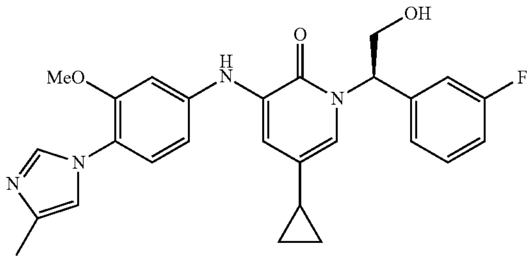 [SMILES: COc1cc(Nc2cc(C3CC3)cn([C@@H](CO)c3cccc(F)c3)c2=O)ccc1-n1cnc(C)c1]
163.1
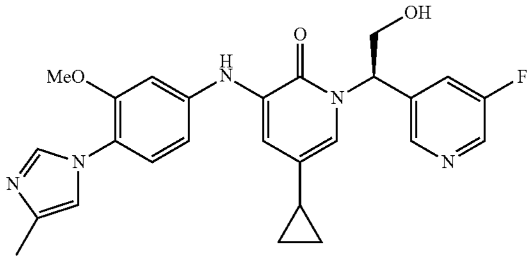

TABLE 4-continued
164.1
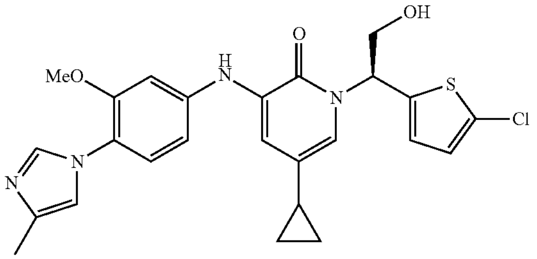 [SMILES: COc1cc(Nc2cc(C3CC3)cn([C@@H](CO)c3ccc(Cl)s3)c2=O)ccc1-n1cnc(C)c1]
165.1
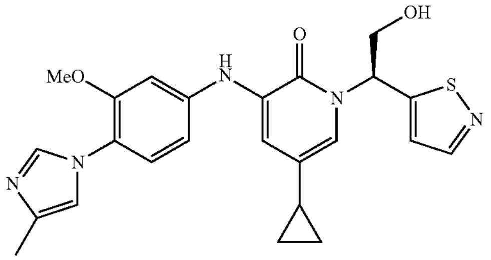 [SMILES: COc1cc(Nc2cc(C3CC3)cn([C@@H](CO)c3ccns3)c2=O)ccc1-n1cnc(C)c1]
166.1
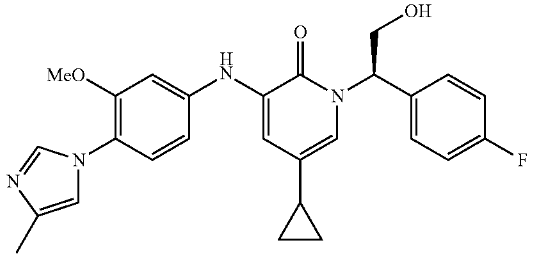 [SMILES: COc1cc(Nc2cc(C3CC3)cn([C@@H](CO)c3ccc(F)cc3)c2=O)ccc1-n1cnc(C)c1]
167.1
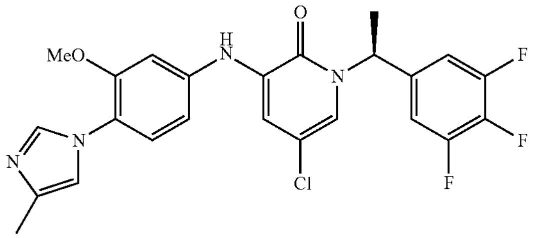 [SMILES: COc1cc(Nc2cc(Cl)cn([C@@H](C)c3cc(F)c(F)c(F)c3)c2=O)ccc1-n1cnc(C)c1]
168.1
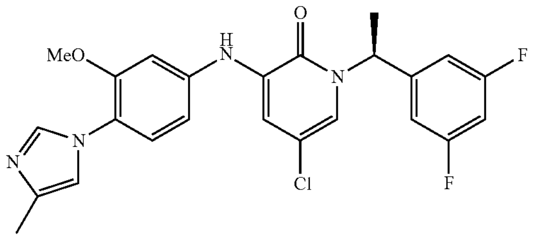 [SMILES: COc1cc(Nc2cc(Cl)cn([C@@H](C)c3cc(F)cc(F)c3)c2=O)ccc1-n1cnc(C)c1]

TABLE 4-continued
169.1
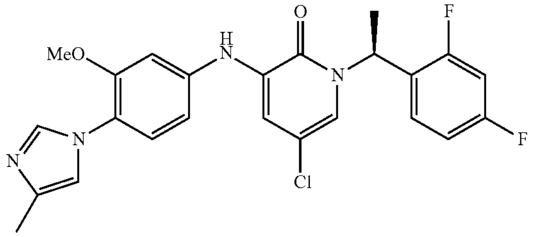 [SMILES: COc1cc(Nc2cc(Cl)cn([C@@H](C)c3ccc(F)cc3F)c2=O)ccc1-n1cnc(C)c1]
170.1
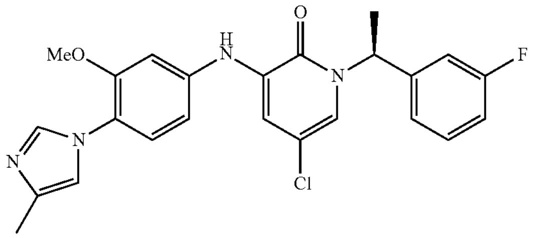 [SMILES: COc1cc(Nc2cc(Cl)cn([C@@H](C)c3cccc(F)c3)c2=O)ccc1-n1cnc(C)c1]
171.1
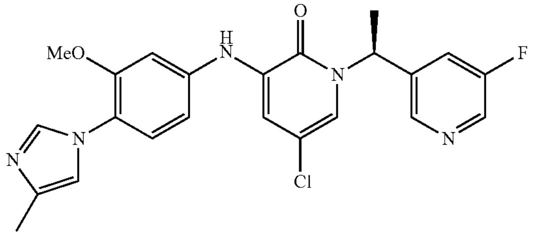 [SMILES: COc1cc(Nc2cc(Cl)cn([C@@H](C)c3cncc(F)c3)c2=O)ccc1-n1cnc(C)c1]
172.1
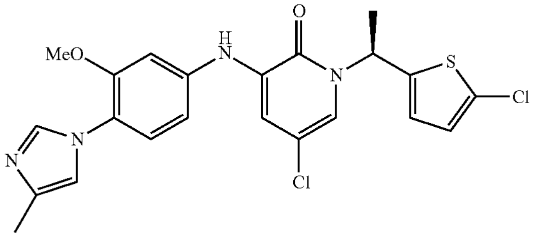 [SMILES: COc1cc(Nc2cc(Cl)cn([C@@H](C)c3ccc(Cl)s3)c2=O)ccc1-n1cnc(C)c1]
173.1
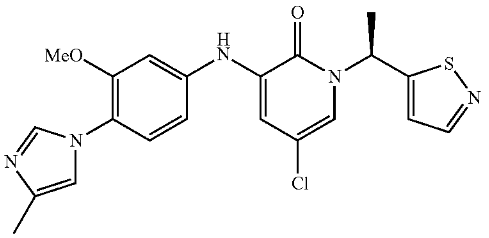 [SMILES: COc1cc(Nc2cc(Cl)cn([C@@H](C)c3ccns3)c2=O)ccc1-n1cnc(C)c1]
174.1
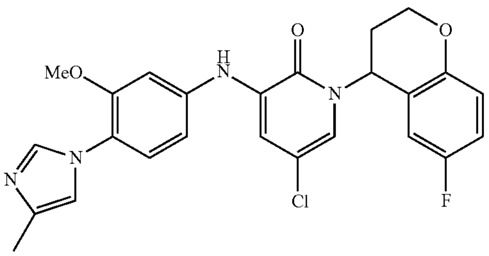 [SMILES: COc1cc(Nc2cc(Cl)cn(C3CCOc4ccc(F)cc43)c2=O)ccc1-n1cnc(C)c1]

TABLE 4-continued
175.1
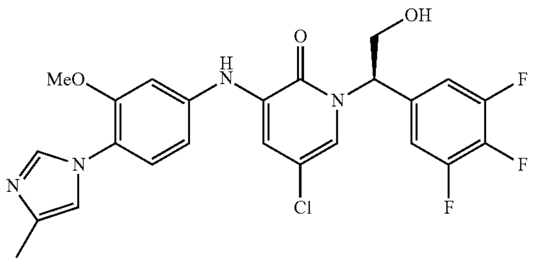
176.1
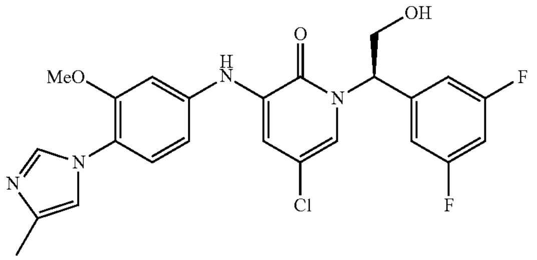 [SMILES: COc1cc(Nc2cc(Cl)cn([C@@H](CO)c3cc(F)cc(F)c3)c2=O)ccc1-n1cnc(C)c1]
177.1
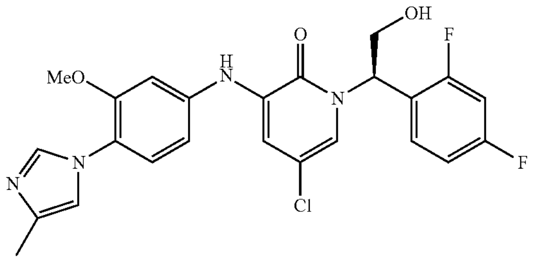 [SMILES: COc1cc(Nc2cc(Cl)cn([C@@H](CO)c3ccc(F)cc3F)c2=O)ccc1-n1cnc(C)c1]
178.1
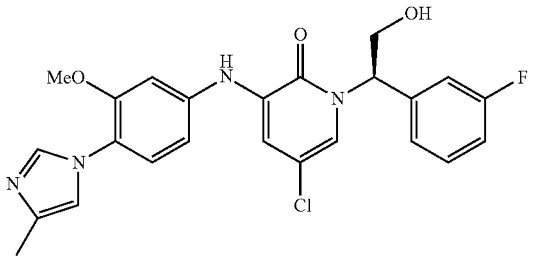 [SMILES: COc1cc(Nc2cc(Cl)cn([C@@H](CO)c3cccc(F)c3)c2=O)ccc1-n1cnc(C)c1]
179.1
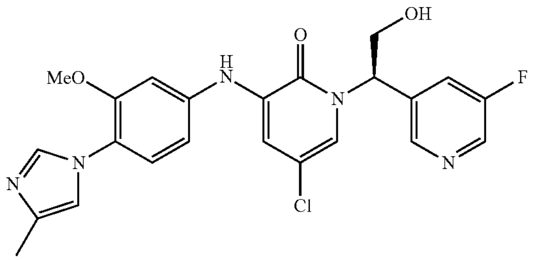 [SMILES: COc1cc(Nc2cc(Cl)cn([C@@H](CO)c3cncc(F)c3)c2=O)ccc1-n1cnc(C)c1]

TABLE 4-continued
180.1
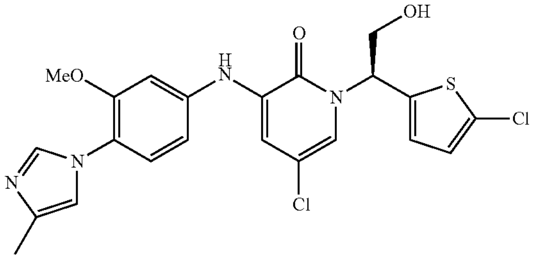 [SMILES: COc1cc(Nc2cc(Cl)cn([C@@H](CO)c3ccc(Cl)s3)c2=O)ccc1-n1cnc(C)c1]
181.1
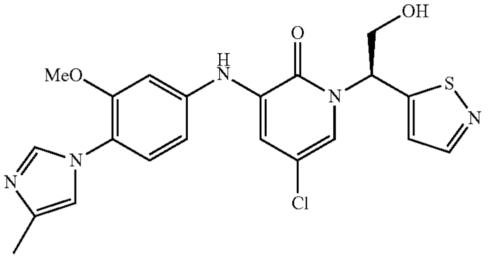 [SMILES: COc1cc(Nc2cc(Cl)cn([C@@H](CO)c3ccns3)c2=O)ccc1-n1cnc(C)c1]
182.1
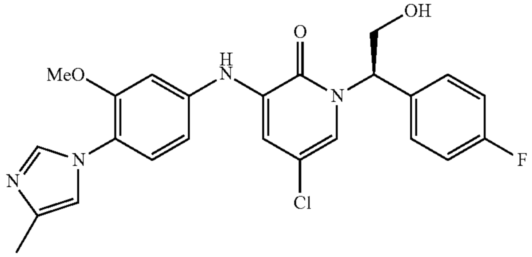 [SMILES: COc1cc(Nc2cc(Cl)cn([C@@H](CO)c3ccc(F)cc3)c2=O)ccc1-n1cnc(C)c1]
183.1
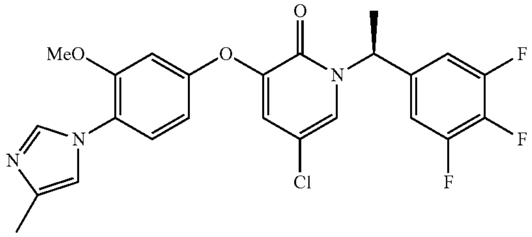 [SMILES: COc1cc(Oc2cc(Cl)cn([C@@H](C)c3cc(F)c(F)c(F)c3)c2=O)ccc1-n1cnc(C)c1]
184.1
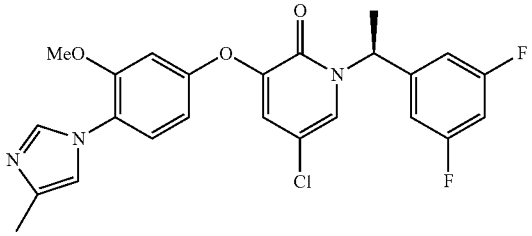 [SMILES: COc1cc(Oc2cc(Cl)cn([C@@H](C)c3cc(F)cc(F)c3)c2=O)ccc1-n1cnc(C)c1]

TABLE 4-continued
185.1
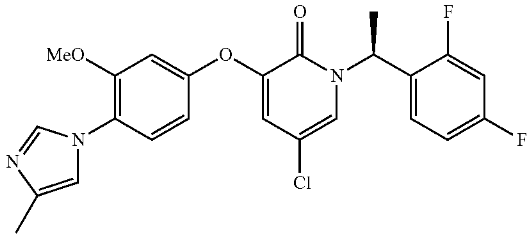 [SMILES: COc1cc(Oc2cc(Cl)cn([C@@H](C)c3ccc(F)cc3F)c2=O)ccc1-n1cnc(C)c1]
186.1
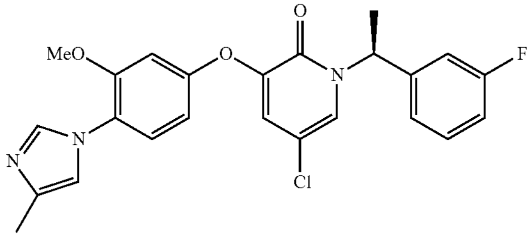 [SMILES: COc1cc(Oc2cc(Cl)cn([C@@H](C)c3cccc(F)c3)c2=O)ccc1-n1cnc(C)c1]
187.1
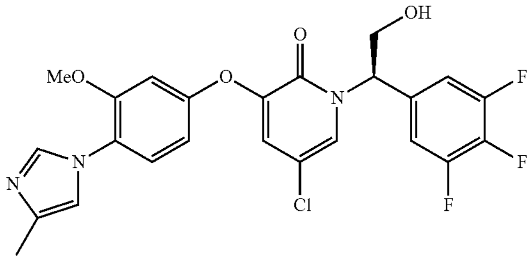 [SMILES: COc1cc(Oc2cc(Cl)cn([C@@H](CO)c3cc(F)c(F)c(F)c3)c2=O)ccc1-n1cnc(C)c1]
188.1
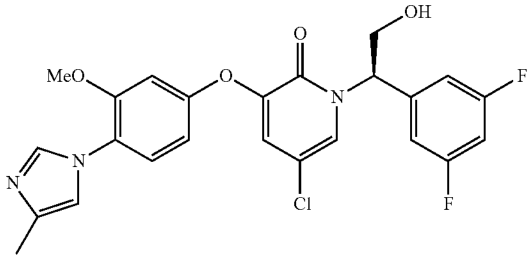 [SMILES: COc1cc(Oc2cc(Cl)cn([C@@H](CO)c3cc(F)cc(F)c3)c2=O)ccc1-n1cnc(C)c1]
189.1
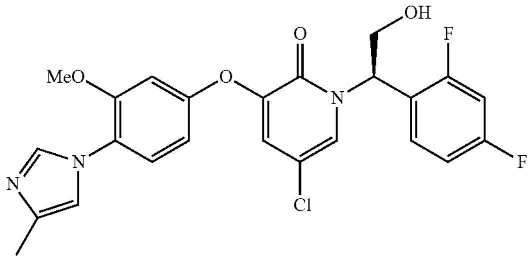 [SMILES: COc1cc(Oc2cc(Cl)cn([C@@H](CO)c3ccc(F)cc3F)c2=O)ccc1-n1cnc(C)c1]

TABLE 4-continued
190.1
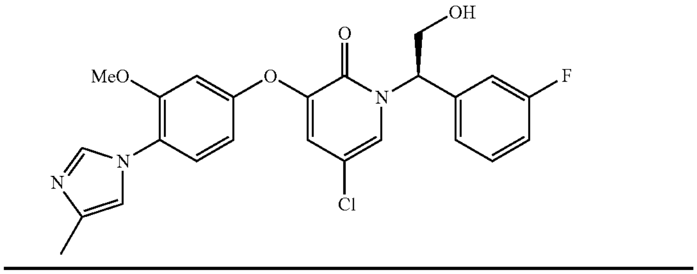
Representative compounds of formula (I) also include, but are not limited to, compounds 263.1-274.1 in Table 5.
TABLE 5
263.1
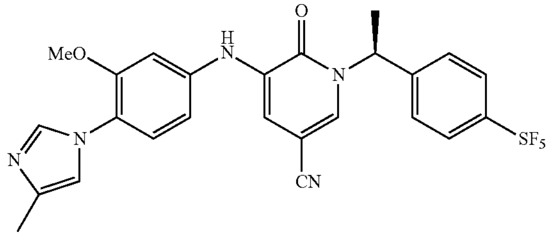
264.1
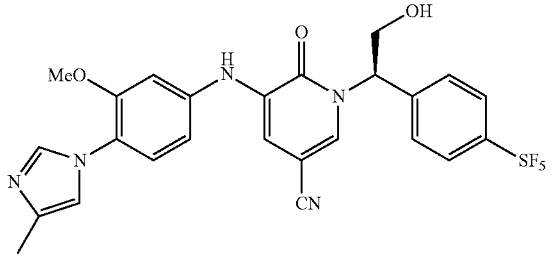
265.1
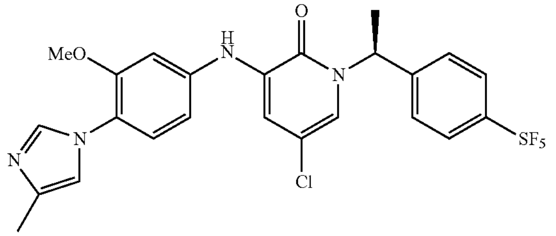
266.1
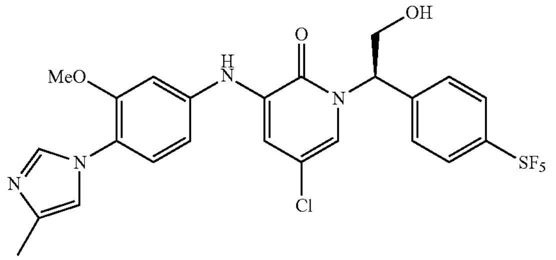

TABLE 5-continued
267.1
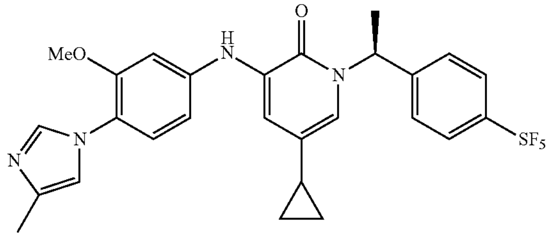
268.1
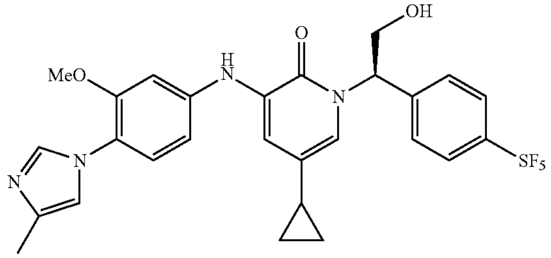
269.1
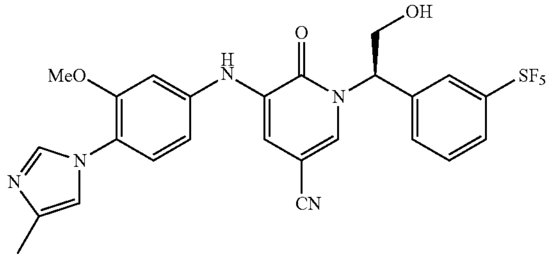
270.1
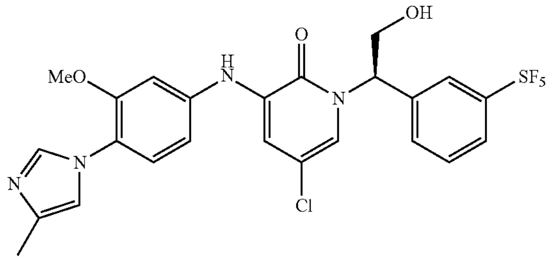
271.1
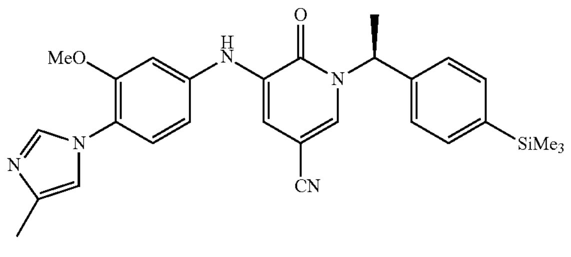

TABLE 5-continued

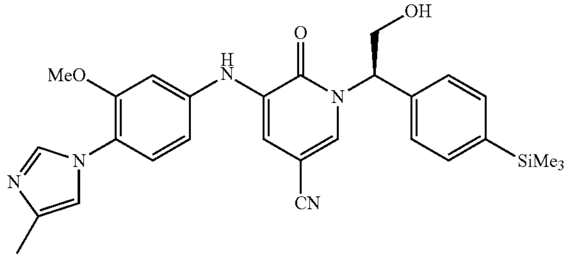

272.1

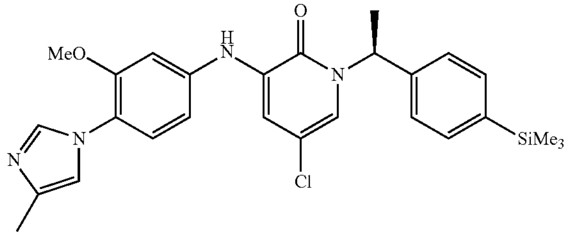 [SMILES: COc1cc(Nc2cc(Cl)cn([C@@H](C)c3ccc([Si](C)(C)C)cc3)c2=O)ccc1-n1cnc(C)c1]

273.1

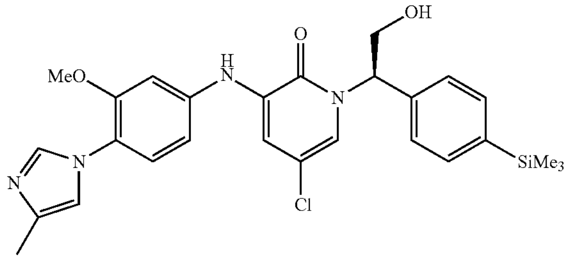 [SMILES: COc1cc(Nc2cc(Cl)cn([C@@H](CO)c3ccc([Si](C)(C)C)cc3)c2=O)ccc1-n1cnc(C)c1]

274.1

In one embodiment of this invention, the compound of formula (I) is compound 1.1.

In one embodiment of this invention, the compound of formula (I) is compound 2.1.

In one embodiment of this invention, the compound of formula (I) is compound 3.1.

In one embodiment of this invention, the compound of formula (I) is compound 4.1.

In one embodiment of this invention, the compound of formula (I) is compound 5.1.

In one embodiment of this invention, the compound of formula (I) is compound 6.1.

In one embodiment of this invention, the compound of formula (I) is compound 6.1.

In one embodiment of this invention, the compound of formula (I) is compound 7.1.

In one embodiment of this invention, the compound of formula (I) is compound 8.1.

In one embodiment of this invention, the compound of formula (I) is compound 9.1.

In one embodiment of this invention, the compound of formula (I) is compound 10.1.

In one embodiment of this invention, the compound of formula (I) is compound 11.1.

In one embodiment of this invention, the compound of formula (I) is compound 12.1.

In one embodiment of this invention, the compound of formula (I) is compound 13.1.

In one embodiment of this invention, the compound of formula (I) is compound 14.1.

In one embodiment of this invention, the compound of formula (I) is compound 15.1.

In one embodiment of this invention, the compound of formula (I) is compound 16.1.

In one embodiment of this invention, the compound of formula (I) is compound 17.1.

In one embodiment of this invention, the compound of formula (I) is compound 18.1.

In one embodiment of this invention, the compound of formula (I) is compound 19.1.

In one embodiment of this invention, the compound of formula (I) is compound 20.1.

In one embodiment of this invention, the compound of formula (I) is compound 21.1.

In one embodiment of this invention, the compound of formula (I) is compound 22.1.

In one embodiment of this invention, the compound of formula (I) is compound 23.1.

In one embodiment of this invention, the compound of formula (I) is compound 24.1.

In one embodiment of this invention, the compound of formula (I) is compound 25.1.

In one embodiment of this invention, the compound of formula (I) is compound 26.1.

In one embodiment of this invention, the compound of formula (I) is compound 27.1.

In one embodiment of this invention, the compound of formula (I) is compound 28.1.

In one embodiment of this invention, the compound of formula (I) is compound 29.1.

In one embodiment of this invention, the compound of formula (I) is compound 30.1.

In one embodiment of this invention, the compound of formula (I) is compound 31.1.

In one embodiment of this invention, the compound of formula (I) is compound 32.1.

In one embodiment of this invention, the compound of formula (I) is compound 33.1.

In one embodiment of this invention, the compound of formula (I) is compound 34.1.

In one embodiment of this invention, the compound of formula (I) is compound 36.1.

In one embodiment of this invention, the compound of formula (I) is compound 37.1.

In one embodiment of this invention, the compound of formula (I) is compound 38.1.

In one embodiment of this invention, the compound of formula (I) is compound 39.1.

In one embodiment of this invention, the compound of formula (I) is compound 40.1.

In one embodiment of this invention, the compound of formula (I) is compound 41.1.

In one embodiment of this invention, the compound of formula (I) is compound 42.1.

In one embodiment of this invention, the compound of formula (I) is compound 43.1.

In one embodiment of this invention, the compound of formula (I) is compound 44.1.

In one embodiment of this invention, the compound of formula (I) is compound 45.1.

In one embodiment of this invention, the compound of formula (I) is compound 46.1.

In one embodiment of this invention, the compound of formula (I) is compound 47.1.

In one embodiment of this invention, the compound of formula (I) is compound 48.1.

In one embodiment of this invention, the compound of formula (I) is compound 49.1.

Another embodiment of this invention is directed to compound 50.1.

Another embodiment of this invention is directed to compound 51.1.

Another embodiment of this invention is directed to compound 52.1.

Another embodiment of this invention is directed to compound 53.1.

Another embodiment of this invention is directed to compound 54.1.

Another embodiment of this invention is directed to compound 55.1.

Another embodiment of this invention is directed to compound 56.1.

Another embodiment of this invention is directed to compound 57.1.

Another embodiment of this invention is directed to compound 58.1.

Another embodiment of this invention is directed to compound 59.1.

Another embodiment of this invention is directed to compound 60.1.

Another embodiment of this invention is directed to compound 61.1.

Another embodiment of this invention is directed to compound 62.1.

Another embodiment of this invention is directed to compound 63.1.

Another embodiment of this invention is directed to compound 64.1.

Another embodiment of this invention is directed to compound 65.1.

Another embodiment of this invention is directed to compound 66.1.

Another embodiment of this invention is directed to compound 67.1.

Another embodiment of this invention is directed to compound 68.1.

Another embodiment of this invention is directed to compound 69.1.

Another embodiment of this invention is directed to compound 70.1.

Another embodiment of this invention is directed to compound 71.1.

Another embodiment of this invention is directed to compound 72.1.

Another embodiment of this invention is directed to compound 73.1.

Another embodiment of this invention is directed to compound 74.1.

Another embodiment of this invention is directed to compound 75.1.

Another embodiment of this invention is directed to compound 76.1.

Another embodiment of this invention is directed to compound 77.1.

Another embodiment of this invention is directed to compound 78.1.

Another embodiment of this invention is directed to compound 79.1.

Another embodiment of this invention is directed to compound 80.1.

Another embodiment of this invention is directed to compound 81.1.

Another embodiment of this invention is directed to compound 82.1.

Another embodiment of this invention is directed to compound 83.1.

Another embodiment of this invention is directed to compound 84.1.

Another embodiment of this invention is directed to compound 85.1.

Another embodiment of this invention is directed to compound 86.1.

Another embodiment of this invention is directed to compound 87.1.

Another embodiment of this invention is directed to compound 88.1.

Another embodiment of this invention is directed to compound 89.1.

Another embodiment of this invention is directed to compound 90.1.

Another embodiment of this invention is directed to compound 91.1.

Another embodiment of this invention is directed to compound 92.1.

Another embodiment of this invention is directed to compound 93.1.

Another embodiment of this invention is directed to compound 94.1.

Another embodiment of this invention is directed to compound 95.1.

Another embodiment of this invention is directed to compound 96.1.

Another embodiment of this invention is directed to compound 97.1.

Another embodiment of this invention is directed to compound 98.1.

Another embodiment of this invention is directed to compound 99.1.

Another embodiment of this invention is directed to compound 100.1.

Another embodiment of this invention is directed to compound 101.1.

Another embodiment of this invention is directed to compound 102.1.

Another embodiment of this invention is directed to compound 103.1.

Another embodiment of this invention is directed to compound 104.1.

Another embodiment of this invention is directed to compound 105.1.

Another embodiment of this invention is directed to compound 106.1.

Another embodiment of this invention is directed to compound 107.1.

Another embodiment of this invention is directed to compound 108.1.

Another embodiment of this invention is directed to compound 109.1.

Another embodiment of this invention is directed to compound 110.1.

Another embodiment of this invention is directed to compound 111.1.

Another embodiment of this invention is directed to compound 112.1.

Another embodiment of this invention is directed to compound 113.1.

Another embodiment of this invention is directed to compound 114.1.

Another embodiment of this invention is directed to compound 115.1.

Another embodiment of this invention is directed to compound 116.1.

Another embodiment of this invention is directed to compound 117.1.

Another embodiment of this invention is directed to compound 118.1.

Another embodiment of this invention is directed to compound 119.1.

Another embodiment of this invention is directed to compound 120.1.

Another embodiment of this invention is directed to compound 121.1.

Another embodiment of this invention is directed to compound 122.1.

Another embodiment of this invention is directed to compound 123.1.

Another embodiment of this invention is directed to compound 124.1.

Another embodiment of this invention is directed to compound 125.1.

Another embodiment of this invention is directed to compound 126.1.

Another embodiment of this invention is directed to compound 127.1.

Another embodiment of this invention is directed to compound 128.1.

Another embodiment of this invention is directed to compound 129.1.

Another embodiment of this invention is directed to compound 130.1.

Another embodiment of this invention is directed to compound 131.1.

Another embodiment of this invention is directed to compound 132.1.

Another embodiment of this invention is directed to compound 133.1.

Another embodiment of this invention is directed to compound 134.1.

Another embodiment of this invention is directed to compound 135.1.

Another embodiment of this invention is directed to compound 136.1.

Another embodiment of this invention is directed to compound 137.1.

Another embodiment of this invention is directed to compound 138.1.

Another embodiment of this invention is directed to compound 139.1.

Another embodiment of this invention is directed to compound 140.1.

Another embodiment of this invention is directed to compound 141.1.

Another embodiment of this invention is directed to compound 142.1.

Another embodiment of this invention is directed to compound 143.1.

Another embodiment of this invention is directed to compound 144.1.

Another embodiment of this invention is directed to compound 145.1.

Another embodiment of this invention is directed to compound 146.1.

Another embodiment of this invention is directed to compound 147.1.

Another embodiment of this invention is directed to compound 148.1.

Another embodiment of this invention is directed to compound 149.1.

Another embodiment of this invention is directed to compound 150.1.

Another embodiment of this invention is directed to compound 151.1.

Another embodiment of this invention is directed to compound 152.1.

Another embodiment of this invention is directed to compound 153.1.

Another embodiment of this invention is directed to compound 154.1.

Another embodiment of this invention is directed to compound 155.1.

Another embodiment of this invention is directed to compound 156.1.

Another embodiment of this invention is directed to compound 157.1.

Another embodiment of this invention is directed to compound 158.1.

Another embodiment of this invention is directed to compound 159.1.

Another embodiment of this invention is directed to compound 160.1.

Another embodiment of this invention is directed to compound 161.1.

Another embodiment of this invention is directed to compound 162.1.

Another embodiment of this invention is directed to compound 163.1.

Another embodiment of this invention is directed to compound 164.1.

Another embodiment of this invention is directed to compound 165.1.

Another embodiment of this invention is directed to compound 166.1.

Another embodiment of this invention is directed to compound 167.1.

Another embodiment of this invention is directed to compound 168.1.

Another embodiment of this invention is directed to compound 169.1.

Another embodiment of this invention is directed to compound 170.1.

Another embodiment of this invention is directed to compound 171.1.

Another embodiment of this invention is directed to compound 172.1.

Another embodiment of this invention is directed to compound 173.1.

Another embodiment of this invention is directed to compound 174.1.

Another embodiment of this invention is directed to compound 175.1.

Another embodiment of this invention is directed to compound 176.1.

Another embodiment of this invention is directed to compound 177.1.

Another embodiment of this invention is directed to compound 178.1.

Another embodiment of this invention is directed to compound 179.1.

Another embodiment of this invention is directed to compound 180.1.

Another embodiment of this invention is directed to compound 181.1.

Another embodiment of this invention is directed to compound 182.1.

Another embodiment of this invention is directed to compound 183.1.

Another embodiment of this invention is directed to compound 184.1.

Another embodiment of this invention is directed to compound 185.1.

Another embodiment of this invention is directed to compound 186.1.

Another embodiment of this invention is directed to compound 187.1.

Another embodiment of this invention is directed to compound 188.1.

Another embodiment of this invention is directed to compound 189.1.

Another embodiment of this invention is directed to compound 190.1.

In one embodiment of this invention, the compound of formula (I) is compound 191.1.

In one embodiment of this invention, the compound of formula (I) is compound 192.1.

In one embodiment of this invention, the compound of formula (I) is compound 193.1.

In one embodiment of this invention, the compound of formula (I) is compound 194.1.

In one embodiment of this invention, the compound of formula (I) is compound 195.1.

In one embodiment of this invention, the compound of formula (I) is compound 196.1.

In one embodiment of this invention, the compound of formula (I) is compound 197.1.

In one embodiment of this invention, the compound of formula (I) is compound 198.1.

In one embodiment of this invention, the compound of formula (I) is compound 199.1.

In one embodiment of this invention, the compound of formula (I) is compound 200.1.

In one embodiment of this invention, the compound of formula (I) is compound 201.1.

In one embodiment of this invention, the compound of formula (I) is compound 202.1.

In one embodiment of this invention, the compound of formula (I) is compound 203.1.

In one embodiment of this invention, the compound of formula (I) is compound 204.1.

In one embodiment of this invention, the compound of formula (I) is compound 205.1.

In one embodiment of this invention, the compound of formula (I) is compound 206.1.

In one embodiment of this invention, the compound of formula (I) is compound 207.1.

In one embodiment of this invention, the compound of formula (I) is compound 208.1.

In one embodiment of this invention, the compound of formula (I) is compound 209.1.

In one embodiment of this invention, the compound of formula (I) is compound 210.1.

In one embodiment of this invention, the compound of formula (I) is compound 211.1.

In one embodiment of this invention, the compound of formula (I) is compound 212.1.

In one embodiment of this invention, the compound of formula (I) is compound 213.1.

In one embodiment of this invention, the compound of formula (I) is compound 214.1.

In one embodiment of this invention, the compound of formula (I) is compound 215.1.

In one embodiment of this invention, the compound of formula (I) is compound 216.1.

In one embodiment of this invention, the compound of formula (I) is compound 217.1.

In one embodiment of this invention, the compound of formula (I) is compound 218.1.

In one embodiment of this invention, the compound of formula (I) is compound 219.1.

In one embodiment of this invention, the compound of formula (I) is compound 220.1.

In one embodiment of this invention, the compound of formula (I) is compound 221.1.

In one embodiment of this invention, the compound of formula (I) is compound 222.1.

In one embodiment of this invention, the compound of formula (I) is compound 223.1.

In one embodiment of this invention, the compound of formula (I) is compound 224.1.

In one embodiment of this invention, the compound of formula (I) is compound 225.1.

In one embodiment of this invention, the compound of formula (I) is compound 226.1.

In one embodiment of this invention, the compound of formula (I) is compound 227.1.

In one embodiment of this invention, the compound of formula (I) is compound 228.1.

In one embodiment of this invention, the compound of formula (I) is compound 229.1.

In one embodiment of this invention, the compound of formula (I) is compound 230.1.

In one embodiment of this invention, the compound of formula (I) is compound 231.1.

In one embodiment of this invention, the compound of formula (I) is compound 232.1.

In one embodiment of this invention, the compound of formula (I) is compound 233.1.

In one embodiment of this invention, the compound of formula (I) is compound 234.1.

In one embodiment of this invention, the compound of formula (I) is compound 235.1.

In one embodiment of this invention, the compound of formula (I) is compound 236.1.

In one embodiment of this invention, the compound of formula (I) is compound 237.1.

In one embodiment of this invention, the compound of formula (I) is compound 238.1.

In one embodiment of this invention, the compound of formula (I) is compound 239.1.

In one embodiment of this invention, the compound of formula (I) is compound 240.1

In one embodiment of this invention, the compound of formula (I) is compound 241.1.

In one embodiment of this invention, the compound of formula (I) is compound 242.1.

In one embodiment of this invention, the compound of formula (I) is compound 243.1.

In one embodiment of this invention, the compound of formula (I) is compound 244.1.

In one embodiment of this invention, the compound of formula (I) is compound 245.1.

In one embodiment of this invention, the compound of formula (I) is compound 246.1.

In one embodiment of this invention, the compound of formula (I) is compound 247.1.

In one embodiment of this invention, the compound of formula (I) is compound 248.1.

In one embodiment of this invention, the compound of formula (I) is compound 249.1.

In one embodiment of this invention, the compound of formula (I) is compound 250.1.

In one embodiment of this invention, the compound of formula (I) is compound 251.1.

In one embodiment of this invention, the compound of formula (I) is compound 252.1.

In one embodiment of this invention, the compound of formula (I) is compound 253.1.

In one embodiment of this invention, the compound of formula (I) is compound 254.1.

In one embodiment of this invention, the compound of formula (I) is compound 255.1.

In one embodiment of this invention, the compound of formula (I) is compound 256.1.

In one embodiment of this invention, the compound of formula (I) is compound 257.1.

In one embodiment of this invention, the compound of formula (I) is compound 258.1.

In one embodiment of this invention, the compound of formula (I) is compound 259.1.

In one embodiment of this invention, the compound of formula (I) is compound 260.1.

In one embodiment of this invention, the compound of formula (I) is compound 261.1.

In one embodiment of this invention, the compound of formula (I) is compound 262.1.

In one embodiment of this invention, the compound of formula (I) is compound 263.1.

In one embodiment of this invention, the compound of formula (I) is compound 264.1.

In one embodiment of this invention, the compound of formula (I) is compound 265.1.

In one embodiment of this invention, the compound of formula (I) is compound 266.1.

In one embodiment of this invention, the compound of formula (I) is compound 267.1.

In one embodiment of this invention, the compound of formula (I) is compound 268.1.

In one embodiment of this invention, the compound of formula (I) is compound 269.1.

In one embodiment of this invention, the compound of formula (I) is compound 270.1.

In one embodiment of this invention, the compound of formula (I) is compound 271.1.

In one embodiment of this invention, the compound of formula (I) is compound 272.1.

In one embodiment of this invention, the compound of formula (I) is compound 273.1.

In one embodiment of this invention, the compound of formula (I) is compound 274.1.

Another embodiment of this invention is directed to a pharmaceutically acceptable salt of a compound selected from the group consisting of: compounds 1.1 to 49.1.

Another embodiment of this invention is directed to a pharmaceutically acceptable salt of a compound selected from the group consisting of: compounds 50.1 to 118.1.

Another embodiment of this invention is directed to a pharmaceutically acceptable salt of a compound selected from the group consisting of: compounds 119.1 to 190.1.

Another embodiment of this invention is directed to a pharmaceutically acceptable salt of a compound selected from the group consisting of: compounds 191.1 to 262.1.

Another embodiment of this invention is directed to a pharmaceutically acceptable salt of a compound selected from the group consisting of: compounds 263.1 to 274.1.

Another embodiment of this invention is directed to a pharmaceutically acceptable ester of a compound selected from the group consisting of: compounds 1.1 to 49.1.

Another embodiment of this invention is directed to a pharmaceutically acceptable ester of a compound selected from the group consisting of: compounds 50.1 to 118.1.

Another embodiment of this invention is directed to a pharmaceutically acceptable ester of a compound selected from the group consisting of: compounds 119.1 to 190.1.

Another embodiment of this invention is directed to a pharmaceutically acceptable ester of a compound selected from the group consisting of: compounds 191.1 to 262.1.

Another embodiment of this invention is directed to a pharmaceutically acceptable ester of a compound selected from the group consisting of: compounds 263.1 to 274.1.

Another embodiment of this invention is directed to a solvate of a compound selected from the group consisting of: compounds 1.1 to 49.1.

Another embodiment of this invention is directed to a solvate of a compound selected from the group consisting of: compounds 50.1 to 118.1.

Another embodiment of this invention is directed to a solvate of a compound selected from the group consisting of: compounds 119.1 to 190.1.

Another embodiment of this invention is directed to a solvate of a compound selected from the group consisting of: compounds 191.1 to 262.1.

Another embodiment of this invention is directed to a solvate of a compound selected from the group consisting of: compounds 263.1 to 274.1.

Another embodiment of this invention is directed to a compound selected from the group consisting of: compounds 1.1 to 49.1, said compound being in pure and isolated form.

Another embodiment of this invention is directed to a solvate of a compound selected from the group consisting of: compounds 50.1 to 118.1, said compound being in pure and isolated form.

Another embodiment of this invention is directed to a solvate of a compound selected from the group consisting of: compounds 119.1 to 190.1, said compound being in pure and isolated form.

Another embodiment of this invention is directed to, to a solvate of a compound selected from the group consisting of: compounds 191.1 to 262.1, said compound being in pure and isolated form.

Another embodiment of this invention is directed to a solvate of a compound selected from the group consisting of: compounds 263.1 to 274.1, said compound being in pure and isolated form.

Another embodiment of this invention is directed to a compound selected from the group consisting of: compounds 1.1 to 49.1, said compound being in pure form.

Another embodiment of this invention is directed to a solvate of a compound selected from the group consisting of: compounds 50.1 to 118.1, said compound being in pure form.

Another embodiment of this invention is directed to a solvate of a compound selected from the group consisting of: compounds 119.1 to 190.1, said compound being in pure form.

Another embodiment of this invention is directed to a solvate of a compound selected from the group consisting of: compounds 191.1 to 262.1, said compound being in pure form.

Another embodiment of this invention is directed to a solvate of a compound selected from the group consisting of: compounds 263.1 to 274.1, said compound being in pure form.

Another embodiment of this invention is directed to a compound selected from the group consisting of: compounds 1.1 to 49.1, said compound being in isolated form.

Another embodiment of this invention is directed to a solvate of a compound selected from the group consisting of: compounds 50.1 to 118.1, said compound being in isolated form.

Another embodiment of this invention is directed to a solvate of a compound selected from the group consisting of: compounds 119.1 to 190.1, said compound being in isolated form.

Another embodiment of this invention is directed to a solvate of a compound selected from the group consisting of: compounds 191.1 to 262.1, said compound being in isolated form.

Another embodiment of this invention is directed to a solvate of a compound selected from the group consisting of: compounds 263.1 to 274.1, said compound being in isolated form.

Another embodiment of this invention is directed to a compound of formula (I) selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a pharmaceutically acceptable salt of a compound of formula (I), said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a pharmaceutically acceptable ester of a compound of formula (I), said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a solvate of a compound of formula (I), said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a compound of formula (I) in isolated form, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a compound of formula (I) in pure form, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (1Y), (IY1), (IZ), (IZ1), (1AB), (IAB1), (IAC3), (IAC6), (IAD3), (IAD6), (IAE), (IAE1), (IAF), and (IAF1).

Another embodiment of this invention is directed to a compound of formula (I) in pure and isolated form, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment is directed to a pharmaceutical composition comprising an effective amount of one or more (e.g., one) compounds of formula (I) and a pharmaceutically acceptable carrier, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment is directed to a pharmaceutical composition comprising an effective amount of a pharmaceutically acceptable salt of one or more (e.g., one) compounds of formula (I) and a pharmaceutically acceptable carrier, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IO1), (IR), (IR1), (IS), (IS1), (IT), (IN), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment is directed to a pharmaceutical composition comprising an effective amount of a pharmaceutically acceptable ester of one or more (e.g., one) compounds of formula (I) and a pharmaceutically acceptable carrier, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IV), (IY1), (IZ), (IZ1), (IAB), (IAB1), (IAC3), (IAC6), (IAD3), (IAD6), (IAE), (IAE1), (IAF), and (IAF1).

Another embodiment is directed to a pharmaceutical composition comprising an effective amount of a solvate of one or more (e.g., one) compounds of formula (I) and a pharmaceutically acceptable carrier, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a pharmaceutical composition comprising an effective amount of one or more (e.g., one) compounds of formula (I), and an effective amount of one or more (e.g., one) other pharmaceutically active ingredients (e.g.,) drugs, and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a pharmaceutical composition comprising an effective amount of one or more (e.g., one) compounds of formula (I), and effective amount of one or more BACE inhibitors, and a pharmaceutically acceptable carrier, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a pharmaceutical composition comprising an effective amount of one or more (e.g., one) compounds selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), and effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), and effective amount of one or more muscarinic antagonists (e.g., $m_1$ or $m_2$ antagonists), and a pharmaceutically acceptable carrier.

The compounds of formulas (IA), (IB), (IC), (ID), (IE), (IE1), (IF), (IF1), (IG), (IG1), (IH), (IH1), (14 (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1) can be useful as gamma secretase modulators and can be useful in the treatment and prevention of diseases such as, for example, central nervous system disorders such as Alzheimers disease and Downs Syndrome.

Thus, another embodiment of this invention is directed to a method for modulating (including inhibiting, antagonizing and the like) gamma-secretase comprising administering an effective (i.e., therapeutically effective) amount of one or more (e.g., one) compounds of formula (I) to a patient in need of such treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method for modulating (including inhibiting, antagonizing and the like) gamma-secretase, comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating one or more neurodegenerative diseases, comprising administering an effective (i.e., therapeutically effective) amount of one or more (e.g., one) compounds of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating one or more neurodegenerative diseases, comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of one or more (e.g., one) compounds of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IO1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IO1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating Alzheimer's disease, comprising administering an effective (i.e., therapeutically effective) amount of one or more (e.g., one) compounds of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IO1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating Alzheimer's disease, comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IO1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating Downs syndrome, comprising administering an effective (i.e., therapeutically effective) amount of one or more (e.g., one) compounds of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IO), (IO1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), and (IAF1), and (IAF1) to a patient in need of treatment.

Another embodiment of this invention is directed to a method of treating Downs syndrome, comprising administering an effective (i.e., therapeutically effective) amount of a compound of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IO), (IO1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1) to a patient in need of treatment.

Another embodiment of this invention is directed to a method of treating mild cognitive impairment, comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating glaucoma, comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (10), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating cerebral amyloid angiopathy, comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating stroke, comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating dementia, comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating microgliosis, comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1) (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating brain inflammation, comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

Another embodiment of this invention is directed to a method of treating olfactory function loss, comprising administering an effective (i.e., therapeutically effective) amount of a compound of formula (I) to a patient in need of treatment, said compound of formula (I) being selected from the group consisting of: (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1).

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), and the administration of one or more (e.g., one) other pharmaceutical active ingredients (e.g., drugs). The compounds of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), and the other drugs can be administered separately (i.e., each is in its own separate dosage form), or the compounds of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1) can be combined with the other drugs in the same dosage form.

Thus, other embodiments of this invention are directed to any one of the methods of treatment, or methods of inhibiting, described herein, wherein the compounds of formulas (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IO1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1) are used in combination with an effective amount of one or more other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Another embodiment of this invention is directed to a method of treating Alzheimer's disease, comprising administering an effective (i.e., therapeutically effective) amount of one or more (e.g., one) compounds of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of a compound of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of one or more (e.g., one) compounds of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), in combination with an effective (i.e., therapeutically effective) amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective (i.e., therapeutically effective) amount of one or more (e.g., one) compounds of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), and (IAF1), and (IAF1), in combination with an effective (i.e., therapeutically effective) amount of one or more BACE inhibitors.

Another embodiment of this invention is directed to a method of treating Downs syndrome, comprising administering an effective (i.e., therapeutically effective) amount of one or more (e.g., one) compounds of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective (i.e., therapeutically effective) amount of a compound of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to combinations (i.e., pharmaceutical compositions) comprising an effective (i.e., therapeutically effective) amount of one or more (e.g., one) compounds of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), and (IAF1), in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

This invention also provides a kit comprising, in separate containers, in a single package, pharmaceutical compositions for use in combination, wherein one container comprises an effective amount of a compound of formula (IA), (IB), (IC), (ID), (IE), (IE1), (IF), (IF1), (IG), (IG1), (IH), (IH1), (IJ), (IJ1), (IJ2), (IJ3), (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), (IAB1), (IAC3), (IAC6), (IAD3), (IAD6), (IAE), (IAE1), (IAF), or (IAF1) in a pharmaceutically acceptable carrier, and another container (i.e., a second container) comprises an effective amount of another pharmaceutically active ingredient (as described above), the combined quantities of the compound of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Another embodiment is directed to a pharmaceutical composition comprising an effective amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) and a pharmaceutically acceptable carrier.

Another embodiment is directed to a pharmaceutical composition comprising an effective amount of a pharmaceutically acceptable salt of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), and a pharmaceutically acceptable carrier.

Another embodiment is directed to a pharmaceutical composition comprising an effective amount of a pharmaceutically acceptable ester of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), and a pharmaceutically acceptable carrier.

Another embodiment is directed to a pharmaceutical composition comprising an effective amount of a solvate of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), and a pharmaceutically acceptable carrier.

Another embodiment of this invention is directed to a pharmaceutical composition comprising an effective amount of one or more (e.g., one) compounds selected from the group consisting of 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), and an effective amount of one or more (e.g., one) other pharmaceutically active ingredients (e.g.,) drugs, and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising an effective amount of one or more (e.g., one) compounds of selected from the group consisting of 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), and effective amount of one or more BACE inhibitors, and a pharmaceutically acceptable carrier.

Another embodiment of this invention is directed to a pharmaceutical composition comprising an effective amount of one or more (e.g., one) compounds selected from the group consisting of 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), and effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds selected from the group consisting of 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), and a pharmaceutically acceptable carrier.

The compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) can be useful as gamma secretase modulators and can be useful in the treatment and prevention of diseases such as, for example, central nervous system disorders such as Alzheimers disease and Downs Syndrome.

Thus, another embodiment of this invention is directed to a method for modulating (including inhibiting, antagonizing and the like) gamma-secretase comprising administering an effective (i.e., therapeutically effective) amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of such treatment.

Another embodiment of this invention is directed to a method for modulating (including inhibiting, antagonizing and the like) gamma-secretase, comprising administering an effective (i.e., therapeutically effective) amount of a compound selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating one or more neurodegenerative diseases, comprising administering an effective (i.e., therapeutically effective) amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating one or more neurodegenerative diseases, comprising administering an effective (i.e., therapeutically effective) amount of a compound selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of one or more (e.g., one) compounds selected from the group consisting of compounds 1.1 to 49.1, and 191.1 to 262.1 (and in one embodiment the compounds are selected from the group consisting of 1.1 to 49.1, and in another embodiment the compounds are selected from the group consisting of 191.1 to 274.1, and in another embodiment the compounds are selected from the group consisting of 263.1 to 274.1) to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of a compound selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating Alzheimer's disease, comprising administering an effective (i.e., therapeutically effective) amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating Alzheimer's disease, comprising administering an effective (i.e., therapeutically effective) amount of a compound selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating Downs syndrome, comprising administering an effective (i.e., therapeutically effective) amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating Downs syndrome, comprising administering an effective (i.e., therapeutically effective) amount of a compound of formula compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating mild cognitive impairment, comprising administering an effective amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating glaucoma, comprising administering an effective amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating cerebral amyloid angiopathy, comprising administering an effective amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating stroke, comprising administering an effective amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating dementia, comprising administering an effective amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating microgliosis, comprising administering an effective amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating brain inflammation, comprising administering an effective amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

Another embodiment of this invention is directed to a method of treating olfactory function loss, comprising administering an effective amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) to a patient in need of treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), and the administration of one or more (e.g., one) other pharmaceutical active ingredients (e.g., drugs). The compounds and the other drugs can be administered separately (i.e., each is in its own separate dosage form), or the compounds of formula can be combined with the other drugs in the same dosage form.

Thus, other embodiments of this invention are directed to any one of the methods of treatment, or methods of inhibiting, described herein, wherein the compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) are used in combination with an effective amount of one or more other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Thus, another embodiment of this invention is directed to a method of treating Alzheimer's disease comprising administering one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1) in combination with an effective amount of one or more other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe), to a patient in need of such treatment.

Another embodiment of this invention is directed to a method of treating Alzheimer's disease, comprising administering an effective (i.e., therapeutically effective) amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), in combination with an effective (i.e., therapeutically effective) amount of one or more cholinesterase inhibitors (such as, for example, (#)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of a compound selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), in combination with an effective (i.e., therapeutically effective) amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective (i.e., therapeutically effective) amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), in combination with an effective (i.e., therapeutically effective) amount of one or more BACE inhibitors.

Another embodiment of this invention is directed to a method of treating Downs syndrome, comprising administering an effective (i.e., therapeutically effective) amount of one or more (e.g., one) compounds selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective (i.e., therapeutically effective) amount of a compound selected from the group consisting of compounds 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to combinations (i.e., pharmaceutical compositions) comprising an effective (i.e., therapeutically effective) amount of one or more (e.g., one) compounds selected from the group consisting of 1.1 to 49.1, and 191.1 to 274.1 (and in one embodiment the compounds are selected from the group consisting of 1.1 to 49.1, and in another embodiment the compounds are selected from the group consisting of 191.1 to 262.1, and in another embodiment the compounds are selected from the group consisting of 263.1 to 274.1), in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

Another embodiment is directed to a pharmaceutical composition comprising an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), and a pharmaceutically acceptable carrier.

Another embodiment is directed to a pharmaceutical composition comprising an effective amount of a pharmaceutically acceptable salt of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), and a pharmaceutically acceptable carrier.

Another embodiment is directed to a pharmaceutical composition comprising an effective amount of a pharmaceutically acceptable ester of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), and a pharmaceutically acceptable carrier.

Another embodiment is directed to a pharmaceutical composition comprising an effective amount of a solvate of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), and a pharmaceutically acceptable carrier.

Another embodiment of this invention is directed to a pharmaceutical composition comprising an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), and an effective amount of one or more (e.g., one) other pharmaceutically active ingredients (e.g.,) drugs, and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), and effective amount of one or more BACE inhibitors, and a pharmaceutically acceptable carrier.

Another embodiment of this invention is directed to a pharmaceutical composition comprising an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), and effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), and effective amount of one or more muscarinic antagonists (e.g., $m_1$ or $m_2$ antagonists), and a pharmaceutically acceptable carrier.

The compounds selected from the group consisting of compounds 50.1 to 190.1 (and in one embodiment the compounds are selected from the group consisting of 50.1-118.1, and in another embodiment the compounds are selected from the group consisting of 119.1-190.1) can be useful as gamma secretase modulators and can be useful in the treatment and prevention of diseases such as, for example, central nervous system disorders such as Alzheimers disease and Downs Syndrome.

Thus, another embodiment of this invention is directed to a method for modulating (including inhibiting, antagonizing and the like) gamma-secretase comprising administering an effective (i.e., therapeutically effective) amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of such treatment.

Another embodiment of this invention is directed to a method for modulating (including inhibiting, antagonizing and the like) gamma-secretase, comprising administering an effective (i.e., therapeutically effective) amount of a compound selected from the group consisting of compounds 50.1 to 190.1 (and in one embodiment the compound is selected from the group consisting of 50.1-118.1, and in another embodiment the compound is selected from the group consisting of 119.1-190.1) to a patient in need of treatment.

Another embodiment of this invention is directed to a method of treating one or more neurodegenerative diseases, comprising administering an effective (i.e., therapeutically effective) amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of treating one or more neurodegenerative diseases, comprising administering an effective (i.e., therapeutically effective) amount of a compound selected from the group consisting of compounds 50.1 to 190.1 (and in one embodiment the compound is selected from the group consisting of 50.1-118.1, and in another embodiment the compound is selected from the group consisting of 119.1-190.1) to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of inhibiting the deposition of amyloid protein (e.g., amyloid beta protein) in, on or around neurological tissue (e.g., the brain), comprising administering an effective (i.e., therapeutically effective) amount of a compound selected from the group consisting of compounds 50.1 to 190.1 (and in one embodiment the compound is selected from the group consisting of 50.1-118.1, and in another embodiment the compound is selected from the group consisting of 119.1-190.1) to a patient in need of treatment.

Another embodiment of this invention is directed to a method of treating Alzheimer's disease, comprising administering an effective (i.e., therapeutically effective) amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of treating Alzheimer's disease, comprising administering an effective (i.e., therapeutically effective) amount of a compound selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of treating mild cognitive impairment, comprising administering an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of treating glaucoma, comprising administering an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of treating cerebral amyloid angiopathy, comprising administering an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of treating stroke, comprising administering an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of treating dementia, comprising administering an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of treating microgliosis, comprising administering an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of treating brain inflammation, comprising administering an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of treating olfactory function loss, comprising administering an effective amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds selected from the group consisting of compounds 50.1 to 190.1 (and in one embodiment the compounds are selected from the group consisting of 50.1-118.1, and in another embodiment the compounds are selected from the group consisting of 119.1-190.1) and the administration of one or more (e.g., one) other pharmaceutical active ingredients (e.g., drugs). The compounds selected from the group consisting of compounds 50.1 to 190.1 (and in one embodiment the compounds are selected from the group consisting of 50.1-118.1, and in another embodiment the compounds are selected from the group consisting of 119.1-190.1) and the other drugs can be administered separately (i.e., each is in its own separate dosage form), or the compounds selected from the group consisting of compounds 50.1 to 190.1 (and in one embodiment the compounds are selected from the group consisting of 50.1-118.1, and in another embodiment the compounds are selected from the group consisting of 119.1-190.1) can be combined with the other drugs in the same dosage form.

Thus, other embodiments of this invention are directed to any one of the methods of treatment, or methods of inhibiting, described herein, wherein the compound is selected from the group consisting of compounds 50.1 to 190.1 (and in one embodiment the compound is selected from the group consisting of 50.1-118.1, and in another embodiment the compound is selected from the group consisting of 119.1-190.1) is used in combination with an effective amount of one or more other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Thus, another embodiment of this invention is directed to a method of treating Alzheimer's disease comprising administering one or more (e.g., one) compounds selected from the group consisting of compounds 50.1 to 190.1 (and in one embodiment the compound is selected from the group consisting of 50.1-118.1, and in another embodiment the compound is selected from the group consisting of 119.1-190.1) in combination with an effective amount of one or more other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe), to a patient in need of such treatment.

Another embodiment of this invention is directed to a method of treating Alzheimer's disease, comprising administering an effective (i.e., therapeutically effective) amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of a compound selected from the group consisting of compounds 50.1 to 190.1 (and in one embodiment the compound is selected from the group consisting of 50.1-118.1, and in another embodiment the compound is selected from the group consisting of 119.1-190.1), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective (i.e., therapeutically effective) amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), in combination with an effective (i.e., therapeutically effective) amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective (i.e., therapeutically effective) amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), in combination with an effective (i.e., therapeutically effective) amount of one or more BACE inhibitors.

Another embodiment of this invention is directed to a method of treating Downs syndrome, comprising administering an effective (i.e., therapeutically effective) amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1) to a patient in need of treatment.

Another embodiment of this invention is directed to a method of treating Downs syndrome, comprising administering an effective (i.e., therapeutically effective) amount of a compound selected from the group consisting of compounds 50.1 to 190.1 (and in one embodiment the compound is selected from the group consisting of 50.1-118.1, and in another embodiment the compound is selected from the group consisting of 119.1-190.1) to a patient in need of treatment.

Another embodiment of this invention is directed to a method of treating Downs syndrome, comprising administering an effective (i.e., therapeutically effective) amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective (i.e., therapeutically effective) amount of a compound selected from the group consisting of compounds 50.1 to 190.1 (and in one embodiment the compound is selected from the group consisting of 50.1-118.1, and in another embodiment the compound is selected from the group consisting of 119.1-190.1), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to combinations (i.e., pharmaceutical compositions) comprising an effective (i.e., therapeutically effective) amount of one or more (e.g., one) compounds selected from the group consisting of compounds 50.1 to 190.1 (and in one embodiment the compounds are selected from the group consisting of 50.1-118.1, and in another embodiment the compounds are selected from the group consisting of 119.1-190.1), in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors. The pharmaceutical compositions also comprise a pharmaceutically acceptable carrier.

Another embodiment of this invention is directed to a kit comprising, in separate containers, in a single package, pharmaceutical compositions for use in combination, wherein one container comprises an effective amount of a compound selected from the group consisting of compounds 50.1 to 190.1 (and in one embodiment the compound is selected from the group consisting of 50.1-118.1, and in another embodiment the compound is selected from the group consisting of 119.1-190.1) in a pharmaceutically acceptable carrier, and another container (i.e., a second container) comprises an effective amount of another pharmaceutically active ingredient (as described above), the combined quantities of the compound selected from the group consisting of compounds 50.1 to 190.1 (and in one embodiment the compound is selected from the group consisting of 50.1-118.1, and in another embodiment the compound is selected from the group consisting of 119.1-190.1) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Other embodiments of this invention are directed to any one of the embodiments directed to the compounds of formulas (IK), (IK1), (IL), (IL1), (IL2), (IL3), (IM), (IM1), (IN), (IN1), (IO), (IO1), (IP), (IP1), (IQ), (IQ1), (IR), (IR1), (IS), (IS1), (IT), (IT1), (IU), (IU1), (IV), (IV1), (IW), (IW1), (IX), (IX1), (IY), (IY1), (IZ), (IZ1), (IAB), and (IAB1), or the their use, except that the -G-$R^{10}$—$R^9$ moiety is bound to position (2) of the compound instead of position (1) and the $(R^{21})_q$ moiety is bound to position (1) of the compound instead of position (2).

Another embodiment of this invention is directed to a kit comprising, in separate containers, in a single package, pharmaceutical compositions for use in combination, wherein one container comprises an effective amount of a compound selected from the group consisting of compounds 1.1 to 49.1 in a pharmaceutically acceptable carrier, and another container (i.e., a second container) comprises an effective amount of another pharmaceutically active ingredient (as described above), the combined quantities of the compound of formulas 1.1 to 49.1 and the other pharmaceutically active ingredient being effective to: (a) treat Alzheimer's disease, or (b) inhibit the deposition of amyloid protein (e.g., amyloid beta protein)

in, on or around neurological tissue (e.g., the brain), or (c) treat neurodegenerative diseases, or (d) modulate the activity of gamma-secretase.

Another embodiment of this invention is directed to a kit comprising, in separate containers, in a single package, pharmaceutical compositions for use in combination, wherein one container comprises an effective amount of a compound selected from the group consisting of compounds 50.1 to 118.1 in a pharmaceutically acceptable carrier, and another container (i.e., a second container) comprises an effective amount of another pharmaceutically active ingredient (as described above), the combined quantities of the compound of formulas 50.1 to 118.1 and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Another embodiment of this invention is directed to a kit comprising, in separate containers, in a single package, pharmaceutical compositions for use in combination, wherein one container comprises an effective amount of a compound selected from the group consisting of compounds 119.1 to 190.1 in a pharmaceutically acceptable carrier, and another container (i.e., a second container) comprises an effective amount of another pharmaceutically active ingredient (as described above), the combined quantities of the compound of formulas 119.1 to 190.1 and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Another embodiment of this invention is directed to a kit comprising, in separate containers, in a single package, pharmaceutical compositions for use in combination, wherein one container comprises an effective amount of a compound selected from the group consisting of compounds 191.1 to 262.1 in a pharmaceutically acceptable carrier, and another container (i.e., a second container) comprises an effective amount of another pharmaceutically active ingredient (as described above), the combined quantities of the compound of formulas 191.1 to 262.1 and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Another embodiment of this invention is directed to a kit comprising, in separate containers, in a single package, pharmaceutical compositions for use in combination, wherein one container comprises an effective amount of a compound selected from the group consisting of compounds 263.1 to 274.1 in a pharmaceutically acceptable carrier, and another container (i.e., a second container) comprises an effective amount of another pharmaceutically active ingredient (as described above), the combined quantities of the compound of formulas 263.1 to 274.1 and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Examples of cholinesterase inhibitors are tacrine, donepezil, rivastigmine, galantamine, pyridostigmine and neostigmine, with tacrine, donepezil, rivastigmine and galantamine being preferred.

Examples of $m_1$ antagonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Examples of BACE inhibitors include those described in: US2005/0119227 published Jun. 2, 2005 (see also WO2005/016876 published Feb. 24, 2005), US2005/0043290 published Feb. 24, 2005 (see also WO2005/014540 published Feb. 17, 2005), WO2005/058311 published Jun. 30, 2005 (see also US2007/0072852 published Mar. 29, 2007), US2006/0111370 published May 25, 2006 (see also WO2006/065277 published Jun. 22, 2006), U.S. application Ser. No. 11/710,582 filed Feb. 23, 2007, US2006/0040994 published Feb. 23, 2006 (see also WO2006/014762 published Feb. 9, 2006), WO2006/014944 published Feb. 9, 2006 (see also US2006/0040948 published Feb. 23, 2006), WO2006/138266 published Dec. 28, 2006 (see also US2007/0010667 published Jan. 11, 2007), WO2006/138265 published Dec. 28, 2006, WO2006/138230 published Dec. 28, 2006, WO2006/138195 published Dec. 28, 2006 (see also US2006/0281729 published Dec. 14, 2006), WO2006/138264 published Dec. 28, 2006 (see also US2007/0060575 published Mar. 15, 2007), WO2006/138192 published Dec. 28, 2006 (see also US2006/0281730 published Dec. 14, 2006), WO2006/138217 published Dec. 28, 2006 (see also US2006/0287294 published Dec. 21, 2006), US2007/0099898 published May 3, 2007 (see also WO2007/050721 published May 3, 2007), WO2007/053506 published May 10, 2007 (see also US2007/099875 published May 3, 2007), U.S. application Ser. No. 11/759,336 filed Jun. 7, 2007, U.S. Application Ser. No. 60/874,362 filed Dec. 12, 2006, and U.S. Application Ser. No. 60/874,419 filed Dec. 12, 2006, the disclosures of each being incorporated herein by reference thereto.

Thus, Embodiments of this invention include (1) to (197):

(1) Compounds of formula (I);

(2) Compounds of formula (I) wherein $R^{10}$ is aryl;

(3) Compounds of formula (I) wherein $R^{10}$ is phenyl;

(4) Compounds of formula (I) wherein $R^{10}$ is aryl substituted with one or more $R^{21}$ groups;

(5) Compounds of formula (I) wherein $R^{10}$ is phenyl substituted with one or more $R^{21}$ groups;

(6) Compounds of formula (I) wherein $R^{10}$ is phenyl substituted with one or more $R^{21}$ groups, and each $R^{21}$ group is the same or different —$OR^{15}$ group.

(7) Compounds of formula (I), as described in (6) above, wherein said $R^{15}$ is alkyl, and each alkyl is independently selected;

(8) Compounds of formula (I), as described in (6) above, wherein said phenyl is substituted with one —$OR^{15}$, and $R^{15}$ is alkyl;

(9) Compounds of formula (I), as described in (8) above, wherein said $R^{15}$ alkyl is methyl;

(10) Compounds of formula (I) wherein said $R^{10}$ group is heteroaryl.

(11) Compounds of formula (I) wherein said $R^{10}$ group is heteroaryl substituted with one or more $R^{21}$ groups.

(12) Compounds of formula (I) wherein said $R^9$ group is heteroaryl;

(13) Compounds of formula (I) wherein said $R^9$ group is heteroaryl substituted with one or more $R^{21}$ groups;

(14) Compounds of formula (I), as described in (13) above, wherein said $R^{21}$ groups are the same or different alkyl;

(15) Compounds of formula (I) wherein said $R^9$ group is heteroaryl substituted with one $R^{21}$ group, and said $R^{21}$ is alkyl;

(16) Compounds of formula (I), as described in (15) above, wherein said alkyl is methyl;

(17) Compounds of formula (I), as described in (12) above, wherein said heteroaryl is imidazoyl;

(18) Compounds of formula (I), as described in (13) above, wherein said $R^9$ heteroaryl is imidazoyl;

(19) Compounds of formula (I), as described in (14) above, wherein the $R^9$ heteroaryl is imidazolyl;

(20) Compounds of formula (I), as described in (15) above, said heteroaryl is imidazolyl;

(21) Compounds of formula (I), as described in (16) above, wherein the $R^9$ heteroaryl is imidazolyl;

(22) Compounds of formula (I) wherein said $R^{10}$ is selected from the group consisting of aryl and aryl substituted with one or more $R^{21}$ groups, and said $R^9$ group is selected from the group consisting of heteroaryl and heteroaryl substituted with one or more $R^{21}$ groups, wherein each $R^{21}$ is independently selected;

(23) Compounds of formula (I) wherein said $R^{10}$ is phenyl substituted with one or more $R^{21}$ groups, and said $R^9$ is imidazolyl substituted with one or more $R^{21}$ groups, wherein each $R^{21}$ is independently selected;

(24) Compounds of formula (I) wherein said $R^{10}$ is phenyl substituted with one $R^{21}$ group, and said $R^9$ is imidazolyl substituted with one $R^{21}$ group, wherein each $R^{21}$ is independently selected;

(25) Compounds of formula (I) wherein said $R^{10}$ is phenyl substituted with one or more independently selected —$OR^{15}$ groups, and said $R^9$ is imidazolyl substituted with one or more independently selected alkyl groups;

(26) Compounds of formula (I), as described in (25) above, wherein each $R^{15}$ is the same or different alkyl group;

(27) Compounds of formula (I) wherein said $R^{10}$ is phenyl substituted with one —$OR^{15}$ group, and said $R^9$ is imidazolyl substituted with one alkyl group;

(28) Compounds of formula (I), as described in (27) above, wherein said $R^{15}$ is alkyl, and wherein the $R^{15}$ alkyl group, and the alkyl group on said imidazolyl are independently selected;

(29) Compounds of formula (I), as described in (28) above, wherein said $R^{15}$ alkyl group is methyl, and said alkyl group on said imidazolyl is methyl;

(30) Compounds of formula (I) wherein the $R^9$-$R^{10}$— moiety is:

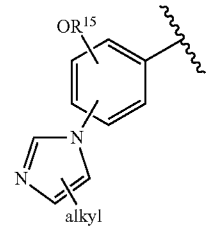

or

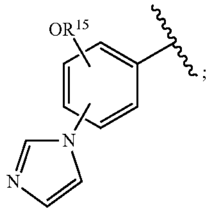

(31) Compounds of formula (I) wherein the $R^9$-$R^{10}$— moiety is:

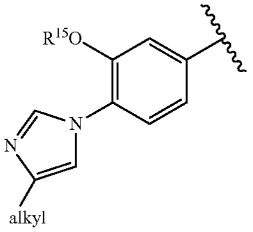

or

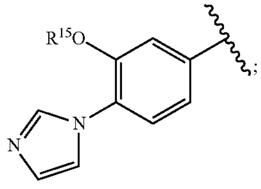

(32) Compounds of formula (I) wherein the $R^9$-$R^{10}$— moiety is:

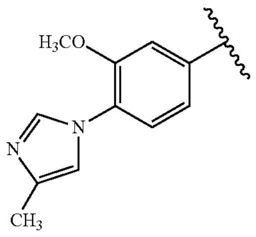

or

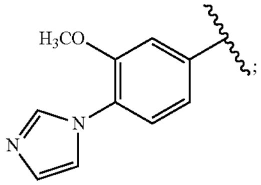

(33) Compounds of formula (I) wherein $R^1$ is an alkyl group substituted with one or more independently selected $R^{21}$ groups;

(34) Compounds of formula (I) wherein $R^1$ is an alkyl group substituted with one $R^{21}$ group;

(35) Compounds of formula (I) wherein $R^1$ is an alkyl group substituted with one $R^{21}$ group, and said $R^{21}$ group is substituted with one or more independently selected $R^{22}$ groups;

(36) Compounds of formula (I) wherein said $R^1$ group is:

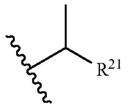

wherein $R^{21}$ is unsubstituted or substituted with one or more independently selected $R^{22}$ groups;

(37) Compounds of formula (I) wherein $R^1$ is an alkyl group substituted with one $R^{21}$ group, and said $R^{21}$ group is an aryl group;

(38) Compounds of formula (I), as described in (37) above, wherein said aryl is phenyl;

(39) Compounds of formula (I), as described in (38) above, wherein the alkyl is ethyl;

(40) Compounds of formula (I), as described in (38) above, wherein said alkyl is methyl;

(41) Compounds of formula (I) wherein $R^1$ is an alkyl group substituted with one $R^{21}$ group, and said $R^{21}$ group is an aryl group, and said aryl group is substituted with one or more $R^{22}$ groups;

(42) Compounds of formula (I), as described in (41) wherein each $R^{22}$ group is the same or different halo;

(43) Compounds of formula (I), as described in (42) above, wherein there is one or two $R^{22}$ halo groups;

(44) Compounds of formula (I), as described in (43) above, wherein the halo is F;

(45) Compounds of formula (I), as described in (41) above, wherein said $R^{21}$ aryl group is phenyl;

(46) Compounds of formula (I), as described in (45) above, wherein each $R^{22}$ group is the same or different halo;

(47) Compounds of formula (I), as described in (46) above, wherein there is one or two $R^{22}$ halo groups;

(48) Compounds of formula (I), as described in (47) above, wherein the halo is F;

(49) Compounds of formula (I), as described in (41) above, wherein said alkyl is ethyl;

(50) Compounds of formula (I), as described in (41) above, wherein said alkyl is methyl;

(51) Compounds of formula (I), as described in (45) above, wherein said alkyl is ethyl;

(52) Compounds of formula (I), as described in (45) above, wherein said alkyl is methyl;

(53) Compounds of formula (I), as described in (47) above, wherein said alkyl is ethyl;

(54) Compounds of formula (I), as described in (47) above, wherein said alkyl is methyl;

(55) Compounds of formula (I), as described in (48) above, wherein said alkyl is ethyl;

(56) Compounds of formula (I), as described in (48) above, wherein said alkyl is methyl;

(57) Compounds of formula (I), as described in (53) above, wherein there is one halo $R^{22}$ group.

(58) Compounds of formula (I), as described in (54) wherein there is one halo $R^{22}$ group.

(59) Compounds of formula (I), as described in (58) above, wherein said halo is F;

(60) Compounds of formula (I) as described in (59) wherein said halo is F;

(61) Compounds of formula (I) wherein said $R^1$ is selected from the group consisting of:

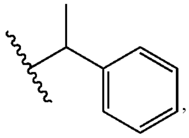,
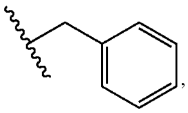,
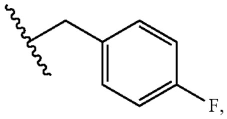
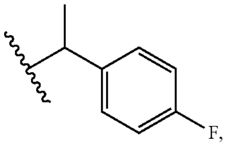
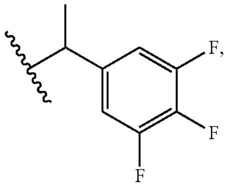
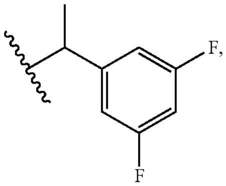
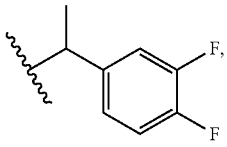
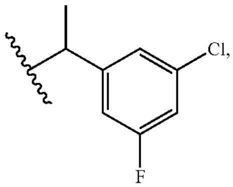
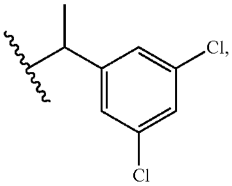
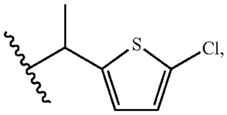
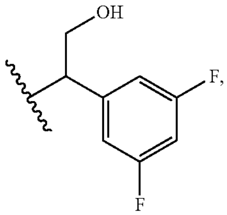
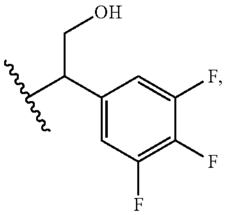

-continued

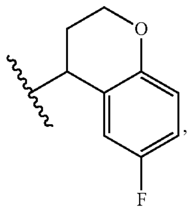,
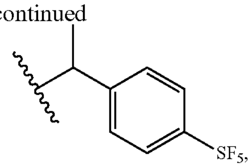
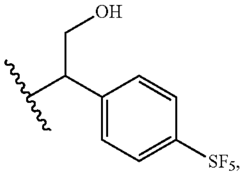
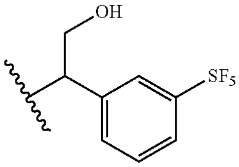,
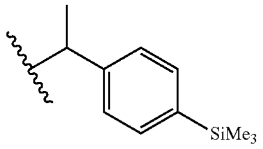 and
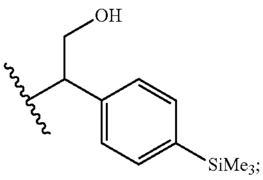

(62) Compounds of formula (I) wherein said $R^{10}$ is selected from the group consisting of heteroaryl and heteroaryl substituted with one or more $R^{21}$ groups, and said $R^9$ group is selected from the group consisting of heteroaryl and heteroaryl substituted with one or more $R^{21}$ groups, and wherein each $R^{21}$ is independently selected;

(63) Compounds of formula (I) wherein:

$R^1$ is an alkyl group substituted with one $R^{21}$ group, or $R^1$ is an alkyl group substituted with one $R^{21}$ group, and said $R^{21}$ group is substituted with one or more independently selected $R^{22}$ groups, and $R^{10}$ is selected from the group consisting of aryl and aryl substituted with one or more independently selected $R^{21}$ groups, and $R^9$ is selected from the group consisting of heteroaryl and heteroaryl substituted with one or more independently selected $R^{21}$ groups;

(64) Compounds of formula (I), as described in (63) above, wherein $R^1$ is an alkyl group substituted with one phenyl, or $R^1$ is an alkyl group substituted with one phenyl, and said phenyl is substituted with one or more independently selected $R^{22}$ groups, and $R^{10}$ is selected from the group consisting of phenyl and phenyl substituted with one or more independently selected $R^{21}$ groups, and $R^9$ is selected from the group consisting of imidazolyl and imidazolyl substituted with one or more independently selected $R^{21}$ groups;

(65) Compounds of formula (I), as described in (64) above, wherein $R^1$ is a methyl or ethyl group substituted with one phenyl, or $R^1$ is an methyl or ethyl group substituted with one phenyl, and said phenyl is substituted with one or more independently selected halos, and $R^{10}$ is selected from the group consisting of phenyl and phenyl substituted with one or more independently selected $—OR^{15}$ groups, and $R^9$ is selected from the group consisting of imidazolyl and imidazolyl substituted with one or more independently selected alkyl groups;

(66) Compounds of formula (I), as described in (65) above, wherein $R^1$ is a methyl or ethyl group substituted with one phenyl, or $R^1$ is an methyl or ethyl group substituted with one phenyl, and said phenyl is substituted with one or two independently selected halos, and $R^{10}$ is selected from the group consisting of phenyl and phenyl substituted with one or two independently selected —$OR^{15}$ groups, wherein $R^{15}$ is alkyl, and $R^9$ is selected from the group consisting of imidazolyl and imidazolyl substituted with one or two independently selected alkyl groups;

(67) Compounds of formula (I), as described in (66) above, wherein $R^1$ is a methyl or ethyl group substituted with one phenyl, or $R^1$ is an methyl or ethyl group substituted with one phenyl, and said phenyl is substituted with one or two F, and $R^{10}$ is selected from the group consisting of phenyl and phenyl substituted with one or two independently selected —$OR^{15}$ groups, wherein $R^{15}$ is methyl, and $R^9$ is selected from the group consisting of imidazolyl and imidazolyl substituted with one or two independently selected methyl groups;

(68) Compounds of formula (I), as described in (67) above, wherein $R^1$ is a methyl or ethyl group substituted with one phenyl, or $R^1$ is an methyl or ethyl group substituted with one phenyl, and said phenyl is substituted with one or two F, and $R^{10}$ is phenyl substituted with one —$OR^{15}$ group, wherein $R^{15}$ is methyl, and $R^9$ is selected from the group consisting of imidazolyl and imidazolyl substituted with one methyl group;

(69) Compounds of formula (I) wherein $R^1$ is selected from the group consisting of:

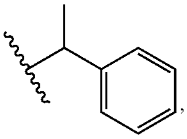,
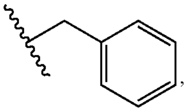,
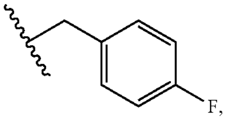
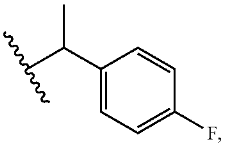
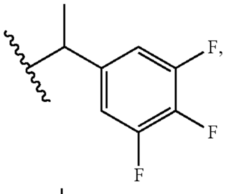
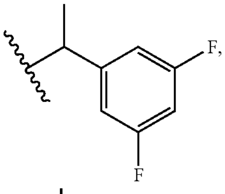
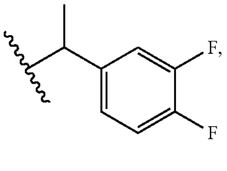
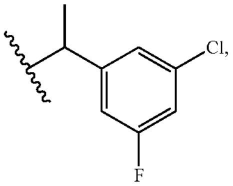
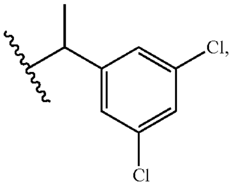
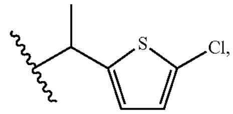

-continued

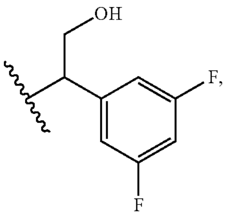
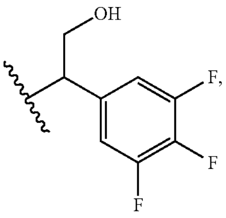
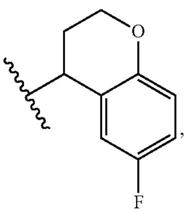,
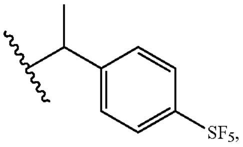
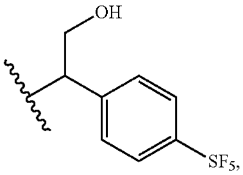
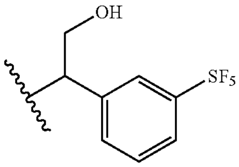,
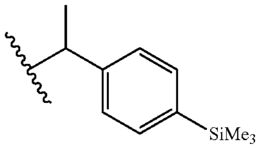 and
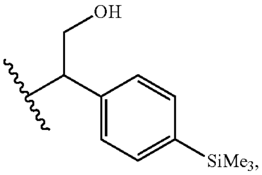

and wherein the $R^9$-$R^{10}$— moiety is:

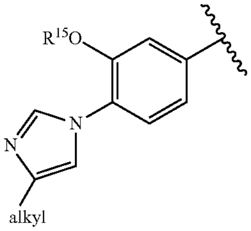 or 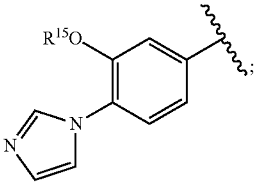;

(70) Compounds of formula (I) wherein $R^1$ is selected from the group consisting of:

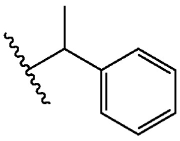,
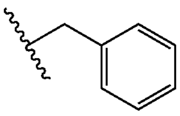,
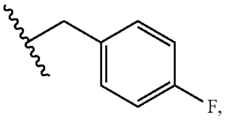
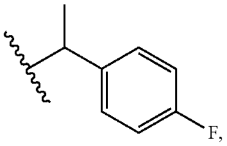

-continued

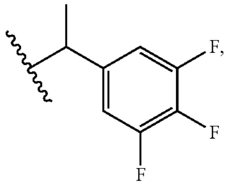
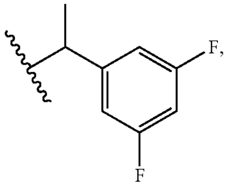

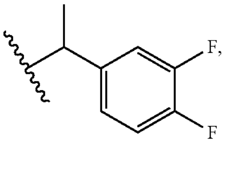
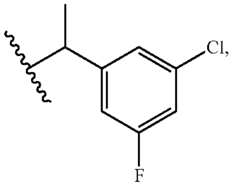

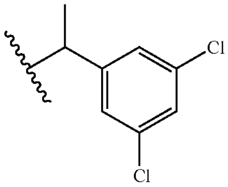
,
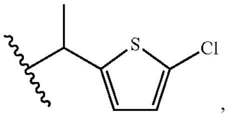
,

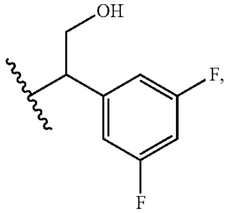
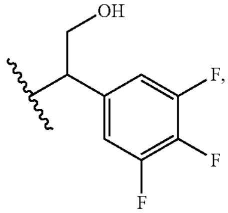

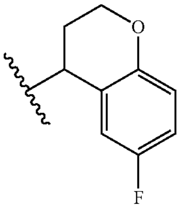
,
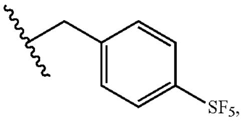

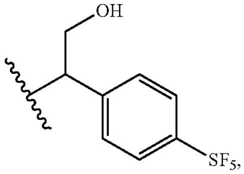
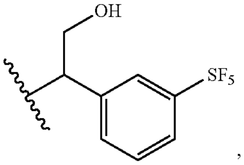
,

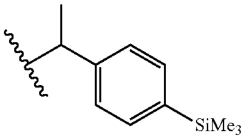
and
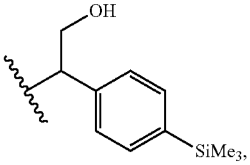

and wherein the $R^9$-$R^{10}$— moiety is:

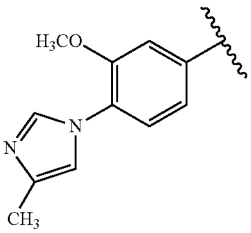
or
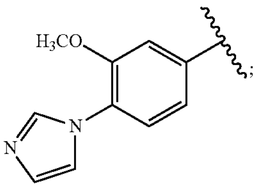

(71) Compounds of formula (I) wherein W is —C(O)—;

(72) Compounds of formula (I) wherein W is —S(O)—;

(73) Compounds of formula (I) wherein W is —$S(O)_2$—;

(74) Compounds of formula (I) wherein is W is —C(=$NR^2$)—;

(75) Compounds of formula (I) wherein G is —NH—;

(76) Compounds of formula (I) wherein G is a direct bond;

(77) Compounds of formula (I), as described in (66) wherein G is selected from the group consisting of —NH—, and a direct bond;

(78) Compounds of formula (I), as described in (67) wherein G is selected from the group consisting of —NH—, and a direct bond;

(79) Compounds of formula (I), as described in (69) above, wherein G is selected from the group consisting of —NH—, and a direct bond;

(80) Compounds of formula (I), as described in (70) above, wherein G is selected from the group consisting of —NH—, and a direct bond;

(81) Compounds of formula (I), as described in (79) above, wherein W is —C(O)—;

(82) Compounds of formula (I), as described in (79) above, wherein W is —S(O)—;

(83) Compounds of formula (I), as described in (79) above, wherein W is —$S(O)_2$—;

(84) Compounds of formula (I), as described in (79) above, wherein is W is —C(=$NR^2$)—;

(85) Compounds of formula (I) selected from the group consisting of:

(IA)

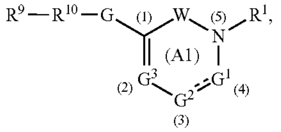

(IB)

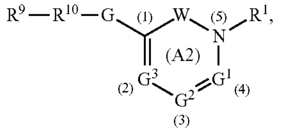

(IC)

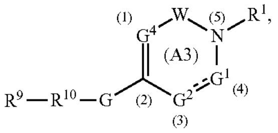
and (ID)

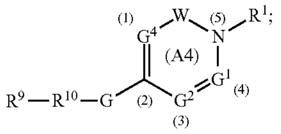

(86) Compounds of formula (I) having the formula:

(IE)

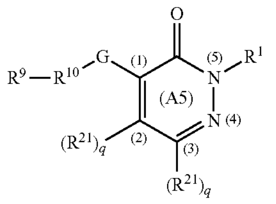

wherein each q is independently 0 or 1, and each $R^{20}$ is independently selected;

(87) Compounds of formula (I), as described in (86) above, wherein:

(a) $R^{21}$ at (2) is —$OR^{15}$, and q at (3) is 0, or (b) $R^{21}$ at (3) is —$OR^{15}$, and q at (2) is 0, or (c) q at (2) and (3) is 0;

(88) Compounds of formula (I), as described in (87) above, wherein $R^{15}$ is alkyl;

(89) Compounds of formula (I), as described in (88) above, wherein said alkyl is methyl or ethyl;

(90) Compounds of formula (I), as described in (89) above, wherein G is selected from the group consisting of: —NH—, and a direct bond;

(91) Compounds of formula (I), as described in (90) above, wherein $R^1$ is a methyl or ethyl group substituted with one phenyl, or $R^1$ is an methyl or ethyl group substituted with one phenyl, and said phenyl is substituted with one or two F, and $R^{10}$ is phenyl substituted with one —$OR^{15}$ group, wherein $R^{15}$ is methyl, and $R^9$ is selected from the group consisting of imidazolyl and imidazolyl substituted with one methyl group;

(92) Compounds of formula (I), as described in (90) above, wherein $R^1$ is selected from the group consisting of:

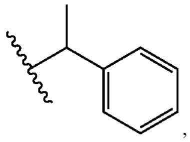, 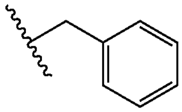,

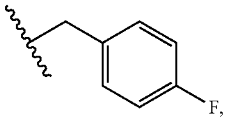 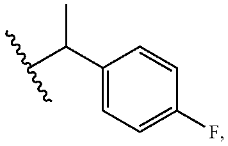

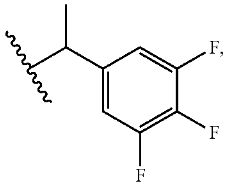 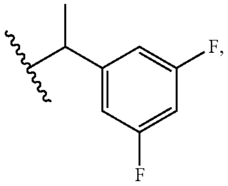

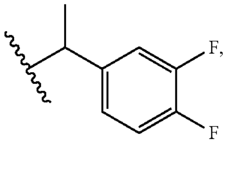 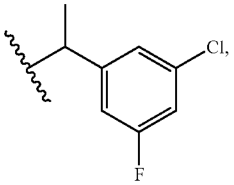

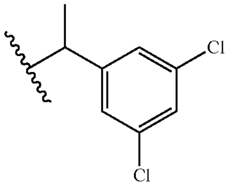, 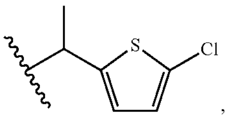,

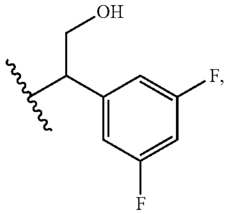 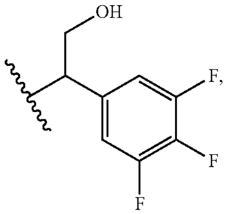

-continued

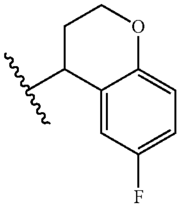, 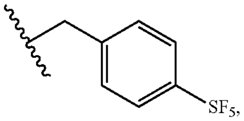

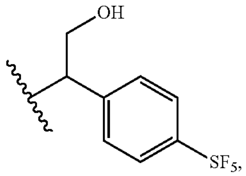 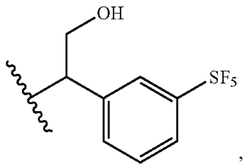,

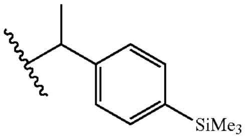 and 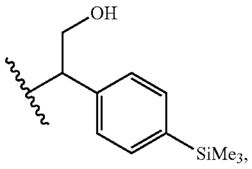

and wherein the $R^9$-$R^{10}$— moiety is:

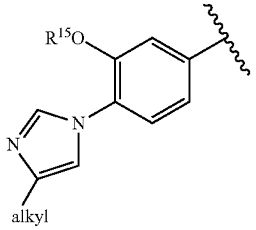 or 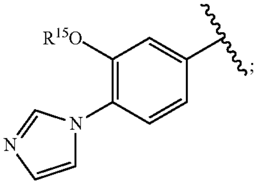;

(93) Compounds of formula (I), as described in (92) above, wherein $R^1$ is selected from the group consisting of:

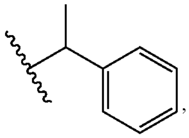, 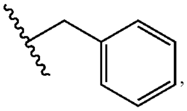,

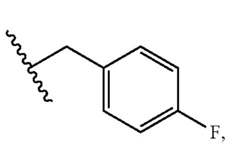 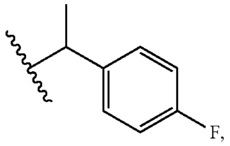

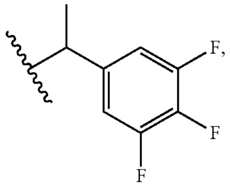 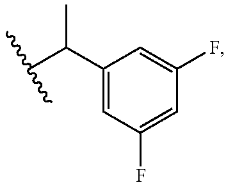

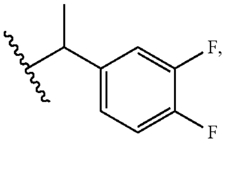 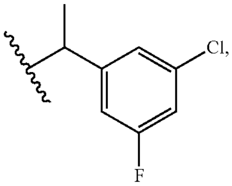

-continued

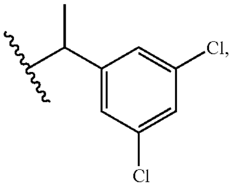
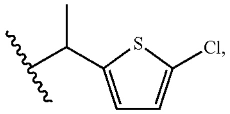

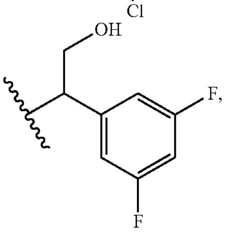
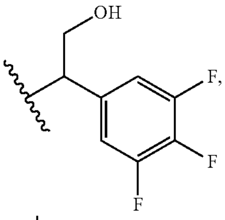

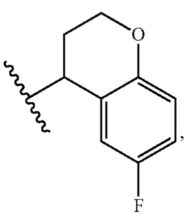
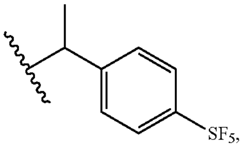

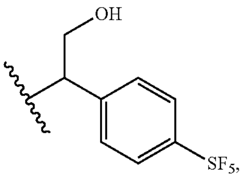
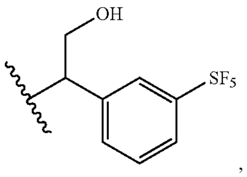

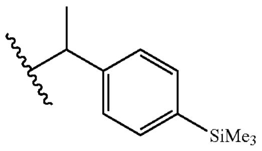
and
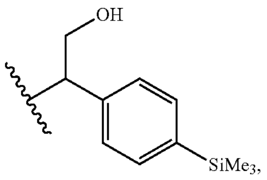

and wherein the $R^9$-$R^{10}$— moiety is:

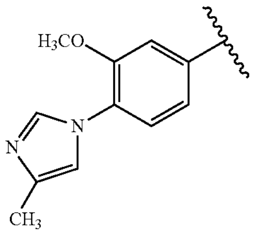
or
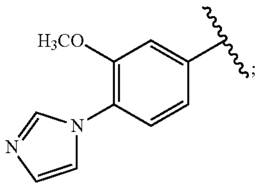

(94) Compounds of formula (I), as described in (86) above, having the formula:

(IE1)

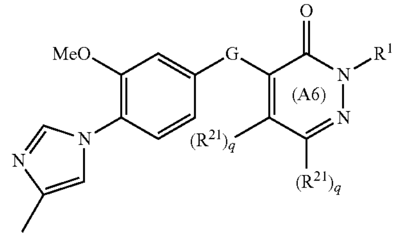

wherein each q is independently 0 or 1, and each $R^{21}$ is independently selected;

(95) Compounds of formula (I) having the formula:

(IF)

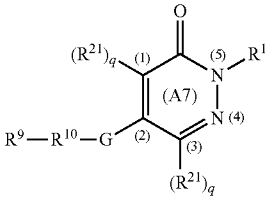

wherein each q is independently 0 or 1, and each $R^{21}$ is independently selected.

(96) Compounds of formula (I), as described in (95) above, wherein $R^{21}$ at (3) is —$OR^{15}$ and q at (1) is 0, or wherein q at (1) and (3) are 0;

(97) Compounds of formula (I), as described in (96) above, wherein $R^{15}$ is alkyl;

(98) Compounds of formula (I), as described in (97) above, wherein said alkyl is methyl or ethyl;

(99) Compounds of formula (I), as described in (98) above, wherein G is selected from the group consisting of: —NH—, and a direct bond;

(100) Compounds of formula (I), as described in (99) above, wherein $R^1$ is a methyl or ethyl group substituted with one phenyl, or $R^1$ is an methyl or ethyl group substituted with one phenyl, and said phenyl is substituted with one or two F, and $R^{10}$ is phenyl substituted with one —$OR^{15}$ group, wherein $R^{15}$ is methyl, and $R^9$ is selected from the group consisting of imidazolyl and imidazolyl substituted with one methyl group;

(101) Compounds of formula (I), as described in (99) above, wherein $R^1$ is selected from the group consisting of:

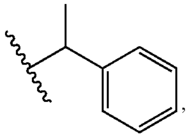
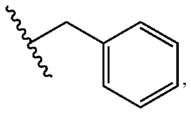

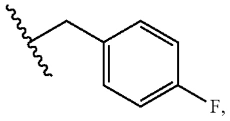
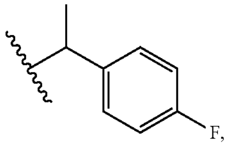

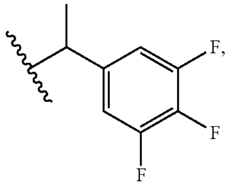
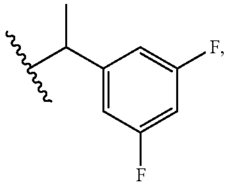

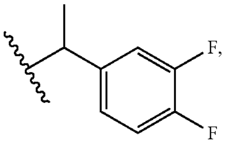
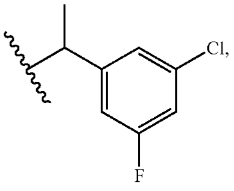

-continued
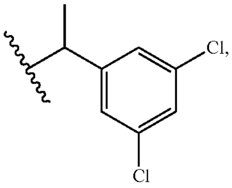
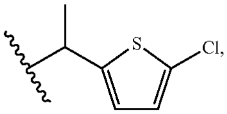
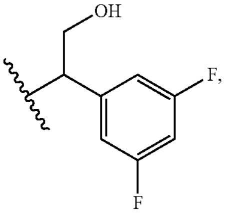
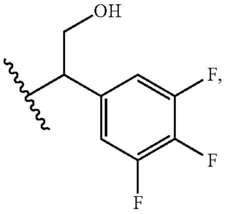
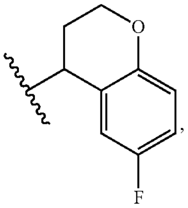
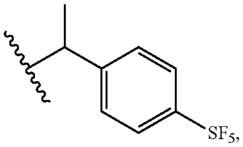
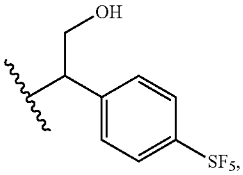
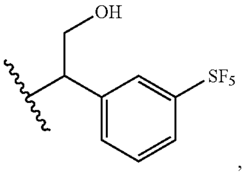
,
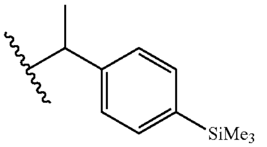
and
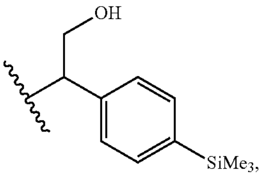
and
wherein the $R^9$-$R^{10}$— moiety is:
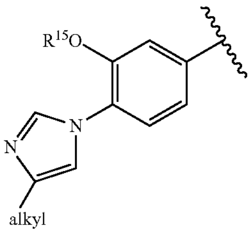
or
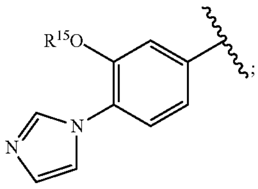
(102) Compounds of formula (I), as described in (99) above, wherein $R^1$ is selected from the group consisting of:
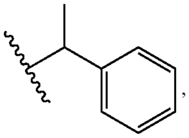
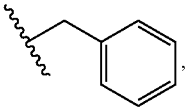
-continued
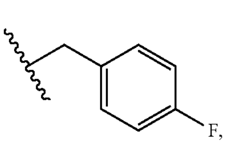
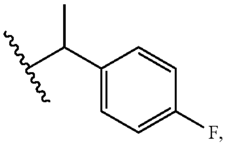
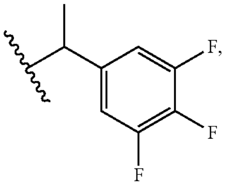
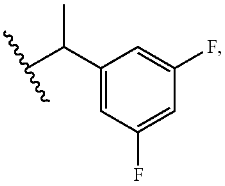
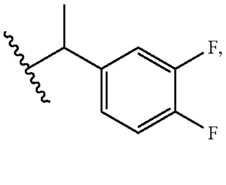
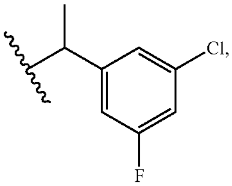
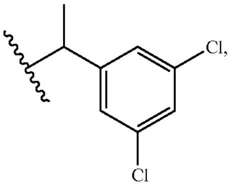
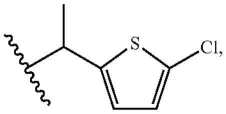
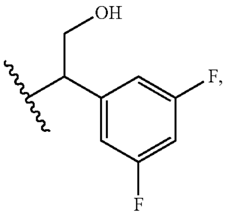
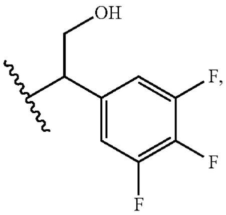
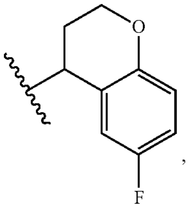
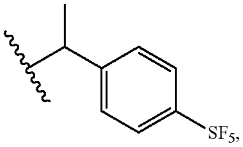
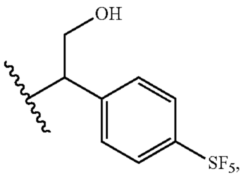
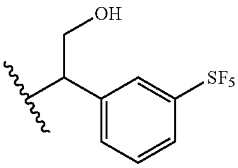
,
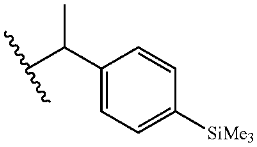
and
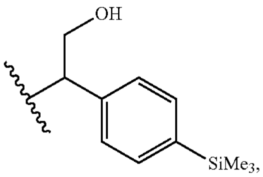

and
wherein the $R^9$-$R^{10}$— moiety is:

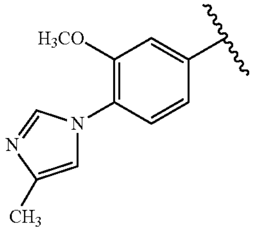

or

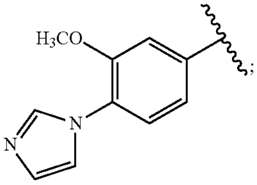

;

(103) Compounds of formula (I), as described in (95) above, having the formula:

(IF1)

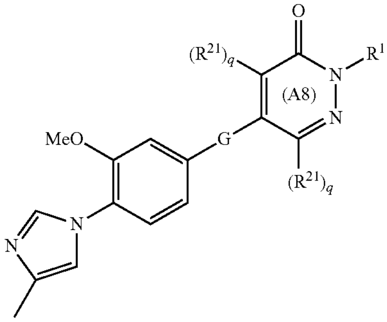

wherein each q is independently 0 or 1, and each $R^{21}$ is independently selected;

(104) Compounds of formula (I) having the formula;

(IG)

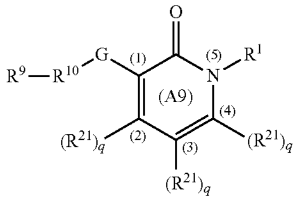

wherein each q is independently 0 or 1, and each $R^{21}$ is independently selected;

(105) Compounds of formula (I), as described in (104) above, wherein:

(a) q at (2) and (4) is 0, and $R^{21}$ at (3) is —C(O)$OR^{15}$, or (b) q at (2) and (4) is 0, and $R^{21}$ at (3) is —C(O)$NR^{15}R^{18}$, or (c) q at (2), (3) and (4) is 0;

(106) Compounds of formula (I), as described in (104) above, wherein:

(a) $R^{15}$ is alkyl in said —C(O)$OR^{15}$ group, and (b) in said —C(O)$NR^{15}R^{16}$ group one of $R^{15}$ or $R^{18}$ is H, and the other is selected from the group consisting of: $(R^{18})_n$-arylalkyl-, $(R^{18})_n$-alkyl-, and cycloalkyl;

(107) Compounds of formula (I), as described in (106) above, wherein:

(a) said $R^{15}$ alkyl group in said —C(O)$OR^{15}$ group is methyl, and (b) in said —C(O)$NR^{15}R^{16}$ group the $R^{18}$ is —$OR^{20}$, n is 1, $R^{20}$ is alkyl, said cycloalkyl is cyclobutyl, and said arylalkyl- is benzyl;

(108) Compounds of formula (I), as described in (107) above, wherein G is selected from the group consisting of: —NH—, and a direct bond;

(109) Compounds of formula (I), as described in (108) above, wherein $R^1$ is a methyl or ethyl group substituted with one phenyl, or $R^1$ is an methyl or ethyl group substituted with one phenyl, and said phenyl is substituted with one or two F, and $R^{10}$ phenyl substituted with one —$OR^{15}$ group, wherein $R^{15}$ is methyl, and $R^9$ is selected from the group consisting of imidazolyl and imidazolyl substituted with one methyl group;

(110) Compounds of formula (I), as described in (108) above, wherein $R^1$ is selected from the group consisting of:

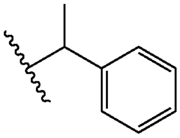,
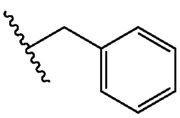,
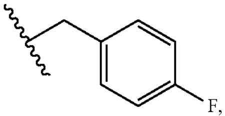,
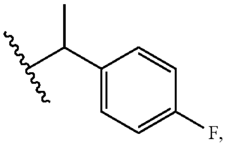,
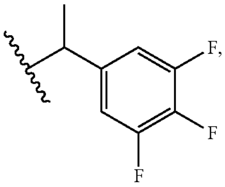,
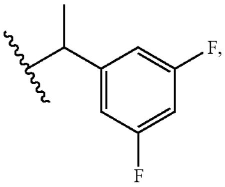,
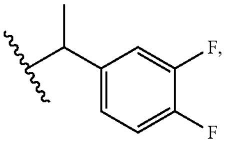,
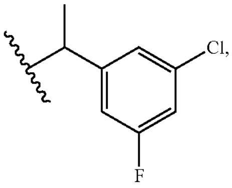,
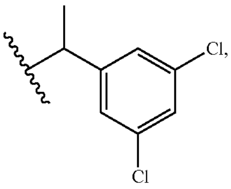,
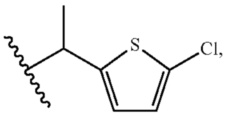,
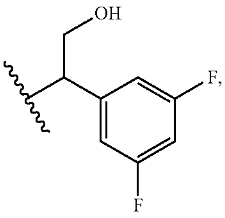,
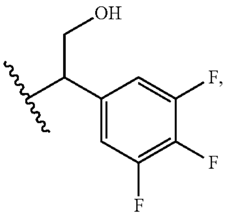,
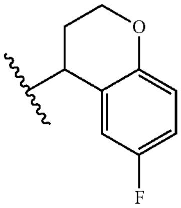,
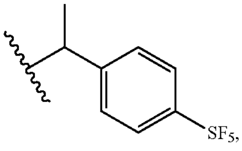, -continued
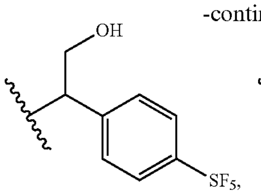
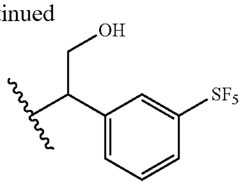
,
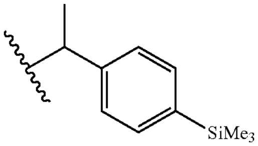
and
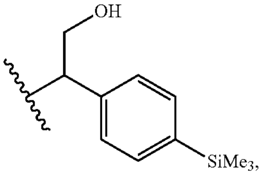
and
wherein the $R^9$-$R^{10}$— moiety is:
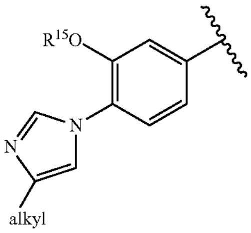
or
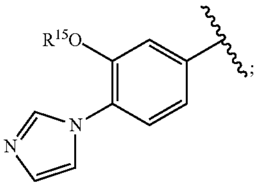
;
(111) Compounds of formula (I), as described in (108) above, wherein $R^1$ is selected from the group consisting of:
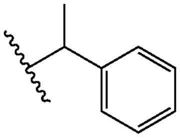
,
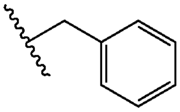
,
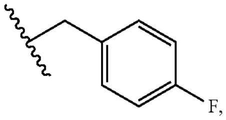
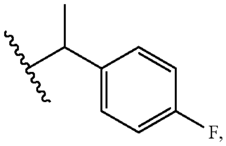
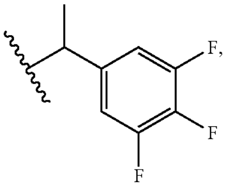
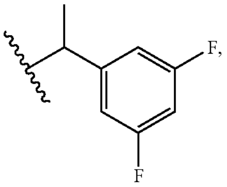
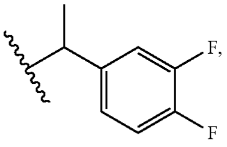
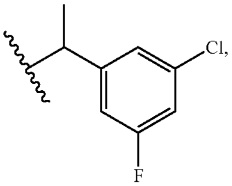
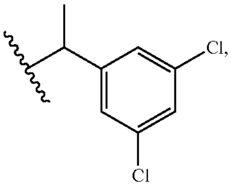
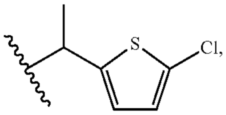
-continued
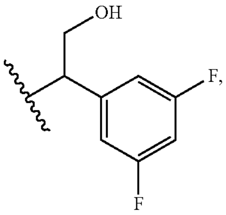
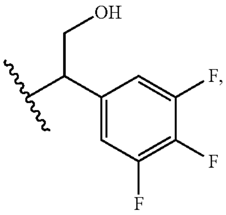
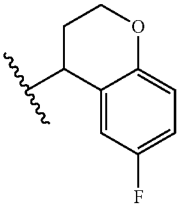
,
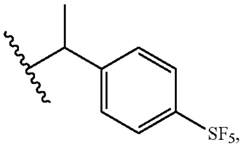
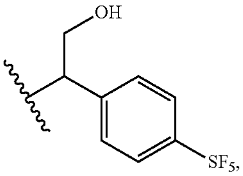
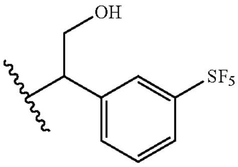
,
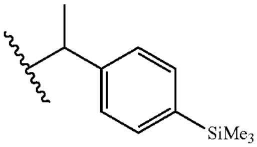
and
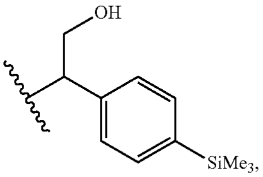
and
wherein the $R^9$-$R^{10}$— moiety is:
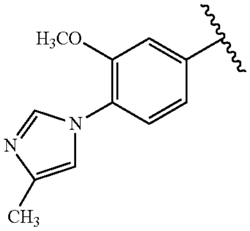
or
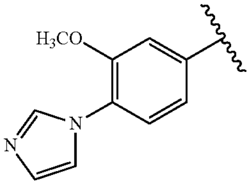
;
(112) Compounds of formula (I), as described in (104) above, having the formula:
(IG1)
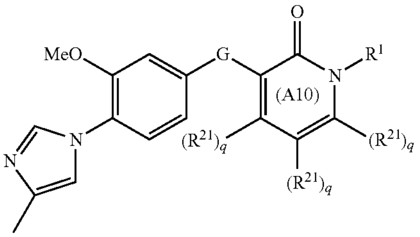
wherein each q is independently 0 or 1, and each $R^{21}$ is independently selected;

(113) Compounds of formula (I) having the formula:

(IH)

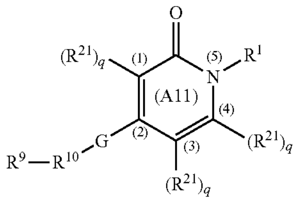

wherein each q is independently 0 or 1, and each $R^{21}$ is independently selected;

(114) Compounds of formula (I), as described in (113) above, wherein G is selected from the group consisting of: —NH—, and a direct bond;

(115) Compounds of formula (I), as described in (114) above, wherein $R^1$ is a methyl or ethyl group substituted with one phenyl, or $R^1$ is an methyl or ethyl group substituted with one phenyl, and said phenyl is substituted with one or two F, and $R^{10}$ is phenyl substituted with one —$OR^{15}$ group, wherein $R^{15}$ is methyl, and $R^9$ is selected from the group consisting of imidazolyl and imidazolyl substituted with one methyl group;

(116) Compounds of formula (I), as described in (114) above, wherein $R^1$ is selected from the group consisting of:

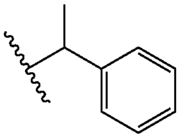,
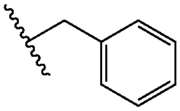,
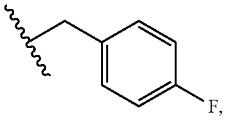
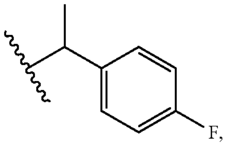
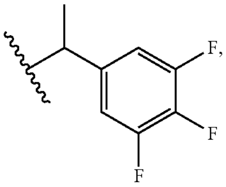
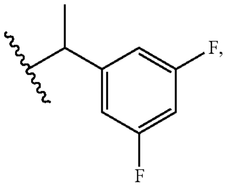
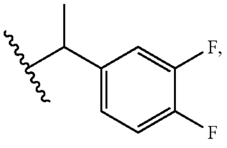
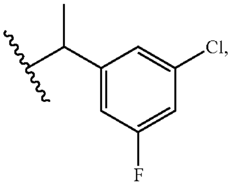
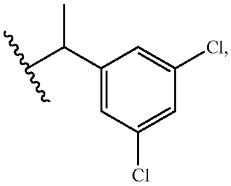
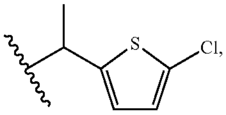

-continued

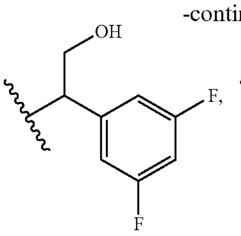
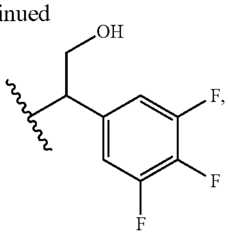
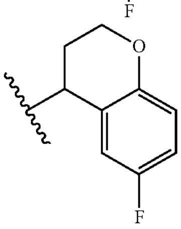,
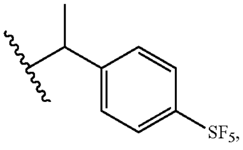
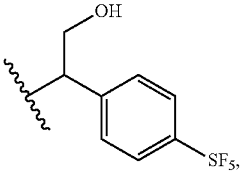
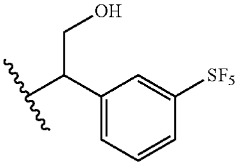,
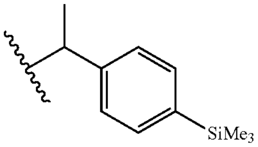 and
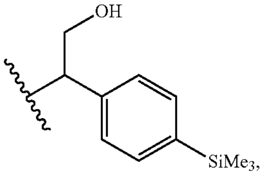

and wherein the $R^9$-$R^{10}$— moiety is:

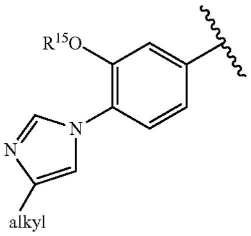
or
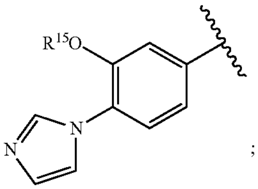
;

(117) Compounds of formula (I), as described in (114) above, wherein $R^1$ is selected from the group consisting of:

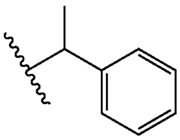,
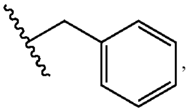,
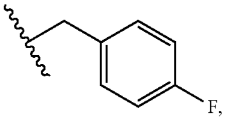
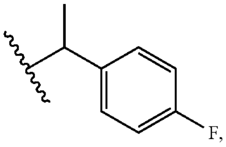
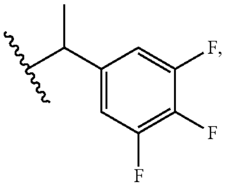
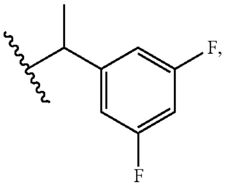

-continued

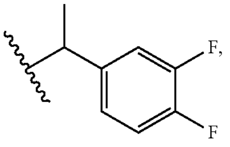
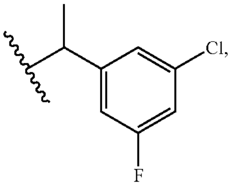
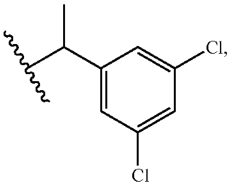
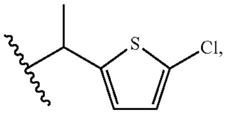
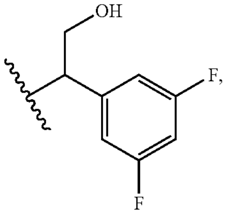
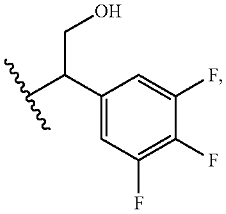
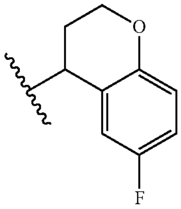
,
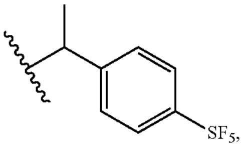
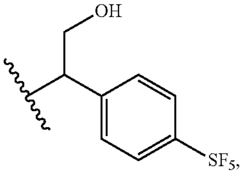
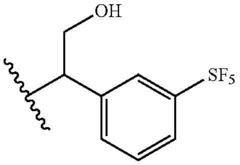
,
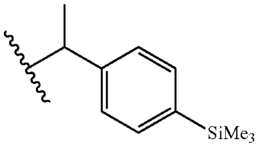
and
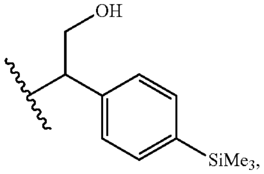

and wherein the $R^9$-$R^{10}$— moiety is:

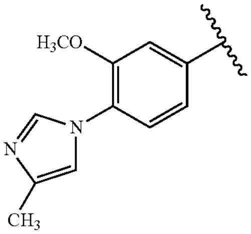
or
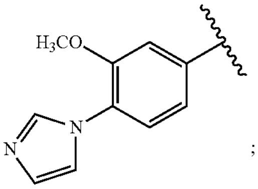
;

(118) Compounds of formula (I), as described in (115) above, wherein:

(a) q at (1) and (4) is 0, and $R^{21}$ at (3) is —C(O)$OR^{15}$, or (b) q at (1) and (4) is 0, and $R^{21}$ at (3) is —C(O)$NR^{15}R^{16}$, or (c) q at (1), (3) and (4) is 0;

(119) Compounds of formula (I), as described in (118) above, wherein (a) $R^{15}$ is alkyl in said —C(O)$OR^{15}$ group, and (b) in said —C(O)$NR^{15}R^{16}$ group one of $R^{15}$ or $R^{15}$ is H, and the other is selected from the group consisting of: $(R^{15})_n$-arylalkyl-, $(R^{18})$-alkyl-, and cycloalkyl;

(120) Compounds of formula (I), as described in (113) above, having the formula:

(IH1)

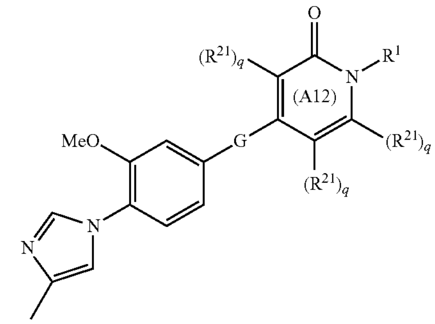

wherein each q is independently 0 or 1, and each $R^{21}$ is independently selected;

(121) Compounds of formula (I) selected from the group consisting of:

(IJ)

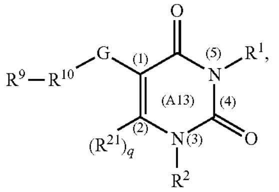

(IJ2)

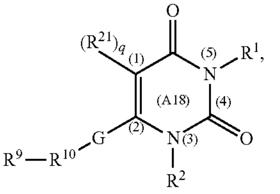

(IK)

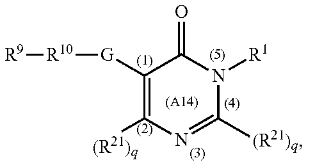

(IL)

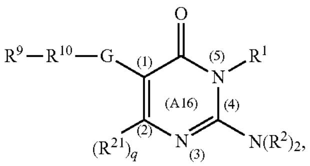

(IL2)

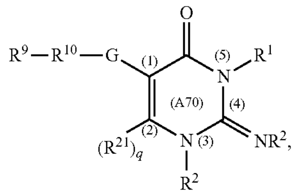

-continued (IM)

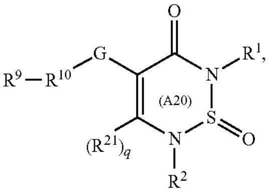

(IN)

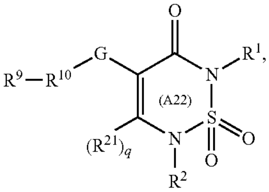

(IO)

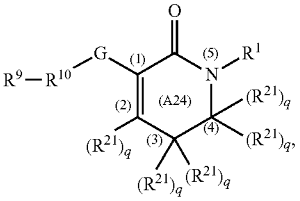

(IP)

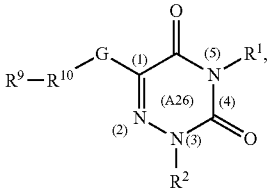

(IQ)

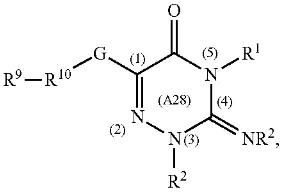

(IR)

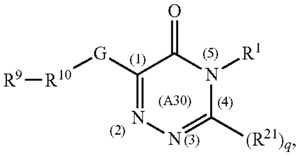

and (IS)

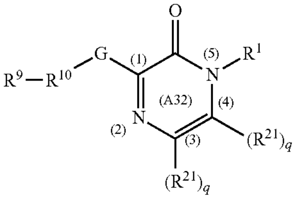

wherein each q is independently 0 or 1, and each $R^{21}$ is independently selected, and each $R^2$ in formula (IL) is independently selected, and each $R^2$ in formula (IL2) is independently selected;

(122) Compounds of formula (I), as described in (121) above, wherein G is selected from the group consisting of: —NH—, and a direct bond;

(123) Compounds of formula (I), as described in (122) above, wherein $R^1$ is a methyl or ethyl group substituted with one phenyl, or $R^1$ is an methyl or ethyl group substituted with one phenyl, and said phenyl is substituted with one or two F, and $R^{10}$ is phenyl substituted with one —$OR^{15}$ group, wherein $R^{15}$ is methyl, and $R^9$ is selected from the group consisting of imidazolyl and imidazolyl substituted with one methyl group;

(124) Compounds of formula (I), as described in (122) above, wherein $R^1$ is selected from the group consisting of:

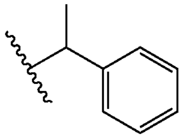,
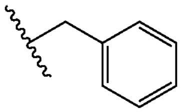,

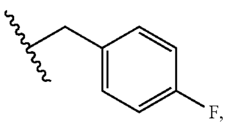
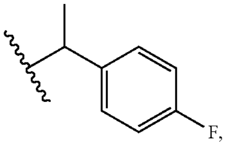

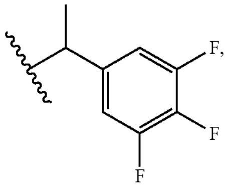
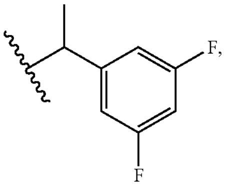

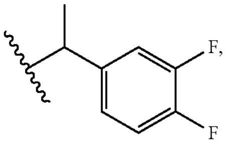
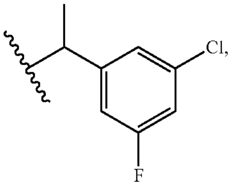

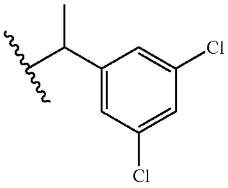,
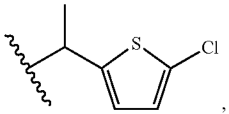,

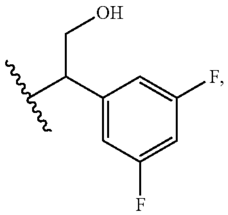
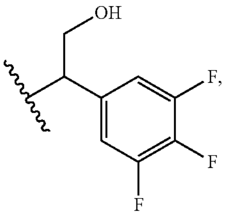

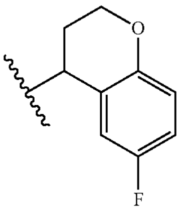,
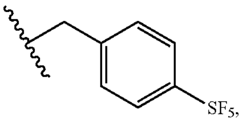

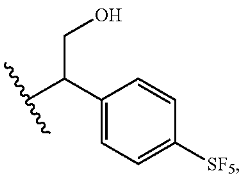
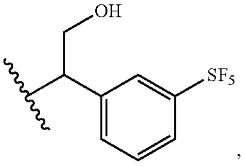,

-continued
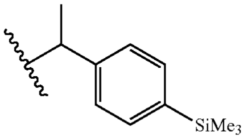 and 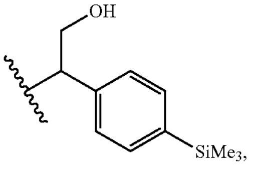
and
wherein the $R^9$-$R^{10}$— moiety is:
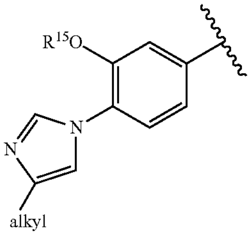 or 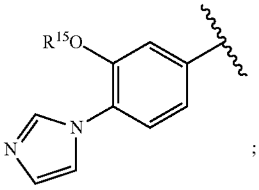 ;
(125) Compounds of formula (I), as described in (122) above, wherein $R^1$ is selected from the group consisting of:
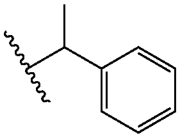 , 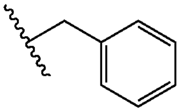 ,
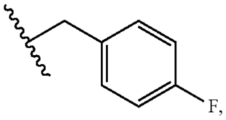
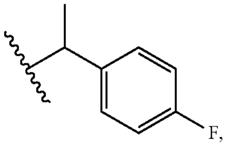
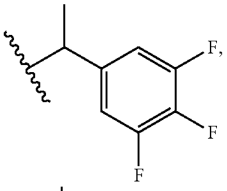
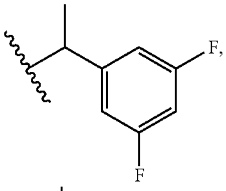
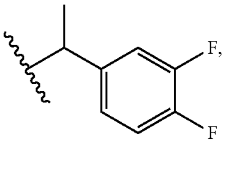
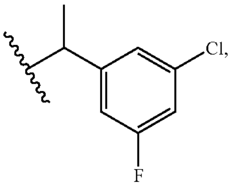
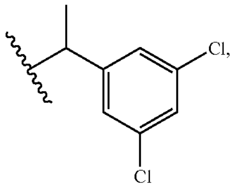
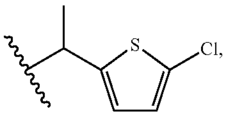
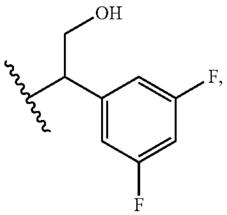
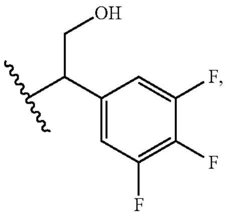
-continued
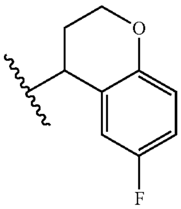 , 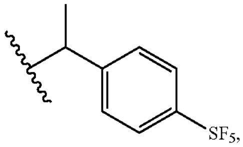
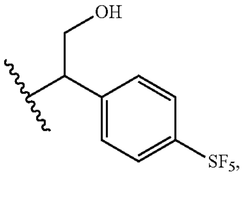
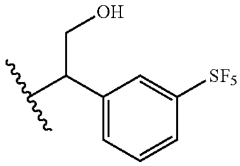 ,
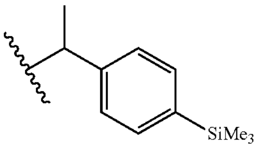 and 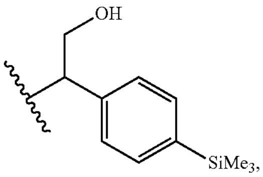
and
wherein the $R^9$-$R^{10}$— moiety is:
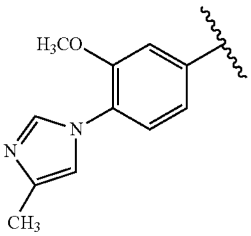 or 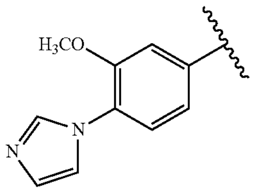 ;
(126) Compounds of formula (I), as described in (121) above, selected from the group consisting of:
(IJ1)
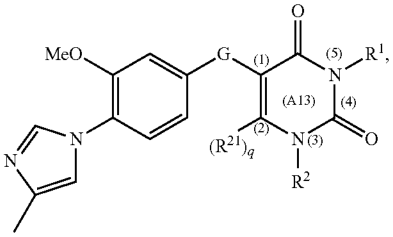
(IJ3)
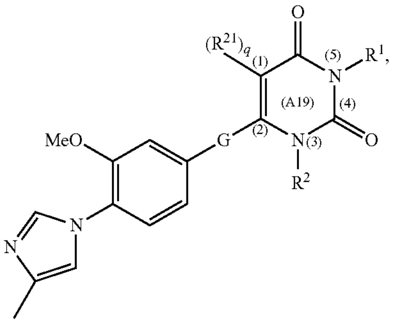

-continued
(IK1)
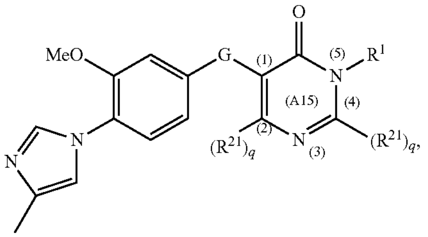
(IL1)
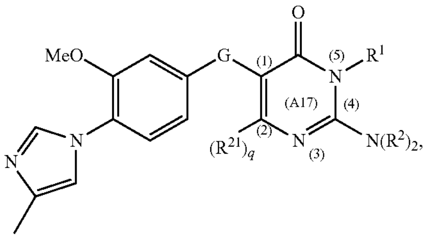
(IL3)
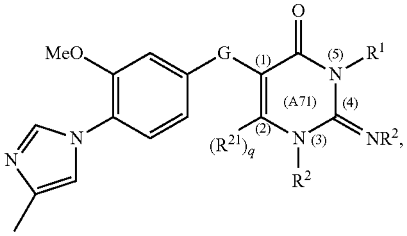
(IM1)
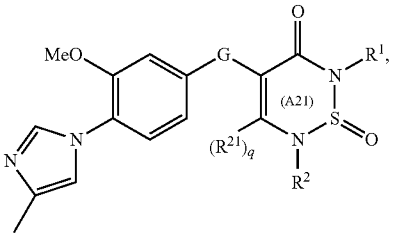
(IN1)
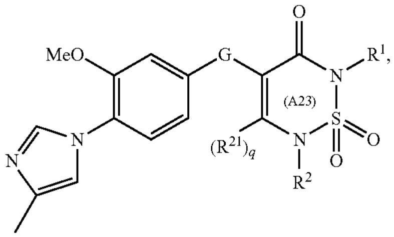
(IO1)
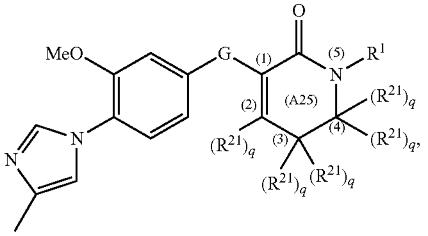
(IP1)
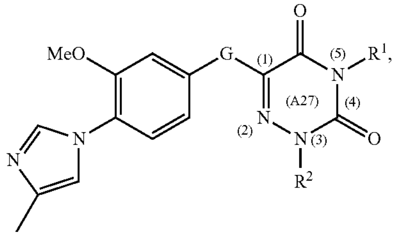
-continued
(IQ1)
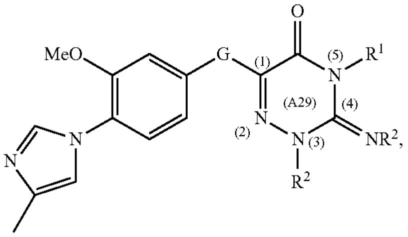
(IR1)
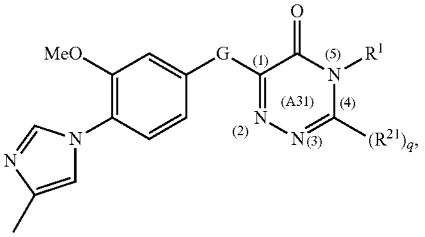
and
(IS1)
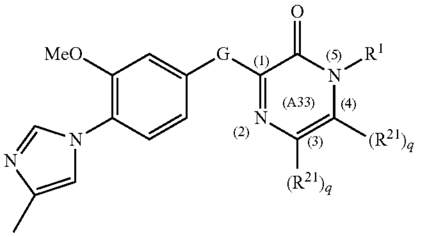
wherein each q is independently 0 or 1, and each $R^{21}$ is independently selected, and each $R^2$ in formula (IL1) is independently selected, and each $R^2$ in formula (IL3) is independently selected;
(127) Compounds of formula (I) having the formula:
(IT)
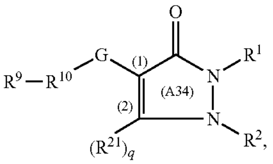
(IU)
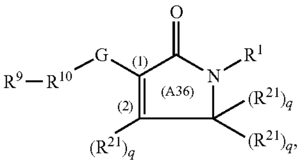
(IV)
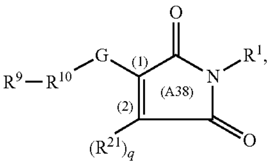
(IW)
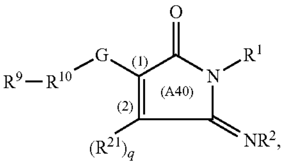

-continued (IX)

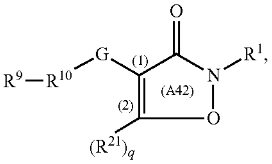

(IY)

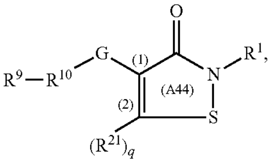

(IZ)

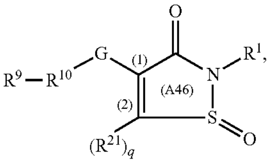 and (IAB)

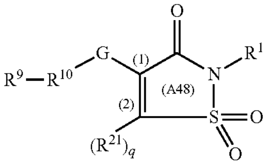

wherein:

(a) each q is independently 0 or 1, and (b) for formula (IU) q for the $R^{21}$ at (2) is 0 or 1, and q for the $R^{21}$ on the carbon adjacent to the N is 0, 1 or 2, and each $R^{21}$ for each q is independently selected;

(128) Compounds of formula (I), as described in (127) above, wherein G is selected from the group consisting of: —NH—, and a direct bond;

(129) Compounds of formula (I), as described in (128) above, wherein $R^1$ is a methyl or ethyl group substituted with one phenyl, or $R^1$ is an methyl or ethyl group substituted with one phenyl, and said phenyl is substituted with one or two F, and $R^{10}$ is 1 phenyl substituted with one —$OR^{15}$ group, wherein $R^{15}$ is methyl, and $R^9$ is selected from the group consisting of imidazolyl and imidazolyl substituted with one methyl group;

(130) Compounds of formula (I), as described in (128) above, wherein $R^1$ is selected from the group consisting of:

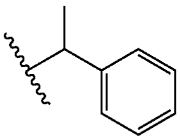,
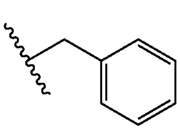,
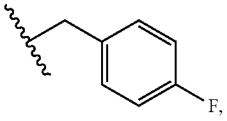
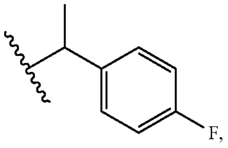

-continued

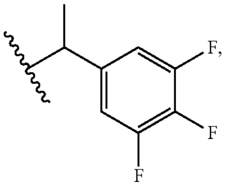
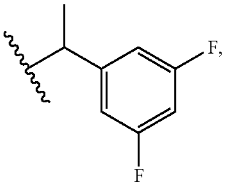
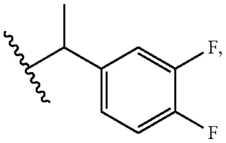
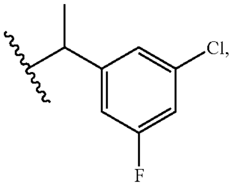
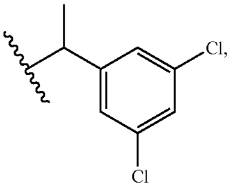
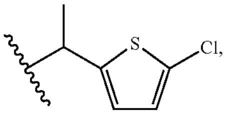
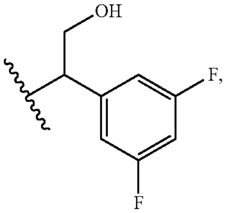
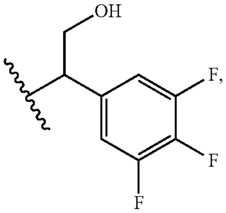
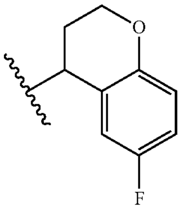,
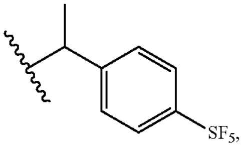
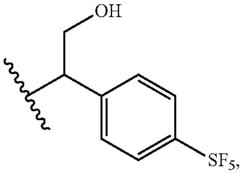
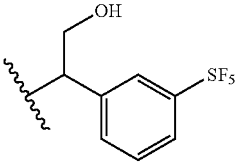,
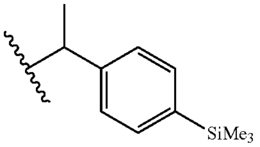 and
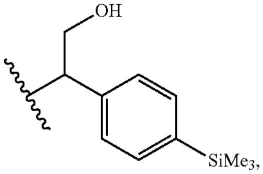

and wherein the $R^9$-$R^{10}$— moiety is:

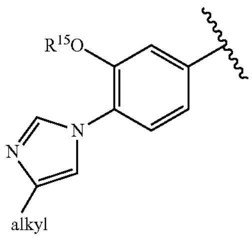 or 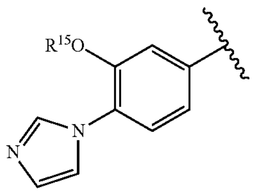 ;

(131) Compounds of formula (I), as described in (128) above, wherein $R^1$ is selected from the group consisting of:
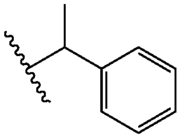
,
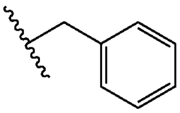
,
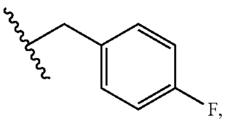
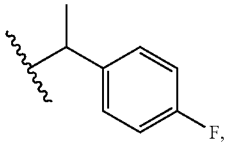
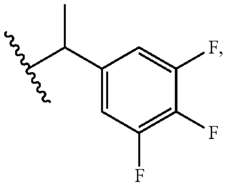
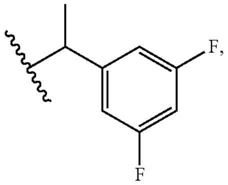
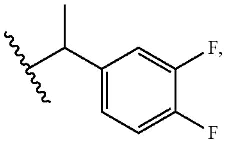
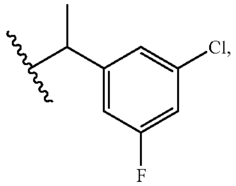
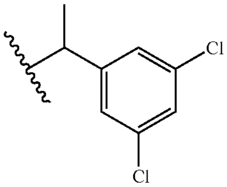
,
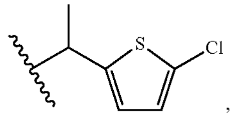
,
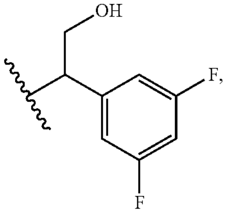
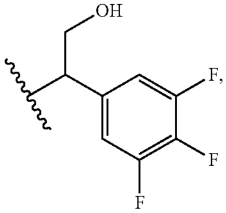
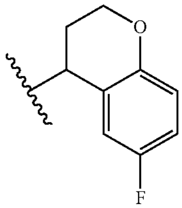
,
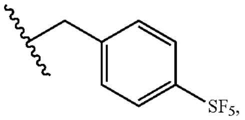
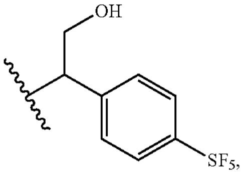
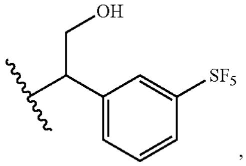
,
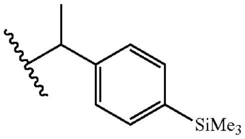
and
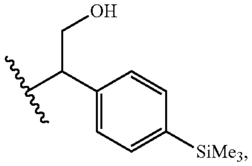
and
wherein the $R^9$-$R^{10}$— moiety is:
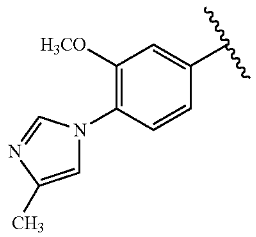
or
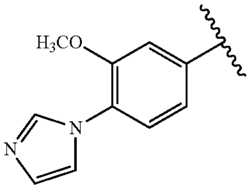
;
(132) Compounds of formula (I), as described in (127) above, having the formula:
(IT1)
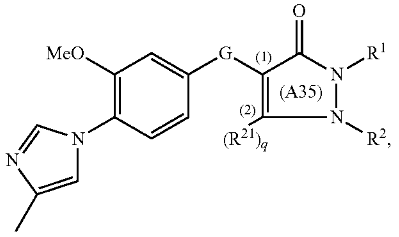
(IU1)
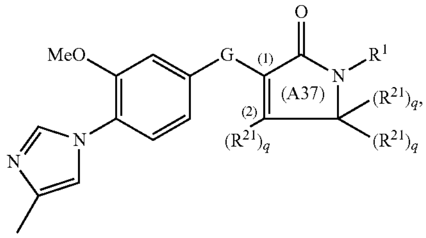
(IV1)
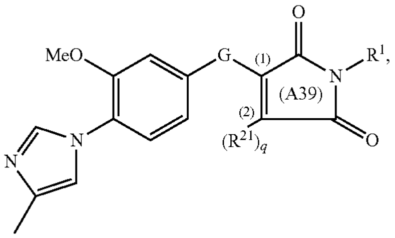
(IW1)
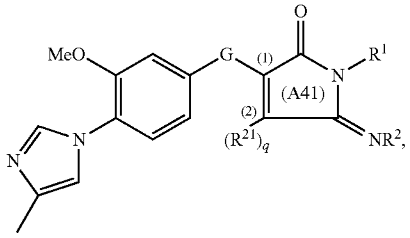
(IX1)
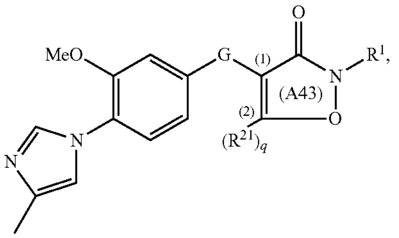

-continued (IY1)

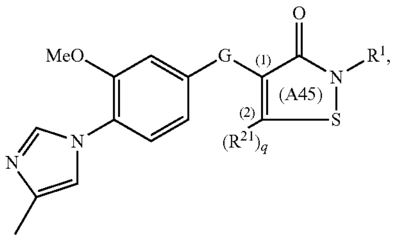

(IZ1)

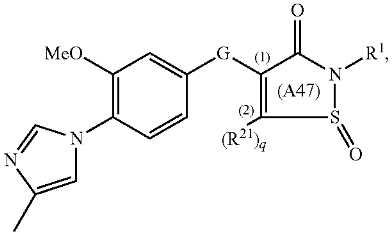 and (IAB1)

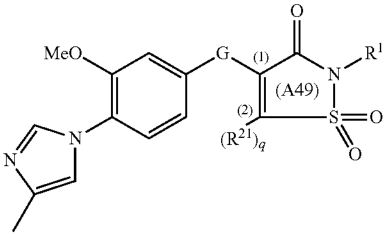

wherein:

(a) each q is independently 0 or 1, and (b) for formula (IU1) q for the $R^{21}$ at (2) is 0 or 1, and q for the $R^{21}$ on the carbon adjacent to the N is 0, 1 or 2, and each $R^{21}$ for each q is independently selected;

(133) Compounds of formula (I) having the formula:

(IAC3)

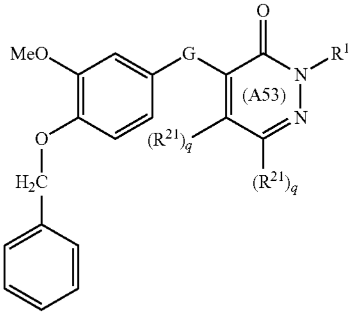

wherein each q is independently 0 or 1, and each $R^{21}$ is independently selected;

(134) compounds of formula (I), as described in (133) above, wherein $R^1$ is selected from the group consisting of:

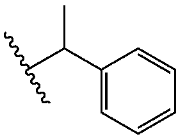, 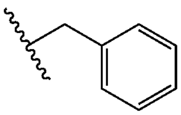,

-continued

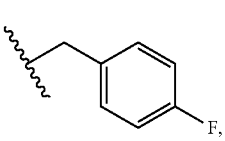 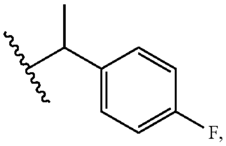

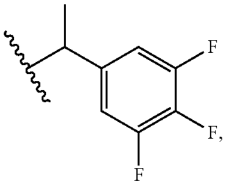 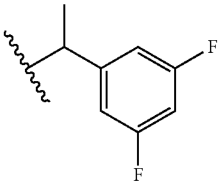,

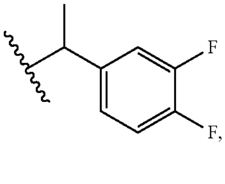 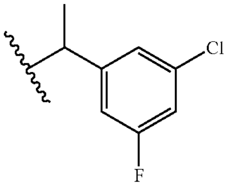,

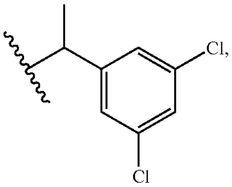 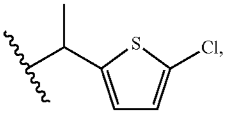

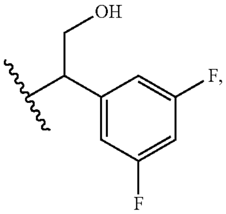 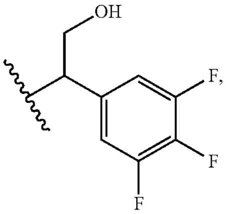

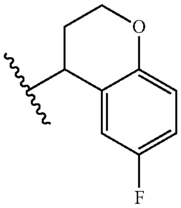, 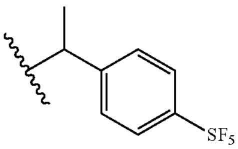,

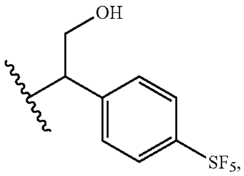 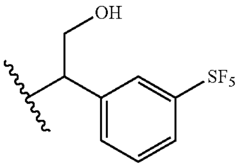,

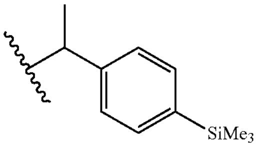 and 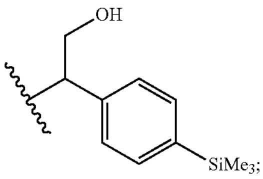

(135) Compounds of formula (I) having the formula:

(IAC6)

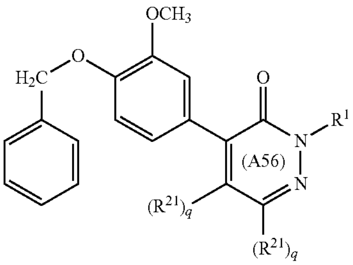

wherein each q is independently 0 or 1, and each $R^{21}$ is independently selected;

(136) Compounds of formula (I) having the formula:

(IAD3)

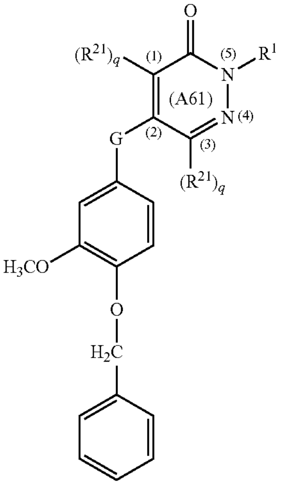

wherein each q is independently 0 or 1, and each $R^{20}$ is independently selected;

(137) Compounds of formula (I) having the formula:

(IAD6)

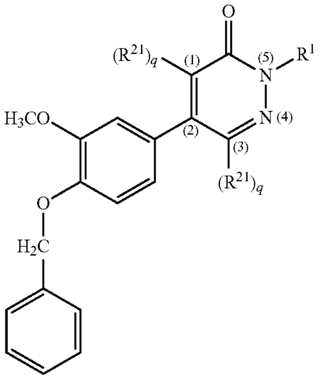

wherein each q is independently 0 or 1, and each $R^{21}$ is independently selected;

(138) compounds of formula (I), as described in (135) above, wherein $R^1$ is selected from the group consisting of:

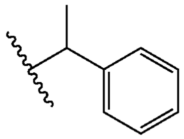,
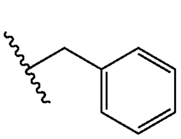,
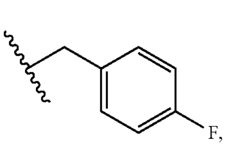
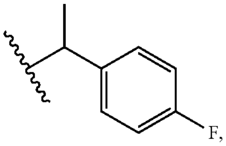
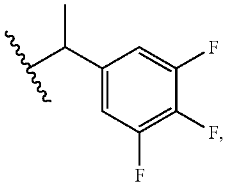
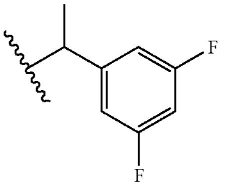,
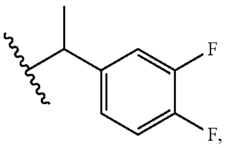
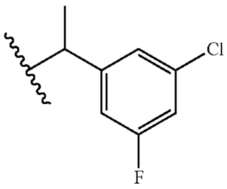,
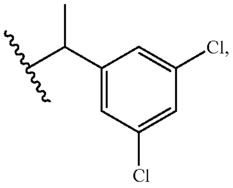
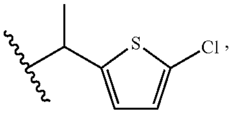
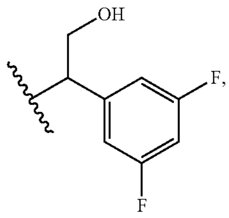
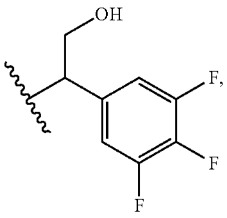
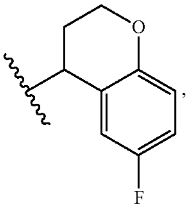,
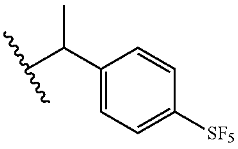,
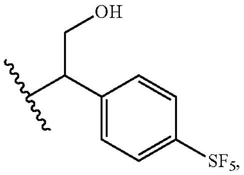
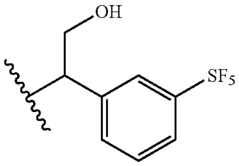,
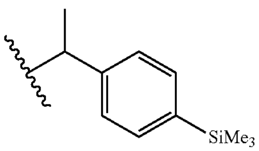 and 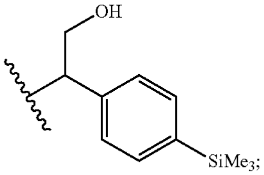

(139) compounds of formula (I), as described in (136) above, wherein $R^1$ is selected from the group consisting of:
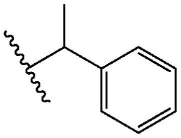, 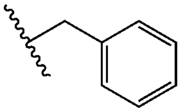, 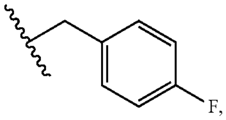, 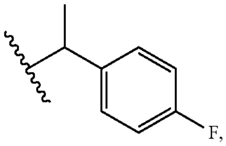, 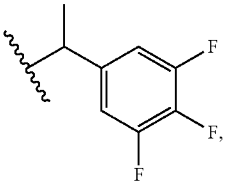, 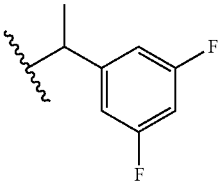, 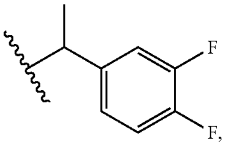, 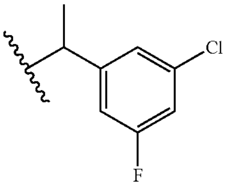, 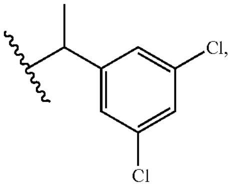, 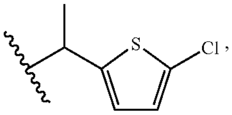, 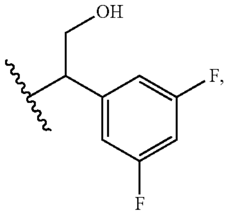, 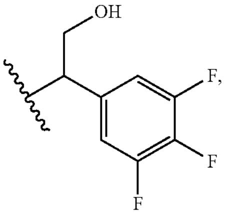, 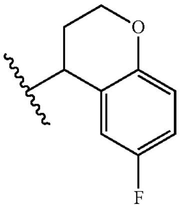, 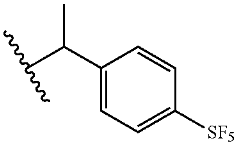, 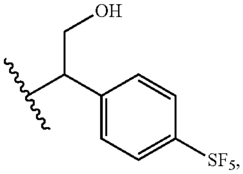, 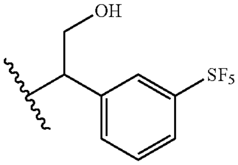, 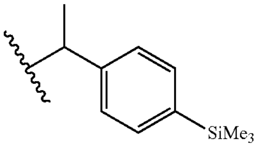 and 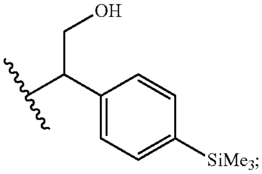;
(140) compounds of formula (I), as described in (137) above, wherein $R^1$ is selected from the group consisting of:
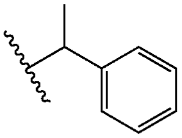, 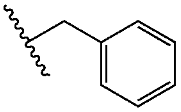, 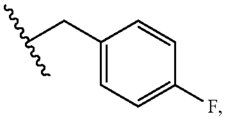, 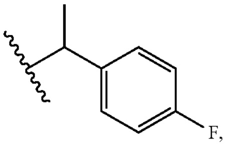, 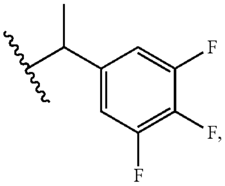, 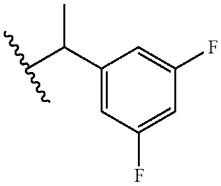, 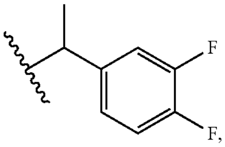, 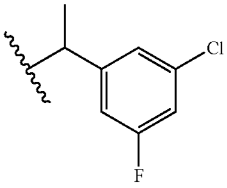, 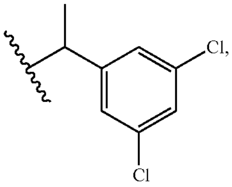, 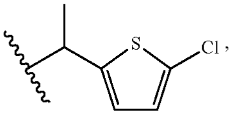, 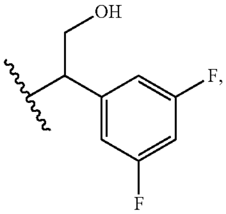, 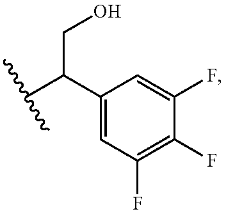, 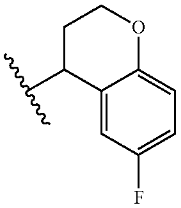, 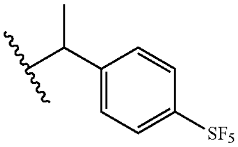, 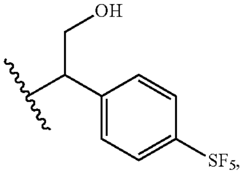, 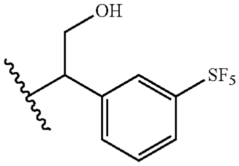, 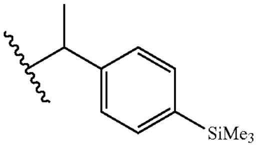 and 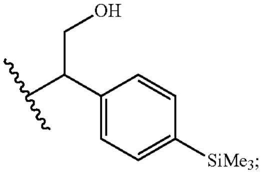;

(141) Compounds of formula (I) selected from the group consisting of: compounds 1.1 to 49.1;

(142) Compounds selected from the group consisting of: compounds 50.1 to 118.1;

(143) Compounds selected from the group consisting of: compounds 119.1 to 190.1;

(144) Compounds of formula (I) selected from the group consisting of: compounds 191.1 to 262.1;

(145) Compounds of formula (I) selected from the group consisting of: compounds 263.1 to 274.1;

(146) Compounds of formula (I) having the formula:

(IAE)

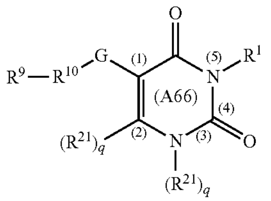

wherein each q is independently 0 or 1, and each $R^{21}$ is independently selected;

(147) Compounds of formula (I), as described in (146) above, wherein q at position (2) is 0 and q at position (3) is 1;

(148) Compounds of formula (I), as described in (146) above, wherein q at position (2) is 0 and q at position (3) is 1, and $R^{21}$ is arylalkyl;

(149) Compounds of formula (I), as described in (146) above, wherein G is selected from the group consisting of: —NH—, and a direct bond;

(150) Compounds of formula (I), as described in (149) above, wherein G is —NH—;

(151) Compounds of formula (I), as described in (149) above, wherein: (a) q at position (2) is 0 and q at position (3) is 1, (b) G is selected from the group consisting of: —NH—, and a direct bond, (c) $R^1$ is a methyl or ethyl group substituted with one phenyl, or (d) $R^1$ is an methyl or ethyl group substituted with one phenyl, and said phenyl is substituted with one or two F, (e) $R^{10}$ is phenyl substituted with one —$OR^{15}$ group, wherein $R^{15}$ is methyl, and (f) $R^9$ is selected from the group consisting of imidazolyl and imidazolyl substituted with one methyl group;

(152) Compounds of formula (I), as described in (149) above, wherein: (a) G is selected from the group consisting of: —NH—, and a direct bond, and (b) $R^1$ is selected from the group consisting of:

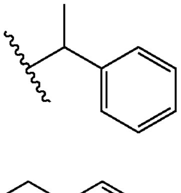,
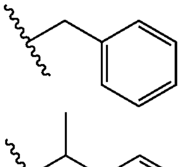,
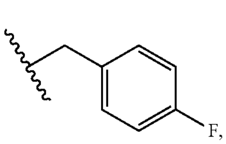
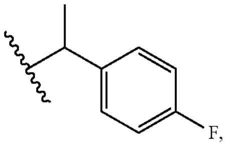

-continued

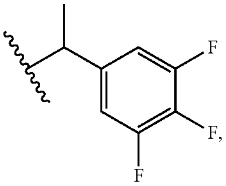
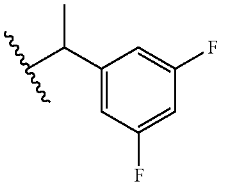,
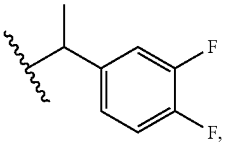
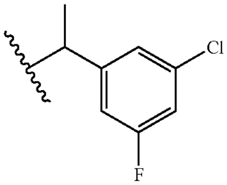,
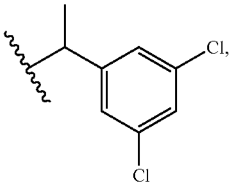
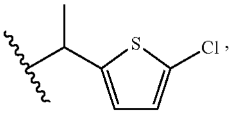
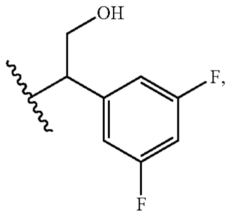
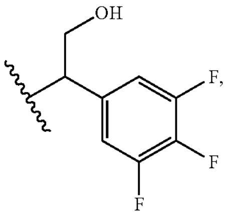
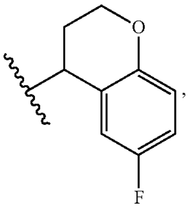,
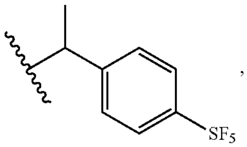,
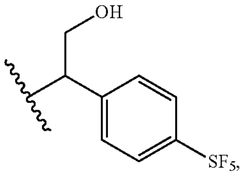
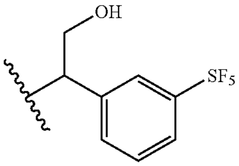,
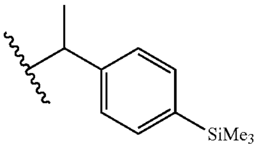 and 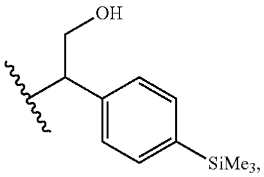

and wherein the $R^9$-$R^{10}$— moiety is:

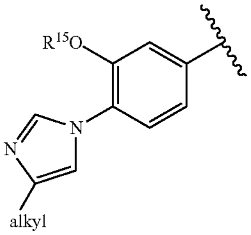 or 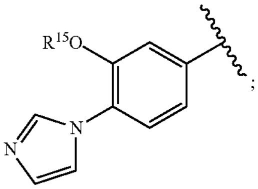;

(153) Compounds of formula (I), as described in (149) above, wherein: (a) G is selected from the group consisting of: —NH—, and a direct bond, and (b) $R^1$ is selected from the group consisting of:

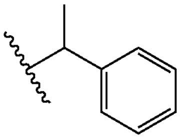,
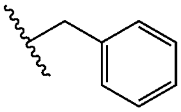,

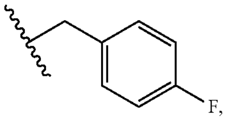
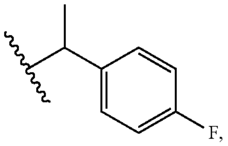

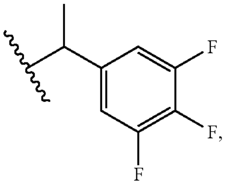
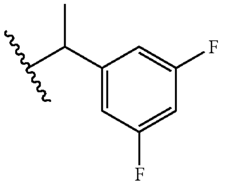,

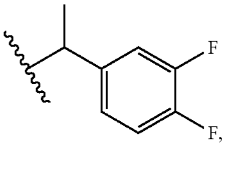
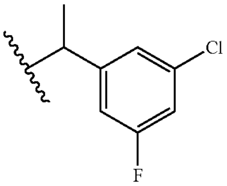,

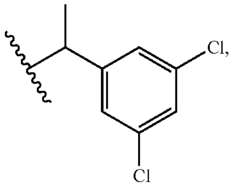
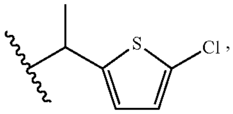

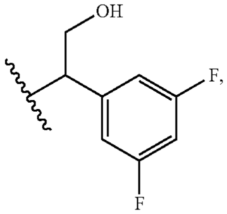
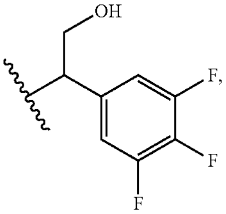

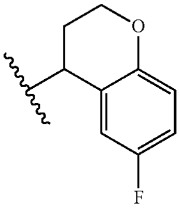,
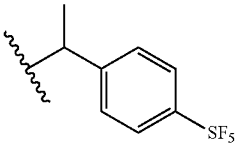,

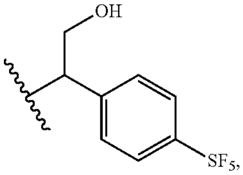
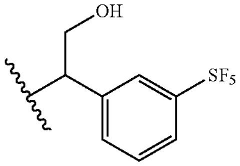,

-continued

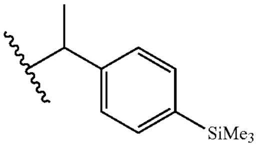
and
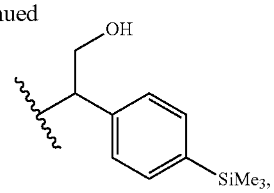

and wherein the $R^9$-$R^{10}$— moiety is:

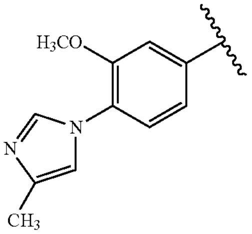
or
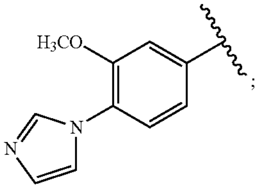;

(154) Compounds of formula (I), as described in (149) above, having the formula:

(IAE1)

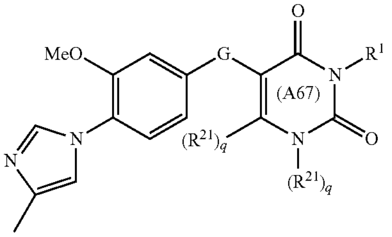

wherein each q is independently 0 or 1, and each $R^{21}$ is independently selected;

(155) Compounds of formula (I) having the formula:

(IAF)

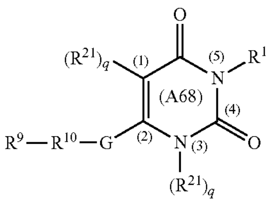

wherein each q is independently 0 or 1, and each $R^{21}$ is independently selected;

(156) Compounds of formula (I), as described in (155) above, wherein q at position (1) is 0 and q at position (3) is 1;

(157) Compounds of formula (I), as described in (155) above, wherein q at position (1) is 0 and q at position (3) is 1, and $R^{21}$ is arylalkyl;

(158) Compounds of formula (I), as described in (155) above, wherein G is selected from the group consisting of: —NH—, and a direct bond;

(159) Compounds of formula (I), as described in (158) above, wherein G is —NH—;

(160) Compounds of formula (I), as described in (158) above, wherein: (a) q at position (2) is 0 and q at position (3)

is 1, (b) G is selected from the group consisting of: —NH—, and a direct bond, (c) $R^1$ is a methyl or ethyl group substituted with one phenyl, or (d) $R^1$ is an methyl or ethyl group substituted with one phenyl, and said phenyl is substituted with one or two F, (e) $R^{10}$ is phenyl substituted with one —$OR^{15}$ group, wherein $R^{15}$ is methyl, and (f) $R^9$ is selected from the group consisting of imidazolyl and imidazolyl substituted with one methyl group;

(161) Compounds of formula (I), as described in (155) above, wherein: (a) G is selected from the group consisting of: —NH—, and a direct bond, and (b) $R^1$ is selected from the group consisting of:

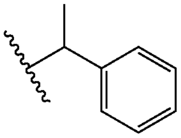,
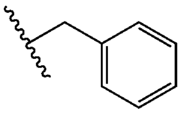,
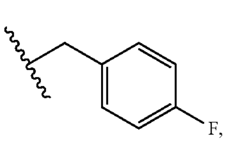
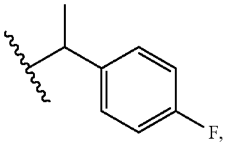
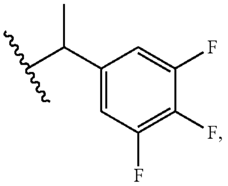
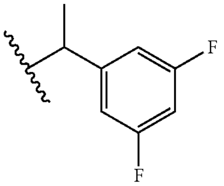,
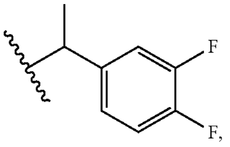
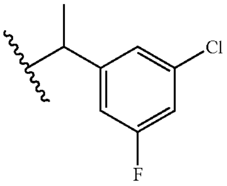,
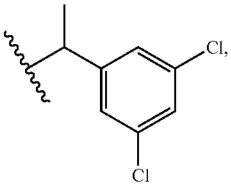
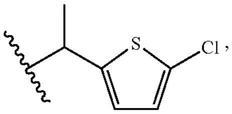
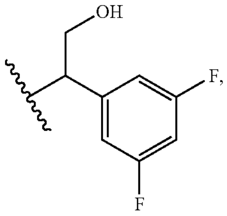
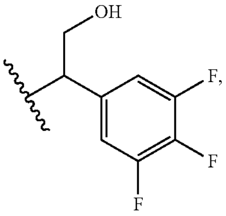
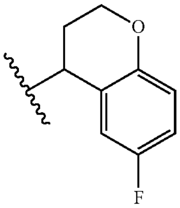,
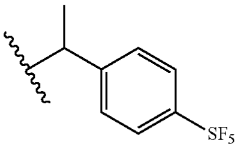, -continued

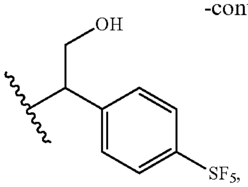
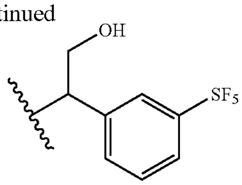,
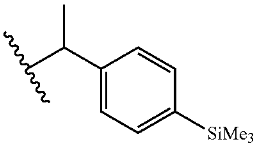
and
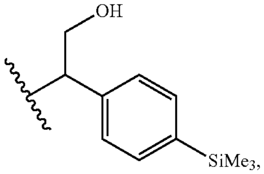

and wherein the $R^9$-$R^{10}$— moiety is:

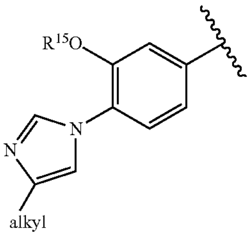
or
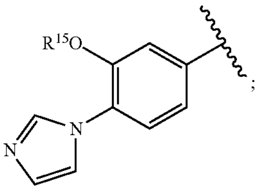;

(162) Compounds of formula (I), as described in (155) above, wherein: (a) G is selected from the group consisting of —NH—, and a direct bond, and (b) $R^1$ is selected from the group consisting of:

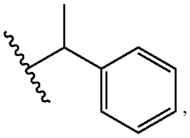,
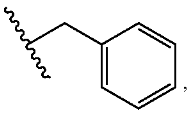,
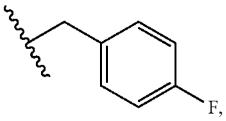
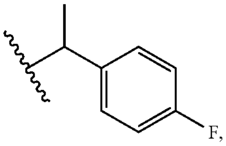
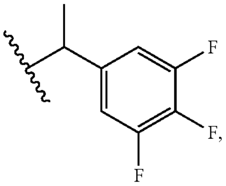
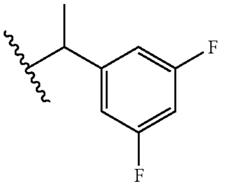,
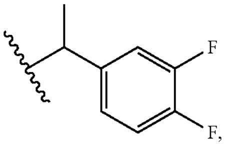
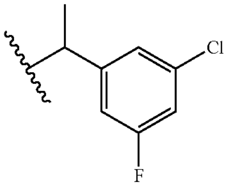, -continued

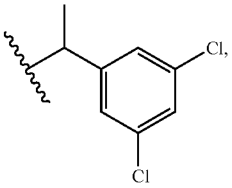

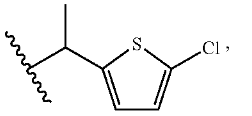

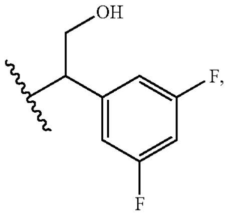

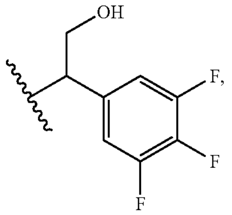

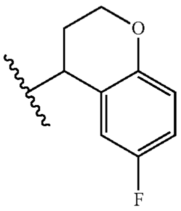
,
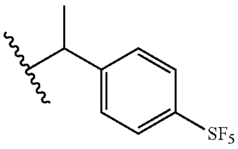
,

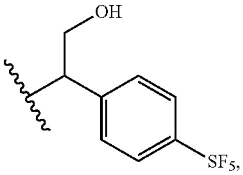

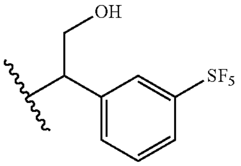
,

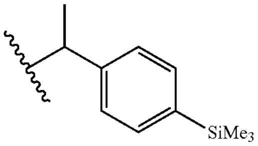
and
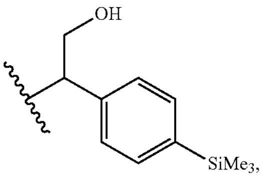

and wherein the $R^9$-$R^{10}$— moiety is:

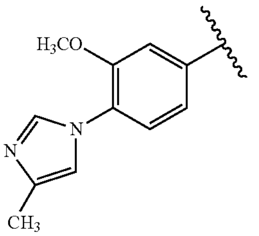
or
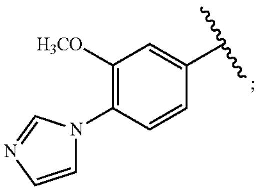
;

(163) Compounds of formula (I), as described in (155) above, having the formula:

(IAF1)

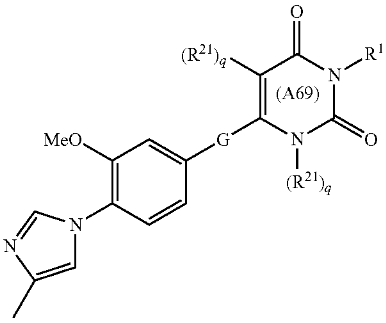

wherein each q is independently 0 or 1, and each $R^{21}$ is independently selected;

(164) A pharmaceutical composition comprising a therapeutically effective amount of at least one compound of formula (I), or a pharmaceutically acceptable salt, solvate, ester or prodrug thereof, and at least one pharmaceutically acceptable carrier;

(165) Compositions of formula (I), as described in (164) above, further comprising a therapeutically effective amount of one or more compounds selected from the group consisting of cholinesterase inhibitors, Aβ antibody inhibitors, gamma secretase inhibitors and beta secretase inhibitors;

(166) Compositions of formula (I), as described in (165) above, wherein said cholinesterase inhibitor is donepezil hydrochloride;

(167) A method of treating a central nervous system disorder comprising administering a therapeutically effective amount of at least one compound of formula (I) to a patient in need of such treatment;

(168) A method of treating a central nervous system disorder comprising administering a therapeutically effective amount of a composition of formula (I), as described in (164) above, to a patient in need of such treatment;

(169) A method of treating a central nervous system disorder comprising administering a therapeutically effective amount of a composition of formula (I), as described in (165) above, to a patient in need of such treatment;

(170) A method of treating a central nervous system disorder comprising administering a therapeutically effective amount of a composition of formula (I), as described in (166) above, to a patient in need of such treatment;

(171) A method of treating Alzheimers disease comprising administering a therapeutically effective amount of at least one compound of formula (I) to a patient in need of such treatment;

(172) A method of treating Alzheimer's disease comprising administering a therapeutically effective amount of at least one compound of formula (I), in combination with a therapeutically effective amount of a BACE inhibitor, to a patient in need of such treatment;

(173) A method of treating Alzheimers disease comprising administering a therapeutically effective amount of at least one compound, as described in (141), (142), (143), (144) or (145) above, to a patient in need of such treatment;

(174) A method of treating Alzheimer's disease comprising administering a therapeutically effective amount of at least one compound, as described in (141), (142), (143), (144)

or (145) above, in combination with a therapeutically effective amount of a BACE inhibitor, to a patient in need of such treatment;

(175) A method of treating Downs syndrome comprising administering a therapeutically effective amount of at least one compound of formula (I) to a patient in need of such treatment;

(176) A method of modulating gamma secretase activity comprising administering an effective amount of a compound of formula (I) to a patient in need of such treatment;

(177) A method of inhibiting the deposition of beta amyloid protein comprising administering an effective amount of a compound of formula (I) to a patient in need of such treatment;

(178) A method of treating one or more neurodegenerative disease comprising administering an effective amount of a compound of formula (I) to a patient in need of such treatment;

(179) A pharmaceutical composition comprising a therapeutically effective amount of at least one compound selected from the group consisting of: 1.1 to 49.1 and 191.1 to 274.1 (and in one example, 1.1 to 49.1, and in another example 191.1 to 274.1, and in another example 263.1 to 274.1), or a pharmaceutically acceptable salt, solvate, ester or prodrug thereof, and at least one pharmaceutically acceptable carrier;

(180) A pharmaceutical composition comprising a therapeutically effective amount of at least one compound selected from the group consisting of: 50.1 to 190.1 (and in one example, 50.1 to 118.1, and in another example 119.1 to 190.1), or a pharmaceutically acceptable salt, solvate, ester or prodrug thereof, and at least one pharmaceutically acceptable carrier;

(181) Compositions, as described in (179) above, further comprising a therapeutically effective amount of one or more compounds selected from the group consisting of cholinesterase inhibitors, Aβ antibody inhibitors, gamma secretase inhibitors and beta secretase inhibitors;

(182) Compositions, as described in (180) above, further comprising a therapeutically effective amount of one or more compounds selected from the group consisting of cholinesterase inhibitors, Aβ antibody inhibitors, gamma secretase inhibitors and beta secretase inhibitors;

(183) Compositions as described in (181) or (182) above, wherein said cholinesterase inhibitor is donepezil hydrochloride;

(184) A method of treating a central nervous system disorder comprising administering a therapeutically effective amount of at least one compound selected from the group consisting of: 50.1 to 190.1 (and in one example, 50.1 to 118.1, and in another example 119.1 to 190.1) to a patient in need of such treatment;

(185) A method of treating Alzheimers disease comprising administering a therapeutically effective amount of at least one compound selected from the group consisting of: 50.1 to 190.1 (and in one example, 50.1 to 118.1, and in another example 119.1 to 190.1) to a patient in need of such treatment;

(186) A method of treating Alzheimer's disease comprising administering a therapeutically effective amount of at least one compound selected from the group consisting of: 50.1 to 190.1 (and in one example, 50.1 to 118.1, and in another example 119.1 to 190.1), in combination with a therapeutically effective amount of a BACE inhibitor, to a patient in need of such treatment;

(187) A method of treating Downs syndrome comprising administering a therapeutically effective amount of at least one compound selected from the group consisting of: 50.1 to 190.1 (and in one example, 50.1 to 118.1, and in another example 119.1 to 190.1) to a patient in need of such treatment;

(188) A method of modulating gamma secretase activity comprising administering an effective amount of a compound selected from the group consisting of: 50.1 to 190.1 (and in one example, 50.1 to 118.1, and in another example 119.1 to 190.1) to a patient in need of such treatment;

(189) A method of inhibiting the deposition of beta amyloid protein comprising administering an effective amount of a compound selected from the group consisting of: 50.1 to 190.1 (and in one example, 50.1 to 118.1, and in another example 119.1 to 190.1) to a patient in need of such treatment;

(190) A method of treating one or more neurodegenerative disease comprising administering an effective amount of a compound selected from the group consisting of: 50.1 to 190.1 (and in one example, 50.1 to 118.1, and in another example 119.1 to 190.1) to a patient in need of such treatment;

(191) A method of treating a central nervous system disorder comprising administering a therapeutically effective amount of at least one compound selected from the group consisting of: 1.1 to 49.1 and 191.1 to 274.1 (and in one example, 1.1 to 49.1, and in another example 191.1 to 274.1, and in another example 263.1 to 274.1) to a patient in need of such treatment;

(192) A method of treating Alzheimers disease comprising administering a therapeutically effective amount of at least one compound selected from the group consisting of: 1.1 to 49.1 and 191.1 to 274.1 (and in one example, 1.1 to 49.1, and in another example 191.1 to 262.1, and in another example 263.1 to 274.1) to a patient in need of such treatment;

(193) A method of treating Alzheimer's disease comprising administering a therapeutically effective amount of at least one compound selected from the group consisting of: 1.1 to 49.1 and 191.1 to 274.1 (and in one example, 1.1 to 49.1, and in another example 191.1 to 262.1, and in another example 263.1 to 274.1), in combination with a therapeutically effective amount of a BACE inhibitor, to a patient in need of such treatment;

(194) A method of treating Downs syndrome comprising administering a therapeutically effective amount of at least one compound selected from the group consisting of: 1.1 to 49.1 and 191.1 to 274.1 (and in one example, 1.1 to 49.1, and in another example 191.1 to 262.1, and in another example 263.1 to 274.1) to a patient in need of such treatment;

(195) A method of modulating gamma secretase activity comprising administering an effective amount of a compound selected from the group consisting of: 1.1 to 49.1 and 191.1 to 274.1 (and in one example, 1.1 to 49.1, and in another example 191.1 to 262.1, and in another example 263.1 to 274.1) to a patient in need of such treatment;

(196) A method of inhibiting the deposition of beta amyloid protein comprising administering an effective amount of a compound selected from the group consisting of: 1.1 to 49.1 and 191.1 to 274.1 (and in one example, 1.1 to 49.1, and in another example 191.1 to 262.1, and in another example 263.1 to 274.1) to a patient in need of such treatment; and (197) A method of treating one or more neurodegenerative disease comprising administering an effective amount of a compound selected from the group consisting of: 1.1 to 49.1 and 191.1 to 274.1 (and in one example, 1.1 to 49.1, and in another example 191.1 to 262.1, and in another example 263.1 to 274.1) to a patient in need of such treatment.

It is noted that the carbons of formula (I) and other formulas herein may be replaced with 1 to 3 silicon atoms so long as all valency requirements are satisfied.

As used above, and throughout this disclosure, the following terms, unless otherwise indicated, shall be understood to have the following meanings:

"Patient" includes both human and animals.

"Mammal" means humans and other mammalian animals.

"One or more" means that there is at least one and there can be more than one, and examples include 1, 2 or 3, or 1 and 2, or 1.

"At least one" means there is at least one and there can be more than one, and examples include 1, 2 or 3, or 1 and 2, or 1.

"ADDP" means 1,1'-(azodicarbonyl)dipiperidine.

"BINAP" means _(R)-(+)-2,2'-bis(diphenylphosphino)-1,1'-binaphthyl

"Bn" means benzyl.

"DAST" means diethylaminosulfur trifluoride.

"DCM" means dichloromethane.

"DEAD" means diethyl azodicarboxylate.

"DIEA" means N,N-diisopropylethylamine.

"DMF" means dimethylforamide.

"EDC" means 1-(3-dimethylaminopropyl)-3-ethylcarbodiimide.

"Et" means ethyl.

"i-pr" means isopropyl.

"ISCO" means brand name of silica gel column chromatography system.

"NBS" means N-bromosuccinimide.

"NMP" means 1-methyl-2-pyrrolidinone.

"-OTBDMS" means tert-butyldimethylsilyloxy.

"$PCy_3$" means tricyclohexylphosphine.

"PDC" means pyridinium dichromate.

"PEG" means polyethyleneglycol.

"Pr" means propyl.

"RT" or "r.t." means room temperature.

"t-Bu" means tert-butyl.

"TBAF" means tetrabutylammonium fluoride.

"TFA" means trifluoroacetic acid.

"THF" means tetrahydrofuran

"Fused benzocycloalkyl ring" means a phenyl ring fused to a cycloalkyl ring (as cycloalkyl is defined below), such as, for example,

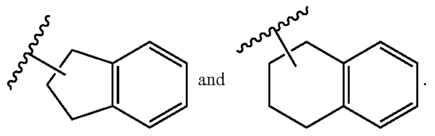

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —$N(alkyl)_2$, —O—C(O)-alkyl, —O—C(O)-aryl, —O—C(O)— cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the'alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine. "Halo" refers to fluoro, chloro, bromo or iodo.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)—cycloalkyl, —C(=N—CN)—$NH_2$, —C(=NH)—$NH_2$, —C(=NH)—NH(alkyl), oxime (e.g., =N—OH), $Y_1Y_2N$—, $Y_1Y_2N$-alkyl-, $Y_1Y_2NC(O)$—, $Y_1Y_2NSO_2$— and —$SO_2NY_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C$(CH_3)_2$— and the like which form moieties such as, for example:

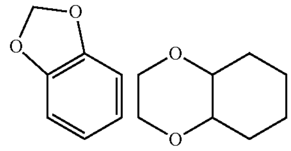

and

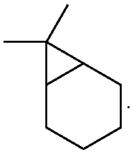

.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" or "heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom on a ring system (i.e., heterocyclyl includes rings having a carbonyl in the ring). An example of such moiety is pyrrolidone:

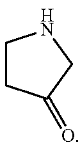

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazotyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom on a ring system (i.e., heterocyclyl includes rings having a carbonyl in the ring). An example of such moiety is pyrrolidinone:

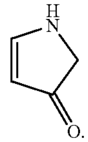

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

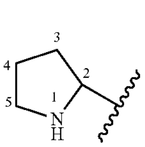

there is no —OH attached directly to carbons marked 2 and 5.

It should also be noted that tautomeric forms such as, for example, the moieties:

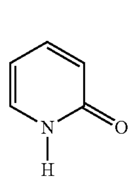 and 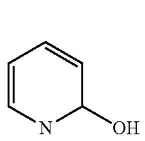

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I), or a compound selected from the group consisting of 50.1 to 190.1, or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, $(C_1-C_2)$alkylcarbamoyl-$(C_1-C_2)$alkyl and piperidino-, pyrrolidino- or morpholino$(C_2-C_3)$alkyl, and the like.

Similarly, for example, if a compound of Formula (I) contains an alcohol functional group, a prodrug can be formed by the replacement of the hydrogen atom of the alcohol group with a group such as, for example, $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, $—P(O)(O(C_1-C_6)alkyl)_2$ or glycosyl (the radical resulting from the removal of a hydroxyl group of the hemiacetal form of a carbohydrate), and the like.

Also, for example, if a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)$OY^1$ wherein $Y^1$ is H, $(C_1-C_6)$alkyl or benzyl, $—C(OY^2)Y^3$ wherein $Y^2$ is $(C_1-C_4)$ alkyl and $Y^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, $—C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.,* 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.,* 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula (I), and the compounds 50.1 to 190.1, can form salts which are also within the scope of this invention. Reference to a compound of Formula (I), or a compound 50.1 to 190.1, herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I), or a compound 50.1 to 190.1, contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I), or compounds 50.1 to 190.1, may be formed, for example, by reacting a compound of Formula (I), or compound 50.1 to 190.1, with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula (I), and compounds 50.1 to 190.1, and salts, solvates, esters and prodrugs thereof, may exist in their tautomeric form (for example, as an amide, enol, keto or imino ether). All such tautomeric forms are contemplated herein as part of the present invention.

The compounds of Formula (I), and compounds 50.1 to 190.1, may contain asymmetric or chiral centers, and, therefore, exist in different stereoisomeric forms. It is intended that all stereoisomeric forms of the compounds of Formula (I), and compounds 50.1 to 190.1, as well as mixtures thereof, including racemic mixtures, form part of the present invention. In addition, the present invention embraces all geometric and positional isomers. For example, if a compound of Formula (I), or a compound 50.1 to 190.1, incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) (and some compounds of 50.1 to 190.1) may be atropisomers (e.g., substituted biaryls) and are considered as part of this invention. Enantiomers can also be separated by use of chiral HPLC column.

It is also possible that the compounds of Formula (I), and compounds 50.1 to 190.1, may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I), or a compound 50.1 to 190.1, incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms “salt”, “solvate”, “ester”, “prodrug” and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{18}F$, and $^{36}Cl$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula (I), and of compounds 50.1 to 190.1, can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula (I), and of the salts, solvates, esters and prodrugs of the compounds of Formula (I), are intended to be included in the present invention.

Polymorphic forms of compounds 50.1 to 190.1, and of the salts, solvates, esters and prodrugs of these compounds, are intended to be included in the present invention.

The compounds according to the invention can have pharmacological properties; in particular, the compounds of Formula (I), and compounds 50.1 to 190.1, can be modulators of gamma secretase (including inhibitors, antagonists and the like).

More specifically, the compounds of Formula (I), and compounds 50.1 to 190.1, can be useful in the treatment of a variety of disorders of the central nervous system including, for example, including, but not limited to, Alzheimer’s disease, AIDS-related dementia, Parkinson’s disease, amyotrophic lateral sclerosis, retinitis pigmentosa, spinal muscular atrophy and cerebellar degeneration and the like.

Another aspect of this invention is a method of treating a mammal (e.g., human) having a disease or condition of the central nervous system by administering a therapeutically effective amount of at least one compound of Formula (I), or at least one compound of 50.1 to 190.1, or a pharmaceutically acceptable salt, solvate, ester or prodrug of said compound to the mammal.

A preferred dosage is about 0.001 to 500 mg/kg of body weight/day of the compound of Formula (I), or the compound of 50.1 to 190.1. An especially preferred dosage is about 0.01 to 25 mg/kg of body weight/day of a compound of Formula (I), or a compound of 50.1 to 190.1, or a pharmaceutically acceptable salt or solvate of said compound.

The compounds of this invention may also be useful in combination (administered together or sequentially) with one or more additional agents listed above.

The compounds of this invention may also be useful in combination (administered together or sequentially) with one or more compounds selected from the group consisting of Aβ antibody inhibitors, gamma secretase inhibitors and beta secretase inhibitors.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of Formula (I), or at least one compound of 50.1 to 190.1, or a pharmaceutically acceptable salt, solvate, ester or prodrug thereof, and an amount of one or more additional agents listed above wherein the amounts of the compounds/treatments result in desired therapeutic effect.

The pharmacological properties of the compounds of this invention may be confirmed by a number of pharmacological assays. Certain assays are exemplified later in this document.

This invention is also directed to pharmaceutical compositions which comprise at least one compound of Formula (I), or at least one compound of 50.1 to 190.1, or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington’s Pharmaceutical Sciences,* $18^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula (I), or at least one compound of 50.1 to 190.1, or a pharmaceutically acceptable salt, solvate, ester or prodrug of said compound and a pharmaceutically acceptable carrier, vehicle or diluent.

Yet another aspect of this invention is a kit comprising an amount of at least one compound of Formula (I), or at least one compound of 50.1 to 190.1, or a pharmaceutically acceptable salt, solvate, ester or prodrug of said compound and an amount of at least one additional agent listed above, wherein the amounts of the two or more ingredients result in desired therapeutic effect.

The invention disclosed herein is exemplified by the following illustrative schemes and examples which should not be construed to limit the scope of the disclosure. Alternative mechanistic pathways and analogous structures will be apparent to those skilled in the art.

The compounds of the invention can be prepared by the schemes and examples below. Compounds of the invention wherein the G moiety is bound to $G^3$ (i.e., position (2)) can be prepared by the same chemistry unless indicated otherwise.

In the Schemes below [O] represents Dess-Martin Periodinane.

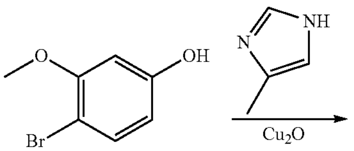

1

-continued

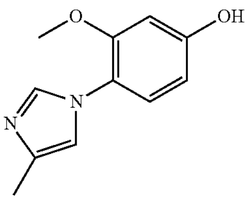

2

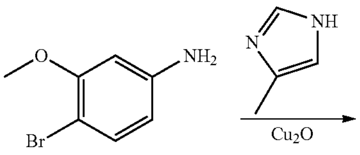

1

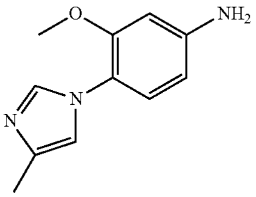

4

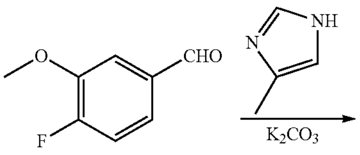

5

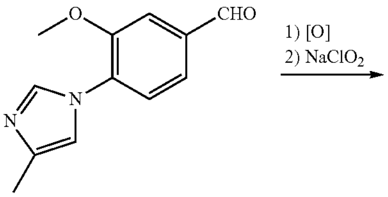

6

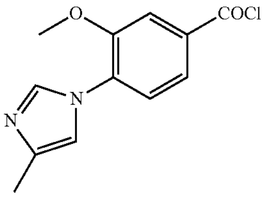

7

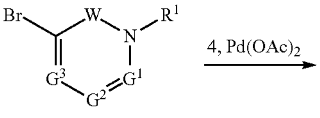

8

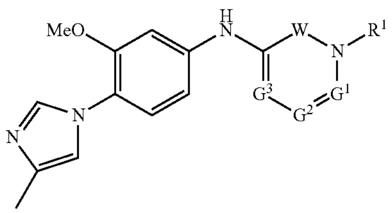

9

-continued
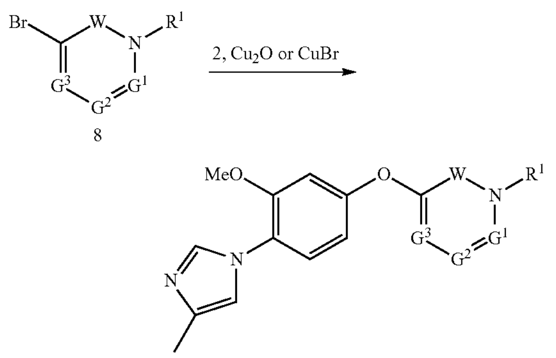
8
or
10
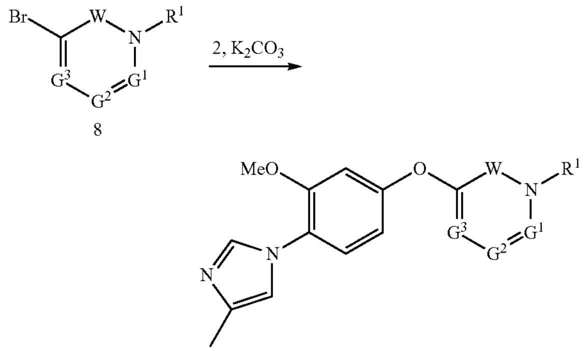
8
10
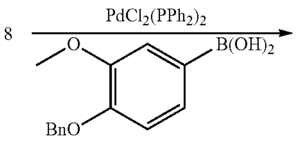
11
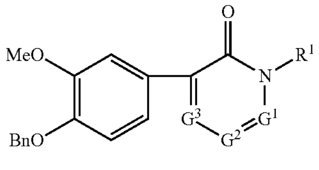
12
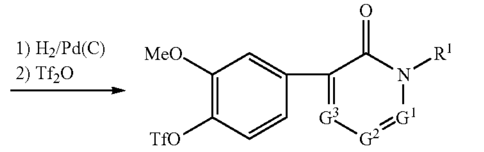
13
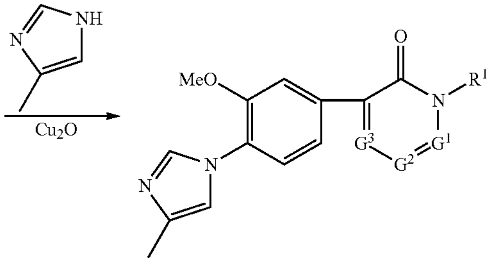
14
-continued
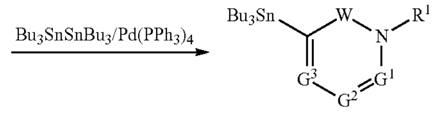
15
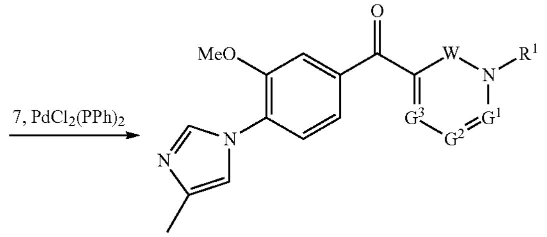
16
or 15→17→16 as follows:
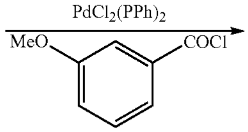
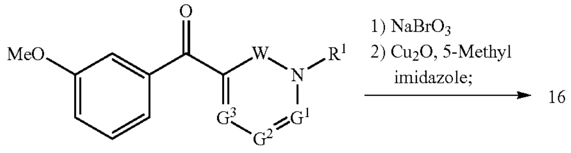
17
or 8→18→16 as follows:
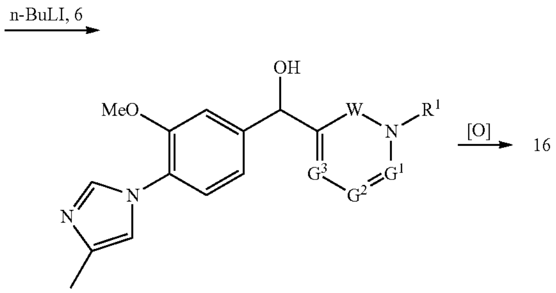
18
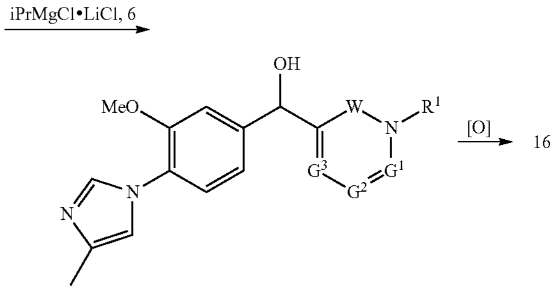
18

-continued
16
DAST
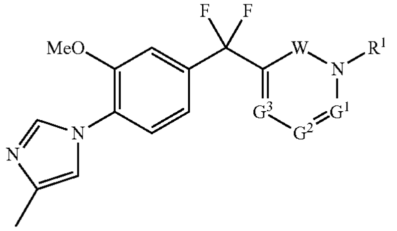
19
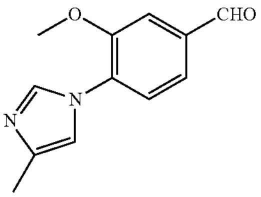
6
$CrCl_2$, $CHI_3$
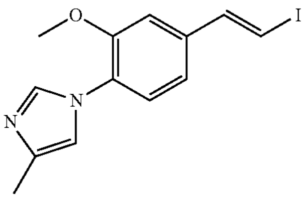
24
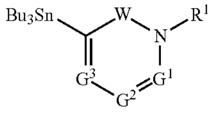
24
15
$Pd(PPh_3)_4$
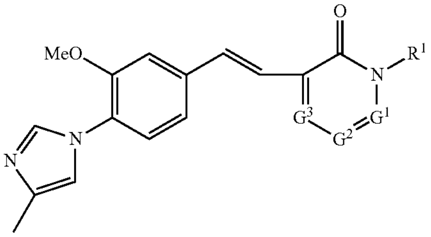
25
25
$H_2/Pd(C)$
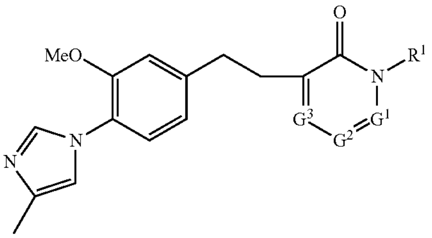
28
1) $Zn(Cu)/CCl_3COCl$
2) Zn/HOAc
25
-continued
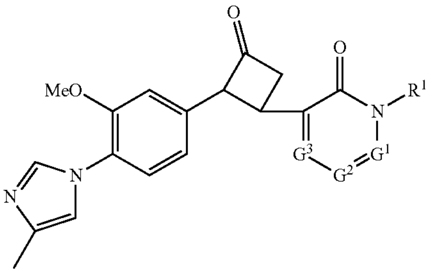
26
$ZnEt_2$,
$ICH_2I$,
25
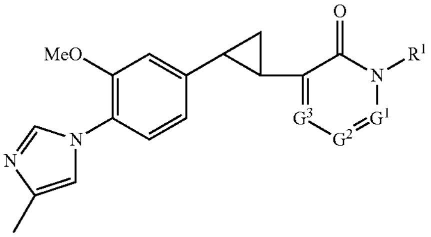
27
6
$TMSCHN_2$
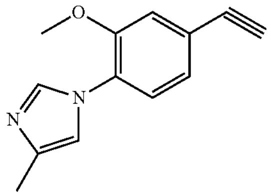
29
15
$Pd(PPh_3)_4$
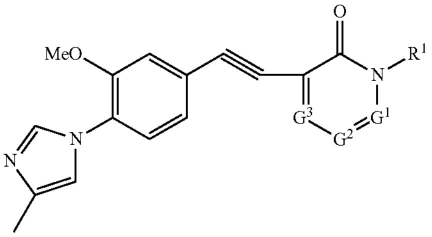
30
$Pd(OAc)_2$/Ligand
CO(g), MeOH
8
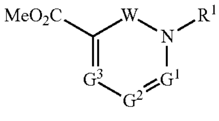
31
DIBAL
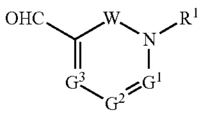
32
m-CPBA
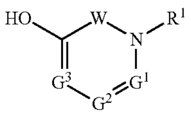
33
31
LiOH
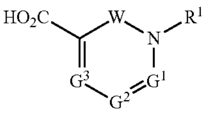
34
DPPA, then $H_2O$
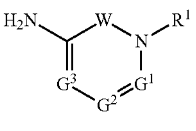
35

-continued
34
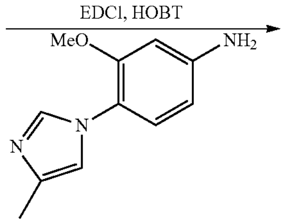
4
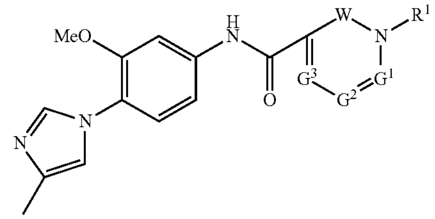
36
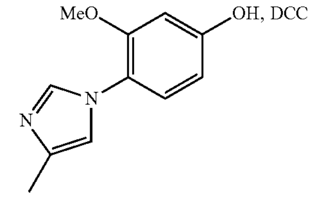
34
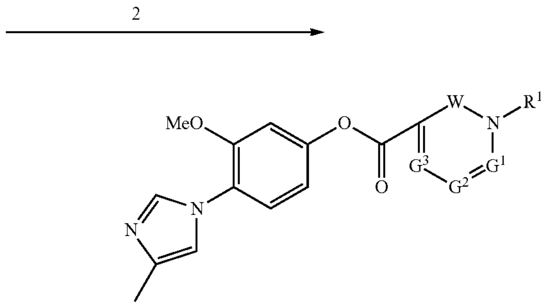
37
6
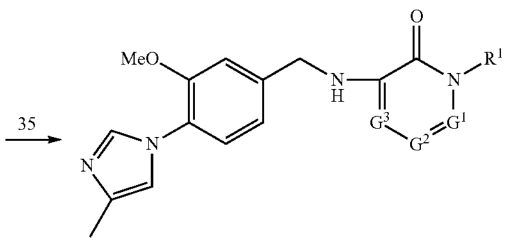
38
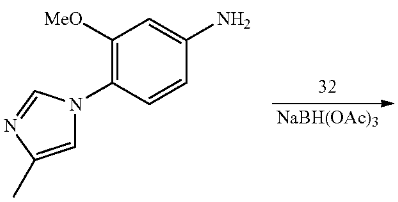
4
-continued
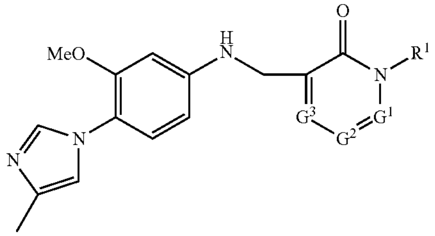
39
6
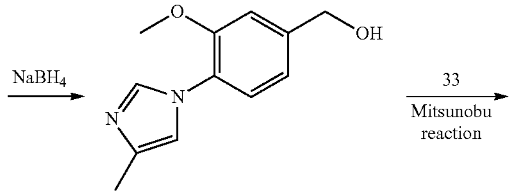
40
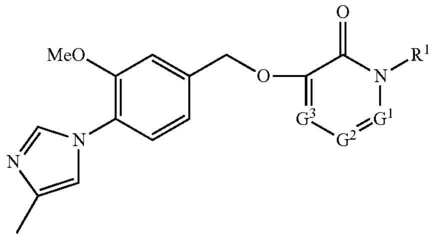
41
32
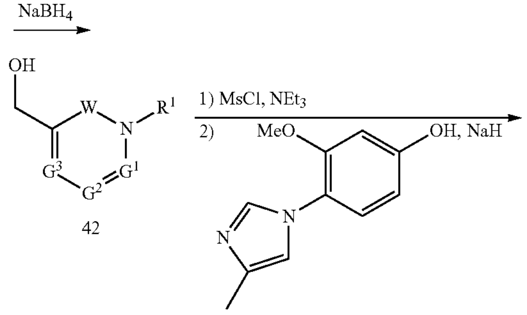
42
2
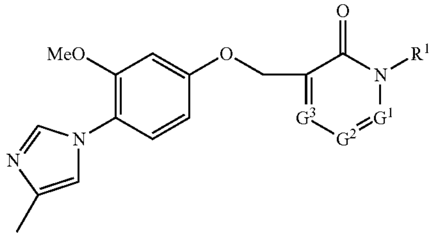
43
6
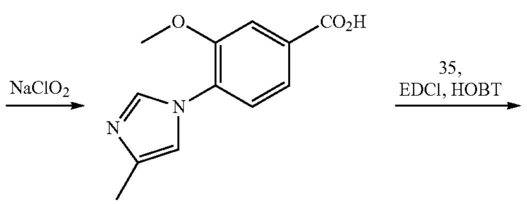
44

-continued
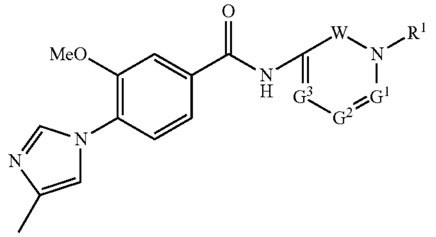
45
44
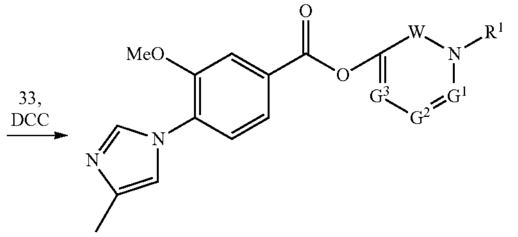
46
4
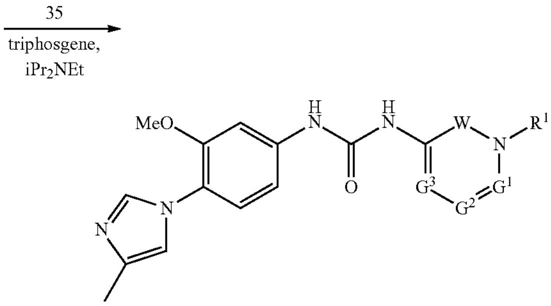
47
4
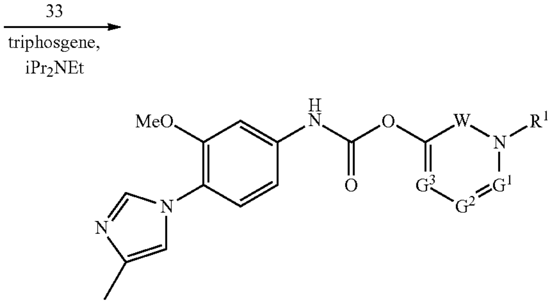
48
2
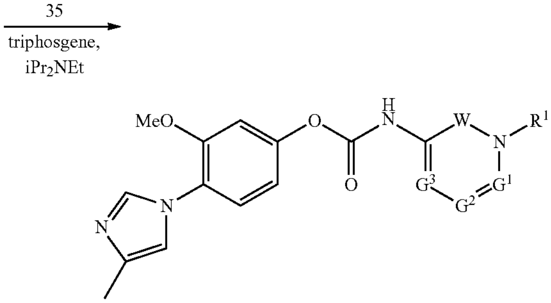
49
4
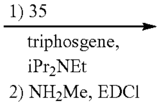
-continued
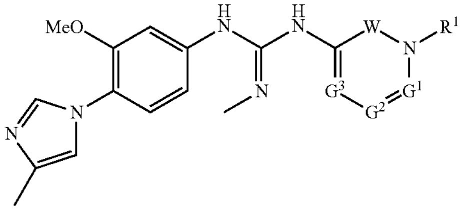
50
4
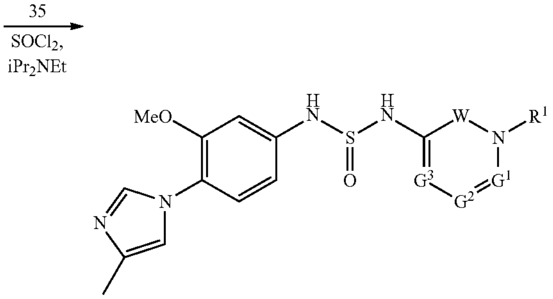
51
4
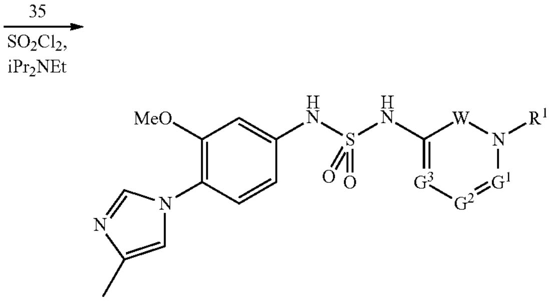
52
3
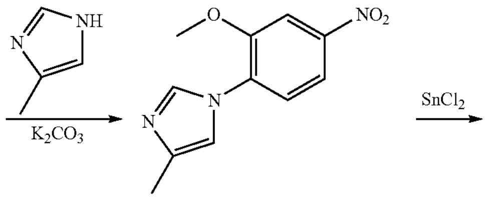
53
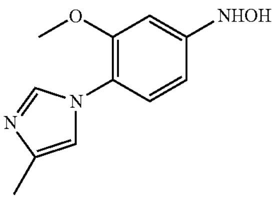
54
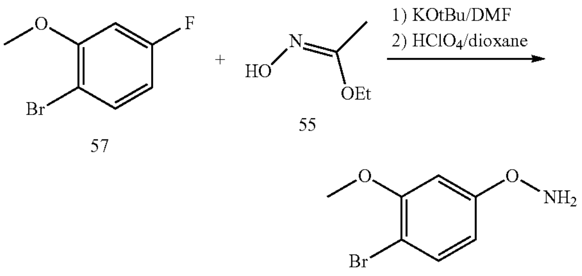
57
55
56

-continued
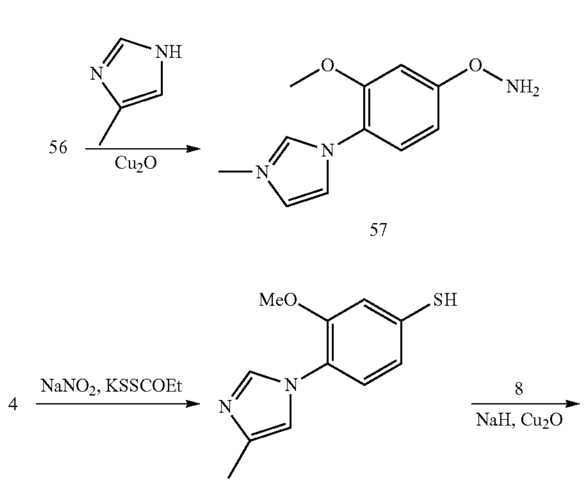
56
57
4
58
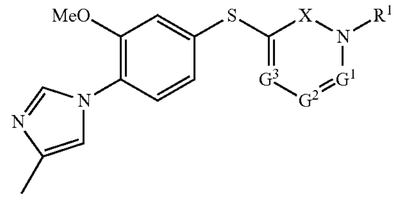
59
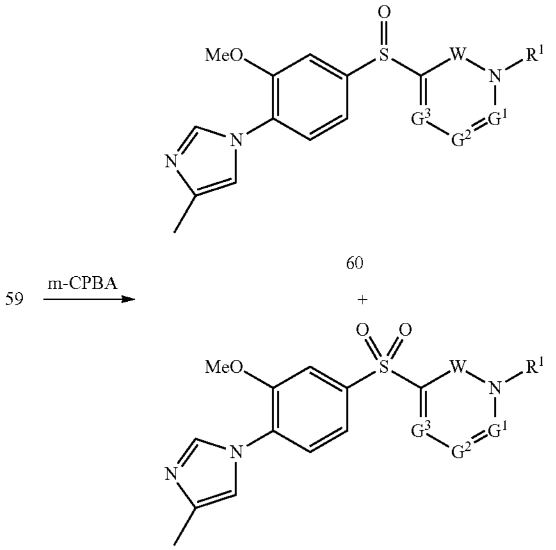
59
60
+
61
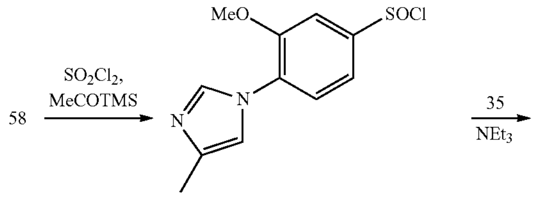
58
62
-continued
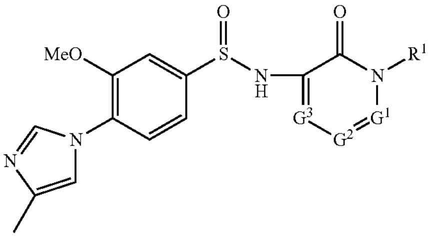
64
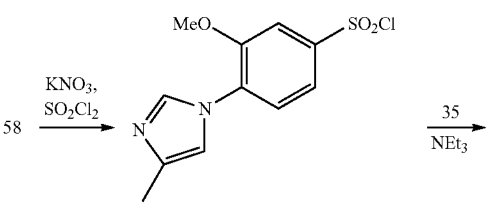
58
63
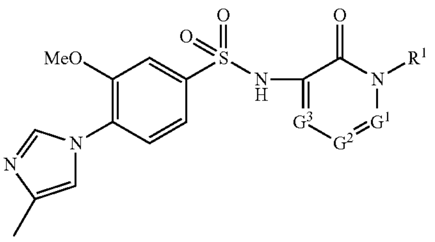
65
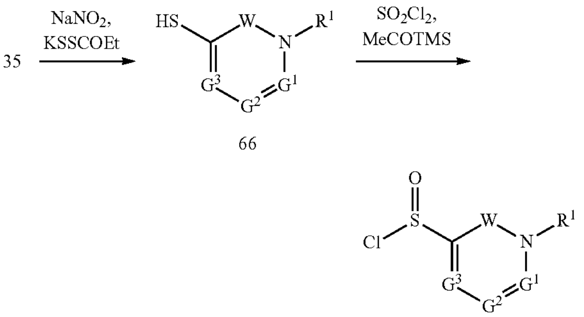
35
66
67
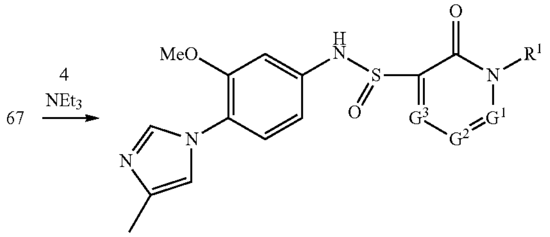
67
68
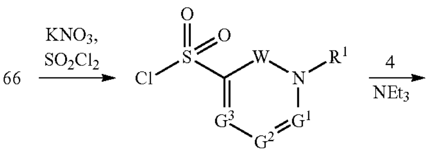
66
69

-continued

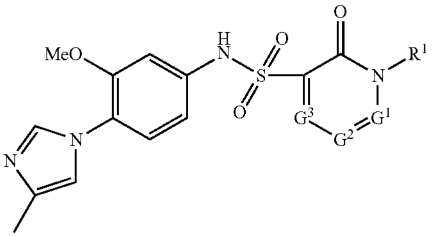

70

Compounds of the invention having —$SF_5$ and —$Si(R^{15})_3$ (e.g., —$Si(CH_3)_3$) groups can be prepared according to the scheme below and by techniques well known in the art. Those skilled in the art will appreciate that any carbon substitutable with a —$CF_3$ group can be substituted with a —$SF_5$ or a —$Si(R^{15})_3$ (e.g., —$Si(CH_3)_3$) group using techniques well known in the art.

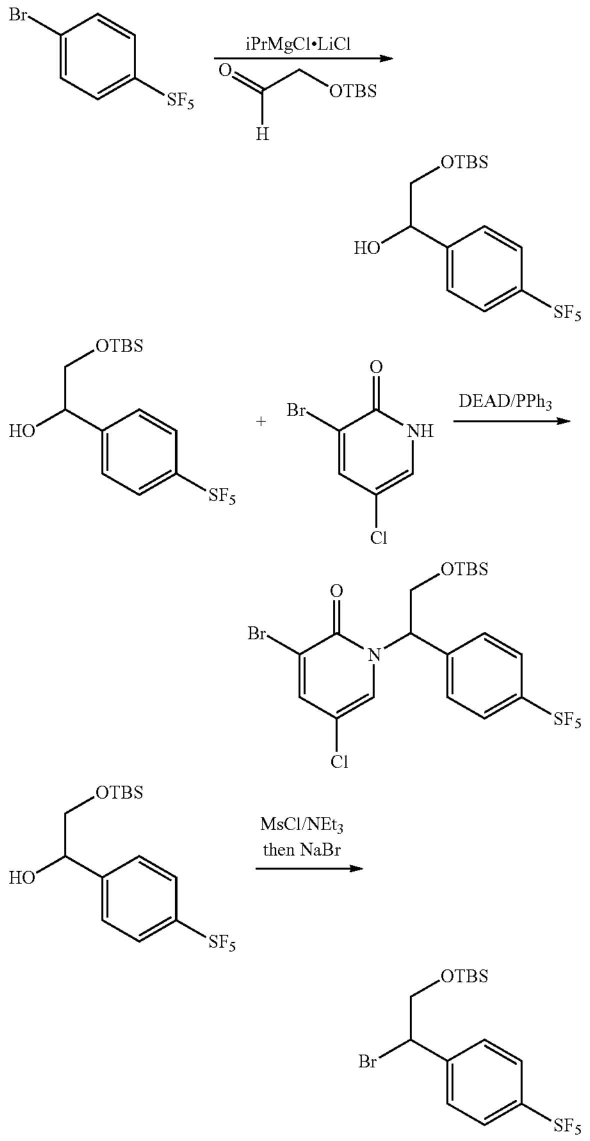

-continued

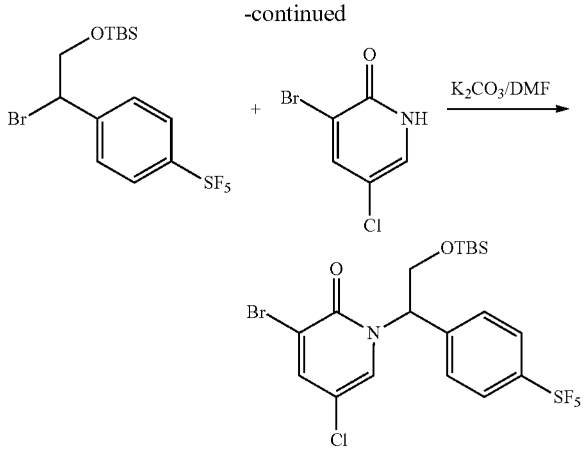

a-e can be prepared in a similar manner:

a

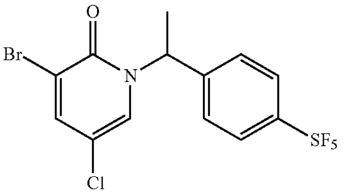

b

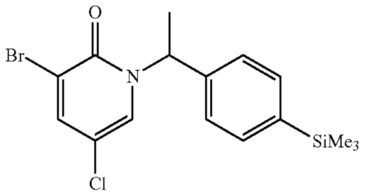

c

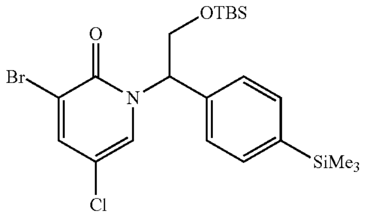

d

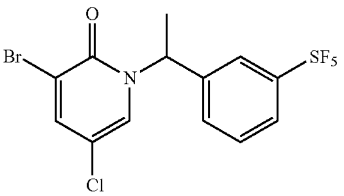

e

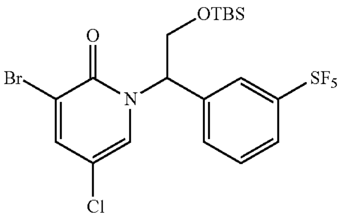

Compounds of the invention having —$OSF_5$ groups can be prepared according to the scheme below and by techniques well known in the art.

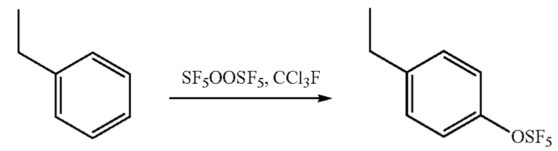

Journal of the Chemical Society; 1962; 2107-2108

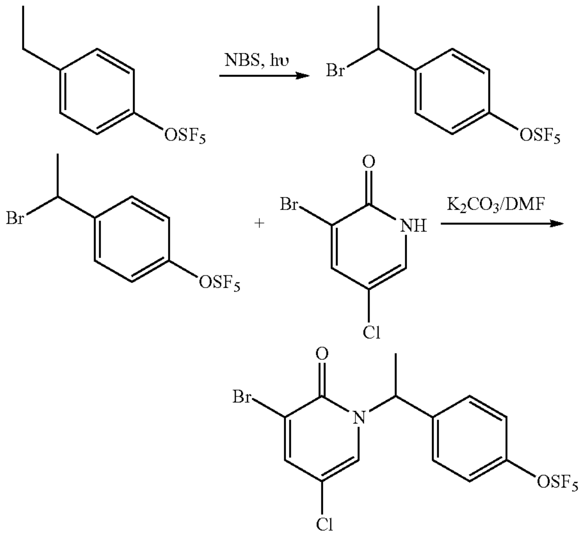

f-h can be prepared in a similar manner:

f

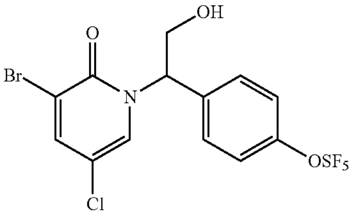

g

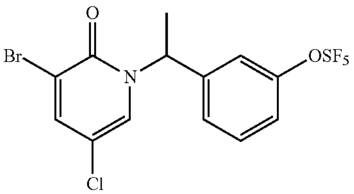

h

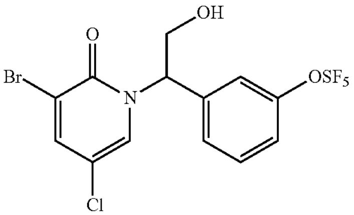

-continued

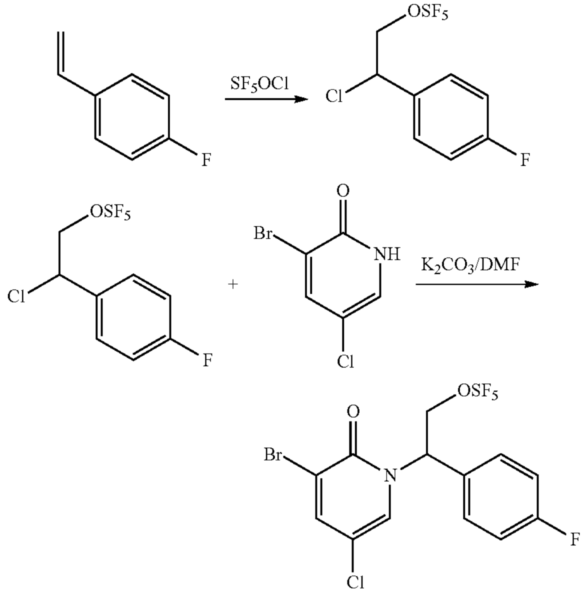

The brominated starting compounds, e.g., compound 8, are commercially available, or can be prepared according to procedures know in the art and the reactions below.

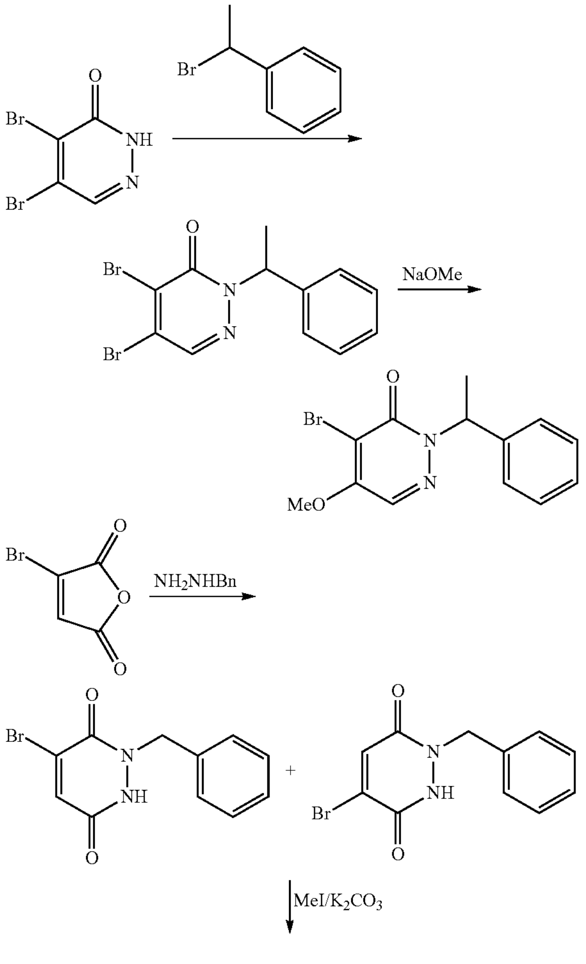

-continued
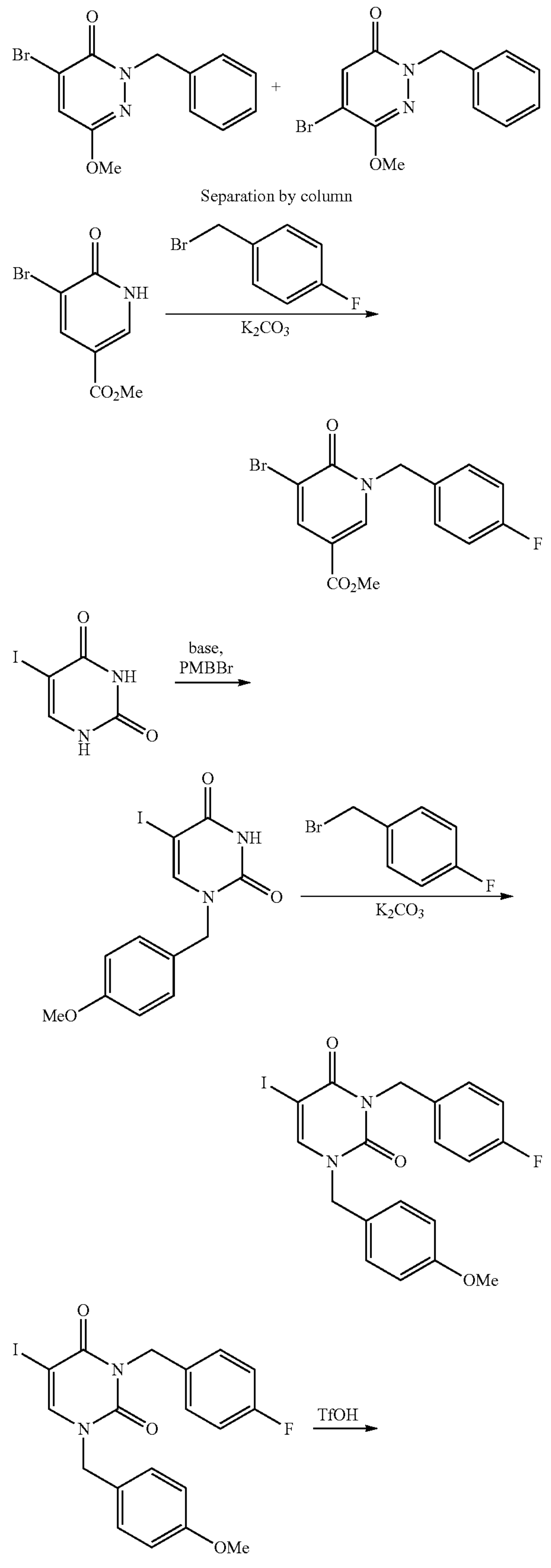
-continued
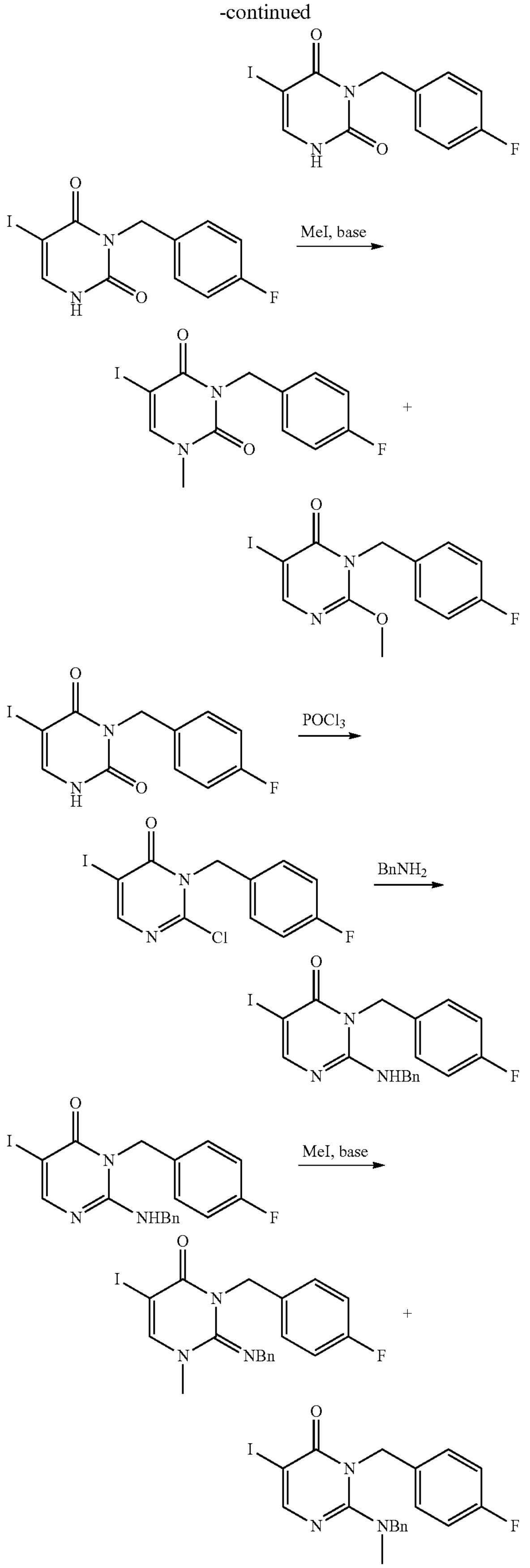

-continued
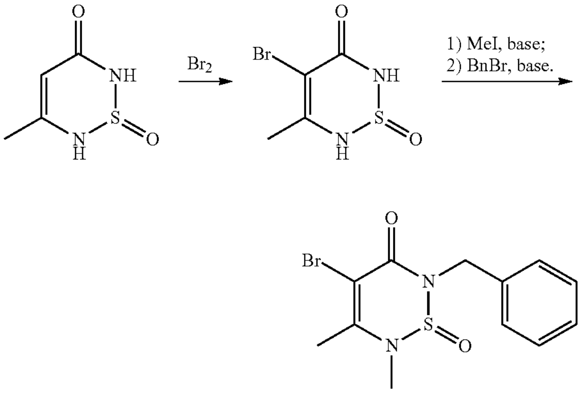
Same procedure will apply to preparing:
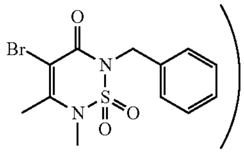
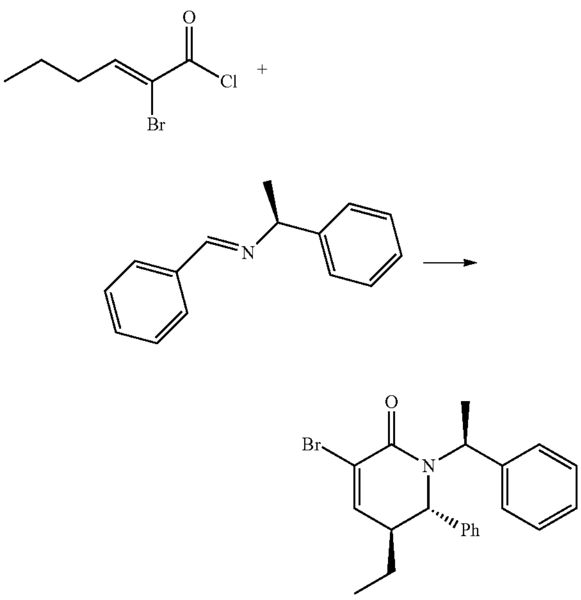
CARDILLO, G.; FABBRONI, S.; GENTILUCCI, L.; PERCIACCANTE, R.; PICCINELLI, F.; TOLOMELLI, A.; Tetrahedron 2004, 60 (23), 5031-5040.
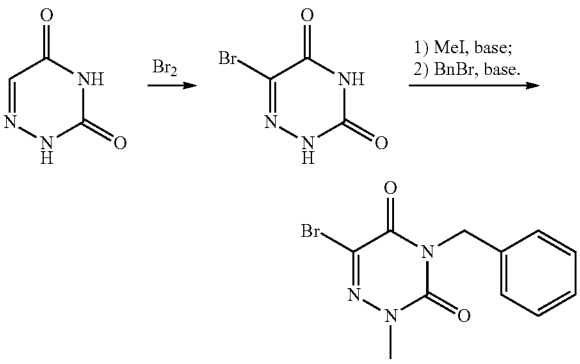
-continued
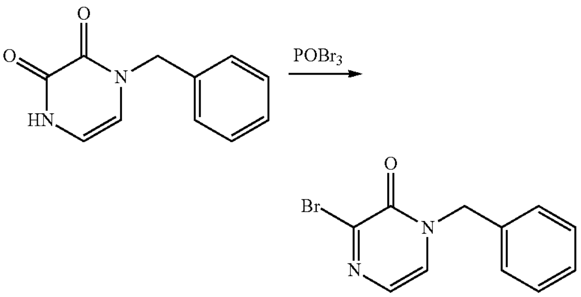
FLEITZ, F. J.; LYLE, T.A.; ZHENG, N.; ARMSTRONG, J. D. III; VOLANTE, R. P.; Synth Commun 2000, 30 (17), 3171-3180.
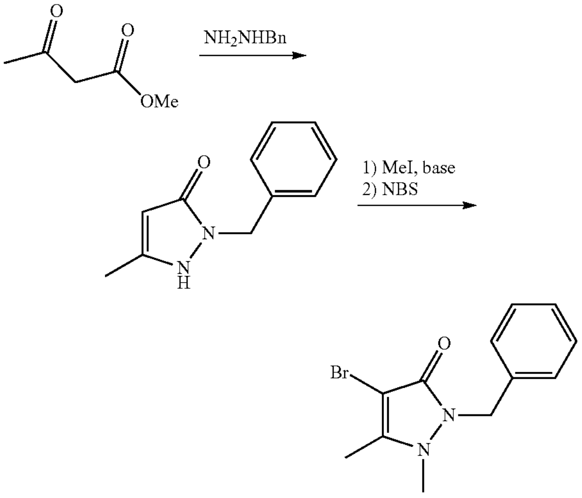
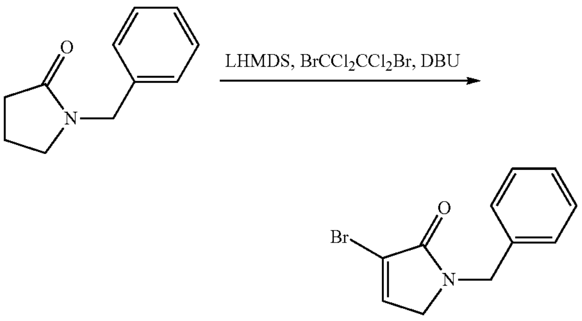
NEWHOUSE, B. J.; MEYERS, A. I.; SIRISOMA, N. S.; BRAUN, M. P.; JOHNSON, C. R.; Synlett 1993, (8), 573-574.
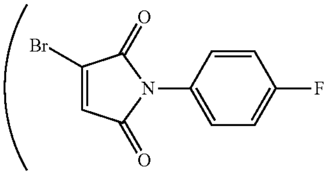
is commercially available
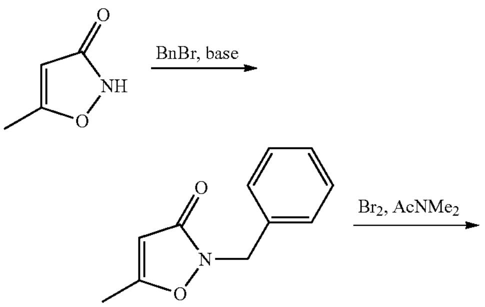

-continued

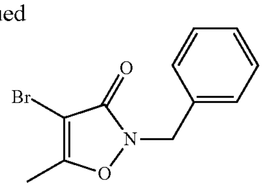

KIM, K.; RYU, E. K.; SEO, Y.; Tetrahedron Lett 1990, 31 (35), 5043-5044.

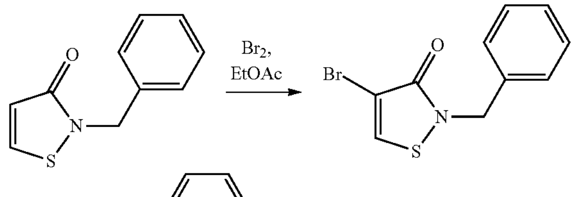

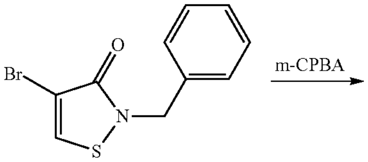

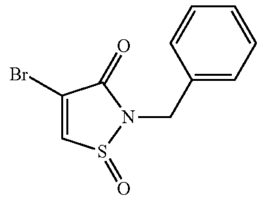

and

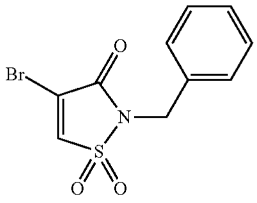

EXAMPLE 1

5.1

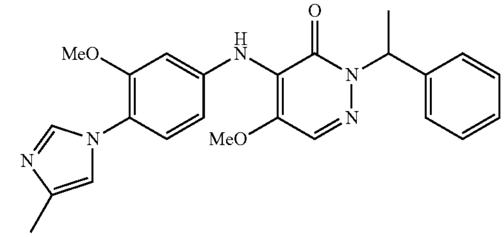

Step A:

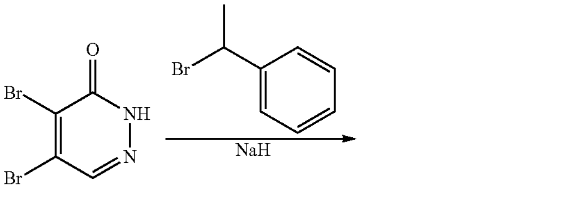

5.1a

NaH (0.397 g, 9.06 mmol, 1.15 eq) was added to a solution of compound 5.1a (2.0 g, 7.88 mmol, 1 eq) in DMF (10 mL) at 0° C. The mixture was stirred for 15 minutes before alpha-methyl benzyl bromide (1.34 mL, 9.85 mmol, 1.25 eq) was added dropwise. The resulting reaction mixture was stirred at room temperature over night. The mixture was diluted with EtOAc (200 mL) and HCl solution (30 mL, 0.5 M). The organic layer was washed with water (3×), brine, dried over $MgSO_4$, and concentrated to give the crude product. The crude residue was purified by column chromatography eluting with EtOAc/hexanes to yield compound 5.1b (2.43 g, 86%).

Step B:

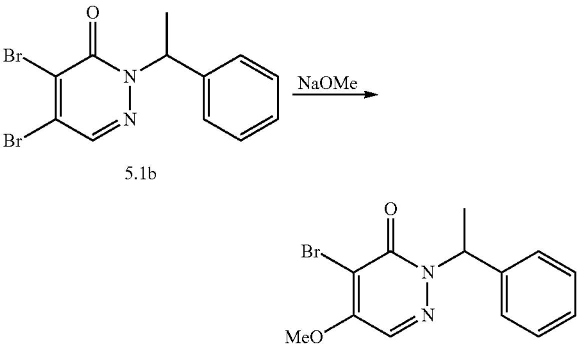

5.1b 5.1c

NaOMe (0.555 mL, 25 wt % in MeOH) was added to a solution of compound 5.1b (0.8 g, 2.24 mmol, 1 eq) in MeOH (4.0 mL) at 0° C. The mixture was stirred for 6 hours at room temperature before solvent was removed under reduced pressure. The crude residue was purified by column chromatography eluting with EtOAc/hexanes to yield compound 5.1c (0.7 g, 100%).

Step C:

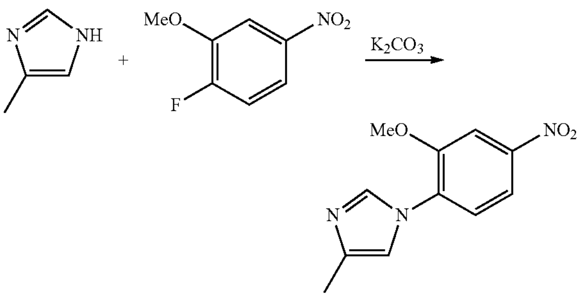

5.1d

Two equivalent of 4-methylimidazole, 1 equivalent of 3-methoxy-4-fluoro-nitrobenzene and 5 eq. of $K_2CO_3$ were stirred in $CH_3CN$ at room temperature over night. The reaction mixture was filtered and concentrated under reduced pressure. The crude product was recrystallized with EtOAc to give desired product 5.1d.

Step D:

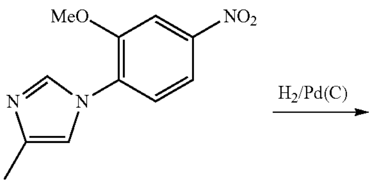

5.1d

-continued

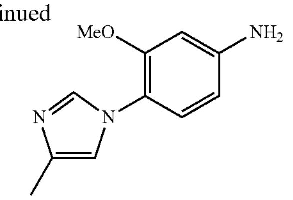

5.1e

Compound 5.1d was hydrogenated with hydrogen balloon in the presence of Pd(C) as the catalyst (10 wt %) in MeOH over night. The mixture was filtered and concentrated under reduced pressure to give product 5.1e.

Step E:

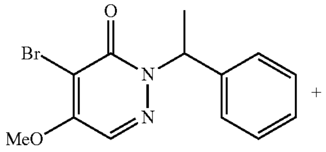

5.1c

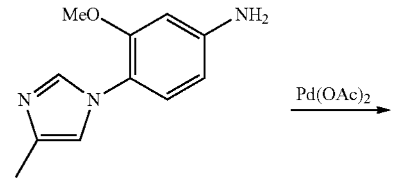

5.1e

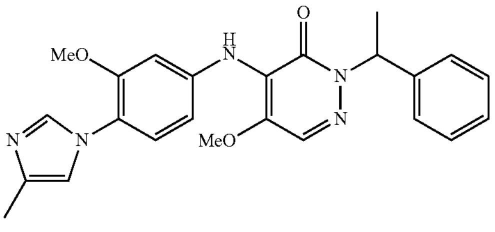

5.1

A mixture of compound 5.1c (36.5 mg, 0.118 mmol), 5.1e (24 mg, 0.118 mmol), $Pd(OAc)_2$ (1.06 mg, 0.00472 mmol), BINAP (2.94 mg, 0.00472 mmol) and $K_2CO_3$ (81.4 mg, 0.59 mmol) in toluene was vacuum/nitrogen exchange degassed for 3 times before it was heated at 120° C. for 48 hours. The reaction mixture was cooled and diluted with EtOAc (50 mL) and $NH_4Cl$ solution (10 mL). The organic layer was washed with water, brine, dried over $MgSO_4$, and concentrated to give the crude product. The crude residue was purified by Gilson reverse phase HPLC to yield Compound 5.1 (37 mg, 73%). Electrospray MS $[M+1]^+$432.2.

EXAMPLE 2

Following a procedure similar to that of Example 1, compounds 6.1, 7.1, 10.1-16.1, 22.1-23.1, 27.1-31.1, 34.1-37.1, 50.1-54.1, 56.1-58.1, 61.1-63.1, 65.1-68.1, 71.1, 76.1, 82.1, and 83.1 were prepared starting with the corresponding bromide or iodide.

EXAMPLE 3

If one were to follow a procedure similar to that of Example 1 one could prepare compounds 119.1-182.1, and 191.1-254.1 starting with the corresponding bromide or iodide.

EXAMPLE 4

8.1

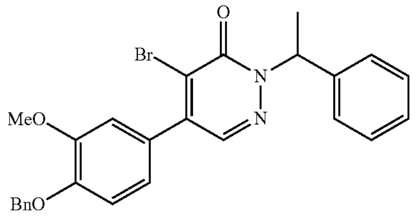

9.1

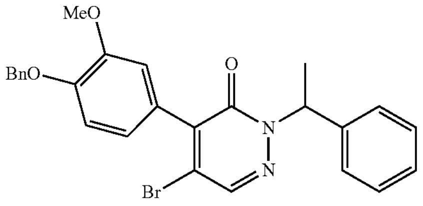

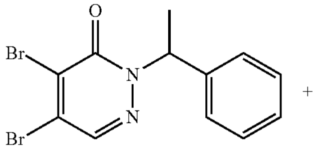

+

5.1b

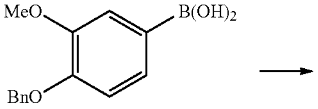

8.1a

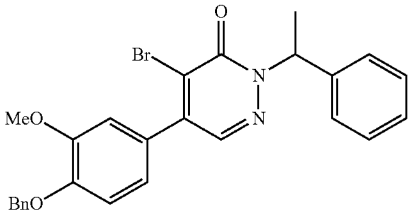

8.1

+

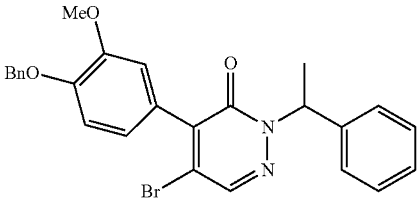

9.1

Compound 5.1b (1.3 g, 3.63 mmol, 1 eq) and 8.1a (1.03 g, 3.99 mmol, 1.1 eq), $Pd(PPh_3)_4$ (0.63 g, 0.545 mmol, 0.15 eq) and $Na_2CO_3$ (10.89 mL, 21.8 mmol, 2N, 6.0 eq) in toluene (10 mL) and MeOH (5 mL) were mixed together in a microwave tube and reacted in a microwave reactor for 1 hour (110° C.). The mixture was diluted with EtOAc (200 mL) and $NaHCO_3$ solution (50 mL). The organic layer was washed with water, brine, dried over $MgSO_4$, and concentrated to give the crude product. The crude residue was purified by column chromatography eluting with EtOAc/hexanes to yield compound 8.1 (0.35 g, Electrospray MS $[M+1]^+$491.0.) and compound 9.1 (0.54 g, Electrospray MS $[M+1]^+$491.0.).

EXAMPLE 5

55.1

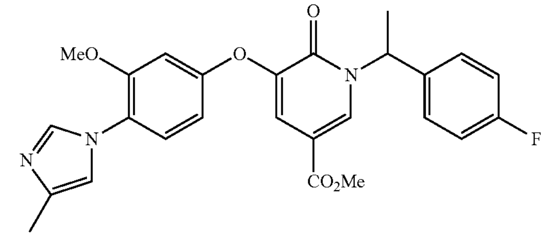

Step A:

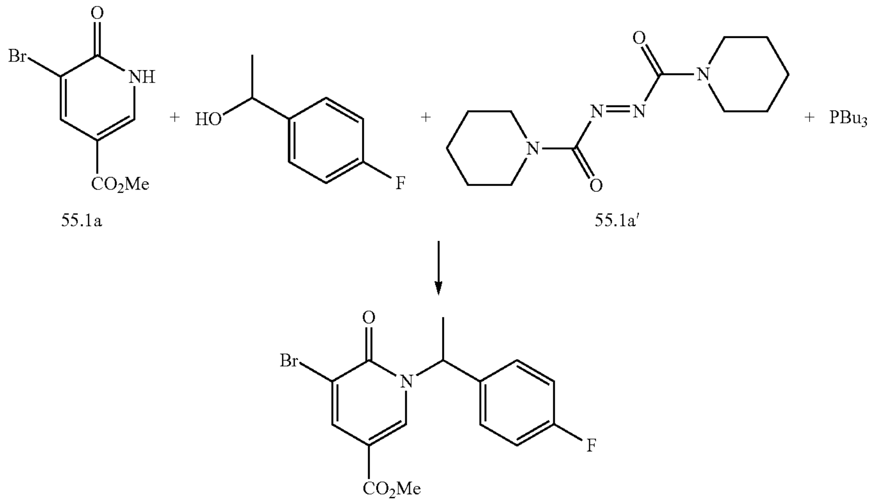

55.1a 55.1a'

55.1b

A mixture of compound 55.1a (0.5 g, 2.15 mmol), 4-fluoro-alpha-methylbenzyl alcohol (0.36 g, 2.58 mmol, 1.2 eq), reagent 55.1a' (0.65 g, 2.58 mmol, 1.2 eq) and $PBu_3$ (0.644 mL, 2.58 mmol, 1.2 eq) in THF (6.0 mL) was stirred at 50° C. overnight. The mixture was then filtered through a short pad of celite and washed with EtOAc. Solvent was concentrated to give the crude product. The crude residue was purified by column chromatography eluting with EtOAc/Hexane to yield compound 55.1b (0.28 g).

Step B:

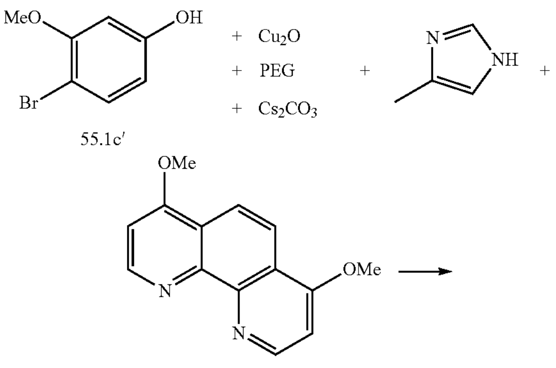

55.1c'

55.1c''

-continued

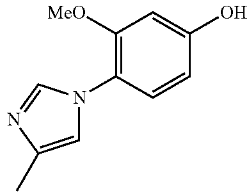

55.1c

A mixture of compound 55.1c' (2.03 g, 10 mmol), $Cu_2O$ (0.288 g, 2 mmol), PEG (4.0), $Cs_2CO_3$ (9.77 g, 30 mmol), 4-methylimidazole (0.98 g, 12 mmol) and 55.1c" (0.72 g, 3 mmol) in NMP (15 mL) was vacuum-nitrogen exchange degassed and stirred in a sealed tube at 120° C. for 48 hours. The mixture was cooled to room temperature and diluted with $CH_2Cl_2$ followed with addition of silica gel. The mixture was stirred for 20 minutes and filtered. The organic layer was washed with water (3×), brine, dried over $MgSO_4$, and concentrated to give the crude product. The crude residue was purified by column chromatography eluting with $CH_2Cl_2$/MeOH to yield compound 55.1c (0.2 g).

Step C:

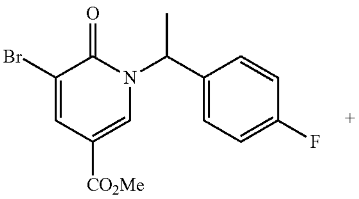

55.1b

-continued

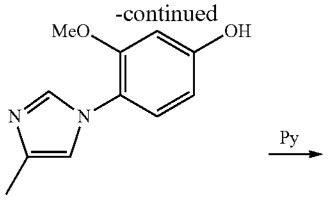

55.1c
$+K_2CO_3$
$+CuBr.Me_2S$

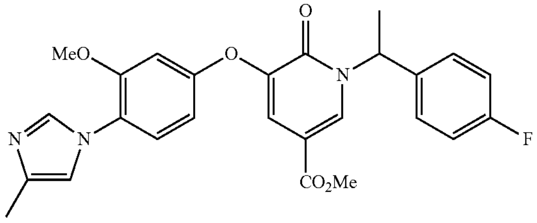

55.1

A mixture of compound 55.1b (48 mg, 0.141 mmol), 55.1c (28.8 mg, 0.141 mmol), $K_2CO_3$ (0.117 g, 0.846 mmol) and $CuBr.Me_2S$ (58 mg, 0.282 mmol) in pyridine (1.0 mL) were heated at 140° C. overnight. The mixture was diluted with EtOAc (50 mL) and $NH_4Cl$ solution (10 mL, saturated). The organic layer was washed with water, brine, dried over $MgSO_4$, and concentrated to give the crude product. The crude residue was purified by Gilson reverse phase HPLC to yield compound 55.1 (4 mg). Electrospray MS $[M+1]^+$478.3.

EXAMPLE 6

17.1

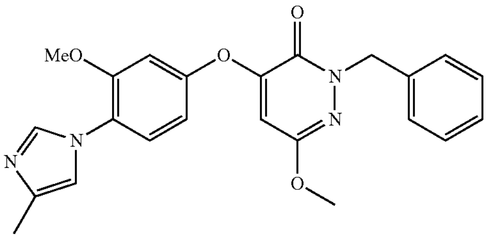

Step A:

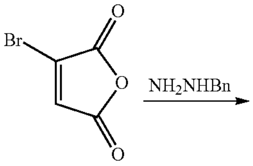

17.1a'

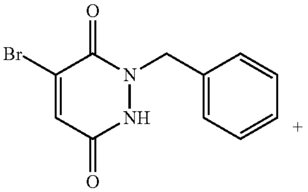

17.1a

+

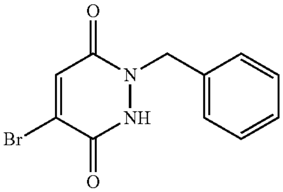

17.1b

Compound 17.1a' (3.0 g, 16.95 mmol) and benzylhydrazine (3.47 g, 17.8 mmol) in water (20 mL) was stirred and heated at 100° C. overnight. The mixture was cooled to room temperature and filtered to collect the solid as a mixture of compound 17.1a and compound 17.1b (4.0 g).

Step B:

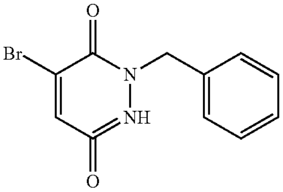

17.1a

+

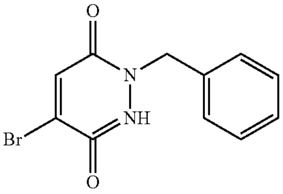

17.1b

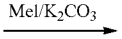

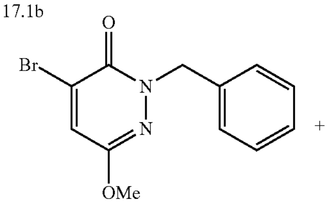

17.1c

+

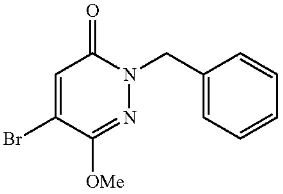

17.1d

A mixture of compound 17.1a and compound 17.1b (1.5 g, 5.34 mmol), MeI (0.646 mL, 10.68 mmol) and $K_2CO_3$ (2.21 g, 16.0 mmol) in DMF (6.0 mL) was stirred at room temperature overnight. The mixture was diluted with EtOAc (150 mL) and HCl solution (30 mL, 0.5 M). The organic layer was washed with water (3×), brine, dried over $MgSO_4$, and concentrated to give the crude product. The crude residue was purified by column chromatography eluting with EtOAc/hexanes to yield compound 17.1c (0.75 g) and compound 17.1d (0.7 g).

Step C:

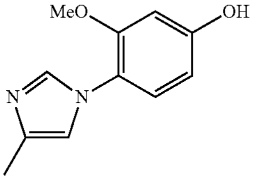

55.1c

+

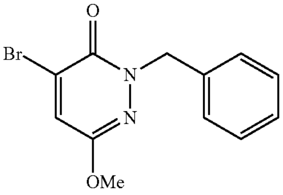

17.1c

-continued

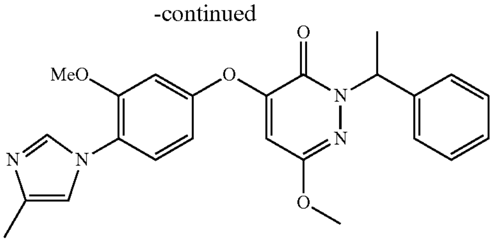

17.1

A mixture of compound 55.1c (21.2 mg, 0.104 mmol) and compound 17.1c (30.6 mg, 0.104 mmol), and $K_2CO_3$ (71.8 mg, 0.52 mmol) in DMF (1.5 mL) was stirred at 80° C. overnight. The mixture was diluted with EtOAc (50 mL) and $NH_4Cl$ solution (10 mL, saturated). The organic layer was washed with water (3×), brine, dried over $MgSO_4$, and concentrated to give the crude product. The crude residue was purified by Gilson reverse phase HPLC to yield compound 17.1 (25 mg). Electrospray MS $[M+1]^+$419.2.

EXAMPLE 7

18.1

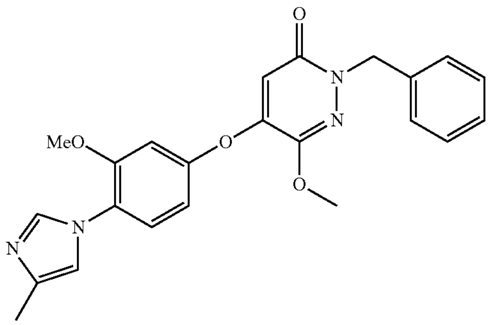

Following a procedure similar to that of Example 6, the compound 18.1 was prepared from compound 17.1d as starting material. Electrospray MS $[M+1]^+$419.2.

EXAMPLE 8

Following a procedure similar to that of Example 55.1, one can prepare compounds 183.1-190.1, 255.1-262.1 starting with the corresponding bromide or iodide.

EXAMPLE 9

77.1

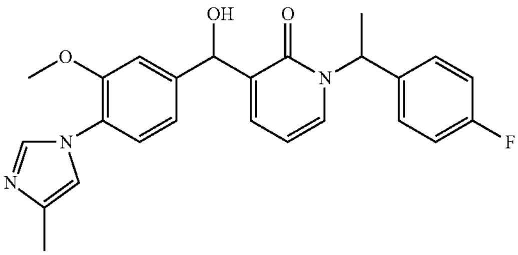

Step A:

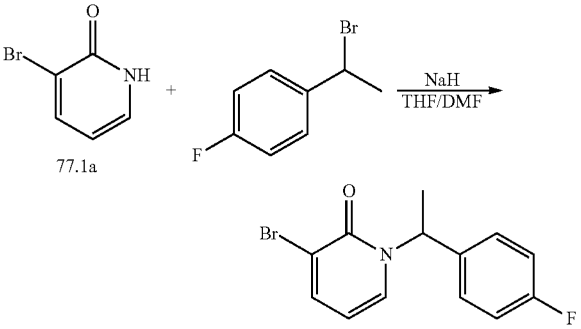

77.1a 77.1b

To a solution of 77.1a (4.0 g, 22.98 mmol) in THF/DMF (20/20 ml) was added NaH (60%, 1.10 g, 27.6 mmol) at 0° C. and stirred for 10 min, followed with addition of 4-fluoro alpha-methyl benzyl bromide (5.57 g, 27.6 mmol). The resulting mixture was stirred overnight, then quenched with saturated aqueous $NH_4Cl$, extracted with EtOAc (3×). The combination of organic layers was washed with brine, dried ($Na_2SO_4$), concentrated and purified by flash chromatography to afford product 77.1b as colorless oil (4.0 g, 59%).

Step B:

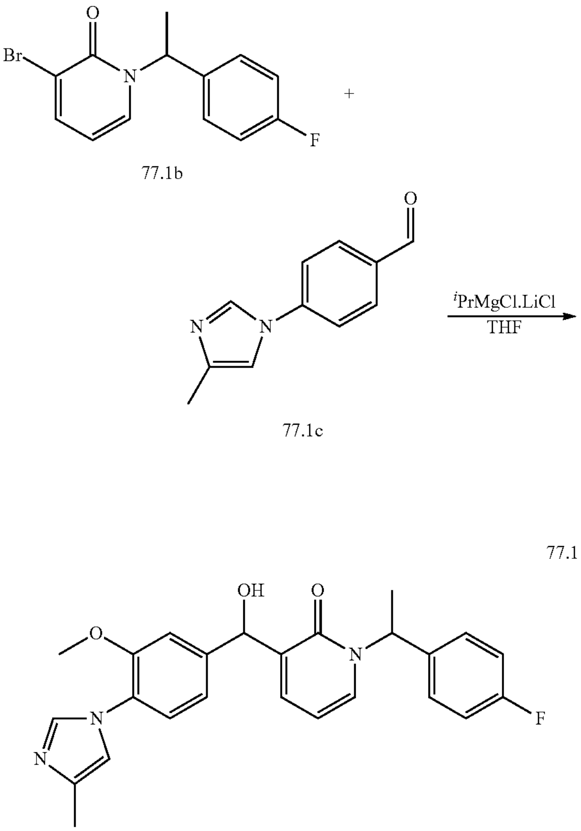

77.1b 77.1c 77.1

To a solution of 77.1b (300 mg, 1.01 mmol) in THF (5 ml) was added $^i$PrMgCl.LiCl (1M in THF, 1.3 ml, 1.3 mmol) and stirred at room temperature for 10 min, followed with addition of 77.1c (216 mg, 1.01 mmol). The resulting mixture was stirred overnight, then quenched with saturated aqueous $NH_4Cl$, extracted with EtOAc (3×). The combination of organic layers was washed with brine, dried ($Na_2SO_4$), concentrated and purified by flash chromatography to afford product 77.1 as colorless oil (210 mg, 48%). $^1H$ NMR ($CDCl_3$, ppm) 7.39-7.36 (m, 1H), 7.31-7.25 (m, 3H), 7.20-7.10 (m, 2H), 7.09-7.02 (m, 4H), 6.44-6.35 (m, 1H), 6.28-6.20 (m, 1H), 5.85 (d, 1H), 3.89 (d, 3H), 2.47 (s, 3H), 1.75-1.70 (m, 3H); MS (ES-LCMS, M+1) 434.2. Retention time: 2.55 min.

EXAMPLE 10

78.1

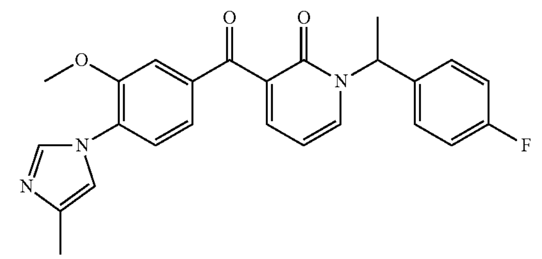

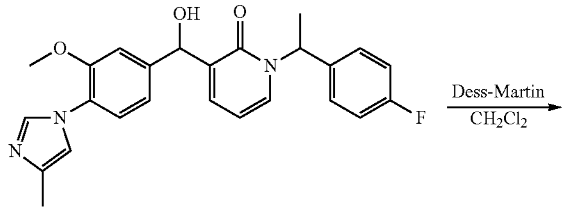

77.1

78.1

To a solution of 77.1 (300 mg, 0.69 mmol) in $CH_2Cl_2$ (5 ml) was added Dess-Martin Periodinane (440 mg, 1.04 mmol) and stirred overnight. Then it was diluted with $CH_2Cl_2$, washed with saturated aqueous $NaHCO_3$, dried ($Na_2SO_4$), concentrated and purified by flash chromatography to afford product 78.1 as colorless oil (200 mg, 67%). $^1H$ NMR ($CDCl_3$, ppm) 7.82 (d, 1H), 7.59 (s, 1H), 7.51-7.47 (m, 1H), 7.46-7.39 (m, 2H), 7.34-7.28 (m, 2H), 7.14 (s, 1H), 7.10-7.03 (m, 2H), 6.42-6.37 (m, 1H), 6.37-6.30 (m, 1H), 3.91 (s, 3H), 2.47 (s, 3H), 1.75 (d, 3H); MS (ES-LCMS, M+1) 432.2. Retention time: 2.48 min.

EXAMPLE 11

80.1

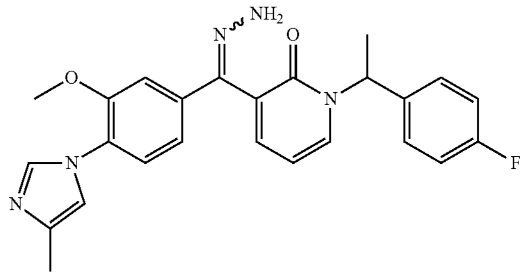

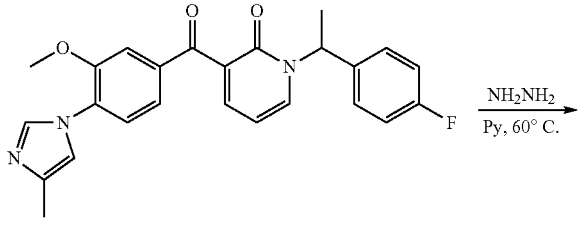

78.1

80.1

A mixture of 78.1 (150 mg, 0.35 mmol) and $NH_2NH_2$ (111 mg, 3.4 mmol) in pyridine (1.5 ml) was heated at 60° C. overnight. Then it was concentrated under vacuum to remove pyridine and the residue was purified by flash chromatography to afford product 80.1 as colorless oil (70 mg, 45%). $^1H$ NMR ($CDCl_3$, ppm) 7.50 (s, 1H), 7.40-7.37 (d, 1H), 7.36-7.32 (m, 3H), 7.16-7.02 (m, 3H), 6.93-6.84 (m, 2H), 6.53-6.46 (m, 1H), 6.34-6.30 (m, 1H), 5.94 (s, 2H), 3.86 (s, 3H), 2.29 (s, 3H), 1.78 (d, 3H); MS (ES-LCMS, M+1) 446.2. Retention time: 2.52 min.

EXAMPLE 12

79.1

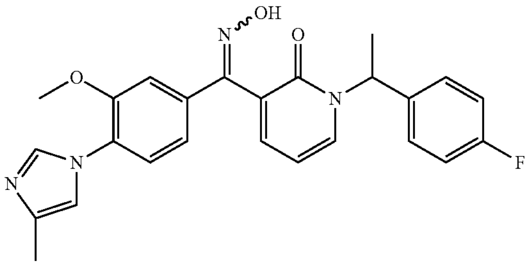

-continued

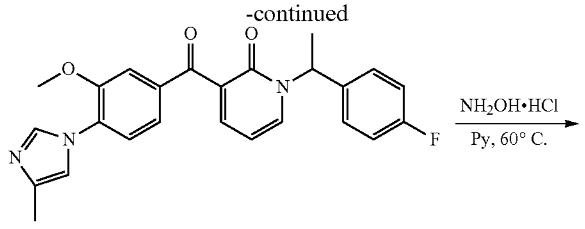

78.1

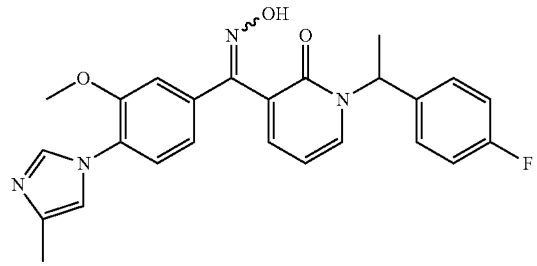

79.1

A mixture of 78.1 (50 mg, 0.12 mmol) and $NH_2OH.HCl$ (94 mg, 1.16 mmol) in pyridine (1.5 ml) was heated at 60° C. overnight. Then it was concentrated under vacuum to remove pyridine and the residue was purified by flash chromatography to afford product 79.1 as colorless oil (30 mg, 58%). $^1$H NMR ($CDCl_3$, ppm): □□□□s, 1H), 7.54-7.18 (m, 7H), 7.17-6.88 (m, 4H), 6.48-6.32 (m, 2H), 3.81 (s, 3H), 2.45 (s, 3H), 1.75 (d, 3H); MS (ES-LCMS, M+1) 447.2. Retention time: 2.50 min.

EXAMPLE 13

84.1

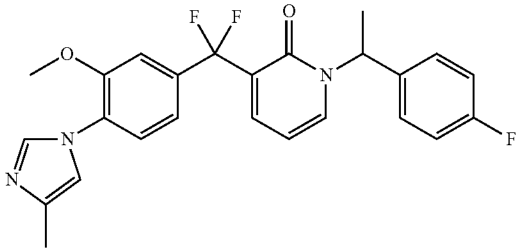

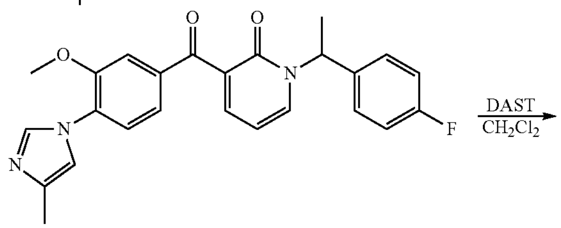

78.1

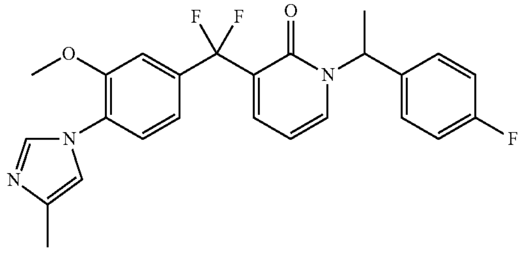

84.1

A mixture of 78.1 (200 mg, 0.46 mmol) and DAST (0.37 ml, 2.3 mmol) in $CH_2Cl_2$ (5 ml) was stirred at room temperature overnight. Then it was diluted with $CH_2Cl_2$, quenched with saturated aqueous $NaHCO_3$. The layers were partitioned and the organic layer was washed with brine, dried ($Na_2SO_4$), concentrated and purified by flash chromatography to afford product 84.1 as off-white powder (110 mg, 52%). $^1$H NMR ($CDCl_3$, ppm) 7.74-7.69 (m, 1H), 7.60 (s, 1H), 7.41-7.37 (m, 2H), 7.36-7.27 (m, 3H), 7.11-7.04 (m, 2H), 6.97 (s, 1H), 6.42-6.35 (m, 1H), 6.34-6.29 (m, 1H), 3.90 (s, 3H), 2.30 (s, 3H), 1.75 (d, 3H); MS (ES-LCMS, M+1) 454.2. Retention time: 2.47 min.

EXAMPLE 14

85.1

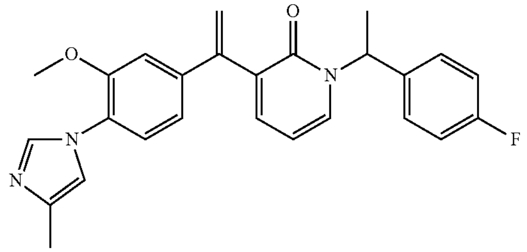

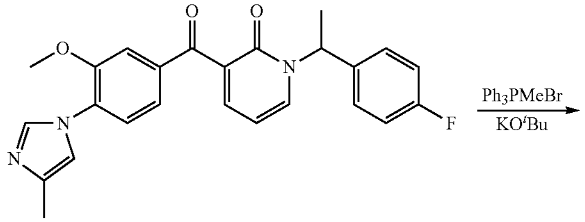

78.1

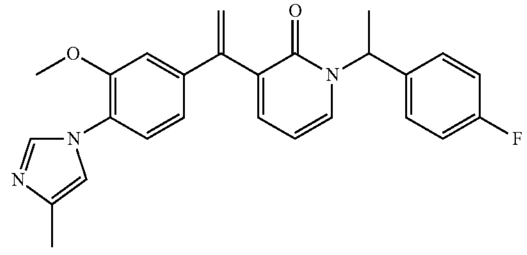

85.1

A mixture of $Ph_3PMeBr$ (124 mg, 0.35 mmol) and $KO^tBu$ (39 mg, 0.35 mmol) in THF (2 ml) was stirred at room temperature for 1 h, followed with addition of 78.1 (100 mg, 0.23 mmol) and heated at reflux overnight. It was then quenched by 1 N HCl, extracted with EtOAc, dried ($Na_2SO_4$), concentrated and purified by flash chromatography to afford product 85.1 as white powder (10 mg, 10%). $^1$H NMR ($CDCl_3$, ppm) 7.39-7.12 (m, 5H), 7.09-6.87 (m, 5H), 6.47-6.35 (m, 1H), 6.23-6.17 (m, 1H), 5.68 (d, 2H), 3.81 (s, 3H), 2.30 (s, 3H), 1.70 (d, 3H); MS (ES-LCMS, M+1) 430.2. Retention time: 2.86 min.

EXAMPLE 15

81.1

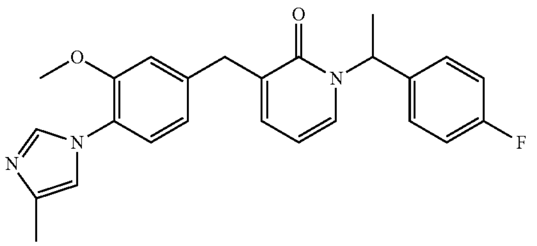

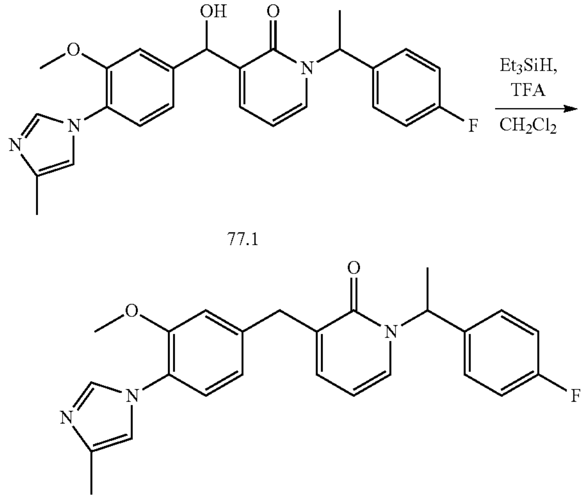

77.1

81.1

To a solution of 77.1 (100 mg, 0.23 mmol) in $CH_2Cl_2$ (5 ml) was added $Et_3SiH$ (268 mg, 2.31 mmol) and TFA (0.18 ml, 2.31 mmol) and stirred overnight. Then it was concentrated and the residue was purified by flash chromatography to afford product 81.1 as colorless oil (60 mg, 62%). $^1H$ NMR ($CDCl_3$, ppm) 7.32-7.27 (m, 2H), 7.18 (d, 1H), 7.10-7.00 (m, 5H), 6.94-6.90 (m, 2H), 6.47-6.40 (m, 1H), 6.15-6.07 (m, 1H), 4.00-3.84 (m, 2H), 3.82 (s, 3H), 2.35 (s, 3H), 1.70 (d, 3H); MS (ES-LCMS, M+1) 418.2. Retention time: 2.67 min.

EXAMPLE 16

Following a procedure similar to that of Examples 77.1 and 78.1, compounds 1.1-4.1, 19.1-21.1, 24.1-26.1, 32.1, 33.1, 38.1, 39.1, 41.1-49.1, 87.1-112.1 were prepared starting with the corresponding bromide or iodide.

EXAMPLE 17

59.1

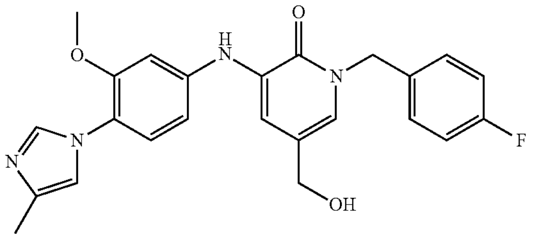

-continued 60.1

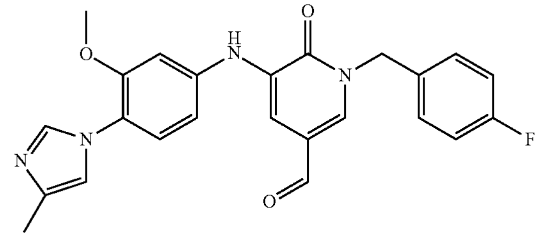

Step A:

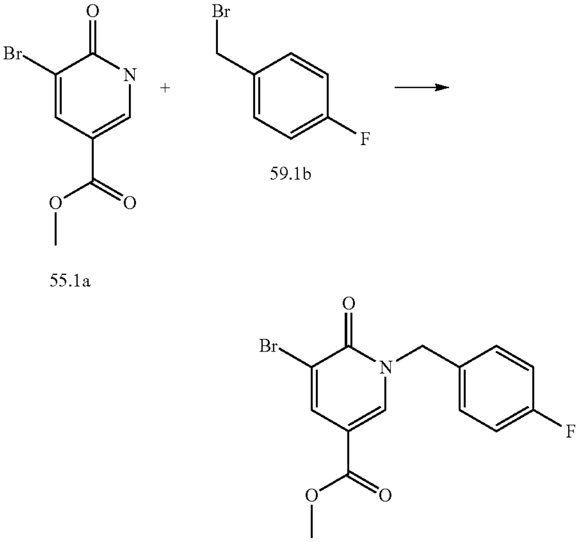

59.1b 55.1a 59.1c

The mixture 55.1a (1.0 g, 4.31 mmol) and $K_2CO_3$ (1.43 g, 10.4 mmol) in DMF (5 ml) was stirring at RT for 10 minutes before the addition of Bromide 59.1b (0.644 ml, 5.17 mmol). The resultant mixture was kept stirring at RT for 16 h. To the mixture was added EtOAc (30 ml) and $H_2O$ (30 ml), the organic was separated and washed with brine (20 ml), dried over anhydrous $MgSO_4$, and concentrated. The residue was purified via Biotage (EtOAc-Hexane=1:4), obtained 59.1c as a white solid (1.32 g). $MH^+$340.2

Step B:

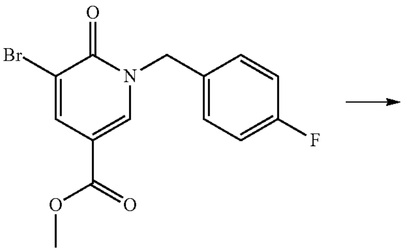

59.1c

-continued

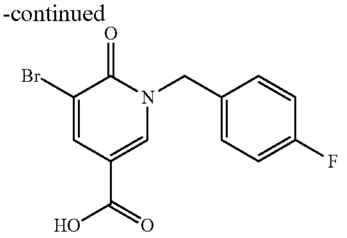

59.1d

To the solution of 59.1c (680 mg, 2 mmol) in MeOH (4 ml) at RT was added 2N NaOH (4 ml). The resultant mixture was kept stirring at RT for 16 h. The organic solvent was removed via rotavapor, the aqueous layer was extracted with EtOAc (5 ml) once, then the aqueous layer was acidified with 2N HCl to pH 2-3. White precipitate formed. Collected the solid, washed with $H_2O$, dried, obtain a white powder 59.1d. $MH^+$326/328

Step C:

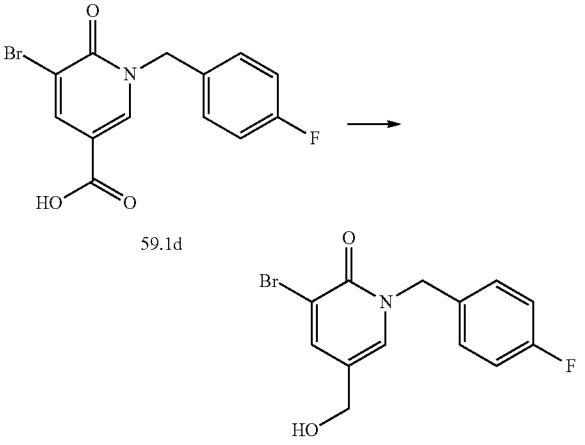

59.1d 59.1e

The solution of 59.1d (530 mg, 1.63 mmol) in DCM (3 ml) and Pyridine (1.63 mmol) was cooled in an ice-salt bath, Cyanuric fluoride (3.25 mmol) was added dropwise, and the mixture was kept stirring at 0° C. for 1 h. Ice water was added to the mixture, the aqueous was extracted once more with DCM (10 ml), the combined organic was washed with ice water (10 ml), dried over anhydrous $MgSO_4$, and concentrated. The residue was taken up in DCM (3 ml), $NaBH_4$ (120 mg, 3.25 mmol) was added, followed by the addition of MeOH (4 ml). The mixture was kept stirring at RT for 16 h. 1N $H_2SO_4$ was added to neutralize the mixture, extracted with DCM (20 ml×2), the combined organic was washed with 1N $H_2SO_4$, dried over anhydrous $MgSO_4$, and concentrated. The residue was purified via Biotage (EtOAc-Hexane=2:1), obtained 59.1e as a white solid (282 mg). $MH^+$313/315

Step D:

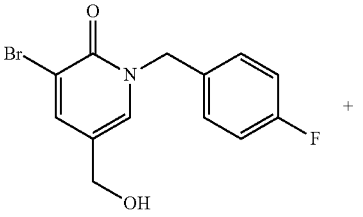

+

59.1e

-continued

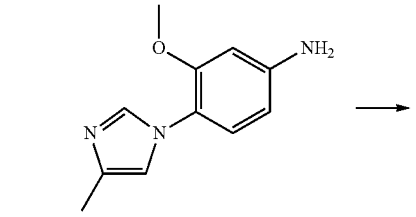

5.1e

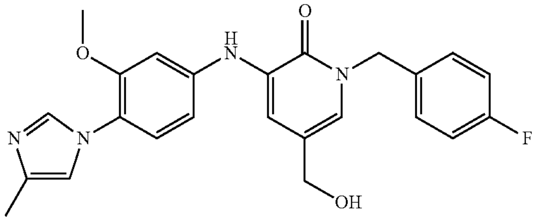

59.1

+

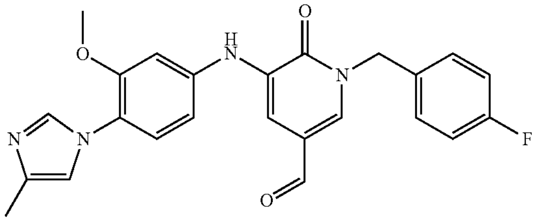

60.1

To the mixture of 59.1e (60 mg, 0.192 mmol) in toluene (100 ml) was added compound 5.1e (40 mg, 0.192 mmol) and solid $K_2CO_3$ (132 g, 0.960 mmol), followed by the addition of BINAP (4.8 mg, 4% mol) and $Pd(OAc)_2$ (1.7 mg, 4% mol), the resultant mixture was kept stirring at 120° C. for 48 h. The mixture was cooled to RT, EtOAc (10 ml) and $NH_4Cl$ (6 ml) were added, the insoluble material was filtered off thru Celite. The filtrate was separated; the aqueous was extracted once more with EtOAc (6 ml). The combined organic was dried over anhydrous $MgSO_4$, and concentrated. The residue was purified via Gilson to obtain 59.1 as yellow syrup (3.6 mg). $MH^+$435 and 60.1 as a yellow powder (8.2 mg). $MH^+$ 433

EXAMPLE 18

64.1

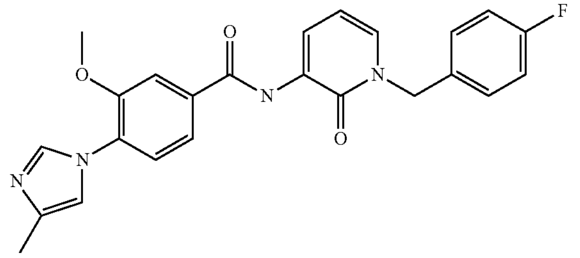

Step A:

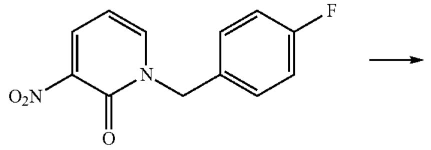

64.1a

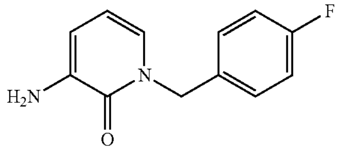

64.1b

To the solution of 64.1a (3.6 g, 14.5 mmol) in mixed solvent of THF (100 ml)-EtOH (30 ml) was added 50% Raney Nickel (aqueous slurry) (0.36 g, 10% wt), and the mixture was placed on the Parr Shaker, hydrogenated at $P_0$=40 Psi for 16 h. The spent catalyst was filtered off, and the filtrate was concentrated, obtain 64.1b as a light yellow solid (3.31 g). $MH^+$219

Step B:

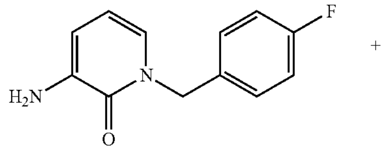

64.1b

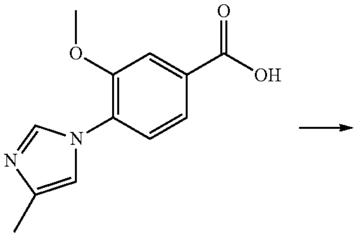

64.1c

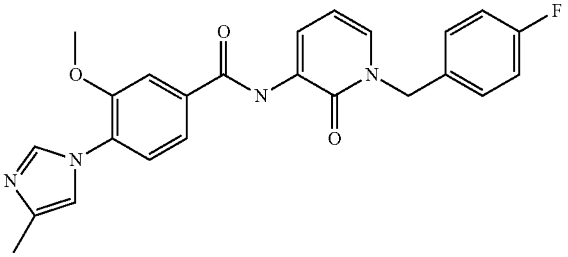

64.1

Compound 64.1b (130 mg, 0.596 mmol), 64.1c (138 mg, 0.596 mmol) were mixed in DCM (4 ml) at RT, followed by the addition of HOBT (96 mg, 0.715 mmol), EDC (136 mg, 0.715 mmol) and DIEA (300 μL, 1.2 mmol). The resultant mixture was kept stirring at RT for 16 h. The mixture was diluted with $CH_2Cl_2$ (10 ml), washed with $NaHCO_3$ (Sat.) (6 ml), and brine (6 ml), respectively, dried over anhydrous $MgSO_4$, and concentrated. The residue was purified via FCC (DCM/MeOH (2N $NH_3$)=30:1), followed by PTLC (DCM/MeOH (2N $NH_3$)=20:1), obtained 64.1 as a cream colored solid. $MH^+$433

EXAMPLE 19

72.1

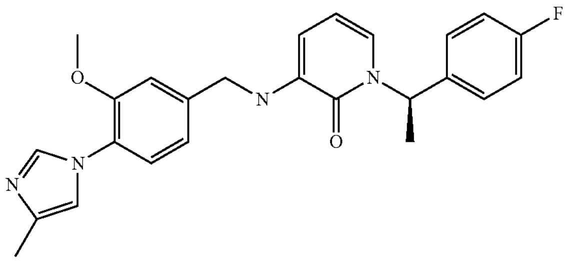

Step A:

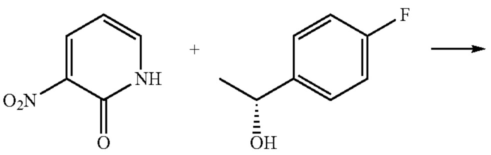

72.1a 72.1b

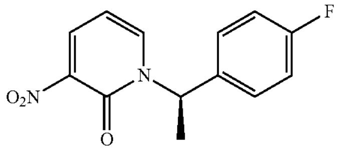

72.1c

The mixture of 72.1a (1.0 g, 7.14 mmol) and 72.1b (0.5 g, 3.57 mmol) in THF (10 ml) was stirring at 0° C., $PBu_3$ (1.78 ml, 7.14 mmol) was added dropwise to the mixture, the mixture was stirring at 0° C. for 0.5 h before the addition of ADDP (1.80 g, 7.14 mmol). The resultant mixture was kept stirring at 0° C. for 0.5 h, the slowly warmed up to 80° C., and kept stirring at 80° C. for 48 h. The mixture was cooled to RT, the white precipitate was filtered off, the filtrate was concentrated and purified via ISCO (EtOAc-Hexane=1:6) to obtain 72.1c as a light orange liquid. (310 mg). $MH^+$263

Step B:

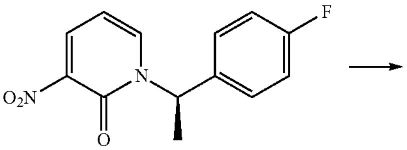

72.1c

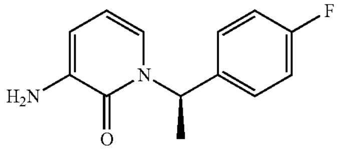

72.1d

Following a procedure similar to that of Step A of Example 18, 72.1d was prepared from 72.1c.

Step C:

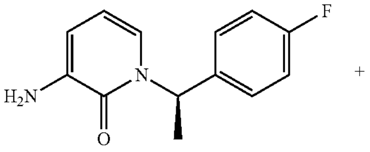

72.1d

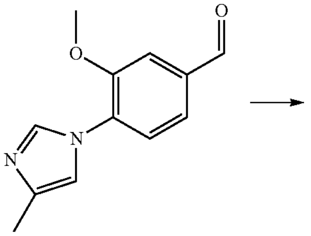

77.1c

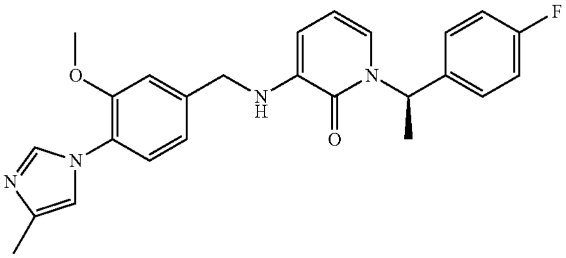

72.1

The mixture of aldehyde 77.1c (14.0 mg, 0.065 mmol) and 72.1d (15.0 mg, 0.065 mmol) in DCM (4 ml) was stirring at RT for 1 h before the addition of $Na(OAc)_3BH$ (28 mg, 0.13 mmol). The resultant mixture was kept stirring at RT for 4 h. The mixture was washed with $NaHCO_3$ (Sat.) (5 ml) and brine (5 ml), respectively, dried over anhydrous $MgSO_4$, and concentrated. The residue was purified via Gilson to obtain 72.1 as a light yellow foam (12 mg). $MH^+$433

EXAMPLE 20

73.1

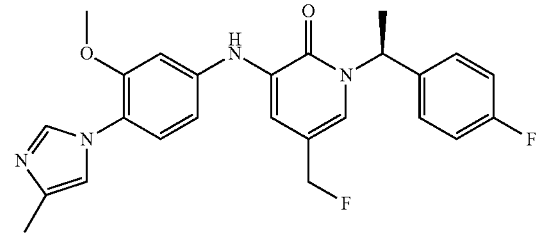

Step A:

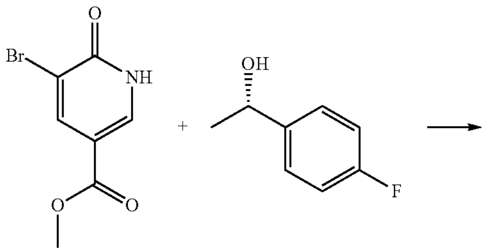

-continued

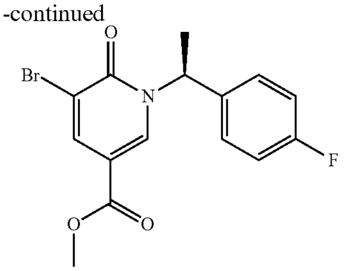

73.1a

Following a procedure similar to that of Step A of Example 19, 73.1A was prepared.

Step B:

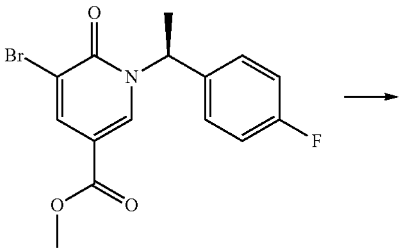

73.1a

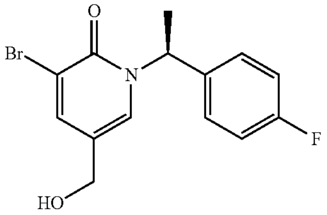

73.1b

Compound 73.1a was converted to compound 73.1b using a procedure similar to that of Example 17, steps B-C.

Step C:

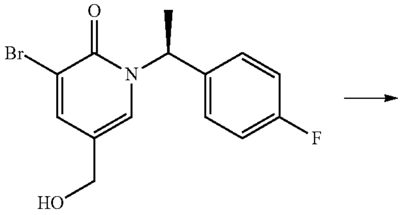

73.1b

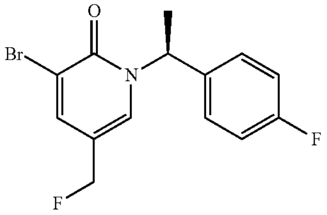

73.1c

DAST (0.690 mmol) was added to the solution of 73.1b (90 mg, 0.276 mmol) in DCM (4 ml), and the resultant mixture was kept stirring at RT for 16 h. The mixture was washed with $H_2O$ (6 ml), $NaHCO_3$ (Sat. 6 ml), respectively, dried over anhydrous $MgSO_4$ and concentrated. The residue was purified via ISCO to obtain 73.1c as a clear syrup (83 mg). $MH^+$328

Step D:

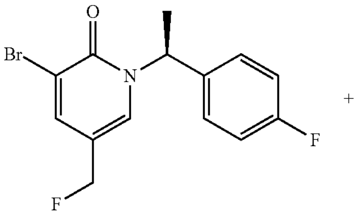

73.1c

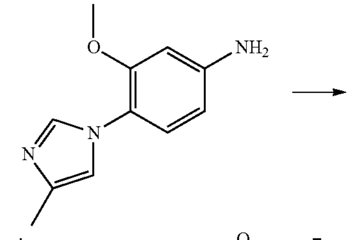

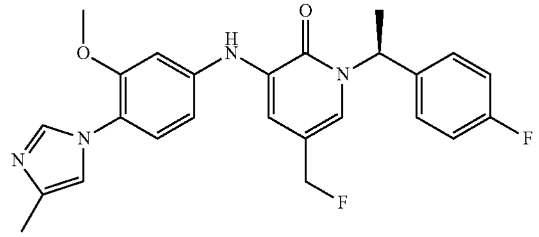

73.1

Compound 73.1c was converted to the title compound 73.1 using a procedure similar to that of Example 17, step D.

EXAMPLE 21

74.1

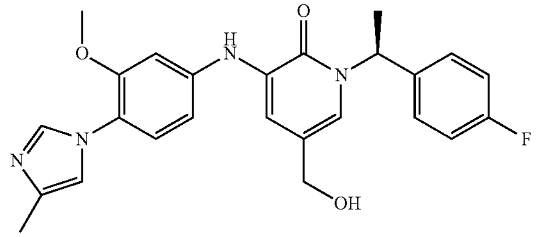

Step A:

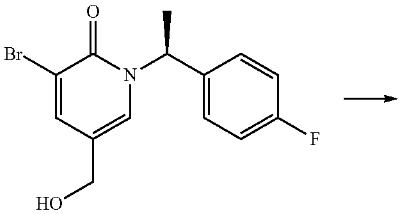

74.1a

-continued

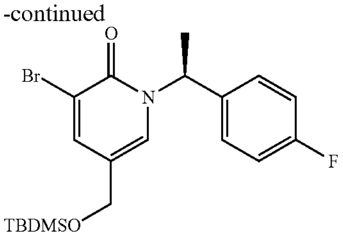

74.1b

To the solution of compound 74.1a (200 mg, 0.613 mmol, DMAP (7.3 mg, 0.06 mmol) and $Et_3N$ (170 μL, 1.22 mmol) in DCM (3 ml) and was added TBDMSCl (140 mg, 0.920 mmol), and the mixture was kept stirring at RT for 2 h. The mixture was washed with $NaHCO_3$ (Sat. 6 ml), dried over anhydrous $MgSO_4$, and concentrated. The residue was purified by ISCO to obtain 74.1b as an offwhie solid (221 mg). $MH^+$442

Step B:

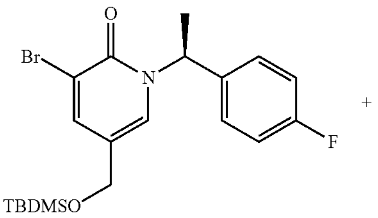

74.1b

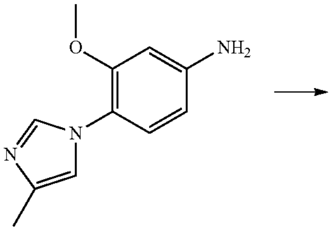

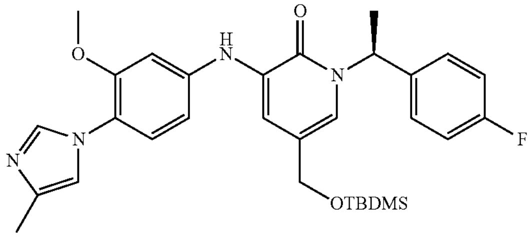

74.1c

Compound 74.1b was converted to compound 74.1c using a procedure similar to that of Example 17, step D.

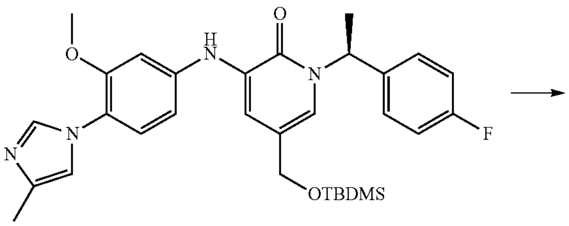

74.1c

-continued

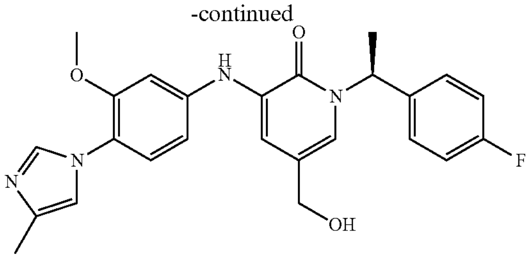

74.1

Step C:

TBAF (114 μL, 0.114 mmol) was added to the solution of 74.1c (32 mg, 0.057 mmol) in THF (1 ml), and the resultant mixture was kept stirring at RT for 4 h. EtOAc (20 ml) and $NH_4Cl$ (Sat. 6 ml) were added, the organic was washed with brine (6 ml), dried over anhydrous $MgSO_4$, and concentrated. The residue was purified via Gilson to obtain 74.1 as a clear syrup (11.2 mg). $MH^+$449

EXAMPLE 22

75.1

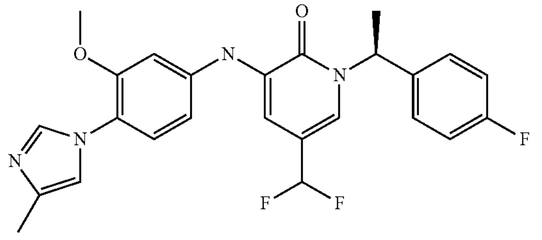

Step A:

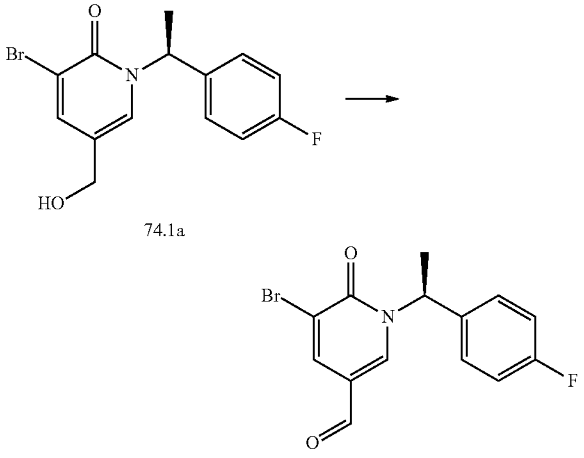

74.1a 75.1a

PDC (190 mg, 0.506 mmol) was added to the solution of 74.1a (110 mg, 0.337 mmol) in DCM (2 ml), and the resultant mixture was kept stirring at RT for 3 h. Celite was added to the mixture and stirred at RT for 5 minutes, the solid was filtered and the filtrate was concentrated. The residue was purified via ISCO (EtOAc-Hexane=1:2) to obtain 75.1a as a clear syrup (23 mg). $MH^+$325

Step B:

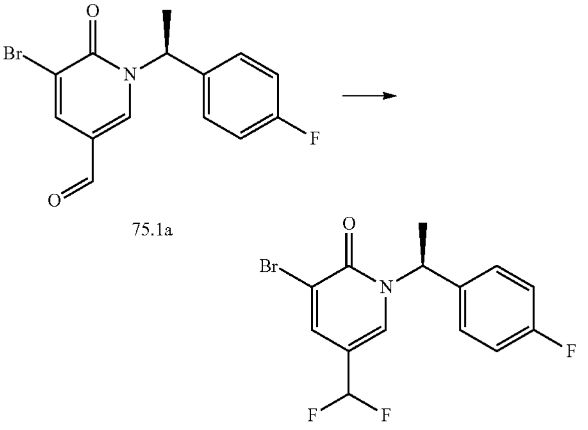

75.1a 75.1b

DAST (23 μL, 0.185 mmol) was added to the solution of 75.1a (20 mg, 0.0617 mmol) in DCM (1 ml), and the resultant mixture was kept stirring at RT for 16 h. EtOAc (20 ml) and $NH_4Cl$ (Sat. 6 ml) were added, the organic was washed with brine (6 ml), dried over anhydrous $MgSO_4$, and concentrated to obtain 75.1b as a yellow syrup (20 mg). $MH^+$348

Step C:

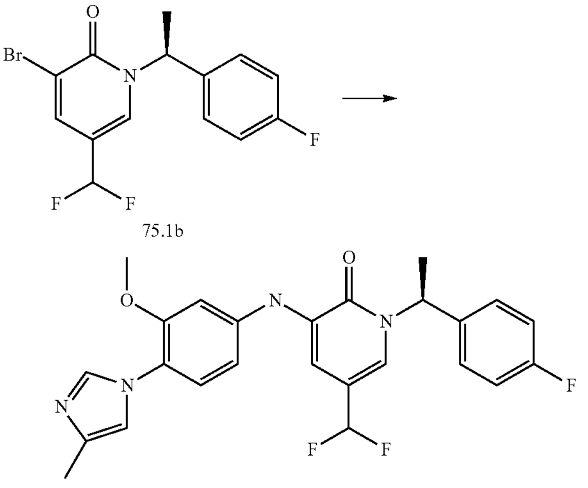

75.1b 75.1

Compound 75.1b was converted to the title compound 75.1 using a procedure similar to that of Example 17, step D.

EXAMPLE 23

117.1

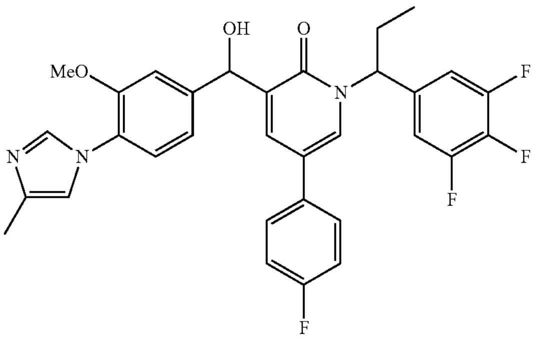

-continued 118.1

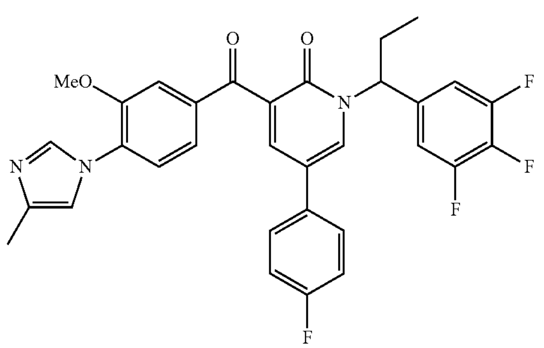

Step A:

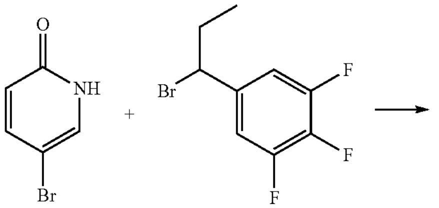

117.1a 117.1b

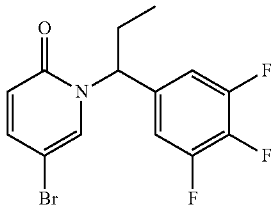

117.1c

To the solution of 117.1a (5.0 g, 28.7 mmol) in 15 ml of DMF was added $K_2CO_3$ (11.9 g, 86.2 mmol) and 117.1b (8.7 g, 34.5 mmol) at r.t. After stirring at r.t. for 24 h, the mixture was extracted with EtOAc and $NH_4Cl$(aq), washed with $H_2O$ and brine, dried over $Na_2SO_4$, filtered, concentrated and purified by Isco to give 5.2 g of 117.1c, yield: 52%.

Step B:

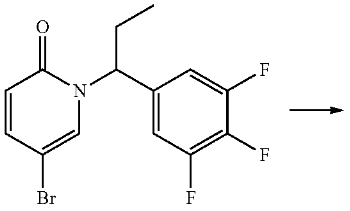

117.1c

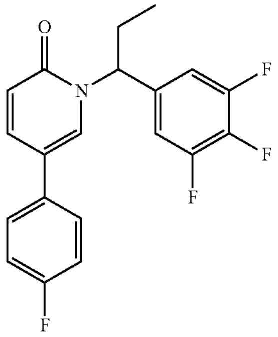

117.1d

To the solution of 117.1c (1.0 g, 2.89 mmol) in 30 ml of DME/$H_2O$ (4:1) were added 4-fluorophenylboronic acid (0.81 g, 5.78 mmol) $PdCl_2(PPh_3)_2$ (0.2 g, 0.289 mmol) and $Na_2CO_3$ (0.92 g, 8.67 mmol) at r.t. After stirring at 90° C. for 3 h and r.t. for 24 h, the mixture was extracted with EtOAc and $H_2O$, washed with brine, dried over $Na_2SO_4$, filtered, concentrated and purified by Isco to give 1.02 g of 117.1d, yield: 97.7%.

Step C:

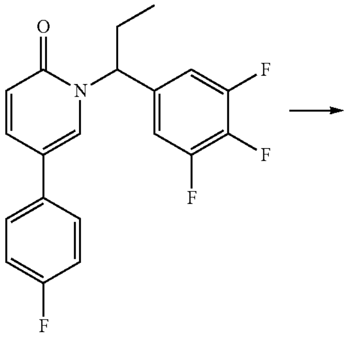

117.1d

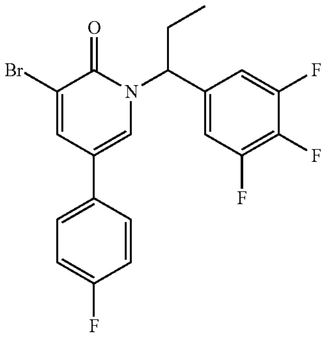

117.1e

To the solution of 117.1d (1.02 g, 2.82 mmol) in 10 ml of DMF was added NBS (0.85 g, 4.78 mmol) at r.t. After stirring at r.t. for 2 h, the mixture was extracted with EtOAc and 10% of $Na_2S_2O_3$(aq), washed with saturated $NaHCO_3$(aq), dried over $Na_2SO_4$, filtered, concentrated and purified by Isco to give 1.1 g of 117.1e, $MH^+$: 439.92, yield: 89%.

Step D:

Compounds 117.1 and 118.1 were prepared from 117.1e using a procedure similar to that of Examples 9 and 10, respectively.

EXAMPLE 24

113.1

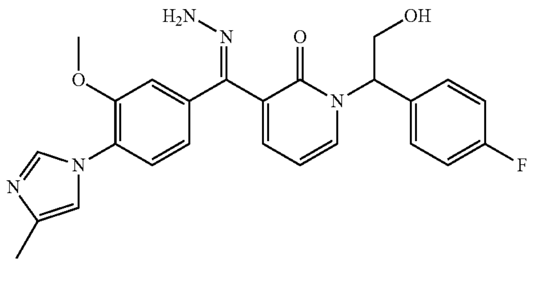

Step A:

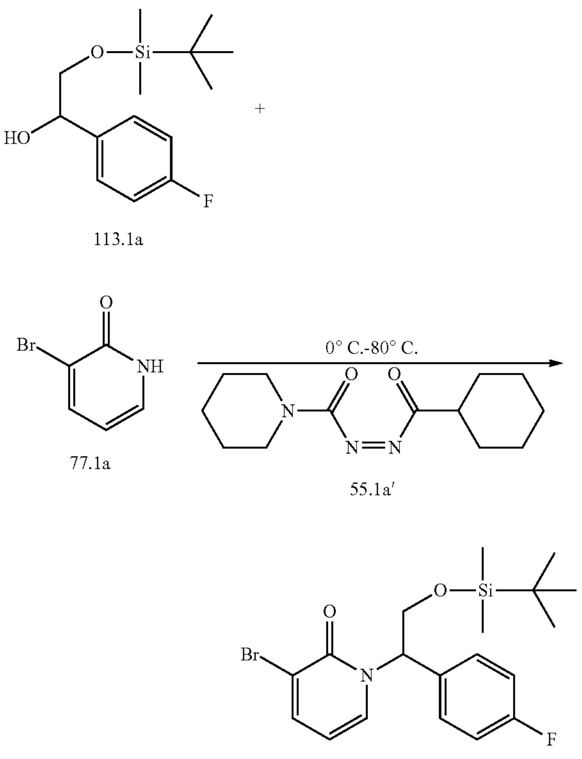

113.1a 77.1a 55.1a'

113.1b

To the solution of 113.1a (7.24 g, 26.8 mmol) in 54 ml of THF was added 77.1a (5.76 g, 32.1 mmol). This mixture was allowed to stir at 0° C. for 30 minutes, followed by the addition of $P(n-Bu)_3$ (10.8 g, 53.6 mmol) and 55.1a' (13.6 g, 53.6 mmol). This mixture was allowed to stir at 0° C. for another 30 minutes. Now the reaction mixture was warmed to room temperature and then allowed to reflux at 80° C. overnight. The reaction mixture was cooled to room temperature and filtered until no solid was observed in the filtrate. The filtrate was concentrated and purified by silica gel chromatography using ethyl acetate/hexanes to afford 3.20 g of 113.1b.

Step B:

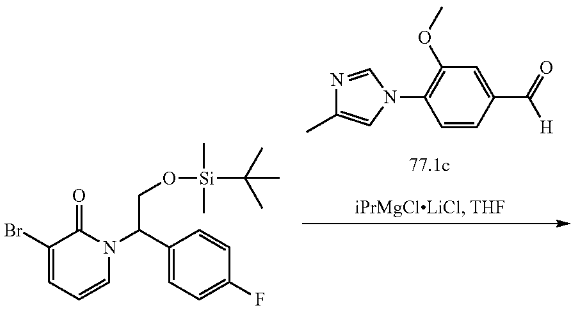

77.1c 113.1b

-continued

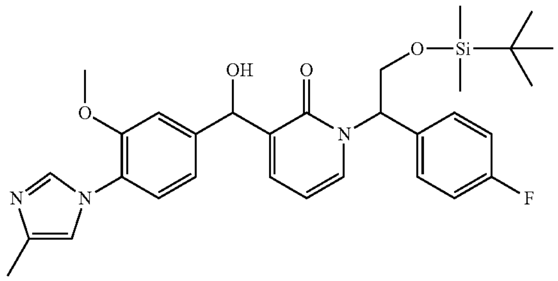

113.1c

To the solution of 113.1b (3.20 g, 7.5 mmol) in 25 ml THF was added, iPrMgCl.LiCl (9.27 ml, 8.96 mmol). This mixture was allowed to stir for 30 minutes followed by the addition of 77.1c (1.79 g, 8.2 mmol). The reaction mixture was allowed to stir overnight. It was quenched with aq. $NH_4Cl$ solution, extracted three times with ethyl acetate. The combined organic layer was dried with $Na_2SO_4$. It was then filtered and concentrated. The residue was purified by silica gel chromatography using (0-5) % $MeOH/CH_2Cl_2$ to give 3.41 g of 113.1c.

Step C:

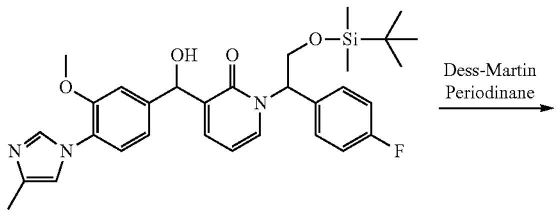

113.1c

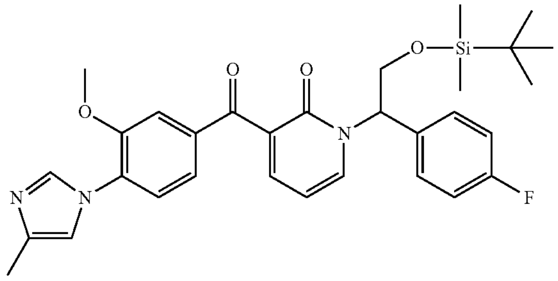

113.1d

To the solution of 113.1c (3.41 g, 6.0 mmol) in 20 ml of $CH_2Cl_2$ was added dess-martin periodinane (5.3 g, 12.1 mmol). The reaction mixture was allowed to stir overnight. The reaction mixture was concentrated and then diluted with ethyl acetate. It was then quenched with aq. $NaHCO_3$ solution and extracted three times with ethyl acetate while continuously removing solids from both layers. The combined organic layer was dried with $Na_2SO_4$ and then filtered. The filtrate was concentrated and the residue was purified by silica gel chromatography using (0-5) % $MeOH/CH_2Cl_2$ to give 1.78 g of 113.1d.

Step D:

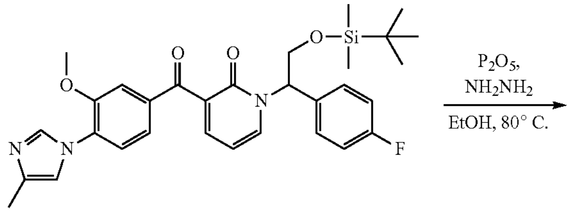

113.1d

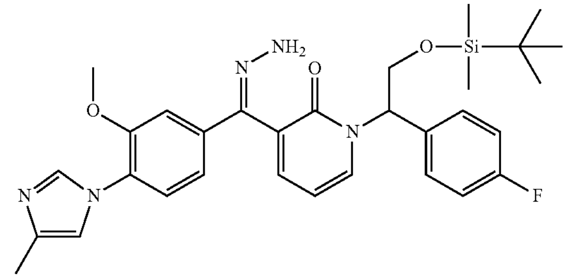

113.1e

To the solution of 113.1d (1.78 g, 3.17 mmol) in 12 ml ethanol was added $P_2O_5$ (1.80 g, 12.7 mmol) followed by $NH_2NH_2$ (1.01 ml, 31.7 mmol). The reaction mixture was allowed to reflux at 80° C. for overnight. The reaction mixture was cooled to room temperature and diluted with ethyl acetate. This was then washed with aq. $NaHCO_3$ solution. The extracted organic layer was dried with $Na_2SO_4$ and then filtered. The filtrate was concentrated and the residue was purified by silica gel chromatography using (0-5) % (2N $NH_3$/MeOH)/$CH_2Cl_2$ to give 880 mg of 113.1e.

Step E:

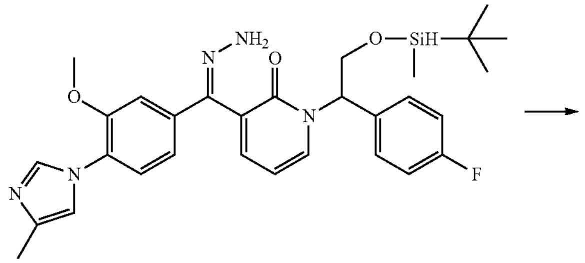

113.1e

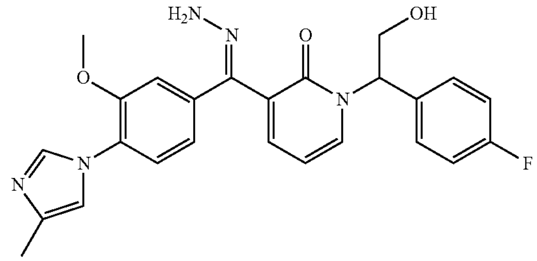

113.1

The solution of 113.1e (880 mg, 1.5 mmol) in 15 ml of $POCl_3$ was stirred at 100° C. for 90 minutes. The reaction mixture was cooled to room temperature and concentrated to get rid of $POCl_3$. The residue was purified by silica gel chromatography using (0-5) % (2N $NH_3$/MeOH)/$CH_2Cl_2$ to give 324 mg of 113.1.

EXAMPLE 25

114.1

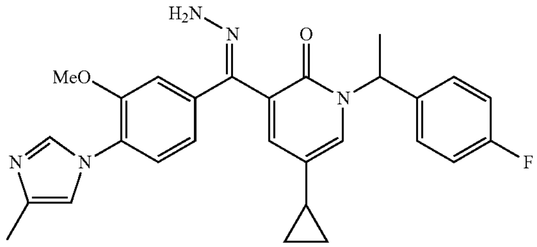

115.1

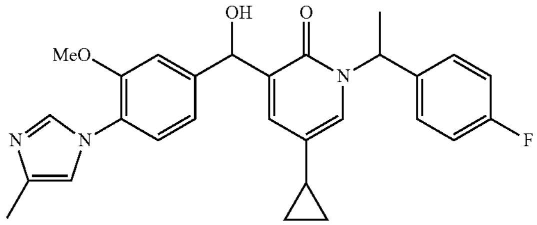

116.1

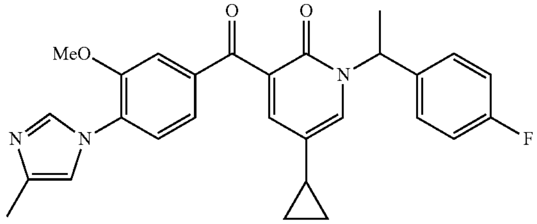

Step A:

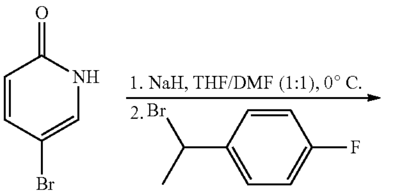

117.1a

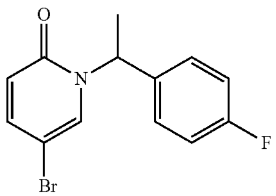

114.1a

To the 0.9M solution 117.1a in THF/DMF (1:1) was added 1.5 eq. of NaH was added at 0° C. After 10 minutes 1.5 eq. of 4-fluoro alpha-methyl benzyl bromide was added. The reaction was then allowed to stir overnight at room temperature. The reaction mixture was quenched with $NH_4Cl$ solution and extracted with ethyl acetate. The combined organic layer was dried with $Na_2SO_4$ and then filtered. The filtrate was concentrated and the residue was purified by silica gel chromatography using ethyl acetate/hexanes to obtain 114.1a.

Step B:

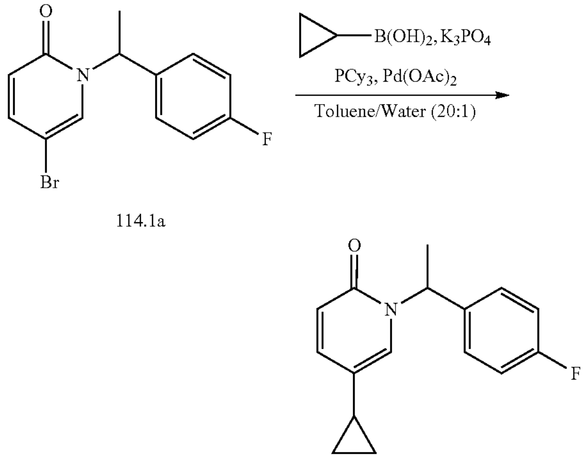

114.1a 114.1b

To the solution of 114.1a (12.95 g, 43.7 mmol) in Toluene/Water (20:1) 231 ml was added Cyclopropyl boronic acid (11.27 g, 131.19 mmol), $K_3PO_4$ (83 g, 393.6 mmol) and $PCy_3$ (3.1 g, 10.9 mmol). Finally $Pd(OAc)_2$ (4.9 g, 21.9) was added. The reaction was stirred overnight at 100° C. The reaction mixture was cooled to room temperature and quenched by the addition of water. It was then extracted with ethyl acetate. The combined organic layer was washed with brine and then dried with $Na_2SO_4$. It was then filtered. The filtrate was concentrated and the residue was purified by silica gel chromatography using (20-60) % ethyl acetate/hexanes to give 7.249 of 114.1b.

Step C:

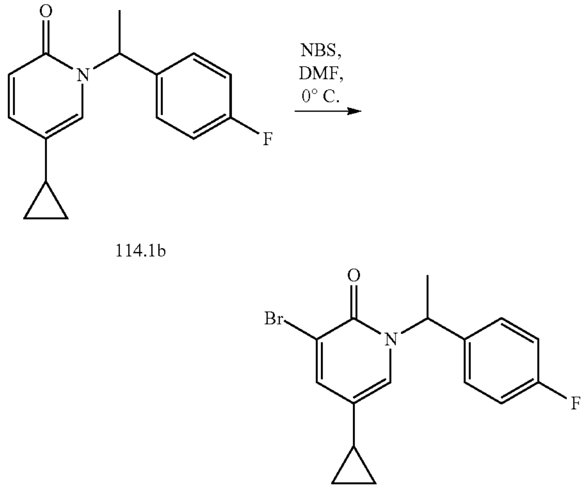

114.1b 114.1c

To the solution of 114.1b (7.24 g, 28.1 mmol) in 47 ml of DMF at 0° C. was added NBS (5.5 g, 30.9 mmol). The reaction was allowed to stir overnight. It was diluted with water and extracted with ethyl acetate three times. The combined organic layer was dried with $Na_2SO_4$ and then filtered. The filtrate was concentrated and the residue was purified by Silica gel chromatography using (10-30) % ethyl acetate/hexanes to obtain 8.1 g of 114.1c.

Step D:

Compounds 114.1, 115.1 and 116.1 were prepared from 114.1c using a procedure similar to that of Examples 11, 9, and 10, respectively.

Assay:

γ-Secretase Reaction and Aβ Analysis in whole cell: HEK293 cells overexpressing APP with Swedish and London mutations are treated with the specified compounds for 5 hour at 37° C. in 100 μL of DMEM medium containing 10% fetal bovine serum. At the end of the incubation, total Aβ and Aβ42 are measured using an electrochemiluminescence (ECL)-based immunoassay. Total Aβ is identified with antibody pairs TAG-W02 and biotin-4G8, while Aβ42 is identified with TAG-G2-11 and biotin-4G8. The ECL signal is measured using MSD technology (Meso Scale Discovery) according to the manufacturer's instructions.

MS analysis of Aβ profile: To analyze Aβ products from conditioned media, cells expressing APP are grown to 90% confluence and re-fed with fresh media containing γ-secretase modulator. The conditioned media, harvested after 16 h of incubation, are incubated overnight with antibody WO2 immobilized on PS20 array (Bio-Rad). The array is then washed three times with PBS plus 0.2% Tween 20 and rinsed twice with water. After briefly drying up the array surface, energy absorbing molecule (EAM, saturated alpha-cyano-4-hydroxycinnamic acid in 50% acetonitrile, 0.1% TFA) is added to the spots and the array is analyzed using ProteinChip SELDI system (Bio-Rad).

Matrix-assisted laser desorption/ionization mass spectrometric (MALDI MS) analysis of Aβ is performed on a Voyager-DE STR mass spectrometer (ABI, Framingham, Mass.). The instrument is equipped with a pulsed nitrogen laser (337 nm). Mass spectra are acquired in the linear mode with an acceleration voltage of 20 kV. Each spectrum presented in this work represents an average of 256 laser shots. To prepare the sample-matrix solution, 1 μL of immunoprecipitated Aβ sample is mixed with 3 μL of saturated α-cyano-4-hydroxycinnamic acid solution in 0.1% TFA/acetonitrile. The sample-matrix solution is then applied to the sample plate and dried at ambient temperature prior to mass spectrometric analysis. All the spectra are externally calibrated with a mixture of bovine insulin and ACTH (18-39 clip).

The Aβ42 $IC_{50}$ of compounds 5.1 to 27.1 was about 20 micromolar or less.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the formula (I):

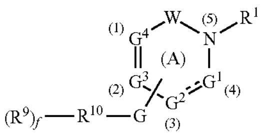

(I)

or a pharmaceutically acceptable salt or ester, thereof, wherein:

(A) in the ring in formula (I) is a reference letter to identify the ring;

the numbers (1), (2), (3), (4), and (5) are reference numbers to identify positions of the Ring (A);

the dotted line (----) between positions (3) and (4) represents an optional bond;

f is 1;

n is 1 to 5;

q is 0, 1 or 2, and each q is independently selected;

r is 1 to 3 ;

t is 1 or 2;

W is selected from the group consisting of: —C(O)—, and —C(═$NR^2$)—;

the moiety -G-$R^{10}$—$(R^9)_f$ is bound through G to positions (1) or (2);

G is selected from the group consisting of: a direct bond, —C(O)—, —(C═$NR^2$)—, —$CHR^3$—, $C(R^4)_2$, —$CF_2$—, —$N(R^2)$—, —O—, —S—, —$S(O)_t$, —$CR^4(OH)$—, —$CR^4(OR^4)$—, —C═C—, alkynyl, —$(CH_2)_rN(R^2)$—, —$(CHR^4)_rN(R^2)$—, —$(C(R^4)_2)_rN(R^2)$—, —$N(R^2)(CH_2)_r$—, —$N(R^2)(CHR^4)_r$—, —$N(R^2)(C(R^4)_2)_r$—$(CH_2)_r$—O—, —$(CHR^4)_r$—O—, —$(C(R^4)_2)_r$—O—, —O—$(CH_2)_r$—, —O—$(CHR^4)_r$—, —O—$(C(R^4)_2)_r$—, —$(CH_2)_r$—O—C(O)—, —$(CHR^4)_r$—O—C(O)—, —$C(R^4)_2)_r$—O—C(O)—, —C(O)—O—$(CH_2)_r$—, —C(O)—O—$(CHR^4)_r$—, C(O)—O—$(C(R^4)_2)_r$—, —C(O)$NR^5$—, —O—C(O)—, —C(O)—O—C(O)—$NR^5$—, —$NR^5$C(O)—,—$(CH_2)_rNR^5$—C(O)—,—$(CHR^4)_rNR^5$—C(O)—, —$(C(R^4)_2)_rNR^5$—C(O)—, —C(O)$NR^5(CH_2)_r$—, —C(O)$NR^5(CHR^4)_r$—, —C(O)$NR^5(C(R^4)_2)_r$—, —$NR^5S(O)_t$—, —$(CH_2)_rNR^5S(O)_t$—, —$(CHR^4)_rNR^5S(O)_t$—, —$(C(R^4)_2)_rNR^5S(O)_t$—$S(O)_tNR^5$—, —$S(O)_tNR^5(CH_2)_r$—, —$S(O)_tNR^5(CHR^4)_r$——$S(O)_tNR^5(C(R^4)_2)_r$—$NR^5$—C(O)—O—, —$NR^5$—C(O)—$NR^5$—, —$NR^5$—$S(O)_t$—$NR^5$, —$NR^5$—C(═$NR^2$)—$NR^5$—, —$NR^5$—C(═$NR^2$)—O—, —O—C(═$NR^2$)—$NR^5$—, —$C(R^4)$═N—O—, —O—N═$C(R^4)$—, —O—$C(R^4)$═N—, —N═$C(R^4)$—O—, —$(CH_2)_{2\text{-}3}$, —$(C(R^4)_2)_{2\text{-}3}$—, —$(CHR^4)_{2\text{-}3}$—, cycloalkyl, and heterocycloalkyl (comprising 1 to 4 heteroatoms independently selected from the group consisting of: —O—, —$NR^2$—, —S—, —S(O)—, and —$S(O)_2$);

$G^1$ is —$C(R^{21})_q$, and with the proviso that when the optional double bond between (3) and (4) is present then:

q for the —$C(R^{21})_q$ group is 0 or 1 and when 0 there is a H on the carbon, $G^2$ is —$C(R^{21})_q$, and C(═$NR^2$)—; and with the proviso that when the optional double bond between (3) and (4) is present then:

(a) q for the —$C(R^{21})_q$ group is 0 or 1 (and when 0 there is a H on the carbon), and (b) $G^2$ is —C(═$NR^2$);

$G^3$ is —$C(R^{21})_q$ wherein q is 0 or 1, and when 0 there is a H on the carbon;

$G^4$ is —$C(R^{21})_g$ wherein q is 0 or 1, and when 0 there is a H on the carbon; and $R^1$ is selected from the group consisting of: alkyl-, alkenyl-, alkynyl-, aryl-, arylalkyl-, alkylaryl-, cycloalkyl, cycloalkenyl, cycloalkylalkyl-, fused benzocycloalkyl-, fused benzoheterocycloalkyl-, fused heteroarylcycloalkyl-, fused heteroarylheterocycloalkyl-, fused cycloalkylaryl, fused heterocycloalkylaryl-, fused cycloalkylheteroaryl-, fused heterocycloalkylheteroaryl-, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, fused heterocycloalkylheteroarylalkyl-, heteroaryl-, heteroarylalkyl-, heterocyclyl-, heterocyclenyl-, and heterocyclyalkyl-; wherein each of said alkyl-, alkenyl-, alkynyl-, aryl-, arylalkyl-, alkylaryl-, cycloalkyl, cycloalkenyl, cycloalkylalkyl-, fused benzocycloalkyl, fused benzoheterocycloalkyl, fused heteroarylcycloalkyl, fused heteroarylheterocycloalkyl, fused cycloalkylaryl, fused heterocycloalkylaryl, fused cycloalkylheteroaryl, fused heterocycloalkylheteroaryl, fused benzocycloalkylalkyl-, fused benzoheterocycloalkylalkyl-, fused heteroarylcycloalkylalkyl-, fused heteroarylheterocycloalkylalkyl-, fused cycloalkylarylalkyl-, fused heterocycloalkylarylalkyl-, fused cycloalkylheteroarylalkyl-, fused heterocycloalkylheteroarylalkyl-, heteroaryl, heteroarylalkyl-, heterocyclyl, heterocyclenyl and heterocyclyalkyl- wherein the $R^1$ groups are optionally substituted with 1-5 independently selected $R^{21}$ groups;

$R^2$ is selected from the group consisting of: H, —OH, —O-alkyl, —O-(halo substituted alky), —$NH(R^4)$, —$N(R^4)_2$, —$NH_2$, —$S(R^4)$, —$S(O)R^4$, —$S(O)(OR^4)$, —$S(O)_2R^4$, —$S(O)_2(OR^4)$, —$S(O)NHR^4$, —$S(O)N(R^4)_2$, —$S(O)NH_2$, —$S(O)_2NHR^4$, —$S(O)_2N(R^4)_2$, —$S(O)_2NH_2$, —ON, —$C(O)_2R^4$, —$C(O)NHR^4$, —$C(O)N(R^4)_2$, —$C(O)NH_2$, —$C(O)R^4$,unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected $R^{21}$ groups;

$R^3$ is selected from the group consisting of; H, —OH, halo, —O-alkyl, —O-(halo substituted alkyl), —$NH(R^4)$, —$N(R^4)_2$ wherein each $R^4$ is independently selected, —$NH_2$, —$S(R^4)$, —$S(O)R^4$, —$S(O)(OR^4)$, —$S(O)_2R^4$, —$S(O)_2(OR^4)$, —$S(O)NHR^4$, —$S(O)N(R^4)_2$, —$S(O)NH_2$, —$S(O)_2NHR^4$, —$S(O)_2N(R^4)_2$, —$S(O)_2NH_2$, —CN, —$C(O)_2R^4$, —$C(O)NHR^4$, —$C(O)N(R^4)_2$, —$C(O)NH_2$, —$C(O)R^4$, unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected $R^{21}$ groups;

Each $R^4$ is independently selected from the group consisting of: unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected $R^{21}$ groups;

Each $R^5$ is independently selected from the group consisting of: H, unsubstituted alkyl, substituted alkyl, unsubstituted alkenyl, substituted alkenyl, unsubstituted alkynyl, substituted alkynyl, unsubstituted cycloalkyl, substituted cycloalkyl, unsubstituted aryl, substituted aryl, unsubstituted heteroaryl and substituted heteroaryl; wherein said substituted groups are substituted with one or more substituents independently selected from: $R^{21}$.

$R^{10}$ is phenyl substituted with one $R^{21}$ group, and said $R^9$ is imidazolyl substituted with one $R^{21}$ group wherein each $R^{21}$ is independently selected;

$R^{14}$ is selected from the group consisting of H, alkyl, alkenyl, alkynyl, cycloalkyl, cycloalkylalkyl, cycloalkenyl, heterocyclyl, heterocyclenyl, heterocyclylalkyl, heterocyclyalkenyl-, aryl, arylalkyl, heteroaryl, heteroarylalkyl, —CN, —C(O)$R^{15}$, —C(O)O$R^{15}$, —C(O)N($R^{16}$)($R^{16}$), —S(O)N($R^{15}$)($R^{16}$), —S(O)$_2$N($R^{13}$)($R^{16}$), —C(=NO$R^{15}$)$R^{16}$, and —P(O)(O$R^{15}$)(O$R^{16}$);

$R^{15}$, $R^{16}$ and $R^{17}$ are independently selected from the group consisting of H, alkyl, alkenyl, alkynyl, cycloalkyl, cycloalkylalkyl-, heterocyclyl, heterocyclyalkyl-, aryl, arylalkyl, heteroaryl, heteroarylalkyl-, arylcycloalkyl-, arylheterocyclyl-, $(R^{18})_n$-alkyl, $(R^{18})_n$-cycloalkyl, $(R^{18})_n$-cycloalkylalkyl-, $(R^{18})_n$-heterocyclyl, $(R^{18})_n$-heterocyclylalkyl-, $(R^{18})_n$-aryl, $(R^{18})_n$-arylalkyl-, $(R^{18})_n$-heteroaryl and $(R^{18})_n$-heteroarylalkyl-;

Each $R^{18}$ is independently selected from the group consisting of alkyl, alkenyl, alkynyl, aryl, arylalkyl-, arylalkenyl-, arylalkynyl-, —$NO_2$, halo, heteroaryl, HO—alkyoxyalkyl-, —$CF_3$, —ON, alkyl-CN, —C(O)OH, —C(O)O$R^{19}$, —C(O)NH$R^{20}$, —C(O)$NH_2$, —C(O)$NH_2$—C(O)N(alkyl)$_2$, —C(O)N(alkyl)(aryl), —C(O)N(alkyl)(heteroaryl), —S$R^{19}$, —S(O)$_2R^{20}$, —S(O)$NH_2$, —S(O)NH(alkyl), —S(O)N(alkyl)(alkyl), —S(O)NH(aryl), —S(O)$_2NH_2$, —S(O)$_2$NH$R^{19}$, —S(O)$_2$NH(heterocyclyl), —S(O)$_2$N(alkyl)$_2$, —S(O)$_2$N(alkyl)(aryl), —$OCF_3$, —OH, —O$R^{20}$, —O-heterocyclyl, —O-cycloalkylalkyl, —O-heterocyclylalkyl, —$NH_2$, —NH$R^{20}$, —N(alkyl)$_2$, —N(arylalkyl)$_2$, —N(arylalkyl)-(heteroarylalkyl), —NHC(O)$R^{20}$, —NHC(O)$NH_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl); or two $R^{18}$ moieties on adjacent carbons can be linked together to form a

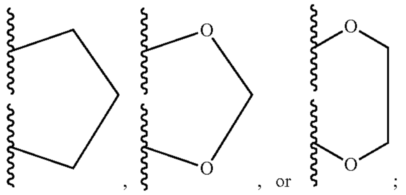

$R^{19}$ is selected from the group consisting of: alkyl, cycloalkyl, aryl, arylalkyl- and heteroarylalkyl-;

$R^{20}$ is selected from the group consisting of: alkyl, cycloalkyl, aryl, halo substituted aryl, heteroaryl and heteroarylalkyl-;

Each $R^{21}$ is independently selected from the group consisting of: alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —O$R^{15}$, —C(O)$R^{15}$, —C(O)O$R^{15}$, —C(O)N($R^{15}$)($R^{16}$), —$SF_5$, —$OSF_5$, —Si($R^{15}$)$_3$ wherein each $R^{15}$ is independently selected, —S(O)N($R^{15}$)($R^{16}$), —CH($R^{15}$)($R^{16}$), —S(O)$_2$N($R^1$)($R^{16}$), C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, $CH_2$—N($R^{15}$)C(O)$R^{16}$, —$CH_2$—N($R^{15}$)C(O)N($R^{16}$)($R^{17}$), —$CH_2$—$R^{15}$; —$CH_2$N($R^{15}$)($R^{16}$), —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —S(O)$R^{15}$, =NO$R^{15}$, —$N_3$, —$NO_2$, —S(O)$_2R^{15}$, —O—N=C($R^4$)$_2$ wherein each $R^4$ is independently selected, and —O—N=C($R^4$)$_2$ wherein $R^4$ is taken together with the carbon atom to which they are bound to form a 5 to 10 membered ring, said ring optionally containing 1 to 3 heteroatoms selected from the group consisting of —O—, —S—, —S(O)—, —S(O)$_2$—, and —N$R^2$—; wherein each of said alkyl, alkenyl, alkynyl, cycloalkyl, cycloalkylalkyl, cycloalkenyl, heterocycloalkyl, heterocycloalkylalkyl, aryl, arylalkyl, heteroaryl, and heteroarylalkyl $R^{21}$ groups are optionally substituted with 1 to 5 independently selected $R^{22}$ groups;

Each $R^{22}$ group is independently selected from the group consisting of alkyl, cycloalkyl, cycloalkenyl, heterocyclcalkyl, aryl, heteroaryl, halo, —$CF_3$, —CN, —O$R^{15}$—C(O)$R^{15}$, —C(O)O$R^{15}$, -alkyl-C(O)O$R^{15}$, C(O)N($R^{15}$)($R^{16}$), —$SF_5$, —$OSF_5$, —Si($R^{15}$)$_3$ wherein each $R^{15}$ is independently selected, —S$R^{15}$, —S(O)N($R^{15}$)($R^{16}$) —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$) -alkyl-N($R^{15}$)($R^{16}$), —N($R^{15}$)C(O)$R^{16}$, —$CH_2$—N($R^{15}$)C(O)$R^{16}$, —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{15}$)($R^{16}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —$N_3$, =NO$R^{15}$, —$NO_2$, —S(O)$R^{15}$ and —S(O)$_2R^{15}$; and provided that (a) when no —$SF_5$ moiety or —Si($R^{15}$)$_3$ is present, and W is C(=0) or C(=N$R^2$), and $G^1$ is $C(R^{21})_q$, and $G^2$ is $C(R^{21})_q$, and $G^3$ is $C(R^{21})_q$, and $G^4$ is C, and G is bound to $G^4$, and the optional bond between $G^1$ and $G^2$ is present, then $R^1$ is not alkyl-, alkenyl-, alkynyl-, aryl, arylalkyl-, alkylaryl-, cycloalkyl, cycloalkenyl, or cycloalkylalkyl-; and (b) When W is C(=O), and $G^1$ is $C(R^{21})_q$, and $G^2$ is $C(R^{21})_q$, and $G^3$ is $C(R^{21})_q$, and $G^4$ is C, and G is bound to $G^4$, then G is not CH$R^3$; and (c) When W is C(=O), and $G^1$ is $C(R^{21})_q$, and $G^2$ is $C(R^{21})_q$, and $G^3$ is $C(R^{21})_q$, and $G^4$ is C, and G is bound to $G^4$, and the optional bond between $G^1$ and $G^2$ is not present, then $R^1$ is not a fused 2-aminopyridylcycloalkyl- moiety.

2. The compound of claim 1 or a pharmaceutically acceptable salt thereof, wherein the $R^9$-$R^{10}$— moiety is:

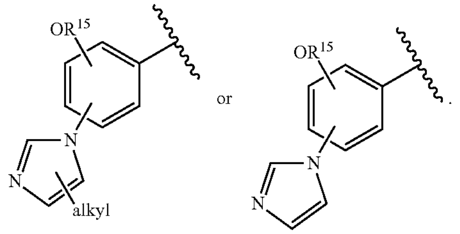

3. The compound of claim 1 or a pharmaceutically acceptable salt thereof, wherein the $R^9$-$R^{10}$— moiety is:

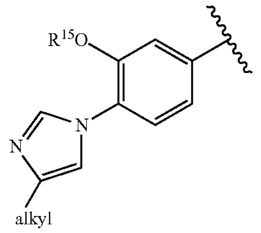 or 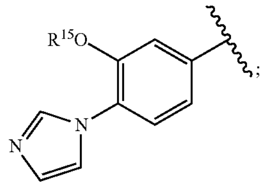

wherein the $R^9$-$R^{10}$— moiety is:

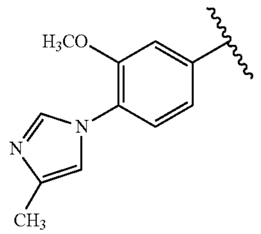 or 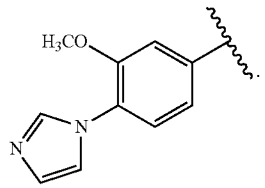

4. The compound of claim 1 or a pharmaceutically acceptable salt thereof, wherein said $R^1$ group is selected from the group consisting of:

(a)

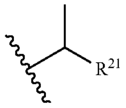

wherein $R^{21}$ is unsubstituted or substituted with one or more independently selected $R^{22}$ groups;

(b)

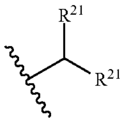

wherein one $R^{21}$ is an unsubstituted or substituted alkyl group, and the other $R^{21}$ is an unsubstituted or substituted aryl group; and (c)

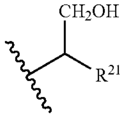

and $R^{21}$ is unsubstituted aryl or aryl substituted with one or more independently selected $R^{22}$ groups.

5. The compound of claim 1 or a pharmaceutically acceptable salt thereof, wherein:

$R^1$ is an alkyl group substituted with one $R^{21}$ group, and said $R^{21}$ group is an aryl group; or $R^1$ is an alkyl group substituted with one $R^{21}$ group, and said $R^{21}$ group is an aryl group, and said aryl is phenyl, and said alkyl group is methyl or ethyl; or $R^1$ is an alkyl group substituted with one $R^{21}$ group, and said $R^{21}$ group is an aryl group, and said aryl group is substituted with one or more $R^{22}$ groups; or $R^1$ is an alkyl group substituted with one $R^{21}$ group, and said $R^{21}$ group is an aryl group, and said aryl group is substituted with one or more $R^{22}$ groups wherein each $R^{22}$ group is the same or different halo; or $R^1$ is an alkyl group substituted with one $R^{21}$ group, and said $R^{21}$ group is an aryl group, and said aryl group is substituted with one or two $R^{22}$ halo groups; or $R^1$ is an alkyl group substituted with one $R^{21}$ group, and said $R^{21}$ group is an aryl group, and said aryl group is substituted with one or two $R^{22}$ halo groups wherein the halo is F.

6. The compound of claim 1 or a pharmaceutically acceptable salt thereof, wherein:

$R^1$ is an alkyl group substituted with one $R^{21}$ group, and said $R^{21}$ group is an aryl group, and said aryl group is substituted with one or more $R^{22}$ groups, and at least one $R^{22}$ group is selected from the group consisting of: $—SF_5$, $—OSF_5$, and $—Si(R^{15})_3$, wherein each $R^{15}$ is independently selected; or $R^1$ is an alkyl group substituted with one $R^{21}$ group, and said $R^{21}$ group is an aryl group, and said aryl group is substituted with one or more $R^{22}$ groups, and at least one $R^{22}$ group is selected from the group consisting of: $—SF_5$, $—OSF_5$, $—Si(R^{15})_3$, and each $R^{15}$ is the same or different alkyl group; or $R^1$ is an alkyl group substituted with one $R^{21}$ group, and said $R^{21}$ group is an aryl group, and said aryl group is substituted with one or more $R^{22}$ groups, and at least one $R^{22}$ group is selected from the group consisting of: $—SF_5$, $—OSF_5$, $—Si(CH_3)_3$; or $R^1$ is an alkyl group substituted with one $R^{21}$ group, and said $R^{21}$ group is phenyl, and said phenyl is substituted with one or more $R^{22}$ groups, and at least one $R^{22}$ is selected from the group consisting of: $—SF_5$, $—OSF_5$, $—Si(R^{15})_3$, wherein each $R^{15}$ is independently selected; or $R^1$ is an alkyl group substituted with one $R^{21}$ group, and said $R^{21}$ group is phenyl, and said phenyl is substituted with one or more $R^{22}$ groups, and at least one $R^{22}$ is selected from the group consisting of: $—SF_5$, $—OSF_5$, $—Si(R^{15})_3$, and each $R^{15}$ is the same or different alkyl group; or $R^1$ is an alkyl group substituted with one $R^{21}$ group, and said $R^{21}$ group is phenyl, and said phenyl is substituted with one or more $R^{22}$ groups, and at least one $R^{22}$ is selected from the group consisting of: $—SF_5$, $—OSF_5$, $—Si(CH_3)_3$; or $R^1$ is an alkyl group substituted with one $R^{21}$ group, and said $R^{21}$ group is phenyl, and said phenyl is substituted with one or more $R^{22}$ groups, and one of the $R^{22}$ groups is selected from the group consisting of: $—SF_5$, $—OSF_5$, $—Si(R^{15})_3$; or $R^1$ is an alkyl group substituted with one $R^{21}$ group, and said $R^{21}$ group is phenyl, and said phenyl is substituted with one or more $R^{22}$ groups, and one of the $R^{22}$ groups is selected from the group consisting of: $—SF_5$, $—OSF_5$, $—Si(R^{15})_3$, and each $R^{15}$ is the same or different alkyl group; or $R^1$ is an alkyl group substituted with one $R^{21}$ group, and said $R^{21}$ group is phenyl, and said phenyl is substituted with one or more $R^{22}$ groups, and one of the $R^{22}$ groups is selected from the group consisting of: $—SF_5$, $—OSF_5$, $—Si(CH_3)_3$; or $R^1$ is an alkyl group substituted with one $R^{21}$ group, and said $R^{21}$ group is phenyl, and said phenyl is substituted with one or more $R^{22}$ groups, and two of the $R^{22}$ groups are selected from the group consisting of: —$SF_5$, —$OSF_5$, —$Si(R^{15})_3$; or $R^1$ is an alkyl group substituted with one $R^{21}$ group, and said $R^{21}$ group is phenyl, and said phenyl is substituted with one or more $R^{22}$ groups, and two of the $R^{22}$ groups are selected from the group consisting of: —$SF_5$, —$OSF_5$, —$Si(R^{15})_3$, and each $R^{15}$ is the same or different alkyl group; or $R^1$ is an alkyl group substituted with one $R^{21}$ group, and said $R^{21}$ group is phenyl, and said phenyl is substituted with one or more $R^{22}$ groups, and two of the $R^{22}$ groups are selected from the group consisting of: —$SF_5$, —$OSF_5$, —$Si(CH_3)_3$; or $R^1$ is an alkyl group substituted with one $R^{21}$ group, and said $R^{21}$ group is phenyl, and said phenyl is substituted with one or more $R^{22}$ groups, and one of the $R^{22}$ groups is —$SF_5$; or $R^1$ is an alkyl group substituted with one $R^{21}$ group, and said $R^{21}$ group is phenyl, and said phenyl is substituted with one or more $R^{22}$ groups, and two of the $R^{22}$ groups are —$SF_5$; or $R^1$ is an alkyl group substituted with one $R^{21}$ group, and said $R^{21}$ group is phenyl, and said phenyl is substituted with one or more $R^{22}$ groups, and one of the $R^{22}$ groups is —$OSF_5$; or $R^1$ is an alkyl group substituted with one $R^{21}$ group, and said $R^{21}$ group is phenyl, and said phenyl is substituted with one or more $R^{22}$ groups, and two of the $R^{22}$ groups are —$OSF_5$; or $R^1$ is an alkyl group substituted with one $R^{21}$ group, and said $R^{21}$ group is phenyl, and said phenyl is substituted with one or more $R^{22}$ groups, and one of the $R^{22}$ groups is —$Si(R^{15})_3$; or $R^1$ is an alkyl group substituted with one $R^{21}$ group, and said $R^{21}$ group is phenyl, and said phenyl is substituted with one or more $R^{22}$ groups, and one of the $R^{22}$ groups is —$Si(R^{15})_3$, and each $R^{15}$ is the same or different alkyl group; or $R^1$ is an alkyl group substituted with one $R^{21}$ group, and said $R^{21}$ group is phenyl, and said phenyl is substituted with one or more $R^{22}$ groups, and one of the $R^{22}$ groups is —$Si(CH_3)_3$; or $R^1$ is an alkyl group substituted with one $R^{21}$ group, and said $R^{21}$ group is phenyl, and said phenyl is substituted with one or more $R^{22}$ groups, and two of the $R^{22}$ groups are —$Si(R^{15})_3$; or $R^1$ is an alkyl group substituted with one $R^{21}$ group, and said $R^{21}$ group is phenyl, and said phenyl is substituted with one or more $R^{22}$ groups, and two of the $R^{22}$ groups are —$Si(R^{15})_3$, and each $R^{15}$ is the same or different alkyl group; or $R^1$ is an alkyl group substituted with one $R^{21}$ group, and said $R^{21}$ group is phenyl, and said phenyl is substituted with one or more $R^{22}$ groups, and two of the $R^{22}$ groups are —$Si(CH_3)_3$.

7. The compound of claim 1 or a pharmaceutically acceptable salt thereof, wherein said $R^1$ is selected from the group consisting of:

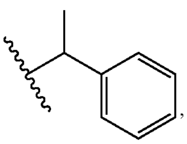
,
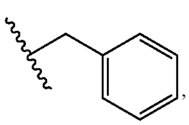
,

-continued

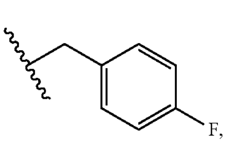
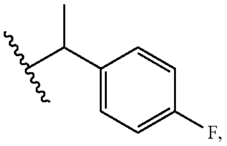
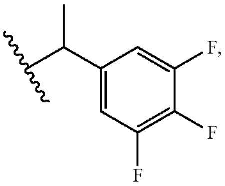
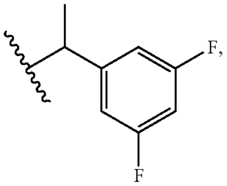
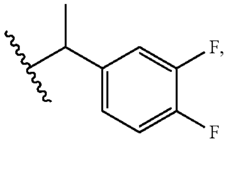
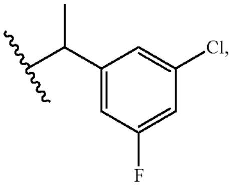
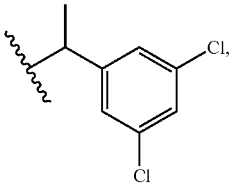
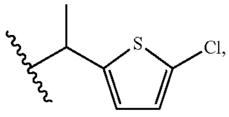
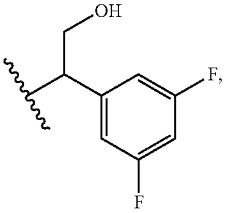
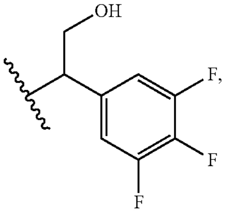
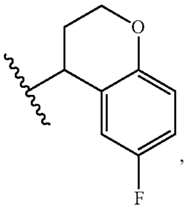
,
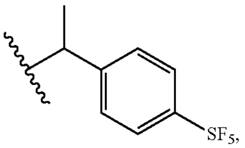
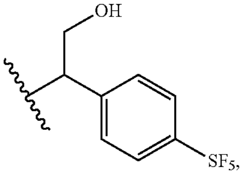
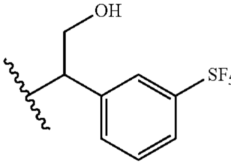
,
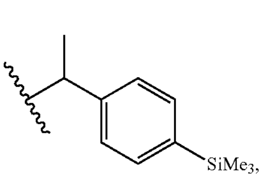
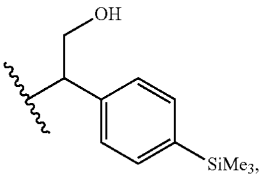
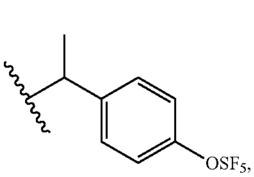
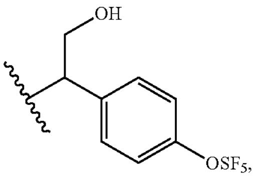

-continued

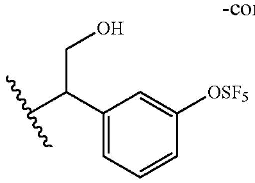 and 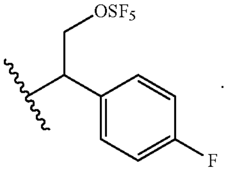 .

8. The compound of claim 1 or a pharmaceutically acceptable salt thereof, wherein:

(1)

$R^1$ is an alkyl group substituted with one $R^{21}$ group, or $R^1$ is an alkyl group substituted with one $R^{21}$ group, and said $R^{21}$ group is substituted with one or more independently selected $R^{22}$ groups; or (2)

$R^1$ is an alkyl group substituted with one phenyl, or $R^1$ is an alkyl group substituted with one phenyl, and said phenyl is substituted with one or more independently selected $R^{22}$ groups; or (3)

$R^1$ is a methyl or ethyl group substituted with one phenyl, or $R^1$ is a methyl or ethyl group substituted with one phenyl, and said phenyl is substituted with one or more independently selected halos, or (4)

$R^1$ is a methyl or ethyl group substituted with one phenyl, or $R^1$ is an methyl or ethyl group substituted with one phenyl, and said phenyl is substituted with one or two independently selected halos, or (5)

$R^1$ is a methyl or ethyl group substituted with one phenyl, or $R^1$ is an methyl or ethyl group substituted with one phenyl, and said phenyl is substituted with one or two F, or (6)

$R^1$ is a methyl or ethyl group substituted with one phenyl, or $R^1$ is an methyl or ethyl group substituted with one phenyl, and said phenyl is substituted with one or two F, or (7)

$R^1$ is selected from the group consisting of:

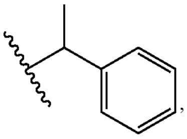, 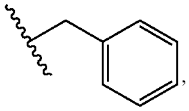,

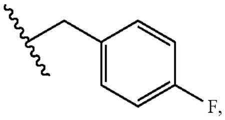 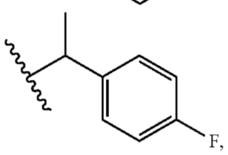

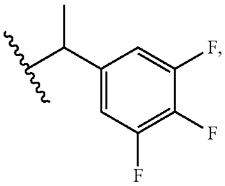 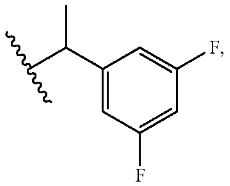

-continued

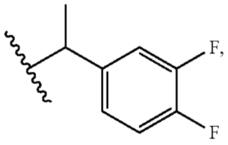 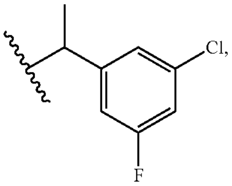

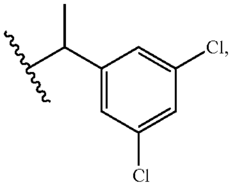 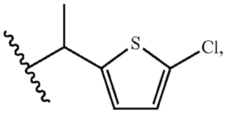

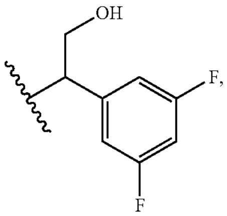 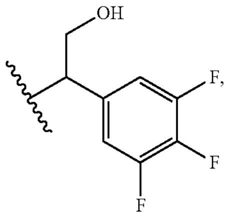

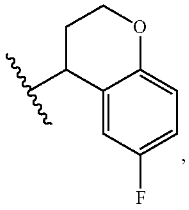, 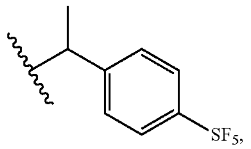

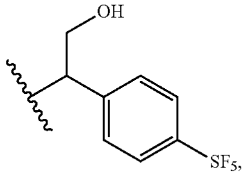 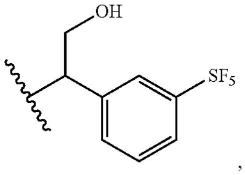,

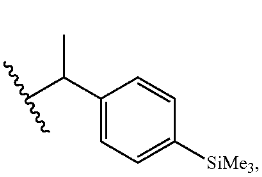 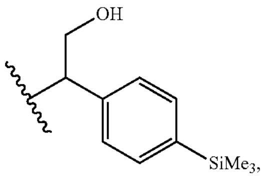

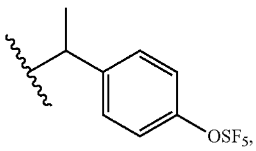 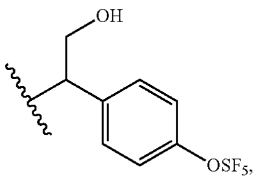

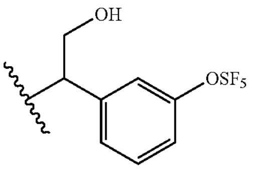 and 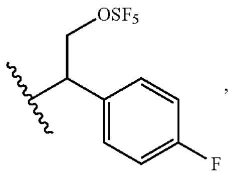, (8)

$R^1$ is selected from the group consisting of:

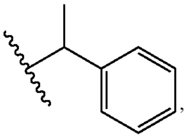
,
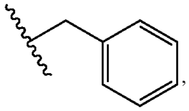
,
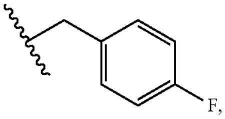
,
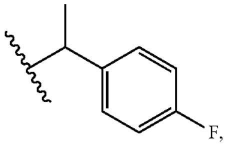
,
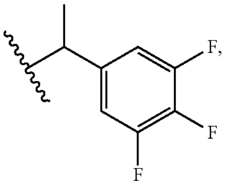
,
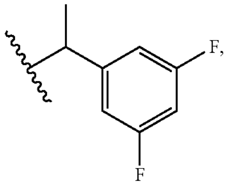
,
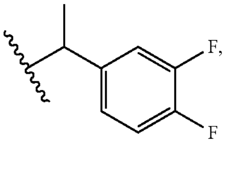
,
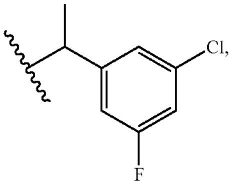
,
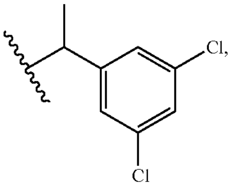
,
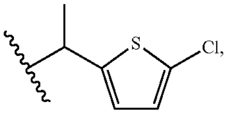
,
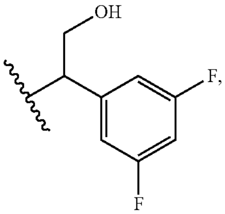
,
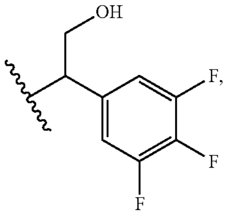
,
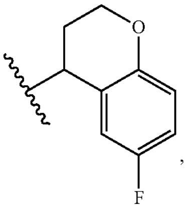
,
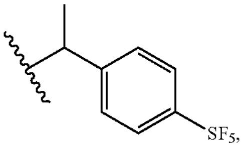
,
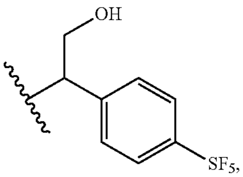
,
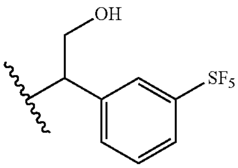
,
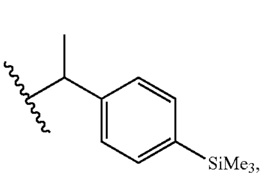
,
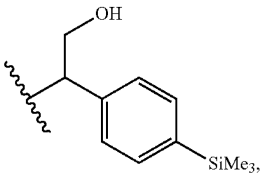
, -continued

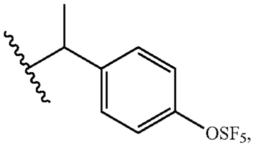
,
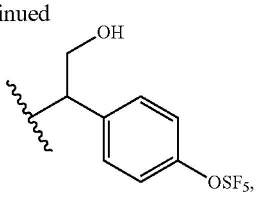
,
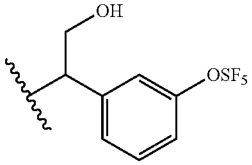
and
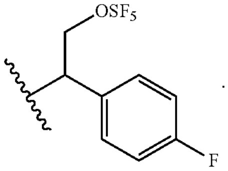
.

9. The compound of claim 8 or a pharmaceutically acceptable salt thereof, wherein W is —C(O)—.

10. The compound of claim 9 or a pharmaceutically acceptable salt thereof, wherein G is selected from the group consisting of —NH—, and a direct bond.

11. The compound of claim 1 or a pharmaceutically acceptable salt thereof selected from the group consisting of having the formula:

(IA)

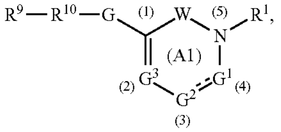
, (IB)

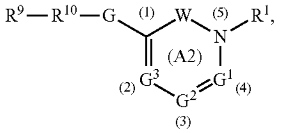
, (IC)

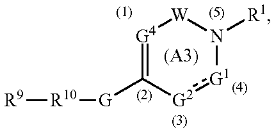
, and (ID)

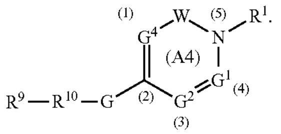
.

12. The compound of claim 1 or a pharmaceutically acceptable salt thereof selected from the group consisting of:

(IG)

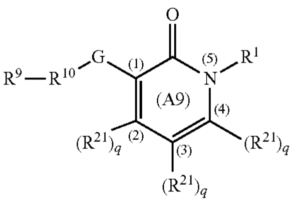

and

-continued
(IH)
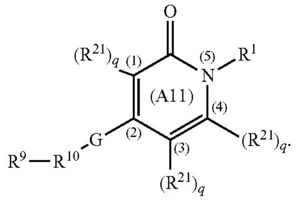
13. The compound of claim 1 or a pharmaceutically acceptable salt thereof selected from the group consisting of:
(IG1)
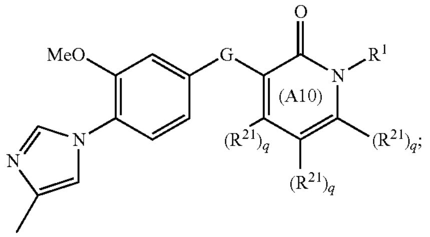
(IH1)
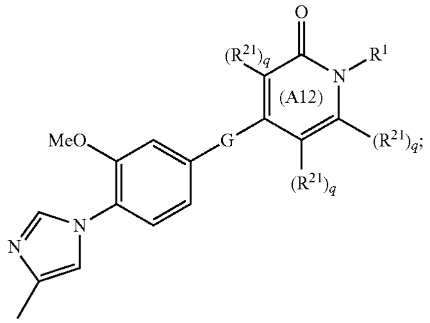
and
(IO1)
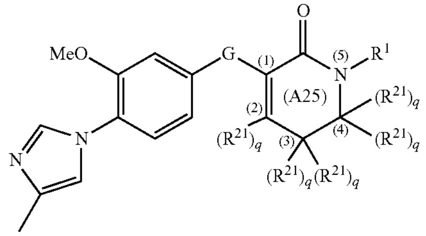
-wherein:
(a) each q is independently 0 or 1, and
(b) each $R^{21}$ is independently selected.
14. The compound of claim 1 or a pharmaceutically acceptable salt thereof selected from the group consisting of:
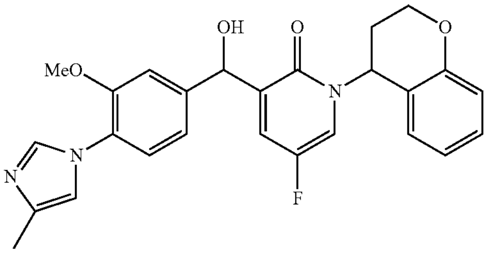
,
-continued
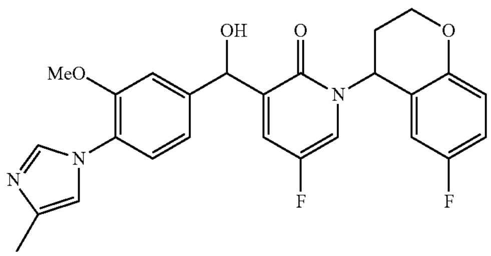
,
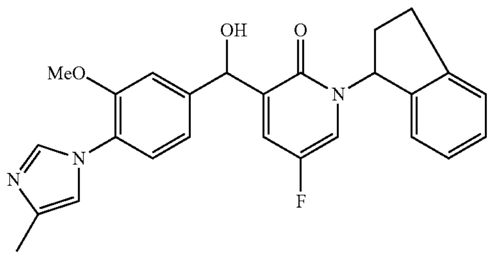
,
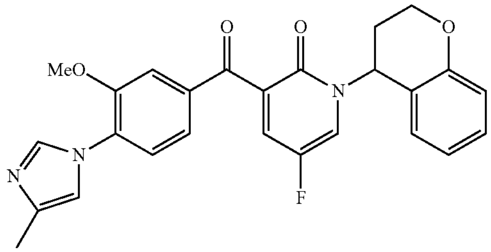
,
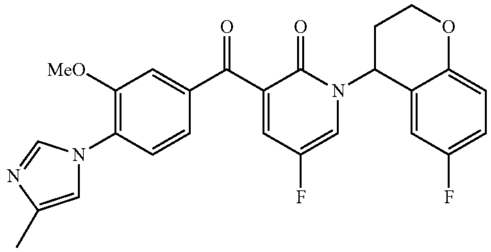
,
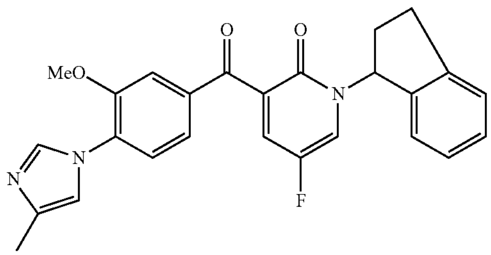
,
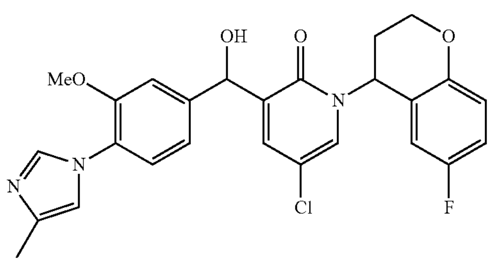
,

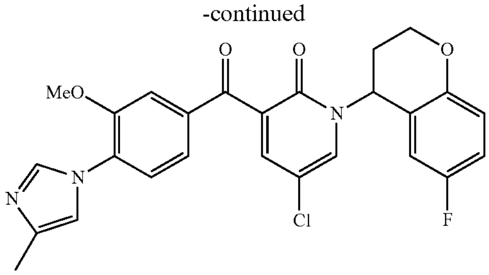
,
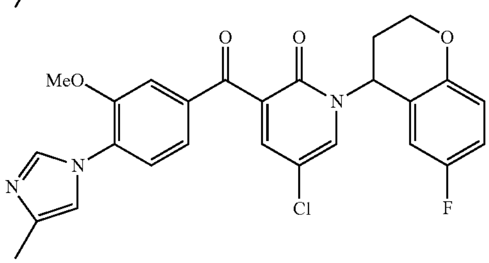
,
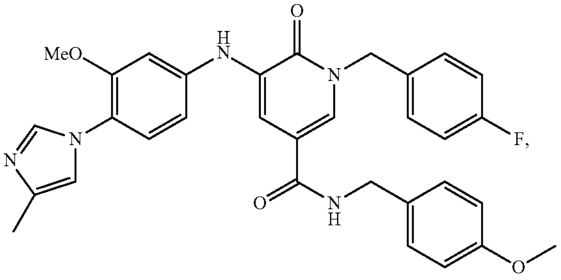
,
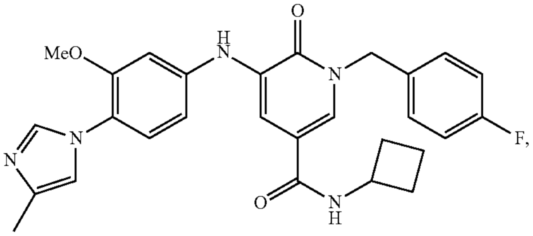
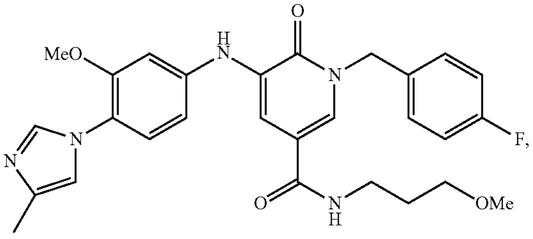
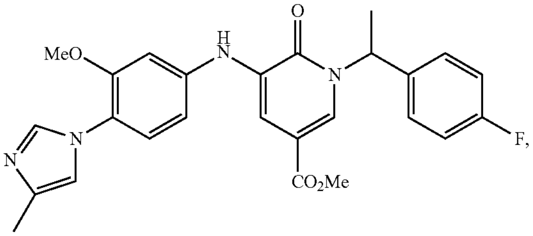
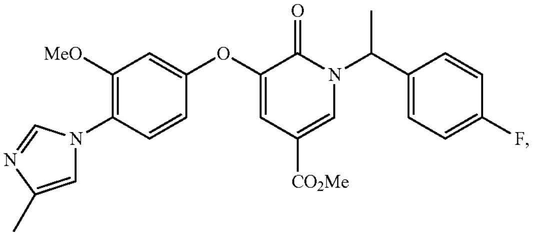
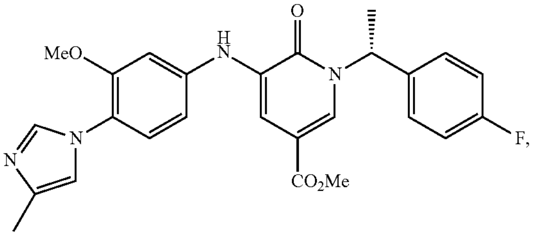
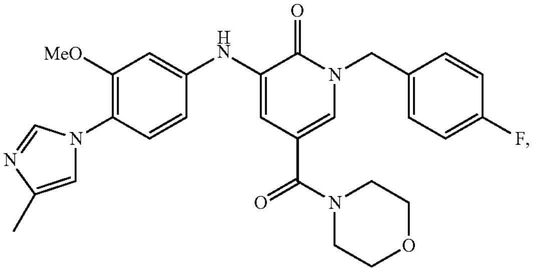
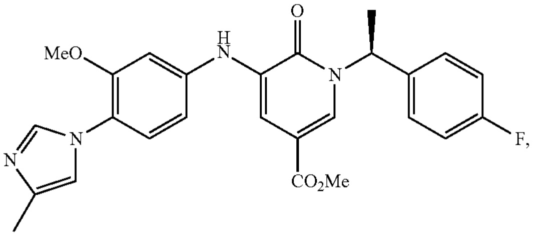
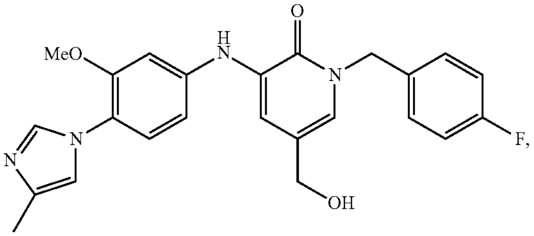
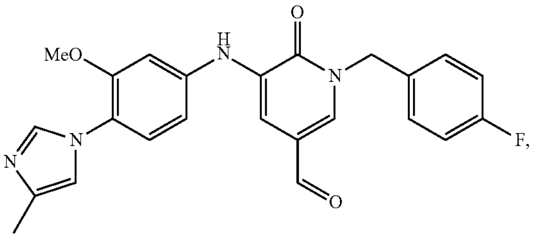
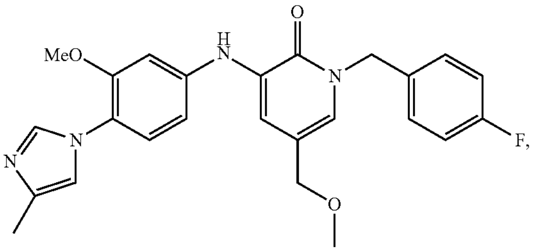
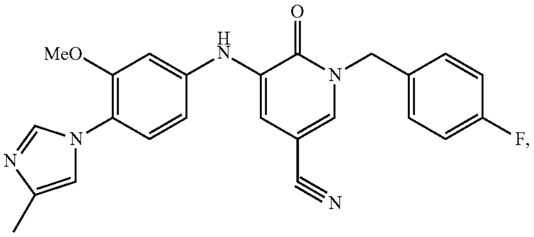

-continued
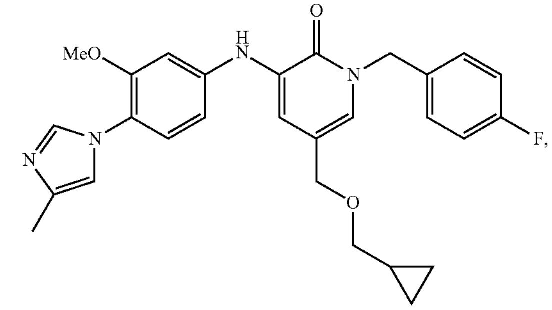
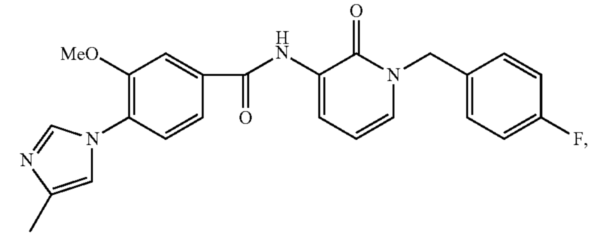
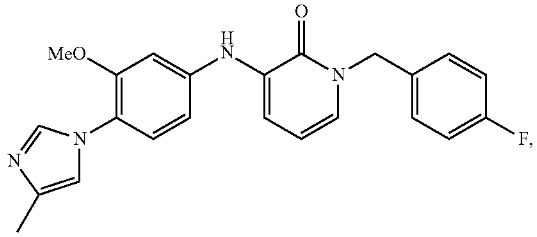
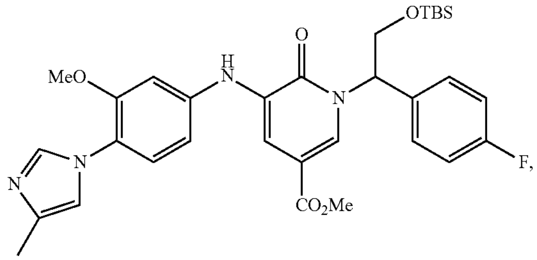
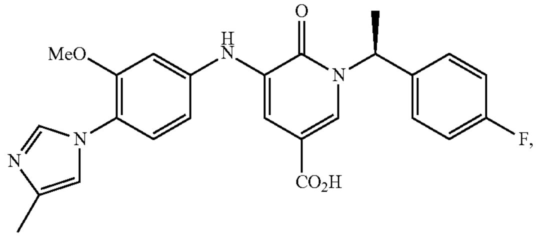
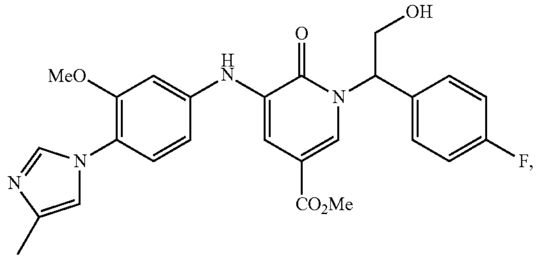
-continued
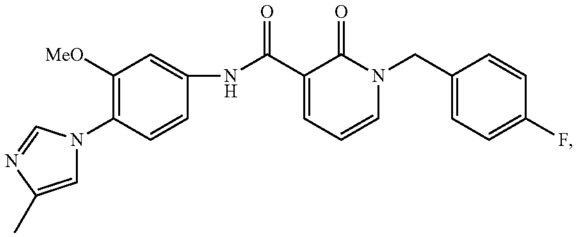
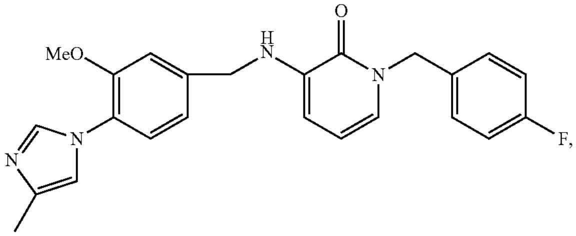
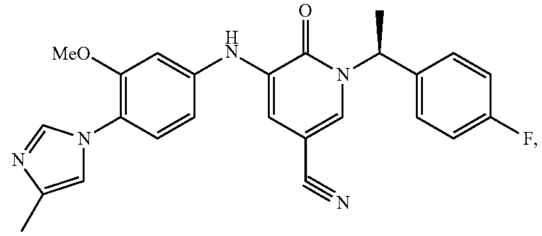
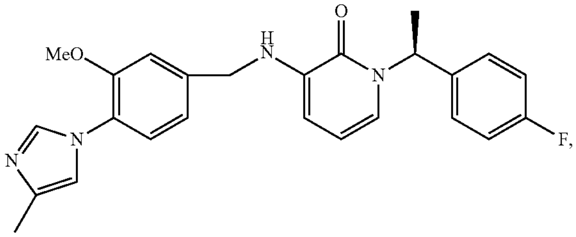
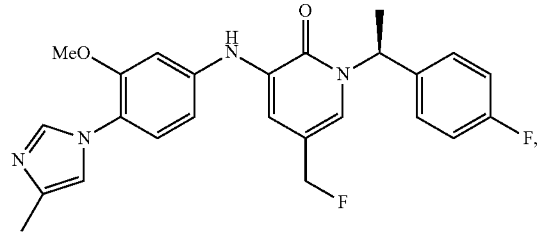
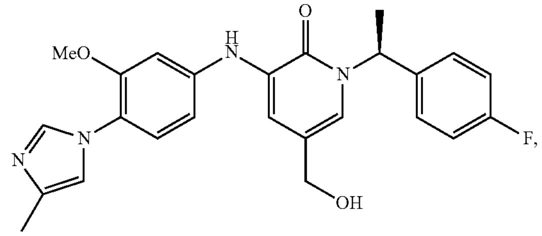
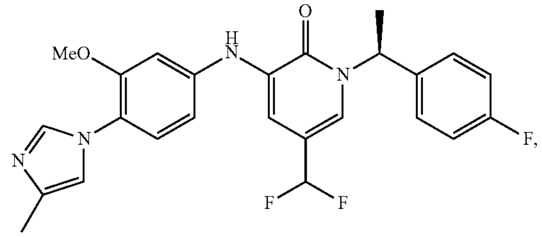

-continued
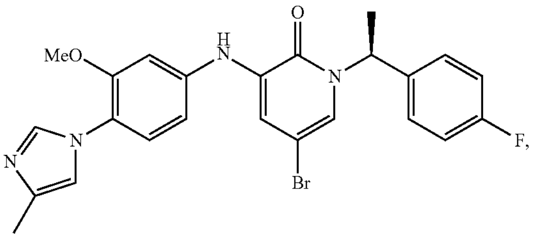
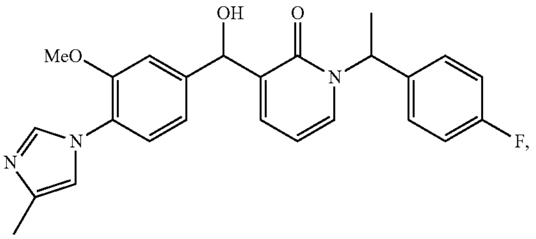
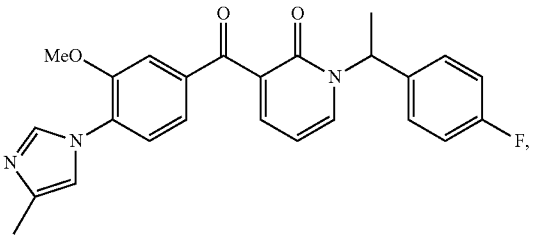
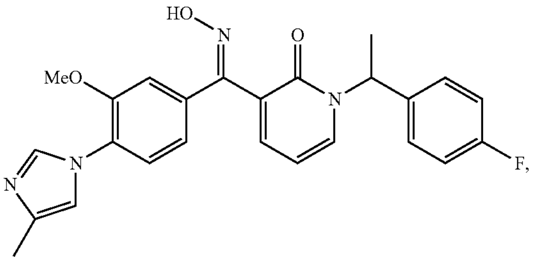
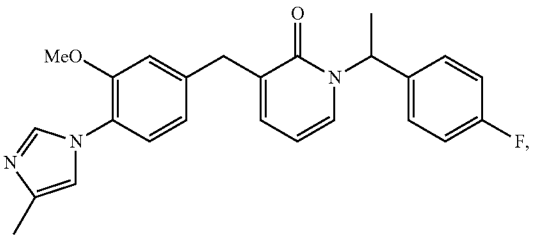
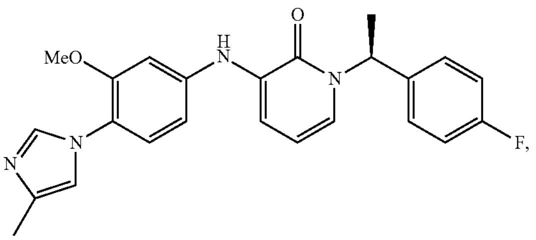
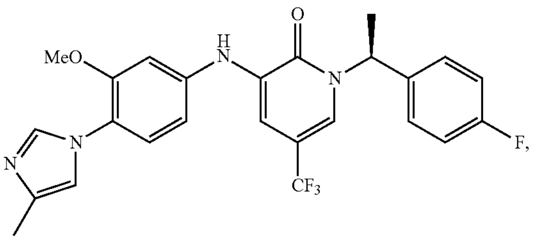
-continued
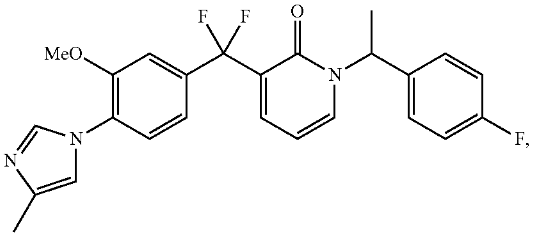
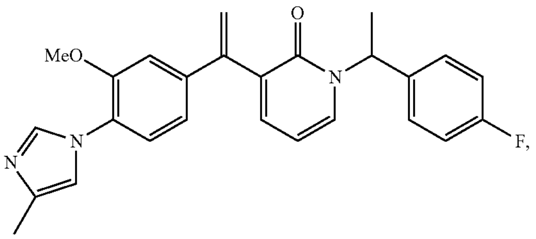
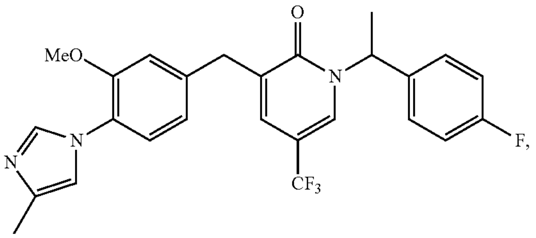
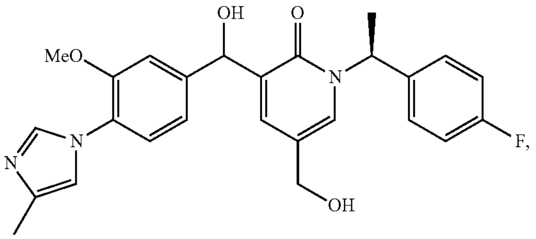
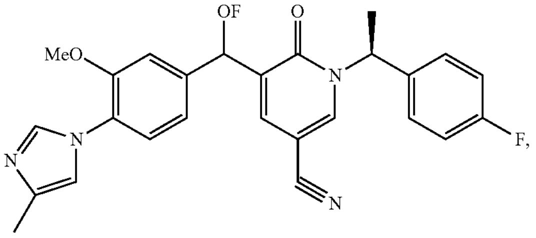
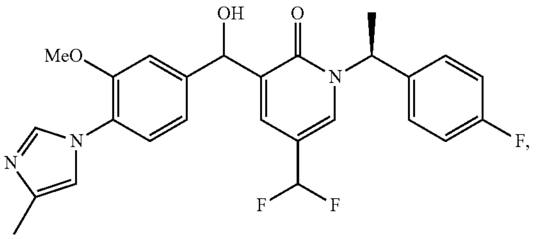
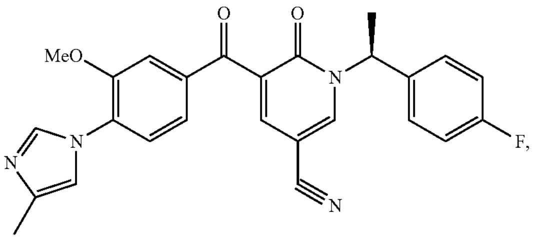

-continued
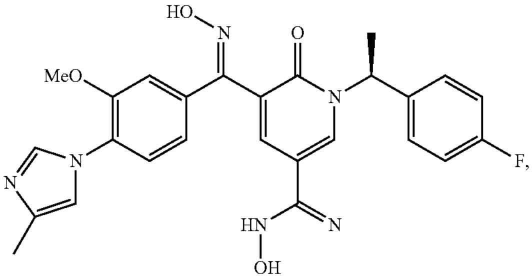
,
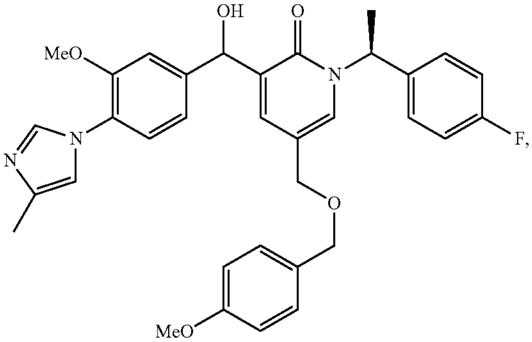
,
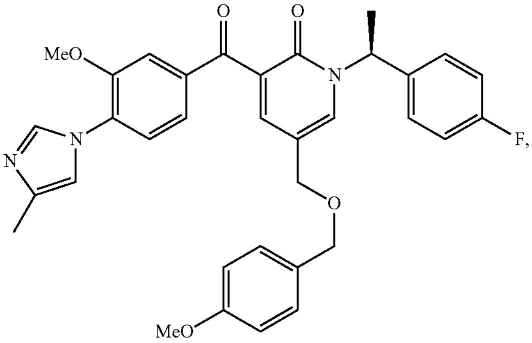
,
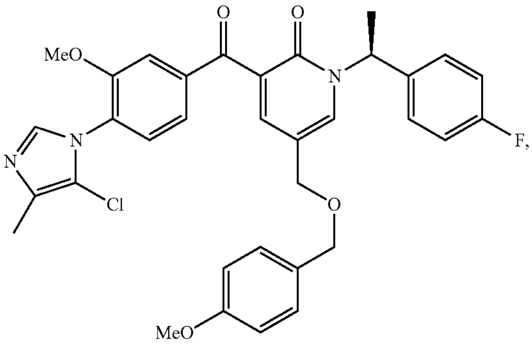
,
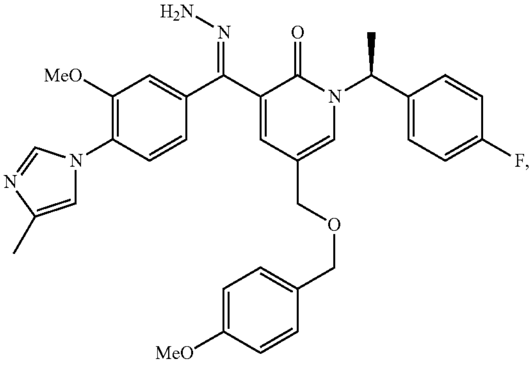
,
-continued
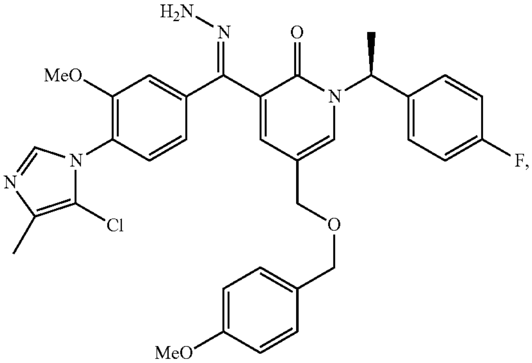
,
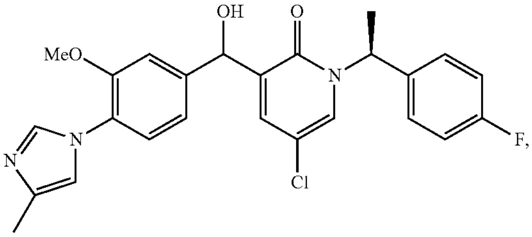
,
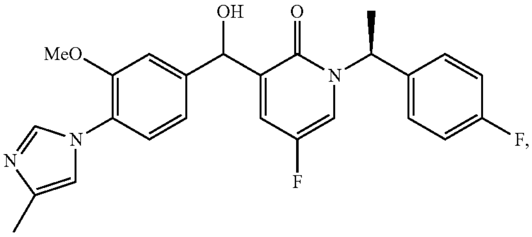
,
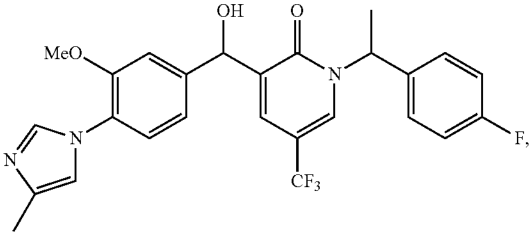
,
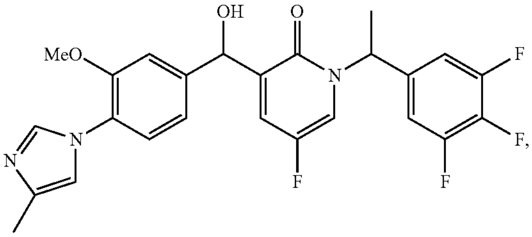
,
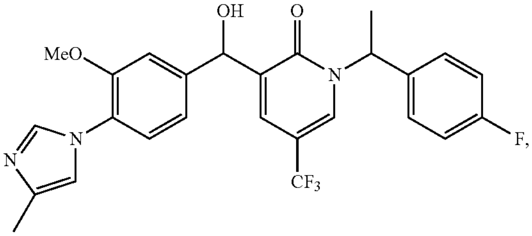
, -continued
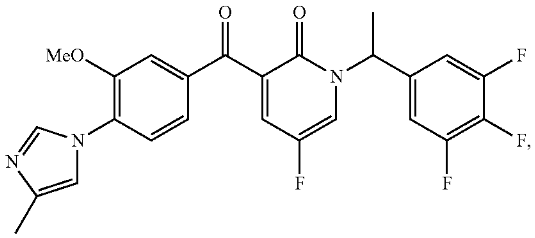
,
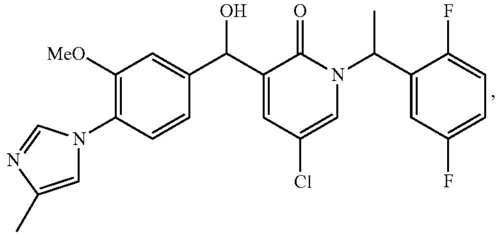
,
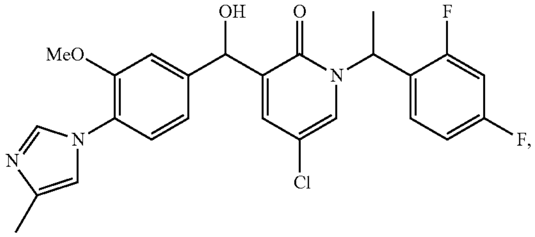
,
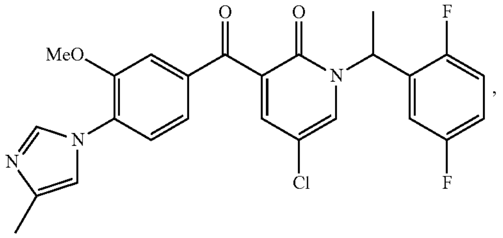
,
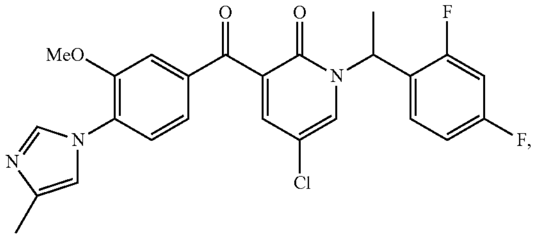
,
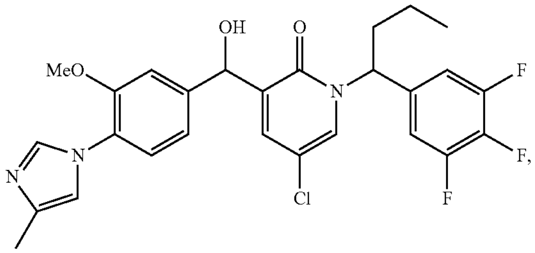
,
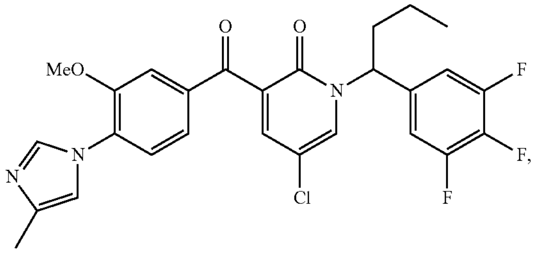
,
-continued
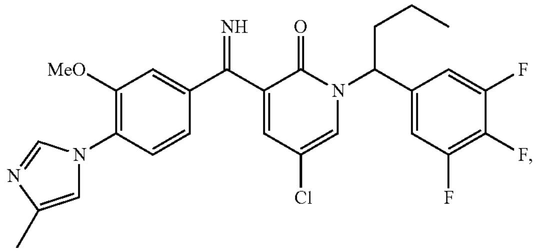
,
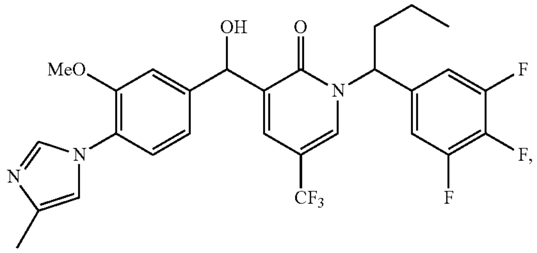
,
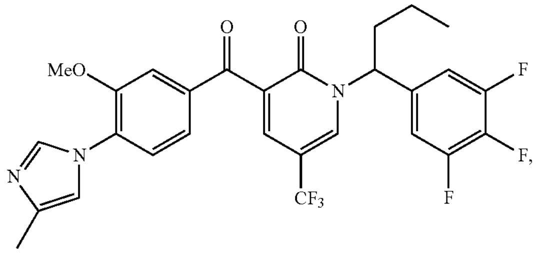
,
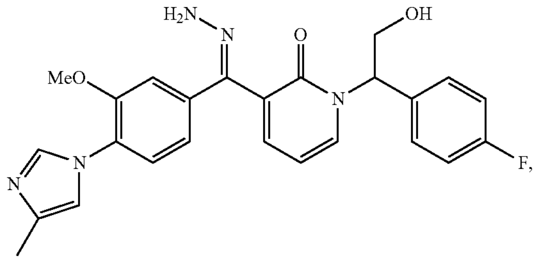
,
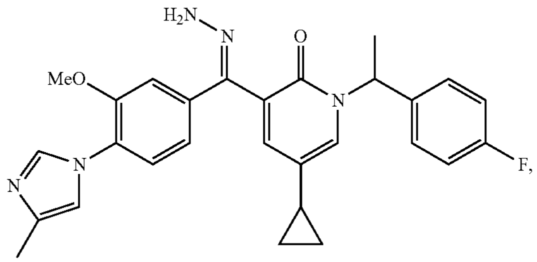
,
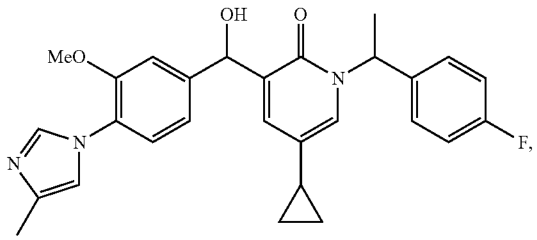
, -continued
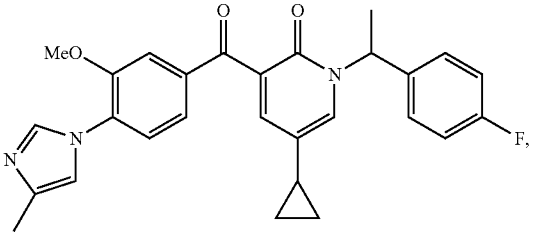
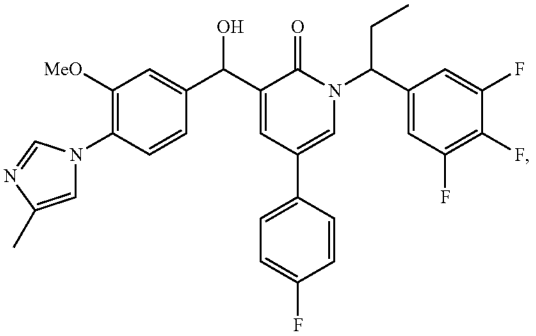
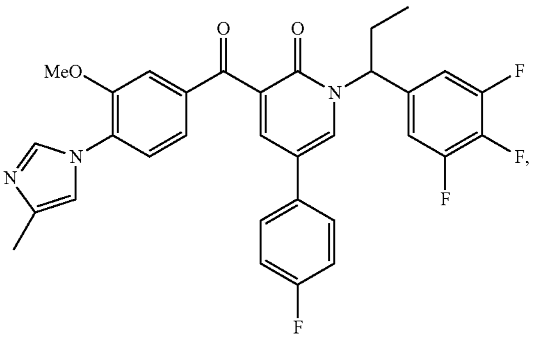
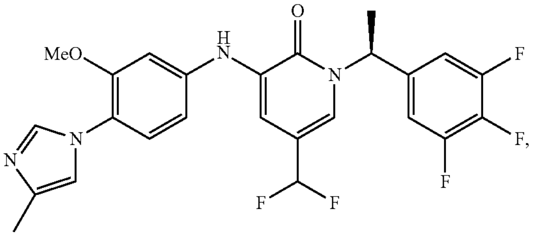
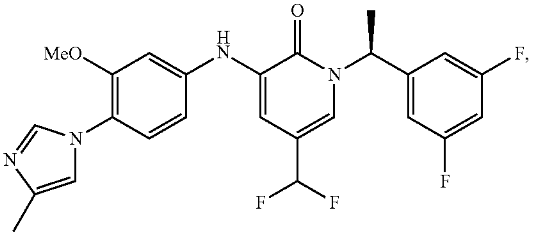
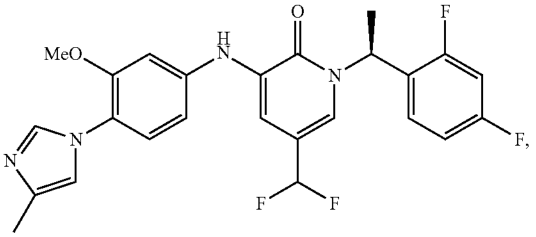
-continued
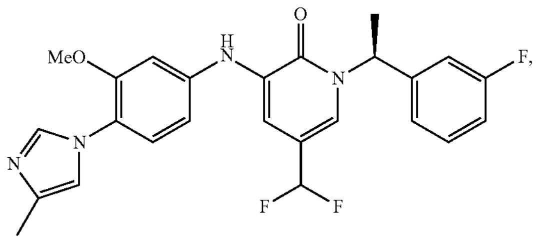
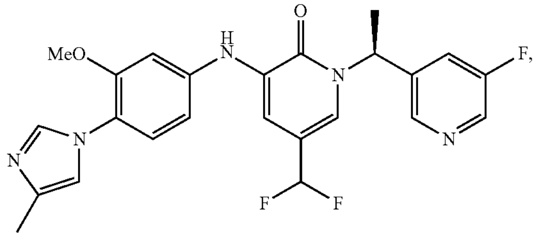
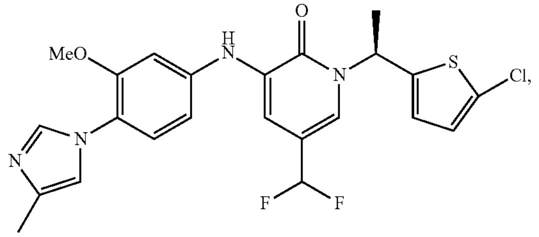
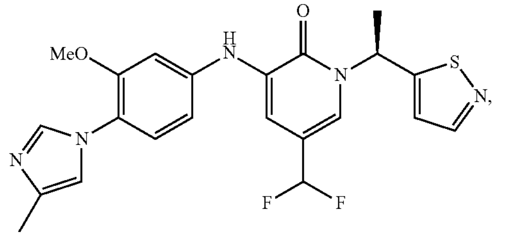
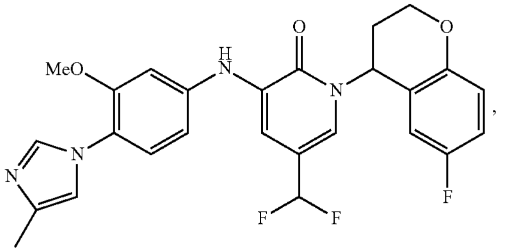
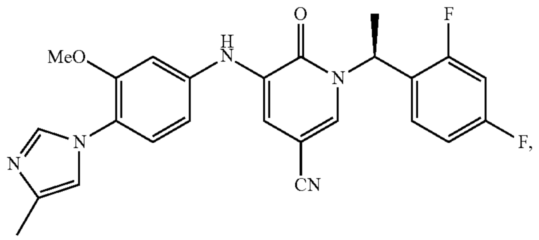
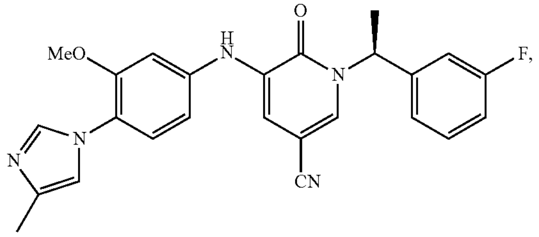

-continued
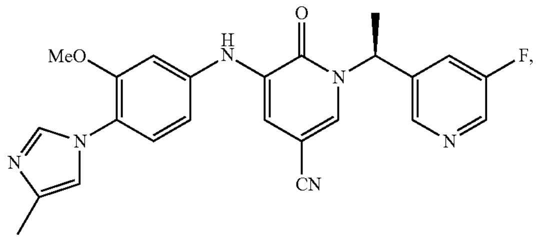
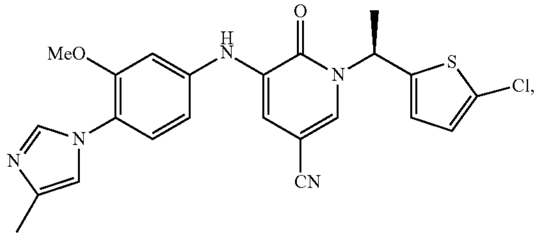
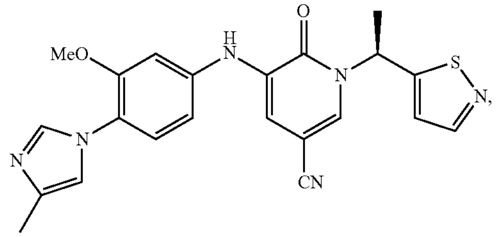
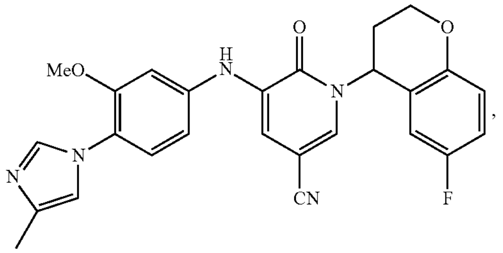
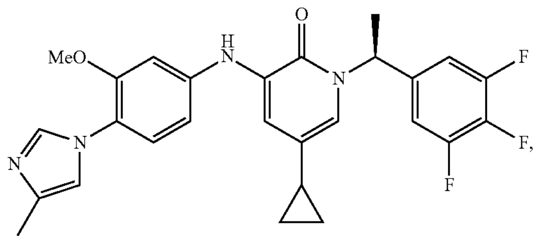
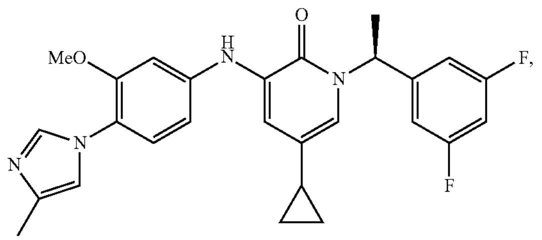
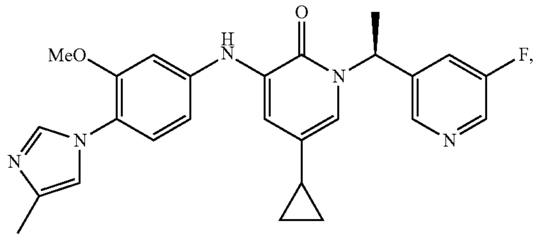
-continued
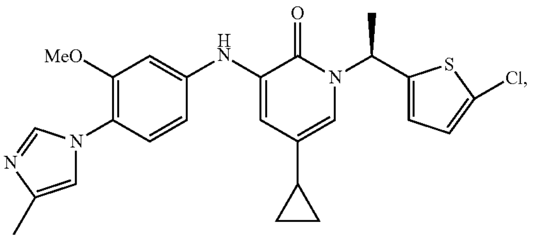
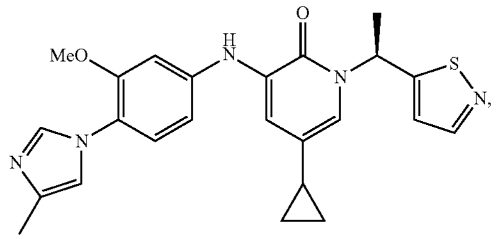
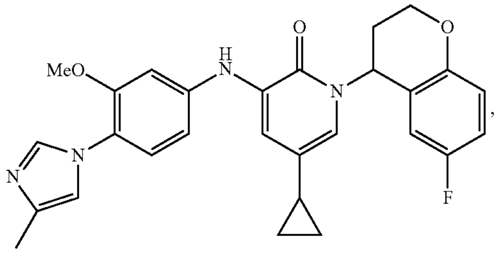
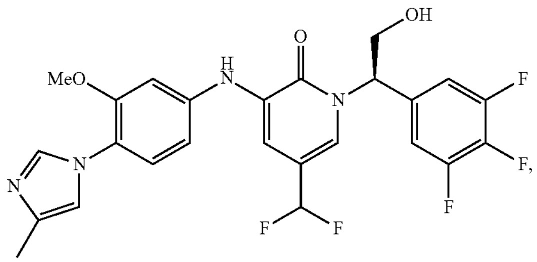
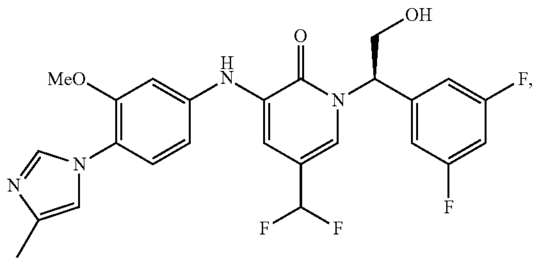
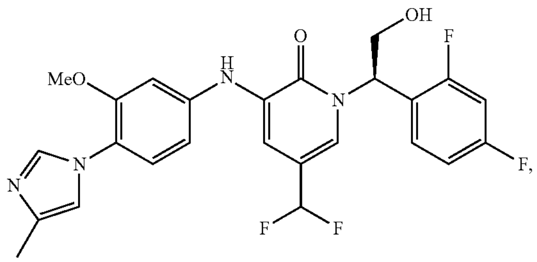

-continued
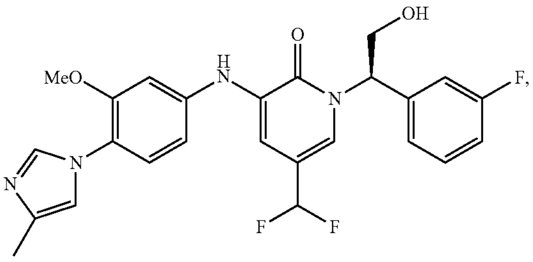
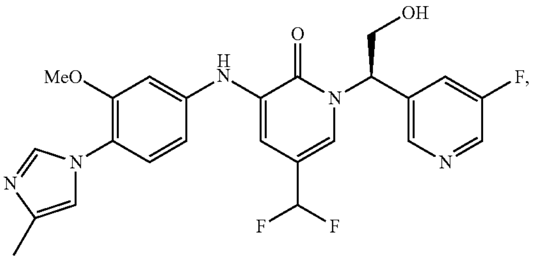
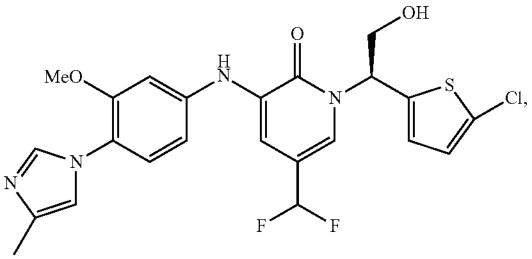
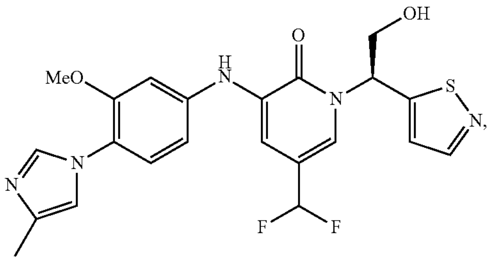
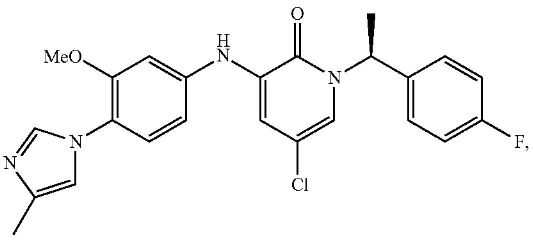
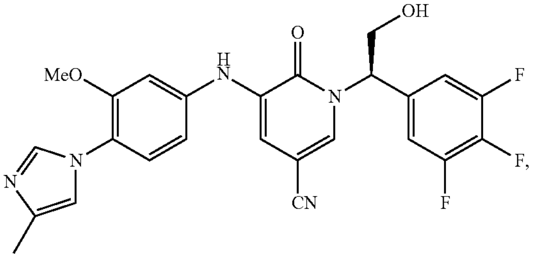
-continued
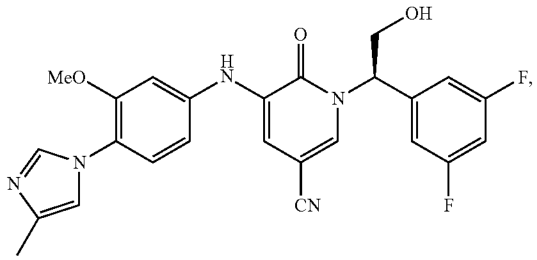
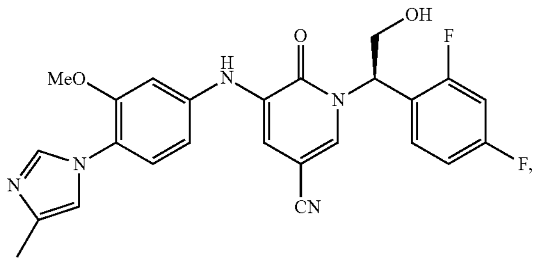
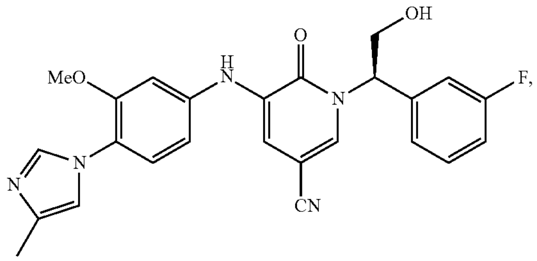
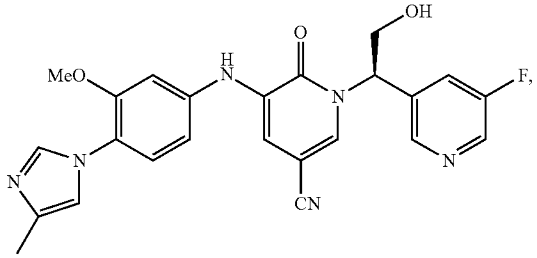
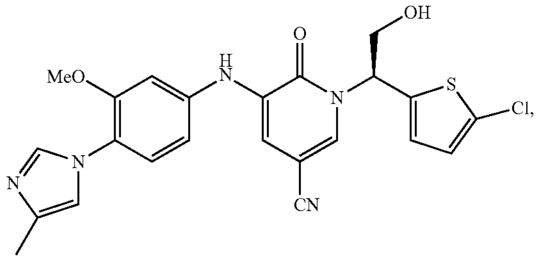
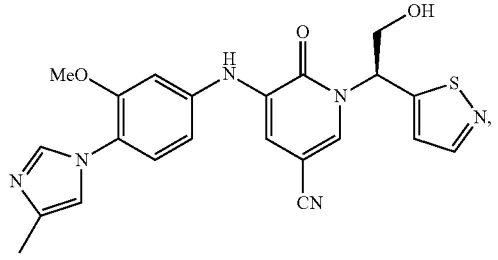

-continued
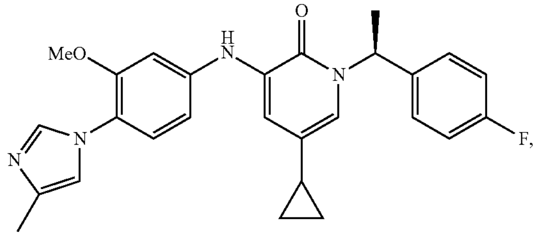
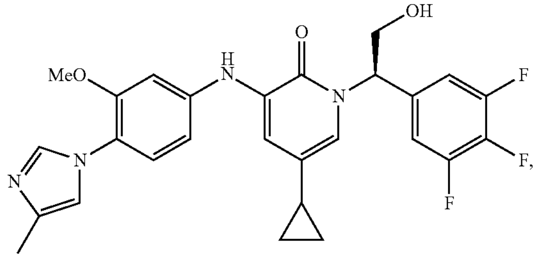
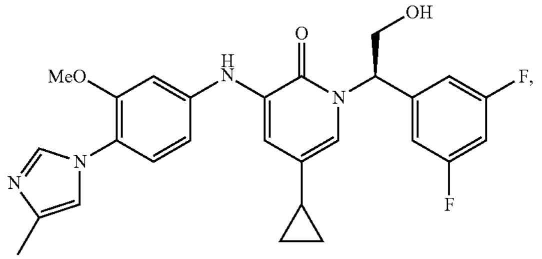
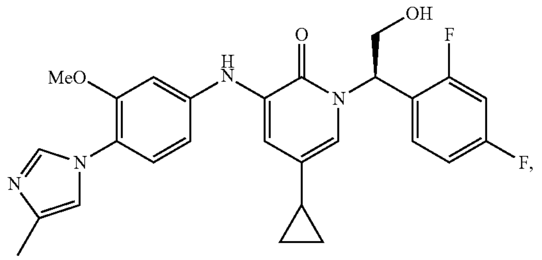
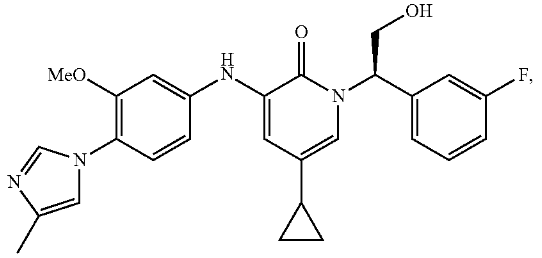
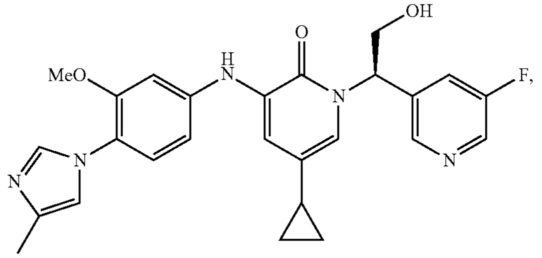
-continued
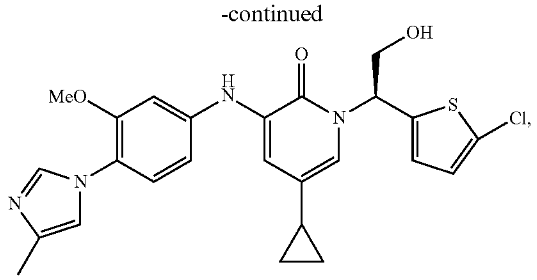
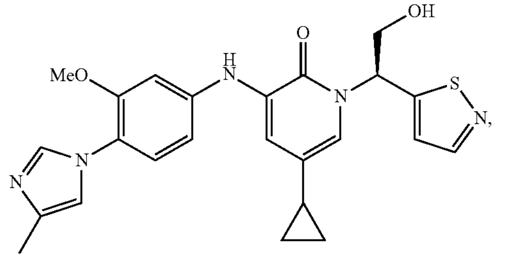
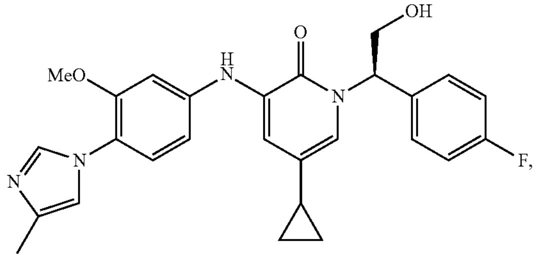
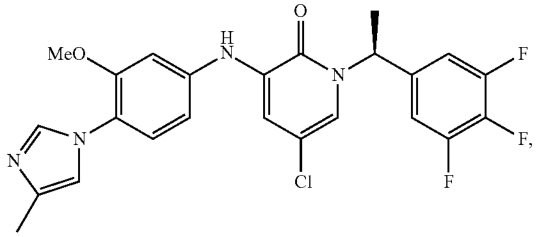
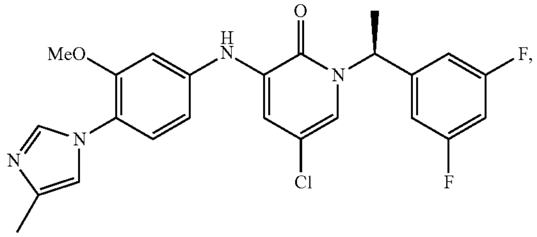
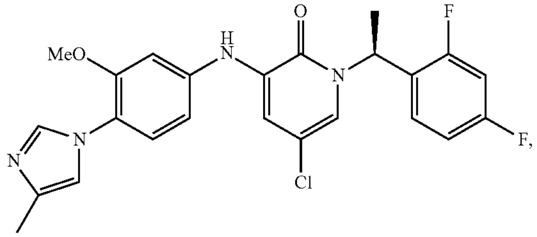
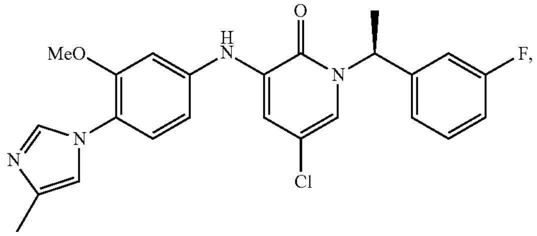

-continued
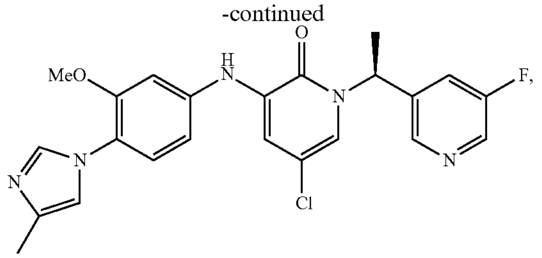
,
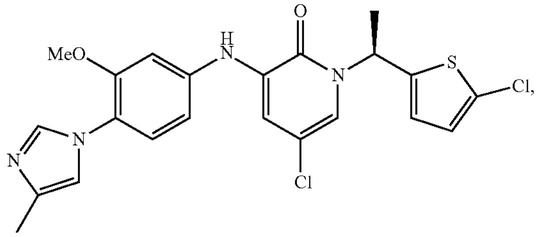
,
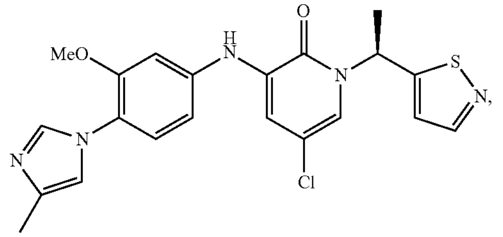
,
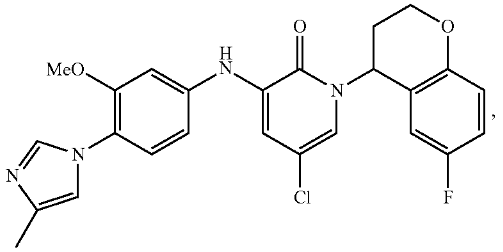
,
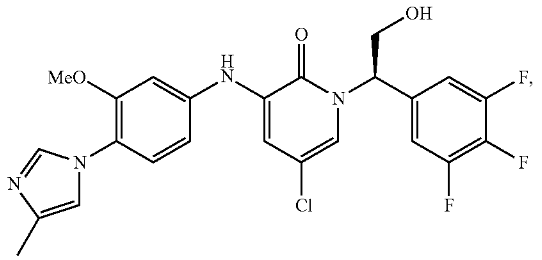
,
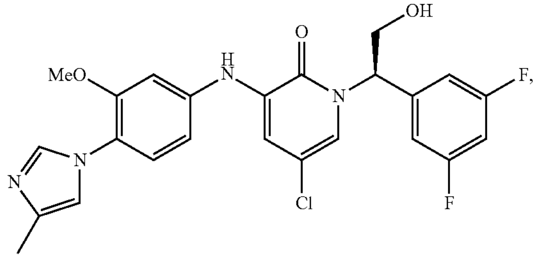
,
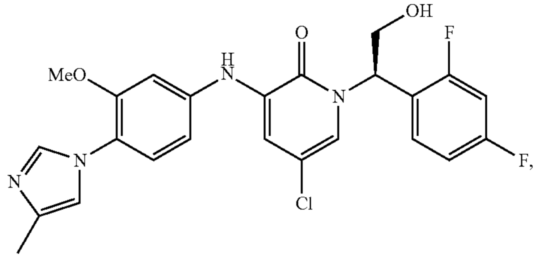
,
-continued
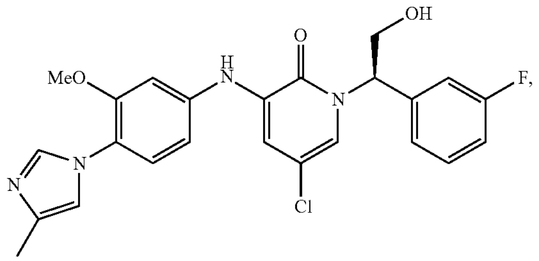
,
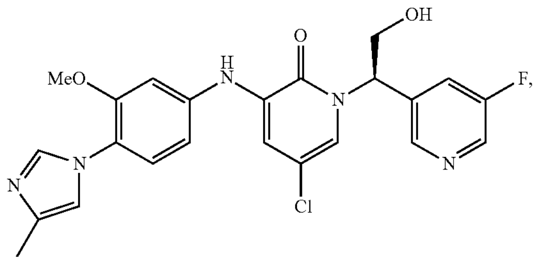
,
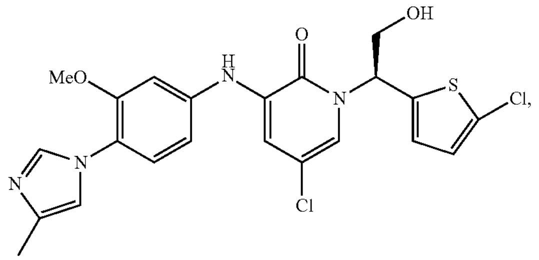
,
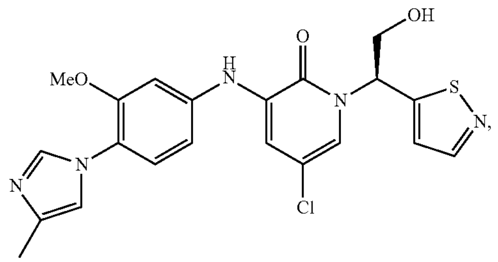
,
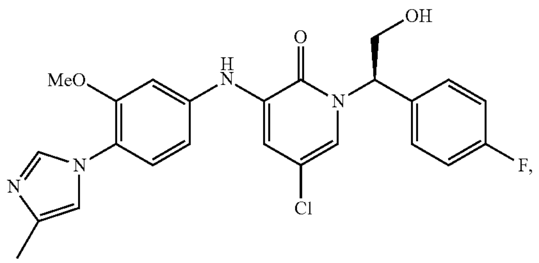
,
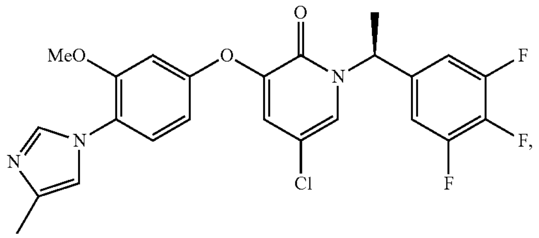
, -continued
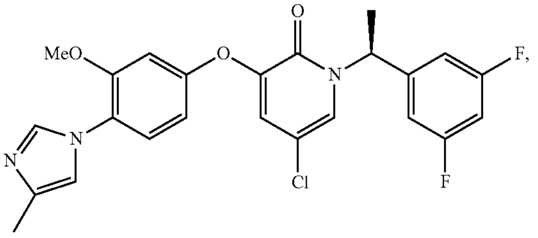
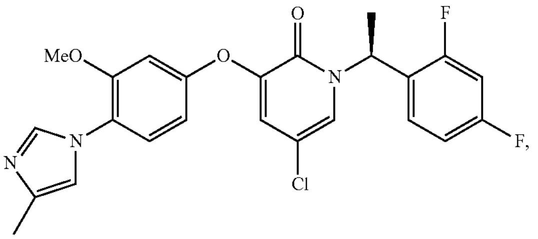
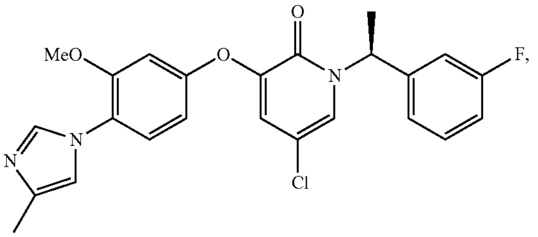
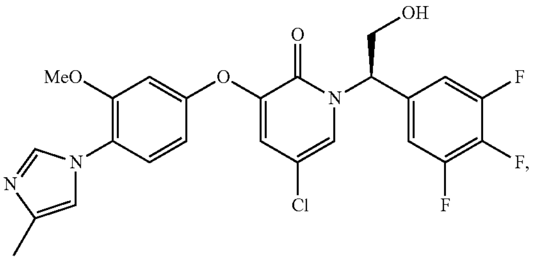
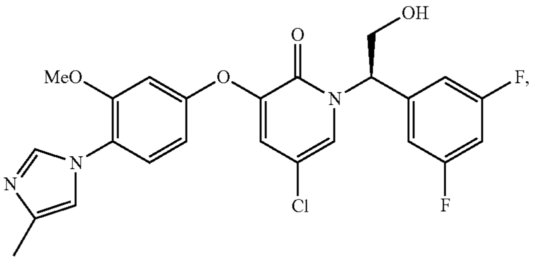
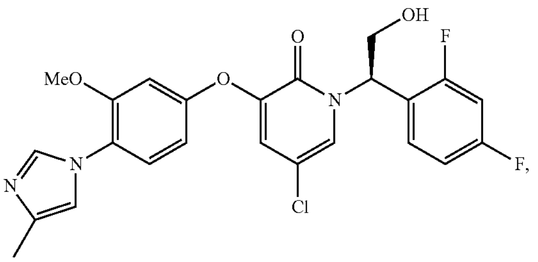
-continued
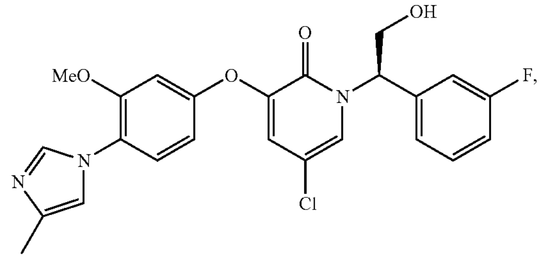
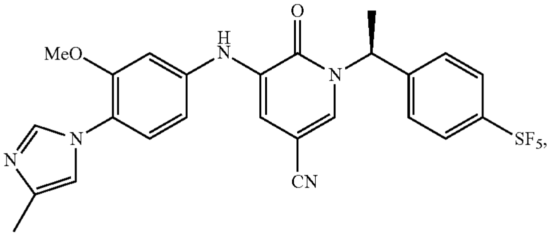
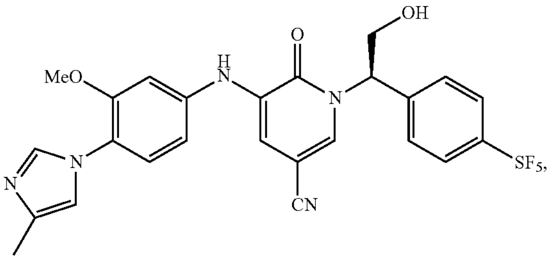
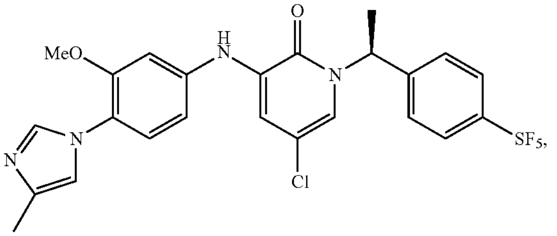
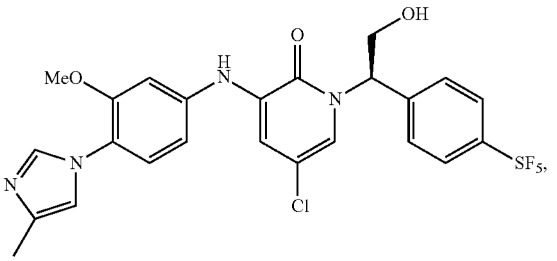
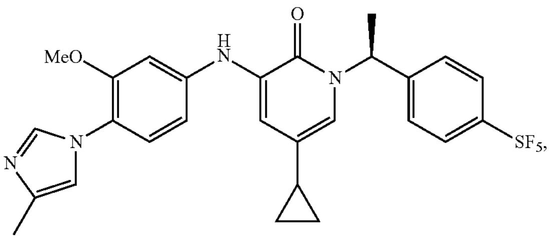

-continued

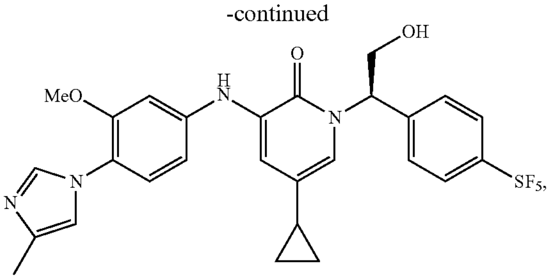

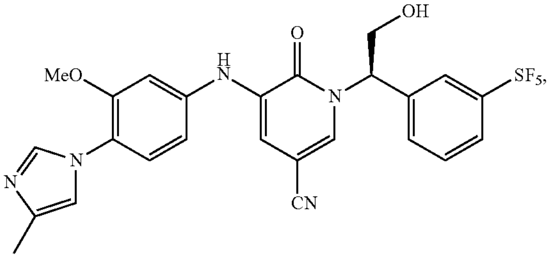

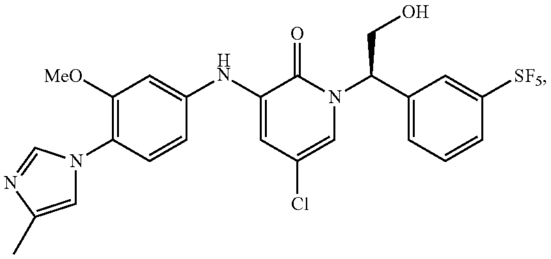

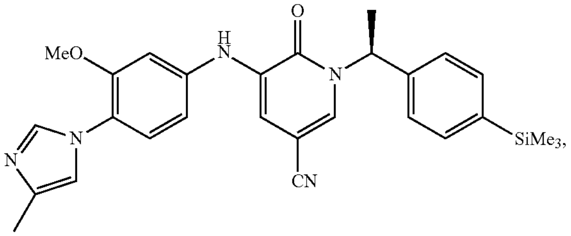

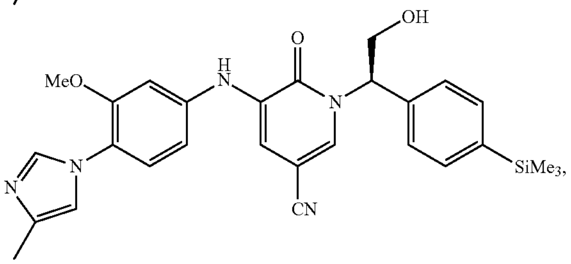

-continued

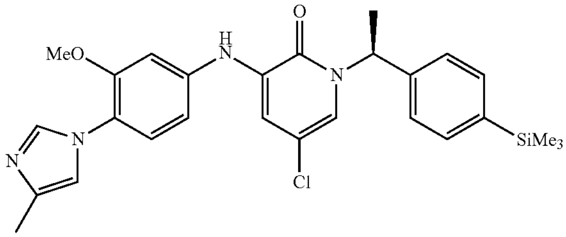

and

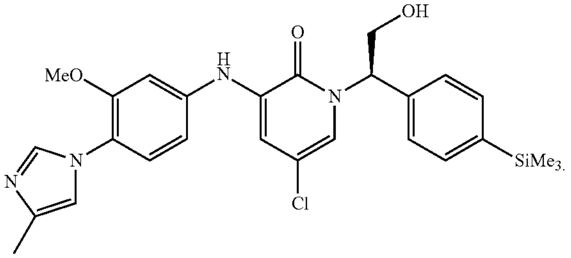

15. A pharmaceutical composition comprising:

(a) therapeutically effective amount of at least one compound of claim 1, or a pharmaceutically acceptable salt or ester thereof, and at least one pharmaceutically acceptable carrier; or (b) therapeutically effective amount of at least one compound of claim 1, or a pharmaceutically acceptable salt or ester thereof, and at least one pharmaceutically acceptable carrier, and a therapeutically effective amount of one or more compounds selected from the group consisting of cholinesterase inhibitors, Aβ antibody inhibitors, gamma secretase inhibitors and beta secretase inhibitors.

* * * * *